US012697341B1

(12) United States Patent
Vogt et al.

(10) Patent No.: US 12,697,341 B1
(45) Date of Patent: *Aug. 4, 2026

(54) METHODS OF USING MELOXICAM FOR PAIN TREATMENT AND MANAGEMENT

(71) Applicant: Viatris Inc., Canonsburg, PA (US)

(72) Inventors: Susanne Vogt, Bad Homburg v.d. Höhe (DE); Jeffrey P. Smith, Morgantown, WV (US); Kathleen Ocasio, Morgantown, WV (US); Joachim Maus, Hanau (DE); Kristina Marschall, Bad Homburg v.d. Höhe (DE); Matthew Hummel, Beaver, PA (US); Scott Haughie, Kent (GB); Abhijit Deshmukh, Hyderabad (IN); Amit Antarkar, Hyderabad (IN)

(73) Assignee: Viatris Inc., Canonsburg, PA (US)

( * ) Notice: Subject to any disclaimer, the term of this patent is extended or adjusted under 35 U.S.C. 154(b) by 16 days.

This patent is subject to a terminal disclaimer.

(21) Appl. No.: 19/397,383

(22) Filed: Nov. 21, 2025

Related U.S. Application Data

(60) Provisional application No. 63/862,494, filed on Aug. 12, 2025, provisional application No. 63/821,323, filed on Jun. 10, 2025, provisional application No. 63/802,518, filed on May 8, 2025, provisional application No. 63/801,585, filed on May 7, 2025.

(51) Int. Cl.
*A61K 31/5415* (2006.01)
*A61K 9/00* (2006.01)
*A61K 9/20* (2006.01)
*A61P 29/00* (2006.01)

(52) U.S. Cl.
CPC ........ *A61K 31/5415* (2013.01); *A61K 9/0053* (2013.01); *A61K 9/2009* (2013.01); *A61K 9/2027* (2013.01); *A61K 9/2054* (2013.01); *A61K 9/2077* (2013.01); *A61P 29/00* (2018.01)

(58) Field of Classification Search
CPC .................................................. A61K 31/5415
See application file for complete search history.

(56) References Cited

U.S. PATENT DOCUMENTS

| | | | |
|---|---|---|---|
| 9,526,734 | B2 | 12/2016 | Bosch |
| 9,649,318 | B2 | 5/2017 | Bosch |
| 9,808,468 | B2 | 11/2017 | Bosch |
| 9,821,075 | B2 | 11/2017 | Tabuteau |
| 10,265,399 | B2 | 4/2019 | Tabuteau |
| 10,265,400 | B2 | 4/2019 | Tabuteau |
| 10,307,484 | B2 | 6/2019 | Tabuteau |
| 10,369,224 | B2 | 8/2019 | Tabuteau |
| 10,369,225 | B2 | 8/2019 | Tabuteau |
| 10,426,839 | B2 | 10/2019 | Tabuteau |
| 10,463,736 | B2 | 11/2019 | Tabuteau |
| 10,709,713 | B2 | 7/2020 | Cooper et al. |
| 2005/0053669 | A1 | 3/2005 | Friedl et al. |
| 2007/0077296 | A1 | 4/2007 | Folger et al. |
| 2011/0160273 | A1 | 6/2011 | Buschmann et al. |
| 2011/0212948 | A1 * | 9/2011 | Pippia ................ A61K 31/5415 514/226.5 |
| 2012/0149692 | A1 | 6/2012 | Hanna et al. |
| 2013/0224151 | A1 | 8/2013 | Pearson et al. |
| 2017/0281640 | A1 | 10/2017 | Romero Medina et al. |
| 2020/0085835 | A1 | 3/2020 | Bosch |
| 2022/0184095 | A1 | 6/2022 | Allan et al. |
| 2023/0172943 | A1 | 6/2023 | Allan et al. |
| 2024/0277726 | A1 | 8/2024 | Patil et al. |
| 2025/0352478 | A1 | 11/2025 | Patil et al. |
| 2025/0352479 | A1 | 11/2025 | Patil et al. |
| 2025/0352552 | A1 | 11/2025 | Patil et al. |

FOREIGN PATENT DOCUMENTS

| | | | |
|---|---|---|---|
| CA | 2976272 | C | 9/2018 |
| CN | 1233323 | C | 12/2005 |
| CN | 107405359 | A | 11/2017 |
| CN | 107970219 | A | 5/2018 |
| EP | 4008319 | B1 | 11/2024 |
| JP | 2011207875 | A | 10/2011 |
| JP | 4965130 | B2 | 4/2012 |
| NZ | 540226 | A | 3/2008 |
| WO | WO-2009094155 | A1 | 7/2009 |
| WO | WO-2011086194 | A1 | 7/2011 |
| WO | WO-2020219406 | A1 | 10/2020 |
| WO | WO-2020262618 | A1 | 12/2020 |
| WO | WO-2021216545 | A1 | 10/2021 |
| WO | WO-2022097024 | A1 | 5/2022 |

OTHER PUBLICATIONS

Tacca et al. Clinical Drug Investigation, 2002, 22(12): 799-818.*

Yocum et al. Archives of Internal Medicine, 2000, 160(19): 2947-2954.*

Abass Met al, "Synergistic efficacy of tramadol and meloxicam on alleviation of pain and selected immunological variables after sciatic nerve ligation in rats", Int J Vet Sci Med, 2014, 2(1):14-20.

Anjeso Package Insert, U.S. Food and Drug Administration, Revised Apr. 2021.

Auvinet et al., "Comparison of the onset and intensity of action of intramuscular meloxicam and oral meloxicam in patients in acute sciatica", Clin Ther, 17(6):1078-90, (1995).

Bittner, J.G., and Clingempeel, N.L. Hernia Repair in the United States: Current Situation and Trends. In: Campanelli, G. (eds) The Art of Hernia Surgery. 2018. Springer, Cham.

Blain H et al., Limitation of the in vitro whole blood assay for predicting the COX selectivity of NSAIDs in clinical use. Br J Clin, (2002) 53(3):255-65.

Bourque S.L. et al., Comparison of buprenorphine and meloxicam for postsurgical analgesia in rats: effects on body weight, locomotor activity, and hemodynamic parameters. J Am Assoc Lab Anim Sci, (2010) 49 (5):617-622.

Breivik, H., et al., Assessment of pain. Br J Anaesth, 2008. 101(1): p. 17-24.

(Continued)

*Primary Examiner* — Rei Tsang Shiao

(57) ABSTRACT

The present invention relates to a method for managing pain, such as acute pain, post-operative pain, or post-procedure pain, by administering meloxicam.

29 Claims, 45 Drawing Sheets

(56) References Cited

OTHER PUBLICATIONS

Bugada, D., et al., Effect of postoperative analgesia on acute and persistent postherniotomy pain: a randomized study. J Clin Anesth, 2015. 27(8): p. 658-664.
Burukoglu D et al., Effects of nonsteroidal anti-inflammatory meloxicam on stomach, kidney, and liver of rats. Toxicol Ind Health, (2016) 32:980-986.
Busch U et al. Pharmacokinetics of Meloxicam in Animals and the Relevance to Humans. Drug Metab Dispos, (1998) 26:576-584.
Cheung, C.W., et al., Oral Oxycodone for Acute Postoperative Pain: A Review of Clinical Trials. Pain Physician, 2017. 20(2S): p. SE33-SE52.
Chou, R., et al., Management of Postoperative Pain: a clinical practice guideline from the American pain society, the American Society of Regional Anesthesia and Pain Medicine, and the American Society of Anesthesiologists' committee on regional anesthesia, executive committee, and administrative council. J Pain, 2016. 17(2): p. 131-157.
Christensen, S.E., et al., A randomized double-blind controlled trial of intravenous meloxicam in the treatment of pain following dental impaction surgery. J Clin Pharm col. 2018. 58(5): p. 593-605.
Clinical Trial NCT04571515, Dose-Response Study of MR-107A-01 in The Treatment of Post-Surgical Dental Pain, https://clinicaltrials.gov/study/NCT04571515?term=NCT04571515&rank=1.
Clinical Trial NCT05317312, Study of MR-107A-02 in the Treatment of Post Surgical Dental Pain, https://clinicaltrials.gov/study/NCT05317312?term=NCT05317312%20&rank=1.
Clinical Trial NCT06215820, Study of MR-107A-02 for the Treatment of Acute Postoperative Pain Following Bunionectomy, https://clinicaltrials.gov/study/NCT06215820?term=NCT06215820&rank=1.
Clinical Trial NCT06215859, Study of MR-107A-02 for the Treatment of Acute Postoperative Pain Following Herniorrhaphy, https://clinicaltrials.gov/study/NCT06215859?term=NCT06215859&rank=1.
ClinicalTrials.gov, "Evaluation of N1539 Following Bunionectomy Surgery", Identifier NCT02675907, Last Updated Nov. 17, 2017. Accessed Oct. 31, 2025. Available at https://clinicaltrials.gov/study/NCT02675907#participation-criteria.
ClinicalTrials.gov. "Evaluation of N1539 Following Abdominoplasty Surgery." Identifier NCT02678286, Last Updated Feb. 14, 2018. Accessed Oct. 31, 2025. Available at https://clinicaltrials.gov/study/NCT02678286#participation-criteria.
Co-pending U.S. Appl. No. 17/920,233, filed Oct. 20, 2022, published as US20230172943.
Co-pending U.S. Appl. No. 18/251,923, filed Nov. 3, 2021, published as US20240277726.
Co-pending U.S. Appl. No. 19/285,261, filed Jul. 30, 2025, published as US20250352478A1.
Co-pending U.S. Appl. No. 19/285,330, filed Jul. 30, 2025, published as US20250352552A1.
Co-pending U.S. Appl. No. 19/285,358, filed Jul. 30, 2025, published as US20250352479A1.
Co-pending U.S. Appl. No. 19/397,231, filed Nov. 21, 2025.
Co-pending U.S. Appl. No. 19/397,290, filed Nov. 21, 2025.
Co-pending U.S. Appl. No. 19/397,427, filed Nov. 21, 2025.
Combe et al., "Comparison of Intramuscular and Oral Meloxicam in Rheumatoid Arthritis Patients", Inflammatory Research, 50(1):10-16, (2001).
Engelhardt et al., "Anti-inflammatory, Analgesic, Antipyretic and Related Properties of Meloxicam, A New Non-steroidal Anti-inflammatory Agent with Favourable Gastrointestinal Tolerance", Inflamm Res, 1995, 44: 423-433.
Engelhardt et al., "General Pharmacology of Meloxicam—Part II: Effects on Blood Pressure, Blood Flow, Heart Rate, ECG, Respiratory Minute vol. and Interactions with Paracetamol, Pirenzepine, Chlorthalidone, Phenprocoumon and Tolbutamide", Gen Pharmac, 27:679-688, (1996).
Engelhardt et al., "Pharmacology of Meloxicam, A New Non-steroidal Anti-inflammatory Drug with An Improved Safety Profile Through Preferential Inhibition of COX-2", British Journal Rheumatology, 35:4-12, (1996).
FDA Guidance for Industry: Multiple Endpoints in Clinical Trials. Oct. 2022.
FDA. Drug Safety Communication: FDA updates prescribing information for all opioid pain medicines to provide additional guidance for safe use. Apr. 13, 2023. Accessed Oct. 28, 2025. Available at https://www.fda.gov/drugs/drug-safety-and-availability/fda-updates-prescribing-information-all-opioid-pain-medicines-provide-additional-guidance-safe-use.
FDA. Guidance for Industry: Development of Non-Opioid Analgesics for Acute Pain. Feb. 2022.
FDA. Guidance for Industry: Development of Non-Opioid Analgesics for Chronic Pain. Sep. 2025.
FDA. Guidance for Industry: E8(R1) General Considerations for Clinical Studies. Apr. 2022.
Foroud M and Vesal N (2015). Evaluation of the anti-nociceptive effects of morphine, tramadol, meloxicam and their combinations using the tail-flick test in rats. In Veterinary Research Forum. 6:4, 313.
Gottlieb et al, "Evaluation of the Safety and Efficacy of an Intravenous Nanocrystal Formulation of Meloxicam in the Management of Moderate-to-severe Pain after Bunionectomy" Journal of Pain Research,16(11): p. 383-393, (2018).
Hudgins, J.D., et al., Prescription opioid use and misuse among adolescents and young adults in the United States: A national survey study. PLoS Med, 2019. 16(11): p. e1002922.
Inal S et al. Comparison of the effects of dexketoprofen trometamol, meloxicam and diclofenac sodium on fibular fracture healing, kidney and liver: an experimental rat model. Injury, (2014) 45:494-500.
Isiordia-Espinoza et al, "Pre-emptive Analgesic Effectiveness of Meloxicam Versus Tramadol After Mandibular Third Molar Surgery: A Pilot Study", J Oral Maxil Surg, 50 (1):31-36, (2012).
Karaca, Z. and McDermott, K.W., High-Volume Invasive, Therapeutic Ambulatory Surgeries Performed in Hospital-Owned Facilities, 2016. HCUP Statistical Brief #252. Sep. 2019. Agency for Healthcare Research and Quality, Rockville, MD. Accessed Nov. 10, 2025. Available at www.hcup-us.ahrq.gov/reports/statbriefs/sb252-Invasive-Ambulatory-Surgeries-2016.pdf.
Kehlet, H., Jensen, T.S., and Woolf, C.J., Persistent postsurgical pain: risk factors and prevention. Lancet, 2006. 367(9522): p. 1618-1625.
Kesaria, A.A., et al., Nationwide surgical trends for bunionectomies in medicare beneficiaries: An increase in lapidus bunionectomy procedure. Journal of Foot and Ankle Surgery, 2025. 64(5): p. 581-587.
Khalikov, S.P., et al., Inguinal Hernia: Prevalence, Risks, Treatment Prospects, American Journal of Medicine and Medical Sciences, 2024. 14(10): p. 2453-2457.
Khan, N.F., et al., Association ofOpioid Overdose With Opioid Prescriptions to Family Members. JAMA Intern Med, 2019. 179(9): p. 1186-1192.
Korwin-Kochanowska, K., et al., PROSPECT guideline for hallux valgus repair surgery: a systematic review and procedure-specific postoperative pain management recommendations. Reg Anesth Pain Med, 2020. 45: p. 702-708.
Kvarda, P., et al., Opioid consumption rate following foot and ankle surgery. Foot Ankle Orthop, 2019. 40(8): p. 905-913.
Maamar M, et al., Ibuprofen results in alterations of human fetal testis development. Scientific Reports, (2017) 7:1-15.
Martinez, V., et al., Chronic postsurgical pain: a European survey. Eur J Anaesthesiol, 2024. 41(5), p. 351-362.
McDermott, K.W. and Liang, L., Overview of Major Ambulatory Surgeries Performed in Hospital-Owned Facilities, 2019. HCUP Statistical Brief #287. Dec. 2021. Agency for Healthcare Research and Quality, Rockville, MD. Accessed Nov. 10, 2025. Available at https://www.ncbi.nlm.nih.gov/books/NBK577044/pdf/Bookshelf_NBK577044.pdf.
MOBIC Label (2024). Approved product labeling for MOBIC® (meloxicam) tablets, for oral use. USFDA. Boehringer Ingelheim Pharmaceuticals Inc.

(56) References Cited

OTHER PUBLICATIONS

Moeremans et al, "Pharmacokinetics and Absolute Oral Bioavailability of Meloxicam in Guinea Pigs (*Cavia porcellus*)", Vet Anesthesia and Analgesia 46:548-555, (2019).
Moore, R.A., et al., Single dose oral analgesics for acute postoperative pain in adults—an overview of Cochrane reviews. Cochrane Database Syst Rev, 2015. 2015(9): p. CD008659.
Nunamaker et al, "Evaluation of Analgesic Efficacy of Meloxicam and 2 Formulations of Buprenorphine After Laparotomy in Female Sprague Dawley Rats", Journal of the American Assoc for Laboratory Animal Science, 57(5): 498-507, (2018).
Vaughn, B. et al., Abstract for P-104, Efficacy and Safety of Meloxicam Co-Crystal and a Rapid-Absorption Formation of Meloxicam in the treatment of Post-Surgical Dental Pain, PainWeek 2024.
PainWeek 2024, Bertoch, Abstract for SAP-05, SAP-05—(Scientific Abstract Poster Live Presentation) Efficacy and Safety of Meloxicam Co-Crystal and a Rapid-Absorption Formulation of Meloxicam in The Treatment of Post-Surgical Dental Pain, https://painweek2024.eventscribe.net/fsPopup.asp?PresentationID=1483713&mode=presInfo.
PainWeek 2025, Abstract for P-039, Efficacy and safety of MR-107A-02 (novel fast-acting meloxicam formulation) for the treatment of acute moderate-to-severe pain following bunionectomy; https://painweek2025.eventscribe.net/SearchByPresentation.asp?pfp=BrowseAbstractsByTitle.
PainWeek 2025, Abstract for P-041, Pharmacokinetics study comparing MR-107A-02 (novel fast-acting meloxicam formulation) 15mg tablet with meloxicam (Mobic®) 15mg in healthy adult male subjects; https://painweek2025.eventscribe.net/SearchByPresentation.asp?pfp=BrowseAbstractsByTitle.
PainWeek 2025, Abstract for P-076, Time to Efficacy Onset of MR-107A-02 (Novel Fast-Acting Meloxicam Formulation) in the Treatment of Acute Postoperative Pain Following Bunionectomy and Herniorrhaphy; https://painweek2025.eventscribe.net/SearchByPresentation.asp?pfp=BrowseAbstractsByTitle.
PainWeek 2025, Abstract for P-40, Opioid sparing effect of MR-107A-02 (novel fast-acting meloxicam formulation) for the treatment of acute moderate-to-severe pain following bunionectomy and herniorrhaphy; https://painweek2025.eventscribe.net/SearchByPresentation.asp?pfp=BrowseAbstractsByTitle.
PainWeek 2025, Abstract for P-038, Efficacy and safety of MR-107A-02 (novel meloxicam fast-acting formulation) for the treatment of acute moderate-to-severe pain following herniorrhaphy; https://painweek2025.eventscribe.net/fsPopup.asp?efp=UEFTRVdOUE0yNTUzNQ&PresentationID=1668898&rnd=0.9800032&mode=presInfo.
Pollak, R.A., et al., Efficacy and Safety of Intravenous Meloxicam in Patients with Moderate-to-Severe Pain Following Bunionectomy: A Randomized, Double-Blind, Placebo-controlled Trial. Clin J Pain, 2018. 34(10): p. 918-926.
PainWeek 2024 Poster #104 (Sep. 3-6, 2024, The Cosmopolitan of Las Vegas, Las Vegas, Nevada).
PainWeek 2025, Poster 38 (Sep. 2-5, 2025, The Cosmopolitan of Las Vegas, Las Vegas, Nevada).
PainWeek 2025, Poster 39 (Sep. 2-5, 2025, The Cosmopolitan of Las Vegas, Las Vegas, Nevada).
PainWeek 2025, Poster 40 (Sep. 2-5, 2025, The Cosmopolitan of Las Vegas, Las Vegas, Nevada).
PainWeek 2025, Poster 41 (Sep. 2-5, 2025, The Cosmopolitan of Las Vegas, Las Vegas, Nevada).
PainWeek 2025, Poster 76 (Sep. 2-5, 2025, The Cosmopolitan of Las Vegas, Las Vegas, Nevada).
QAMZOVA [package insert]. U.S. Food and Drug Administration. Revised [Apr. 2025]. Accessed Oct. 31, 2025.
Romer D (1980). Pharmacological evaluation of mild analgesics. Br J Clin Pharmacol, 10: 247S-251S.
Santos AR et al., Antinociceptive effect of meloxicam, in neurogenic and inflammatory nociceptive models in mice. Inflam Res, (1998) 47(7):302-307.
Small, C. and Laycock, H., Acute postoperative pain management. Br J Surg, 2020. 107(2): p. e70-e80.
Tubbs et al., "Effects of Buprenorphine, Meloxicam, and Flunixin Meglumine as Postoperative Analgesia in Mice" Journal American Assoc Lab Animal Sci, 2:185-191, (2011).
U.S. Centers for Disease Control and Prevention, CDC Reports Nearly 24% Decline in U.S. Drug Overdose Deaths. Released 2025. Accessed Oct. 15, 2025. Available at https://www.cdc.gov/media/releases/2025/2025-cdc-reports-decline-in-us-drug-overdose-deaths.html.
Viatris Aug. 1, 2025 Press Release, "Viatris Announces Five Data Presentations on Novel Fast-Acting Meloxicam (MR-107A-02) at PainWeek 2025 Conference", https://newsroom.viatris.com/2025-08-01-Viatris-Announces-Five-Data-Presentations-on-Novel-Fast-Acting-Meloxicam-MR-107A-02-at-PAINWeek-2025-Conference.
Viatris May 8, 2025 Press Release, Viatris Announces Positive Top-Line Results from Two Pivotal Phase 3 Studies of Novel Fast-Acting Meloxicam (MR-107A-02) for the Treatment of Moderate-to-Severe Acute Pain, https://newsroom.viatris.com/2025-05-08-Viatris-Announces-Positive-Top-Line-Results-from-Two-Pivotal-Phase-3-Studies-of-Novel-Fast-Acting-Meloxicam-MR-107A-02-for-the-Treatment-of-Moderate-to-Severe-Acute-Pain.
XIFYRM [package insert]. U.S. Food and Drug Administration. Revised [Jun. 2025]. Accessed Oct. 31, 2025.
Yocum et al. "Archives of Internal Medicine", 2000, 160(19):2947-5954.

* cited by examiner

| No. at Risk | | | | | | | | | | | | | | |
|---|---|---|---|---|---|---|---|---|---|---|---|---|---|---|
| 1.25 mg BID | 28 | 10 | 8 | 8 | 7 | 7 | 7 | 7 | 7 | 7 | 7 | 7 | 0 | 0 |
| 5 mg BID | 28 | 7 | 7 | 7 | 7 | 7 | 7 | 7 | 7 | 7 | 7 | 7 | 1 | 0 |
| 15 mg BID | 27 | 1 | 1 | 1 | 1 | 1 | 1 | 1 | 1 | 1 | 1 | 1 | 0 | 0 |
| Placebo | 27 | 18 | 17 | 17 | 17 | 17 | 17 | 17 | 17 | 17 | 17 | 17 | 2 | 0 |

| No. at Risk | | | | | | | | | | | | | |
|---|---|---|---|---|---|---|---|---|---|---|---|---|---|
| 1.25 mg BID | 28 | 23 | 20 | 18 | 15 | 15 | 14 | 14 | 14 | 14 | 14 | 14 | 1 | 0 |
| 5 mg BID | 28 | 21 | 19 | 17 | 15 | 15 | 15 | 15 | 15 | 15 | 15 | 15 | 2 | 0 |
| 15 mg BID | 27 | 13 | 9 | 8 | 8 | 8 | 8 | 8 | 8 | 8 | 8 | 8 | 0 | 0 |
| Placebo | 27 | 25 | 21 | 21 | 21 | 21 | 21 | 21 | 21 | 21 | 21 | 21 | 3 | 0 |

| No. at Risk | | | | | | | | | | | | | | |
|---|---|---|---|---|---|---|---|---|---|---|---|---|---|---|
| 1.25 mg BID | 28 | 21 | 18 | 17 | 17 | 16 | 16 | 16 | 16 | 16 | 16 | 16 | 0 | 0 |
| 5 mg BID | 28 | 22 | 15 | 15 | 14 | 12 | 12 | 12 | 12 | 12 | 12 | 12 | 1 | 0 |
| 15 mg BID | 27 | 25 | 24 | 24 | 23 | 20 | 19 | 19 | 19 | 19 | 19 | 19 | 1 | 0 |
| Placebo | 27 | 15 | 9 | 8 | 8 | 7 | 7 | 7 | 7 | 7 | 7 | 7 | 1 | 0 |

| No. at Risk | | | | | | | | |
|---|---|---|---|---|---|---|---|---|
| Meloxicam 15mg BID | 137 | 49 | 33 | 26 | 21 | 17 | 16 | |
| Tramadol 50mg q6h | 137 | 53 | | 20 | 16 | 13 | 11 | 10 |
| Placebo | 136 | 66 | | 32 | 23 | 20 | 16 | 15 |

No. at Risk

| | | | | | |
|---|---|---|---|---|---|
| Meloxicam 15mg BID | 137 | 17 | 4 | 2 | 0 |
| Tramadol 50mg q6h | 137 | 15 | 7 | 3 | 0 |
| Placebo | 136 | 20 | 7 | 6 | 0 |

No. at Risk

| | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| Meloxicam 15mg BID | 137 | 84 | 77 | 77 | 77 | 76 | 76 | 76 | 76 | 76 | 76 | 76 | 76 | 76 | 76 | 76 | 76 | 76 | 69 | 25 | 14 | 8 | 2 | 2 | 1 | 1 | 1 | 1 | 1 | 1 | 1 | 1 | 1 |
| Tramadol 50mg q6h | 137 | 73 | 64 | 62 | 59 | 58 | 58 | 58 | 58 | 58 | 58 | 58 | 58 | 58 | 58 | 58 | 58 | 58 | 53 | 24 | 7 | 1 | 1 | 1 | 1 | 1 | 1 | 1 | 0 | 0 | 0 | 0 | 0 |
| Placebo | 138 | 50 | 43 | 43 | 42 | 42 | 42 | 42 | 42 | 42 | 42 | 42 | 42 | 42 | 42 | 42 | 42 | 42 | 40 | 18 | 6 | 1 | 1 | 1 | 0 | 0 | 0 | 0 | 0 | 0 | 0 | 0 | 0 |

| No. at Risk | | | | | | | | |
|---|---|---|---|---|---|---|---|---|
| Meloxicam 15mg BID | 230 | 119 | 99 | 89 | 51 | 38 | | |
| Tramadol 50mg q6h | 115 | 59 | 51 | 49 | 29 | 20 | 19 | |
| Placebo | 227 | 148 | 127 | 118 | 89 | 72 | | 55 |

No. at Risk

| | | | | | | | |
|---|---|---|---|---|---|---|---|
| Meloxicam 15mg BID | 230 | 107 | 51 | 41 | 30 | 25 | |
| Tramadol 50mg q6h | 115 | 53 | 33 | 28 | 19 | 15 | 14 |
| Placebo | 227 | 133 | 83 | 64 | 56 | 37 | |

| No. at Risk | | | | | | | | | | | | | | | | | | | |
|---|---|---|---|---|---|---|---|---|---|---|---|---|---|---|---|---|---|---|---|
| Meloxicam 15mg BID | 230 | 164 | 161 | 161 | 161 | 39 | 5 | 2 | 2 | 2 | 2 | 2 | 2 | 1 | 1 | 1 | 1 | 1 | 1 |
| Tramadol 50mg q8h | 115 | 76 | 76 | 76 | 76 | 12 | 1 | 0 | 0 | 0 | 0 | 0 | 0 | 0 | 0 | 0 | 0 | 0 | 0 |
| Placebo | 227 | 133 | 133 | 133 | 133 | 27 | 3 | 1 | 0 | 0 | 0 | 0 | 0 | 0 | 0 | 0 | 0 | 0 | 0 |

No. at Risk

| | | | | | | | | | | |
|---|---|---|---|---|---|---|---|---|---|---|
| Meloxicam 15mg BID | 230 | 108 | 101 | 101 | 101 | 101 | 72 | 12 | 2 | 1 |
| Tramadol 50mg q6h | 115 | 41 | 38 | 38 | 39 | 39 | 27 | 2 | 0 | 0 |
| Placebo | 227 | 55 | 53 | 53 | 53 | 53 | 40 | 1 | 0 | 0 |

MR-107A-02 are tablets according to Composition 8

METHODS OF USING MELOXICAM FOR PAIN TREATMENT AND MANAGEMENT

CROSS REFERENCE TO RELATED APPLICATIONS

This application claims priority to U.S. Provisional Application Ser. No. 63/801,585, filed May 7, 2025, U.S. Provisional Application Ser. No. 63/802,518 filed May 8, 2025, U.S. Provisional Application Ser. No. 63/821,323, filed Jun. 10, 2025, and U.S. Provisional Application Ser. No. 63/862,494, filed Aug. 12, 2025. The entire disclosure of each of the above-cited prior applications is incorporated herein by reference in their entireties.

FIELD OF THE INVENTION

The present invention relates to the treatment and management of pain, particularly acute pain.

BACKGROUND OF THE INVENTION

Acute pain affects millions of people in the United States annually, with over 80 million prescriptions written each year (Hincapie-Castillo et al., 2020; changes in opioid use after Florida's restriction law for acute pain prescriptions; *JAMA Network Open,* 3 (2), e200234-e200234).

Acute pain has to be treated in a timely manner with suitable pain medication. Alarmingly, nearly half of the prescriptions prescribed for treating pain are filled with an opioid. Opioids, although effective, come with significant risks, including addiction, overdose, and other adverse effects (Hincapie-Castillo et al., 2020, supra). Almost 10% of acute pain patients treated initially with an opioid will have prolonged opioid use.

Acute pain affects millions of Americans each year, and opioids are still commonly prescribed despite their well-documented risks. In a national U.S. survey of 300 adults who had undergone surgery within the previous 5 years, 86% of patients experienced postsurgical pain overall, and 75% of those who reported pain described its severity as moderate to extreme during the immediate postoperative period (Gan, et al., 2014; incidence, patient satisfaction, and perceptions of post-surgical pain: results from a US national survey; *Curr Med Res Opin,* 30 (1), 149-160). A prospective cohort study of 523 patients reported that up to 47.2% of patients experienced severe pain (numerical rating scale score at least 8) in the first 24 hours after surgery, depending on the type of surgery performed. Postoperative pain typically follows a predictable trajectory:

Acute pain peaks within the first 24-72 hours after surgery.

Moderate to severe pain is common during this period, especially after major surgeries.

Pain generally decreases over the first week, but some patients experience persistent pain lasting weeks to months (Hah et al., 2019; factors associated with acute pain estimation, postoperative pain resolution, opioid cessation, and recovery: secondary analysis of a randomized clinical trial; *JAMA Network Open,* 2 (3), e190168-e190168).

Therefore, it is also crucial to provide patients with highly effective oral pain medications at discharge with a favorable safety profile that provides effective pain relief during the first few days after a surgical procedure.

Despite existing options, current non-opioid treatments—such as traditional NSAIDs or acetaminophen—are often inadequate for treating more severe pain. As a result, patients are commonly prescribed opioids, which are associated with substantial risks, including addiction, overdose, and prolonged use (Dowell et al., 2022; CDC clinical practice guideline for prescribing opioids for pain—United States, 2022; MMQR Recommendations and Reports, 71 (3), 1-95).

NSAIDs and acetaminophen, which are generally known as suitable medication for treating pain and well-tolerated by patients, do not exhibit sufficient efficacy in managing severe pain. As such, more effective analgesic/anesthetic measures in the perioperative period are needed to prevent the progression to persistent pain (Gan, 2017; poorly controlled postoperative pain: prevalence, consequences, and prevention; *Journal of Pain Research,* 2287-2298), and there still remains a large unmet medical need for developing effective, well tolerated non-opioid treatments for treating acute moderate-to-severe pain.

SUMMARY OF THE INVENTION

This disclosure relates to methods of pain management comprising the administration of meloxicam as a pharmaceutically effective active ingredient.

One of the objectives of the present invention is to provide methods for the treatment of acute pain comprising meloxicam administration. Inventors of the methods herein have now found that this objective can be achieved by use of pharmaceutical compositions, such as those disclosed herein, providing rapid meloxicam release with increased rate of absorption.

Another objective of the present invention is to provide methods for the treatment of acute pain comprising meloxicam administration in human subjects.

Another objective of the present invention is to provide methods for the treatment of acute pain comprising meloxicam administration in human subjects under fasting or semi-fasting conditions.

Inventors of the methods of using meloxicam described herein have now surprisingly found that meloxicam, in a solid oral dosage form, can treat acute pain, post operative pain or post- or peri-procedural pain, or moderate-to-severe pain, including moderate-to-severe acute pain.

DRAWINGS OF THE INVENTION

FIG. 1 is a graph showing the LS Means of NRS Pain Scores at Each Nominal Time Point (W6LOCF) (Population: Modified Intent-to-treat Analysis Set); BID=twice daily; CI=confidence interval; LS=least squares; NRS=numeric rating scale; W6LOCF=6-hour windowed last observation carried forward;

FIG. 2 is a graph showing the LS Means of NRS Pain Scores at Each Nominal Time Point Through Hour 4 (W6LOCF) (Population: Modified Intent-to-treat Analysis Set); BID=twice daily; CI=confidence interval; LS=least squares; NRS=numeric rating scale; W6LOCF=6-hour windowed last observation carried forward;

FIG. 3 is a graph showing the LS Means of NRS Pain Difference Scores at Each Nominal Time Point (W6LOCF) (Population: Modified Intent-to-treat Analysis Set); BID=twice daily; CI=confidence interval; LS=least squares; NRS=numeric rating scale; W6LOCF=6-hour windowed last observation carried forward;

FIG. 4 is a graph showing the LS Means of NRS Pain Difference Scores at Each Time Point Through Hour 4 (W6LOCF) (Population: Modified Intent-to-treat Analysis Set); BID=twice daily; CI=confidence interval; LS=least squares; NRS=numeric rating scale; W6LOCF=6-hour windowed last observation carried forward;

FIG. 5 is a graph showing the Time to First Perceptible Pain Relief (Population: Modified Intent-to-treat Analysis Set); BID=twice daily;

FIG. 6 is a graph showing the First Meaningful Pain Relief (Population: Modified Intent-to-treat Analysis Set); BID=twice daily; Note that the vertical rise in the graph for the meloxicam 5 mg group at 24 hours is due to Subject 201-0107, who had meaningful pain relief with the timer stopped at 24.22 hours and therefore was not censored;

FIG. 7 is a graph showing the Time to First Rescue Medication Use (Population: Modified Intent-to-treat Analysis Set); BID=twice daily;

FIG. 8 is a dot graph showing the Rescue Medication Use (Population: Modified Intent-to-treat Analysis Set); BID=twice daily; Note: Each vertical line represents a subject; dots show the time of rescue medication use; subjects who did not use rescue medication are represented with "+" at 24 hours;

FIG. 9 is a series of two graphs showing the Plasma Meloxicam Concentration (ng/ml) (Population: Pharmacokinetic Analysis Set); A=meloxicam 1.25 mg BID; B=meloxicam 5 mg BID; C=meloxicam 15 mg BID; D=placebo BID; BID=twice daily;

Figure 13:
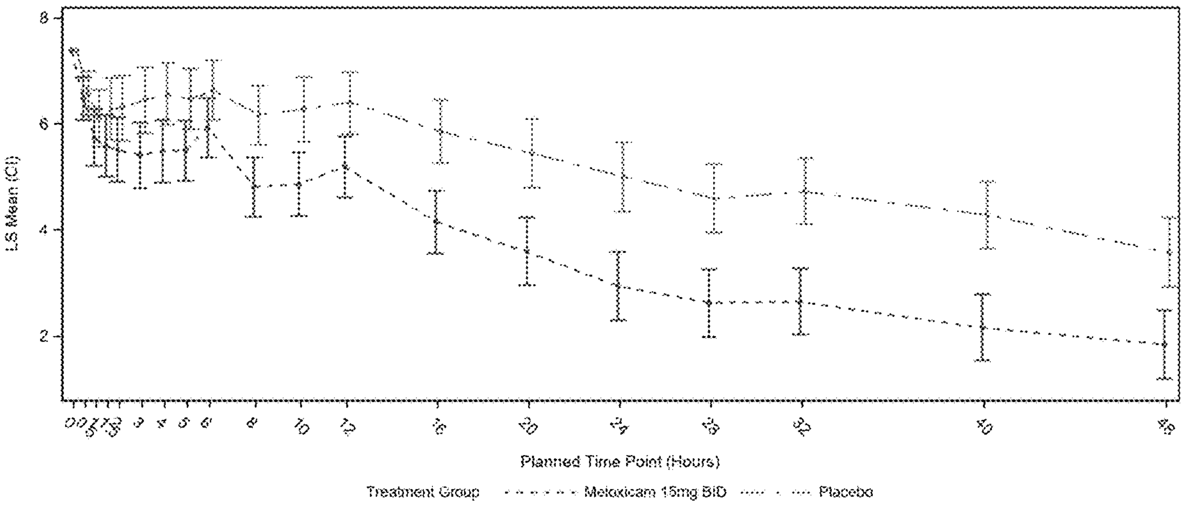
Figure 14:
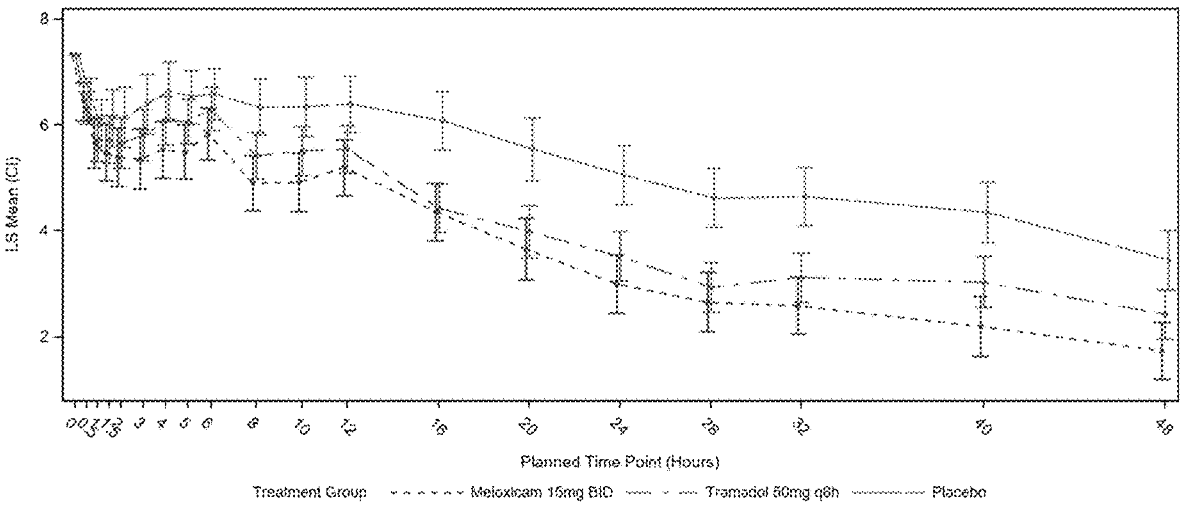

FIG. 13 is a graph showing the NRS-R Pain Scores, ANCOVA by Timepoint (MR-107A-02 and Placebo Only) (Full Analysis Set); ANCOVA=Analysis of covariance; APAP=Acetaminophen; BID=Twice daily; CI=Confidence interval; LS=Least squares; MI=Multiple imputation; NRS-R=Numeric Rating Scale at rest; q6h=Once every 6 hours; SAP=Statistical Analysis Plan; SE=Standard error; WLOCF=Windowed last observation carried forward; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase); Note: For any rescue medication use, a WLOCF was used, whereby the last observed pain intensity score prior to taking rescue medication was carried forward to replace the observed pain intensity scores during the period of time following the rescue medication intake. The window for APAP ($1^{st}$ step) rescue medication was 6 hours; the window for oxycodone ($2^{nd}$ step) rescue medication was 4 hours; the window for morphine ($3^{rd}$ step) rescue medication was 2 hours; Note: The LS means and CIs were based on an ANCOVA model with fixed, categorical effects for treatment (MR-107A-02 and placebo), age group (<65 years, ≥65 years), and study site and baseline pain intensity score as a continuous covariate. The 95% CIs are presented for MR-107A-02 and Placebo;

FIG. 14 is a graph showing the NRS-R Pain Scores, ANCOVA by Timepoint (Full Analysis Set); ANCOVA=Analysis of covariance; APAP=Acetaminophen; BID=Twice daily; CI=Confidence interval; LS=Least squares; MI=Multiple imputation; NRS-R=Numeric Rating Scale at rest; q6h=Once every 6 hours; SE=Standard error; WLOCF=Windowed last observation carried forward; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase); Note: For any rescue medication use, a WLOCF was used, whereby the last observed pain intensity score prior to taking rescue medication was carried forward to replace the observed pain intensity scores during the period of time following the rescue medication intake. The window for APAP ($1^{st}$ step) rescue medication was 6 hours; the window for oxycodone ($2^{nd}$ step) rescue medication was 4 hours; the window for morphine ($3^{rd}$ step) rescue medication was 2 hours; Note: The LS means and CIs were based on an ANCOVA model with fixed, categorical effects for treatment (MR-107A-02, tramadol, and placebo), age group (<65 years, ≥65 years), and study site and baseline pain intensity score as a continuous covariate. The 95% CIs are presented for MR-107A-02 and placebo.

Figure 15:
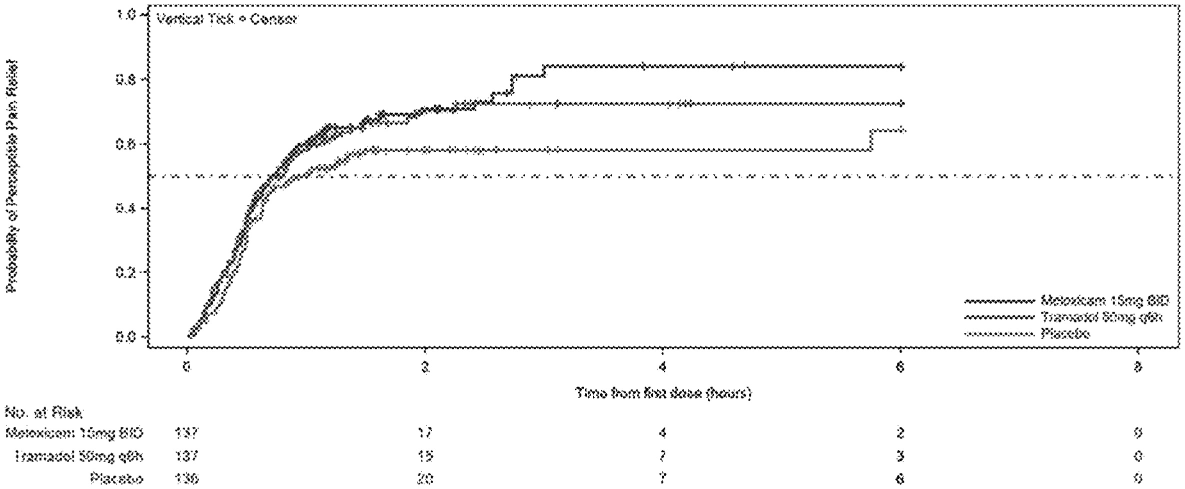
Figure 16:
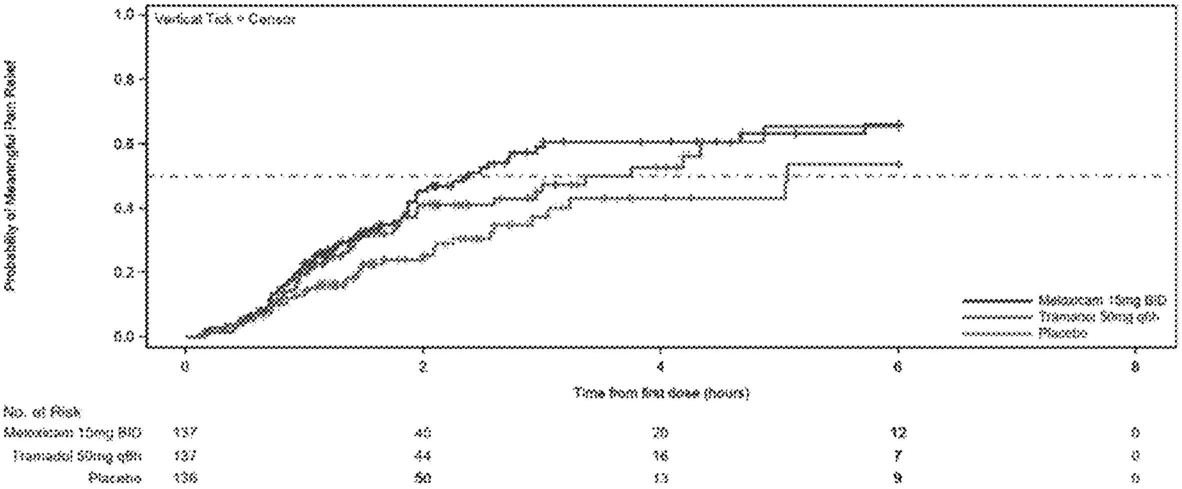
Figure 17:
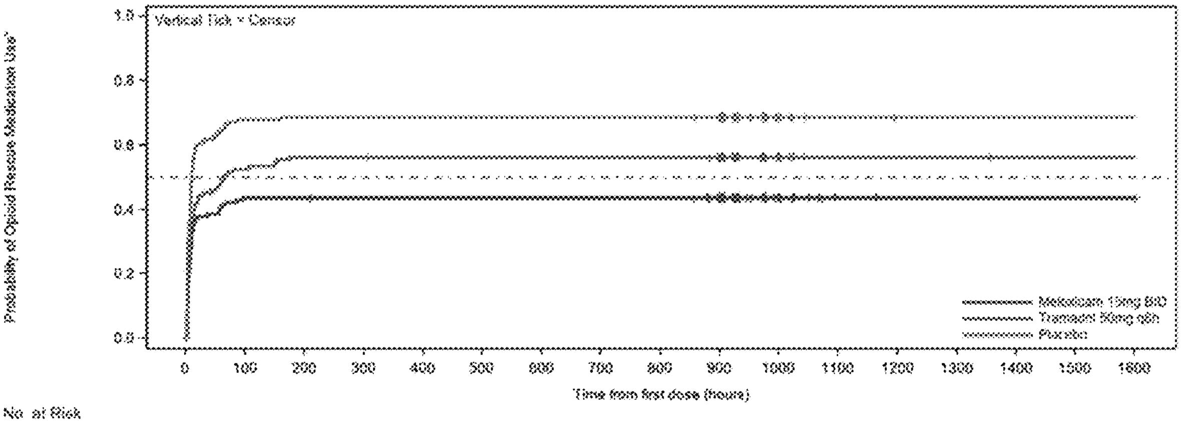
Figure 18:
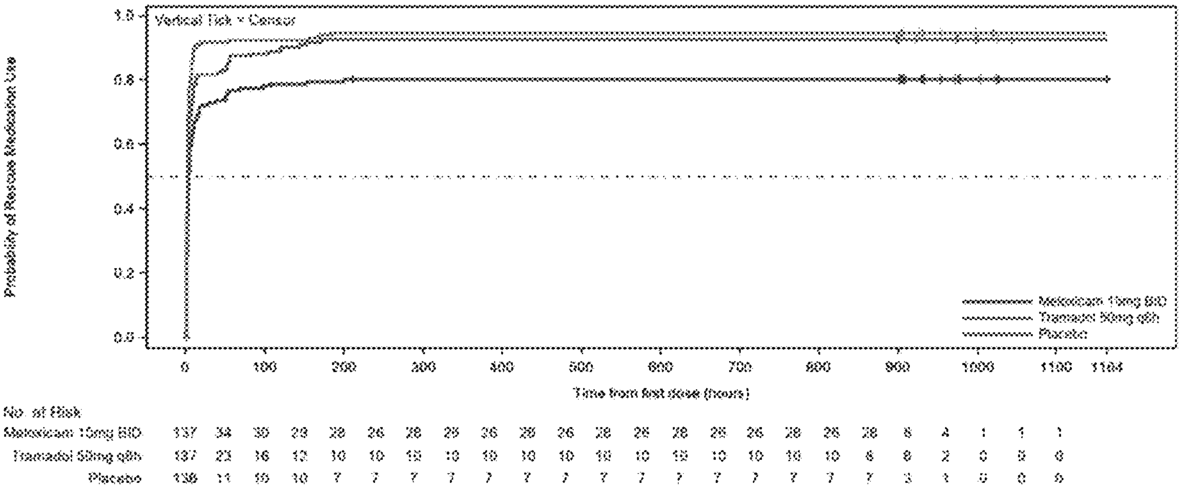
Figure 19:
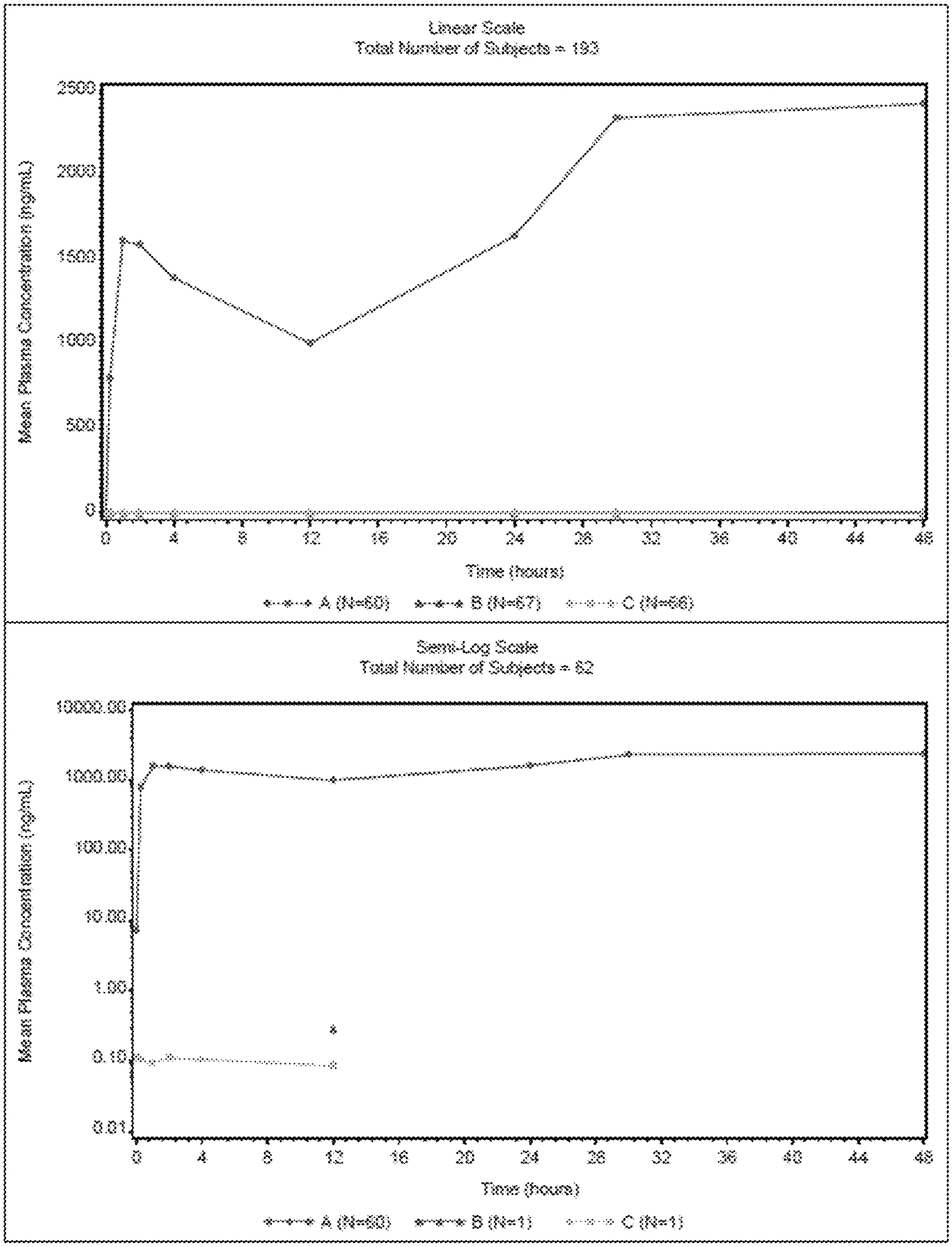
Figure 20:
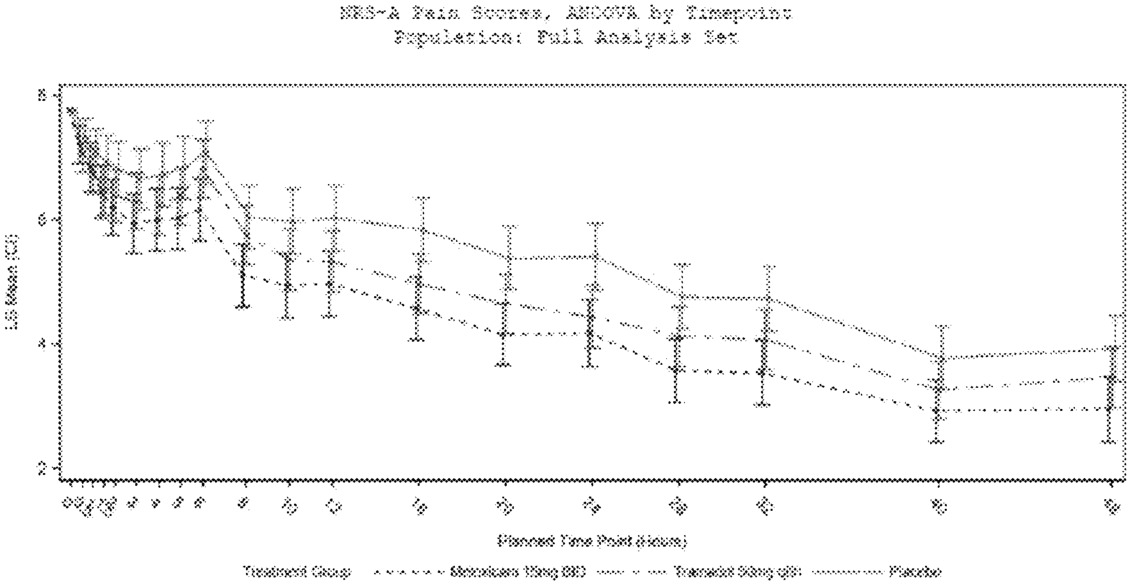
Figure 21:
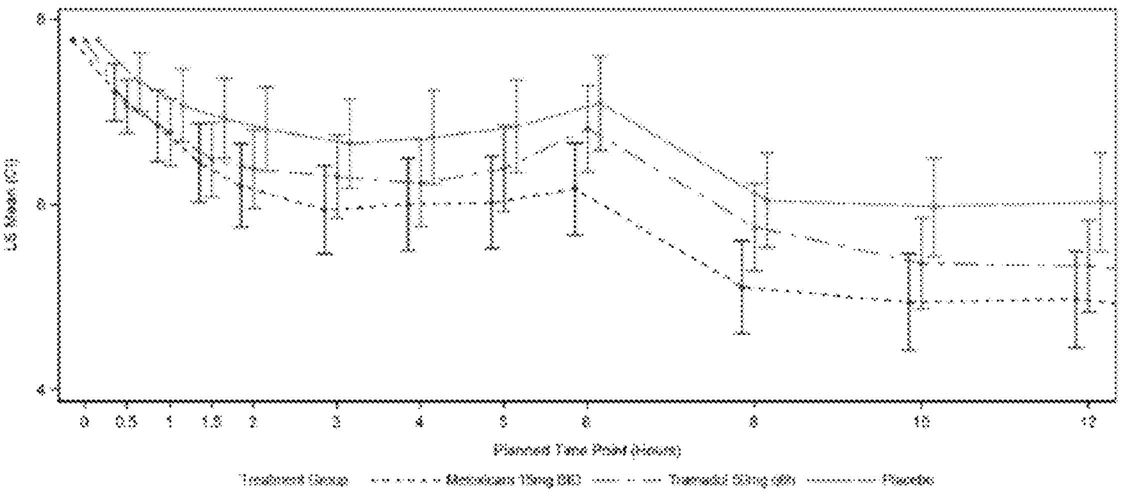
Figure 22:
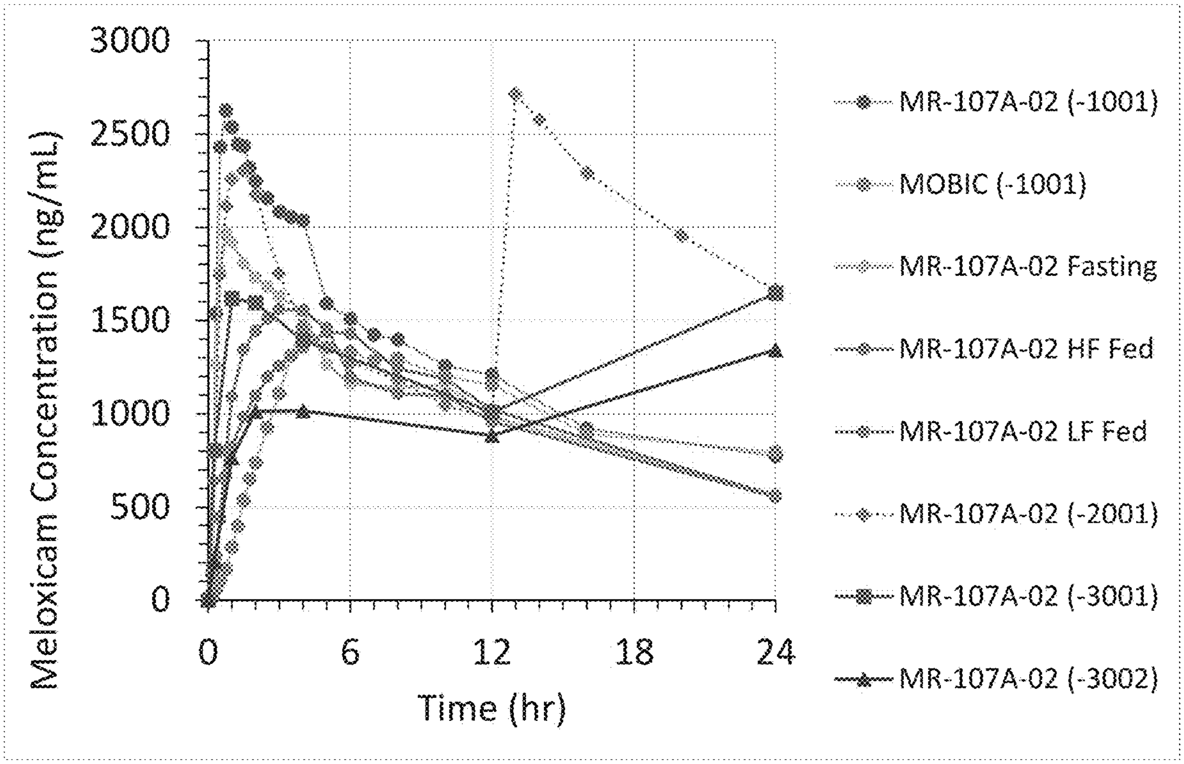

FIG. 15 is a graph showing Kaplan-Meier Plot for Time to Perceptible Pain Relief (Full Analysis Set); BID=Twice daily; q6h=Once every 6 hours; Note: During the in-patient treatment phase, participants received MR-107A-02 (15 mg BID), tramadol (50 mg q6h), or placebo (q6h); Note: The time to first perceptible pain relief was determined using the double-stopwatch technique. The time to onset of first perceptible relief (time that the first watch was stopped) was defined as the post-dose time at which the participant first began to feel pain relief at their estimation; Note: For participants who took rescue medication, the time to perceptible pain relief was censored at the time of first rescue medication use. For participants who did not report perceptible time relief within the assessment period (within 6 hours), the time to perceptible pain relief was censored at 6 hours, or at the time of study discontinuation, whichever was sooner;

FIG. 16 is a graph showing the Kaplan-Meier Plot for Time to Meaningful Pain Relief (Full Analysis Set); BID=Twice daily; q6h=Once every 6 hours; Note: During the in-patient treatment phase, participants received MR-107A-02 (15 mg BID), tramadol (50 mg q6h), or placebo (q6h); Note: The time to first meaningful pain relief was determined using the double-stopwatch technique. The time to meaningful pain relief (time that the second watch was stopped) was defined as the post-dose time at which the participant began to feel meaningful pain relief at their estimation; Note: For participants who took rescue medication, the time to meaningful pain relief was censored at the time of first rescue medication use. For participants who did not report meaningful time relief within the assessment period (within 6 hours), the time to meaningful pain relief was censored at 6 hours, or at the time of study discontinuation, whichever was sooner;

FIG. 17 is a graph showing the Kaplan-Meier Plot for Time to First Opioid (Oxycodone and/or Morphine) Rescue Medication Use (Full Analysis Set); BID=Twice daily; q6h=Once every 6 hours; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase); Note: The time of first oxycodone and/or morphine rescue medication administration for those participants who discontinued early was censored at the time of discontinuation;

FIG. 18 is a graph showing the Kaplan-Meier Plot for Time to First Rescue Medication Use (Full Analysis Set); BID=Twice daily; q6h=Once every 6 hours; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase); Note: The time of first rescue medication administration for those participants who discontinued early was censored at the time of discontinuation;

FIG. 19 is a graph showing the Mean Plasma Meloxicam Concentrations (PK Analysis Set); A=MR-107A-02 Group; B=Placebo Group; BID=Twice daily; C=Tramadol Group; N=Number of participants per treatment group in the PK Analysis Set; PK=Pharmacokinetic; q6h=once every 6 hours; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase); Note: Participants 101-32, 104-011, 104-076, 111-024 were not included in the summary tables due to insufficient available concentration data;

FIG. 20 is a graph showing a graph showing the efficacy results of in-patient treatment phase in the 3002 study as a function of NRS-A Pain Scores (ANCOVA by Timepoint-FAS) (Meloxicam 15 mg are tablets according to MR-107A-02);

FIG. 21 is a graph showing the efficacy results in the 3002 study as a function of NRS-A Pain Scores (ANCOVA by Timepoint-FAS) truncated to 12 hours. (Meloxicam 15 mg are tablets according to MR-107A-02);

FIG. 22 is a graph showing the mean meloxicam profiles across phase 1, 2 and 3 pharmacokinetic studies (0-24 hrs.).

Figure 23:
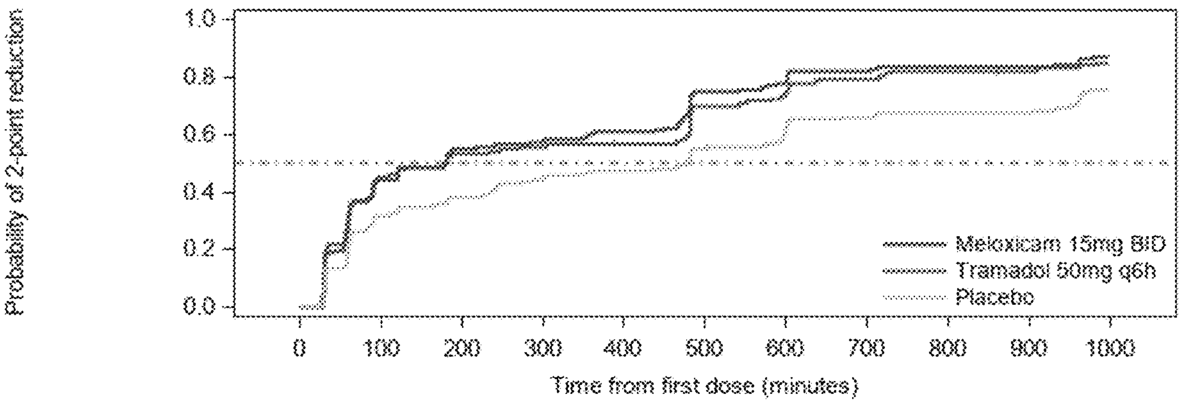
Figure 24:
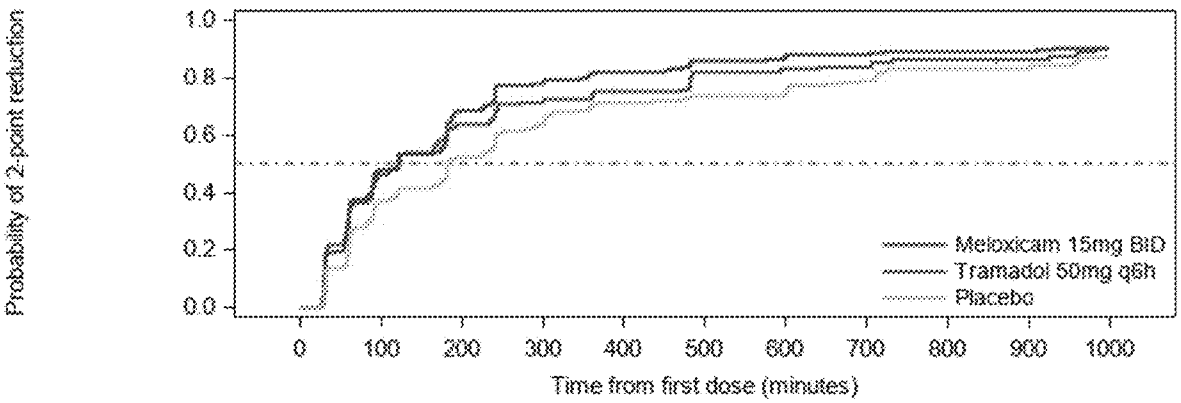
Figure 25:
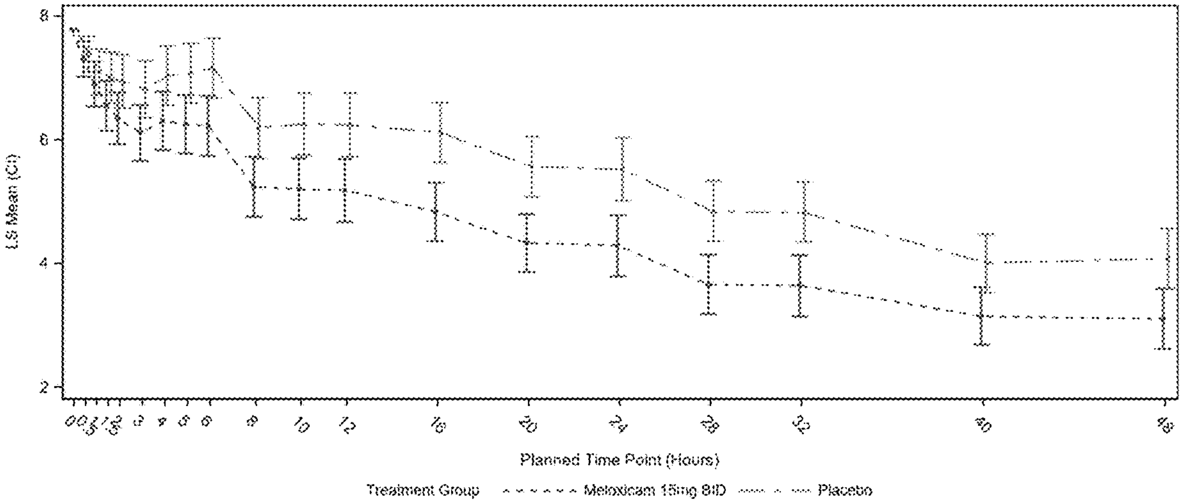

FIG. 23 is a graph showing the time to 2-point Reduction in NRS-A, with WLOCF Censoring following Rescue Use;

FIG. 24 is a graph showing the time to 2-point Reduction in NRS-A, with No Censoring following Rescue Use;

FIG. 25 is a graph showing the NRS-A Pain Scores, ANCOVA by Timepoint (Full Analysis Set); ANCOVA=Analysis of covariance; APAP=Acetaminophen; BID=Twice daily; CI=Confidence interval; LS=Least squares; MI=Multiple imputation; NRS-A=Numeric Rating Scale with activity; q6h=Once every 6 hours; SAP-Statistical Analysis Plan; SE-Standard error; WLOCF=Windowed last observation carried forward; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase); Note: For any rescue medication use, a WLOCF was used, whereby the last observed pain intensity score prior to taking rescue medication was carried forward to replace the observed pain intensity scores during the period of time following the rescue medication intake. The window for APAP ($1^{st}$ step) rescue medication was 6 hours; the window for oxycodone ($2^{nd}$ step) rescue medication was 4 hours; the window for morphine ($3^{rd}$ step) rescue medication was 2 hours; Note: The LS means and CIs were based on an ANCOVA model with fixed, categorical effects for treatment (MR-107A-02 and placebo), age group (<65 years, ≥65 years), and study site and baseline pain intensity score as a continuous covariate. The 95% CIs are presented for MR-107A-02 and Placebo.

Figure 26:
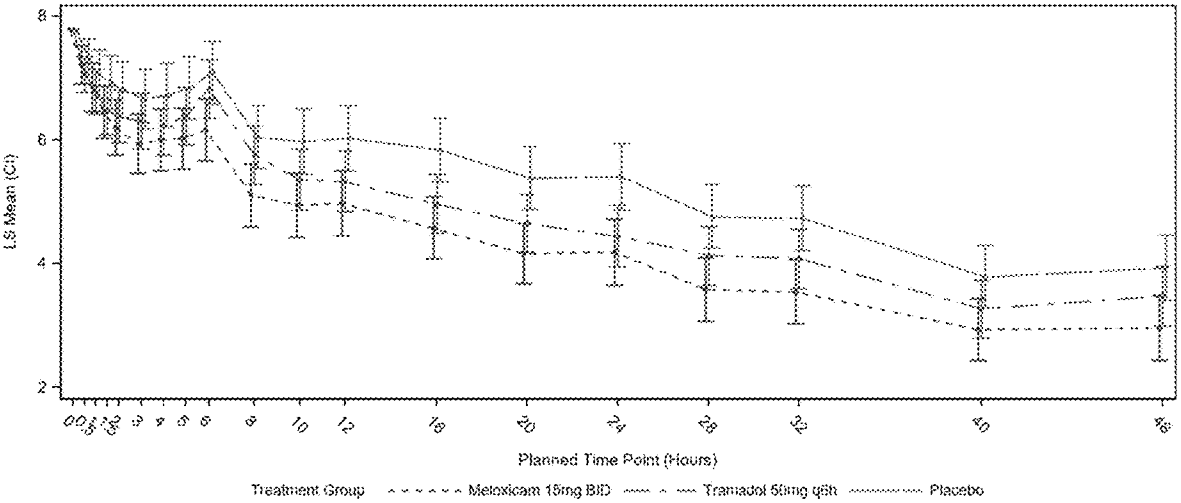
Figure 27:
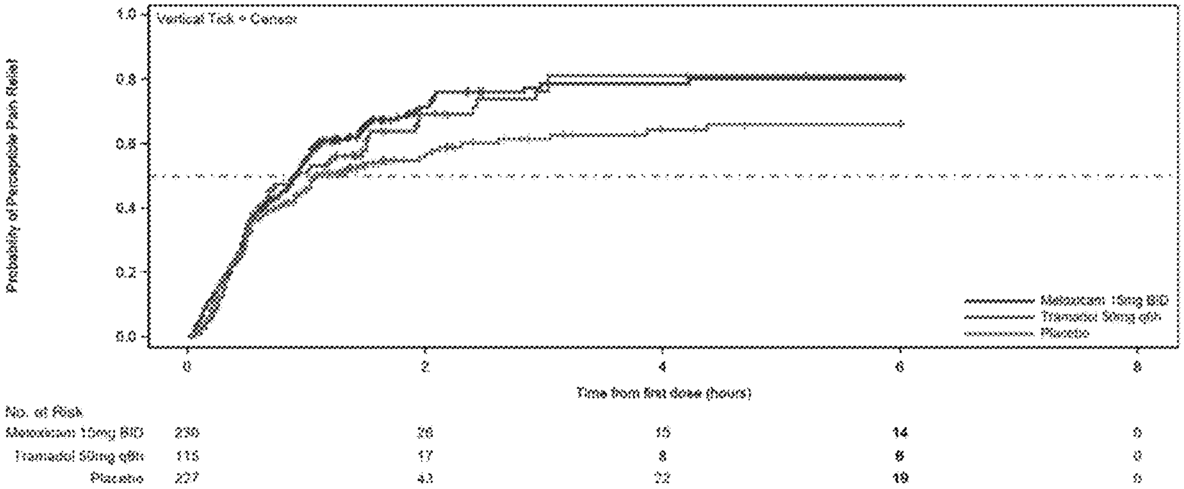
Figure 28:
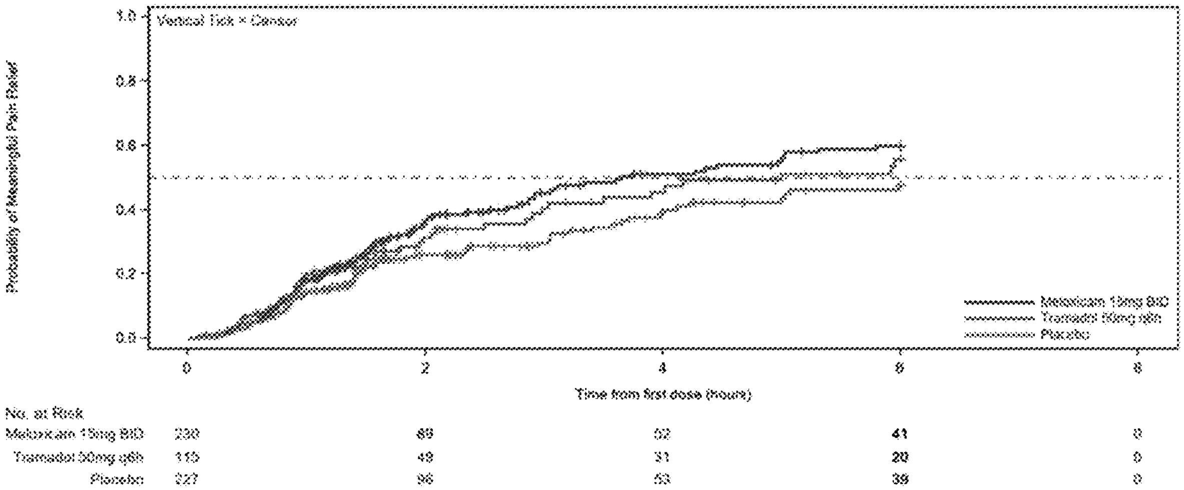
Figure 29:
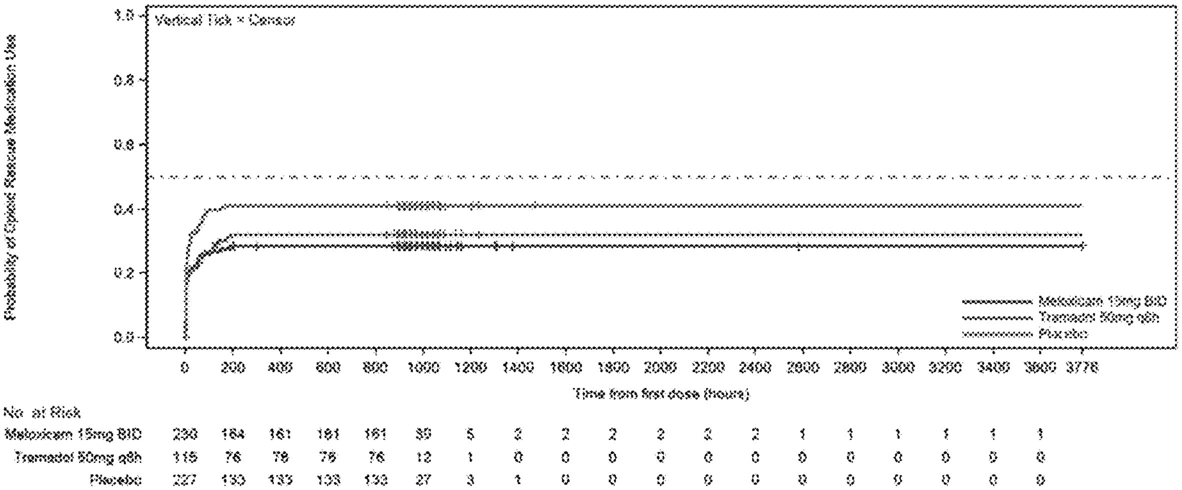
Figure 30:
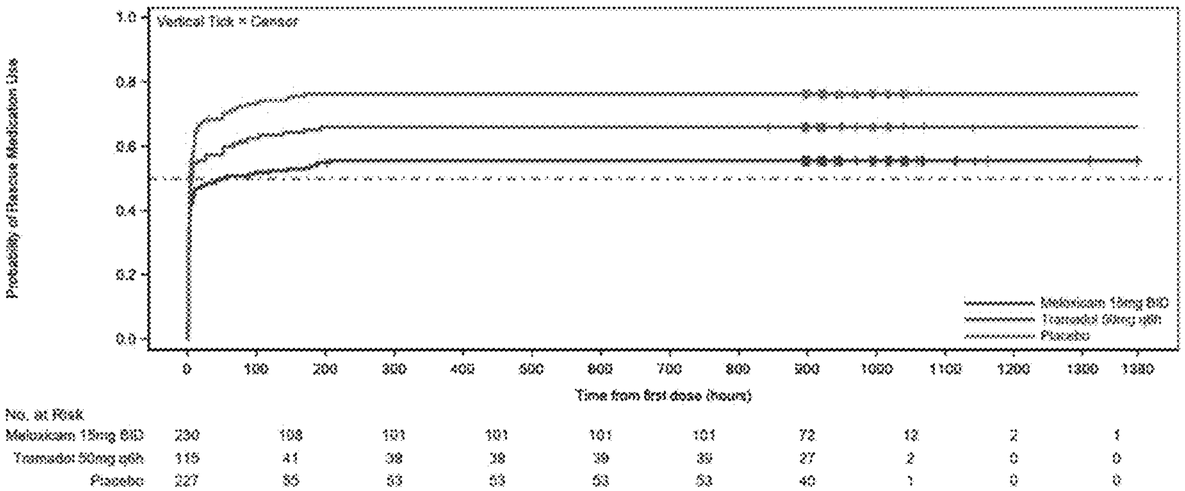

FIG. 26 is a graphs showing the NRS-A Pain Scores, ANCOVA by Timepoint (Full Analysis Set); ANCOVA=Analysis of covariance; APAP=Acetaminophen; BID=Twice daily; CI=Confidence interval; LS=Least squares; MI=Multiple imputation; NRS-A=Numeric Rating Scale with activity; q6h=Once every 6 hours; SE=Standard error; WLOCF=Windowed last observation carried forward; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase); Note: For any rescue medication use, a WLOCF was used, whereby the last observed pain intensity score prior to taking rescue medication was carried forward to replace the observed pain intensity scores during the period of time following the rescue medication intake. The window for APAP ($1^{st}$ step) rescue medication was 6 hours; the window for oxycodone ($2^{nd}$ step) rescue medication was 4 hours; the window for morphine ($3^{rd}$ step) rescue medication was 2 hours; Note: The LS means and CIs were based on an ANCOVA model with fixed, categorical effects for treatment (MR-107A-02, tramadol, and placebo), age group (<65 years, ≥65 years), and study site and baseline pain intensity score as a continuous covariate. The 95% CIs are presented for MR-107A-02 and placebo and 90% CI for tramadol; The LS mean pain scores (NRS-A) over time for the MR-107A-02, Tramadol, and Placebo groups in the FAS based on the ANCOVA model used for the primary efficacy estimand with additional windows for rescue medication use in place of the WLOCF in the calculation of the primary estimand (i.e., no censoring, a 4-hour APAP window, a 6-hour oxycodone window, alternative censoring, and all values censored, respectively) show that similar to the primary analysis (FIG. 25), the LS mean pain scores decreased with time for all groups, with the MR-107A-02 group showing the largest reductions over the period of 0-48 hours, for all sensitivity analyses. The magnitude of the LS mean pain scores over time was dependent on the analysis method, with the biggest impact on the LS mean pain scores over time in the analysis with all values censored;

FIG. 27 is a in a graph showing the Kaplan-Meier Plot for Time to Perceptible Pain Relief (Full Analysis Set); BID=Twice daily; q6h=Once every 6 hours; Note: During the in-patient treatment phase, participants received MR-107A-02 (15 mg BID), tramadol (50 mg q6h), or placebo (q6h); Note: The time to first perceptible pain relief was determined using the double-stopwatch technique. The time to onset of first perceptible relief (time that the first watch was stopped) was defined as the post-dose time at which the participant first began to feel pain relief at their estimation; Note: For participants who took rescue medication, the time to perceptible pain relief was censored at the time of first rescue medication use. For participants who did not report perceptible time relief within the assessment period (within 6 hours), the time to perceptible pain relief was censored at 6 hours, or at the time of study discontinuation, whichever was sooner;

FIG. 28 is a graph showing a Kaplan-Meier Plot for Time to Meaningful Pain Relief (Full Analysis Set); BID=Twice daily; q6h=Once every 6 hours; Note: During the in-patient treatment phase, participants received MR-107A-02 (15 mg BID), tramadol (50 mg q6h), or placebo (q6h); Note: The time to first meaningful pain relief was determined using the double-stopwatch technique. The time to meaningful pain relief (time that the second watch was stopped) was defined as the post-dose time at which the participant began to feel meaningful pain relief at their estimation; Note: For participants who took rescue medication, the time to meaningful pain relief was censored at the time of first rescue medication use. For participants who did not report meaningful time relief within the assessment period (within 6 hours), the time to meaningful pain relief was censored at 6 hours, or at the time of study discontinuation, whichever was sooner;

FIG. 29 is a graph showing a Kaplan-Meier Plot for Time to First Opioid (Oxycodone and/or Morphine) Rescue Medication Use (Full Analysis Set); BID=Twice daily; q6h=Once every 6 hours; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase); Note: The time of first oxycodone and/or morphine rescue medication administration for those participants who discontinued early was censored at the time of discontinuation;

FIG. 30 is a series of graphs showing a Kaplan-Meier Plot for Time to First Rescue Medication Use (Full Analysis Set); BID=Twice daily; q6h=Once every 6 hours; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase); Note: The time of first rescue medication administration for those participants who discontinued early was censored at the time of discontinuation.

Figure 31:
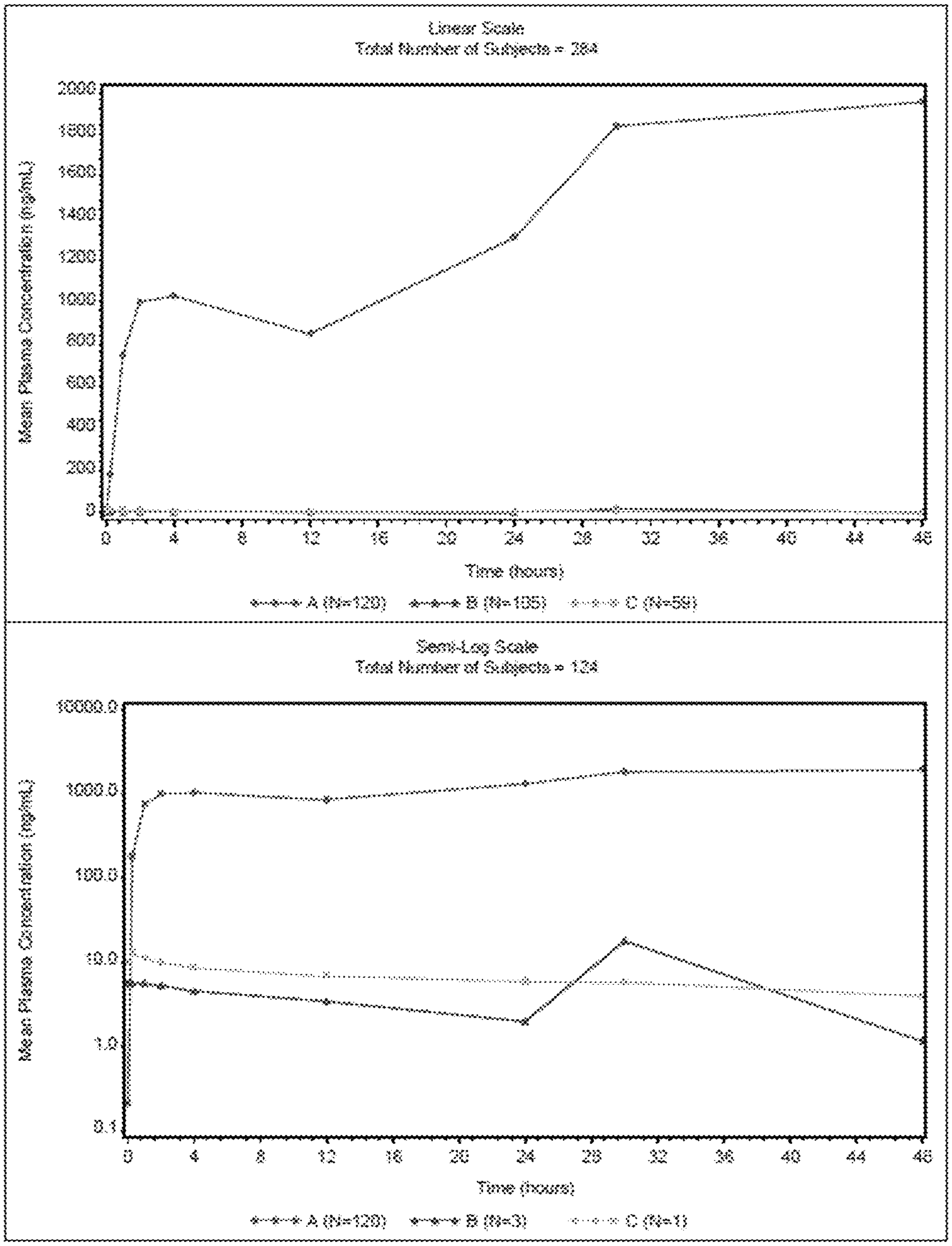
Figure 32:
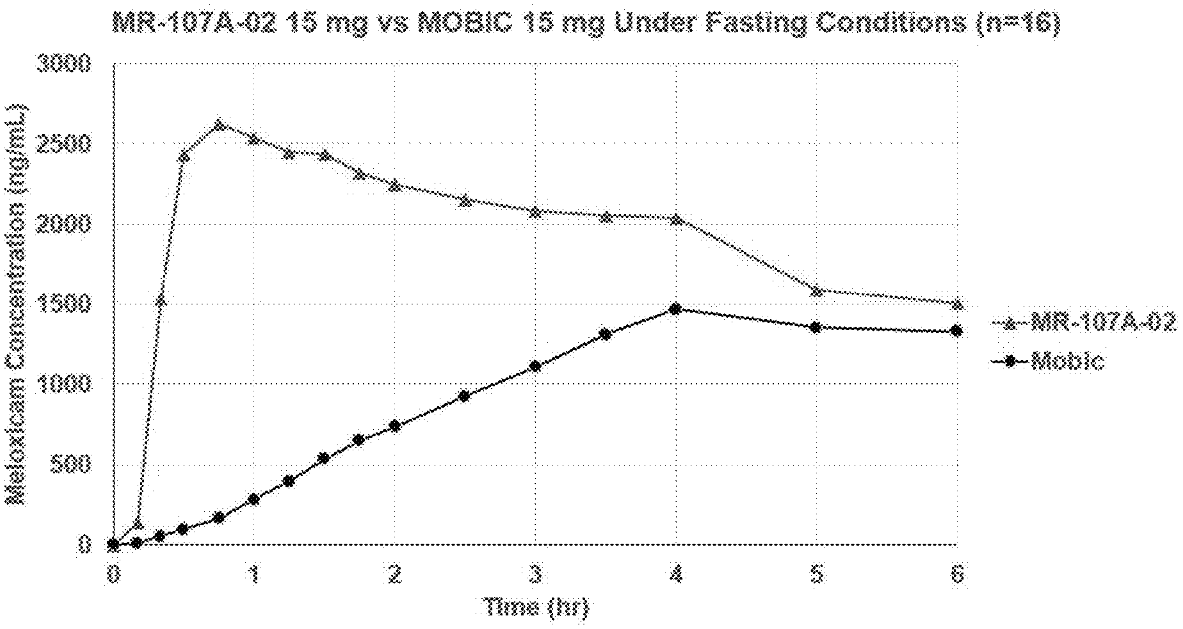
Figure 33:
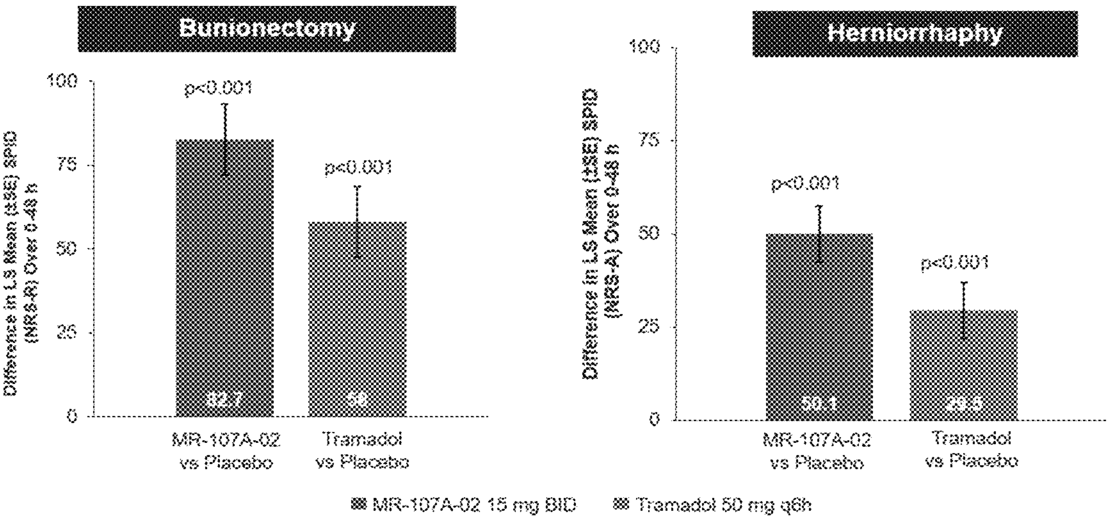
Figure 34:
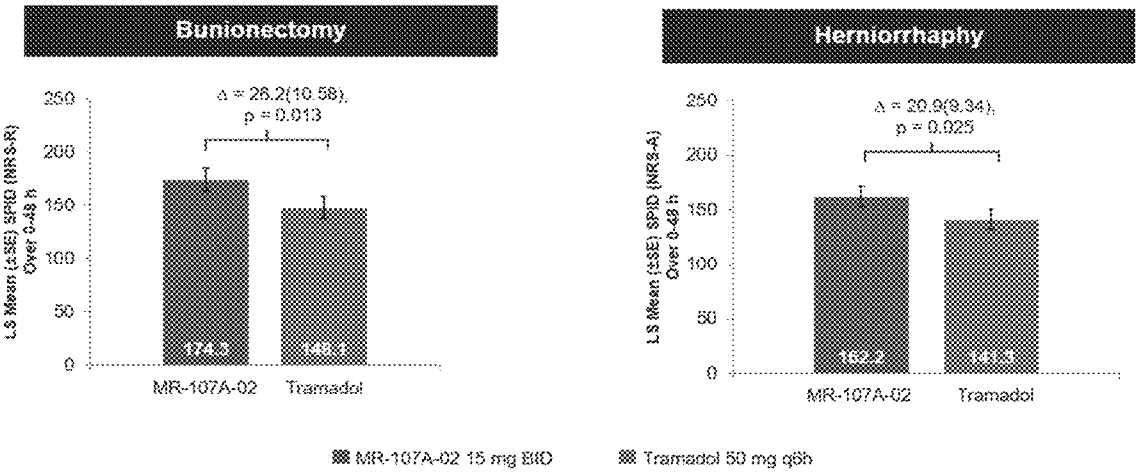
Figure 35:
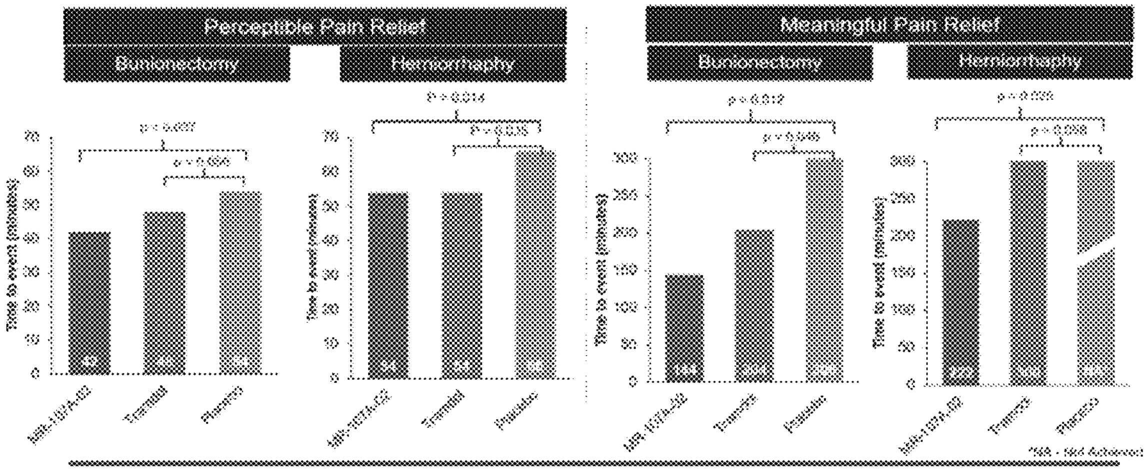
Figure 36:
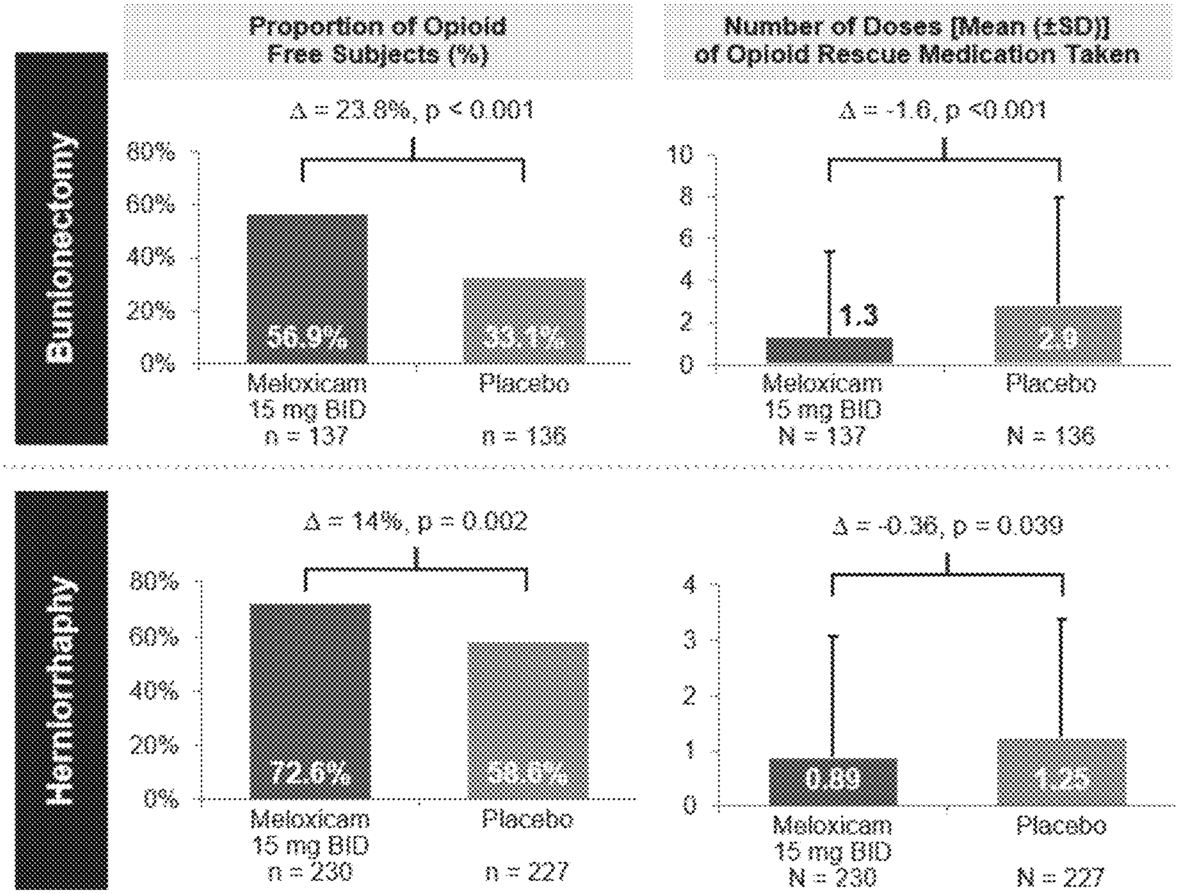
Figure 37:
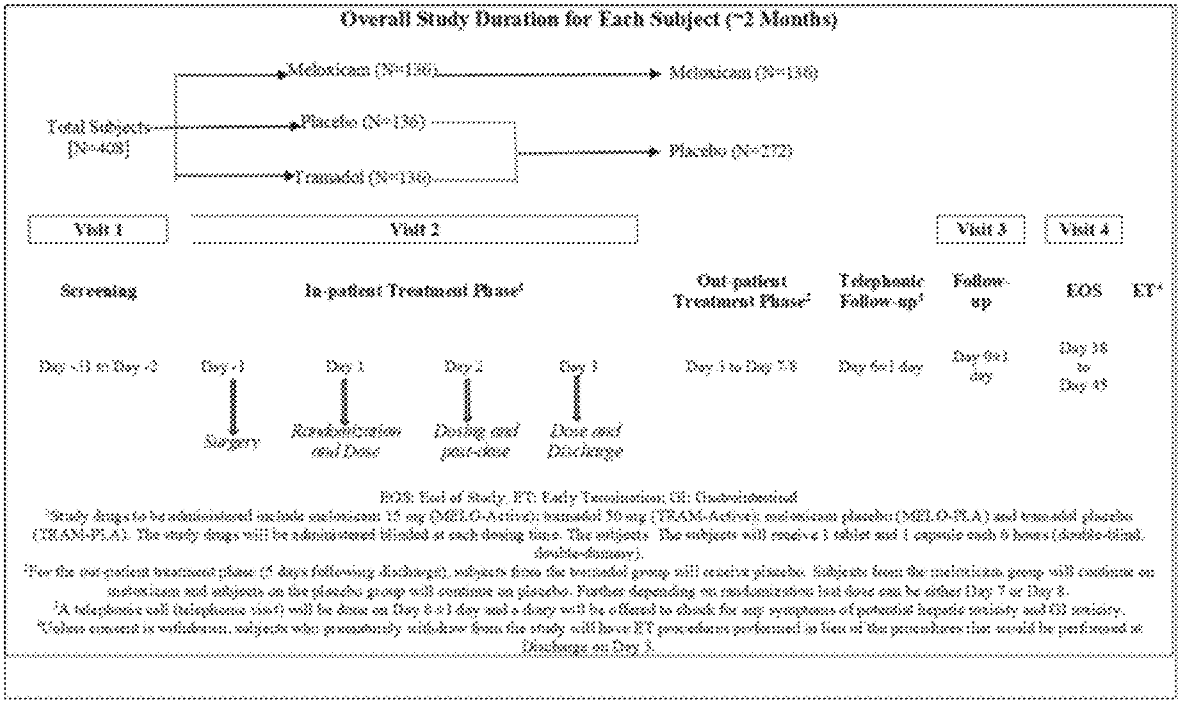
Figure 38:
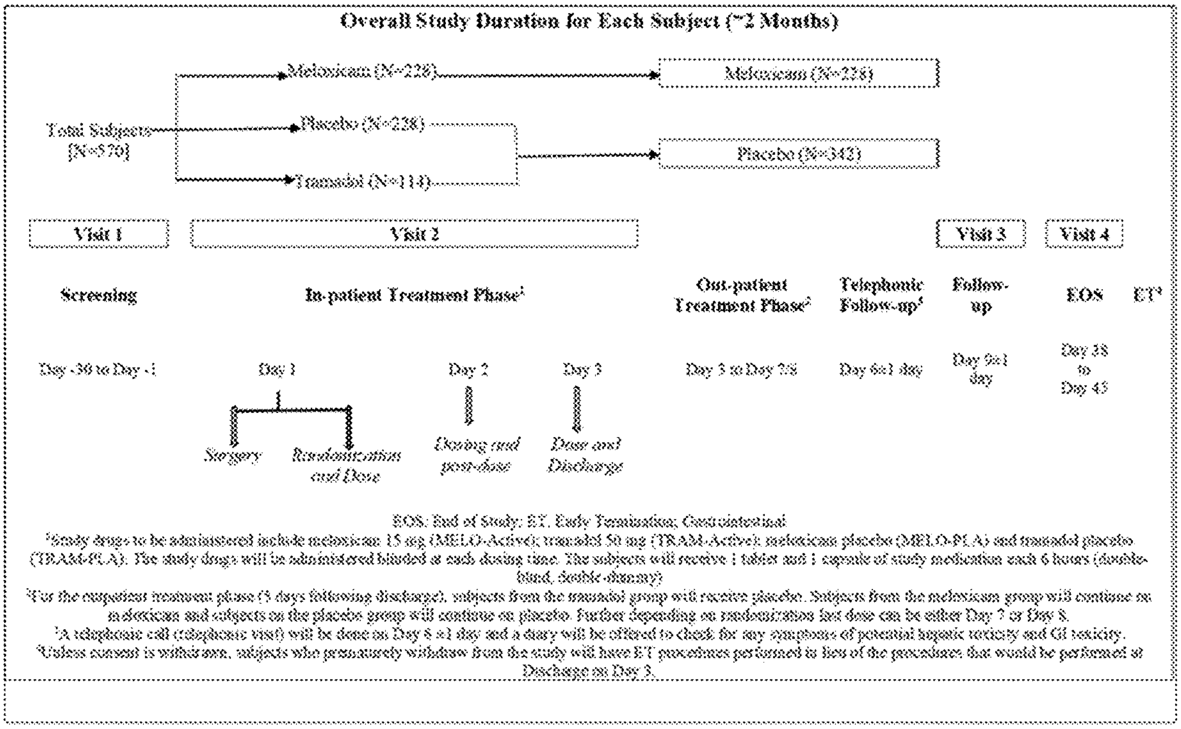
Figure 39:
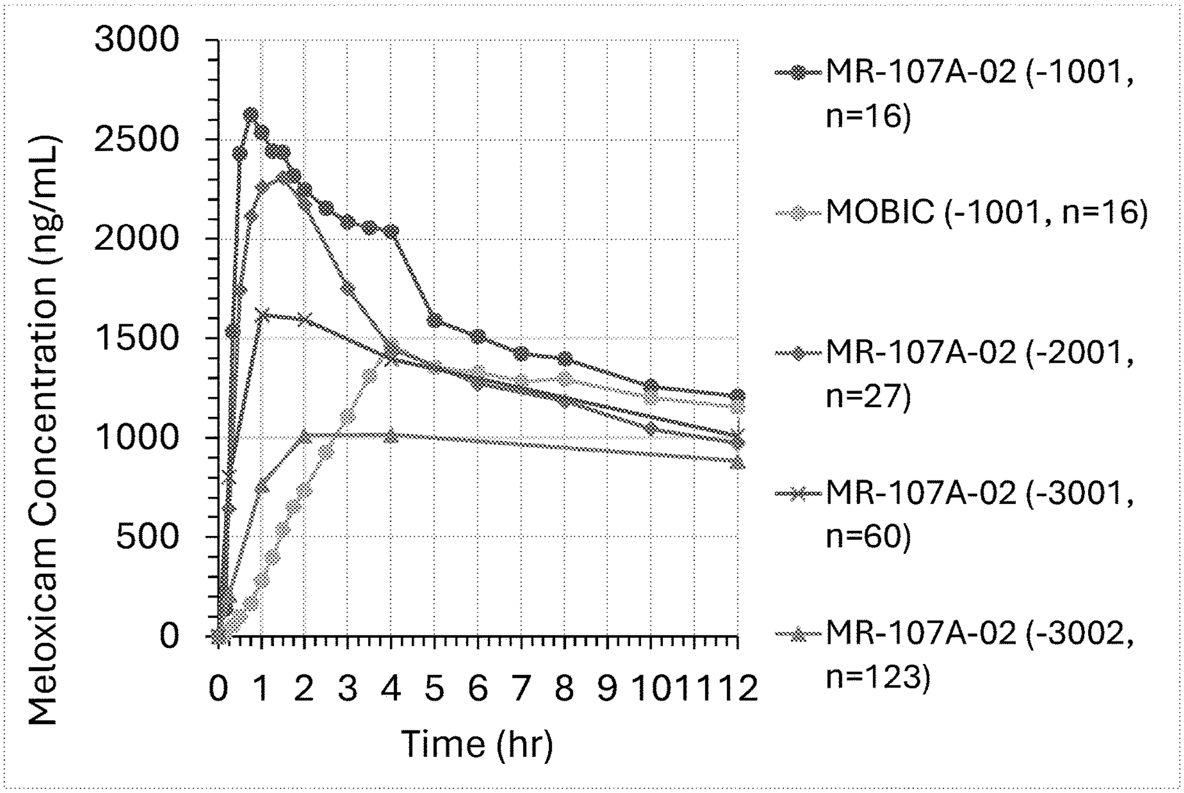
Figure 40:
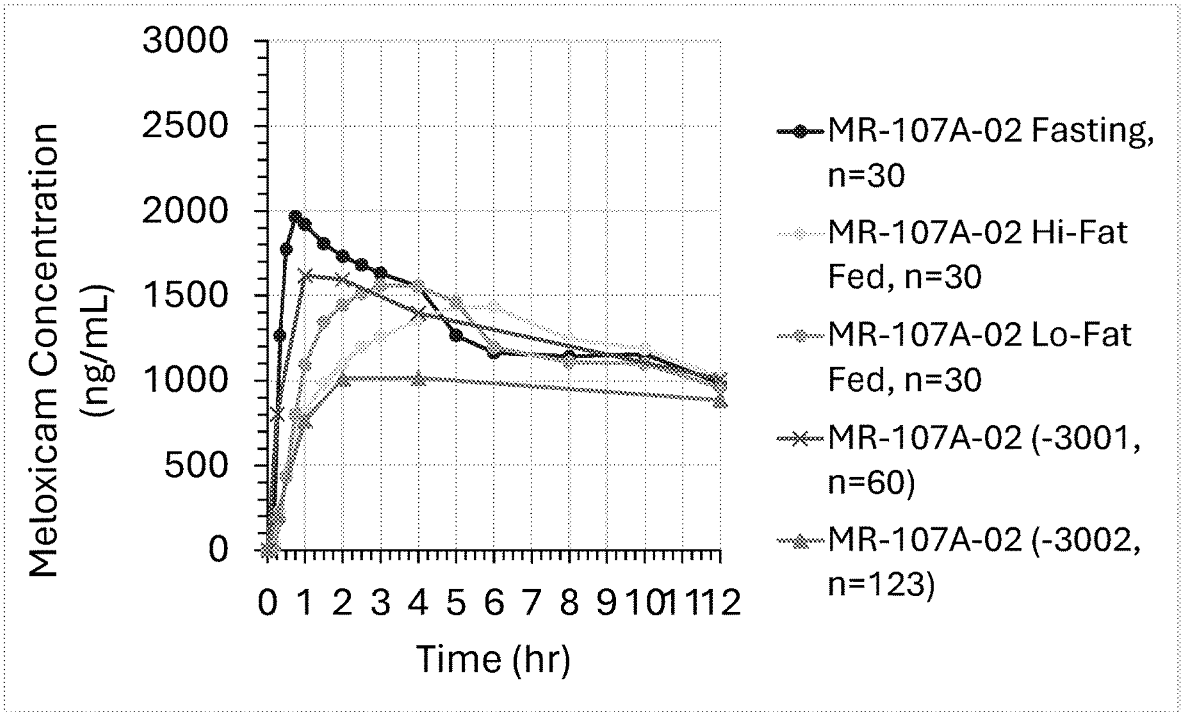
Figure 41:
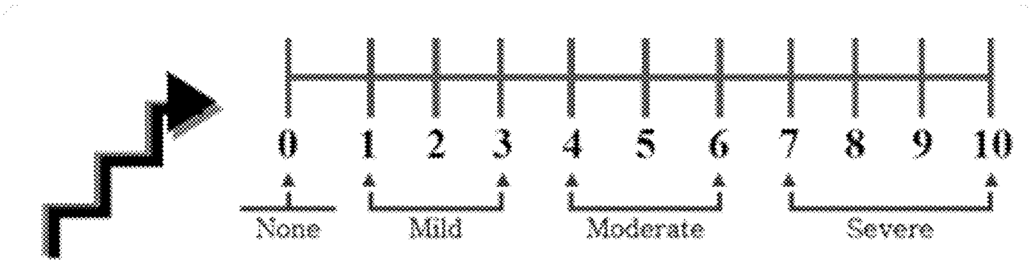
Figure 42:
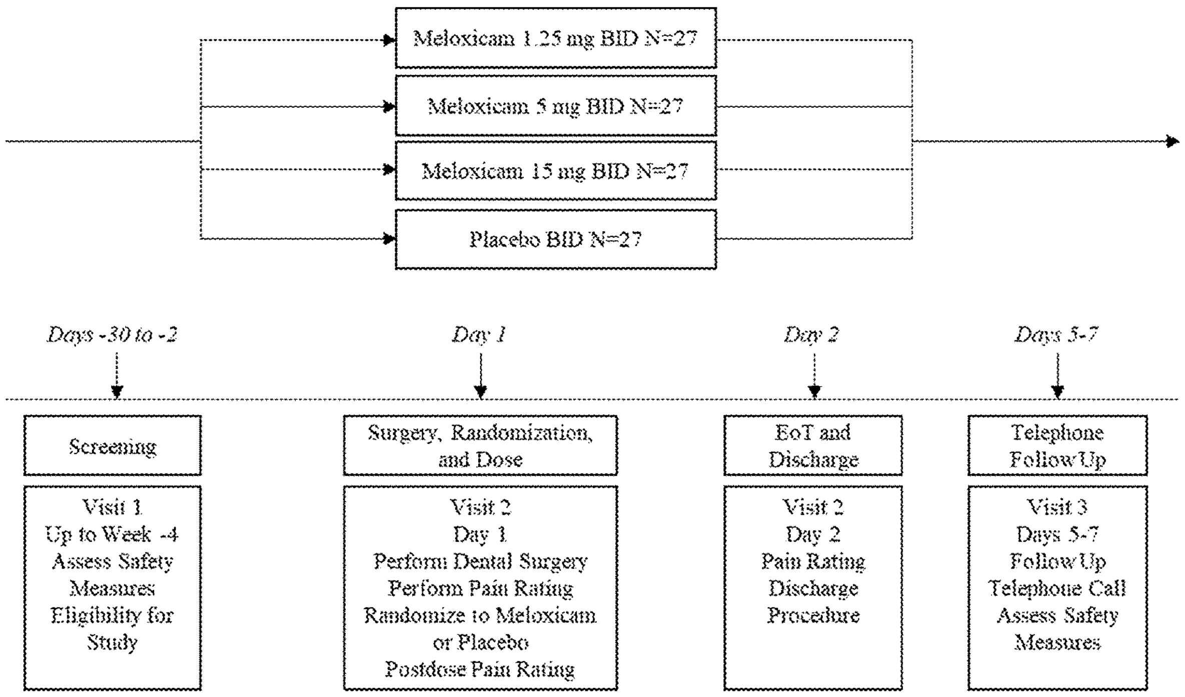
Figure 43:
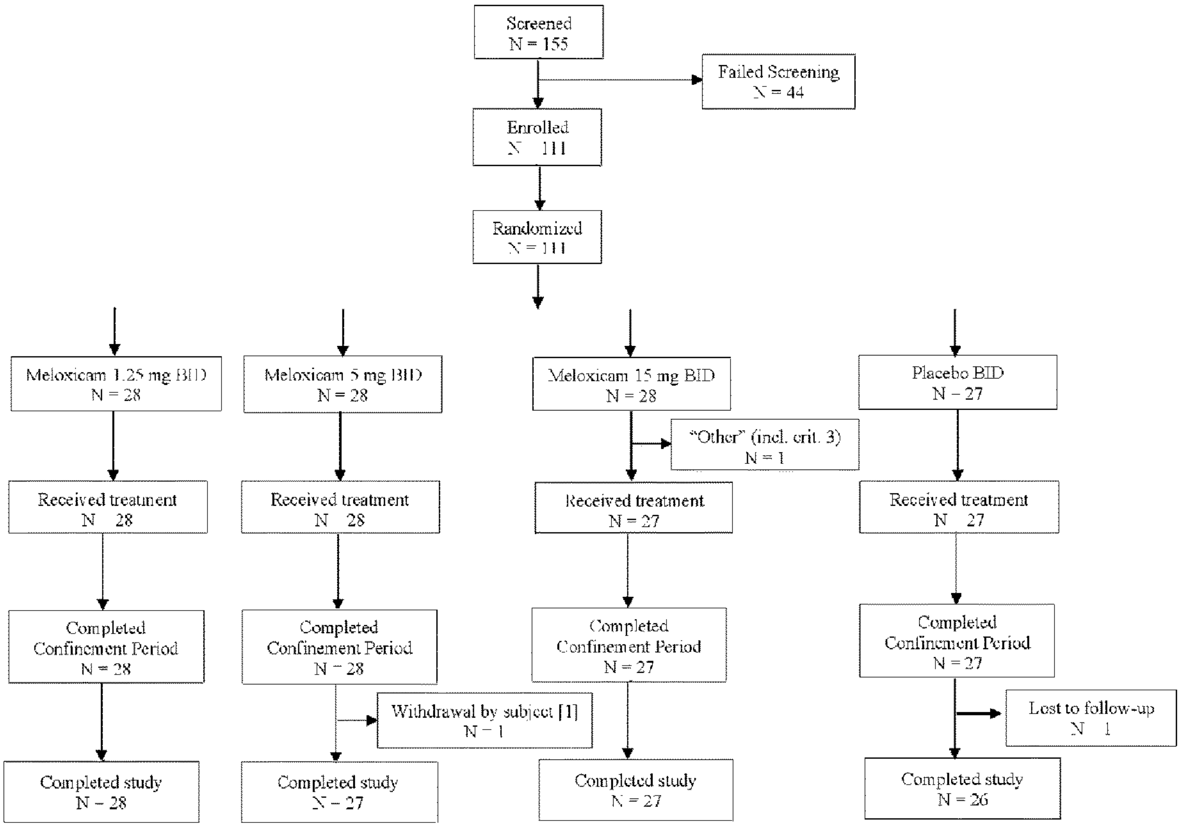
Figure 44:
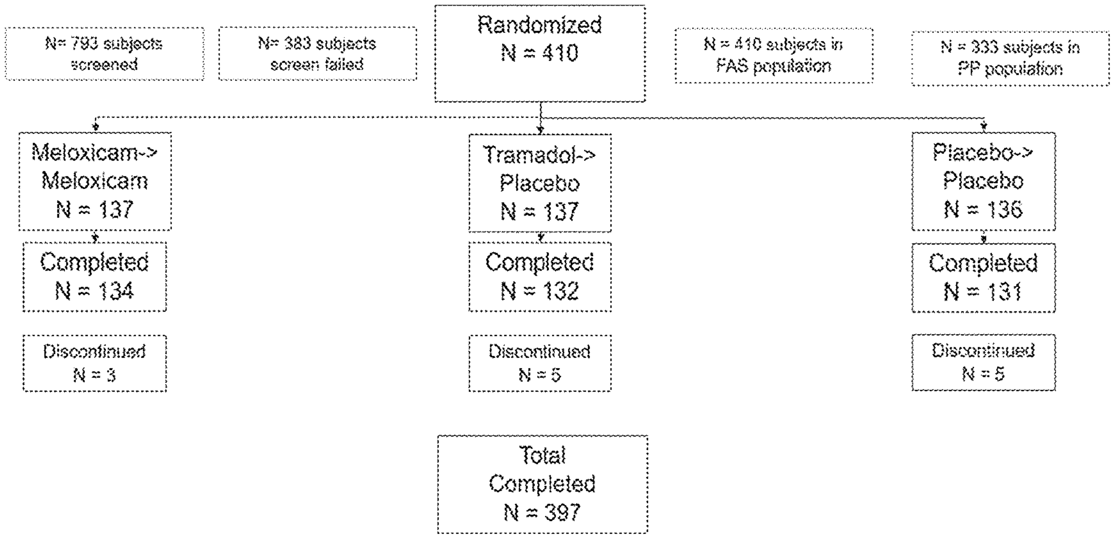
Figure 45:
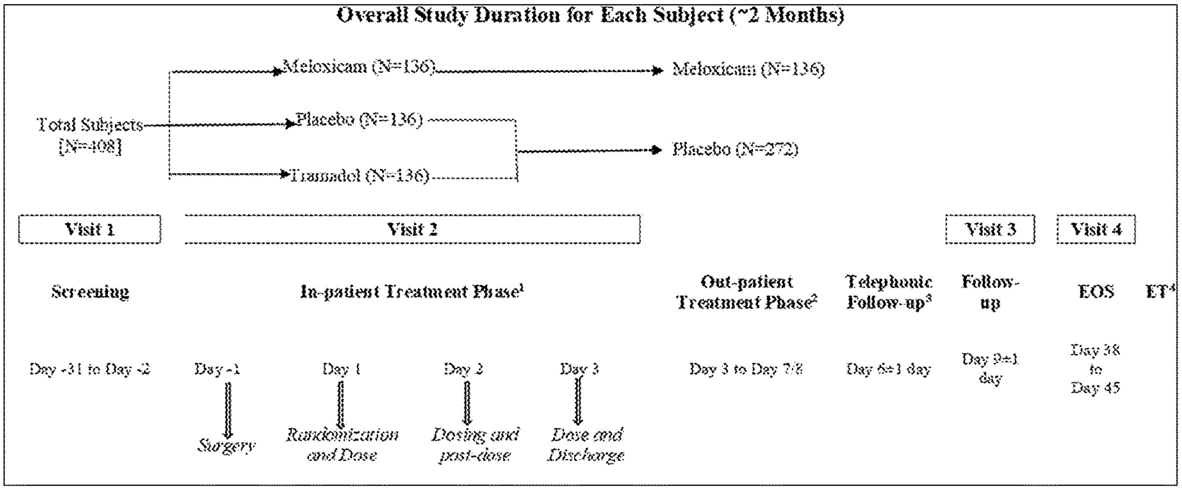
Figure 46:
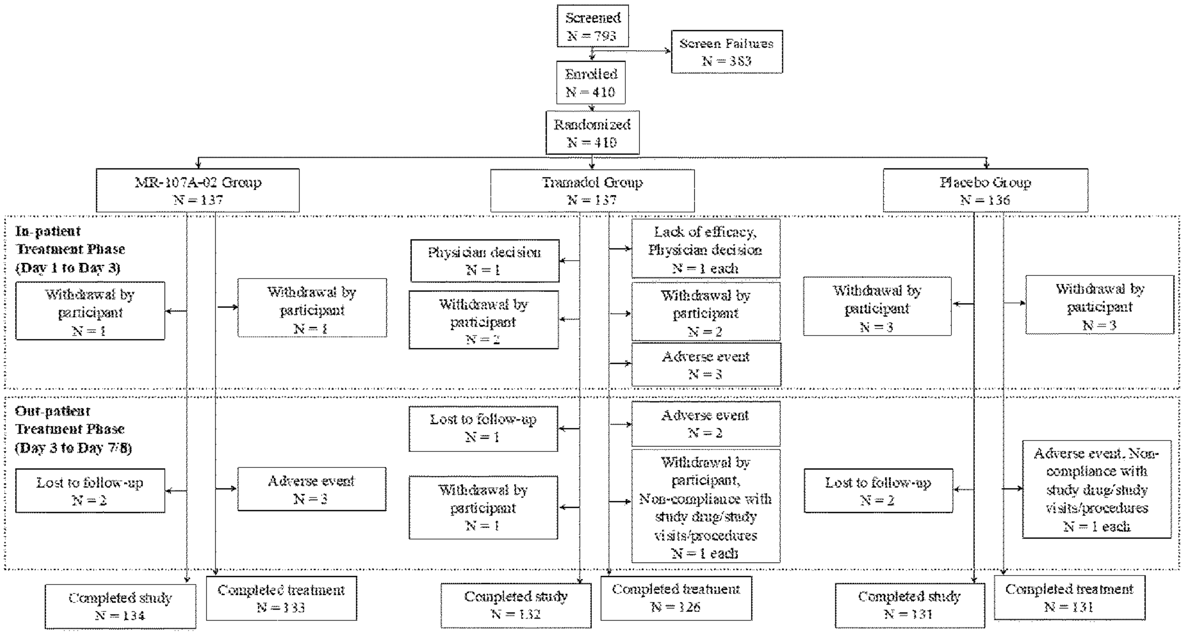
Figure 47:
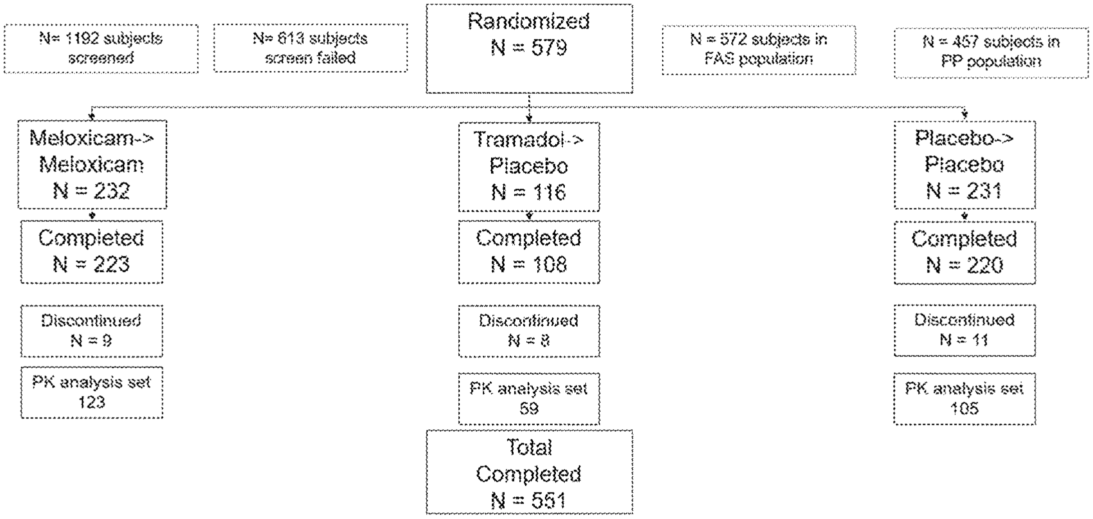
Figure 48:
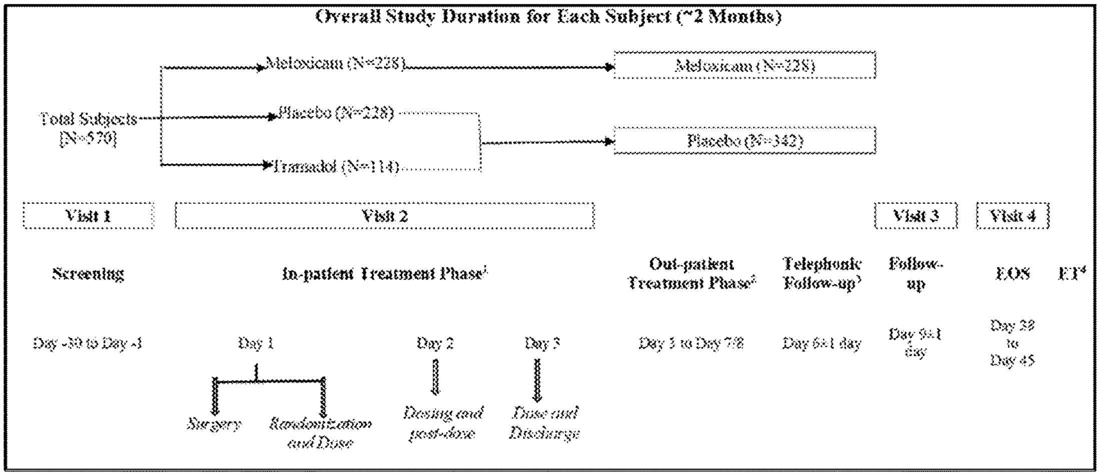
Figure 49:
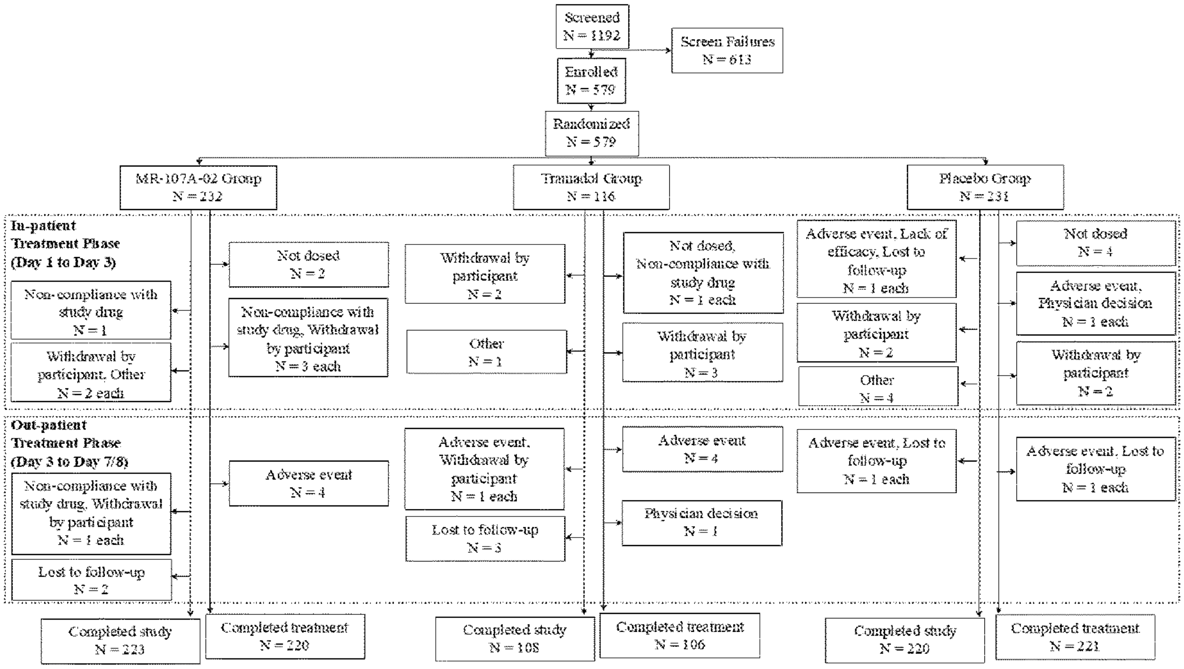

FIG. 31 is series of graphs showing a Mean Plasma Meloxicam Concentrations (PK Analysis Set); A=MR-107A-02 Group; B=Placebo Group; BID=Twice daily; C=Tramadol Group; N=Number of participants per treatment group in the PK Analysis Set; PK=Pharmacokinetic; q6h=once every 6 hours; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase); Note: Participants 201-100 and 204-007 were not included in the summary figures due to insufficient available concentration data and participant 212-121 was not included due to Time 0 pre-dose concentration greater than $C_{max}$;

FIG. 32 a graph showing data as to the rapid dissolution and absorption of Composition 4 relative to MOBIC;

FIG. 33 is a graph showing data of MR-107A-02 vs. placebo and Tramadol vs. placebo in achieving pain control after a Bunionectomy and Herniorrhaphy;

FIG. 34 a graph showing data for the time it takes for MR-107A-02 and tramadol to obtain perceptive and meaningful pain relief after a Bunionectomy and Herniorrhaphy;

FIG. 35 a graph showing data for the time it takes for MR-107A-02 and tramadol to obtain perceptive and meaningful pain relief after a Bunionectomy and Herniorrhaphy;

FIG. 36 shows a series of graphs directed towards an analysis of rescue opioid usage after a Bunionectomy and Herniorrhaphy; the "Meloxicam 15 mg" intervention are tablets according to MR-107A-02. Calculation of Number of opioid doses included all subjects who received the study treatment. *Percentage reduction in #opioid doses based on ratio of Least Squares geometric means. **Second rescue: 5 mg oral oxycodone, third rescue up to 2 mg IV morphine (first rescue acetaminophen=APAP);

FIG. 37 shows the study diagram of the 3001 study;

FIG. 38 shows the study diagram of the 3002 study;

FIG. 39 is a graph showing the mean meloxicam pharmacokinetic profiles across phase 1, 2 and 3 studies (0-12 hrs); the number of subjects who from each study with pK data is identified in parentheses;

FIG. 40 is a graph showing the meloxicam concentrations of phase 3 pharmacokinetic studies compared to MR-107A-02 food effect study (0-12 hrs.) results; n is the number of subjects with pK data from each study;

FIG. 41 is a graph showing an overview of a pain scale;

FIG. 42 shows a study scheme;

FIG. 43 shows a scheme of the disposition of subjects in Phase 2b Study; BID=twice daily; incl. crit.=inclusion criterion [1] Of the 28 subjects in the meloxicam 5 mg group who completed the confinement period, 1 subject (Subject 201-0035) received only 1 dose of study drug during the confinement period because he withdrew consent before receiving the second dose; however, the subject completed the follow-up telephone call on Day 6;

FIG. 44 is a scheme showing the Subject Disposition in a Bunionectomy Surgery Study;

FIG. 45 is a scheme showing a study design; BID=Twice daily; EOS=End of Study; ET=Early Termination; GI=Gastrointestinal; Meloxicam=MR-107A-02; q6h=Once every 6 hours; [1]Study drugs administered included MR-107A-02 (15 mg BID; tablet), tramadol (50 mg; q6h; over-encapsulated tablet), and placebo (one for MR-107A-02 BID [tablet] and one for tramadol q6h [over-encapsulated tablet]). The study drugs were administered blinded at each dosing time. The participants received one tablet and one over-encapsulated tablet q6h (double-blinded, double-dummy); [2]For the out-patient treatment phase (5 days following discharge), participants from the tramadol group received placebo. Participants from the MR-107A-02 group continued on MR-107A-02, and participants in the Placebo group continued on placebo. Further, depending on randomization, the last dose could have been on either Day 7 or Day 8; [3]A telephonic call (telephonic visit) was to be done on Day 6±1 day, and a diary was to be offered to check for any symptoms of potential hepatic toxicity and GI toxicity. Unless consent was withdrawn, participants who prematurely withdrew from the study were to have ET procedures performed in lieu of the procedures that would have been performed at Discharge on Day 3;

FIG. 46 is a scheme showing the participant disposition for all participants, wherein BID=Twice daily; N=Number of participants; q6h=Once every 6 hours; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase;

FIG. 47 is a scheme showing the subject disposition in a Herniorrhaphy Surgery Study;

FIG. 48 is a scheme showing a study design; BID=Twice daily; EOS=End of Study; ET=Early Termination; GI=Gastrointestinal; Meloxicam=MR-107A-02; q6h=Once every 6 hours; [1]Study drugs administered included MR-107A-02 (15 mg BID; tablet), tramadol (50 mg; q6h;

over-encapsulated tablet), and placebo (one for MR-107A-02 BID [tablet] and one for tramadol q6h [over-encapsulated tablet]). The study drugs were administered blinded at each dosing time. The participants received one tablet and one over-encapsulated tablet q6h (double-blinded, double-dummy). [2]For the out-patient treatment phase (5 days following discharge), participants from the tramadol group received placebo. Participants from the MR-107A-02 group continued on MR-107A-02, and participants in the Placebo group continued on placebo. Further, depending on randomization, the last dose could have been on either Day 7 or Day 8. [3]A telephonic call (telephonic visit) was to be done on Day 6±1 day, and a diary was to be offered to check for any symptoms of potential hepatic toxicity and GI toxicity. Unless consent was withdrawn, participants who prematurely withdrew from the study were to have ET procedures performed in lieu of the procedures that would have been performed at Discharge on Day 3; and FIG. 49 is a scheme showing the participant disposition for all participants, wherein BID=Twice daily; N=Number of participants; q6h=Once every 6 hours; Note: During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase. Note: Seven participants were not dosed; they were indicated to have discontinued from the study under the reason of "Other."

DETAILED DESCRIPTION OF THE EMBODIMENTS OF THE INVENTION

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

The term "acute pain," as used herein, unless otherwise indicated, refers to pain arising relatively suddenly, usually from a specific cause (injury, infection, inflammation, surgery etc.), sometimes lasting for a limited period of time (as opposed to chronic pain).

The term "chronic pain," as used herein, unless otherwise indicated, refers to a persistent state of pain. Chronic pain is often associated with long-term incurable or intractable medical conditions or diseases.

The term "procedural pain," as used herein, unless otherwise indicated refers to pain arising from a medical procedure, including but not limited to a dental procedure or a dental surgery, any type of surgery, or any other medical procedure wherein the procedure may be planned or associated with acute trauma. The procedure may be conducted without anesthesia or with a patient under anesthesia, such as general, twilight, or local anesthesia or a combination thereof. "Procedural pain," includes post-operative pain, post-procedural pain and peri-procedural pain.

The term "pain," as used herein, refers to all types of pain, including but not limited to moderate to severe pain. Pain may be moderate or severe. "Moderate to severe" pain encompasses moderate pain, severe pain, and pain that changes or variates between moderate and severe. Pain also includes neuropathic pain, post-operative pain, chronic lower back pain, cluster headaches, herpes neuralgia, phantom limb pain, central pain, dental pain, visceral pain, surgical pain, bone injury pain, pain during labor and delivery, pain resulting from burns, postpartum pain, migraine, angina pain, genitourinary tract-related pain, including but not limited to cystitis and nociceptive pain.

The term "post-operative pain," or "post-surgical pain," as used herein refers to an individual's pain after surgery.

"Perceptible pain relief" and "Meaningful pain relief," as used herein, unless otherwise indicated, are terms known to those or ordinary skill in the art. For example, Miller et al. (Miller, C and Farrar, J: "Methodology for determining minimally clinically important differences in acute pain intensity with the double stopwatch technique," The Journal of Pain, Vol. 30, May 2025, 104759) states that the double stopwatch technique is the gold standard for determining the time to meaningful acute pain relief; participants in a double stopwatch technique indicate when they experience perceptible and meaningful pain relief with two stopwatches.

Measures of bioavailability are well known in the art and include parameters such as the area under the plasma concentration-time curve (AUC), the maximum concentration (Cmax), and the time to reach Cmax (Tmax).

The term "AUC" is a measurement of the area under the plasma concentration-time curve and is representative of the amount of drug absorbed following administration of a single dose of a drug (Remington: The Science and Practice of Pharmacy, (Alfonso R. Gennaro ed. 2000), page 999). AUC represents how much drug reaches an individual's bloodstream over a given period of time after a dose of a drug is given.

The term "Cmax" is the maximum plasma concentration achieved after oral drug administration (Remington, page 999).

The term "Tmax" is the amount of time necessary to achieve the Cmax after oral drug administration and is related to the rate of absorption of a drug (Remington, page 999).

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within one (1) or more than one (1) standard deviations, per the practice in the art. Alternatively, "about" can mean a range of up to 20%, preferably up to 10% of a given value.

As used herein, the term "subject" or "patient" or "individual" and other like terms refer to any animal, including human and non-human animals (mammals such as dogs, cats, cows, horses, sheep; and other non-human mammals, e.g., poultry, fish, crustaceans, etc.). As used herein, the term “patient” typically refers to a subject that is being treated for a disease or condition.

The phrase “individual in need thereof” as used herein refers to an individual who is in a physical or mental state of needing a particular treatment or intervention. Unless otherwise indicated, an “individual in need thereof” refers to an individual suffering from or experiencing any type of pain. In some embodiments of the invention described herein, the “individual in need thereof” is an individual experiencing pain who has received no other analgesic before receiving treatment of pain as described herein. Although the individual in need thereof may have received no other analgesic before receiving treatment of pain as described herein, the individual may or may not have received anesthesia, including local, general, and/or twilight anesthesia.

As used herein, the terms “administration” and “administering” refer to the act of giving a drug, prodrug, or other agent, or therapeutic treatment to a subject or a subject receiving such drug or therapeutic. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term “significant,” unless otherwise indicated herein, refers to statistical significance, meaning a result is unlikely to have occurred by random chance.

The term “statistical significance” means a result is unlikely due to random chance, suggesting a real effect or relationship in the data. Statistical significance can be determined by a p-value, where a low p-value (typically ≤0.05, or ≤0.04, or ≤0.03, or ≤0.02) indicates statistical significance, meaning the observed effect is unlikely to have occurred by chance alone.

The term “clinically significant,” as used for example in “clinically significant pain relief,” refers to a reduction in pain that is meaningful and noticeable by or with respect to the patient, not just a small or statistically insignificant change. “Clinical significance” refers to a set of indices selected to evaluate whether the impact of a treatment or intervention translates to meaningful changes in a patient, and “clinically significant” as used herein, unless otherwise indicated, refers to an effect, measurement, or observation, following a treatment or intervention, regarding a patient that is meaningful with respect to the patient’s health or well-being.

The term “pain intensity” refers to the degree or severity of pain experienced by an individual. It describes how strong or intense the pain feels, ranging from mild discomfort to excruciating agony. A simple and quick way is to ask the patient to assess pain intensity on a scale of 0-10 (verbal analogue scale, where 0 means no pain at all, and 10 the most excruciating pain imagined). A Numerical Rating Scale (NRS) is a type of self-report measure used to assess the intensity of a symptom, most commonly pain, by asking individuals to rate it on a numerical scale, wherein where 0 represents no pain and 10 represents the worst possible pain. Typically, the minimum for moderate pain is 4, whereas an NRS score of 7 or greater is classified as severe. FIG. 41 is an overview of pain scales.

The terms “rescue analgesia medication,” “rescue analgesic,” “rescue medication,” and other like terms, refer to any pain medication provided to an individual when the existing analgesia the individual is receiving is not working well enough on its own. Rescue analgesia medication may be used to manage sudden intense pain (sometimes referred to as “breakthrough pain”). Here, in the current studies, a rescue medication was used as an additional analgesic agent for obtaining pain relief for patients who did not experience sufficient pain relief from the treatment (study drug, comparator, or placebo).

The term “breakthrough pain (BTP),” as used herein, unless otherwise indicated, refers to a sometimes sudden, sometimes transitory increase in pain in a patient already receiving a pain therapy, for example a pain medication regimen. This pain is often described as “breaking through,” the effects of the “around-the-clock” medication being used to manage the underlying chronic pain.

The term “peri-procedural pain” refers to the pain experienced by a patient during or around the time of a medical procedure. It encompasses pain felt both during the procedure itself and in the immediate period before and/or after. This pain can stem from the physical acts involved with the procedure, related tissue damage, or complications arising from the procedure.

The term “herniorrhaphy” refers to a surgical procedure to repair a hernia. A hernia occurs when an organ or tissue protrudes through a weak spot in a muscle or connective tissue. Herniorrhaphy involves reinforcing the weakened area and pushing the protruding organ or tissue back into its proper position.

The term “postoperative pain” and references herein to an individual having undergone an operation or surgery or being “postoperative,” unless otherwise indicated, mean the person has undergone a surgery or operation of any type within a preceding hours of time, such as within about 72 hours or less. A postoperative individual may have received anesthesia, such as general, twilight, or local anesthesia, during the operation. Such individual may be “postoperative” for a period of time after emerging from general or twilight anesthesia, such as from about 24 hours or less, about 12 hours or less, about 6 hours or less, about 3 hours or less, about 2 hours or less, or about 1 hour or less after emerging from general or twilight anesthesia. An individual may be postoperative after reversal of a local anesthetic block, for example about 3 hours or less, about 2 hours or less, or about 1 hour or less after the anesthetic block reverses.

The term “adverse event” refers to any undesirable medical occurrence, such as a symptom, sign, or disease, that happens during treatment or research, regardless of whether it is related to the treatment or intervention. It encompasses any negative outcome, even if not directly caused by the medical care provided.

The term “Kaplan-Meier plot,” also known as a “Kaplan-Meier curve,” refers to a graphical representation of survival data, illustrating the proportion of a population that survives over a specific period. It’s a statistical tool used to estimate the probability of survival (or the probability of another event occurring) over time.

The term “SPID” or “Sum of Pain Intensity Difference” refers to a metric used in pain research to quantify the change in pain intensity over a period of time, often in clinical trials of analgesics. It’s calculated by summing the differences in pain intensity scores, typically recorded at regular intervals, from a baseline measurement.

The term “Overall Benefit of Analgesic Score (OBAS)” refers to a multi-dimensional assessment tool used to measure a patient’s perception of benefit from pain management, particularly in the context of postoperative pain therapy. It considers pain intensity, opioid-related side effects, and patient satisfaction to provide a more comprehensive evaluation than simple pain scores.

The term "Modified Post-anesthetic Discharge Scoring System (MPADSS)" refers to a tool used to assess a patient's readiness for discharge from post-anesthesia care, specifically after procedures like colonoscopies performed under sedation. It builds upon the original Post-Anesthetic Discharge Scoring System (PADSS), often incorporating elements of the Modified Aldrete Score (MAS). The MPADSS evaluates various criteria, including vital signs, ambulation, pain, nausea/vomiting, and surgical bleeding, to determine if a patient can be safely discharged.

The term "Post-Anesthetic Discharge Scoring System (PADSS)" refers to a tool used to objectively assess a patient's readiness for discharge following anesthesia, particularly in ambulatory surgery settings. It evaluates patients based on several criteria, including vital signs, ambulation, nausea/vomiting, pain, bleeding, and voiding, assigning scores to each to determine overall readiness for discharge.

The term "Modified Aldrete Score (MAS)" refers to a widely used tool to assess a patient's readiness for discharge from the post-anesthesia care unit (PACU) following surgery. It evaluates five key criteria: activity, respiration, circulation, consciousness, and oxygen saturation. Each criterion is scored from 0 to 2, with a maximum total score of 10. A score of 9 or higher generally indicates that a patient is ready to be discharged from the PACU.

The term "Patient Global Assessment (PGA)" refers to a patient's subjective evaluation of their overall health or disease activity. It's a single-item, self-reported measure, often used in rheumatoid arthritis (RA) and other pain conditions, to gauge how the disease is affecting them. Typically, patients rate their condition on a scale (e.g., 0-10 or 0-100), with higher scores indicating worse perceived health or disease activity.

The terms "fed state," "fasted state," and "semi-fasted state" are known to those of ordinary skill in the art and typically refer to a condition with respect to food intake a human is in that is similar qualitatively and/or quantitatively to a condition with the same term ("fed," "fasted," or "semi-fasted") of a subject in a clinical study to evaluate the effects of food on the pharmacokinetics of a drug. A "fed" state may for example be having just recently (for example within one hour or less) eaten a meal similar with respect to fat and calories as a breakfast of 2 eggs fried in butter, 2 strips of bacon, 2 slices of toast with butter, 4 ounces of hash brown potatoes, and 8 ounces of whole milk. This type of meal is sometimes referred to as a "high fat meal." A semi-fasted state may be after having recently (for example within one hour or less) eaten a light meal or snack, such as a meal or snack similar in fat content and calories as a breakfast of 1 boiled egg, one packet of flavored instant oatmeal made with water, and 8 ounces of 1% fat milk. This type of meal is sometimes referred to as a "low fat meal.'

A regulatory agency may approve a drug with instructions to be taken "with food," which simply means an individual should not take the medication on an empty stomach. Instructions to take a medication "with food" means an individual can take the medicine just before, right after, or while having a meal. A period of 30 minutes before or after a meal is typically considered taking a medicine "with food."

A regulatory agency may approve a drug with instructions to be taken "without food" or "on an empty stomach." Taking a medication "without food" or "on an empty stomach" usually does not mean that a meal needs to be skipped. Rather, it means a medication should be taken before or after a meal, such as breakfast, lunch, or dinner. When taking a medication "without food" or "on an empty stomach," waiting for at least 30 minutes before beginning to eat or after completing a meal is usually enough time.

A regulatory agency may approve a drug with instructions such as "may be taken with or without food." Or a regulatory agency may approve a drug without any instructions regarding whether to take the medication with food or without food.

The terms "opioid drug," "opioid," and other like terms are known to a person of skill in the art. Opioids can be described as a class of drugs that derive from, or mimic, natural substances found in the opium poppy plant. Another way of describing an opioid drug, is a molecule (naturally occurring or synthetic) that binds to or interacts with one or more of opioid receptors within the nervous system. Opioids work in the brain to produce a variety of effects, including pain relief. Examples of opioid drugs include oxycodone, oxymorphone, hydrocodone, morphine, and tramadol.

Opioid-sparing behavior refers to the use of an intervention (such as non-opioid medications, regional anesthesia, or non-pharmacological techniques) to reduce the total dosage or duration of opioid medications required to achieve adequate pain relief.

Meloxicam is a nonsteroidal anti-inflammatory drug (NSAID) that exhibits anti-inflammatory, analgesic and anti-pyretic activities, and is classified under BCS class II. Like other NSAIDs, the primary mechanism of action of meloxicam is via inhibition of the cyclooxygenase (COX-2) enzyme system resulting in decreased prostaglandin synthesis.

Meloxicam, an oxicam derivative, is a member of the enolic acid group of NSAIDs. It is chemically designated as 4-hydroxy-2-methyl-N-(5-methyl-2-thiazolyl)-2H-1,2-benzothiazine-3-carboxamide-1,1-dioxide and is depicted by the following chemical structure:

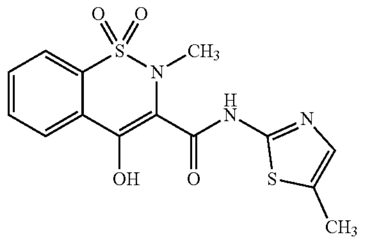 [SMILES: Cc1cnc(NC(=O)C2=C(O)c3ccccc3S(=O)(=O)N2C)s1]

Meloxicam was developed originally by Boehringer Ingelheim and marketed in Europe as Meloxyl as an oral suspension for the treatment of rheumatoid arthritis, short term use in osteoarthritis, and ankylosing spondylitis. In the United States, MOBIC® (7.5 mg and 15 mg meloxicam oral tablets) has been approved by the Food and Drug Administration for osteoarthritis, rheumatoid arthritis, and Juvenile Rheumatoid Arthritis in patients who weigh at least 60 kg.

The absorption of meloxicam has been studied following its administration via intramuscular, oral, and rectal routes. The bioavailability of a single 30 mg oral dose of meloxicam is 89% as compared to a 30 mg intravenous bolus injection. Meloxicam capsules have been shown to be bioequivalent to MOBIC® (Meloxicam) 15 mg tablets. Following single intravenous doses, dose-proportional pharmacokinetics were shown in the range of 5 mg to 60 mg. After administration of multiple oral doses of meloxicam, the pharmacokinetics are dose-proportional in the range of 7.5 to 15 mg. The rate or extent of absorption is not affected by multiple dose administration. Mean Cmax was achieved in 4-5 hours after a 7.5 mg meloxicam tablet was taken under fasted conditions, indicating prolonged drug absorption. A second meloxicam concentration peak occurring at approximately 12 to 14 hours post-dose, suggested gastrointestinal recirculation. Furthermore, studies under steady state fed conditions in healthy adult males showed that administration of 7.5 mg tablets (MOBIC®) have a mean Cmax of 1.05 μg/mL, a Tmax of 4.9 hrs., and a t½ of 20.1 hours. Under steady state fed conditions in elderly males and females, administration of 15 mg tablets (MOBIC®) have a Cmax of 2.3 and 3.2 μg/ml respectively, a Tmax of 5 and 6 hrs. respectively, and a t½ of 21 and 24 hrs. respectively [See MOBIC® (meloxicam): Prescribing Information and Medication Guide; approved by U.S. FDA for osteoarthritis Apr. 13, 2000].

Next, additional studies of a 15 mg meloxicam capsule showed that a maximum meloxicam plasma concentration (Cmax) of was achieved after 5-6 hours (Tmax) when administered after breakfast. The onset of action of meloxicam, however, occurred much earlier than Tmax. The $C_{max}$ occurred later (Tmax was doubled) when a meloxicam capsule was administered in a fasted state [Turck D, Busch U, Heinzel G, Narjes H. Clinical pharmacokinetics of meloxicam. *Eur. J. Rheumatol. Inflamm.* 1995; 15:22-34] [Turck D, Busch U, Heinzel G, Narjes H., Nehmiz G. Effect of Food on the Pharmacokinetics of Meloxicam after Oral Administration. *Clin. Drug Invest.* 1995; 9 (5): 270-276] [Turck D, Roth W, Busch U. A Review of the Clinical Pharmacokinetics of Meloxicam. *British Journal of Rheumatology* 1996; 35 (suppl. 1): 13-16]. When used chronically, NSAIDs are typically administered after a meal; thus, Cmax (5-6 hours) is the more clinically relevant figure, but it is still not suitable for the treatment of acute pain.

Although current pharmaceutical products containing meloxicam are effective in treating pain, the onset of pain relief does take multiple hours, and, thus, having a formulation that exhibits a faster onset of pain relief would also be desirable.

The present invention provides methods of administering meloxicam for adequate pain relief, such as relief of moderate-to-severe pain, within a sufficient amount of time, for example within about 4 hours or less, or within less than the amount of time currently approved oral and IV meloxicam formulations take to provide adequate pain relief. In some embodiments, the methods comprise administering to an individual in need thereof a solid oral pharmaceutical dosage form comprising meloxicam such as the pharmaceutical compositions described herein. The methods described herein are therefore useful in treating pain when more rapid pain relief is needed, for example when treating acute pain, post-operative pain, or post-procedural or peri-procedural pain.

Compositions useful in the methods described herein can comprise meloxicam as an active ingredient in its free form or in the form of a pharmaceutically acceptable salt of meloxicam. The word "meloxicam" generally refers herein, unless otherwise indicated, to the free form of meloxicam, i.e., the molecule with the structure depicted above not combined with any counter-ion.

U.S. Patent Application Publication No. US 2024/0277726 A1, Publication Date Aug. 22, 2024, which is hereby incorporated by reference in its entirety, describes a randomized bioequivalence study in healthy adult volunteers under fasted conditions comparing single-dose pharmacokinetics following administration of 15 mg MOBIC® to pharmacokinetics following administration of a 15 mg meloxicam tablet representative of novel oral meloxicam dosage forms described therein. The novel oral meloxicam dosage form showed a 5 times faster median Tmax compared to MOBIC®, and a more rapid absorption than MOBIC®, as evidenced by a higher Cmax, higher pAUCs, shorter Tmax, and a more rapid time to achieve 1090 ng/ml meloxicam.

US 2024/0277726 A1 discloses a meloxicam solid oral composition having the following pK parameters when tested in a bioavailability study in 16 (N) healthy adult volunteers under fasted conditions:

| Parameter | N | Arithmetic mean ± Std. Deviation (Coeff of Variation (%)) |
|---|---|---|
| Tmax (hr)◂ | 16 | 0.750 (0.333-3.500) |
| T1090 (hr)◂ | 16 | 0.333 (0.333-0.500) |
| Cmax (ng/mL) | 16 | 2786.072 ± 558.429 (20.044) |
| AUCt (ng/mL)*(hr) | 16 | 49700.363 ± 16123.474 (32.441) |
| AUCi (ng/mL)*(hr) | 16 | 55910.213 ± 24751.922 (44.271) |

T1090 = Time at which concentration first exceed 1090 ng/mL
◂T1090 and Tmax are presented as Median (Range)

In some embodiments, the solid oral meloxicam composition is a composition that is bioequivalent in healthy adult humans to a composition having the parameters described in the Table above. In some embodiments of the methods, the solid oral meloxicam composition is a composition that has a meloxicam Cmax in healthy adult humans that is about 30% less to about 30% more than the Cmax described in the Table above. In some embodiments of the methods, the solid oral meloxicam composition is a composition that has a meloxicam Cmax in healthy adult humans that is about 20% less to about 25% more than the Cmax described in the Table above. In some embodiments of the methods, the solid oral meloxicam composition is a composition that has a meloxicam AUCt in healthy adult humans that is about 30% less to about 30% more than the AUCt described in the Table above. In some embodiments of the methods, the solid oral meloxicam composition is a composition that has a meloxicam AUCt in healthy adult humans that is about 20% less to about 25% more than the AUCt described in the Table above.

In some embodiments of the methods described herein, the solid oral meloxicam composition has one or more pK parameters (Tmax, Cmax, AUCt) having a value in healthy adult humans falling within the numeric range given for each such parameter as described in the following Table, wherein the column entitled "Value" indicates an example of one formulation useful in the subject methods and having a Tmax, Cmax, and AUCt in healthy adult humans that fall within the indicated ranges:

| Parameter | 30% less | 20% less | Value | 20% more | 25% more | 30% more |
|---|---|---|---|---|---|---|
| ◂Tmax (hr) | 0.525 (31.5 min) | 0.645 (38.7 min) | 0.75 (0.333-3.500) | 0.855 (51.3 min) | 0.93 | 0.975 |

-continued

| Parameter | 30% less | 20% less | Value | 20% more | 25% more | 30% more |
|---|---|---|---|---|---|---|
| Cmax (ng/mL) | 1950.25 | 2228.86 | 2786.072 ± 558.429 (20.044%) | 3343.29 | 3482.59 | 3621.89 |
| AUCt | 34790.25 | 39760.29 | 49700.363 ± 16123.474 (32.441%) | 59640.44 | 62125.45 | 64610.47 |

US 2024/0277726 A1 discloses oral dosage forms of meloxicam that can be used in the methods described herein. Example 1 below describes specific examples of such dosage forms and their manufacture, which are also described in US 2024/0277726 A1 (see, e.g., Paras. [0027] through [0033] and Paras. [0055] through [0073]), that can be used in the therapeutic methods described in the present application.

The pending application describes administration of such compositions as are described in US 2024/0277726 A1 to effectively and safely manage pain in human subjects afflicted with acute or moderate-to-severe pain. Specifically, this application describes Phase 2 and Phase 3 clinical studies of a composition described in US 2024/0277726 A1 in three different established clinical models for acute pain, including pain models representing both bony and soft tissue injury. As described in further detail herein, the results of these clinical studies in established pain models (dental surgery, bunionectomy and herniorrhaphy) revealed more effective and timely pain relief relative to placebo and in some cases relative to a positive comparator, tramadol. In addition to efficacious pain management, the clinical studies described herein revealed other beneficial properties, such as minimal side effects and/or minimal use of rescue medication, including opioids.

In one embodiment in the methods of treating pain of the present invention, the composition of the meloxicam solid oral dosage form comprises an alkalizing agent less than about 400 mg; preferably about 100-400 mg; or any amount in a range bounded by, or between, any of these values.

In some embodiments, the methods of treating pain of the present invention comprise administering to a subject in need thereof a meloxicam solid oral dosage form in the form of a tablet or capsule or any other solid oral dosage form comprising meloxicam, a hydrophilic polymer and one or more alkalizing agents or the combinations thereof.

In some embodiments, the methods for treating pain of the invention comprise administering a solid dispersion of meloxicam with at least a hydrophilic polymer and one or more alkalizing agents, or combinations thereof.

In some embodiments, the methods for treating pain of the invention comprise administering an oral pharmaceutical composition as described herein, the composition further comprising one or several pharmaceutically acceptable excipients.

In some embodiments, the methods for treating pain of the invention comprise administering a meloxicam solid oral pharmaceutical composition as described, the composition comprising meloxicam or a pharmaceutically acceptable salt thereof in an amount effective for treating pain, one or more alkalizing agents, and one or more hydrophilic polymers.

In some embodiments, the methods for treating pain of the invention comprise administering a meloxicam solid oral pharmaceutical composition as described, comprising drug granules or drug pellets comprising the meloxicam or pharmaceutically acceptable meloxicam salt, one or more alkalizing agents, and one or more hydrophilic polymers.

In some embodiments of the methods for treating pain of the invention, the drug granules in the solid oral dosage form are manufactured by a method comprising (a) obtaining alkalizer based granules comprising a first alkalizing agent and a first hydrophilic polymer, (b) granulating the alkalizer based granules of step (a) with a solution comprising the meloxicam or the pharmaceutically acceptable meloxicam salt dispersed in a solution comprising a second alkalizing agent and a second hydrophilic polymer, and (c) granulating the meloxicam granules of step (b) with a solution comprising a third alkalizing agent and a third hydrophilic polymer, thereby obtaining the drug granules. In some such compositions the first, second and third hydrophilic polymers are each independently selected from the group consisting of copovidone, hypromellose, povidone, hydroxy propyl cellulose, hydroxy ethyl cellulose, PEG 6000, PEG 8000, PEG 20000, Lutrol F-127, and any combination thereof. In some such compositions as described in the immediately preceding sentence, the first and the third hydrophilic polymers are hypromellose and the second hydrophilic polymer is copovidone. In some such compositions, the first, second and third alkalizing agents are each independently selected from the group consisting of ammonium hydroxide, sodium phosphate, sodium acetate, sodium carbonate, sodium bicarbonate, meglumine, ethylamine, triethylamine, ethanediamine, tromethamine, lysine, arginine, histidine, sodium hydroxide, and any combination thereof.

In some embodiments of these compositions, the drug granules are formed into an oral tablet by blending them with one or more pharmaceutically acceptable excipients including a diluent, lubricant, glidant, disintegrant, or binder.

In some embodiments of the methods for treating pain of the invention, the drug pellets in the solid oral dosage form are manufactured by a method comprising (a) coating pharmaceutically acceptable inert spheres with a solution comprising a first alkalizing agent to obtain alkalized spheres, (b) coating the alkalized spheres of step (a) with a solution comprising the meloxicam or the pharmaceutically acceptable meloxicam salt dispersed in a solution comprising a second alkalizing agent and a first hydrophilic polymer to obtain drug loaded pellets, and (c) coating the drug loaded pellets of step (b) with a solution comprising a third alkalizing agent and a second hydrophilic polymer, thereby obtaining the drug pellets. In some embodiments, the solution coating the inert spheres of step (a) further comprises a third hydrophilic polymer.

In some embodiments of the methods for treating pain of the invention, an oral tablet comprised of (a) drug granules, wherein the drug granules comprise (i) about 5 mg to about 50 mg meloxicam, (ii) one or more hydrophilic polymers, and (iii) one or more alkalizing agents is administered to the individual in need thereof. In some embodiments, the alkalizing agents in the drug granules are selected from the group consisting of sodium bicarbonate, sodium carbonate, meglumine, and any combination thereof. In some embodiments, the oral tablet comprises from about 100 mg to about 400 mg sodium bicarbonate. In some embodiments, the oral tablet comprises from about 100 mg to about 400 mg sodium bicarbonate, about 15 mg meloxicam, and the hydrophilic polymers are selected from the group consisting of copovidone, hypromellose, povidone, hydroxy propyl cellulose, hydroxy ethyl cellulose, PEG 6000, PEG 8000, PEG 20000, Lutrol F-127, and any combination thereof. In some embodiments, the drug granules in such oral tablet contain at least one hydrophilic polymer selected from copovidone. In some embodiments, the oral tablet comprises from about 100 mg to about 400 mg sodium bicarbonate, about 15 mg meloxicam, and the hydrophilic polymers in the drug granules are copovidone and hypromellose. In some embodiments of the methods, the oral tablet comprising the drug granules further comprises a disintegrant, a lubricant, and/or a binder. In some embodiments of the methods, the oral tablet comprising the drug granules further comprises crospovidone and a lubricant and/or a binder.

In some embodiments of the methods for treating pain of the invention, the meloxicam or pharmaceutically acceptable meloxicam salt is embedded in alkaline surroundings in the solid oral composition. In some embodiments of the methods, the composition comprises granules or pellets comprising meloxicam or a pharmaceutically acceptable salt thereof embedded in alkaline surroundings. In some such embodiments, the alkaline surroundings further comprise granules and/or pellets comprising one or more pharmaceutically acceptable excipients selected from alkalizing agents, hydrophilic polymers, and any combination thereof. In some such embodiments, the alkalizing agents or agents include ammonium hydroxide, sodium phosphate, sodium acetate, sodium carbonate, sodium bicarbonate, meglumine, ethylamine, triethylamine, ethanediamine, tromethamine, lysine, arginine, histidine, or sodium hydroxide, or any combination thereof, and wherein the hydrophilic polymer or polymers include copovidone, hypromellose, povidone, hydroxy propyl cellulose, hydroxy ethyl cellulose, PEG 6000, PEG 8000, PEG 20000, or Lutrol F-127, or any combination thereof.

In some embodiments of the methods for treating pain of the invention, the solid oral pharmaceutical composition comprises a solid dispersion of the meloxicam or the pharmaceutically acceptable meloxicam salt. In some embodiments of the methods, the composition comprises a solid dispersion of the meloxicam or pharmaceutically acceptable meloxicam salt, and the meloxicam or pharmaceutically acceptable meloxicam salt is embedded in alkaline surroundings in the solid oral composition. In some embodiments of the methods, the solid oral pharmaceutical composition comprises a solid dispersion of meloxicam or the pharmaceutically acceptable meloxicam salt, and the solid dispersion comprises a hydrophilic polymeric matrix. In some embodiments, the solid dispersion is made by spray drying, slow evaporation at low temperature, rotary evaporation, freeze drying, spin drying, traditional melt cool method hot stage extrusion, melt agglomeration, or solvent evaporation.

In some embodiments of the methods for treating pain of the invention, the solid oral pharmaceutical composition is prepared by embedding the meloxicam or pharmaceutically acceptable meloxicam salt in the alkaline surroundings. The embedding may comprise dispersing the meloxicam or pharmaceutically acceptable meloxicam salt in at least one hydrophilic polymer. Crystalline meloxicam or crystalline pharmaceutically acceptable meloxicam salt may be dispersed in at least one hydrophilic polymer. In some embodiments the embedding comprises granulating the meloxicam or pharmaceutically acceptable meloxicam salt with one or more pharmaceutically acceptable excipients providing an alkaline microenvironment. Crystalline meloxicam or crystalline pharmaceutically acceptable meloxicam salt may be granulated with one or more excipients providing the alkaline microenvironment. The excipients providing an alkaline microenvironment comprise an alkalizing agent, a hydrophilic polymer, or a combination thereof. In some embodiments, the embedding comprises coating the meloxicam or pharmaceutically acceptable meloxicam salt with one or more pharmaceutically acceptable excipients providing an alkaline microenvironment.

In some embodiments of the methods for treating pain of the invention, the solid oral pharmaceutical composition comprises a therapeutically effective amount of meloxicam or a pharmaceutically acceptable salt thereof and one or more pharmaceutically acceptable excipients, wherein said meloxicam or pharmaceutically acceptable salt thereof is embedded in surroundings in the composition to provide an alkaline pH microenvironment in acidic dissolution media sufficient to prevent precipitation of the meloxicam or meloxicam salt in such acidic dissolution media. In such embodiments, the alkaline pH microenvironment may in some cases comprise one or more pharmaceutically acceptable excipients selected from alkalizing agents, hydrophilic polymers, or a combination thereof. In such embodiments, the alkaline pH microenvironment may in some cases comprise granules and/or pellets. The alkaline pH microenvironment may in some cases comprise a solid dispersion, and in some cases the solid dispersion may comprise a hydrophilic polymeric matrix.

In some embodiments of the methods for treating pain of the invention, the solid oral pharmaceutical composition comprises a therapeutically effective amount of meloxicam or a pharmaceutically acceptable salt thereof and one or more pharmaceutically acceptable excipients, wherein the meloxicam or meloxicam salt in the composition does not precipitate in acidic dissolution media. In some such embodiments, the composition comprises one or more pharmaceutically acceptable excipients selected from a hydrophilic polymer, an alkalizing agent, or any combination thereof. The hydrophilic polymer may, for example, be selected from copovidone, hypromellose, povidone, hydroxy propyl cellulose, hydroxy ethyl cellulose, PEG 6000, PEG 8000, PEG 20000, and Lutrol F-127. The alkalizing agent may for example be selected from ammonium hydroxide, sodium phosphate, sodium acetate, sodium carbonate, sodium bicarbonate, meglumine, ethylamine, triethylamine, ethanediamine, tromethamine, lysine, arginine, histidine, sodium hydroxide, and any combination thereof. In some such embodiments the composition comprises at least one hydrophilic polymer and at least one alkalizing agent.

In some embodiments, the methods for treating pain of the present invention comprise administering to an individual in need thereof a solid oral pharmaceutical composition comprising meloxicam or a pharmaceutically acceptable meloxicam salt and at least one pharmaceutically acceptable excipient, wherein the composition is free of cyclodextrin and its derivatives.

Excipients to be used in the compositions of the present invention are preferably selected from the group consisting of diluents, binders, hydrophilic polymers, lubricants, glidants, disintegrants, alkalizing agents, coating materials and solvents. Any other excipient known to the skilled person and found suitable for the composition according to the invention may also be used in the composition according to the invention.

Solid oral meloxicam compositions useful in the present invention may comprise one or more suitable inert pharmaceutical diluents selected from the group consisting of sucrose, dextrose, lactose, mannitol, microcrystalline cellulose, fructose, xylitol, sorbitol, starches, and the like, and mixtures thereof.

One or several binders are preferably selected from the group consisting of polyvidone (used synonymously for povidone), methylcellulose, hydroxypropyl methylcellulose (HPMC), hypromellose, starch, gelatin, and hydroxy methylcellulose. Any other binder known to the skilled person may also be used.

Solid oral meloxicam pharmaceutical compositions useful in the present invention may also comprise one or more disintegrants selected from the group consisting of croscarmellose sodium, sodium starch glycolate, pregelatinized starch and cross-linked polyvinylpyrrolidone. Any other disintegrant known to the skilled person and found suitable for the meloxicam compositions for treating pain according to the invention may be used.

Solid oral meloxicam compositions for use in the methods of the present invention may also comprise one or more lubricants selected from the group consisting of magnesium stearate, calcium stearate, glyceryl behenate, polyethylene glycol, stearic acid, and talc. Any other lubricant known to the skilled person and found suitable for the meloxicam compositions for treating pain according to the invention may be used.

Solid oral meloxicam compositions for use in the methods of the present invention may also comprise one or more glidants including, but not limited to, calcium phosphate, calcium silicate, powdered cellulose, magnesium trisilicate, silicon dioxide, talc, colloidal silica, colloidal silica anhydrous and the like.

Solid oral meloxicam compositions for use in the methods of the present invention may also comprise one or more solvents that include, but are not limited to, isopropyl alcohol, methanol, ethanol, dichloromethane, acetone and the like. Other Suitable solvents can also be selected from dimethylacetamide (DMA), dimethyl sulfoxide (DMSO), 1-methyl-2-pyrrolidone (NMP), 1,3-dimethyl-2-imidazolidinone (DMI), acetone, tetrahydrofuran (THF), dimethylformamide (DMF), propylene carbonate (PC), glycerin, dimethyl isosorbide and mixtures thereof. Aqueous solvent includes water. Combination of aqueous and non-aqueous solvents can also be used.

Solid oral meloxicam compositions for use in the methods of the present invention may also comprise one or more coating materials that include, but are not limited to, film-forming substances, e.g. hydroxypropyl methyl cellulose (hypromellose), hydroxyl propyl cellulose, methyl cellulose, polyvinyl alcohol. Optionally, other auxiliary substances, such as plasticizers, and colorants, may be present. Preferred plasticizers are polyethylene glycol (Macrogols e.g. Macrogol6000), triethyl citrate and triacetin. The film coating may also contain excipients such as, excipients for better film adhesion, preferably lactose and/or stearic acid, release agents/antiadhesive agents, preferably talcum and/or glycerol monostearate, and colorants (pigments and lakes). A preferred blend of hydroxypropyl methylcellulose, a plasticizer and a colorant is commercially available under the tradename Opadry®.

The present invention relates to methods for treating pain comprising administration of meloxicam to an individual in need thereof. The present invention also relates to methods for treating pain comprising administering a therapeutically effective amount of meloxicam in a pharmaceutical formulation with pharmaceutically acceptable excipients. In some embodiments, from 0.5 to 100 mg of meloxicam is administered to the individual. In some embodiments, 1 to 50 mg of meloxicam or 5 to 50 mg of meloxicam are so administered. In other embodiments, 1 to 20 mg of meloxicam, 1.25 to 15 mg meloxicam, or 7.5 to 15 mg of meloxicam are so administered. In some embodiments, the solid oral pharmaceutical composition is administered as multiple units of dose such as from two to five parts.

In any of the embodiments herein, the composition administered to the individual comprises 1.25, 5, 7.5, or 15 mg meloxicam.

In some embodiments, the solid oral meloxicam dosage form used in the methods for treating pain of the present invention comprises a solid dispersion, wherein the meloxicam and one or more of the various components of the dosage form are in an immediate release part. Such components include, but are not limited to, an alkalizer component, a drug-binder component, an extra granular component, and a coating component.

Another aspect of the current invention is the treatment of acute pain, post-operative pain, post-surgical pain (e.g., somatic pain, visceral pain, nociceptive pain, or neuropathic pain; pain due to acute tissue, organ or bone injury), post-procedural pain, or peri-procedural pain in a patient in need thereof by administering meloxicam to the patient as described herein. In such embodiments, the pain to be treated is due to a pain-effecting incident, i.e., any incident resulting in pain, e.g., an accidental injury, operation, and/or procedure. Such pain can be treated by the methods herein within about 48 hours or less, about 36 hours or less, about 24 hours or less, about 12 hours or less, about 8 hours or less, about 6 hours or less, about 4 hours or less, about 2 hours or less, or about 1 hour or less after the pain effecting incident. In some embodiments, such pain can be prophylactically reduced by administering meloxicam according to the methods herein about 24 hours prior to an operation or procedure, for example, about 20 hours, about 18 hours, about 16 hours, about 14 hours, about 12 hours, about 8 bours, about 6 hours, about 4 hours, about 2 hours, about 1 hour, or about 0.5 hours prior to the operation or procedure.

In any case of treating pain according to the present invention, the pain may be mild, moderate, severe, or moderate-to-severe, or any other severity of pain. In another aspect, the current invention provides for the treatment of moderate to severe pain. Examples of pain (mild or moderate to severe) that may be treated by administering meloxicam according to the present invention include bony pain, tissue pain, arthritis pain, signs and/or symptoms of arthritis, pain associated with osteoarthritis, rheumatoid arthritis, juvenile rheumatoid arthritis, erosive osteoarthritis, sero-negative (non-rheumatoid) arthropathies, non-articular rheumatism, peri-articular disorders, neuropathic arthropathies including Charcot's foot, axial spondylarthrites including ankylosing spondylitis, and SAPHO syndrome. In some embodiments of the methods of treating moderate to severe pain by administering meloxicam according to the present invention, the pain is acute. In some embodiments of the methods of treating moderate to severe pain according to the present invention, the pain is chronic.

In some embodiments of the methods the present invention, pain associated with an inflammatory disease or condition, pain from or symptoms of an inflammatory disease, pain associated with a toothache, an ache after tooth extraction, a sore throat, otalgia, arthralgia, lumbago, myalgia, a headache, muscle stiffness of shoulder, pain from a pulled muscle or sprain, pain from tense muscles, pain from swelling, pain of contusion, pain of fracture, pain of sprain or bruising, pain from burns, menstrual pain (dysmenorrhea), traumatic pain, chill, exothermic reaction, and/or cold and various symptoms of cold such as sore throat, chill, pyrexia or fever, arthralgia, or muscle pain are treated.

Acute pain can in one aspect be described as pain lasting less than about three months and typically having a sudden or rapid onset, usually resulting from tissue injury, surgical intervention or acute illness. In some embodiments, acute pain that can be treated by the present invention can be bony pain and/or soft tissue pain (soft body tissue pain). In some embodiments the bony pain results from a bone injury or fracture or a bone surgery, such as a bunionectomy surgery. The bone may be a bone in any part of the body, including a bone in the foot of an individual or in the tooth of an individual. In some embodiments the soft tissue pain results from a surgery involving soft tissue, such as a herniorrhaphy. In some embodiments the soft tissue pain results from an injury to a soft body tissue. The soft tissue can be in any soft body tissue, for example a tendon, a muscle or skin (externally or skin surrounding an organ internally).

In some embodiments, moderate to severe pain, acute pain, post-operative pain or post-procedure pain or peri-procedural pain is treated by the methods and described herein without the need for supplemental administration of a different analgesic, i.e., a “rescue medication,” to achieve adequate or meaningful pain relief. In some embodiments, the moderate to severe pain, acute pain, post-operative pain or post-procedural pain or peri-procedural pain is treated by the methods described herein without the need for supplemental administration of an opioid medication or opioid medications to achieve adequate or meaningful pain relief. In some embodiments, the individual does not receive a rescue medication for at least 48 hours after administration of the solid oral meloxicam pharmaceutical composition. In some embodiments, the individual does not receive a rescue medication for at least 48 hours after administration of the solid oral meloxicam pharmaceutical composition.

In some embodiments, the individual experiences perceptible pain relief within one hour after administration of the meloxicam pharmaceutical composition. In some embodiments, the individual experiences perceptible pain relief between about thirty minutes to about one hour following administration of the meloxicam pharmaceutical composition. In some embodiments, the individual experiences perceptible pain relief between about 40 minutes and one hour following administration of the meloxicam pharmaceutical composition. In some embodiments, the individual experiences perceptible pain relief about 45 minutes after administration of the meloxicam pharmaceutical composition. In some embodiments, the individual experiences perceptible pain relief about 50 minutes or about 55 minutes after administration of the meloxicam pharmaceutical composition. In some embodiments, the individual receiving a meloxicam pharmaceutical composition as described herein experiences perceptible pain relief sooner than an individual who had not received said meloxicam pharmaceutical composition.

In some embodiments, the individual experiences meaningful pain relief between about two hours and six hours after administration of the meloxicam pharmaceutical composition. In some embodiments, the individual experiences meaningful pain relief between about three hours and about six hours following administration of the meloxicam pharmaceutical composition. In some embodiments, the individual experiences meaningful pain relief between about three hours and about 4 hours, about 4.5 hours, about 5 hours, or about 5.5 hours following administration of the meloxicam pharmaceutical composition. In some embodiments, the individual experiences meaningful pain relief between from about 2.5 hours and about 3.5 hours, about 4 hours, about 4.5 hours, about 5 hours, or about 5.5 hours after administration of the meloxicam pharmaceutical composition. In some embodiments, the individual experiences meaningful pain relief faster than an individual who received an opioid analgesic but did not receive said meloxicam pharmaceutical composition.

In some embodiments, the individual experiences perceptible pain relief or meaningful pain relief at the same time when achieving a meloxicam Tmax after the disclosed solid oral pharmaceutical composition has been orally administered to said individual suffering from pain. In such embodiments, the meloxicam Tmax can be achieved within about 6 hours or less, about 5 hours or less, about 4 hours or less, about 3 hours or less, about 2 hours or less, or within about 1 hour or less after administration of the oral solid pharmaceutical composition disclosed herein. In other words, a meloxicam Tmax can be achieved in an individual within about 1 hour or less, about 2 hours or less, about 3 hours or less, about 4 hours or less, about 5 hours or less, or within about 6 hours or less after administration of the disclosed solid oral pharmaceutical composition. A skilled artisan would be aware that these Tmax can be modulated by the individual’s fasted, semi-fasted, or fed state. For example, a Tmax of about 3 hours or less can be provided in the disclosed methods when the disclosed solid oral pharmaceutical composition is administered to an individual in a fasted or semi-fasted state.

In some embodiments, administration of the disclosed solid oral pharmaceutical composition to an individual suffering from pain in the disclosed methods provides a meloxicam Tmax in the individual about 6 hours earlier, about 5 hours earlier, about 4 hours earlier, about 2 hours earlier or about 1 hour earlier than a meloxicam Tmax provided in an individual by MOBIC when administered in a same or similar fed or fasted condition.

In some embodiments, the individual experiences perceptible pain relief or meaningful pain relief at the same time as or prior to a meloxicam Cmax is achieved after the disclosed solid oral pharmaceutical composition has been orally administered to said individual suffering from pain. In such embodiments, the meloxicam Cmax can be achieved within about 6 hours or less, about 5 hours or less, about 4 hours or less, about 3 hours or less, about 2 hours or less, or within about 1 hour or less after administration of the oral solid pharmaceutical composition disclosed herein. In other words, a meloxicam Cmax can be achieved in an individual within about 1 hour or less, about 2 hours or less, about 3 hours or less, about 4 hours or less, about 5 hours or less, or within about 6 hours or less after administration of the disclosed solid oral pharmaceutical composition. A skilled artisan would be aware that the Cmax can be modulated by the individual’s fasted, semi-fasted, or fed state. For example, a Cmax of about 3 hours or less can be provided in the disclosed methods when the disclosed solid oral pharmaceutical composition is administered to an individual in a fasted or semi-fasted state. In some embodiments, the Cmax is obtained when Tmax has been reached.

The meloxicam blood plasma concentration of Cmax (i.e., at the time of Tmax) can vary depending on the state of the individual, i.e., fasted, semi-fasted or not fasted. In some embodiments, the meloxicam plasma concentration at Cmax ranges from about 2200 ng/ml to about 800 ng/mL, from about 2000 ng/ml to about 1000 ng·ml, or from about 1500 ng/ml to about 2000 ng/mL. In some embodiments, the meloxicam blood plasma concentration of Cmax of an individual post administration of the disclosed oral pharmaceutical composition is at least about 800 ng/mL, at least about 900 ng/ml, at least about 1,000 ng/mL, at least about 1100 ng/mL, at least 1,200 ng/mL, at least 1,300 ng/ml, at least 1,400 ng/mL, at least 1,500 ng/mL, at least 1,600 ng/ml, at least 1,700 ng/mL, at least 1,800 ng/mL, at least 1,900 ng/mL, or at least 2,000 ng/mL. Such Cmax values can be obtained after a single or multiple (e.g., 2, 3 or 4) administrations of the disclosed solid oral pharmaceutical composition.

In some embodiments, administration of the disclosed solid oral pharmaceutical composition to an individual suffering from pain in the disclosed methods provides a higher meloxicam Cmax in the individual than a meloxicam Cmax provided in an individual by MOBIC when administered in a same or similar fed or fasted condition.

In some embodiments, administration of the disclosed solid oral pharmaceutical composition to an individual in need thereof reaches and/or maintains a meloxicam blood plasma concentration, which ranges from about 2200 ng/ml to about 800 ng/mL, from about 2000 ng/ml to about 1000 ng·ml, or from about 1500 ng/ml to about 2000 ng/ml. Such a meloxicam blood plasma concentration can be referred to as the steady state or threshold meloxicam plasma concentration. In some embodiments, such a meloxicam blood plasma concentration is at least about 800 ng/ml, at least about 900 ng/ml, at least about 1,000 ng/mL, at least about 1100 ng/ml, at least 1,200 ng/mL, at least 1,300 ng/ml, at least 1,400 ng/mL, at least 1,500 ng/mL, at least 1,600 ng/mL, at least 1,700 ng/mL, at least 1,800 ng/mL, at least 1,900 ng/mL, or at least 2,000 ng/ml, after a single or multiple (e.g., 2, 3, or 4) administration(s) to an individual in need thereof. For example, in some embodiments, the meloxicam blood plasma concentration of an individual reaches at least about 1,000 ng/mL after administration of the solid oral pharmaceutical composition to the individual in need thereof. In another example, the meloxicam blood plasma concentration of an individual is maintained above about 800 ng/ml after the second administration of the oral solid pharmaceutical composition to the individual in need thereof.

The amount of time between multiple administration of the disclosed solid oral pharmaceutical composition can vary as well. For example, in some embodiments, the time between administration ranges from about 1 hour to about 24 hours, from about 2 hours to about 20 hours, from about 4 hours to about 16 hours, from about 6 hours to about 14 hours, or from about 8 hours to about 12 hours. In some embodiments, the time between administrations of the solid oral pharmaceutical composition disclosed herein is about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

In some embodiments, the disclosed solid oral pharmaceutical composition is administered to an individual in need thereof once during a 24 hour period. In some embodiments, the disclosed solid oral pharmaceutical compositions is administered more than one time during a 24 hour period such as two times, three times, or four times or more during a 24 hour period.

The duration of administration of the disclosed oral solid pharmaceutical composition can vary. In some embodiments, the disclosed solid oral pharmaceutical composition is administered to an individual in need thereof for more than 12 hours starting from the first administration of the composition. In some embodiments, the disclosed solid oral pharmaceutical compositions is administered for more than 24 hours, more than 28 hours, more than 72 hours, more than 4, 5, 6, 7, 8, 9, 10, 11, 12, 13, 14, 15, 16, 17, 18, 19, 20, 21, 22, 23, 24, 25, 26, 27, 28, 29, or more than 30 days. In some embodiments, the disclosed solid oral pharmaceutical composition is administered for any number of days or parts of a day equal to or less than 30 days.

In some embodiments, the disclosed solid oral pharmaceutical composition is administered to an individual in need thereof two times per day (i.e., 24 hours) for more than 1 day or for any number of days less than or equal to 30 days, i.e., for 30, 29, 28, 27, 26, 25, 24, 23, 22, 21 20, 19, 18, 17, 16, 15, 14, 13, 12, 11, 10, 9, 8, 7, 6, 5, 4, 3, or 2 days. In some such embodiments, the composition is administered two times per day (i.e., 24 hours), the administrations being about 12 hours apart from one another.

The present invention also provides drug containers containing a certain number of units to provide for dosing the pharmaceutical meloxicam composition to a patient as described herein. In some embodiments the container is a medicine container with a cap. In some embodiments the container contains sixty (60) 15 mg meloxicam composition units to provide for up to thirty days of administration when the 15 mg composition is given two times per day (24 hours). In some embodiments the container contains 30 (thirty) 15 mg meloxicam composition units to provide for up to fifteen (15) days of administration when the 15 mg composition administered two times per day (24 hours). In some embodiments the container is a blister pack. In some embodiments of the blister pack, the blister pack contains fourteen (14) 15 mg meloxicam composition units to provide for up to seven days of administration at two units per 24 hour period. In some embodiments of the blister pack, the blister pack contains 13, 12, 11, 10, 9, 8, 7, 6, 5, 4, 3, or two (2) 15 mg meloxicam composition units, each such blister pack containing enough units to provide for administration of the meloxicam composition for a day or up to 6.5 days, two times per day, each administration approximately every 12 hours.

In some embodiments of the methods for treating pain described herein, the meloxicam composition administered to the individual in need thereof provides meloxicam dosages ranging from 0.5 mg to 100 mg, in single or divided dosage units (for example, tablets or capsules). In one embodiment, 60 mg of meloxicam are administered to the individual in need thereof, preferably by administering four 15 mg meloxicam tablets or capsules of the novel meloxicam composition to the individual. In another embodiment, 45 mg of meloxicam is administered to the individual in need thereof, for example by administering three 15 mg meloxicam tablets or capsules of the composition described herein to the individual. In another embodiment, 30 mg of meloxicam are administered to the individual in need thereof, for example by administering two 15 mg meloxicam tablets or capsules having a composition as described herein to the individual. In another embodiment, 15 mg of meloxicam are administered to the individual in need thereof, for example by administering one 15 mg meloxicam tablet or capsule as described herein to the individual.

In some embodiments, the meloxicam solid oral dosage form is administered to the individual upon onset of pain or prior to onset of pain. In some embodiments, the meloxicam solid oral dosage form is administered on an as needed basis or at periodic time periods, for example at intervals ranging in length from 30 minutes to 24 hours, such as at 24-hour intervals, at twelve-hour intervals, at six-hour intervals, at four-hour intervals, at two-hour intervals, or at one-hour intervals.

In any of the above-mentioned embodiments, the individual can be in a fasted, semi-fasted, or fed state. In some embodiments, the solid oral pharmaceutical composition is administered in any of the above-mentioned embodiments to an individual without food or on an empty stomach, for example about one hour or more before or after eating, or one hour or more both before and after eating. In some embodiments, the pharmaceutical composition is administered to the individual about one or two hours or more before eating. In some embodiments, the pharmaceutical composition is administered about two hours or more after eating. In some embodiments, the pharmaceutical composition is administered about two hours or more before eating and about one or two hours or more after eating. In some embodiments, the solid oral pharmaceutical composition is administered in any of the above-mentioned embodiments to an individual without food or on an empty stomach about 1-12 hours before eating, about 1-10 hours before eating, about 1-8 hours, about 1-6 hours before eating, or about 1-4 hours before eating. In some embodiments, the solid oral pharmaceutical composition is administered in any of the above-mentioned embodiments to an individual without food or on an empty stomach about 4-16 hours after eating, about 6-14 hours before eating, about 8-14 hours, or about 10-12 hours after eating.

In any of the above-mentioned embodiments, the individual exhibits an opioid-sparing behavior after administration of the solid oral pharmaceutical composition. Such a behavior is indicative of requiring and/or needing lower amounts of an opioid analgesic being administered to such an individual and/or requiring a decrease in the frequency of an opioid analgesic being administered to such an individual (e.g., a human) compared to an individual suffering from the same pain but not having been administered a solid oral pharmaceutical composition as disclosed herein. Thus, in some embodiments, individuals can exhibit an opioid-sparing effect to not require or need administration of an opioid analgesic at all. As such, in some embodiments, the disclosed methods comprise no opioid analgesic being administrated to said individuals (e.g., no opioid analgesic administered orally, nasally, or transdermally to the individual). In any of these opioid-sparing embodiments, the opioid can be an opioid analgesic that is not administered as an IV infusion, but rather the opioid is an opioid analgesic administered as, for example an oral pill, an oral solution, a transdermal patch, or an intramuscular or subcutaneous injection. Alternatively, in some embodiments of the methods described herein, the opioid-sparing activity includes administration of an opioid analgesic by IV infusion, albeit with less opioid than would have been required to manage the individual's pain if the individual had not been administered the subject solid oral meloxicam composition.

In some embodiments, the disclosed methods do comprise administration of an opioid analgesic to said individual, e.g., after administration of said solid oral pharmaceutical composition. In such instances, the opioid analgesic is primarily administered to treat breakthrough pain but should not be limited thereto. In such embodiments, the individual is administered less opioid analgesic than the amount of opioid analgesic administered to an individual (e.g., a human) suffering from the same pain who did not receive the disclosed solid oral pharmaceutical composition. In some embodiments, the disclosed methods comprise that the individual is administered an opioid analgesic less frequently compared to an individual (e.g., a human) suffering from the same pain who did not receive the disclosed solid oral pharmaceutical composition (in other words, the frequency of administration of an opioid analgesic is reduced after administration of the solid oral pharmaceutical composition to an individual when compared to the frequency of opioid analgesic administration to an individual (e.g., a human) suffering from the same pain not having the disclosed solid oral pharmaceutical composition administered). As such, when an opioid analgesic is administered in the disclosed methods it is administered after administration of the disclosed solid oral pharmaceutical composition, e.g., not until about at least 0.5 hours, about at least 1 hour, about at least 1.5 hour, about at least 2 hours, about at least 2.5 hours, about at least 3 hours, about at least 3.5 hours, or about at least 4 hours after administration of the solid oral pharmaceutical composition.

Opioid analgesics are know to persons of ordinary skill in the art and the term "opioid analgesic," unless otherwise qualified, means any such known opioid analgesic. In any of the embodiments, the opioid analgesic may be selected from the group consisting of morphine, oxycodone, fentanyl, methadone, hydromorphone, codeine, tramadol, tapentadol, buprenorphine, alfentanil, and hydrocodone. In any of these embodiments, the opioid used with the oral pharmaceutical meloxicam composition can be administered by any means known for administering such drug, for example as an oral pill, an oral solution, a transdermal patch, an IV infusion or an intramuscular or subcutaneous injection.

In some embodiments, the opioid analgesic is administered to the individual as a rescue medication. In some embodiments, the individual experiences meaningful pain relief before administration of the opioid analgesic.

In some embodiments, the disclosed methods do comprise administration of a non-opioid analgesic to said individual, e.g., before, at the same time, or after administration of said solid oral pharmaceutical composition. For example, the non-opioid analgesic can be administered not until about at least 0.5 hour, about at least 1 hour, about at least 1.5 hours, about at least 2.5 hours, about at least 3 hours, about at least 3.5 hours, or about at least 4 hours after administration of the solid oral pharmaceutical composition. In some instances, the non-opioid analgesic is administered as a rescue medication to treat breakthrough pain. In any of the embodiments, the non-opioid may be administered orally, nasally, intravenously, or transdermally to said individual. In some embodiments, the non-opioid analgesic is selected from an anesthetic and/or an NSAID. Exemplary anesthetic and/or NSAIDS include, but are not limited to, acetaminophen, diclofenac, celecoxib, indomethacin, ketorolac, mefenamic acid, nabumetone, piroxicam, sulindac, naproxen, aspirin, ibuprofen, bupivacaine, gabapentin, glucosamine, duloxetine, pregabalin, lidocaine and/or ropivacaine.

In some embodiments, the non-opioid analgesic is administered to the individual as a rescue medication. In some embodiments, the individual experiences meaningful pain relief before administration of a non-opioid analgesic.

The duration of treatment for an individual in need thereof (i.e., suffering from pain) with the disclosed solid oral pharmaceutical composition can vary. In some embodiments, the disclosed methods treat pain for any number of days less than 30, less than 29, less than 28, less than 27, less than 26, less than 25, less than 24, less than 23, less than 22, less than 21, less than 20, less than 19, less than 18, less than 17, less than 16, less than 15, less than 14, less than 13, less than 12, less than 11, less than 10, less than 9, less than 8, less than 7, less than 6, less than 5, less than 4, less than 3, less than 2 days, or less than 1 day following an administration of the solid oral pharmaceutical composition to the individual in need thereof. For example, in some embodiments, the disclosed methods treat pain for 12 hours, 24 hours, 48 hours, 72 hours, 4 days, 5 days, 6 days, 7 days, 8 days, 9 days, 10 days, 11 days, 12 days, 13 days, 14 days, 15 days, 16 days, 17 days, 18 days, 19 days, 20 days, 1 days, 22 days, 23 days, 24 days, 25 days, 26 days, 27 days, 28 days, 29 days, or 30 days following an administration of the solid oral pharmaceutical composition to the individual in need thereof.

In some embodiments, a solid oral meloxicam dosage form used in the methods for treating pain described herein is a tablet, a capsule, a pill, a dragée, a sachet, or a granule powder.

Individuals in need receiving one or more administrations of the disclosed solid oral pharmaceutical composition exhibit a favorable safety profile. For instance, treatment with the disclosed solid oral pharmaceutical compositions proceeded without significant risk to the individual having a gastrointestinal bleeding adverse event (e.g., gastrointestinal hemorrhage, ulceration, and/or perforation) and/or cardiovascular event (e.g., myocardial infarction, unstable angina, stroke, transient ischemic attach, heart failure, or cardiac arrhythmia). The Examples below further describe the beneficial safety profile of the disclosed solid oral pharmaceutical compositions Exemplary methods based on the above-described embodiments may be any one of the following:

A method or treating pain in an individual in need thereof comprising orally administering to the individual a solid oral pharmaceutical composition comprising a therapeutically effective amount of meloxicam or a pharmaceutically acceptable salt thereof and one or more pharmaceutically acceptable excipients, wherein the administered composition provides meloxicam Tmax in the individual within about 5 hours or less, within about 4 hours or less, within about 3 hours or less, or within about one hour or less after administration.

Another method is directed towards treating pain in and individual in need thereof comprising orally administering to the individual a solid oral pharmaceutical composition comprising a therapeutically effective amount of meloxicam or a pharmaceutically acceptable salt thereof and one or more pharmaceutically acceptable excipients, wherein he administered composition provides a meloxicam Tmax in the individual about 5 hours earlier than a meloxicam Tmax provided in an individual by MOBIC when administered in a same or similar fed or fasted conditions.

Another method is directed towards treating pain in an individual in need thereof comprising orally administering to the individual a solid oral pharmaceutical composition comprising a therapeutically effective amount of meloxicam or a pharmaceutically acceptable salt thereof and one or more pharmaceutically acceptable excipients, wherein the time to the individual's first perceptible pain relief is about 2 hours or less, about 1.5 hours or less, or about 1 hour or less following the administration of the solid oral pharmaceutical composition, or any amount of time after the administration encompassed therewithin.

Another method is directed towards treating pain in an individual in need thereof comprising orally administering to the individual a solid oral pharmaceutical composition comprising a therapeutically effective amount of meloxicam or a pharmaceutically acceptable salt thereof and one or more pharmaceutically acceptable excipients, wherein the time to the individual's first the individual's first meaningful pain relief is about 5.5 hours or less, about 4 hours or less, about 3 hours or less, about 2.5 hours or less, or about 2 hours or less following the administration of the solid oral pharmaceutical composition, or any amount of time after the administration encompassed therewithin.

Another method is directed towards treating pain in an individual in need thereof comprising orally administering to the individual a solid oral pharmaceutical composition comprising a therapeutically effective amount of meloxicam or a pharmaceutically acceptable salt thereof and one or more pharmaceutically acceptable excipients, wherein the administered composition provides a meloxicam Tmax in the individual within about 5 hours or less after administration of the composition, and wherein no opioid medication is administered to the individual after administration of the composition.

Another method is directed towards treating pain in an individual in need thereof comprising orally administering to the individual a solid oral pharmaceutical composition comprising a therapeutically effective amount of meloxicam or a pharmaceutically acceptable salt thereof and one or more pharmaceutically acceptable excipients, wherein the administered composition provides a meloxicam Tmax in the individual within about 5 hours or less after administration of the composition, and wherein the individual exhibits opioid-sparing behavior after administration of the solid oral pharmaceutical composition Another method is directed towards treating pain in an individual in need thereof comprising orally administering to the individual a solid oral pharmaceutical composition comprising a therapeutically effective amount of meloxicam or a pharmaceutically acceptable salt thereof and one or more pharmaceutically acceptable excipients, wherein the administered composition provides a meloxicam Tmax in the individual within about 5 hours or less after administration of the composition, and wherein less opioid analgesic is administered to the individual than opioid analgesic administered to a human suffering from pain not administered the solid oral pharmaceutical composition.

Another method is directed towards treating pain in an individual in need thereof comprising orally administering to the individual a solid oral pharmaceutical composition comprising a therapeutically effective amount of meloxicam or a pharmaceutically acceptable salt thereof and one or more pharmaceutically acceptable excipients, wherein the administered composition provides a meloxicam Tmax in the individual within about 5 hours or less after administration of the composition, and wherein frequency of administration of an opioid analgesic after administration of the solid oral pharmaceutical composition to the individual is reduced compared to frequency of opioid analgesic administration to a human suffering from pain not administered the solid oral pharmaceutical composition The following embodiments further exemplify various features of the methods of managing pain using meloxicam disclosed herein:

1. This embodiment is directed to a method of treating pain within about four hours after onset of the pain in an individual in need thereof comprising orally administering a therapeutically effective amount of meloxicam to the individual, wherein the therapeutically effective amount of meloxicam so administered is in a solid oral dosage form comprising meloxicam or a pharmaceutically acceptable salt thereof and one or more pharmaceutically acceptable excipients.

2. This embodiment is directed to the method of treating pain of the first embodiment, wherein the pain is acute pain, post-surgical pain, procedural pain or any combination thereof.

3. This embodiment is directed to the method of treating pain of any of the preceding embodiments, wherein the pain comprises moderate to severe pain.

4. This embodiment is directed to the method of treating pain of any of the preceding embodiments, wherein the pain comprises bony pain.

5. This embodiment is directed to the method of treating pain of any of the preceding embodiments, wherein the pain comprises soft tissue pain.

6. This embodiment is directed to the method of treating pain of any of the preceding embodiments, wherein the pain is post-surgical pain following bunionectomy.

7. This embodiment is directed to the method of treating pain of any of the preceding embodiments, wherein the pain is post-surgical pain following herniorrhaphy.

8. This embodiment is directed to the method of treating pain of any of the preceding embodiments, wherein the first perceptible pain relief is provided to the individual within about thirty minutes, about 45 minutes, about one hour or less, about 1.5 hours, about two hours, about 2.5 hours, about three hours, or about 3.5 hours following administration of the solid oral dosage form.

9. This embodiment is directed to the method of treating pain of any of the preceding embodiments, wherein the first perceptible pain relief is provided to the individual within about thirty minutes, about 45 minutes, or within about one hour or less following administration of the solid oral dosage form.

10. This embodiment is directed to the method of treating pain of any of the preceding embodiments, wherein first perceptible pain relief is provided to the individual within about less than one hour or within about 55 minutes, about 50 minutes, about 45 minutes, or about 40 minutes following administration of the solid oral dosage form.

11. This embodiment is directed to the method of treating pain of any of the preceding embodiments, wherein meaningful pain is first provided to the individual within about 4 hours or less, about 3.5 hours, about 3 hours, about 2.5 hours, or about 2 hours following administration of the solid oral dosage form.

12. This embodiment is directed to the method of treating pain of any of the preceding embodiments, wherein the solid oral dosage form is administered, in single or divided doses, to the individual one time, two times, three times, or any other number of times.

13. This embodiment is directed to the method of treating pain of any of the preceding embodiments, wherein the solid oral dosage form is administered to the individual about once every twenty-four, twelve, eight, six, or four hours.

14. This embodiment is directed to the method of treating pain of any of the preceding embodiments, wherein the solid oral dosage form is administered to the individual once, twice, three times or four times per day.

15. This embodiment is directed to the method of treating pain of any of the preceding embodiments, wherein the solid oral dosage form is administered to the individual twice per day. 16. This embodiment is directed to the method of treating pain of any of the preceding embodiments, wherein each administration comprises single or divided doses of the solid oral dosage form.

17. This embodiment is directed to the method of treating pain of any of the preceding embodiments, wherein the solid oral dosage form is administered for no more than 30, 15, 14, 13, 12, 11, 10, 9, 8, 7, 6, 5, 4, 3 or 2 days or for no more than one day.

18. This embodiment is directed to the method of treating pain of any of the preceding embodiments, wherein the therapeutically effective amount of meloxicam in the solid oral dosage form is between about 0.5 to about 100 mg.

19. This embodiment is directed to the method of treating pain of any of the preceding embodiments, wherein the therapeutically effective amount of meloxicam in the solid oral dosage form is between about 5 to about 50 mg, about 1 to about 20 mg, about 1.25 to about 15 mg or about 7.5 to about 15 mg.

20. This embodiment is directed to the method of treating pain of any of the preceding embodiments, wherein the therapeutically effective amount of meloxicam in the solid oral dosage form is 1 mg, 1.25 mg, 2.5 mg, 5 mg, 7.5 mg, 10 mg, 12.5 mg or 15 mg.

21. This embodiment is directed to the method of treating pain of any of the preceding embodiments, wherein the solid oral dosage form comprises a solid dispersion of the meloxicam or the pharmaceutically acceptable meloxicam salt.

22. This embodiment is directed to the method of treating pain of any of the preceding embodiments, wherein the solid oral dosage form comprises an alkaline microenvironment comprising the meloxicam or the pharmaceutically acceptable meloxicam salt. In some embodiments, the alkaline surrounding comprises a solid dispersion of the meloxicam or pharmaceutically acceptable meloxicam salt. In some embodiments, the solid dispersion comprises a hydrophilic polymeric matrix. In some embodiments, the solid oral dosage form comprises drug granules or drug pellets comprising (a) the meloxicam or the pharmaceutically acceptable meloxicam salt, and (b) one or more alkalizing agents, one or more hydrophilic polymers, or any combination thereof.

23. This embodiment is directed to the method of treating pain of any of the preceding embodiments, wherein the alkaline microenvironment comprises granules and/or pellets.

24. This embodiment is directed to the method of treating pain of any of the preceding embodiments, wherein the solid oral dosage form comprises one or more pharmaceutically acceptable alkalizing agents, hydrophilic polymers, or a combination thereof.

25. This embodiment is directed to the method of treating pain of any of the preceding embodiments, wherein the meloxicam or pharmaceutically acceptable meloxicam salt is embedded in alkaline surroundings in the dosage form.

26. This embodiment is directed to the method of treating pain according to embodiment 25, wherein the alkaline surroundings comprise a solid dispersion of the meloxicam.

27. This embodiment is directed to the method of treating pain of any of the preceding embodiments, wherein the solid oral dosage form comprises granules and/or pellets comprising the meloxicam or the pharmaceutically acceptable meloxicam salt and one or more pharmaceutically acceptable excipients including an alkalizing agent or agents, a hydrophilic polymer or hydrophilic polymers, and any combination thereof.
28. This embodiment is directed to the method of treating pain of any of the preceding embodiments, wherein the solid oral dosage form is a capsule, a tablet, a sachet, or a granule powder.
29. This embodiment is directed to the method of treating pain of any of the preceding embodiments, wherein the individual is in a fasted state when administered the solid oral dosage form. In some embodiments of the method, the individual is administered the solid oral dosage form without food or on an empty stomach.
30. This embodiment is directed to the method of treating pain of any of the preceding embodiments, wherein the treatment is not significantly impacted by a fed or a fasted state in the individual. In some embodiments of the method, the individual may take the solid oral dosage form with food or without food.
31. This embodiment is directed to the method of treating pain of any of the preceding embodiments, wherein the solid oral dosage form is first administered to the individual approximately upon onset of perception of the pain.
32. This embodiment is directed to the method of treating pain of any of the preceding embodiments, wherein the solid oral dosage form is administered to the individual prior to surgery or procedure.
33. This embodiment is directed to the method of treating pain of any of the preceding embodiments, wherein the solid oral dosage form is administered to the individual after a surgery or procedure, prior to the onset of pain perception.
34. This embodiment is directed to the method of treating pain of any of the preceding embodiments, wherein the solid oral dosage form is first administered to the individual about one hour or less after a surgery or procedure.
35. This embodiment is directed to the method of treating pain of any of the preceding embodiments, wherein the solid oral dosage form is first administered to the individual about one-half hour or less after a surgery or procedure.
36. This embodiment is directed to the method of treating pain of any of the preceding embodiments, wherein the solid oral dosage form is first administered to the individual within about fifteen minutes after a surgery or procedure.
37. This embodiment is directed to the method of treating pain of any of the preceding embodiments without significant risk to the individual of a gastrointestinal bleeding adverse event.
38. This embodiment is directed to the method of treating pain of any of the preceding embodiments without significant risk to the individual of a gastrointestinal bleeding adverse event for 96 hours, 72 hours, 48 hours, or 24 hours after the first administration of the solid oral dosage form.
39. This embodiment is directed to the method of treating pain of any of the preceding embodiments without significant risk to the individual of a gastrointestinal bleeding adverse event for at least 10 days, at least 9 days, at least 8 days, at least 7 days, at least 6 days, at least 5 days, at least 4 days, at least 3 days, at least 2 days, or at least 1 day after the first administration of the solid oral dosage form.
40. This embodiment is directed to the method of treating pain of any of the preceding embodiments without significant risk to the individual of a gastrointestinal bleeding adverse event when the solid oral dosage form is administered to the individual for 10 days or any number of days less than 10, two times per day.
41. This embodiment is directed to the method of treating pain of any of the preceding embodiments without significant risk to the individual of a gastrointestinal bleeding adverse event when the solid oral dosage form is administered to the individual for 10 days or any number of days less than 10, about once every 12 hours.
42. This embodiment is directed to the method of treating pain of any of the preceding embodiments without significant risk to the individual of a gastrointestinal hemorrhage, ulceration, or perforation.
43. This embodiment is directed to the method of treating pain of any of the preceding embodiments without significant risk to the individual of a gastrointestinal hemorrhage, ulceration, or perforation for 96 hours, 72 hours, 48 hours, or 24 hours after the first administration of the solid oral dosage form.
44. This embodiment is directed to the method of treating pain of any of the preceding embodiments without significant risk to the individual of a gastrointestinal hemorrhage, ulceration, or perforation for 10 days or any number of days less than 10 after the first administration of the solid oral dosage form.
45. This embodiment is directed to the method of treating pain of any of the preceding embodiments without significant risk to the individual of a gastrointestinal hemorrhage, ulceration, or perforation when the solid oral dosage form is administered to the individual for 10 days or any number of days less than 10, two times per day.
46. This embodiment is directed to the method of treating pain of any of the preceding embodiments without significant risk to the individual of a gastrointestinal hemorrhage, ulceration, or perforation when the solid oral dosage form is administered to the individual for 10 days or any number of days less than 10, about once every 12 hours.
47. This embodiment is directed to the method of treating pain of any of the preceding embodiments without significant risk to the individual of a cardiovascular adverse event.
48. This embodiment is directed to the method of treating pain of any of the preceding embodiments without significant risk to the individual of a myocardial infarction, unstable angina, stroke, transient ischemic attack, heart failure, or cardiac arrhythmia.
49. This embodiment is directed to the method of treating pain of any of the preceding embodiments without significant risk to the individual of a cardiovascular adverse event for 96 hours, 72 hours, 48 hours, or 24 hours after the first administration of the solid oral dosage form.
50. This embodiment is directed to the method of treating pain of any of the preceding embodiments without significant risk to the individual of a cardiovascular adverse event for 10 days or any number of days less than 10 after the first administration of the solid oral dosage form.

51. This embodiment is directed to the method of treating pain of any of the preceding embodiments without significant risk to the individual of a cardiovascular adverse event when the solid oral dosage form is administered to the individual for 10 days or any number of days less than 10, two times per day.
52. This embodiment is directed to the method of treating pain of any of the preceding embodiments without significant risk to the individual of a cardiovascular bleeding adverse event when the solid oral dosage form is administered to the individual for 10 days or any number of days less than 10, about once every 12 hours.
53. This embodiment is directed to the method of treating pain of any of the preceding embodiments, wherein the therapeutically amount of meloxicam in the solid oral dosage form administered, in single or divided doses, is 15 mg.
54. This embodiment is directed to a method of treating acute pain, post-surgical pain, and/or procedural pain in an individual in need thereof comprising orally administering a therapeutically effective amount of meloxicam to the individual, wherein the therapeutically effective amount of meloxicam so administered is in a solid oral dosage form comprising meloxicam or a pharmaceutically acceptable salt thereof and one or more pharmaceutically acceptable excipients, and wherein the method does not comprise administering an opioid drug to the individual to treat the pain.
55. This embodiment is directed to the method of treating pain of embodiment 54, wherein the pain is treated within about four hours of onset of the pain.
56. This embodiment is directed to the method of treating pain of embodiment 54 or 55, wherein the pain comprises moderate to severe pain.
57. This embodiment is directed to the method of treating pain of any one of embodiments 54-56, wherein the pain comprises bony pain.
58. This embodiment is directed to the method of treating pain of any one of embodiments 54-57, wherein the pain comprises soft tissue pain.
59. This embodiment is directed to the method of treating pain of any one of embodiments 54-58, wherein the pain is post-surgical pain following bunionectomy.
60. This embodiment is directed to the method of treating pain of any one of embodiments 54-58, wherein the pain is post-surgical pain following herniorrhaphy.
61. This embodiment is directed to the method of treating pain of any one of embodiments 54-60, wherein the therapeutically effective amount of meloxicam in the solid oral dosage form is between about 0.5 to about 100 mg.
62. This embodiment is directed to the method of treating pain of any one of embodiments 54-61, wherein the therapeutically effective amount of meloxicam in the solid oral dosage form is between about 5 to about 50 mg, about 1 to about 20 mg, about 1.25 to about 15 mg or about 7.5 to about 15 mg.
63. This embodiment is directed to the method of treating pain of any one of embodiments 54-61, wherein the therapeutically effective amount of meloxicam in the solid oral dosage form is 1 mg, 1.25 mg, 2.5 mg, 5 mg, 7.5 mg, 10 mg, 12.5 mg or 15 mg.
64. This embodiment is directed to the method of treating pain of any one of embodiments 54-63, wherein the solid oral dosage form comprises a solid dispersion of the meloxicam or the pharmaceutically acceptable meloxicam salt.
65. This embodiment is directed to the method of treating pain of any one of embodiments 54-64, wherein the solid oral dosage form comprises an alkaline microenvironment comprising the meloxicam or the pharmaceutically acceptable meloxicam salt.
66. This embodiment is directed to the method of treating pain of embodiment 65, wherein the alkaline microenvironment comprises granules and/or pellets.
67. This embodiment is directed to the method of treating pain of any one of embodiments 54-66, wherein the solid oral dosage form comprises one or more pharmaceutically acceptable alkalizing agents, hydrophilic polymers, or a combination thereof.
68. This embodiment is directed to the method of treating pain of any one of embodiments 42-67, wherein the meloxicam or pharmaceutically acceptable meloxicam salt is embedded in an alkaline surrounding in the solid oral dosage form. In some embodiments, the alkaline surrounding comprises a solid dispersion of the meloxicam or pharmaceutically acceptable meloxicam salt. In some embodiments, the solid dispersion comprises a hydrophilic polymeric matrix. In some embodiments, the solid oral dosage form comprises drug granules or drug pellets comprising (a) the meloxicam or the pharmaceutically acceptable meloxicam salt, and (b) one or more alkalizing agents, one or more hydrophilic polymers, or any combination thereof.
69. This embodiment is directed to the method of treating pain of any one of embodiments 54-68, wherein the solid oral dosage form comprises granules and/or pellets comprising the meloxicam or the pharmaceutically acceptable meloxicam salt and one or more pharmaceutically acceptable excipients including an alkalizing agent or agents, a hydrophilic polymer or hydrophilic polymers, and any combination thereof.
70. This embodiment is directed to the method of treating pain of any one of embodiments 54-69, wherein the solid oral dosage form is a capsule, a tablet, a sachet, or a granule powder.
71. This embodiment is directed to the method of treating pain of any one of embodiments 54-70, wherein the individual is in a fasted state when administered the solid oral dosage form. In some embodiments of the method, the individual is administered the solid oral dosage form without food or on an empty stomach.
72. This embodiment is directed to the method of treating pain of any one of embodiments 54-71, wherein the treatment is not significantly impacted by a fed or a fasted state in the individual. In some embodiments of the method, the individual may take the solid oral dosage form with food or without food.
73. This embodiment is directed to the method of treating pain of any one of embodiments 54-72, wherein the solid oral dosage form is first administered to the individual approximately upon onset of perception of the pain.
74. This embodiment is directed to the method of treating pain of any one of embodiments 54-72, wherein the solid oral dosage form is administered to the individual prior to surgery or procedure.
75. This embodiment is directed to the method of treating pain of any one of embodiments 54-72, wherein the solid oral dosage form is administered to the individual after a surgery or procedure, prior to the onset of pain perception.
76. This embodiment is directed to the method of treating pain of any one of embodiments 54-72, wherein the solid oral dosage form is first administered to the individual about one hour or less after a surgery or procedure.

77. This embodiment is directed to the method of treating pain of any one of embodiments 54-72, wherein the solid oral dosage form is first administered to the individual about one-half hour or less after a surgery or procedure.

78. This embodiment is directed to the method of treating pain of any one of embodiments 54-72, wherein the solid oral dosage form is first administered to the individual within about fifteen minutes after a surgery or procedure.

79. This embodiment is directed to the method of treating pain of any one of embodiments 54-78, without significant risk to the individual of a gastrointestinal bleeding adverse event.

80. This embodiment is directed to the method of treating pain of any one of embodiments 54-79 without significant risk to the individual of a gastrointestinal bleeding adverse event for 96 hours, 72 hours, 48 hours, or 24 hours after the first administration of the solid oral dosage form.

81. This embodiment is directed to the method of treating pain of any one of embodiments 54-80 without significant risk to the individual of a gastrointestinal bleeding adverse event for 10 days or any number of days less than 10 after the first administration of the solid oral dosage form.

82. This embodiment is directed to the method of treating pain of any one of embodiments 54-81 without significant risk to the individual of a gastrointestinal bleeding adverse event when the solid oral dosage form is administered to the individual for days or any number of days less than 10, two times per day.

83. This embodiment is directed to the method of treating pain of any one of embodiments 54-82 without significant risk to the individual of a gastrointestinal bleeding adverse event when the solid oral dosage form is administered to the individual for 10 days or any number of days less than 10, about once every 12 hours.

84. This embodiment is directed to the method of treating pain of any one of embodiments 54-83 without significant risk to the individual of a gastrointestinal hemorrhage, ulceration, or perforation.

85. This embodiment is directed to the method of treating pain of any one of embodiments 54-85 without significant risk to the individual of a gastrointestinal hemorrhage, ulceration, or perforation for 96 hours, 72 hours, 48 hours, or 24 hours after the first administration of the solid oral dosage form.

86. This embodiment is directed to the method of treating pain of any one of embodiments 54-85 without significant risk to the individual of a gastrointestinal hemorrhage, ulceration, or perforation for 10 days or any number of days after 10 after the first administration of the solid oral dosage form.

87. This embodiment is directed to the method of treating pain of any one of embodiments 54-86 without significant risk to the individual of a gastrointestinal hemorrhage, ulceration, or perforation when the solid oral dosage form is administered to the individual for 10 days or any number of days less than 10, two times per day.

88. This embodiment is directed to the method of treating pain of any one of embodiments 54-87 without significant risk to the individual of a gastrointestinal hemorrhage, ulceration, or perforation when the solid oral dosage form is administered to the individual for 10 days or any number of days less than 10, about once every 12 hours.

89. This embodiment is directed to the method of treating pain of any one of embodiments 54-88 without significant risk to the individual of a cardiovascular adverse event.

90. This embodiment is directed to the method of treating pain of any one of embodiments 54-89 without significant risk to the individual of a myocardial infarction, unstable angina, stroke, transient ischemic attack, heart failure, or cardiac arrhythmia.

91. This embodiment is directed to the method of treating pain of any one of embodiments 54-90 without significant risk to the individual of a cardiovascular adverse event for 96 hours, 72 hours, 48 hours, or 24 hours after the first administration of the solid oral dosage form.

92. This embodiment is directed to the method of treating pain of any one of embodiments 54-91 without significant risk to the individual of a cardiovascular adverse event for 10 days or any number of days less than 10 after the first administration of the solid oral dosage form.

93. This embodiment is directed to the method of treating pain of any one of embodiments 54-92 without significant risk to the individual of a cardiovascular adverse event when the solid oral dosage form is administered to the individual for 7 days, two times per day.

94. This embodiment is directed to the method of treating pain of any one of embodiments 54-93 without significant risk to the individual of a cardiovascular bleeding adverse event when the solid oral dosage form is administered to the individual for 10 days or any number of days less than 10, about once every 12 hours.

95. This embodiment is directed to the method of treating pain of any one of embodiments 54-94, wherein the therapeutically amount of meloxicam in the solid oral dosage form administered, in single or divided doses, is 15 mg.

EXAMPLES

List of Abbreviations and Definitions of Terms

| Abbreviation | Definition |
|---|---|
| ACE | Angiotensin converting enzyme |
| ACLS | Advanced Cardiac Life Support |
| ADaM | Analysis Data Model |
| ADHD | Attention-deficit/hyperactivity disorder |
| AE | Adverse event |
| AESI | AE of special interest |
| ALLOCF | all values censored after rescue medication use |
| ALT | Alanine aminotransferase |
| ANCOVA | Analysis of covariance |
| ANOVA | Analysis of variance |
| APAP | Acetaminophen |
| AST | Aspartate aminotransferase |
| ATC | Anatomical Therapeutic Chemical |
| AUC | Area under the curve |
| $AUC_{0-2}$ | AUC from time 0 to 2 hours after dosing |
| $AUC_{0-4}$ | AUC from time 0 to 4 hours after dosing |
| $AUC_{0-8}$ | AUC from time 0 to 8 hours after dosing |
| $AUC_{0-12}$ | AUC from time 0 to 12 hours after dosing |
| $AUC_{0-24}$ | AUC from time 0 to 24 hours after dosing |
| $AUC_{12-24}$ | AUC from time 12 to 24 hours after dosing |
| $AUC_{0-48}$ | AUC from time 0 to 48 hours after dosing |
| $AUC_{Inf}$ | AUC extrapolated to infinity |

List of Abbreviations and Definitions of Terms

| Abbreviation | Definition |
| --- | --- |
| AUCt | AUC from time 0 after dosing until last measurable concentration above the limit of quantitation of the assay |
| ATC | Anatomical Therapeutic Chemical |
| BCS | Biopharmaceutics classification system |
| BDR | Blinded data review |
| BID | Twice daily |
| BILI | Bilirubin |
| BLQ | Below lower limit of quantification |
| BMI | Body mass index |
| BP | Blood pressure |
| bpm | Beats per minute |
| BUN | Blood urea nitrogen |
| CDC | Centers for Disease Control and Prevention |
| CI | Confidence interval |
| Cm | Centimeter |
| $C_{max}$ | Maximum plasma concentration |
| $CO_2$ | Carbon dioxide |
| COVID-19 | Coronavirus disease 2019 |
| CRF | Case report form |
| CRO | Contact research organization |
| CT | Computerized tomography |
| CV | Coefficient of variance |
| CYP | Cytochrome P450 |
| CYP2C9 | CYP family 2 subfamily C member 9 |
| $E_{max}$ | Term referring to the asymptotic maximum dose effect (model) |
| dL | Deciliter |
| DNA | Deoxyribonucleic acid |
| ECG | Electrocardiogram |
| eCRF | Electronic case report form |
| EDC | Electronic data capture |
| eGFR | Estimated glomerular filtration rate |
| $E_{max}$ | Maximum effect; term referring to the asymptotic maximum dose effect (model) |
| EOS | End of Study |
| ER | Emergency room |
| E-R | Exposure-response |
| ET | Early Termination |
| FAS | Full Analysis Set |
| FDA | Food and Drug Administration |
| FSH | Follicle stimulating hormone |
| g | Gram |
| GCP | Good Clinical Practice |
| GI | Gastrointestinal |
| HCG | Human chorionic gonadotropin |
| HIV | Human immunodeficiency virus |
| ICF | Informed consent form |
| ICH | International Council for Harmonization of Technical Requirements for Pharmaceuticals for Human Use |
| ID | Identification |
| IMMPACT | Initiative on Methods, Measurement, and Pain Assessment in Clinical Trials |
| IP | Investigational product |
| IR | Immediate release |
| IRB | Institutional Review Board |
| IU | International units |
| IV | Intravenous |
| IVRS/IWRS | Interactive Voice Response System/Interactive Web Response System |
| ITT | Intent-to-treat |
| Ka | First order absorption rate constant |
| kg | Kilogram |
| LLE | Lower limb extremity |
| LOCF | Last observation carried forward |
| L | Liter |
| LS | Least squares |
| m | Meter |
| MAR | Missing at random |
| MCMC | Markov Chain Monte Carlo |
| MECC-SA | Meloxicam (Co-crystal formulation of meloxicam:salicyclic acid) |
| MedDRA | Medical Dictionary for Regulatory Activities |
| mFAS | Modified Full Analysis Set |
| mg | Milligram |
| MI | Multiple imputation |

List of Abbreviations and Definitions of Terms

| Abbreviation | Definition |
| --- | --- |
| mITT | Modified ITT |
| mL | Milliliter |
| mmHg | Millimeter of mercury |
| mmol | Millimolar |
| MMRM | Mixed model for repeated measures |
| MPADSS | Modified Post-anesthetic Discharge Scoring System |
| MRI | Magnetic resonance imaging |
| ng | Nanogram |
| NR | Normal range |
| NRS | Numeric Rating Scale |
| NRS-A | NRS with activity |
| NRS-R | NRS at rest |
| NSAID | Non-steroidal anti-inflammatory drug |
| NYHA | New York Heart Association |
| OBAS | Overall Benefit of Analgesic Score |
| ORAE | Opioid-related AE |
| PGA | Patient's Global Assessment |
| PI | Principal Investigator |
| PID | Pain intensity difference |
| PK | Pharmacokinetic(s) |
| Pop PK | Population PK |
| PP | Per-protocol |
| PROC MI | Multiple imputation procedure |
| PROSPECT | PROcedure SPECific Postoperative Pain ManagemenT |
| PT | Preferred term |
| q2 h | Once every 2 hours |
| q6 h | Once every 6 hours |
| q12 h | Once every 12 hours |
| Q1 | Quartile for 25th percentile, representing the time beyond which 25% of the participants had the endpoint of interest |
| QD | Once daily |
| QID | 4 times daily |
| QoL | Quality of life |
| QTc | QT corrected for heart rate |
| QTcF | QTc using Fridericia's method |
| RA | Rheumatoid arthritis |
| RBC | Red blood cell |
| RNA | Ribonucleic acid |
| RR | Reference range |
| SAE | Serious AE |
| SAP | Statistical Analysis Plan |
| SAS | Statistical Analysis System |
| SD | Standard deviation |
| SDTM | Study Data Tabulation Model |
| SE | Standard error |
| SES | Standardized effect size |
| SOC | System organ class |
| SOP | Standard operating procedure |
| SPID | Summed pain intensity difference (PID) |
| $SPID_{0-2}$ | SPID over 0-2 hours |
| $SPID_{0-4}$ | SPID over 0-4 hours |
| $SPID_{0-8}$ | SPID over 0-8 hours |
| $SPID_{0-12}$ | SPID over 0-12 hours |
| $SPID_{12-24}$ | SPID over 12-24 hours |
| $SPID_{0-24}$ | SPID over 0-24 hours |
| $SPID_{0-48}$ | SPID over 0-48 hours |
| $SPO_2$ | Peripheral oxygen saturation |
| SNRI | Serotonin-norepinephrine reuptake inhibitor |
| SRI | Serotonin-reuptake inhibitor |
| SSRI | Selective Serotonin Reuptake inhibitor |
| $t_{1/2}$ | Half-life |
| TEAE | Treatment-emergent AE |
| TIA | Transient ischemic attack |
| $T_{max}$ | Time of maximum concentration |
| TSFD | Time-since-first dose |
| U | Units |
| ULN | Upper limit of normal |
| US | United States |
| WBC | White blood cell |
| WHO | World Health Organization |
| WHO-DD | WHO Drug Dictionary |
| WLOCF | Windowed last observation carried forward |
| W2LOCF | 2-Hour Windowed last observation carried forward |
| W4LOCF | 4-Hour Windowed last observation carried forward |
| W6LOCF | 6-Hour Windowed last observation carried forward |

-continued

| List of Abbreviations and Definitions of Terms | |
|---|---|
| Abbreviation | Definition |
| W8LOCF | 8-Hour Windowed last observation carried forward |
| WoCBP | Women of child-bearing potential |

Example I: Meloxicam Compositions

The following compositions are examples of meloxicam solid oral dosage forms that can be used in the methods of the invention described in this patent application.

TABLE 1

Composition of Meloxicam tablets 15 mg

| | Ingredients<br>Alkalizer solution 1 | Ex. 1<br>mg/tab | Ex. 2<br>mg/tab | Ex. 3<br>mg/tab | Ex. 4<br>mg/tab | Ex. 5<br>mg/tab | Ex. 6<br>mg/tab | Ex. 7<br>mg/tab |
|---|---|---|---|---|---|---|---|---|
| 1 | Sodium bicarbonate (Part 1) | 50.000 | 50.000 | 50.000 | 50.000 | 50.000 | 50.000 | 10.000 |
| 2 | Hypromellose E3LV (Part 1) | 5.000 | 5.000 | 5.000 | 5.000 | 5.000 | 5.000 | 1.000 |
| 3 | Purified water | q.s | q.s | q.s | q.s | q.s | q.s | q.s |
| | Dry mix | | | | | | | |
| 4 | Microcrystalline cellulose PH101 | 270.00 | 220.000 | 220.000 | 220.000 | 220.00 | 220.000 | 220.000 |
| 5 | Crospovidone (Polyplasdone XL 10) | 30.000 | 30.000 | 30.000 | 30.000 | 30.000 | 30.000 | 30.000 |
| 6 | Colloidal Silicon dioxide (Aerosil 200) | 25.000 | 15.000 | 15.000 | 15.000 | 15.000 | 15.000 | 15.000 |
| 7 | Sodium bicarbonate (Part 2) | 130.000 | 70.000 | 70.000 | 70.000 | 70.000 | 70.000 | 10.000 |
| | Drug-Binder solution | | | | | | | |
| 8 | Meloxicam API | 15.000 | 15.000 | 15.000 | 15.000 | 15.000 | 15.000 | 15.000 |
| 9 | Sodium bicarbonate (Part 3) | 60.000 | 60.000 | 60.000 | 60.000 | 60.000 | 60.000 | 60.000 |
| 10 | Copovidone (Plasdone S 630) | 105.000 | 95.000 | 95.000 | 95.000 | 95.000 | 95.000 | 95.000 |
| 11 | Purified water | q.s | q.s | q.s | q.s | q.s | q.s | q.s |
| 12 | Isopropyl alcohol | q.s | q.s | q.s | q.s | q.s | q.s | q.s |
| | Alkalizer solution 2 | | | | | | | |
| 13 | Sodium bicarbonate (Part 4) | 150.000 | 150.000 | 150.000 | 120.000 | 30.000 | 120.000 | 20.000 |
| 14 | Hypromellose E3LV (Part 2) | 15.000 | 15.000 | 15.000 | 12.000 | 3.000 | 12.000 | 2.000 |
| 15 | Purified water | q.s | q.s | q.s | q.s | q.s | q.s | q.s |
| | Extragranular | | | | | | | |
| 16 | Crospovidone (Polyplasdone XL ) | 110.000 | 205.00 | 107.000 | 100.000 | 109.000 | 100.000 | 104.000 |
| 17 | Sodium carbonate | — | 50.00 | — | — | — | — | — |
| 18 | Colloidal silicon dioxide (Syloid 244FP) | 50.000 | 40.00 | 10.000 | 10.000 | 10.000 | 10.000 | 10.000 |
| 20 | Meglumine | — | — | — | — | — | — | 50.00 |
| 21 | Magnesium stearate | 10.000 | 10.00 | 8.000 | 8.000 | 8.000 | 8.000 | 8.000 |
| | Core Tablet Weight | 1025.00 | 1030.00 | 850.000 | 810.000 | 720.00 | 810.00 | 650.000 |
| 22 | opadry yellow 03F82657 | 30.750 | — | — | 20.250 | — | — | — |
| 23 | Isopropyl alcohol | q.s | — | — | q.s | — | — | — |
| 24 | P. water | q.s | — | — | q.s | — | — | — |
| | Coated tablet weight | 1055.75 | — | — | 830.25 | — | — | — |

*Varying concentration of alkalizing agents such as Sodium bicarbonate, Sodium carbonate and meglumine, were evaluated.

**Total sodium bicarbonate quantity per tablet varied from 100 mg to 400 mg and observed dissolution was found to be very rapid.

Brief Manufacturing Process:

1. Alkalizer-1 solution was prepared by dissolving Sodium bicarbonate (part 1) and hypromellose E3LV (part 1) in purified water.
2. Microcrystalline cellulose PH101, Crospovidone, colloidal silicon dioxide and sodium bicarbonate were sifted together and granulated with alkalizer-1 solution in first step to obtain alkalizer based granules.
3. Sodium bicarbonate (part 3) and Copovidone were dissolved in purified water and Meloxicam was added to this solution to form dispersion. Isopropyl alcohol is added in the dispersion with stirring to obtained meloxicam solution.
4. Alkalized granules were further granulated using meloxicam suspension of third step in fluid bed processer.
5. Alkalizer solution-2 was prepared by dissolving the Sodium bicarbonate (part 4) and hypromellose E3LV (part 2) in purified water.
6. The drug granules were further granulated using alkalizer-2 solution of fifth step to obtain drug granules.

The Extragranular

7. Crospovidone (Polyplasdone XL) and Colloidal silicon dioxide (Syloid 244FP) were sifted through suitable mesh and blended with drug granules in blender. The blend is lubricated with magnesium stearate in blender.
8. The lubricated blend was compressed using suitable tooling on rotary compression machine. The core tablets were finally coated using hydro-alcoholic dispersion of opadry in automated coating pan.

TABLE 2

Composition of Meloxicam tablets 15 mg-MUPS formulation

| | Ingredients | Ex. 7<br>mg/tab |
|---|---|---|
| | Alkalizer solution 1 | |
| 1 | Sugar Sphere (60/80) | 100.00 |
| 2 | Hypromellose E5LV (Part 1) | 20.00 |
| 3 | Sodium Bicarbonate (Part 1) | 100.00 |
| 4 | Purified water | q.s. |
| | Drug-Binder solution | |
| 5 | Meloxicam API | 15.000 |
| 6 | Sodium bicarbonate (Part 2) | 60.000 |
| 7 | Copovidone (Plasdone S 630) | 95.000 |

TABLE 2-continued

| Composition of Meloxicam tablets 15 mg-MUPS formulation | | |
|---|---|---|
| | Ingredients | Ex. 7 mg/tab |
| 8 | Purified water | q.s |
| 9 | Isopropyl alcohol | q.s |
| | Alkalizer solution 2 | |
| 10 | Sodium Bicarbonate (Part 3) | 170.000 |
| 11 | Hypromellose ESLV (Part 2) | 40.000 |
| 12 | Purified water | q.s |
| | Extragranular | |
| 13 | Crospovidone (Polyplasdone XL) | 20.000 |
| 14 | Microcrystalline Cellulose PH 102 (Avicel PH 102) | 365.000 |
| 15 | Magnesium stearate | 10.000 |
| | Core Tablet Weight | 995.00 |
| 16 | Opadry White 03F58750 | 25.000 |
| 17 | P. water | q.s |
| | Coated tablet weight | 1020.00 |

*Alkalizing agent and drug binder solution sprayed on sugar beads. Order of addition of alkalizing agent, drug binder solution and again alkalizing agent was kept same.

Brief Manufacturing Process:

1. Alkalizer 1 solution is prepared by dissolving Sodium bicarbonate (part 1) and hypromellose E5LV (part 1) in purified water.
2. Sugar sphere (60/80) was coated with Alkalizer solution-1 of first step to obtained alkalized sugar sphere. 10
3. Sodium bicarbonate (part 2) and Copovidone were dissolved in purified water and Meloxicam was added to this solution to form dispersion. Isopropyl alcohol is added in the dispersion with stirring to obtained meloxicam solution.
4. Alkalized sugar sphere were further coated using meloxicam solution of third step in fluid bed processer.
5. Alkalizer solution 2 was prepared by dissolving the Sodium bicarbonate (part 3) and hypromellose E5LV (part 2) in purified water. The drug loaded pellets were further coated using alkalizer 2 solution to obtain drug pellets.

The Extragranular

6. Crospovidone (Polyplasdone XL), Microcrystalline cellulose PH 102 (Avicel PH 102) and Colloidal silicon dioxide (Syloid 244FP) were sifted through suitable mesh and blended with drug loaded pellets in blender.
7. The blend is lubricated with magnesium stearate in blender.
8. The lubricated blend was compressed using suitable tooling on a rotary compression machine.
9. The core tablets were finally coated using hydro-alcoholic dispersion of Opadry in automated coating pan.

Meloxicam 15 mg Tablet—MR-107A-02

Composition 8 and Ex. 4 of Table 1 are each sometimes referred to herein as MR-107A-02. Composition 8 uses low peroxide (ultra grade) crospovidone and copovidone. Example 4 of Table 1 uses standard grade crospovidone and copovidone.

Fifteen mg meloxicam tablets of the present invention with the following composition can be made by the process indicated in Table 3:

TABLE 3

| Unit Composition for Meloxicam Tablets 15 mg (Composition 8) | | | |
|---|---|---|---|
| Sr. No | Ingredients | mg/tablet | % w/w |
| | Alkalizer solution 1 | | |
| 1. | Sodium bicarbonate USP (Part 1) | 50.000 | 6.17 |
| 2. | Hypromellose USP (Methocel E3 premium LV) (Part 1) | 5.000 | 0.62 |
| 3. | Purified water | q.s | — |
| | Dry mix | | |
| 4. | Microcrystalline cellulose NF (Avicel PH 101) | 220.000 | 27.16 |
| 5. | Colloidal silicon dioxide NF (Aerosil 200 pharma) | 15.000 | 1.85 |
| 6. | Crospovidone NF (Polyplasdone Ultra 10) | 30.000 | 3.70 |
| 7. | Sodium bicarbonate USP (Part 2) | 70.000 | 8.64 |
| | Drug binder solution | | |
| 8. | Meloxicam USP | 15.000 | 1.85 |
| 9. | Copovidone NF (Plasdone S 630 Ultra) | 95.000 | 11.73 |
| 10. | Sodium bicarbonate USP (Part 3) | 60.000 | 7.41 |
| 11. | Iso propyl alcohol | q.s | — |
| 12. | Purified water | q.s | — |
| | Alkalizer solution 2 | | |
| 13. | Sodium bicarbonate USP (Part 1) | 120.000 | 14.81 |
| 14. | Hypromellose USP (Methocel E3 premium LV) (Part 2) | 12.000 | 1.48 |
| 15. | Purified water | q.s | — |
| | Extra granular | | |
| 16. | Silicon dioxide (Syloid 244 FP) | 10.000 | 1.23 |
| 17. | Crospovidone NF (Polyplasdone Ultra) | 100.000 | 12.35 |
| 18. | Magnesium stearate NF (Ligamed MF-2-K) | 8.000 | 0.99 |
| | Core tablets weight (mg) | 810.000 | 100 |
| | Film coating | | |
| 19. | Opadry yellow 03F82657 | 20.250 | — |
| 20. | Iso propyl alcohol | q.s | — |
| 21. | Purified water | q.s | — |
| | Coated tablets weight (mg) | 830.250 | — |

Particle Size Distribution Specification of Meloxicam API:

D (0.1): Not More than 2.0 µm
D (0.5): Not more than 5.0 µm
D (0.9): Between 2.0 µm and 10 µm Brief Manufacturing Procedure for Composition 8:

1. Dissolve sodium bicarbonate (Part 1) in purified water under stirring to get clear solution.
2. Add hypromellose (Part 1) in step 1 under stirring to get clear solution.
3. Co-sift microcrystalline cellulose, sodium bicarbonate (Part 2), Crospovidone and colloidal silicon dioxide through suitable sieve.
4. Load ingredients of step 3 in fluid bed granulator.
5. Granulate material of step 4 with step 2 alkalizer solution 1 in fluid bed processor.
6. Dissolve sodium bicarbonate (Part 3) in purified water under stirring to get clear solution.
7. Add copovidone in step 6 under stirring to get clear solution.
8. Add meloxicam in step 7 under stirring to get uniform dispersion.
9. Add IPA in step 8 under stirring to get clear solution.
10. Continue granulation process of step 5 by using step 9 drug binder solution.
11. Dissolve sodium bicarbonate (Part 4) in purified water under stirring to get clear solution.
12. Add hypromellose (part 2) in step 11 under stirring to get clear solution.

13. Continue granulation process of step 10 by using step 12 alkalizer solution 2.
14. Dry the material of step 13 in fluid bed processor.
15. Sift dried granules of step 14 through suitable sieve.
16. Co-sift crospovidone and silicon dioxide through suitable sieve.
17. Sift magnesium stearate was sifted through suitable sieve.
18. Add granules of step 15 and material of step 16 into the blender and blend for suitable time.
19. Add Step 17 into step 18 and blend suitable time.
20. Compress lubricated blend of step 19 using compression machine with suitable tooling.
21. Disperse opadry yellow 03F82657 in purified water and isopropyl alcohol under stirring.
22. Coat the core tablets of step 20 by using coating dispersion of step 21.

Example II. Post-Operative Dental Pain, Phase 2B Study

A Phase 2b study investigated the efficacy and safety of three different dose regimens (1.25 mg BID, 5 mg BID, and 15 mg BID) of MR-107A-02. The MR-107A-02 formulation of meloxicam included within the formulation 300 mg of bicarbonate for the 15 mg strength, 100 mg of bicarbonate for the 5 mg strength, and 25 mg of bicarbonate for the 1.25 mg strength to increase the rate of absorption of meloxicam by increasing its solubility and dissolution.

Rescue medication of immediate-release hydrocodone/acetaminophen (5/325 mg) was allowed to treat breakthrough pain. Subjects were encouraged to refrain from rescue medication until at least 1.5-hours post dose. A dose of rescue medication was allowed as needed up to once every 2 hours. A maximum of six tablets (equivalent to 30 mg hydrocodone and 1950 mg acetaminophen) were allowed; if a subject required greater than this, the subject was to be withdrawn from the study.

Table 4 shows rescue medication for each of the three dosage strengths of study drug and for placebo.

TABLE 4

Summary of Subjects Using Rescue Medication During Hours 0-24 Modified Intent-to-treat Analysis Set

| Response Statistic | MELO-TFZ 1.25 mg BID (N = 28) | MELO-TFZ 5 mg BID (N = 28) | MELO-TFZ 15 mg BID (N = 27) | Placebo (N = 27) |
|---|---|---|---|---|
| Rescue Medication Used within 24 h | | | | |
| Yes | 12 (42.9) | 16 (57.1) | 8 (29.6) | 20 (74.1) |
| No | 16 (57.1) | 12 (42.9) | 19 (70.4) | 7 (25.9) |
| Diff. vs PBO | −31.2% | −16.9% | −44.4% | |
| (95% CI) | (−55.9%, −6.5%) | (−41.6%, 7.8%) | (−68.3%, −20.6%) | |
| P-value vs PBO | 0.019 | 0.187 | 0.001 | |

Note:
Difference in proportions estimates, confidence intervals and p-values are based on the difference in proportions Z test (equivalent to the Pearson's Chi Squared).

The three study drug dose regimens evaluated in the Phase 2b study were generally safe and well tolerated. No dose-effect pattern was observed with respect to treatment-emergent AEs (TEAEs), vital signs, or ECG findings.

The two primary objectives of this study were to evaluate the efficacy of MR-107A-02 in subjects following dental surgery and to establish the dose-response relationship.

The primary endpoint was the summed pain intensity difference (SPID) over 0-24 hours ($SPID_{0-24}$) for meloxicam versus placebo for the Modified Intent-to-treat (mITT) analysis was set under the assumption that rescue medication use is managed by a 6-hour windowed last observation carried forward (W6LOCF) principle.

Secondary efficacy endpoints were also evaluated in the mITT Analysis Set. The secondary efficacy endpoints in this study were as follows:

- Overall SPID over 0-2 hours, 0-4 hours, 0-8 hours, 0-12 hours, and 12-24 hours after initial dose of study drug
- Pain Intensity Score and Pain Intensity Difference (PID) from baseline over time
- Time to perceptible relief (as measured by double-stopwatch technique) after first dose
- Time to meaningful pain relief (as measured by double-stopwatch technique) after first dose
- Proportion of subjects with overall pain reductions from baseline of ≥30% and ≥50% within 4 hours following the first dose
- Patients Global Assessment (PGA) of pain control from 0-24 hours
- Elapsed time from the start of study drug to first rescue medication administration
- Proportion of subjects using rescue medication from 0-24 hours
- Number of subjects using zero doses of rescue medication from 0-24 hours
- Number of times rescue medication used from 0-24 hours The safety endpoints in this study were as follows:

- Adverse events (AEs)
- Laboratory safety tests
- Electrocardiograms (ECGs)
- Vital signs The pharmacokinetic (PK) endpoints in this study were the population PK parameters for meloxicam $C_{max}$; time to maximum plasma concentration ($t_{max}$); and area under the concentration-versus-time curve from time 0 to 2 hours after dosing (first dose) ($AUC_{0-2}$), from time 0 to 4 hours after dosing ($AUC_{0-4}$), from time 0 to 8 hours after dosing ($AUC_{0-8}$), from time 0 to 12 hours after dosing ($AUC_{0-12}$), and from time 0 to 24 hours after dosing ($AUC_{0-24}$).

2.1 Overall Study Design and Plan

This was a randomized, double-blind, placebo-controlled, parallel-group, dose-ranging study, randomizing approximately 108 male or female subjects who had dental surgery (removal of ≥2 third molars) performed. Subjects received a dose of study drug on Day 1 after surgery and an additional dose approximately 12 hours later.

The dental surgery and related anesthesia, sedation, and prophylactic antibiotics were not investigational and would have occurred regardless of research.

The dental surgery (extraction of ≥2 third molars, at least 1 of which involved partial or complete mandibular bony impaction) was performed on Visit 2 (Day 1). The procedure was performed using appropriate local anesthesia and sedation (performed using nitrous oxide and a local injection of lidocaine with epinephrine). Subjects also received prophylactic antibiotics post surgically. End of Study was defined as the date of the last subject's last visit. Visits and procedures were conducted as presented in FIG. 42 and in Table 5 below.

Based on data from a previous Phase 2 study on a different investigative meloxicam formulation, an appropriate censoring period to account for the use of rescue medication in this present study was needed. The previous Phase 2 study explored the effect of the censoring period on the data and indicated that 2 hours (i.e., a W2LOCF approach) would not be sufficient and that a 4-6 hour window would be a better balance of a) accounting for the analgesic effect of the rescue medication and b) not censoring a large amount of data in placebo or low doses of study drug. For this reason, a W6LOCF approach was adopted for the primary analysis, with pre-specified sensitivity analyses of W4LOCF and W8LOCF also explored.

This present study was designed to specifically identify if meloxicam has efficacy in a model of acute postoperative pain and to enable the identification of the most appropriate dose of meloxicam to continue in development.

Subject eligibility was to be reviewed and documented by an appropriate medically qualified member of the investigator's study team before a subject was included in the study. Subjects must have met all of the following inclusion criteria to be eligible for enrollment into the study:

1. Males and females≥18 years of age. Females could have been of either childbearing or non-childbearing potential. All females of childbearing potential must have been using an acceptable, highly effective method of contraception and had a negative serum pregnancy test at Screening
2. Requirement for dental surgery for extraction of ≥2 third molars, at least 1 of which involved partial or complete mandibular bony impaction
3. Pain intensity using a Numeric Rating Scale (NRS)≥5 during the 5 hours following the end of surgery in the eligibility assessment as well as in the baseline assessment immediately predosing.
4. Rating of moderate or severe pain on a 4-point categorical pain rating scale (i.e., none, mild, moderate, severe) during the 5 hours following the end of surgery
5. Was able to understand and complete the study requirements (including literacy, to enable diary and questionnaire completion), provide written informed consent, and agree to abide by the study protocol and its restrictions Subjects were randomized to receive either meloxicam study drug (1.25 mg BID, 5 mg BID, or 15 mg BID) or corresponding placebo utilizing a double-dummy design. Subjects received a dose of study drug on Day 1 after surgery and randomization and a second dose approximately 12 hours later. At Visit 2 (Day 1) eligible subjects were randomized to receive meloxicam (1.25 mg BID, 5 mg BID, or 15 mg BID) or matching placebo in a 1:1:1:1 ratio.

Gastrointestinal AEs were the most frequently reported AEs in all treatment groups across MOBIC trials, reflective of the safety profile of meloxicam.

Higher doses of MOBIC (22.5 mg and greater) have been associated with an increased risk of serious gastrointestinal events; however, the predicted exposure associated with 22.5 mg MOBIC is greater than that which was observed with the present formulation of meloxicam 15 mg in the Phase 1 Study of MR-107A-02 discussed in US 2024/0277726, supra.

Furthermore, in an earlier Phase 2 study of a different investigational meloxicam tablet at three different dosages (15 mg QD, 10 mg QD, 15 mg BID, and 10 mg BID) in adult patients who had undergone dental surgery, the doses up to 15 mg BID were well tolerated. The most common treatment-emergent AEs (TEAEs) in this previous Phase 2 Study, by preferred term, were nausea, headache, and dizziness.

While the $C_{max}$ of meloxicam following dosing with the present study drug containing 15 mg meloxicam was approximately 70% greater than that of 15 mg MOBIC in the Phase 1 study discussed in US 2024/0277726, the overall exposure (AUC) was similar. The similar overall exposure of the present formulation of meloxicam to MOBIC at 15 mg meloxicam meant that use of the present formulation containing 15 mg meloxicam should be safe, especially as ANJESO (IV meloxicam) 30 mg has a reported $C_{max}$ of 7972.5 ng/ml and an AUC extrapolated to infinity ($AUC_{inf}$) of 121437.6 ng·hr/mL.

Using data from the Phase 1 study discussed in US 2024/0277726, it was predicted an exposure for 15 mg BID (i.e., 2 doses over 24 hours) of the present formulation of meloxicam exceeding that of a single dose of 15 mg meloxicam or MOBIC; however, the overall exposure and $C_{max}$ (after the second dose) would be similar to or less than that of ANJESO and therefore, for use in the treatment of acute pain, one hypothesized that the present formulation of meloxicam would be well tolerated. Furthermore, comparing the data from both the Phase 1 study discussed in US 2024/0277726 and the food effect Phase 1 study (Example IV herein), the inventors estimated that a 15 mg dose of meloxicam using the present tablet formulation would have rapid absorption.

As previously described, subjects were randomized to receive either meloxicam (1.25 mg BID, 5 mg BID, or 15 mg BID) or placebo through the IWRS, and study drugs were administered on Day 1 following randomization and approximately 12 hours following the first dose, regardless of treatment arm.

The study tablets had three different sizes, depending on the dose: 1.25 mg, 5 mg, or 15 mg. To maintain the blind for the double-dummy design, each subject received a total of three (3) tablets at each administration as follows:

Placebo arm: 3 placebo tablets, one each matching sizes of 1.25 mg, 5 mg, and 15 mg;

1.25 mg study drug arm: one (1) tablet with 1.25 mg active, plus 2 placebo tablets, one each for the 5 mg size and the 15 mg size;

5 mg study drug arm: one (1) tablet with 5 mg active, plus 2 placebo tablets, one each for the 1.25 mg size and the 15 mg size; and 15 ng study drug arm: one (1) tablet with 15 mg active, plus 2 placebo tablets, one each for the 1.25 mg size and the 5 mg size.

The tablets were administered to each subject on Day 1 following surgery and again 12 hours later. Due to the double-dummy design, neither the subject nor the investigator knew what treatment a subject received.

Any use of rescue medication while the subject was in the clinic was recorded, including the dose and time of administration. If an enrolled subject (i.e., a subject who was not a screen failure) required the use of rescue medication prior to administration of study drug, the subject was not eligible for randomization. After administration of study drug, rescue medication of immediate-release hydrocodone/acetaminophen (5/325 mg) was allowed to treat breakthrough pain. Subjects were encouraged to refrain from rescue medication until at least 1.5 hours post dose. A dose of rescue medication was allowed as needed up to once every 2 hours. A maximum of 6 tablets (equivalent to 30 mg hydrocodone and 1950 mg acetaminophen) was allowed; if a subject required more than this, the subject was to be withdrawn from the study. Pain intensity was measured immediately before any rescue medication was administered.

In order to avoid interference with sedation and operative procedures, subjects were to fast from midnight prior to the surgery. Subjects were allowed to eat food after 2 hours following the first dose. Meals served in the clinic were to be low-fat in composition. Subjects were not to consume any water or other drinks for 2 hours prior to the surgery. Subjects were allowed to consume water and other drinks ad libitum following completion of the surgery. Subjects were given snacks and meals at appropriate times (after the fasting period) during confinement in the clinic.

2.2 Efficacy Assessments

Pain intensity (using a 0-10-point NRS where 0 was no pain and 10 was the worst pain imaginable) [Breivik, H., et al., Assessment of pain. Br J Anaesth, 2008. 101 (1): p. 17-24] was assessed during the 5 hours following surgery. If the subject scored an NRS≥5 (and moderate or severe pain on the categorical scale) within 5 hours following surgery, they were eligible for randomization, and the randomization process was initiated. Immediately prior to dosing, the NRS was checked to confirm that the subject still met NRS≥5, and this value served as the baseline NRS score.

Assessments were made at 15, 30, and 45 minutes and 1, 1.5, 2, 3, 4, 5, 6, 7, 8, 10, 12, 14, 16, 20, and 24 hours after the first dose of study drug and immediately before any rescue medication and/or at the time of Early Termination.

Assessments were also made immediately following the time of first relief and time of first meaningful relief. The pain intensity was recorded in a diary.

A pain rating using a 4-point categorical rating scale (i.e., none, mild, moderate, severe) was used to assess eligibility for randomization. If the subject recorded moderate or severe on this scale (and an NRS≥5) within 5 hours following surgery, they were eligible for randomization.

Following surgery and prior to randomization, pain rating assessments were made until eligible pain scores were achieved. Following randomization and prior to dosing, at most, 2 attempts were made to achieve a baseline NRS rating that was ≥5. If this did not occur, the subject was discontinued from the study. The categorical pain rating was recorded in a diary.

A patient's global assessment (PGA) of pain control was rated on a 5-point scale, ranging from 0 to 4, where 0=poor, 1=fair, 2=good, 3=very good, or 4=excellent. Assessments were made 24 hours after the first dose of study drug or at time of Early Termination if applicable. The PGA was recorded in a diary.

Time to first perceptible pain relief was assessed using a double-stopwatch approach. The time to onset of first perceptible pain relief (time that the first watch stopped) was defined as the post dose time at which the subject first began to feel pain relief. If a subject took rescue medication prior to recording perceptible pain relief, the stopwatches were collected, and no further assessment of perceptible pain relief was collected.

Time to meaningful pain relief was assessed using a double-stopwatch approach. The time to onset of meaningful pain relief (time that the second watch stopped) was defined as the post dose time at which the subject first began to feel meaningful pain relief. If a subject took rescue medication prior to recording meaningful pain relief, the stopwatches were collected, and no further assessment of meaningful pain relief was collected.

Rescue medication of immediate-release hydrocodone/acetaminophen was allowed at any time, but subjects were encouraged to wait until at least 1.5 hours post dose if possible. A pain intensity score assessment was made immediately prior to any rescue medication. The time and dose of any rescue medication taken by a subject was recorded in the CRF.

Given that meloxicam is an NSAID, adverse events of special interest (AESIs) included the following:

Myocardial infarction/unstable angina.

Stroke/transient ischemic attack (TIA).

Heart failure.

Cardiac arrhythmia (atrial and ventricular).

Gastrointestinal hemorrhages, not elsewhere classified

Gastrointestinal ulceration and perforation

Blood samples for analysis of meloxicam concentration were collected at the following times, with the date and time of each sample recorded in the CRF: predose and 15, 30, and 45 minutes and 1, 1.5, 2, 3, 4, 5, 6, 8, 10, 12, 13, 14, 16, 20, and 24 hours after the first dose of study drug.

All efforts were made to obtain the PK samples at the exact nominal time relative to dosing, with the following permitted windows:

±3 minutes for all time points within the first hour

±5 minutes for all time points>1 hour and ≤8 hours

±10 minutes for all time points>8 hours

Samples were analyzed using validated analytical methods.

The following analysis sets were used for this study:

- All Subjects Analysis Set: This included all subjects consented and screened and was used for the reporting of subject populations and dispositions.
- Safety Analysis Set: The Safety Analysis Set included all subjects who received at least 1 dose of study drug. Data were summarized according to the treatment a subject actually received.
- Modified Intent-to-treat Analysis Set: The mITT Analysis Set included all randomized subjects who received study drug and provided at least 1 postbaseline pain intensity score. Subjects who were dosed in error but had a baseline pain intensity score<5 were included in this analysis set. This was used for all efficacy analyses; data were summarized and analyzed according to the treatment a subject was randomized to receive.
- Per-protocol (PP) Analysis Set: The PP Analysis Set included all subjects in the mITT Analysis Set who had no major protocol violation that would have impacted the primary efficacy endpoint. For instance, subjects who were dosed but had a baseline pain intensity score of <5 were excluded from this analysis set. The list of major protocol deviations was finalized prior to database lock and unblinding as part of the final blinded data review, with the following exception: In the case of mis-dispensation of study drug, these subjects were excluded from the PP Analysis Set, unless the misdispensed drug matched their randomized study arm; this was evaluated following unblinding. Thus, for all subjects in the PP Analysis Set, the actual treatment matched the randomized treatment. Additionally, subjects who did not receive both doses were excluded from the PP Analysis Set.

PK Analysis Set: The PK Analysis Set included all subjects who received a dose of study drug and who provided at least 1 post dose concentration sample for the population PK analysis. Data were summarized and analyzed according to the treatment a subject actually received at randomization.

The number and percentage of subjects screened, enrolled (marked as meeting inclusion criteria and not a screen failure), randomized, received treatment, completed the study, and discontinued from the study, were reported, along with the reason for discontinuation (counts only were reported for screened and enrolled subjects). Percentages were out of the number of subjects randomized. Additionally, the number and percentage of subjects who completed the treatment were reported. Subjects screened and enrolled were reported overall; the remaining items were reported by treatment group and overall. Subjects randomized included all subjects for whom randomization was checked on the CRF; subjects receiving treatment included all subjects who had any study drug administered; subjects completing the study were based on the recorded disposition. Subjects who completed the confinement period included those that had a termination date on or after Day 2.

Reasons for discontinuation included the following:

Adverse event
Death
Lack of efficacy
Lost to follow-up
Noncompliance with study drug
Physician decision
Pregnancy
Protocol deviation
Site terminated by sponsor
Study terminated by sponsor
Withdrawal by subject.
Other Additionally, the number and percentage of subjects in each analysis set were reported by treatment. Screen failures were also included in a by-subject listing.

All hypotheses were tested at a 2-sided significance level of 0.05. Because this was a Phase 2 study, all p-values presented for secondary endpoints were nominal and did not have adjustment for multiple comparisons.

2.3 Study Subjects

One hundred fifty-five subjects were screened for the study, of whom 111 were enrolled and randomized (28 subjects to meloxicam 1.25 mg, 28 subjects to meloxicam 5 mg, 28 subjects to meloxicam 15 mg, and 27 subjects to placebo). This is shown in Table 5 and FIG. 43. All except 3 of the randomized subjects, or 108 (97.3%) subjects total, completed the study. One subject in the meloxicam 15 mg group (Subject 201-0155) was discontinued from the study prior to completing the confinement period for failing to meet inclusion criterion 3 (baseline pain assessment was below eligible pain level). A subject in the meloxicam 5 mg group (Subject 201-0035) elected to withdraw from the study after receiving the first dose of study drug, and a subject in the placebo group (Subject 201-0142) was lost to follow-up after completing study treatment. The 4 treatment groups were comparable with respect to subject disposition.

TABLE 5

Summary of Subject Dispositions and Reasons for Discontinuation (Population: All Subjects Analysis Set)

| | MELO-TFZ 1.25 mg BID n (%) | MELO-TFZ 5 mg BID n (%) | MELO-TFZ 15 mg BID n (%) | Placebo n (%) | Total n (%) |
|---|---|---|---|---|---|
| Number of subjects screened | | | | | 155 |
| Number of subjects enrolled | | | | | 111 |
| Number of subjects randomized | 28 | 28 | 28 | 27 | 111 |
| Number of subjects in Safety Analysis Set | 28 (100.0) | 28 (100.0) | 27 (96.4) | 27 (100.0) | 110 (99.1) |
| Number of subjects in mITT Analysis Set | 28 (100.0) | 28 (100.0) | 27 (96.4) | 27 (100.0) | 110 (99.1) |
| Number of subjects in Per Protocol Analysis Set | 23 (100.0) | 27 (96.4) | 27 (96.4) | 27 (100.0) | 109 (98.2) |
| Number of subjects in Pharmacokinetic Analysis Set | 28 (100.0) | 28 (100.0) | 27 (96.4) | 27 (100.0) | 110 (99.1) |
| Number of subjects who completed confinement period [1] | 28 (100.0) | 28 (100.0) | 27 (96.4) | 27 (100.0) | 110 (99.1) |
| Number of subjects who completed study | 28 (100.0) | 27 (96.4) | 27 (96.4) | 26 (96.3) | 108 (97.3) |
| Number of subjects who discontinued study | 0 | 1 (3.6) | 1 (3.6) | 1 (3.7) | 3 (2.7) |

TABLE 5-continued

Summary of Subject Dispositions and Reasons for Discontinuation (Population: All Subjects Analysis Set)

| | MELO-TFZ 1.25 mg BID n (%) | MELO-TFZ 5 mg BID n (%) | MELO-TFZ 15 mg BID n (%) | Placebo n (%) | Total n (%) |
|---|---|---|---|---|---|
| Reason for Discontinuation | | | | | |
| Lost To Follow-Up | 0 | 0 | 0 | 1 (3.7) | 1 (0.9) |
| Withdrawal By Subject | 0 | 1 (3.6) | 0 | 0 | 1 (0.9) |
| Other | 0 | 0 | 1 (3.6) | 0 | 1 (0.9) |

mITT = Modified Intent-to-treat;
PP = Per-protocol;
PK = Pharmacokinetic
Note:
Percentages are out of the number of subjects randomized.
Note:
The Safety Analysis Set included all subjects treated with investigational product.
Note:
The mITT Analysis Set included all subjects who were randomized, received study drug, and reported at least 1 post-baseline pain intensity.
Note:
The PK Analysis Set included all subjects who received study drug, had at least 1 measurable plasma concentration, and received both doses; in the case of misdispensation, the actual dose aligned with a planned dose group for the study.
Note:
The PP Analysis Set included all subjects in the mITT Analysis Set who additionally did not have any protocol deviations that would have impacted the primary efficacy endpoint, took both doses, and took the planned dose that they were randomized to receive.
[1] Of the 28 subjects in the meloxicam 5 mg group who completed the confinement period, 1 subject (Subject 201-0035) received only 1 dose of study drug during the confinement period because he withdrew consent before receiving the second dose; however, the subject completed the follow-up telephone call on Day 6.

2.4 Efficacy Evaluation

The Safety, mITT, and PK Analysis Sets were each composed of 110 subjects, with 28 subjects in the meloxicam 1.25 mg group, 28 subjects in the meloxicam 5 mg group, 27 subjects in the meloxicam 15 mg group, and 27 subjects in the placebo group.

The PP Analysis Set was composed of 109 subjects, with 1 less subject in the meloxicam 5 mg group than in the meloxicam 5 mg group of the mITT, Safety, and PK Analysis Sets (27 subjects versus 28 subjects). The subject excluded from the PP Analysis Set was Subject 201-0035, who did not receive the second dose of study drug.

One subject randomized to meloxicam 15 mg (Subject 201-0155) was excluded from all 4 analysis sets; the subject was discontinued prior to receiving any study drug for not meeting inclusion criterion 3.

Concomitant medications included all medications taken after the administration of the investigational product, including those that were initiated prior to the administration of investigational product and were ongoing. Most subjects (108 of 110 [98.2%] in the Safety Analysis Set were taking at least 1 concomitant medication. The most common (≥20% of all subjects) ATC level 3 drug classes of concomitant medications were anti-inflammatory and antirheumatic products (non-steroids) (87.3%), beta-lactam antibacterials/penicillins (85.5%), and opioids (57.3%). The most common preferred terms of concomitant medications were ibuprofen (under anti-inflammatory and antirheumatic products [non-steroids]; 87.3%), amoxicillin (under beta-lactam antibacterials/penicillins; 85.5%), and hydrocodone bitartrate/paracetamol (under opioids; 57.3%).

The 4 treatment groups were comparable with respect to the proportion of subjects who used anti-inflammatory and antirheumatic products (nonsteroids) and ibuprofen (85.7%, 82.1%, 92.6%, and 88.9% for meloxicam 1.25 mg, meloxicam 5 mg, meloxicam 15 mg, and placebo groups, respectively), as well as the proportion who used beta-lactam antibacterials/penicillins and amoxicillin (96.4%, 92.9%, 70.4%, and 81.5%, respectively). The percentage of subjects who used opioids (hydrocodone bitartrate/paracetamol) was greater (by a factor of 1.5 or more) in the placebo group (74.1%) than in the meloxicam 1.25 mg and meloxicam 15 mg groups (46.4% and 44.4%, respectively), with less difference seen for the meloxicam 5 mg group (64.3%).

The primary efficacy endpoint was the $SPID_{0-24}$ for meloxicam versus placebo in the mITT Analysis Set with rescue medication use managed by W6LOCF. In the W6LOCF approach, the pain intensity score obtained before any rescue medication was carried forward to replace pain intensity scores collected at each observation within 6 hours following the rescue dose.

The following Table 6 below summarizes $SPID_{0-24}$ for the mITT Analysis Set, as well as SPIDs for other time intervals. Mean values for $SPID_{0-24}$ increased with meloxicam dose, ranging from 74.5 in the meloxicam 1.25 mg group, to 82.4 in the meloxicam 5 mg group, to 96.8 in the meloxicam 15 mg group. Each of these mean $SPID_{0-24}$ values was higher than the mean value of 50.5 in the placebo group. Mean $E_{max}$ estimates showed a similar dose-effect pattern, ranging from 70.7 in the meloxicam 1.25 mg group, to 86.7 in the meloxicam 5 mg group, to 94.8 in the meloxicam 15 mg group, compared with 52.0 in the placebo group. The difference between meloxicam and placebo in $E_{max}$ estimates was statistically significant for the meloxicam 5 mg ($p<0.001$) and meloxicam 15 mg groups ($p<0.001$), but not for the meloxicam 1.25 mg group ($p=0.123$).

TABLE 6

Summary of SPIDs: mITT W6LOCF (Population: Modified Intent-to-treat Analysis Set)

| Interval<br>Statistic | MELO-TFZ<br>1.25 mg BID<br>(N = 28) | MELO-TFZ<br>5 mg BID<br>(N = 28) | MELO-TFZ<br>15 mg BID<br>(N = 27) | Placebo<br>(N = 27) |
|---|---|---|---|---|
| $SPID_{0-24}$ | | | | |
| n | 28 | 28 | 27 | 27 |
| Mean | 74.5 | 82.4 | 96.8 | 50.5 |
| SD | 46.49 | 37.78 | 35.31 | 37.26 |
| Median | 74.8 | 90.3 | 100.6 | 44.7 |
| (Min, Max) | (−6, 174) | (7, 147) | (40, 167) | (−11, 117) |
| Emax Estimates [1] | | | | |
| Mean (SE) | 70.7 (7.86) | 86.7 (4.88) | 94.8 (7.47) | 52.0 (7.85) |
| 95% CI | (55.1, 86.3) | (77.0, 96.4) | (80.0, 109.6) | (36.4, 67.5) |
| Emax Estimated Difference vs PBO [1] | | | | |
| Mean (SE) | 18.7 (12.08) | 34.7 (10.25) | 42.8 (9.53) | |
| 95% CI | (−5.2, 42.7) | (14.4, 55.0) | (23.9, 61.7) | |
| p-value | 0.123 | <0.001 | <0.001 | |
| $SPID_{0-2}$ | | | | |
| n | 28 | 28 | 27 | 27 |
| Mean | 1.5 | 2.9 | 3.5 | 0.3 |
| SD | 3.13 | 2.53 | 2.51 | 2.45 |
| Median | 1.9 | 2.2 | 3.3 | 0.0 |
| (Min, Max) | (−5, 8) | (−1, 8) | (−3, 9) | (−5, 7) |
| Emax Estimates [1] | | | | |
| Mean (SE) | 1.6 (0.41) | 2.8 (0.33) | 3.5 (0.46) | 0.3 (0.50) |
| 95% CI | (0.8, 2.4) | (2.2, 3.5) | (2.6, 4.5) | (−0.7, 1.2) |
| Emax Estimated Difference vs PBO [1] | | | | |
| Mean (SE) | 1.3 (0.61) | 2.6 (0.64) | 3.3 (0.66) | |
| 95% CI | (0.1, 2.5) | (1.3, 3.9) | (2.0, 4.6) | |
| p-value | 0.031 | <0.001 | <0.001 | |
| $SPID_{0-4}$ | | | | |
| n | 28 | 28 | 27 | 27 |
| Mean | 5.1 | 7.9 | 10.9 | 0.8 |
| SD | 7.53 | 6.13 | 6.45 | 5.92 |
| Median | 5.7 | 6.5 | 10.9 | 0.0 |
| (Min, Max) | (−11, 18) | (−1, 20) | (−7, 22) | (−11, 12) |
| Emax Estimates [1] | | | | |
| Mean (SE) | 4.7 (1.09) | 8.4 (0.85) | 10.6 (1.19) | 0.9 (1.25) |
| 95% CI | (2.5, 6.8) | (6.7, 10.1) | (8.2, 13.0) | (−1.5, 3.4) |
| Emax Estimated Difference vs PBO [1] | | | | |
| Mean (SE) | 3.7 (1.64) | 7.5 (1.67) | 9.6 (1.62) | |
| 95% CI | (0.5, 7.0) | (4.2, 10.8) | (6.4, 12.9) | |
| p-value | 0.026 | <0.001 | <0.001 | |
| $SPID_{0-8}$ | | | | |
| n | 28 | 28 | 27 | 27 |
| Mean | 15.2 | 19.5 | 27.3 | 5.5 |
| SD | 17.17 | 14.19 | 14.45 | 14.15 |
| Median | 16.8 | 18.2 | 28.4 | 0.6 |
| (Min, Max) | (−16, 47) | (−1, 43) | (−12, 53) | (−21, 35) |
| Emax Estimates [1] | | | | |
| Mean (SE) | 13.4 (2.68) | 21.4 (2.15) | 26.4 (2.94) | 6.2 (3.02) |
| 95% CI | (8.1, 18.7) | (17.2, 25.7) | (20.6, 32.2) | (0.2, 12.2) |
| Emax Estimated Difference vs PBO [1] | | | | |
| Mean (SE) | 7.2 (4.21) | 15.2 (4.25) | 20.2 (3.73) | |
| 95% CI | (−1.1, 15.6) | (6.8, 23.6) | (12.8, 27.6) | |
| p-value | 0.090 | <0.001 | <0.001 | |
| $SPID_{0-12}$ | | | | |
| n | 28 | 28 | 27 | 27 |
| Mean | 26.2 | 32.6 | 42.4 | 14.4 |

TABLE 6-continued

Summary of SPIDs: mITT W6LOCF (Population: Modified Intent-to-treat Analysis Set)

| Interval<br>Statistic | MELO-TFZ<br>1.25 mg BID<br>(N = 28) | MELO-TFZ<br>5 mg BID<br>(N = 28) | MELO-TFZ<br>15 mg BID<br>(N = 27) | Placebo<br>(N = 27) |
|---|---|---|---|---|
| SD | 24.26 | 18.04 | 18.56 | 18.85 |
| Median | 26.6 | 35.1 | 42.2 | 8.0 |
| (Min, Max) | (−16, 78) | (−1, 64) | (6, 79) | (−11, 50) |
| Emax Estimates [1] | | | | |
| Mean (SE) | 23.8 (3.31) | 34.4 (3.13) | 42.0 (3.98) | 15.5 (4.00) |
| 95% CI | (17.2, 30.4) | (28.2, 40.6) | (34.1, 49.8) | (7.6, 23.5) |
| Emax Estimated Difference vs PBO [1] | | | | |
| Mean (SE) | 8.2 (5.30) | 18.9 (5.95) | 26.4 (4.93) | |
| 95% CI | (−2.2, 18.7) | (7.1, 30.7) | (16.6, 36.2) | |
| p-value | 0.122 | 0.002 | <0.001 | |
| $SPID_{12-24}$ | | | | |
| n | 28 | 28 | 27 | 27 |
| Mean | 48.3 | 49.7 | 54.4 | 36.1 |
| SD | 25.07 | 22.76 | 19.96 | 22.13 |
| Median | 48.5 | 52.5 | 56.9 | 40.0 |
| (Min, Max) | (−4, 96) | (0, 84) | (22, 88) | (−5, 70) |
| Emax Estimates [1] | | | | |
| Mean (SE) | 47.5 (4.43) | 51.6 (2.50) | 52.9 (3.68) | 36.4 (4.19) |
| 95% CI | (38.7, 56.3) | (46.6, 56.5) | (45.7, 60.2) | (28.1, 44.7) |
| Emax Estimated Difference vs PBO [1] | | | | |
| Mean (SE) | 11.1 (6.32) | 15.2 (4.92) | 16.5 (5.36) | |
| 95% CI | (−1.4, 23.6) | (5.4, 24.9) | (5.9, 27.2) | |
| p-value | 0.082 | 0.003 | 0.003 | |

BID = twice daily;
CI = confidence interval;
$E_{max}$ = term referring to the asymptotic maximum dose effect (model);
max = maximum;
min = minimum;
mITT = modified intent-to-treat;
NRS = numeric rating scale;
PBO = placebo;
SAP = statistical analysis plan;
SD = standard deviation;
SE = standard error;
SPID = summed pain intensity difference;
W6LOCF = 6-hour windowed last observation carried forward
Note:
SPID was calculated using the trapezoidal rule and available NRS pain scores at actual times. Full details of SPID calculation can be found in the SAP.
Note:
W6LOCF utilized "pain right now" just prior to rescue medication use and censored subsequent pain intensity values for 6 hours when calculating SPIDs.
[1] Model estimates, CIs, and p-values were based on a 3-parameter Emax model with covariate for baseline NRS score. Full details are described in the SAP.

The standardized effect sizes of SPIDs using W6LOCF for the mITT Analysis Set. The findings support the observed dose-effect pattern in the primary endpoint analysis, with standardized effect sizes for mean $SPID_{0-24}$ of 0.57, 0.85, and 1.28 for the meloxicam 1.25 mg, meloxicam 5 mg, and meloxicam 15 mg groups, respectively. A similar pattern was observed for standardized effect sizes for $E_{max}$ estimate of the difference from placebo, with values of 0.44, 0.92, and 1.18, respectively.

The analysis of the primary endpoint was repeated for the PP Analysis Set, and the findings were similar to those for the mITT Analysis Set.

As sensitivity analyses, the primary endpoint analysis was repeated using both a W4LOCF and a W8LOCF approach, whereby the pain intensity score obtained before a given rescue medication was carried forward to replace the pain intensity scores collected at each observation within 4 hours and 8 hours, respectively, following the rescue dose. The results using W4LOCF and W8LOCF were similar to those for the primary endpoint analysis, with a dose-effect pattern for $SPID_{0-24}$ and statistically significant $E_{max}$ estimates of the difference from placebo for the meloxicam 5 mg ($p<0.001$ for W4LOCF; $p=0.002$ for W8LOCF) and meloxicam 15 mg ($p<0.001$ for both approaches) groups, but not the meloxicam 1.25 mg group ($p=0.101$ for W4LOCF; $p=0.159$ for W8LOCF).

A third sensitivity analysis of the primary endpoint analysis used the W6LOCF approach but excluded time points with perceptible and meaningful pain relief. This analysis also showed $SPID_{0-24}$ to increase with meloxicam dose, with significant treatment group differences (meloxicam versus placebo) for the meloxicam 5 mg ($p<0.001$) and meloxicam 15 mg ($p<0.001$) groups, but not the meloxicam 1.25 mg group ($p=0.122$).

Although not sensitivity analyses, $SPID_{0-24}$ was also evaluated with no censoring and with all values censored following rescue medication use (ALLOCF). Both approaches showed statistically significant $E_{max}$ estimate differences (meloxicam versus placebo) for the meloxicam 5 mg (p=0.016 for no censoring; p<0.001 for ALLOCF) and meloxicam 15 mg (p<0.001 for both approaches) groups, but not for the meloxicam 1.25 mg group (p=0.249 for no censoring; p=0.079 for ALLOCF).

The results for $SPID_{0-2}$, $SPID_{0-4}$, $SPID_{0-8}$, $SPID_{0-12}$, and $SPID_{12-24}$ using W6LOCF for the mITT Analysis Set were similar to those for the primary endpoint of $SPID_{0-24}$ using W6LOCF (See Table 7 above). Mean SPID values and $E_{max}$ estimates for each time interval showed a dose-effect pattern, with the $E_{max}$ estimate of the difference from placebo being statistically significant (p<0.05) in favor of meloxicam 5 mg and meloxicam 15 mg over placebo. In addition, the $E_{max}$ estimate of the difference between meloxicam 1.25 mg and placebo were statistically significant for $SPID_{0-2}$ and $SPID_{0-4}$. For all other time intervals, the mean SPID value and $E_{max}$ estimate was numerically greater in the meloxicam 1.25 mg group than in the placebo group, but the treatment group difference was not statistically significant.

Figure 1:
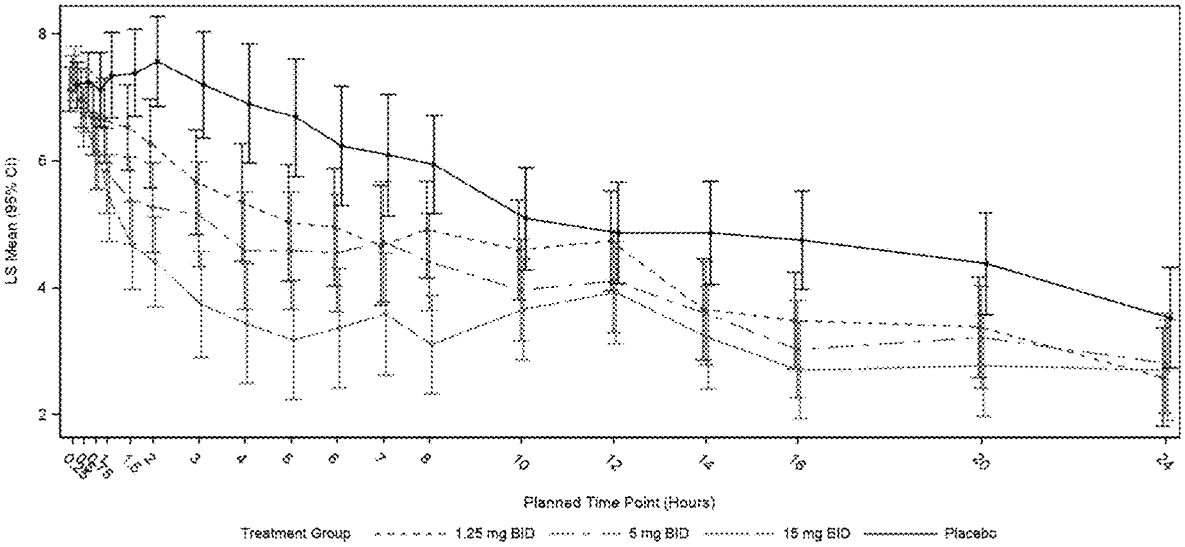
Figure 2:
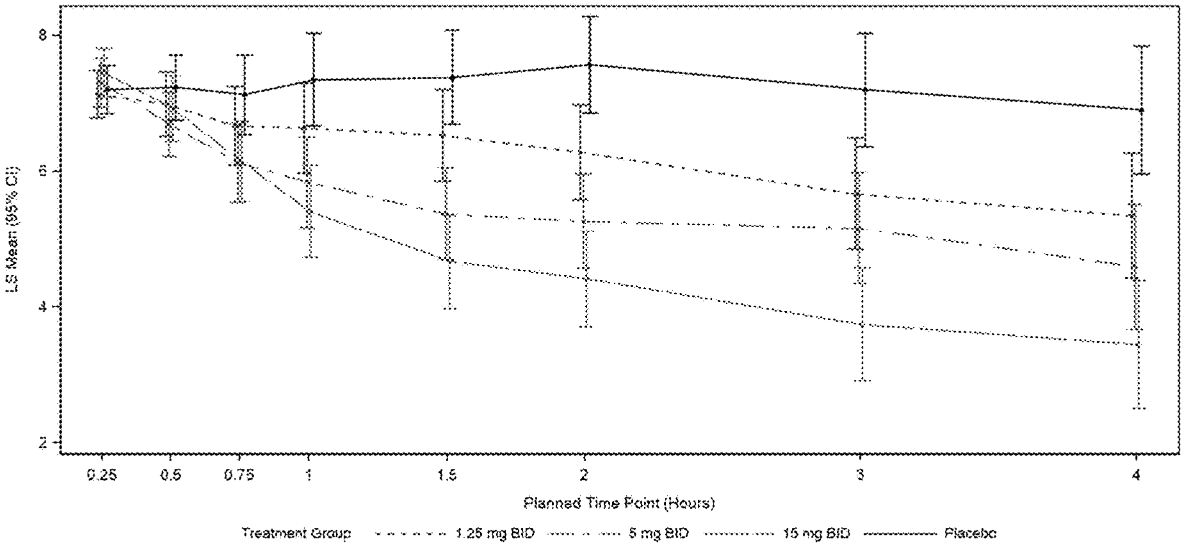

The analyses of SPID by time interval using the other censoring approaches or the PP Analysis Set followed a pattern similar to that described above for the W6LOCF approach in the mITT Analysis Set. These SPID analyses included the following, with exceptions from the mITT W6LOCF analysis noted:

- W6LOCF in the PP Analysis Set
- W4LOCF in the mITT Analysis Set; the $SPID_{0-8}$ treatment group difference (meloxicam versus placebo) was also statistically significant for meloxicam 1.25 mg
- W8LOCF in the mITT Analysis Set
- W6LOCF excluding time points with perceptible and meaningful pain relief in the mITT Analysis Set
- ALLOCF in the mITT Analysis Set; the $SPID_{12-24}$ treatment group difference (meloxicam versus placebo) was also statistically significant for meloxicam 1.25 mg
- No censoring in the mITT Analysis Set The NRS pain scores at each nominal time point for the mITT Analysis Set using W6LOCF were summarized next. FIGS. 1 and 2, which depict the LS mean NRS pain scores at each time nominal point from Hour 0 through Hour 24 and from Hour 0 through Hour 4, respectively. At baseline, mean NRS pain scores were similar across the 4 treatment groups, ranging from 7.2 in the meloxicam 15 mg group to 7.9 in the meloxicam 5 mg group. A similar pattern was observed at Hour 0.25, with LS mean NRS pain scores ranging from 7.0 in the meloxicam 1.25 mg group to 7.7 in the meloxicam 15 mg group. By Hour 0.5, LS mean scores were numerically lower in all 3 meloxicam groups than in the placebo group, and they remained lower than in the placebo group through Hour 24. From Hour 0.5 to Hour 2, LS mean scores in the meloxicam groups showed a greater downward trend than scores in the placebo group, with placebo scores increasing slightly between Hour 0.75 and Hour 2. From Hour 2 to Hour 4, LS mean scores in the 3 meloxicam dose groups continued to show a downward trend, while scores in the placebo group began to decrease. From Hour 4 to Hour 12 (before the second dose of study drug), LS mean scores in the meloxicam groups tended to stabilize or even increase at times, whereas scores in the placebo group continued to decrease but continued to remain higher than in the meloxicam groups. From Hour 12 (after the second dose of study drug) to Hour 16, LS mean scores in each of the meloxicam dose groups decreased, whereas scores in the placebo group remained generally stable. From Hour 16 to 24, LS mean scores in the meloxicam groups tended to be stable, while scores in the placebo group decreased.

At all nominal time points from Hour 1 to Hour 20, LS mean NRS pain scores were numerically lowest in the meloxicam 15 mg group; after Hour 20, at Hour 24, scores were similar across the meloxicam dose groups (2.6, 2.8, and 2.7 for meloxicam 1.25 mg, meloxicam 5 mg, and meloxicam 15 mg, respectively), but still lower than in the placebo group (3.5). At all nominal time points from Hour 0.5 to Hour 20, excluding Hour 7, LS mean NRS pain scores were numerically lower in the meloxicam 5 mg group than in the meloxicam 1.25 mg group; at Hour 7, scores in the meloxicam 1.25 mg and meloxicam 5 mg groups were the same (4.7).

Figure 3:
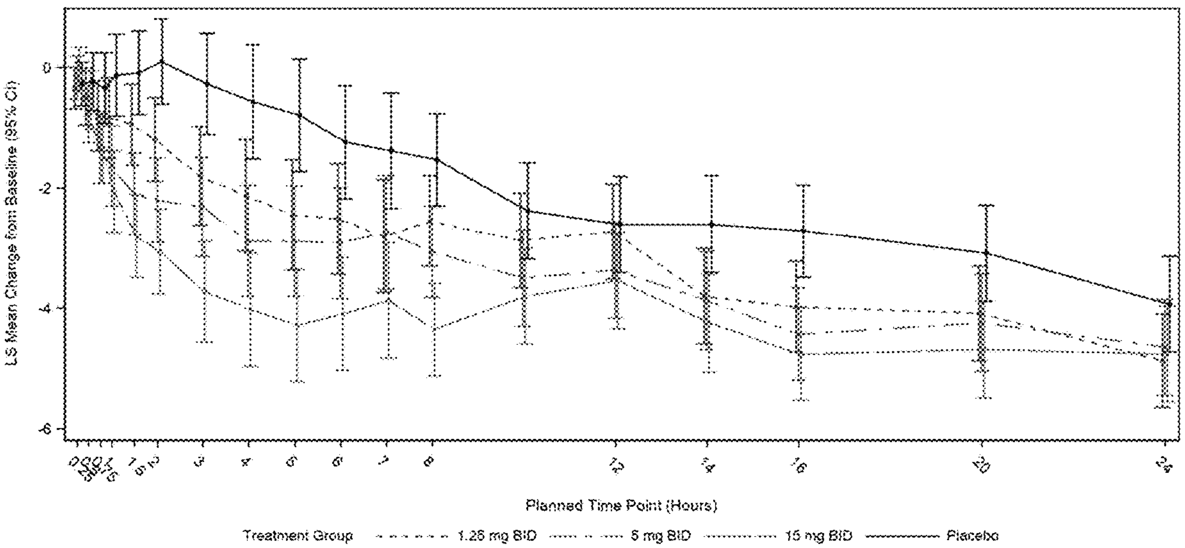
Figure 4:
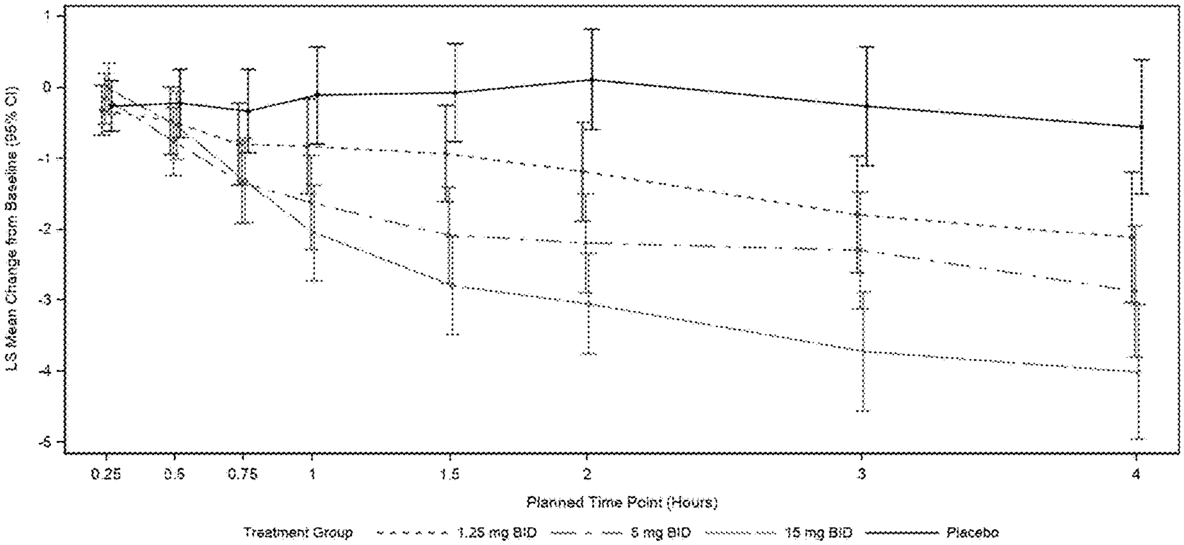

The inventors summarized the NRS PIDs at each nominal time point from Hour 0 to Hour 24 for the mITT Analysis Set using W6LOCF. FIGS. 3 and 4 depict LS mean PIDs at each nominal time point from Hour 0 through Hour 24 and from Hour 0 to Hour 4, respectively. The pattern for PIDs over time was consistent with that for NRS pain scores over time; the PID at each time point was proportional to the NRS pain score at that time point such that larger PIDs corresponded with lower NRS pain scores. All 3 meloxicam groups had a numerically greater LS mean PID than the placebo group by Hour 0.5, and the PID remained larger in the meloxicam groups through Hour 24. At all time points from Hour 1 to Hour 20, LS mean PIDs were numerically greatest in the meloxicam 15 mg group, with all 3 meloxicam groups showing similar PIDs at Hour 24 (−4.9, −4.6, and −4.8 for meloxicam 1.25 mg, meloxicam 5 mg, and meloxicam 15 mg, respectively, versus −3.9 for placebo). At all time points from Hour 0.5 to Hour 20, excluding Hour 7, the LS mean PID was greater in the meloxicam 5 mg group than in the meloxicam 1.25 mg group. At Hour 7, the LS mean PIDs for meloxicam 1.25 mg and meloxicam 5 mg were −2.8 and −2.7, respectively.

Figure 5:
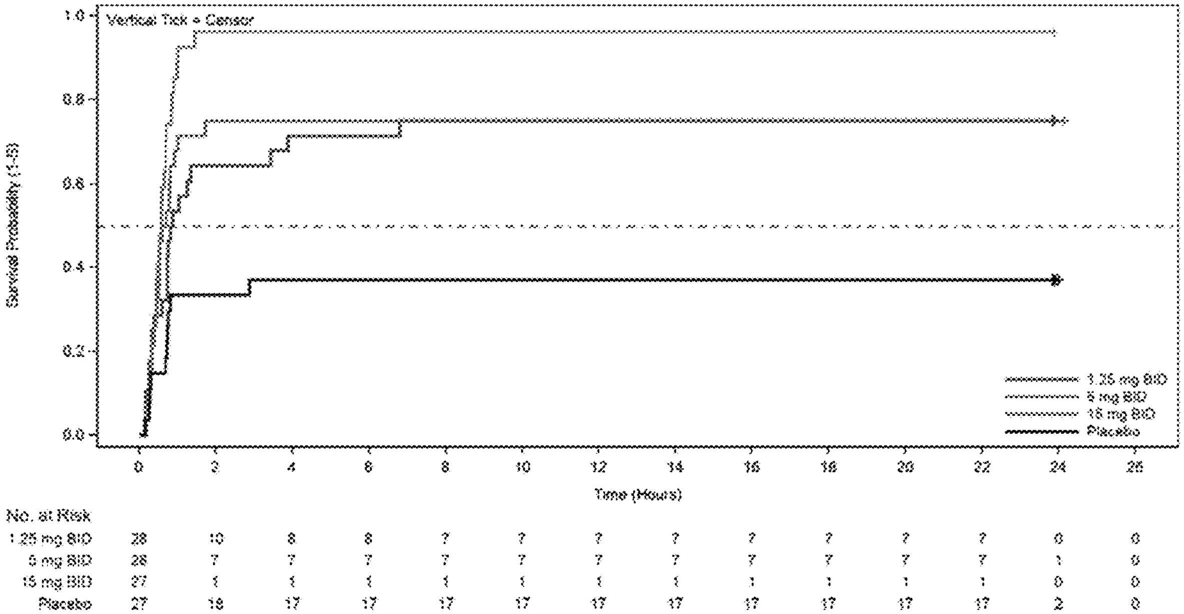

The following Table 7 and FIG. 5 summarize the time to first perceptible relief of pain for the mITT Analysis Set. Seventy-five percent of subjects in the meloxicam 1.25 mg and meloxicam 5 mg groups and 96.3% of subjects in the meloxicam 15 mg group had perceptible pain relief at some point during the study. In contrast, less than half of subjects (37.0%) in the placebo group reported perceptible pain relief.

The median time to first perceptible relief of pain tended to decrease with an increase in meloxicam dose: 0.9, 0.7, and 0.6 hours for meloxicam 1.25 mg, meloxicam 5 mg, and meloxicam 15 mg groups, respectively. Each of these median times was significantly less than in the placebo group (p=0.021 for meloxicam 1.25 mg; p=0.004 for meloxicam 5 mg; and p<0.001 for meloxicam 15 mg). The median time to first perceptible relief of pain in the placebo group was not estimable because of an insufficient number of events.

Similar findings were observed when the analysis of time to perceptible relief of pain was conducted with censoring at first rescue medication. See Table 8 below for results.

TABLE 7

Summary of Time to Perceptible Relief (Population: Modified Intent-to-treat Analysis Set) in Phase 2b Study

| | MELO-TFZ 1.25 mg BID (N = 28) | MELO-TFZ 5 mg BID (N = 28) | MELO-TFZ 15 mg BID (N = 27) | Placebo (N = 27) |
|---|---|---|---|---|
| Subjects with event | | | | |
| n (%) | 21 (75.0) | 21 (75.0) | 26 (96.3) | 10 (37.0) |
| Time to first event (hrs) [1] | | | | |
| 75th percentile (95% CI) | NA (1.0, NA) | NA (0.8, NA) | 0.9 (0.6, 1.0) | NA (NA, NA) |
| Median (95% CI) | 0.9 (0.6, 3.4) | 0.7 (0.5, 0.9) | 0.6 (0.4, 0.7) | NA (0.8, NA) |
| 25th percentile (95% CI) | 0.4 (0.2. 0.8) | 0.4 (0.2, 0.5) | 0.4 (0.2, 0.5) | 0.8 (0.3, NA) |
| P-value (Pooled vs Placebo) | | | | <0.001 |
| P-value (Pairwise vs Placebo) | 0.021 | 0.004 | <0.001 | |

BID = twice daily;
CI = confidence interval:
NA = not applicable
Note:
Subjects were censored at 24 hours if they did not report relief.
[1] Percentiles and comparisons were based on Kaplan-Meier method and log-rank test. Values marked NA had insufficient counts of events to be estimable from the Kaplan-Meier methodology.

Figure 6:
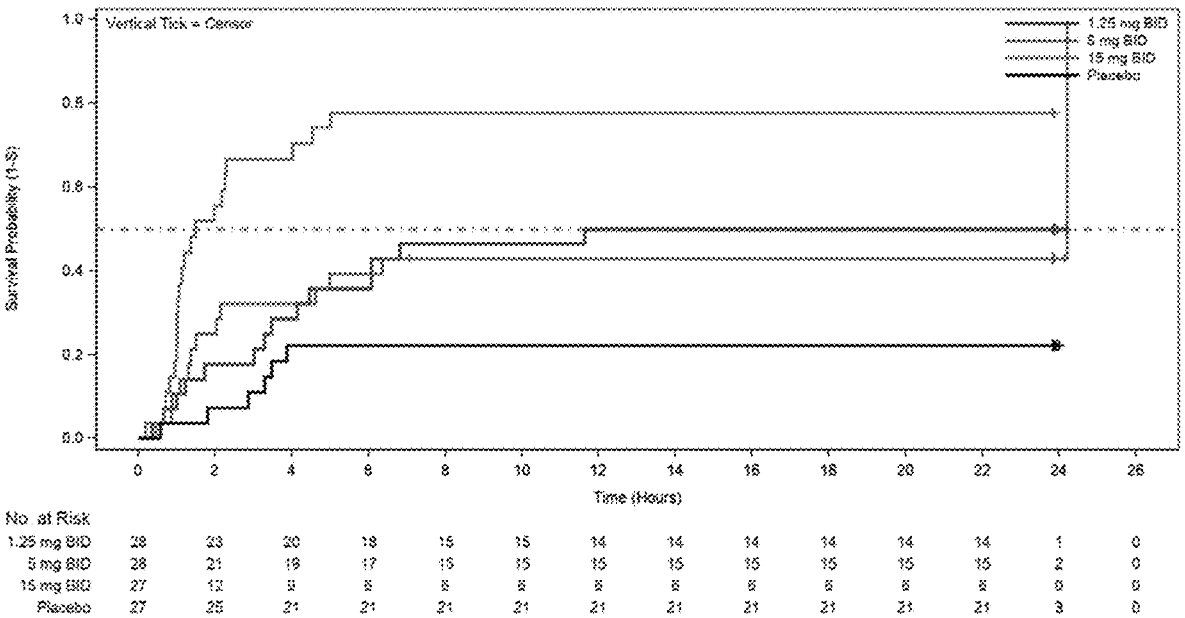

Table 8 and FIG. 6 summarize the time to first meaningful relief of pain for the mITT Analysis Set. Fifty percent of subjects in the meloxicam 1.25 mg group, 46.4% of subjects in the meloxicam 5 mg group, and 77.8% of subjects in the meloxicam 15 mg group had meaningful pain relief at some point during the study. In contrast, only 22.2% of subjects in the placebo group reported meaningful pain relief.

The median time to first meaningful relief of pain was less in the meloxicam 15 mg group than in the meloxicam 5 mg group (1.5 versus 24.2 hours) and was not estimable in the meloxicam 1.25 mg and placebo groups due to an insufficient number of events. The difference from placebo in median time to first meaningful relief was statistically significant for meloxicam 15 mg (p<0.001), but not for meloxicam 1.25 mg (p=0.095) or meloxicam 5 mg with the timer stopped at 24.22 hours, resulting in the subject not being censored. If this subject had been censored, the median time to meaningful pain relief would not have been estimable.

When the analysis was conducted with censoring at first rescue medication, the median time to first meaningful relief of pain was less in the meloxicam 15 mg group (1.5 hours) than in both the meloxicam 1.25 and meloxicam 5 mg groups (4.5 and 5.0 hours, respectively) and placebo group (3.9 hours). As in the analysis without censoring at first rescue, the treatment group difference from placebo was statistically significant for meloxicam 15 mg (p<0.001), but not for meloxicam 1.25 mg (p=0.411) or meloxicam 5 mg (p=0.383). See Table 8 for results.

TABLE 8

Summary of Time to Meaningful Pain Relief (Population: Modified Intent-to-treat Analysis Set), Phase 2b Study

| | MELO-TFZ 1.25 mg BID (N = 28) | MELO-TFZ 5 mg BID (N = 28) | MELO-TFZ 15 mg BID (N = 27) | Placebo (N = 27) |
|---|---|---|---|---|
| Subjects with event | | | | |
| n (%) | 14 (50.0) | 13 (46.4) | 21 (77.8) | 6 (22.2) |
| Time to first event (hrs) [1] | | | | |
| 75th percentile (95% CI) | NA (NA, NA) | 24.2 (NA, NA) | 5.0 (2.2, NA) | NA (NA, NA) |
| Median (95% CI) | NA (4.1, NA) | 24.2 (2.1, NA) | 1.5 (1.0, 4.0) | NA (NA, NA) |
| 25th percentile (95% CI) | 3.4 (0.7, 6.1) | 1.8 (0.9, 6.4) | 1.0 (0.7, 1.1) | NA (1.8, NA) |
| P-value (Pooled vs Placebo) | | | | 0.003 |
| P-value (Pairwise vs Placebo) | 0.095 | 0.146 | <0.001 | |

BID = twice daily;
CI = confidence interval;
NA = not applicable
Note:
Subjects are censored at 24 hours if they do not report relief. One subject in the meloxicam 5 mg BID group (Subject 201-0107) was recorded as having meaningful pain relief with the timer stopped at 24.22 hours and therefore was not censored.
[1] Percentiles and comparisons are based on Kaplan-Meier method and log-rank test. Values marked NA have insufficient counts of events to be estimable from the Kaplan-Meier methodology.

(p=0.146). It should be noted that, for this analysis, subjects were censored at 24 hours if they did not report pain relief; however, 1 subject in the meloxicam 5 mg group (Subject 201-0107) was recorded as having meaningful pain relief The following Table 9 summarizes the number and proportion of 30% and 50% pain responders in the mITT Analysis Set. A responder was a subject who reported a 30% or 50% reduction in pain at any time point through 4 hours.

The proportion of 30% pain responders was greater (by a factor of 2 or more) in each of the meloxicam dose groups than in the placebo group: 57.1%, 60.7%, and 92.6% for meloxicam 1.25 mg, meloxicam 5 mg, and meloxicam 15 mg, respectively, versus 25.9% for placebo. For each of the meloxicam dose groups, the difference from placebo in the proportion of 30% pain responders was statistically significant: p=0.019 for meloxicam 1.25 mg; p=0.009 for meloxicam 5 mg; and p<0.001 for meloxicam 15 mg.

Each of the meloxicam dose groups also had a greater (by factor of 1.5 or more) proportion of 50% pain responders than the placebo group: 42.9%, 46.4%, and 74.1% for meloxicam 1.25 mg, meloxicam 5 mg, and meloxicam 15 mg, respectively, versus 25.9% for placebo. The treatment group difference (meloxicam versus placebo) in the proportion of 50% pain responders was statistically significant for meloxicam 15 mg (p<0.001), but not for meloxicam 1.25 mg (p=0.187) or meloxicam 5 mg (p=0.114).

TABLE 9

Summary of 30% and 50% Pain Responders (Population: Modified Intent-to-treat Analysis Set), Phase 2b Study

| Response Statistic | MELO-TFZ 1.25 mg BID (N = 28) | MELO-TFZ 5 mg BID (N = 28) | MELO-TFZ 15 mg BID (N = 27) | Placebo (N = 27) |
|---|---|---|---|---|
| 30% Pain Responder | | | | |
| Yes | 16 (57.1) | 17 (60.7) | 25 (92.6) | 7 (25.9) |
| No | 12 (42.9) | 11 (39.3) | 2 (7.4) | 20 (74.1) |
| Diff. vs PBO | 31.2% | 34.8% | 66.7% | |
| (95% CI) | (6.5%, 55.9%) | (10.3%, 59.3%) | (47.4%, 85.9%) | |
| P-value vs PBO | 0.019 | 0.009 | <0.001 | |
| 50% Pain Responder | | | | |
| Yes | 12 (42.9) | 13 (46.4) | 20 (74.1) | 7 (25.9) |
| No | 16 (57.1) | 15 (53.6) | 7 (25.9) | 20 (74.1) |
| Diff. vs PBO | 16.9% | 20.5% | 48.1% | |
| (95% CI) | (−7.8%, 41.6%) | (−4.3%, 45.3%) | (24.8%, 71.5%) | |
| P-value vs PBO | 0.187 | 0.114 | <0.001 | |

BID = twice daily;
CI = confidence interval;
diff = difference;
PBO = placebo
Note:
Difference in proportions estimates, CIs, and p-values were based on the difference in proportions Z test (equivalent to the Pearson's Chi Squared).
Note:
A subject was considered a responder if they reported a reduction in pain of 30% or 50% at any time point through 4 hours. If rescue was used, values following the use were imputed with the value taken just prior to rescue use.

The proportion of subjects with different PGA ratings and the proportion of PGA responders in the mITT Analysis Set has been summarized. Responders were subjects with a PGA rating of good, very good, or excellent; subjects with missing values were counted as non-responders. The proportion of PGA responders was numerically greatest in the meloxicam 15 mg group and greater (by a factor of 1.5 or more) in all 3 meloxicam groups than in the placebo group: 60.7%, 67.9%, and 85.2% for meloxicam 1.25 mg, meloxicam 5 mg, and meloxicam 15 mg, respectively, versus 33.3% for placebo. The difference from placebo was statistically significant for each of the meloxicam dose groups (p=0.042 for meloxicam 1.25 mg; p=0.010 for meloxicam 5 mg; and p<0.001 for meloxicam 15 mg).

The proportion of subjects in the mITT Analysis Set who used rescue medication from Hour 0 through Hour 24 were summarized. The proportion of subjects who used rescue medication over this time period was smallest in the meloxicam 15 mg group and was numerically smaller in each of the meloxicam groups than in the placebo group: 42.9%, 57.1%, and 29.6% for meloxicam 1.25 mg, meloxicam 5 mg, and meloxicam 15 mg, respectively, versus 74.1% for placebo. The difference from placebo in rescue medication use was statistically significant for the meloxicam 1.25 mg (p=0.019) and meloxicam 15 mg (p<0.001) groups, but not for the meloxicam 5 mg group (p=0.187).

The proportion of subjects who used rescue medication prior to the second dose was also smallest in the meloxicam 15 mg group and was numerically smaller in each of the meloxicam groups than in the placebo group: 42.9%, 57.1%, and 29.6% for meloxicam 1.25 mg, meloxicam 5 mg, and meloxicam 15 mg, respectively, versus 74.1% for placebo. The difference from placebo in rescue medication use prior to the second dose was statistically significant for the meloxicam 1.25 mg (p=0.019) and meloxicam 15 mg (p<0.001) groups, but not for the meloxicam 5 mg group (p=0.187).

Figure 7:
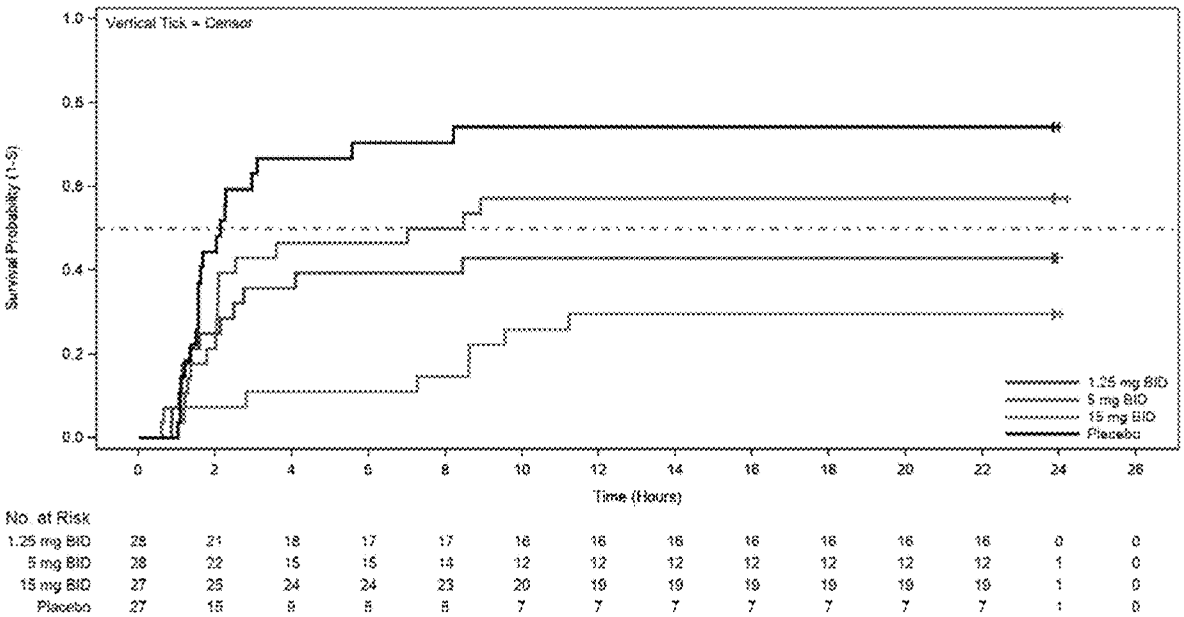

FIG. 7 depicts the time to first rescue medication administration in the mITT Analysis Set. The median time to first rescue medication use was longer in the meloxicam 5 mg group than in the placebo group (7.7 versus 2.1 hours), with the median times in the meloxicam 1.25 mg and meloxicam 15 mg groups not being estimable due to an insufficient number of events. The difference from placebo in median time to first rescue medication use was statistically significant for the meloxicam 1.25 mg (p=0.017) and meloxicam 15 mg (p<0.001) groups, but not for the meloxicam 5 mg group (p=0.148).

Figure 8:
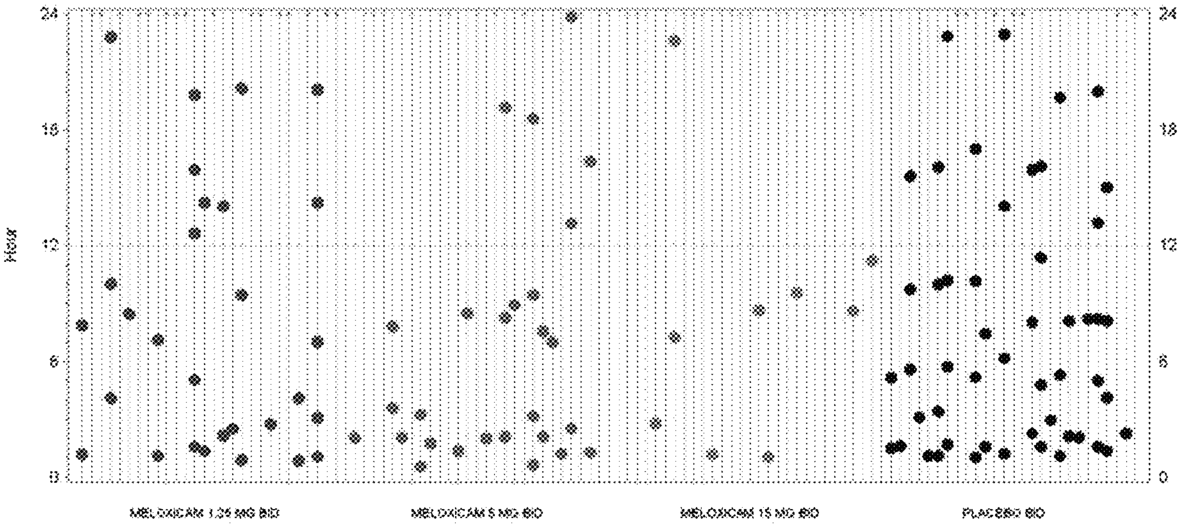

The following Table 10 summarizes the frequency of rescue medication use in the mITT Analysis Set, and FIG. 8 depicts each subject's use of rescue medication by time point. The meloxicam 15 mg group had the lowest mean number of rescue medication uses (0.3 use), followed by the meloxicam 1.25 mg and meloxicam 5 mg groups (1.0 use each) and, lastly, by the placebo group (1.9 uses). The difference from placebo in rescue medication use was statistically significant for each of the meloxicam dose groups (p=0.031 for meloxicam 1.25 mg; p=0.044 for meloxicam 5 mg, and p<0.001 for meloxicam 15 mg).

TABLE 10

Summary of Total Frequency of Rescue Medication Usage (Population: Modified Intent-to-treat Analysis Set), Phase 2b Study

| Statistic | MELO-TFZ 1.25 mg BID (N = 28) | MELO-TFZ 5 mg BID (N = 28) | MELO-TFZ 15 mg BID (N = 27) | Placebo (N = 27) |
|---|---|---|---|---|
| Number of Rescue Medication Uses | | | | |
| n | 28 | 28 | 27 | 27 |
| Mean | 1.0 | 1.0 | 0.3 | 1.9 |

TABLE 10-continued

| Summary of Total Frequency of Rescue Medication Usage (Population: Modified Intent-to-treat Analysis Set), Phase 2b Study | | | | |
|---|---|---|---|---|
| Statistic | MELO-TFZ 1.25 mg BID (N = 28) | MELO-TFZ 5 mg BID (N = 28) | MELO-TFZ 15 mg BID (N = 27) | Placebo (N = 27) |
| SD | 1.50 | 1.22 | 0.55 | 1.65 |
| Median | 0.0 | 1.0 | 0.0 | 1.0 |
| Range (Min, Max) | (0, 5) | (0, 5) | (0, 2) | (0, 5) |
| P-value vs Placebo | 0.031 | 0.044 | <0.001 | |

BID = twice daily;
max = maximum;
min = minimum;
SD = standard deviation
Note:
All subjects in the population were summarized; those with no rescue medication uses were reported as 0.
Note:
P-values were from a pairwise comparison to placebo using the Wilcoxon Rank Sum Test.

From Hour 0 to Hour 24, opioid use was less frequent in each of the meloxicam dose groups than in the placebo group, with the frequency decreasing with increasing meloxicam dose. Use of opioids after Hour 24 (up to Hour 42) was infrequent (3 uses each in the meloxicam 1.25 mg, meloxicam 15 mg, and placebo groups; 6 uses in the meloxicam 5 mg group).

All hypotheses were tested at a 2-sided significance level of 0.05. Nominal p-values were presented for some secondary endpoints without adjustment for multiple comparisons (because this was a Phase 2 study).

The mITT Analysis Set included all randomized subjects who received study drug and provided at least 1 post-baseline pain intensity score. Subjects who were dosed in error but had a baseline pain intensity score<5 were included in this analysis set. The mITT Analysis Set was used for all efficacy analyses; data were summarized and analyzed according to the treatment a subject was randomized to receive.

Figure 9:
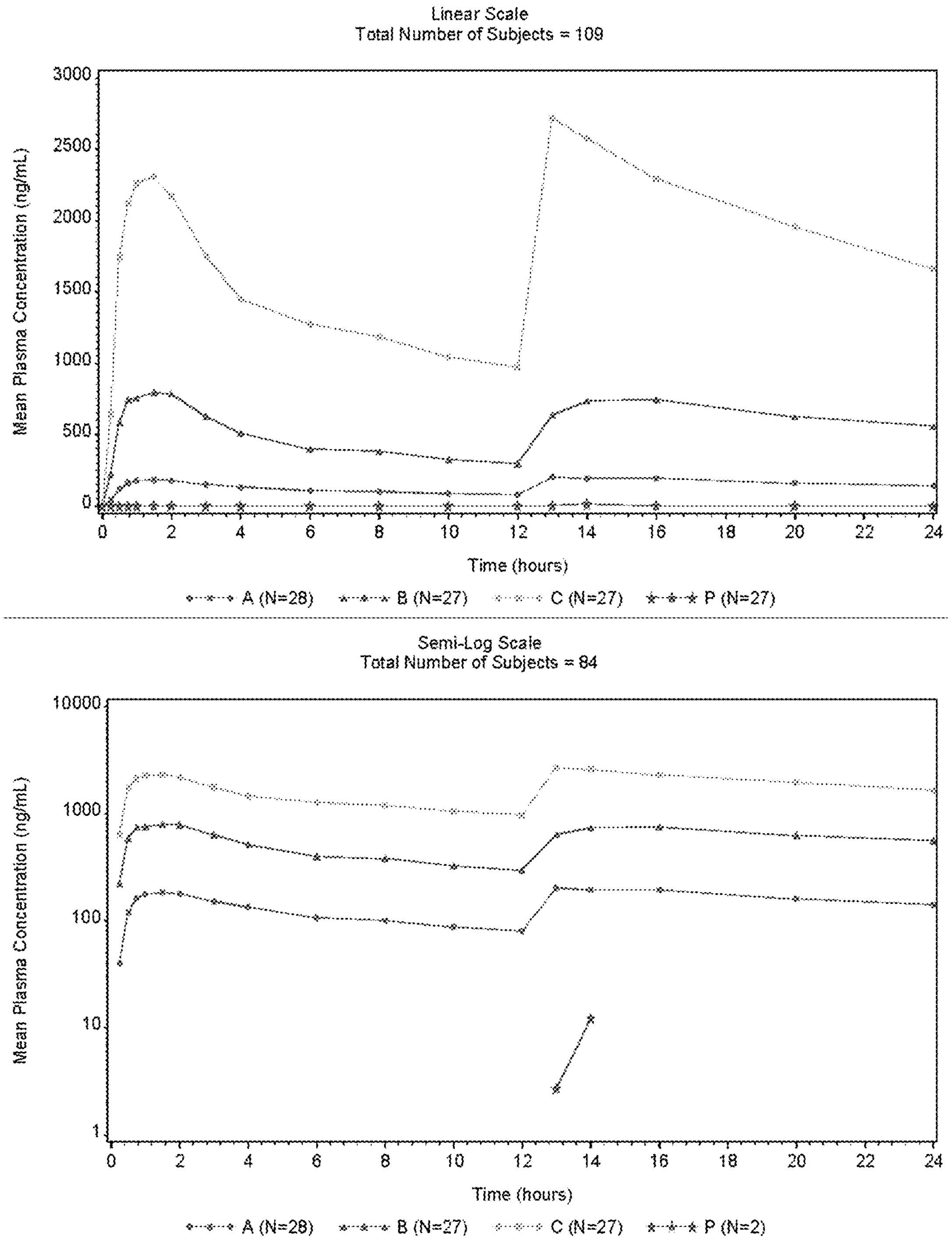

Both $C_{max}$ and AUC showed linear kinetics (FIG. 9 and Table 11 below). Mean plasma concentrations of meloxicam over time were dose proportional, with accumulation after the second dose of meloxicam. Mean $C_{max}$ after the first and second doses ranged from 196.6 ng/mL and 231.7 ng/ml, respectively, for meloxicam 1.25 mg to 2517.9 ng/ml and 2976.1 ng/ml, respectively, for meloxicam 15 mg. Mean $AUC_{0-24}$ ranged from 3418.3 ng*hr/mL for meloxicam 1.25 mg BID to 41741.9 ng*hr/mL for 15 mg BID. Mean values for $AUC_{0-12}$ and $AUC_{12-24}$ for each treatment group are included in Table 12 below.

All subjects in the meloxicam 15 mg group achieved a plasma meloxicam concentration greater than 1090 ng/ml by 1 hour after the first dose, and all except 1 subject in this dose group achieved a plasma concentration greater than 1090 ng/ml by 1 hour after the second dose. One subject in the meloxicam 15 mg group had plasma concentrations of 937.90 ng/ml and 908.00 ng/ml at Hour 13 and Hour 14, respectively (1 and 2 hours, respectively, following the second dose); however, the subject's plasma concentration increased to 1449.0 ng/mL at Hour 15 (3 hours following the second dose).

No subject in the meloxicam 1.25 mg dose group achieved a plasma meloxicam concentration of 1090 ng/mL or greater, and only 4 subjects in the meloxicam 5 mg group achieved this plasma concentration.

TABLE 11

| Mean Values for Meloxicam Pharmacokinetic Parameters (Population: Pharmacokinetic Analysis Set) | | | | |
|---|---|---|---|---|
| | MELO-TFZ 1.25 mg BID | MELO-TFZ 5 mg BID | MELO-TFZ 15 mg BID | Placebo 1.25 mg BID |
| After first dose | | | | |
| Mean $C_{max}$ (ng/ml) | 196.6 | 858.8 | 2517.9 | 0 |
| Mean $t_{max}$ (hr) | 1.465 | 1.531 | 1.447 | — |
| Mean $AUC_{0-12}$ ng*hr/mL | 1388.3 | 5558.9 | 16633.8 | 0 |
| After second dose | | | | |
| Mean $C_{max}$ (ng/mL) | 231.7 | 844.1 | 2976.1 | 14.9 [1] |
| Mean $t_{max}$ (hr) | 2.476 | 2.836 | 1.830 | 1.450 [1] |
| Mean $AUC_{12-24}$ ng*hr/mL | 2030.0 | 7739.1 | 25108.1 | 21.5 [1] |
| After both doses | | | | |
| Mean $AUC_{0-24}$ (ng*hr/mL) | 3418.3 | 13298.1 | 41741.9 | 21.6 [1] |

AUC = area under the concentration-versus-time curve;
$AUC_{0-12}$ = AUC from time 0 to 12 hours after dosing (first dose);
$AUC_{0-24}$ = AUC from time 0 to 24 hours after dosing (first dose);
$AUC_{12-24}$ = AUC from 12 to 24 hours after dosing (first dose but includes second dose);
BID = twice daily;
$C_{max}$ = maximum plasma concentration;

TABLE 11-continued

| Mean Values for Meloxicam Pharmacokinetic Parameters (Population: Pharmacokinetic Analysis Set) | | | |
| --- | --- | --- | --- |
| MELO-TFZ 1.25 mg BID | MELO-TFZ 5 mg BID | MELO-TFZ 15 mg BID | Placebo 1.25 mg BID |

PK = pharmacokinetic;

$t_{max}$ = time to maximum plasma concentration

[1] Subject 201-0024 in the meloxicam 1.25 group and Subject 201-0027 in the placebo group had an apparent PK sample swap at the 14-hour time point. Subject 201-0024 had no meloxicam inher sample, and Subject 201-0027 had measurable meloxicam in his sample. The laboratory assumed this was a sample swap because the samples were collected on the same date within 5 minutes of each other.

In addition, the 13-hour sample for Subject 201-0116 in the placebo group appeared to have been swapped with another subject's based on his treatment assignment and what the PK sample showed. The laboratory was not able to identify the subject with whom the sample had been swapped.

The following Table 12 further shows AUC for different parts of the 24 hours after first dose.

TABLE 12

| Mean (% CV) Meloxicam PK Parameters from Phase 2b Study 2001 | | | |
| --- | --- | --- | --- |
| Parameter | 1.25 mg BID (n = 28) | 5 mg BID (n = 27) | 15 mg BID (n = 27) |
| Cmax, after 1st Dose (ng/mL) | 196.6 (24.6%) | 858.8 (19.9%) | 2517.9 (21.6%) |
| Cmax, after 2nd Dose (ng/mL) | 231.7 (32.9%) | 844.1 (22.7%) | 2976.1 (28.7%) |
| Cmax, overall (ng/mL) | 241.6 (27.5%) | 927.1 (18.5%) | 3123.3 (21.6%) |
| Tmax, after 1st Dose (hr)[1] | 1.225 (0.5-2.967) | 1.00 (0.483-8.017) | 0.967 (0.467-5.950) |
| Tmax, after 2nd Dose (hr)[1] | 1.958 (0.867-7.950) | 1.967 (0.900-11.88) | 1.033 (0.817-7.883) |
| Tmax, after 2nd Dose (hr) [1,2] | 13.958 (12.867-19.967) | 13.967 (12.933-23.917) | 13.033 (12.833-19.883) |
| $AUC_{0-2}$ h (ng*hr/mL) | 283.9 (29.4%) | 1269.3 (24.4%) | 3680.3 (28.6%) |
| $AUC_{0-4\,h}$ (ng*hr/mL) | 589.4 (25.4%) | 2538.7 (19.5%) | 7218.7 (19.0%) |
| $AUC_{0-8\,h}$ (ng*hr/mL) | 1034.4 (25.6%) | 4232.1 (16.5%) | 12389.2 (16.7%) |
| $AUC_{0-12\,h}$ (ng*hr/mL) | 1388.3 (25.8%) | 5558.9 (16.0%) | 16633.8 (16.7%) |
| $AUC_{12-24\,h}$ (ng*hr/mL) | 2030.0 (28.8%) | 7739.1 (19.6%) | 25108.1 (25.1%) |
| $AUC_{0-24\,h}$ (ng*hr/mL) | 3418.3 (25.8%) | 13298.1 (17.6%) | 41741.9 (21.0%) |

[1]Median (Minimum – Maximum)

[2] Tpeak after 2nd dose relative to first dose administration (Time 0)

2.5 Efficacy Conclusions from Phase 2b Study

The primary efficacy endpoint was the $SPID_{0-24}$ for meloxicam versus placebo in the mITT Analysis Set with rescue medication use managed by W6LOCF. In the primary endpoint analysis, mean $E_{max}$ estimates for $SPID_{0-24}$ increased with meloxicam dose: 70.7, 86.7, and 94.8 for meloxicam 1.25 mg, meloxicam 5 mg, and meloxicam 15 mg, respectively, versus 52.0 for placebo. The $E_{max}$ estimate difference between meloxicam and placebo was statistically significant for meloxicam 5 mg (p<0.001) and meloxicam 15 mg (p<0.001), but not for meloxicam 1.25 mg (p=0.123). The results of the sensitivity analyses using W4LOCF and W8LOCF were similar to those for the primary endpoint analysis using W6LOCF, with a dose-effect pattern for $SPID_{0-24}$ and statistically significant $E_{max}$ estimate of the difference from placebo for the meloxicam 5 mg (p<0.001 for W4LOCF; p=0.002 for W8LOCF) and meloxicam 15 mg (p<0.001 for W4LOCF; p<0.001 for W8LOCF) groups, but not the meloxicam 1.25 mg group (p=0.101 for W4LOCF; p=0.159 for W8LOCF).

A third sensitivity analysis of the primary endpoint analysis using the W6LOCF approach but excluding time points with perceptible and meaningful pain relief also showed an increase in $SPID_{0-24}$ with increased meloxicam dose, with significant treatment group differences (meloxicam versus placebo) for the meloxicam 5 mg (p<0.001) and meloxicam 15 mg (p<0.001) groups, but not the meloxicam 1.25 mg group (p=0.122).

The analysis of the primary endpoint was also repeated for the PP Analysis Set, and the findings were similar to those for the mITT Analysis Set.

The $SPID_{0-24}$ was also evaluated with no censoring and with all values censored following rescue medication use (ALLOCF). Both approaches showed statistically significant $E_{max}$ estimates of the difference from placebo for the meloxicam 5 mg (p=0.016 for no censoring; p<0.001 for ALLOCF) and meloxicam 15 mg (p<0.001 for both approaches) groups, but not for the meloxicam 1.25 mg group (p=0.249 for no censoring; p=0.079 for ALLOCF).

The results for $SPID_{0-2}$, $SPID_{0-4}$, $SPID_{0-8}$, $SPID_{0-12}$, and $SPID_{12-24}$ using W6LOCF for the mITT Analysis Set were similar to those for the primary endpoint of $SPID_{0-24}$ using W6LOCF, with the addition of a statistically significant $E_{max}$ estimate of the difference between the meloxicam 1.25 mg and placebo groups for $SPID_{0-2}$ and $SPID_{0-4}$. Other censoring approaches for SPID by time interval followed a pattern similar to that for the W6LOCF censoring approach.

In the analysis of NRS pain scores over time using the W6LOCF approach, LS mean scores were numerically lower in all 3 meloxicam groups than in the placebo group by Hour 0.5 and remained lower than in the placebo group through Hour 24. At all nominal time points from Hour 1 to Hour 20, LS mean scores were numerically lowest in the meloxicam 15 mg group; after Hour 20, at Hour 24, scores were similar across the meloxicam dose groups (2.6, 2.8, and 2.7 for meloxicam 1.25 mg, meloxicam 5 mg, and meloxicam 15 mg, respectively), but still lower than in the placebo group (3.5). At all nominal time points from Hour 0.5 to Hour 20, excluding Hour 7, LS mean NRS pain scores were numerically lower in the meloxicam 5 mg group than in the meloxicam 1.25 mg group; at Hour 7, scores in the meloxicam 1.25 mg and meloxicam 5 mg groups were the same (4.7).

In analyses of NRS pain scores over time using other censoring approaches, LS mean NRS pain scores in the 3 meloxicam dose groups showed a greater downward trend than the scores in the placebo group from Hour 0.5 to Hour 2. With only a few exceptions, LS mean scores in each of the meloxicam dose groups remained numerically lower than in the placebo group from Hour 0.5 through Hour 24.

When matched for censoring approach, the analyses of PIDs over time were consistent with the analyses of NRS pain scores over time; the PID at each time point was proportional to NRS pain score at that time point such that larger PIDs corresponded with lower NRS pain scores.

The 15 mg meloxicam group also showed the following statistically significant analgesic effects over placebo, with statistically significant findings for the other 2 meloxicam dose groups noted:

Shorter median time to first perceptible relief of pain ($p<0.001$); also, statistically significant for meloxicam 1.25 mg ($p=0.021$) and meloxicam 5 mg ($p=0.004$)

- Shorter median time to first meaningful pain relief ($p<0.001$)
- Greater proportion of 30% pain responders ($p<0.001$); also, statistically significant for meloxicam 1.25 mg ($p=0.019$) and meloxicam 5 mg ($p=0.009$)
- Greater proportion of 50% pain responders ($p<0.001$)
- Greater proportion of PGA responders ($p<0.001$); also, statistically significant for meloxicam 1.25 mg ($p=0.042$) and meloxicam 5 mg ($p=0.010$)
- Smaller proportion of subjects using rescue medication ($p<0.001$); also, statistically significant for meloxicam 1.25 mg ($p=0.019$)
- Smaller proportion of subjects using rescue medication prior to the second dose of study drug ($p<0.001$); also, statistically significant for meloxicam 1.25 mg ($p=0.019$)
- Longer median time to first rescue medication use ($p<0.001$); also, statistically significant for meloxicam 1.25 mg ($p=0.017$)
- Lower number of times rescue medication was used ($p<0.001$); also, statistically significant for meloxicam 1.25 mg ($p=0.031$) and meloxicam 5 mg ($p=0.044$)

For each of the dosing regimens, meloxicam exposure was as expected with respect to dose proportionality and accumulation for the dosing regimen. All subjects in the meloxicam 15 mg group achieved a plasma meloxicam concentration greater than 1090 ng/ml by 1 hour after the first dose.

The Phase 2b study described herein met the primary objectives of evaluating the efficacy of MR-107A-02 in subjects following dental surgery and establishing the dose-response relationship. Compared with placebo, both the meloxicam 5 mg BID and the meloxicam 15 mg BID regimens resulted in a significantly greater reduction in acute postoperative dental pain, as measured by $SPID_{0-24}$. The analgesic response was dose related, with meloxicam 1.25 mg dose achieving a numerically, but not statistically significant, greater reduction in $SPID_{0-24}$ than placebo.

The following Table 13 presents an overall summary of TEAEs in the Safety Analysis Set. Overall, 33 subjects (30.0%) reported 45 TEAEs during the study. The proportion of subjects reporting TEAEs was greater (by a factor of 2 or more) in the meloxicam 5 mg, meloxicam 15 mg, and placebo groups (39.3%, 37.0%, and 29.6%, respectively) than in the meloxicam 1.25 mg group (14.3%). Sixteen subjects (14.5%) reported at least 1 TEAE considered related to treatment, with the proportion being greater in the meloxicam 5 mg, meloxicam 15 mg, and placebo groups (17.9%, 14.8%, and 18.5%, respectively) than in the meloxicam 1.25 mg group (7.1%). All TEAEs were either mild or moderate in severity, with no severe TEAEs reported. No subject experienced a serious TEAE or discontinued from the study because of a TEAE.

TABLE 13

Summary of Adverse Events (Population: Safety Analysis Set), Phase 2b

| | MELO-TFZ 1.25 mg BID (N = 28) n (%) | MELO-TFZ 5 mg BID (N = 28) n (%) | MELO-TFZ 15 mg BID (N = 27) n (%) | Placebo (N = 27) n (%) | Total (N = 110) n (%) |
|---|---|---|---|---|---|
| TEAEs | | | | | |
| Total Number | 4 | 14 | 14 | 13 | 45 |
| Number of subjects with any | 4 (14.3) | 11 (39.3) | 10 (37.0) | 8 (29.6) | 33 (30.0) |
| TEAEs by Severity | | | | | |
| Mild | 3 (10.7) | 9 (32.1) | 7 (25.9) | 7 (25.9) | 26 (23.6) |
| Moderate | 1 (3.6) | 2 (7.1) | 3 (11.1) | 1 (3.7) | 7 (6.4) |
| Severe | 0 | 0 | 0 | 0 | 0 |
| TEAEs resulting in study discontinuation | | | | | |
| Total Number | 0 | 0 | 0 | 0 | 0 |
| Number of subjects with any | 0 | 0 | 0 | 0 | 0 |

TABLE 13-continued

Summary of Adverse Events (Population: Safety Analysis Set), Phase 2b

| | MELO-TFZ 1.25 mg BID (N = 28) n (%) | MELO-TFZ 5 mg BID (N = 28) n (%) | MELO-TFZ 15 mg BID (N = 27) n (%) | Placebo (N = 27) n (%) | Total (N = 110) n (%) |
|---|---|---|---|---|---|
| Treatment-related TEAEs | | | | | |
| Total Number | 2 | 5 | 6 | 5 | 18 |
| Number of subjects with any | 2 (7.1) | 5 (17.9) | 4 (14.8) | 5 (18.5) | 16 (14.5) |
| Serious TEAEs | | | | | |
| Total Number | 0 | 0 | 0 | 0 | 0 |
| Number of subjects with any | 0 | 0 | 0 | 0 | 0 |

BID = twice daily; TEAE = treatment-emergent adverse event

Note:

Treatment-emergent adverse events included all events starting after the administration of investigational product.

The following Table 14 summarizes the subject incidence of TEAEs in the Safety Analysis Set by SOC and preferred term. The most common (≥10% of all subjects) SOCs of TEAEs were gastrointestinal disorders (14.5%) and nervous system disorders (11.8%). The incidence of TEAEs in each of these SOCs was greater (by a factor of 2 or more) in the meloxicam 5 mg, meloxicam 15 mg, and placebo groups than in the meloxicam 1.25 mg group (gastrointestinal disorders: 21.4%, 14.8%, and 18.5%, for meloxicam 5 mg, meloxicam 15 mg, and placebo, respectively, versus 3.6% for meloxicam 1.25 mg; nervous system disorders: 17.9%, 11.1%, and 14.8% for meloxicam 5 mg, meloxicam 15 mg, and placebo, respectively, versus 3.6% for meloxicam 1.25 mg).

The most common (≥2% of all subjects) preferred terms of TEAEs were nausea (9.1%), headache (5.5%), dizziness (3.6%), vomiting (2.7%), and syncope (2.7%). All other preferred terms of TEAEs were each reported in no more than 2 subjects. The incidence of the most common preferred term, nausea, was greater in the meloxicam 5 mg group (17.9%) than in the meloxicam 1.25 mg, meloxicam 15 mg, and placebo groups (3.6%, 7.4%, and 7.4%, respectively), whereas the incidence of the second most common preferred term, headache, was greater in the placebo group (11.1%) than in the meloxicam 1.25 mg, meloxicam 5 mg, and meloxicam 15 mg groups (0%, 3.6%, and 7.4%, respectively). Comparisons of the incidence of other preferred terms of TEAEs across treatment groups were limited by the low number of subjects (n≤2) reporting events in any treatment group. Overall, no dose-effect pattern was observed with respect to the incidence of common TEAEs.

TABLE 14

Summary of Treatment-Emergent Adverse Events by System Organ Class, Preferred Term, and Treatment (Population: Safety Analysis Set), Phase 2b

| System Organ Class Preferred Term | MELO-TFZ 1.25 mg BID (N = 28) n(%) [count] | MELO-TFZ 5 mg BID (N = 28) n(%) [count] | MELO-TFZ 15 mg BID (N = 27) n(%) [count] | Placebo (N = 27) n(%) [count] | Total (N = 110) n(%) [count] |
|---|---|---|---|---|---|
| Subjects with any event | 4 (14.3) [4] | 11 (39.3) [14] | 10 (37.0) [14] | 8 (29.6) [13] | 33 (30.0) [45] |
| Gastrointestinal disorders | 1 (3.6) [1] | 6 (21.4) [7] | 4 (14.8) [6] | 5 (18.5) [6] | 16 (14.5) [20] |
| Nausea | 1 (3.6) [1] | 5 (17.9) [6] | 2 (7.4) [2] | 2 (7.4) [2] | 10 (9.1) [11] |
| Vomiting | 0 (0.0) [0] | 0 (0.0) [0] | 2 (7.4) [3] | 1 (3.7) [1] | 3 (2.7) [4] |
| Diarrhoea | 0 (0.0) [0] | 0 (0.0) [0] | 0 (0.0) [0] | 2 (7.4) [2] | 2 (1.8) [2] |
| Abdominal pain | 0 (0.0) [0] | 1 (3.6) [1] | 0 (0.0) [0] | 0 (0.0) [0] | 1 (0.9) [1] |
| Abdominal pain upper | 0 (0.0) [0] | 0 (0.0) [0] | 1 (3.7) [1] | 0 (0.0) [0] | 1 (0.9) [1] |
| Aphthous ulcer | 0 (0.0) [0] | 0 (0.0) [0] | 0 (0.0) [0] | 1 (3.7) [1] | 1 (0.9) [1] |
| Injury, poisoning and procedural complications | 0 (0.0) [0] | 0 (0.0) [0] | 1 (3.7) [1] | 0 (0.0) [0] | 1 (0.9) [1] |
| Incision site discharge | 0 (0.0) [0] | 0 (0.0) [0] | 1 (3.7) [1] | 0 (0.0) [0] | 1 (0.9) [1] |
| Investigations | 2 (7.1) [2] | 0 (0.0) [0] | 1 (3.7) [1] | 0 (0.0) [0] | 3 (2.7) [3] |
| Blood bilirubin increased | 2 (7.1) [2] | 0 (0.0) [0] | 0 (0.0) [0] | 0 (0.0) [0] | 2 (1.8) [2] |
| White blood cell count increased | 0 (0.0) [0] | 0 (0.0) [0] | 1 (3.7) [1] | 0 (0.0) [0] | 1 (0.9) [1] |
| Metabolism and nutrition disorders | 0 (0.0) [0] | 1 (3.6) [1] | 1 (3.7) [1] | 0 (0.0) [0] | 2 (1.8) [2] |
| Dehydration | 0 (0.0) [0] | 1 (3.6) [1] | 0 (0.0) [0] | 0 (0.0) [0] | 1 (0.9) [1] |
| Hyperglycemia | 0 (0.0) [0] | 0 (0.0) [0] | 1 (3.7) [1] | 0 (0.0) [0] | 1 (0.9) [1] |
| Nervous system disorders | 1 (3.6) [1] | 5 (17.9) [5] | 3 (11.1) [4] | 4 (14.8) [7] | 13 (11.8) [17] |
| Headache | 0 (0.0) [0] | 1 (3.6) [1] | 2 (7.4) [2] | 3 (11.1) [4] | 6 (5.5) [7] |
| Dizziness | 0 (0.0) [0] | 1 (3.6) [1] | 2 (7.4) [2] | 1 (3.7) [2] | 4 (3.6) [5] |
| Syncope | 1 (3.6) [1] | 1 (3.6) [1] | 0 (0.0) [0] | 1 (3.7) [1] | 3 (2.7) [3] |
| Hypoaesthesia | 0 (0.0) [0] | 1 (3.6) [1] | 0 (0.0) [0] | 0 (0.0) [0] | 1 (0.9) [1] |
| Migraine | 0 (0.0) [0] | 1 (3.6) [1] | 0 (0.0) [0] | 0 (0.0) [0] | 1 (0.9) [1] |
| Respiratory, thoracic and mediastinal disorders | 0 (0.0) [0] | 1 (3.6) [1] | 1 (3.7) [1] | 0 (0.0) [0] | 2 (1.8) [2] |

TABLE 14-continued

Summary of Treatment-Emergent Adverse Events by System Organ Class, Preferred Term, and Treatment (Population: Safety Analysis Set), Phase 2b

| System Organ Class Preferred Term | MELO-TFZ 1.25 mg BID (N = 28) n(%) [count] | MELO-TFZ 5 mg BID (N = 28) n(%) [count] | MELO-TFZ 15 mg BID (N = 27) n(%) [count] | Placebo (N = 27) n(%) [count] | Total (N = 110) n(%) [count] |
|---|---|---|---|---|---|
| Cough | 0 (0.0) [0] | 1 (3.6) [1] | 0 (0.0) [0] | 0 (0.0) [0] | 1 (0.9) [1] |
| Epistaxis | 0 (0.0) [0] | 0 (0.0) [0] | 1 (3.7) [1] | 0 (0.0) [0] | 1 (0.9) [1] |

BID = twice daily;

MedDRA = Medical Dictionary for Regulatory Activities

Note:

n is the number of unique subjects with at least 1 occurrence of the event; count is the number of events.

Note:

A subject reporting more than 1 adverse event for a system organ class and preferred term was counted only once for that system organ class and preferred term combination.

Note:

Adverse events are sorted alphabetically by system organ class and then by descending order of frequency for the total subject column within each system organ class.

Note:

Treatment-emergent adverse events included all events starting after the administration of investigational product.

Note:

Adverse events were coded using MedDRA Version 25.0.

All TEAEs reported during the study were either mild or moderate in severity, with 23.6% of the Safety Analysis Set reporting a maximum severity of mild and 6.4% reporting a maximum severity of moderate. The incidence of a maximum TEAE severity of mild was greater (by a factor of 2 or more) in the meloxicam 5 mg, meloxicam 15 mg, and placebo groups (32.1%, 25.9%, and 25.9%, respectively) than in the meloxicam 1.25 mg group (10.7%). The incidence of a maximum TEAE severity of moderate was greater in the meloxicam 15 mg group (11.1%) than in the meloxicam 1.25 mg and placebo groups (3.6% and 3.7%, respectively), with the incidence in the meloxicam 5 mg group (7.1%) falling between the higher and lower of these.

The moderate TEAEs included nausea (3 subjects [2.7%] overall), vomiting (2 subjects [1.8%]), diarrhea (1 subject [0.9%]), incision site discharge (1 subject [0.9%]), and dehydration (1 subject [0.9%]). Except for diarrhea, all moderate events were reported in 1 or more of the meloxicam treatment groups, with diarrhea being reported only in the placebo group.

A total of 16 subjects (14.5% of the Safety Analysis Set and 48.5% of the 33 subjects reporting TEAEs) reported at least 1 TEAE considered related to study drug. The incidence of related TEAEs was greater (by a factor of 2 or more) in the meloxicam 5 mg, meloxicam 15 mg, and placebo groups (17.9%, 14.8%, and 18.5%, respectively) than in the meloxicam 1.25 mg group (7.1%).

The preferred terms of related TEAEs included nausea (9 subjects [8.2%] overall), vomiting (3 subjects [2.7%], diarrhea (2 subjects [1.8%]), abdominal pain (1 subject [0.9%]), abdominal pain upper (1 subject [0.9%]), and blood bilirubin increased (1 subject [0.9%]). The incidence of the most common related preferred term, nausea, was 3.6% in the meloxicam 1.25 mg group, 14.3% in the meloxicam 5 mg group, 7.4% in the meloxicam 15 mg group, and 7.4% in the placebo group. Other preferred terms of related TEAEs reported in subjects treated with meloxicam included vomiting (2 subjects [7.4%] in the meloxicam 15 mg group versus 1 subject [3.7%] in the placebo group), abdominal pain (1 subject [3.6%] in the meloxicam 5 mg group versus 0 subjects [0%] in the placebo group), abdominal pain upper (1 subject [3.7%] in the meloxicam 15 mg group versus 0 subjects [0%] in the placebo group), and blood bilirubin increased (1 subject [3.6%] in the meloxicam 1.25 mg group versus 0 subjects [0%] in the placebo group). Diarrhea considered related to study drug was reported only in the placebo group (2 subjects [7.4%]).

No deaths were reported during the study. No SAEs were reported during the study. No AE led to discontinuation of study treatment. No AESIs were reported during the study.

2.6 Safety Conclusions from Phase 2b Study

During the study, 33 subjects (30.0%) in the Safety Analysis Set reported at least 1 TEAE. The proportion of subjects reporting TEAEs was greater (by a factor of 2 or more) in the meloxicam 5 mg, meloxicam 15 mg, and placebo groups (39.3%, 37.0%, and 29.6%, respectively) than in the meloxicam 1.25 mg group (14.3%). The most common (overall incidence≥2%) preferred terms of TEAEs were nausea (9.1%), headache (5.5%), dizziness (3.6%), vomiting (2.7%), and syncope (2.7%). The incidence of the most common preferred term of TEAE, nausea, was greater in the meloxicam 5 mg BID group (17.9%) than in the meloxicam 1.25 mg, meloxicam 15 mg, and placebo groups (3.6%, 7.4%, and 7.4%, respectively), whereas the incidence of the second most common preferred term, headache, was greater in the placebo group (11.1%) than in the meloxicam 1.25 mg, meloxicam 5 mg, and meloxicam 15 mg groups (0%, 3.6%, and 7.4%, respectively). Overall, no dose-effect pattern was observed with respect to the incidence of common TEAEs.

Sixteen subjects (14.5% of the Safety Analysis Set) reported at least 1 TEAE considered related to study drug, with the proportion being greater (by a factor of 2 or more) in the meloxicam 5 mg, meloxicam 15 mg, and placebo groups (17.9%, 14.8%, and 18.5%, respectively) than in the meloxicam 1.25 mg group (7.1%). The most common related TEAEs were nausea (8.2% overall) and vomiting (2.7%).

All TEAEs reported during the study were either mild or moderate in severity. No deaths, SAEs, AEs leading to discontinuation of study treatment, or AESIs were reported.

Clinical laboratory tests showed a possible dose-related pattern for the mean change in lymphocyte count from baseline, with a possible inverse dose-related pattern for the mean change in leukocyte, monocyte, and neutrophil counts from baseline. These findings may reflect an anti-inflammatory effect of meloxicam; however, the size of the treatment groups (N=27 to 28) limits interpretation of these descriptive data. Vital sign measurements and ECG findings showed no clinically meaningful trends or abnormalities to suggest a drug effect.

Treatment with MR-107A-02 1.25 mg BID, meloxicam 5 mg BID, and meloxicam 15 mg BID in subjects with acute postoperative pain following dental surgery was generally safe and well tolerated. No dose effect pattern was observed with respect to TEAEs, vital signs, or ECG findings.

2.7 Conclusion

This Phase 2b, randomized, double-blind, placebo-controlled, dose-ranging study evaluated the efficacy and dose-response relationship of 3 different doses of our investigatory meloxicam composition administered BID in subjects following dental surgery. The primary efficacy endpoint was the $SPID_{0-24}$ for meloxicam versus placebo in the mITT Analysis Set with rescue medication use managed by W6LOCF censoring. The W6LOCF approach was employed to account for the analgesic effect of the rescue medication while avoiding censoring of large amounts of data in the placebo and lower-dose meloxicam groups. The W4LOCF and W8LOCF censoring approaches were also explored as sensitivity analyses of the primary endpoint.

Both the meloxicam 5 mg and meloxicam 15 mg dose groups met the primary efficacy endpoint, with statistically significant differences from placebo in the $E_{max}$ estimates for $SPID_{0-24}$ ($p<0.001$ for both treatment groups). The treatment effect was numerically largest for the meloxicam 15 mg group. The sensitivity analyses using W4LOCF and W8LOCF censoring approaches showed similar results, as did a third sensitivity analysis using W6LOCF but excluding time points with perceptible and meaningful pain relief. The treatment effect for the meloxicam 1.25 mg dose in the primary efficacy and sensitivity analyses was not statistically significant, although the $SPID_{0-24}$ $E_{max}$ estimates for the 1.25 mg dose were numerically greater than placebo.

All 3 meloxicam dose groups showed statistically significant ($p\leq0.05$) results over placebo for other measures of analgesic efficacy, including the median time to first perceptible relief of pain, proportion of 30% pain responders, proportion of PGA responders, and mean number of times rescue medication was used. Further, compared with placebo, both the meloxicam 1.25 mg and meloxicam 15 mg dose groups had significantly smaller proportions of subjects using rescue medication and longer median times to rescue medication use. In addition, the meloxicam 15 mg group, but not the meloxicam 1.25 mg and meloxicam 5 mg groups, had a significantly shorter median time to first meaningful pain relief and greater proportion of 50% pain responders. For all measures of analgesic efficacy, the meloxicam 15 mg group showed the numerically largest effect.

For each of the dosing regimens, meloxicam exposure was as expected with respect to dose proportionality and accumulation for the dosing regimen. Both $C_{max}$ and AUC showed linear pharmacokinetics. All subjects in the meloxicam 15 mg group achieved a plasma meloxicam concentration greater than 1090 ng/mL by 1 hour after the first dose.

The most common TEAEs in the study were nausea, headache, dizziness, vomiting, and syncope, which were consistent with the postoperative state and prior clinical experience with meloxicam. All TEAEs were mild or moderate in severity, with no deaths, SAEs, AEs leading to discontinuation of study treatment, or AESIs reported. No dose-effect pattern was observed with respect to the incidence of common TEAEs. Clinical laboratory test results, vital sign measurements, and ECG findings showed no clinically meaningful trends or abnormalities to suggest a drug effect.

In conclusion, in this Phase 2b study, treatment with our meloxicam formulation 5 mg BID and meloxicam 15 mg BID resulted in a statistically significant greater reduction in acute postoperative dental pain, as measured by $SPID_{0-24}$, than treatment with placebo. The response was dose related, with the meloxicam 1.25 mg dose achieving a numerically, but not statistically significant, greater reduction in $SPID_{0-24}$ than placebo. For the primary and all secondary efficacy endpoints, the meloxicam 15 mg dose showed the largest numeric treatment effect and was the only dose with a statistically significant treatment effect for every endpoint. With respect to a potential opioid-sparing effect, the meloxicam 15 mg group had lowest frequency of rescue medication use and the fewest subjects using rescue medication.

The 3 meloxicam dose regimens were generally safe and well tolerated. No dose effect pattern was observed with respect to TEAEs, vital signs, or ECG findings. Several laboratory tests associated with white blood cells showed a possible dose-related or inverse dose-related pattern, which could reflect an anti-inflammatory effect of meloxicam. The clinical meaningfulness of these findings is limited by small treatment group size (N=27 to 28).

Example III. Phase 3 Study Evaluating Efficacy and Safety of a Meloxicam Pharmaceutical Composition Following Surgery Two Phase 3 studies to demonstrate efficacy, safety, and opioid-reducing capacities of MR-107A-02 were conducted. Each study used a pain model (bunionectomy or herniorrhaphy) that is mentioned in the U.S. FDA's Guidance for Industry entitled, *Development of Non-Opioid Analgesics for Acute Pain* (FDA, 2022). The trials included a repeat-dose design based on the pain model. Both studies were active-(tramadol 50 mg immediate release) and placebo-controlled, had a 48-hour dosing in a hospital with study drug (MR-107A-02, placebo, and tramadol), followed by 5 days of out-patient treatment with study drug (MR-107A-02 or placebo).

In accordance with clinical standards to limit duration of opioid exposure to the shortest possible duration, the fixed opioid dose regimen was limited to the in-patient treatment phase; following discharge, subjects assigned to the tramadol arm received placebo. In case of insufficient pain control, subjects had access to rescue medication (first step acetaminophen, second step oxycodone) during the in-patient period as well as during the out-patient treatment period (5 days after discharge).

The primary endpoint for both studies was $SPID_{0-48}$ following the guidance recommendations (which is based on the change in pain intensity over a suitable time period). Also, in accordance with the guidance, there was a continued safety evaluation for 30 days after the last intake of study medication. Secondary endpoints for both studies included the number of doses of opioid rescue medication over the combined in-patient and out-patient treatment phases (key secondary endpoint), proportion of subjects using no opioid rescue medication (opioid-free) during various time intervals and scores to confirm the association of clinical benefit with reduced opioid use. Furthermore, secondary objectives included confirmation of the safety of MR-107A-02 in subjects following bunionectomy and herniorrhaphy surgery. Both studies were powered for the primary and the key secondary endpoint.

Bunionectomy and open inguinal herniorrhaphy are ideal surgical models to evaluate the safety and efficacy of analgesics for several reasons. Although both procedures are relatively common procedures performed either on inpatient or outpatient basis, they are considered painful and debilitating, suggesting the demonstration of efficacy in these surgical models likely provides more useful information than from less painful procedures. Both procedures are relatively benign surgical procedures and rarely result in life-threatening complications.

Study 3001 (Example III A herein) evaluated MR-107A-02 in the bony pain model of bunionectomy, and Study 3002 (Example III B herein) evaluated MR-107A-02 in the soft tissue pain model of herniorrhaphy.

Study 3001 enrolled 410 subjects undergoing bunionectomy and Study 3002 enrolled 579 subjects undergoing herniorrhaphy. Subjects were mostly female in Study 3001 (85.9%), whereas subjects were mostly male in Study 3002 (96.3%). Mean age and mean baseline Numeric Rating Scale at Rest (NRS-R) scores were similar across treatment groups in each study. Most subjects completed the study (96.8% in Study 3001 and 95.2% in Study 3002).

Example III A. MR-107A-02 Following Bunionectomy Surgery (Study 3001)

The study included both male and female human patients, all >18 years of age. Subject Disposition during the course of this study is depicted in FIG. 37 and FIG. 44.

In FIG. 44, "FAS" means Full Analysis Set: Randomized who received at least one (1) dose of study drug (MR-107A-02). "PP" means Per Protocol: Modified FAS with no major violations impacting 1° efficacy. Dosed subjects with baseline Pain Intensity score of <4 were excluded from PP.

Patients experiencing the requisite level of pain (score≥4 on an 11-point numeric rating scale-rest (NRS-R] from 0=no pain to 10=worst possible pain) after bunionectomy were randomized in a 1:1:1 ratio to receive MR-107A-02, 15 mg meloxicam (BID), placebo, or tramadol 50 mg (QID). The primary endpoint was the summed pain intensity difference over 0-48 hours ($SPID_{0-48}$) based on NRS-R for MR-107A-02 versus placebo. To quantify the onset of pain relief, times to perceptible and meaningful pain relief were measured using the double-stopwatch technique after the first dose.

In-patient Treatment Phase: Patients were dosed every six (6) hours over 48 hours for a total of eight (8) doses. The in-patient phase included MR-107A-02, tramadol and placebo. (To maintain the blind, subjects in the MR-107A-02 group received meloxicam active and meloxicam placebo alternately to allow for a q6h dosing of all subjects during the subject in-patient treatment phase.)

Out-patient Treatment Phase: Patients were dosed for five (5) days. Dosing was twice daily for a total of 10 doses. The out-patient phase included just MR-107A-02 and placebo. The tramadol subjects from the in-patient phase were given placebo for the out-patient phase.

Figure 10:
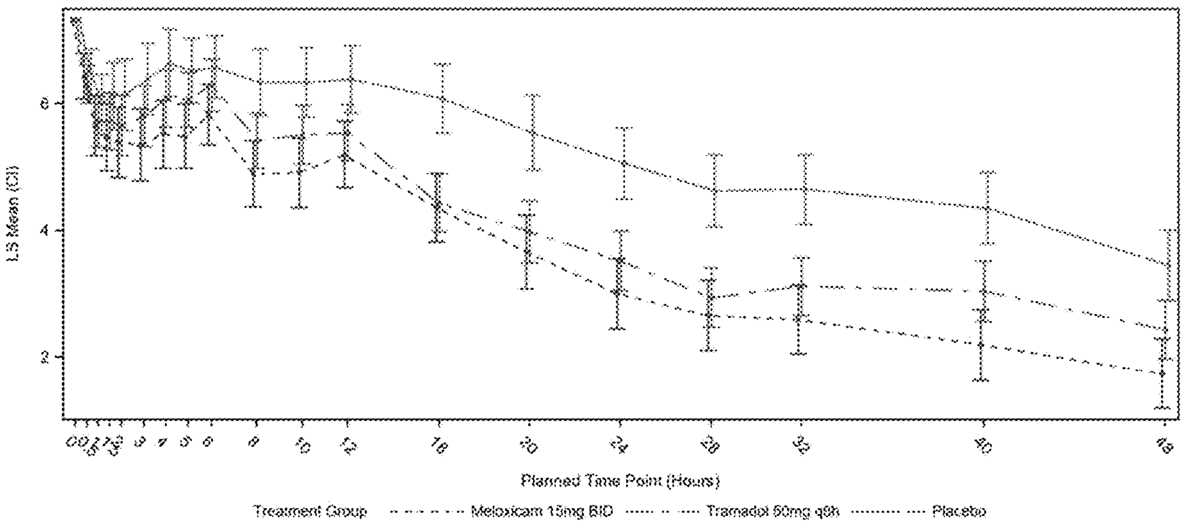
FIG. 10 is a graph showing the Efficacy results of the inpatient treatment phase of Study 3001 as a function of NRS-R Pain Scores (ANCOVA by Timepoint-FAS)

Certain efficacy results are shown in FIG. 10. The group given MR-107A-02 BID showed the lowest NRS-R scores (Numeric Rating Scale scores at rest) among all treatment groups over the whole in-patient treatment phase. "ANCOVA" means "analysis of covariance".

Table 15 details the number of doses of opioid (oxycodone and/or morphine) rescue medication over the entire treatment phase for the FAS (full analysis set). The group given MR-107A-02 had a 30% lower mean opioid use versus the placebo group (3 doses versus 4.3 doses) over the entire treatment period (including in-patient and out-patient treatment phase).

TABLE 15

Number of Doses of Opioid (Oxycodone and/or Morphine) Rescue Medication During Entire Treatment Phase (In- and Out-Patient) of Bunionectomy Study

| Variable<br>Statistic | Meloxicam<br>15 mg BID<br>(N = 137) | Placebo<br>(N = 136) |
|---|---|---|
| Number of doses of Opioid (Oxycodone and/or Morphine) | | |
| Rescue Medication | | |
| Mean | 3.0 | 4.3 |
| Median | 2 | 3 |
| Standard Deviation | 2.37 | 3.69 |
| Difference in Means | −1.3 | |
| LS Geometric Mean | 0.38 | 0.56 |
| 95% CI | (0.27, 0.54) | (0.41, 0.76) |
| Ratio of LS Geometric Means versus Placebo | 0.69 | |
| 95% CI for Ratio of LS Geometric Means | (0.53, 0.89) | |
| p-value for Ratio | 0.004 | |

Table 16 details the number and proportion of opioid-free subjects during the entire treatment phase for the FAS. The group given MR-107A-02 had 24% more opioid-free patients versus the placebo group (57% vs. 33%).

TABLE 16

Number and Proportion of Opioid (Oxycodone and/or Morphine) Free Subjects (Entire Treatment Phase)*

| | Meloxicam<br>15 mg BID<br>(N = 137) | Placebo<br>(N = 136) |
|---|---|---|
| Opioid (Oxycodone and/or Morphine) Free | 78 (56.9) | 45 (33.1) |
| Not Opioid (Oxycodone and/or Morphine) Free | 59 (43.1) | 91 (66.9) |
| Difference in proportions (95% CI ) versus Placebo | 23.8% (12.4%, 35.3%) | |
| p-value | <0.001 | |

*"Meloxicam 15 mg" is MR-107A-02.

The group given Composition 8 had a shorter time to perceptible pain relief versus both the group given placebo and the group given tramadol. Details are shown in Table 17. In Table 17, "Meloxicam 15 mg" is MR-107A-02.

TABLE 17

Time to Perceptible Pain Relief Bunionectomy Study; Population: Full Analysis Set

| | Meloxicam<br>15 mg BID<br>(N = 137) | Tramadol<br>50 mg q6h<br>(N = 137) | Placebo<br>(N = 136) |
|---|---|---|---|
| Subjects with event, n (%) | 97 (70.8) | 90 (65.7) | 76 (55.9) |
| Subjects censored, n (%) | 40 (29.2) | 47 (34.3) | 60 (44.1) |
| Time to event (hours) | | | |
| Q1 | 0.4 | 0.4 | 0.5 |
| Median (CI) [1] | 0.7 (0.6, 0.9) | 0.8 (0.6, 0.9) | 0.9 (0.6, 5.8) |
| Q3 | 2.6 | NA | NA |
| p-value (versus Placebo) [2] | 0.037 | 0.056 | |

[1] 95% CI for MR-107A-02 ("Meloxicam) and placebo. 90% CI for tramadol.
[2] 2-sided p-value for meloxicam. 1-sided p-value for tramadol.

Also, the group given MR-107A-02 had a shorter time to meaningful pain relief versus both the placebo group and the tramadol group (details in Table 18, wherein "Meloxicam 15 mg" is MR-107A-02).

TABLE 18

Time to Meaningful Pain Relief Bunionectomy Study; Population: Full Analysis Set

| | Meloxicam 15 mg BID (N = 137) | Tramadol 50 mg q6h (N = 137) | Placebo (N = 136) |
|---|---|---|---|
| Subjects with event, n (%) | 65 (47.4) | 55 (40.1) | 39 (28.7) |
| Subjects censored, n (%) | 72 (52.6) | 82 (59.9) | 97 (71.3) |
| Time to event (hours) | | | |
| Q1 | 1.1 | 1.2 | 2.0 |
| Median (CI) [1] | 2.4 (1.9, 3.0) | 3.4 (2.6, 4.9) | 5.1 (3.1, NA) |
| Q3 | NA | NA | NA |
| p-value (versus Placebo) [2] | 0.012 | 0.046 | |

[1] 95% CI for MR-107A-02 ("Meloxicam) and placebo. 90% CI for tramadol.
[2] 2-sided p-value for meloxicam. 1-sided p-value for tramadol.

With regard to Study 3001, MR-107A-02 BID demonstrated efficacy in treating acute pain following bunionectomy. The assay sensitivity was also shown as tramadol efficacy versus placebo was shown. MR-107A-02 $SPID_{0-48}$ h SES (0.66) was numerically higher than tramadol SES (0.48). In addition, less patients took opioid rescue medication in the group given MR-107A-02 than in the tramadol group (44% vs. 56%). The MR-107A-02 group had the longest median time to first rescue use (first opioid rescue use) among all groups. Subjects given MR-107A-02 BID had a shorter time to perceptible and meaningful pain relief versus both placebo and tramadol. The group given MR-107A-02 BID was numerically better than tramadol 50 mg q6h, thus showing MR-107A-02 provides at least comparable analgesic efficacy to an opioid.

Of the 410 randomized participants (137 MR-107A-02, 136 placebo, 137 tramadol; 85.9% females; 60% whites; mean [SD] age, 48 [13.4] years; weight range, 45-126 kg), 397 participants completed the study. Baseline NRS-R scores (mean [SD]) were similar across all the three groups (7.2 [1.67] MR-107A-02, 7.6 [1.73] placebo and 7.2 [1.64] tramadol).

The primary endpoint $SPID_{0-48}$ (NRS-R), comparing MR-107A-02 to placebo, was met. The least squares mean (SE) [95% CI] of $SPID_{0-48}$ (NRS-R) for MR-107A-02 was 183.9 (10.64) [163.0, 204.7] vs. 101.2 (10.83) [80.0, 122.4] for placebo with a treatment difference of 82.7 (10.54) [62.0, 103.4]; p<0.001. Assay sensitivity was demonstrated with tramadol versus placebo, showing a treatment difference of 58.0 (10.39) [40.9, 75.1]; p<0.001.

In a post-hoc analysis, MR-107A-02 showed a higher $SPID_{0-48}$ compared to tramadol: 174.3 (10.45) [153.8, 194.7] vs. 148.1 (10.66) [130.5, 165.6], with a treatment difference of 26.2 (10.58) [8.8, 43.6]; p=0.013.

MR-107A-02 had a shorter time to perceptible pain relief compared to placebo (median [CI], hours) (0.7 [0.6, 0.9] vs 0.9 [0.6, 5.8]; p=0.037) and tramadol (0.8 [0.6, 0.9]).

Time to meaningful pain relief was also shorter for MR-107A-02 compared to placebo (median [CI], hours) (2.4 [1.9, 3.0] vs 5.1 [3.1, NA]; p=0.012) and tramadol (3.4 [2.6, 4.9]). Both endpoints demonstrated a significantly faster onset of action for MR-107A-02 compared to placebo.

Overall, MR-107A-02 was well-tolerated with the fewest treatment emergent adverse events (TEAEs) among all groups. There were no severe or serious TEAEs reported in the MR-107A-02 group. During the in-patient treatment period, the most common adverse events (AEs) in the MR-107A-02 group were nausea (5.8%, MR-107A-02; 10.3%, placebo; 38.0%, tramadol), dizziness (2.9%, 6.6%, 18.2%), headache (6.6%, 4.4%, 6.6%) and pruritus (5.1%, 2.9%, 8.8%).

In Study 3001, the MR-107A-02 group had 24% more opioid-free patients compared to placebo (78 [56.9%] vs. 45 [33.1%]) with a significant difference in proportions (95% [CI]) (23.8% [12.4, 35.3], p<0.001). The MR-107A-02 group showed a 59% lower mean opioid rescue use vs. placebo (mean [SD]) (1.3 [2.16] vs. 2.9 [3.64] doses) with a significant ratio of LS geometric mean (95% [CI]) (0.41 [0.29, 0.58], p<0.001). Additionally, MR-107A-02 had fewer patients requiring opioid rescue (60 [43.8%] MR-107A-02, 92 [67.6%] placebo, 77 [56.2%] tramadol) or any rescue medication (110 [80.3%] MR-107A-02, 128 [94.1%] placebo, 127 [92.7%] tramadol), and the longest median time (hours) to first opioid or any rescue medication compared to placebo and tramadol groups.

To recapitulate, the investigational drug, MR-107A-02 (15 mg BID), was compared with an active control (tramadol 50 mg every 6 hours) and a placebo arm using a double-dummy design in patients having undergone bunionectomy.

Figure 11:
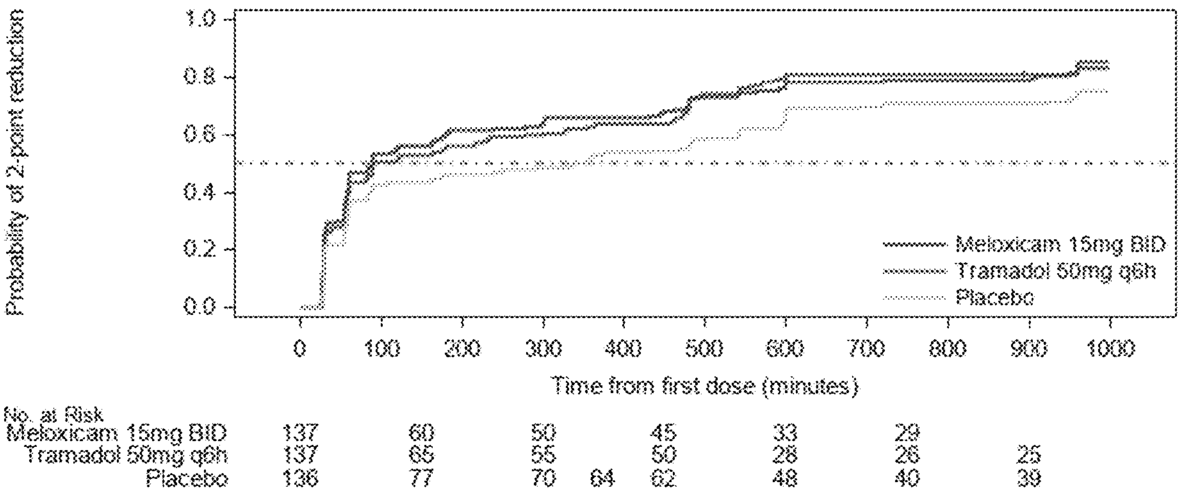
FIG. 11 is a graph showing the Time to 2-point Reduction in NRS-R, with WLOCF Censoring following Rescue Use.

Four hundred and ten (410) subjects were randomized and treated in 3 study arms (137:137:136; MELO:TRAM:PBO), with 397 completing the study. FIG. 11 shows that the median time to 2-point reduction (in minutes) in the NRS-R (95% CI) was 90.0 (60.0, 168.0) and 346.0 (90.0, 499.0) for MR-107A-02 and placebo, respectively. The MR-107A-02 arm was statistically separated from placebo at p<0.001 (post-hoc). For Tramadol, the median time to 2-point reduction in the NRS-R (90% CI) was 91.0 (60.0, 216.0), with the median time similar to that of the MR-107A-02 group.

Figure 12:
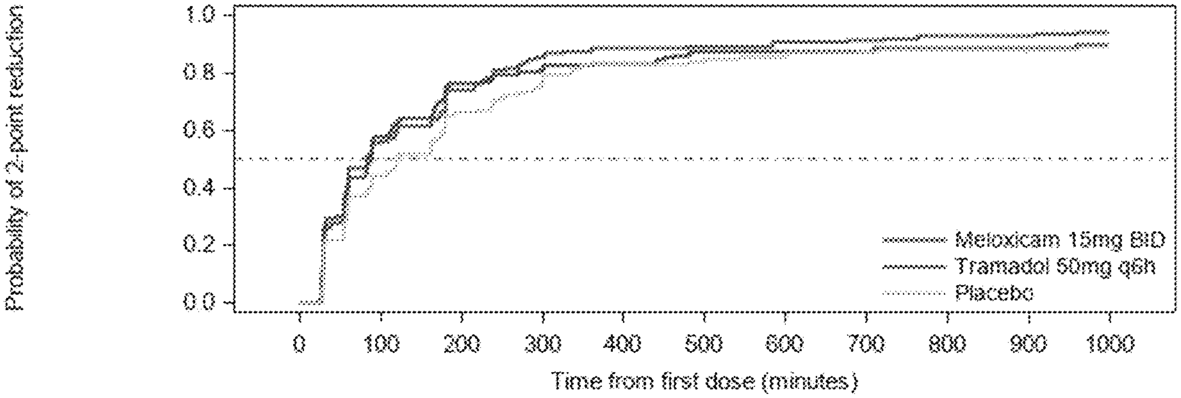
FIG. 12 is a graph showing the Time to 2-point Reduction in NRS-R, with No Censoring following Rescue Use.

FIG. 12 shows that the median time to 2-point reduction (in minutes) in the NRS-R (95% CI) was 83.0 (60.0, 109.0) and 120 (90.0, 174.0) for MR-107A-02 and placebo, respectively. The MR-107A-02 arm was statistically separated from placebo at p=0.044 (post-hoc). For Tramadol, the median time to 2-point reduction in the NRS-R (90% CI) was 90.0 (60.0, 109.0), which was comparable to the MR-107A-02 group.

The median time to 2-point reduction (in minutes) in the NRS-R (95% CI) was 83.0 (60.0, 109.0) and 120 (90.0, 174.0) for MR-107A-02 and placebo, respectively. The MR-107A-02 arm was statistically separated from placebo at p=0.044 (post-hoc). For Tramadol, the median time to 2-point reduction in the NRS-R (90% CI) was 90.0 (60.0, 109.0), which was comparable to the MR-107A-02 group. See Table 19.

TABLE 19

Comparison of Censoring Methods for Time to 2-point NRS-R Reduction

| WLOCF rescue censoring | Meloxicam | Tramadol | Placebo |
|---|---|---|---|
| Subjects with/without 2-point reduction | 135/2 | 132/5 | 125/11 |
| Median time (minutes) | 90 | 91 | 346 |
| p-value (versus placebo) | <0.001[a] | <0.001[b] | |

TABLE 19-continued

| No rescue censoring | Meloxicam | Tramadol | Placebo |
|---|---|---|---|
| Subjects with/without 2-point reduction | 136/1 | 136/1 | 131/5 |
| Median time (minutes) | 83 | 90 | 120 |
| p-value (versus placebo) | 0.044[a] | 0.010[b] | |

[a]2-sided p-value;

[b]1-sided p-value; all tests are post-hoc and exploratory.

The primary objective of the study was to confirm the efficacy of MR-107A-02 in treating acute pain following bunionectomy surgery.

The secondary objectives of the study were as follows:

- To confirm the opioid-sparing effect associated with the use of MR-107A-02
- To further confirm the efficacy of MR-107A-02 in participants following bunionectomy surgery using additional efficacy measures
- To confirm the association of clinical benefit with reduced opioid use.
- To confirm the efficacy of tramadol in the study
- To estimate the difference in efficacy between MR-107A-02 and tramadol.
- To confirm the safety of MR-107A-02 in participants following bunionectomy surgery
- To confirm the exposure of meloxicam in participants following bunionectomy surgery.

The primary efficacy endpoint in this study was the summed pain intensity difference over 0-48 hours ($SPID_{0-48}$)

The key secondary efficacy endpoint in this study was the number of doses of opioid rescue medication over the entire treatment phase (in- and out-patient treatment phases).

An additional secondary efficacy endpoint in this study was the number and proportion of participants using no opioid rescue medication (opioid-free) during the entire treatment phase (in- and out-patient treatment phases).

The other secondary efficacy endpoints in this study were as follows:

- The $SPID_{0-48}$ (tramadol versus placebo)
- The $SPID_{0-48}$ (MR-107A-02 versus tramadol)
- The number of doses of opioid rescue medication during:
  - The last 24 hours before discharge (i.e., 24-48 hours after randomization)
  - The last 36 hours before discharge (i.e., 12-48 hours after randomization)
  - The full in-patient treatment phase (i.e., 0-48 hours after randomization)
  - The full out-patient treatment phase (5 days following discharge)
  - 0-24 hours after randomization
  - Post-discharge (up to 30 days post-discharge)
- The number and proportion of participants using no opioid rescue medication (opioid-free) during:
  - The last 24 hours before discharge (i.e., 24-48 hours after randomization)
  - The last 36 hours before discharge (i.e., 12-48 hours after randomization)
  - The full in-patient treatment phase (i.e., 0-48 hours after randomization)
  - The full out-patient treatment phase (5 days following discharge)
  - 0-24 hours after randomization
  - Post-discharge (up to 30 days after discharge)

- The SPID over 0-4 hours ($SPID_{0-4}$), 0-8 hours ($SPID_{0-8}$), 0-12 hours ($SPID_{0-12}$), 12-24 hours ($SPID_{12-24}$), and 0-24 hours ($SPID_{0-24}$) after initial dose of study drug
- Pain intensity difference (PID) over time
- Time to perceptible relief (as measured by two-stopwatch technique) after first dose of study drug.
- Time to meaningful pain relief (as measured by two-stopwatch technique) after first dose of study drug.
- Proportion of participants with overall pain reductions from baseline of ≥30% and ≥50% within 0-4 hours, 0-8 hours, 0-12 hours, 12-24 hours, 0-24 hours, 24-48 hours, and 0-48 hours after the first dose of study drug
- Patient's Global Assessment (PGA) of pain control over 0-24 hours, 24-48 hours, and on Day 9
- Elapsed time from the start of study drug to first opioid rescue medication administration
- Elapsed time from the start of study drug to first rescue medication administration
- Modified Post-anesthetic Discharge Scoring System (MPADSS), Overall Benefit of Analgesic Score (OBAS) and numeric rating scale (NRS) with activity (NRS-A) at 24 hours, 48 hours, Visit 3, and Early Termination (ET; if applicable)

The safety endpoints in this study were as follows:

- Incidence and quality of AEs (i.e., by severity, duration, and outcome).
- Incidence and quality of opioid-related AEs (ORAEs; i.e., by severity, duration and outcome)
- Absolute values and changes from baseline in vital signs, laboratory tests (hematology, chemistry, and urinalysis [qualitative]), and 12-lead electrocardiogram (ECG)

The pharmacokinetic (PK) endpoints in this study were as follows:

- Exposure measures for meloxicam (maximum plasma concentration [$C_{max}$], time of maximum concentration [$T_{max}$], area under the curve [(AUC): AUC from time 0 to 4 hours after dosing ($AUC_{0-4}$), AUC from time 0 to 24 hours after dosing ($AUC_{0-24}$) and AUC from time 0 to 48 hours after dosing ($AUC_{0-48}$)]) based on observed data
- Exposure measures for meloxicam based on Population PK (Pop PK) methods, which were conducted and reported separately 3A. 1 Overall Study Design and Plan This was a multi-center, randomized, double-blind, placebo (double-dummy)- and active-controlled, parallel-group study, randomizing and dosing 410 male and female participants (approximately 408 planned) following bunionectomy surgical procedure. Participants received doses of study drug on Day 1 until Day 3 during in-patient treatment phase (8 doses of study drug) as well as on the 5 consecutive days following discharge during the out-patient treatment phase (10 doses of study drug).

During in-patient treatment phase (Day 1 to Day 3), all participants received either MR-107A-02, tramadol, or placebo.

During the out-patient treatment phase (Day 3 to Day 7/8), participants received either MR-107A-02 or placebo. Participants who received tramadol during the in-patient treatment phase received placebo during the out-patient treatment phase.

Participants had the bunionectomy performed on Day −1 (Visit 2) under IV sedation, a regional popliteal block (up to 30 mL of 0.5% ropivacaine) and a local Mayo block (up to 20 mL of 2% xylocaine plain). Peri-operative IV sedation was achieved using any of the following: midazolam (total dose 2-4 mg), fentanyl (not to exceed total dose of 200 μg), and propofol titrated as needed to provide the required effect. Up to 20 mg of IV lidocaine (no epinephrine) for IV placement or before propofol was allowed if required. Maintenance of sedation varied by participant; use of additional propofol via multidose or continuous infusion was possible. The surgery was to be completed in ≤120 minutes to qualify for randomization.

The popliteal infusion plus permissible boluses of additional ropivacaine were to be the first line of analgesic treatment for all participants during the post-procedure time period, prior to randomization. In case of pain control that was inadequate based on the participant's self-assessment during the post-procedure time period, any or all of the following may have been used: ketorolac 30 mg IV q6h for patients<65 years and ketorolac 15 mg IV q6h for patients≥65 years as required up to 09:00 p.m. and/or morphine 2 to 4 mg IV once every 2 hours (q2h) up to midnight on the day of surgery, and use of topical ice up to 03:00 a.m. on the post-operative day (Day 1) (i.e., the day following the surgical procedure). Regional anesthesia as popliteal block was to be maintained from the beginning of the surgery until 03:00 a.m. to 06:00 a.m. on Day 1 (i.e., the day following the surgical procedure).

Blood samples (1×4 mL) for PK analysis were to be collected for a subset of 100 participants per treatment group at pre-dose (post-randomization) and 15 minutes and 1, 2, 4, 12, 24, 30-34 hours (one sample collected freely during the interval), and 48 hours post-dose, relative to the first dose at Day 1. The samples at 12, 24, and 48 hours were collected prior to administration of the scheduled dose.

The End of Study (EOS) was considered to be the date of last participant's last visit (telephonic) or the date of ET of the study, whichever was the later.

Visits and procedures were conducted as presented in the study design (see FIG. 45) provided in the section below.

A urine drug screening (for amphetamines, barbiturates, benzodiazepines, cannabinoids (tetrahydrocannabinol; marijuana), cocaine, methadone, opiates, phencyclidine) was to be performed at Visit 1 and on admission at Visit 2. A positive drug screen test at Visit 1 and/or at Visit 2 excluded the participants for study participation. Participants with a positive drug screen who were taking an allowed, prescribed medication that was known to result in a positive drug test (e.g., amphetamine and dextroamphetamine for ADHD, benzodiazepine for anxiety disorder) were not excluded if, in the opinion of the investigator, the participant was taking as prescribed and their use would not have confounded the determination or safety or efficacy during the study. Note: Scheduled Events needed to be obtained within 10% of the nominal time (e.g., within 6 minutes of a 60-minute sample) and ±1 hour for 12 hour and subsequent samples from first dosing.

The study design was consistent with research design recommendations of the Initiative on Methods, Measurement, and Pain Assessment in Clinical Trials (IMMPACT) group for studies involving participants with short-duration acute pain (Cooper et al., 2016).

This study was placebo-(double-dummy) and active-controlled (with tramadol used as an active comparator during the in-patient treatment phase). The rationale for the inclusion of the active comparator, tramadol, in this study was twofold: (1) to confirm the sensitivity of the study with a comparison of the tramadol and placebo treatment groups based on the primary endpoint and (2) to estimate the effect of MR-107A-02 versus that of tramadol using the primary endpoint. Tramadol is an opioid analgesic approved for the management of moderate to moderately severe pain in adults, and the pain level expected for bunionectomy pain studies (mean baseline level is expected to be between NRS 6.7-7.7) aligns with this indication (Daniels et al., 2010; Gottlieb et al., 2018; Pollak et al., 2018; Riff et al., 2009; Singla et al., 2020; Viscusi et al., 2023).

The use of tramadol as an active comparator allowed compatibility with the study's rescue medication strategy. In this study, acetaminophen (APAP) was used as the first-step rescue medication, and if escalation to stronger rescue analgesia was required, oxycodone as second step rescue medication was available. Tramadol's availability as a single-agent opioid enabled first step rescue medication APAP. In contrast, hydrocodone—available only in fixed-dose combination with APAP—was not suitable for use as an active comparator in this study, as its use could have resulted in exceeding the maximum daily dose of APAP. Moreover, oxycodone was also not suitable as an active comparator due to its use as second step rescue medication. Oxycodone is a preferred opioid rescue medication due to its rapid onset of action and reliable analgesic efficacy in postoperative settings.

As opioid use should be limited to the shortest possible duration, participants in the tramadol group received tramadol during the in-patient treatment phase (0-48 hours) and placebo during the out-patient treatment phase.

This study included a repeat-dose design based on the bunionectomy pain model and had 48-hour dosing in-patient (MR-107A-02, tramadol, or placebo), followed by 5 days of out-patient treatment with study drug (MR-107A-02 or placebo). In case of pain control that was inadequate based on the participant's self-assessment, participants had access to rescue medication during the in-patient treatment phase ($1^{st}$ step APAP, $2^{nd}$ step oxycodone and for the first 4 hours following intake of first dose of study medication $3^{rd}$ step rescue morphine) as well as during the first 5 days after discharge ($1^{st}$ step APAP, $2^{nd}$ step oxycodone). This was an adequate duration of treatment as post-operative pain decreases in the first few days in the majority of participants (Small and Laycock, 2020). For cases in which participants still suffered from pain following 5 days of treatment with study drug after discharge, they received standard-of-care treatment. Also, in accordance with the guidance, there was a continued safety evaluation for 30 days after the last dose of study drug.

The post-operative pain immediately after bunionectomy has been reported to be overwhelming, and therefore, a multimodal approach including local blocks and opioids for the treatment of breakthrough pain is recommended for adequate pain management (Chou et al., 2016; Korwin-Kochanowska et al., 2020). Therefore, opioid analgesia was allowed to treat breakthrough pain during the post-procedure time period on Day −1, including ketorolac IV (30 mg IV q6h for patients<65 years and ketorolac 15 mg IV q6h for patients≥65 years) administered as required up to 09:00 p.m. and/or morphine IV (2 to 4 mg IV q2h) administered as required up to midnight on the day of surgery, and use of topical ice up to 03:00 a.m. on the post-operative day (Day 1). Regional anesthesia as popliteal block should have been maintained until 03:00 a.m. to 06:00 a.m. on Day 1 (i.e., the day following the procedure). Pain intensity was assessed during the 9 hours following cessation of the local anesthesia on Day 1. If the participant scored a NRS≥4 and a rating of moderate or severe pain on a 4-point categorical pain rating scale during this time, the participant was eligible for randomization.

Participant eligibility for enrollment into the study included:

1. Pain intensity using a NRS at rest (NRS-R)≥4 at any given timepoint during the 9 hours after removal of the popliteal sciatic block on Day 1 in the eligibility assessment as well as in the baseline assessment (NRS-R) immediately pre-dosing.
2. Rating of moderate or severe pain on a 4-point categorical pain rating scale (i.e., none, mild, moderate, severe) during the 9 hours after removal of the popliteal sciatic block on Day 1.

Participant candidates were not enrolled in the study if they met certain criteria including any of the following:

1. History of gastrointestinal (GI) bleeding or peptic ulcer disease.
2. Known active inflammatory bowel disease, e.g., Crohn's Disease or ulcerative colitis.
3. A history of bleeding disorders that may have affected coagulation.
4. Participants with prior stroke or transient ischemic attack (TIA) in the past 12 months prior to Screening.
5. Participants with moderate or severe hypertension with systolic blood pressure (BP) of ≥160 mmHg and/or diastolic BP≥100 mmHg on two measurements, at least 5 minutes apart.
6. A clinically significant history of respiratory insufficiency, hypotension, bradycardia, migraine, frequent headaches, seizures, renal, hepatic, cardiovascular, metabolic, neurologic or psychiatric disease in the opinion of the investigator.
7. History of human immunodeficiency virus (HIV) or current infection with Hepatitis B or Hepatitis C (based on laboratory testing). Treated Hepatitis C (positive antibody test but undetectable viral load) was not permitted.
8. History of alcohol or drug abuse within the last 5 years prior to consent.
9. History of myocardial infarction or coronary artery bypass graft surgery within the 12 months prior to consent.
10. Clinically significant abnormality on the 12-lead ECG at Screening which in the judgment of the investigator would have put the participant at potential risk if enrolled into the study (these participants should not have been rescreened). Clinically significant abnormalities included but were not limited to the following: left bundle branch block, Wolff-Parkinson-White syndrome, clinically significant arrhythmias (e.g., ventricular tachycardia).
11. Current or history of long QT syndrome or screening ECG with QT corrected for heart rate (QTc) using Fridericia's method (QTcF)>470 milliseconds for female or >450 milliseconds for male participants. One repeat measure was allowed in case of failure of the limits. If the initial tracing was exclusionary and the repeat measure was within the allowed limits, inclusion was possible based on investigator's judgement.
12. Current evidence of, or history within the 6 months prior to Screening of unstable ischemic heart disease, New York Heart Association (NYHA) Class III, or IV right or left ventricular failure.
13. History of malignancy of any organ system treated or untreated, within the past 5 years, whether or not there was evidence of local recurrence or metastases. The only exceptions were previous in situ carcinoma of the cervix, localized basal cell carcinoma of the skin, or localized squamous carcinoma of the skin if the participant had been treated and was considered cured.
14. Use of any investigational drug within 28 days or 5 half-lives (t½) prior to Screening, whichever was longer.
15. Use of medications with the potential to interact with meloxicam, or medications required during the study such as local anesthesia or sedatives, or medications with the potential to affect or confound pain status during the study. This included use of any of the following medications:

a. Strong cytochrome P450 (CYP) family 2 subfamily C member 9 (CYP2C9) inhibitors or inducers (orally or parenterally administered) within 28 days or 5 half-lives (whichever was longer) prior to Screening.

b. Strong CYP2C9 inhibitors or inducers (topically or locally administered) within 7 days prior to Screening.

c. Long-term opioid use (>30 consecutive days in the past year) known or suspected daily use of opioids for 7 or more consecutive days within the previous 6 months and/or use of extended-release opioids within 30 days of the bunionectomy.

d. Antiepileptic drugs within 60 days prior to Screening.

e. Tricyclic antidepressants, monoamine oxidase inhibitors within 60 days prior to Screening.

f. Serotonin-norepinephrine reuptake inhibitors (SNRIs) within 7 days prior to Screening.

g. Serotonin-reuptake inhibitors (SRIs) including selective serotonin reuptake inhibitors (SSRIs) within 7 days prior to Screening, unless on an unchanged, stable dose for at least 60 days prior to Screening.

h. Sedative or hypnotic drugs within 14 days prior to surgery (other than permitted sedatives or hypnotic drugs used during the operation).

i. Positive drug screen test (for amphetamines, barbiturates, benzodiazepines, cannabinoids [tetrahydrocannabinol; marijuana], cocaine, methadone, opiates, phencyclidine) at Screening and/or Visit 2 prior to surgery. Participants with a positive drug screen who were taking an allowed, prescribed medication that was known to result in a positive drug test (e.g., amphetamine and dextroamphetamine for attention-deficit/hyperactivity disorder [ADHD], benzodiazepine for anxiety disorder) were not excluded if, in the opinion of the investigator, the participant was taking as prescribed and their use would not have confounded the determination or safety or efficacy during the study.

j. Vitamin K antagonists, (e.g., warfarin) within 28 days prior to Screening.

k. Factor Xa-inhibitors (e.g., apixaban) within 28 days prior to Screening.

l. Lithium within 28 days prior to Screening.

m. Methotrexate within 28 days prior to Screening.

n. Calcineurin inhibitors (e.g., cyclosporine and tacrolimus) within 28 days prior to Screening o. Pemetrexed within 28 days prior to Screening.

p. Combination of diuretics with angiotensin converting enzyme (ACE) inhibitor or angiotensin receptor blocker within 28 days prior to Screening.

q Gabapentin or pregabalin within 7 days prior to Screening.

r. Cholestyramine within 7 days prior to Screening.

s. Meloxicam within 7 days prior to the bunionectomy.

t. Aspirin within 7 days prior to the bunionectomy, unless taken for cardiac or cardiovascular prophylaxis.

u. Analgesics (including opioids, APAP and NSAIDs) within 72 hours prior to the bunionectomy.

v. Analgesics (including opioids and NSAIDs) during whole in- and out-patient treatment phase with exception of allowed rescue medication.

3A.2 Study Treatments

Treatments administered during the study included one of the following during the in-patient treatment phase:

1. MR-107A-02 (15 mg twice daily [BID])
2. Tramadol (50 mg q6h)
3. Placebo (q6h)

During the in-patient treatment phase, study drugs were administered orally following randomization and approximately 6 hours following the previous doses (8 doses in total). MR-107A-02 was administered BID and tramadol was administered q6h. To maintain the blind, participants in the MR-107A-02 group received MR-107A-02 active and MR-107A-02 placebo alternately starting with MR-107A-02 active to allow for a q6h dosing of all participants during the in-patient treatment phase. The participants received one tablet and one over-encapsulated tablet of study drug each 6 hours (double-blind, double-dummy); the dosing scheme is summarized for the three treatment groups in Table 20.

TABLE 20

Dosing Scheme of Study Medication During In-patient Treatment Phase

| Group | Dose 1 (T0) | Dose 2 (T6) | Dose 3 (T12) | Dose 4 (T18) | Dose 5 (T24) | Dose 6 (T30) | Dose 7 (T36) | Dose 8 (T42) |
|---|---|---|---|---|---|---|---|---|
| MELO; N = 137 | MELO-Active | MELO-PLA | MELO-Active | MELO-PLA | MELO-Active | MELO-PLA | MELO-Active | MELO-PLA |
| | TRAM-PLA | TRAM-PLA | TRAM-PLA | TRAM-PLA | TRAM-PLA | TRAM-PLA | TRAM-PLA | TRAM-PLA |
| PLA: N =1 36 | MELO-PLA | MELO-PLA | MELO-PLA | MELO-PLA | MELO-PLA | MELO-PLA | MELO-PLA | MELO-PLA |
| | TRAM-PLA | TRAM-PLA | TRAM-PLA | TRAM-PLA | TRAM-PLA | TRAM-PLA | TRAM-PLA | TRAM-PLA |
| TRAM; N = 137 | MELO-PLA | MELO-PLA | MELO-PLA | MELO-PLA | MELO-PLA | MELO-PLA | MELO-PLA | MELO-PLA |
| | TRAM-Active | TRAM-Active | TRAM-Active | TRAM-Active | TRAM-Active | TRAM-Active | TRAM-Active | TRAM-Active |

MELO = MR-107A-02 (15 mg);
PLA = Placebo;
TRAM = Tramadol (50 mg);
T0 = Time of first intake of study drug;
T6 = 6 hours following first intake of study drug;
T12 = 12 hours following first intake of study drug;
T18 = 18 hours following first intake of study drug;
T24 = 24 hours following first intake of study drug;
T30: 30 hours following first intake of study drug;
T36 = 36 hours following first intake of study drug;
T4 = 42 hours following first intake of study drug.

During the out-patient treatment phase, participants in the MR-107A-02 and placebo groups received MR-107A-02 or placebo as assigned during the in-patient treatment phase. Tramadol active and tramadol placebo were discontinued during the out-patient treatment phase. Participants in the Tramadol group received placebo during the out-patient treatment phase. Dosing was BID (10 doses in total). The dosing scheme is summarized for the three treatment groups in Table 21:

TABLE 21

Dosing Scheme of Study Medication During Out-patient Treatment Phase

| Group | Dose 9 - Dose 18 (BID) |
|---|---|
| MELO [N = 137] | MELO-Active |
| PLA [N = 136] | MELO-PLA |
| TRAM [N = 137] | MELO-PLA |

BID = Twice daily;
MELO = MR-107A-02 (15 mg);
PLA = Placebo;
TRAM = Tramadol

Selection of Doses Used in the Study

MR-107A-02 has been developed to provide rapid absorption of meloxicam via an oral dose.

The Phase 2b study discussed above investigated the efficacy and safety of three different dose regimens (1.25 mg BID, 5 mg BID, and 15 mg BID) of study drug. Treatment with study drug, 5 mg BID and 15 mg BID, resulted in a significantly greater reduction in acute post-operative dental pain, as measured by $SPID_{0-24}$, than placebo. The response was dose related, with the study drug 1.25 mg dose achieving a numerically, but not statistically significant, greater reduction in $SPID_{0-24}$ than placebo. For the primary and all secondary efficacy endpoints, the drug 15 mg BID dose showed the largest numeric treatment effect and was the only dose with a statistically significant treatment effect for every endpoint.

The three study drug dose regimens evaluated in the Phase 2b study were generally safe and well tolerated. No dose-effect pattern was observed with respect to treatment-emergent AEs (TEAEs), vital signs, or ECG findings.

In-Patient Treatment Phase:

Participants were to take the study drugs with approximately 240 mL of water at ambient temperature or refrigerated under the supervision of trained study personnel. The same procedure applied for the intake of $1^{st}$ step and $2^{nd}$ step rescue medications (if required). Dose administration was to be followed by mouth check and hand check of the participants to assess compliance to dosing while in-patient. Study drugs were instructed to be swallowed as a whole and must not have been chewed, crushed, or divided. In the event of any significant dosing errors, the medical monitor, or Sponsor study contact should have been contacted immediately.

Out-Patient Treatment Phase:

Following discharge, participants received MR-107A-02 active or placebo, for BID dosing for 5 days (dosed morning and evening, 10 doses in total). Study drug was to be taken once every 12 hours (q12h). If a dose of study drug was missed, the missed dose should have been taken as soon as the participant remembered. The interval between two doses should not have been less than 10 hours. The exact date and time of study drug intake was documented in the diary. Participants in the MR-107A-02 and Placebo groups continued to receive MR-107A-02 or placebo as assigned during the in-patient treatment phase. Participants in the Tramadol group received placebo during the out-patient treatment phase. Study drug (MR-107A-02 15 mg or corresponding placebo) was taken at each dosing time.

Participants swallowed the study drug whole and intact with a glass of water at ambient temperature or refrigerated (approximately 240 mL). The same procedure was applied for the intake of $1^{st}$ step and $2^{nd}$ step rescue medications (if required).

Blinding

To maintain the blind during the in-patient treatment phase when MR-107A-02 was to be administered BID and tramadol was to be administered q6h, participants received one tablet and one over-encapsulated tablet of study drug q6h. Participants in the MR-107A-02 group received one MR-107A-02 active tablet and one MR-107A-02 placebo tablet alternately q6h, starting with MR-107A-02 active to allow for a q6h dosing of all participants; they also received a tramadol placebo over-encapsulated tablet q6h according to the dosing scheme shown in Table 21. In the out-patient treatment phase, participants received one MR-107A-02 active tablet or one MR-107A-02 placebo tablet. Neither the participant nor the investigator knew which treatment a participant received during the in-patient treatment phase (double-dummy design) or during the out-patient treatment phase.

Unblinding of the study was performed after the database was locked and followed the corresponding Sponsor and contract research organization (CRO) standard operating procedures (SOPs).

Prior and Concomitant Therapy

All medications taken during the study (from signing informed consent to post-study follow-up) were recorded with indication, daily dose, and start and stop dates of administration in the CRF. All participants were questioned about concomitant medication at each clinic visit and at follow-up.

Medications taken prior to dosing with study drug were documented as a prior medication. Medications taken after dosing with study drug were documented as concomitant medications or rescue medications, which are described in more detail below.

Participants were to abstain from all prohibited medications as described in more detail below. Use of prohibited medication during the study was deemed a protocol deviation and such participants were assessed by the Sponsor or designee regarding potential need to early terminate study drug (e.g., for safety reasons). Exclusion criterion 23 indicated the start point for the period of prohibited medication per substance. The endpoint for the period of prohibited medication period was Visit 3 (Day 9).

Rescue Medication

Rescue medication was characterized by the following issues: its use had impact on the interpretation of the primary endpoint and therefore, it needed to be particularly regulated by the protocol and hence, its use required particular documentation in the CRF or diary.

Use of any rescue medication while the participant was in the clinic, as well as until end of out-patient treatment phase (Day 7/8), was to be recorded, including the dose and time of administration. After the end of out-patient treatment phase until 30 days following first intake of study drug, intake of opioid pain medication was to be documented in the diary and discussed with the site at EOS.

If a participant required rescue medication other than allowed per protocol prior to administration of study drug, the participant was not eligible for randomization.

Participants should only have received rescue medication upon request, in case of pain control that was inadequate based on the participant's self-assessment. The participants were to be trained on pain assessment during the Screening visit and prior to the surgery on Day −1. Post-randomization rescue medication was to be administered using a stepwise approach.

Rescue medication of APAP ($1^{st}$ step rescue) was to be allowed at any time [up to 1 g (2×500 mg) q6h, maximum daily dose of 4 g], but participants were encouraged to wait until at least 1-hour post-dose of any intake of study drug, if possible.

Immediate-release oxycodone ($2^{nd}$ step rescue) was allowed in case of inadequate pain control by APAP rescue medication that was based on the participant's self-assessment. Oxycodone was allowed at any time (up to 5 mg q4h, maximum daily dose of 30 mg) during the APAP lockout periods (6 hours between two APAP doses), but participants were encouraged to wait until at least 1-hour post-dose of any APAP dose, if possible. If APAP could have been given based on maximum allowed APAP dosing schedule, APAP should have always been given first.

In addition, within the first 4 hours following intake of first dose of study medication, rescue medication of IV morphine sulfate was allowed up to 2 mg every hour in case of inadequate pain control based on the participant's self-assessment after the second rescue medication, oxycodone. After the first 4 hours following intake of first dose of study medication, use of morphine sulfate as a rescue medication was no longer allowed.

While in-patient, a pain intensity score assessment (NRS-R) was to be made immediately prior to any rescue medication.

Similar to in-patient, rescue medication during the out-patient treatment phase consisted of a stepwise approach ($1^{st}$ step APAP 2×500 mg, $2^{nd}$ step oxycodone 5 mg). The participants were instructed to take APAP (up to 1 g q6h) only in case of pain control that was inadequate under study drug, based on the participant's self-assessment. In case of inadequate pain control that was based on the participant's self-assessment under study drug and APAP, oxycodone (up to 5 mg q6h) was allowed. The participant was encouraged to wait for at least 1 hour following intake of any dose of study drug before taking $1^{st}$ step rescue medication and at least another 1 hour after 1st step rescue medication before proceeding with $2^{nd}$ step rescue medication.

Before intake of any rescue medication, pain intensity assessment (NRS-R) should have been performed and documented in the diary. Also, all rescue medication type and dose, time and date, were to be captured in the diary. Participants were to complete a diary to record if they took any rescue medication between 48 hours and Day 7/8 (end of out-patient treatment phase) and any intake of opioid pain medication after the end of the out-patient treatment phase until Day 37/38 (30 days after last dose of study medication).

3A. 3 Efficacy Assessments

The following parameters were evaluated to assess the efficacy:

Pain Intensity Assessment (Numeric Rating Scale)

Pain intensity scores were assessed using an 11-point NRS (0-10) where 0 represented “no pain” and 10 represented “worst pain imaginable” (Breivik et al., 2008). In this study, the main pain intensity score was based on NRS-R as defined below:

- Participants were to be in supine position. Measurements were to be obtained after the participant was in the resting position for at least 5 minutes.

Pain assessments (pain intensity and categorical pain rating) were to be performed for up to 9 hours following cessation of the regional anesthesia (popliteal block) on Day 1. Participants with NRS-R≥4 and a rating of moderate or severe pain on a 4-point categorical pain rating scale (described below) during this time were to be eligible for randomization (eligibility assessment).

An additional pain intensity assessment (NRS-R) was to be made immediately prior to dosing which was used as the baseline value; a participant was to be dosed only if this NRS-R was ≥4 (baseline assessment). In case the initial pre-dose pain intensity NRS score was <4, the pre-dose pain intensity assessment could have been repeated once. If the $2^{nd}$ pre-dose assessment was ≥4, the patient was to be dosed. If the $2^{nd}$ pre-dose assessment was <4, the participant should have been discontinued. Randomization should have taken place between eligibility and baseline pain intensity assessment.

The pain intensity scores using NRS-R were to be measured on Days 1-3 at 0.5, 1, 1.5, 2, 3, 4, 5, 6, 8, 10, 12, 16, 20, 24, 28, 32, 40, and 48 hours after the first dose of study drug, and immediately before any rescue medication. If the participant was sleeping, they were to be awakened for pain assessment.

The pain intensity scores using NRS-A, as defined below, were to be measured at 24 and 48 hours after the first dose of study drug.

- Participants were to be seated with the plantar surface of the ball of the surgically attended foot touching the floor (no weightbearing).

NRS-R and NRS-A were also to be assessed during the Follow-up Visit (Visit 3) on Day 9 (+1 day) and during ET (if applicable).

NRS assessments were also to be made immediately following the time to first perceptible pain relief and time to first meaningful pain relief (spontaneously reported, not defined as NRS-R or NRS-A).

The pain intensity assessments were to be recorded in a diary. Participants were to be asked to evaluate their current pain level at scheduled time points after surgery. Participants received training by the site on how to provide pain intensity assessments.

Categorical Pain Rating

A pain rating using a 4-point categorical rating scale (none, mild, moderate, severe) was used to assess eligibility for randomization. The rating was to be performed for up to 9 hours post-cessation of regional anesthesia. If the participant recorded moderate or severe (and an NRS-R pre-randomization and pre-dose≥4) within 9 hours following surgery, they were eligible for randomization. The categorical pain rating was to be recorded in a diary.

Rescue Medication Use

Rescue medication was to be used with greatest care as it may have compromised the efficacy assessments.

Use of any rescue medication while the participant was in the clinic as well as until the end of the out-patient treatment phase (Day 7/8) was to be recorded, including the dose and time of administration. After the end of the out-patient treatment phase until 30 days following first intake of study drug, intake of opioid pain medication was to be documented in the diary.

- Opioid Rescue Medication through 48 hours: The name, dose, and route as well as the date and time of administration of any rescue medication must have been recorded in the participant’s eCRF during entire treatment phase.
- Participant Daily Diary of Rescue Medication Use from 48 hours through Day 30: Participants were to be provided with a daily diary to record if they took any rescue medication from 48 hours through Day 30 (type, dose, date, and time).

Time to First Perceptible Pain Relief

Time to first perceptible pain relief was to be assessed using a double stopwatch approach.

The time to onset of first perceptible pain relief (time that the first watch stopped) was defined as the post-dose time at which the participant first began to feel pain relief at their estimation.

If a participant took rescue medication prior to recording perceptible pain relief, the stopwatches were to be collected, and no further stopwatch assessment of perceptible pain relief was to be done.

If the participant did not press/stop the stopwatches within 6 hours after Time 0, the use of the stopwatches was to be collected, and no further stopwatch assessment of perceptible pain relief was to be done.

Time to Meaningful Pain Relief

Time to meaningful pain relief was to be assessed using a double stopwatch approach. The time to onset of meaningful pain relief (time that the second watch stopped) was defined as the post-dose time at which the participant first began to feel meaningful pain relief at their estimation. If a participant took rescue medication prior to recording meaningful pain relief, the stopwatches were to be collected, and no further stopwatch assessment of meaningful pain relief was to be done. If the participant did not press/stop the stopwatches within 6 hours after Time 0, the use of the stopwatches was to be collected, and no further stopwatch assessment of meaningful pain relief was to be done.

Patient Global Assessment of Pain Control

A PGA of pain control was to be rated on a 5-point scale, ranging from 0 to 4, where 0=poor, 1=fair, 2=good, 3=very good, or 4=excellent.

Assessments were to be made at 24 and 48 hours after the first dose of study drug as well as at Follow-up Visit on Day 9 (±1 day) or at time of ET, if applicable. The PGA was to be recorded in a diary.

Modified Post-Anesthetic Discharge Scoring System

The MPADSS has proved to be an efficient system that assists safe discharge. The MPADSS considers six criteria: vital signs, ambulation, nausea/vomiting, pain, and bleeding as presented in Table 22 (Chung, 1995).

TABLE 22

| Modified Post-anesthetic Discharge Scoring System | |
|---|---|
| Vital Signs (blood pressure, pulse, heart rate) | 0 = >40% of preoperative value<br>1 = 20-40% of preoperative value<br>2 = within 20% of preoperative value |
| Ambulation | 0 = None/dizziness<br>1 = with assistance<br>2 = steady gait/no dizziness |
| PONV | 0 = severe<br>1 = moderate<br>2 = minimal |
| Pain | 0 = severe<br>1 = moderate<br>2 = minimal |
| Surgical bleeding | 0 = severe<br>1 = moderate<br>2 = minimal |
| Total* | |

PONV = Post-operative nausea/vomiting
Note:
This study instrument assessed a participant's potential readiness to be discharged and should have been repeated at all scheduled timepoints. It was not meant to be used to decide on whether or not to discharge a participant from the in-patient facility. Participants were required to remain in the hospital/research facility for 48 hours following randomization.

The MPADSS assessment was to be completed at 24 and 48 hours post-dose, at the Follow-up Visit (Visit 3) and at ET (if applicable). For the MPADSS assessment at 24 hours, the scheduled vital signs values nearest to the MPADSS assessment should have been used; for the MPADSS assessment at 48 hours, the vital signs assessed as part of the discharge assessment should have been used.

Overall Benefit of Analgesic Score

The OBAS is a simple, multi-dimensional tool that has been developed and validated to assess pain intensity and ORAEs and also patient satisfaction (Lehmann et al., 2010; Table 23). The OBAS has been designed to guide post-operative pain therapy in daily clinical practice.

TABLE 23

Overall Benefit of Analgesia Score Items

| | Item | Score |
|---|---|---|
| 1 | Please rate your current pain at rest on a scale between 0 and 4 | 0 = minimal pain to 4 = maximum imaginable pain |
| 2 | Please grade any distress and bother from vomiting in the past 24 hours | 0 = not at all to 4 = very much |
| 3 | Please grade any distress and bother from itching in the past 24 hours | 0 = not at all to 4 = very much |
| 4 | Please grade any distress and bother from sweating in the past 24 hours | 0 = not at all to 4 = very much |
| 5 | Please grade any distress and bother from freezing in the past 24 hours | 0 = not at all to 4 = very much |
| 6 | Please grade any distress and bother from dizziness in the past 24 hours | 0 = not at all to 4 = very much |
| 7 | How satisfied are you with your pain treatment during the past 24 hours | 0 = not at all to 4 = very much |
| | Total score | Sum of responses to items 1-6 + (4-item 7 response) |

Assessment was to be completed at 24 and 48 hours post-dose, at the Follow-up Visit (Visit 3) and at ET (if applicable).

3A.4 Safety Assessments

The following parameters were evaluated to assess safety:

Adverse Event/Opioid-Related Adverse Event Assessment

If a participant reported any symptoms before drug administration, they were to be evaluated by medical staff and necessary measurements were to be performed. The PI or medical sub-investigator was to be notified before dosing to determine the course of action.

Findings from screening procedures, e.g., laboratory tests or physical examinations were to be recorded as medical history. Clinically significant worsening from the screening procedures was to be recorded as AEs.

Participants were to be routinely queried in regard to the presence or absence of AEs using open-ended questions. The clinic was to provide documentation of any AEs in the participant's CRF. The AE source documentation was to minimally include the following information: date and time of assessment, the outcome of the response, and ID of the clinic staff member collecting the information.

Given that meloxicam is an NSAID, AEs of special interest (AESIs) included the AEs related to GI, particularly bleeds, and those related to cardiovascular events:

Myocardial infarction/unstable angina

Stroke/TIA

Heart failure

Cardiac arrhythmia (atrial and ventricular)

Gastrointestinal hemorrhages.

Gastrointestinal ulceration and perforation.

Any AESI should have been reported per the serious AE (SAE) reporting process.

The ORAEs relevant for the short-term opioid treatment were defined as nausea, vomiting, dizziness, somnolence, constipation, pruritus, respiratory depression, changes in mental status, ileus, urinary retention, and falls that were not present on admission (Visit 2).

In case of respiratory depression or other medical emergencies, a study site emergency management plan should have included, at a minimum, immediate access to oxygen, naloxone, and resuscitation equipment. The site staff/study personnel who were qualified to manage medical emergencies (i.e., Advanced Cardiac Life Support [ACLS] certified) were to be present in the clinic during the in-patient treatment phase.

Unless consent was withdrawn, participants who prematurely terminated study drug were to have discharge procedures performed prior to leaving the clinic or at an ET visit scheduled as soon as possible.

All AEs (including ORAEs) were to be recorded from time of consent until 30 days after the last dose of study drug. The investigator was also responsible for notifying the Sponsor if they became aware of any AE after the study period had ended, and it was considered related to the study drug.

Primary Efficacy Variable(s)

The primary efficacy variable was the $SPID_{0-48}$.

Drug Concentration Measurements

Blood samples were to be collected in a subset of 100 participants per treatment group at the following times, and the date and exact time of each sample were to be recorded in the CRF:

Pre-dose (post-randomization) and 15 minutes and 1, 2, 4, 12, 24, 30-34 (one sample collected freely during the interval), and 48 hours post-dose relative to the first dose at Day 1 (time-since-first dose [TSFD]). The samples at 12, 24, and 48 hours were to be collected prior to administration of the scheduled dose.

All efforts were to be made to obtain the PK samples at the exact nominal time relative to dosing.

However, samples obtained±10% or ±1 hour (for samples≥12 hours) of the nominal time were considered per protocol. The dates and times of each administration of study drug during the in-patient treatment phase were to be recorded in the CRF.

Pharmacokinetic sample handling instructions were provided in the Central Laboratory Manual. Plasma samples were analyzed using a validated bioanalytical method in compliance with Sponsor SOPs.

Prior and Concomitant Medications

Prior and concomitant medications were summarized for the Safety Analysis Set.

Medications were coded according to the WHO-DD, September 2023. Medications reported on the CRF were categorized for analysis as prior and/or concomitant to study treatment, by comparing the medication start and stop dates with the first and last dose of study drug administration.

Prior medications were those with a start and stop date prior to the first dose of study drug administration. Concomitant medications had either the start date or stop date on or after the first dose of study drug and on or before the last dose of study drug. A medication was either classed as prior or concomitant. Note that rescue medications were summarized separately and not included in displays of concomitant medications.

For medications with a partial start and/or end date, dates were imputed for analysis according to the rules described in more detail below. If it could not be determined whether a medication was prior or concomitant due to partial dates, it was assumed to be concomitant.

The number and percentage of participants receiving prior and concomitant medications were presented by medication class (level 3) and overall. When reporting the number of participants receiving the medication, a participant was only counted once if they ever received the medication within that medication class. Percentages were based on the number of participants in the Safety Analysis Set.

Concomitant medications were summarized by analysis phase (in-patient and out-patient). If a participant took one concomitant medication during both the in-patient and out-patient treatment phase, that medication was summarized under both analysis phases. Prior and concomitant medications were also listed for the Safety Analysis Set.

3A. 5 Efficacy Analyses

The primary objective of this study was to confirm the efficacy of MR-107A-02 in treating acute pain following bunionectomy surgery. This was measured using the primary estimand described below:

- Variable: The $SPID_{0-48}$
- Population: Patients experiencing moderate to severe pain following bunionectomy surgery as defined by the protocol inclusion/exclusion criteria
- Intercurrent events:
- For the intercurrent event of rescue medication use, a windowed last observation carried forward (WLOCF) approach was used, whereby the last observed pain intensity score prior to taking rescue medication was carried forward to replace the observed pain intensity scores during a defined period of time (window) following the rescue medication intake.
- For imputing the data following the intercurrent event of participants discontinuing treatment early due to lack of efficacy, or an AE related to study drug, a multiple imputation (MI) approach was to be utilized using the pre-dose distribution by sampling from a trimmed normal that had the mean and standard deviation (SD) of the baseline values across the MR-107A-02 and placebo treatment groups. The distribution was trimmed to a value of 4-10.
- Population-level summary: The mean for MR-107A-02 versus the mean for placebo Analysis of the Primary Estimand:

Only NRS-R scores were used in the calculation of the primary estimand variable. First, the pre-dose NRS-R was subtracted from each pain score for a PID. The SPID was calculated using these values and actual times of collection with the trapezoidal rule; the primary analysis did not include the NRS scores recorded at the time of perceptible pain relief and at the time of meaningful pain relief. For any participants with a missing baseline (pre-dose) NRS-R assessment, the NRS-R value recorded at the eligibility assessment was used as baseline. To ensure that all SPIDs were calculated over a uniform time interval of 48 hours (e.g., when the time point at 48 hours was missing), the calculated sum was divided by the observed time in hours (e.g., 47 hours) and then multiplied by 48 to get the final SPID. Due to the short duration involved in the computation of the primary endpoint, missing data was expected to be minimal.

Analysis of covariance (ANCOVA) was used to assess the difference between MR-107A-02 and placebo for the primary estimand. The ANCOVA model included treatment (MR-107A-02 and placebo), age (<65 years, ≥65 years), and study site as fixed class effects and baseline pain intensity score as a continuous covariate. The difference between MR-107A-02 and placebo was estimated from the least squares (LS) means along with the 2-sided 95% confidence interval (CI) and associated 2-sided p-value. The primary analysis was based on the FAS and the WLOCF approach used windows of 6 hours, 4 hours, and 2 hours for APAP, oxycodone and morphine, respectively.

A line graph for the LS means (and CIs) of the NRS-R scores from 0 to 48 hours post-first dose was also generated.

A sensitivity analysis was conducted for the primary estimand by using the same ANCOVA model described for the primary analysis above but with the tramadol treatment included. An additional sensitivity analysis was performed for the primary estimand, based on the pooled data from the MR-107A-02 and placebo groups (i.e., alternate MI).

Other sensitivity analyses for the primary analysis of the primary estimand included the application of additional windows for rescue medication use in place of the WLOCF in the calculation of the primary estimand:

- No censoring: used all actual pain scores following rescue medication used in the calculation of the SPID.
- Shortening the APAP window to 4 hours
- Increasing the oxycodone window to 6 hours.
- Not reverting to observed scores if the window for a previous rescue medication step still applied (alternative censoring)
- All values censored: censored all pain score values following rescue medication use (at the pain score value just prior to $1^{st}$ step rescue medication use).

Sensitivity analyses for the primary estimand were not included in the statistical testing hierarchy. Line graphs for the LS means (and CIs) of the NRS-R scores from 0 to 48 hours post-first dose were also generated, applying the different rules for the censoring of pain scores in the bulleted list above. The analyses for the primary estimand were repeated for the mFAS and the PP Analysis Set. Supplementary analyses for the primary estimand were not included in the statistical testing hierarchy. Line graphs for the LS means (and CIs) of the NRS-R scores from 0 to 48 hours post-first dose were also generated, for the mFAS and the PP Analysis Set. The primary analysis was repeated for each age group (<65 years and ≥65 years), for each race, and for each sex for the FAS.

Separate line graphs for the LS means (and CIs) of the NRS-R scores from 0 to 48 hours post-first dose were also generated by age group (<65 years and ≥65 years), by sex and by race.

Analysis for the Secondary Estimand

The key secondary efficacy objective for this study was to confirm the opioid-sparing effect associated with the use of MR-107A-02. This was measured using the following estimand:

- Variable: Number of doses of opioid rescue medication over the entire in-patient and out-patient treatment phases. The number of doses of opioid was defined as the number of doses of oxycodone and/or morphine taken. For any participants who reported taking a rescue medication without reporting the type taken, or if the rescue medication was noted to be Norco/hydrocodone, that rescue medication was counted as an opioid.
- Population: Patients experiencing moderate to severe pain following bunionectomy surgery as defined by the protocol inclusion/exclusion criteria
- Intercurrent events: For imputing the data following the intercurrent event of participants discontinuing treatment early due to lack of efficacy or an AE related to study drug, a MI approach was utilized by sampling from a negative binomial distribution based on the values of the placebo group only. For the MI stage, values were to be imputed using the Markov Chain Monte Carlo (MCMC) method implemented with the SAS MI procedure (PROC MI).
- Population-level summary: The ratio of geometric means for MR-107A-02 versus placebo Comparisons between MR-107A-02 and placebo for the key secondary estimand were based on a negative binomial regression model with a log link. Treatment (MR-107A-02 and placebo only), age (<65 years, ≥65 years), and study site were included as fixed class effects. The number of doses for each participant was scaled by using the natural log of the participant's duration as an offset. The difference between MR-107A-02 and placebo was estimated from the LS means along with the 2-sided 95% CI and associated 2-sided p-values. The LS means, LS mean differences and associated 2-sided 95% CIs were exponentiated to back-transform these quantities to the original scale.

A sensitivity analysis counting the number of doses of oxycodone only was also undertaken. An additional sensitivity analysis for the number of doses of opioid was performed, with imputation done using a negative binomial distribution based on the pooled data from the MR-107A-02 and placebo groups.

The key secondary estimand analysis was repeated for each age group (<65 years and ≥65 years), for each race, and for each sex for the FAS.

The proportion of participants who were opioid-free during the entire treatment phase was defined as the proportion of participants who had not taken oxycodone and/or morphine during the in-patient and out-patient treatment phases. For any participants who reported taking a rescue medication without reporting the type taken, or if the rescue medication was noted to be Norco/hydrocodone, that rescue medication was counted as an opioid. The number and percentage of responders in each treatment group were summarized. The proportion of participants who were opioid-free during the entire treatment phase were evaluated with the difference in proportions (MR-107A-02 versus placebo) Z-test (equivalent to Pearson's Chi Squared), with the corresponding 95% CI and associated 2-sided p-values.

A sensitivity analysis based on the proportion of participants who had not taken oxycodone during the entire treatment phase was also undertaken.

Other secondary efficacy objectives for this study were to further confirm the efficacy of MR-107A-02 in participants following bunionectomy surgery using additional efficacy measures, to confirm the association of clinical benefit with reduced opioid use, to confirm the efficacy of tramadol in the study, and to estimate the difference in efficacy between MR-107A-02 and tramadol. These were measured using the endpoints described below.

Summed Pain Intensity Difference:

- A comparison of tramadol versus placebo was performed by using a similar ANCOVA model used to perform the analysis of the primary estimand but containing only tramadol and placebo. The difference between tramadol and placebo was estimated from the LS means along with the 2-sided 90% CI and associated (nominal) 1-sided p-value.
- This analysis was repeated using the same ANCOVA model, but with the MR-107A-02 treatment group included, as a sensitivity analysis.
- An ANCOVA was used to assess the difference between MR-107A-02 and tramadol. The ANCOVA model included treatment (MR-107A-02 and tramadol), age (<65 years, ≥65 years), and study site as fixed class effects and baseline pain intensity score as a continuous covariate. The difference between MR-107A-02 and tramadol was estimated from the LS means along with the 2-sided 90% CI. No p-value was planned to be presented for this analysis.
- This analysis was repeated using the same ANCOVA model, but with the placebo treatment group included, as a sensitivity analysis.
- An approach identical to the primary computation for the $SPID_{0-48}$ in sections below was to be employed for the partial SPID for hours 0-4, 0-8, 0-12, 12-24, and 0-24 hours after initial dose of study drug.

Frequency of Opioid Rescue Medication Use:

The number of times opioid (oxycodone and/or morphine) rescue medication used was analyzed in an identical manner to the key secondary endpoint, for the following time intervals: during 0-24 hours, 0-48 hours, 12-48 hours and 24-48 hours after randomization, during the 5 days of out-patient treatment phase, and during post-discharge phase (up to 30 days). All p-values were considered nominal.

Number and Proportion of Opioid Free Participants (Other Time Intervals):

- The number and proportion of participants who were opioid-free during the last 24 hours before discharge (i.e., 24-48 hours after randomization), the last 36 hours before discharge (i.e., 12-48 hours after randomization), the full in-patient treatment phase (i.e., 0-48 hours after randomization), the full out-patient treatment phase (i.e., 5 days following discharge), 0-24 hours after randomization, and post-discharge phase (up to 30 days) were evaluated in the same manner as for the entire treatment phase. All p-values were considered nominal.

Pain Intensity Differences Over Time:

Pain intensity differences over time were analyzed using a Mixed Model for Repeated Measures (MMRM). The LS means estimates, associated standard error (SE), and CIs were based on the MMRM, which included main effects for the treatment group, time point, treatment by time point interaction, and baseline pain intensity score. Kenward-Rogers Degrees of Freedom (option DDFM=KR) and an Unstructured Covariance Matrix (option TYPE=UN) were utilized. Since this analysis was performed for every time point post-dose, no p-values were presented.

Time-to-Event Outcomes:

The four time-to-event outcomes were analyzed in a similar manner. These were as follows:

- Time to perceptible pain relief (as measured by double-stopwatch technique) after first dose
- Time to meaningful pain relief (as measured by double-stopwatch technique) after first dose
- Elapsed time from the start of study drug to first opioid (oxycodone and/or morphine) rescue medication administration
- Elapsed time from the start of study drug to first rescue medication administration The time-to-event outcomes were all analyzed using Kaplan-Meier plots, to generate median times for each treatment group (MR-107A-02 and placebo) together with 2-sided 95% CIs (where estimable). The time to perceptible pain relief and time to meaningful pain relief were censored at the time of first rescue medication use. Additionally, the time to perceptible pain relief, time to meaningful pain relief, time to first rescue medication use, and time to first opioid rescue medication use were censored at the time of study discontinuation, if this occurred prior to the event of interest. Additionally, 2-sided p-values were generated (MR-107A-02 versus placebo) using log-rank tests. All p-values were considered nominal.

Proportion of Participants with Overall Pain Reductions and PGA of Pain Control:

The following two endpoints were analyzed in an identical manner. These were as follows:

- Proportion of participants with overall pain reductions from baseline of ≥30% and ≥50% within 0-4 hours, 0-8 hours, 0-12 hours, 12-24 hours, 0-24 hours, 24-48 hours, and 0-48 hours after the first dose. Percentage pain reductions were based on the NRS-R pain scores.
- Patient's Global Assessment of pain control for 0-24 hours, 24-48 hours and on Day 9

The proportion of participants with overall pain reductions from baseline of ≥30% and ≥50% within 0-4 hours, 0-8 hours, 0-12 hours, 12-24 hours, 0-24 hours, 24-48 hours, and 0-48 hours after the first dose and the PGA of pain control for 0-24 hours, 24-48 hours and on Day 9 were evaluated with the difference in proportions (MR-107A-02 versus placebo) Z-test (equivalent to Pearson's Chi Squared), with the corresponding 95% CI and associated 2-sided p-values. All p-values were considered nominal.

Rescue Medication Use:

The number of participants who received no rescue medication was also summarized by randomized treatment group, for the in-patient, out-patient, and entire treatment phases. A separate summary table was generated, summarizing the amount of APAP rescue medication administered in grams by randomized treatment group, for the in-patient, out-patient and entire treatment phases.

Clinical Benefits:

- The MPADSS, OBAS and NRS-A at 24 hours, 48 hours, Visit 3, and ET (if applicable)

Results of the MPADSS, OBAS, and NRS-A were summarized using descriptive statistics at 24 hours, 48 hours, Visit 3, and ET (if applicable).

Pharmacokinetic Analyses

For all PK data analyses, the PK Analysis Set was used.

Samples for PK determination of drug concentrations of meloxicam in plasma were analyzed by a bioanalytical laboratory using a validated bioanalytical method. Details of the validated bioanalytical method used are provided in a separate bioanalytical report.

The plasma concentration data for meloxicam was listed, summarized based on the nominal time, and plotted using a scatter plot with time relative to the initial MR-107A-02 dosing time. Actual times were used when plotting individual data and for the derivations of PK parameters; summaries by time point grouped values were listed by the nominal times. Summary statistics (mean, SD, minimum, maximum, number of participants, and coefficient of variation) were calculated for plasma concentrations for each time interval and by treatment group.

Additional Pop PK analyses of meloxicam concentrations were performed; these analyses are reported separately.

Safety Analyses

All AEs were classified by SOC and PT, according to MedDRA Version 26.1. The severity of AEs was classified on the CRF using the grades: Mild, Moderate and Severe.

Extent of Exposure

Extent of exposure was summarized by actual treatment group, by treatment phase (in-patient and out-patient) and overall. For each treatment, exposure was measured as:

- The total number of days taking that treatment, defined as last dose date−first dose date+1.
- The total number of doses taken (i.e., each scheduled dose of study drug taken [Table 20 and Table 21]).
- The total number of tablets taken.
- The total number of over-encapsulated tablets taken.
- The total dose taken (mg).

The above data were also provided in a listing, for all participants in the Safety Analysis Set.

Analysis of Adverse Events

Two overall summary tables (one for each analysis phase) presented by treatment group and overall included the total number of:

- Treatment-emergent AEs.
- Serious TEAEs.
- Severe TEAEs.
- Treatment-emergent AEs related to study drug.
- Treatment-emergent AEs leading to study discontinuation
- Treatment-emergent AEs that were ORAEs
- Treatment-emergent AEs of special interest.

Additionally, the number and percentage of participants with at least one of the following were included:

- Participants with at least one TEAE
- Participants with at least one serious TEAE.
- Participants with at least one severe TEAE.
- Participants with at least one TEAE related to study drug
- Participants with at least one TEAE leading to study discontinuation.
- Participants with at least one TEAE that was an ORAE.
- Participants with at least one TEAE of special interest.
- Participants with at least one TEAE leading to death.

Additionally, summary tables by SOC and PT, treatment group and overall were created for the following categories, for each analysis phase:

- All TEAEs
- Serious TEAEs.
- Severe TEAEs
- Treatment-emergent AEs related to study drug
- Treatment-emergent AEs leading to study discontinuation.
- Treatment-emergent AEs that were ORAEs
- Treatment-emergent AEs of special interest Treatment-emergent AEs leading to death.

A data listing was provided for all AEs for the Safety Analysis Set.

Deaths, Serious Adverse Events, and Other Significant Adverse Events

Listings were created for all SAEs, severe AEs, AEs related to study drug, ORAEs, AESIs, AEs leading to study discontinuation and AEs leading to death.

The following post-hoc analyses were also performed:

The analysis of partial SPIDs, time to perceptible pain relief, time to meaningful pain relief, 30% and 50% responders, PGA, time to first opioid, and time to first rescue medication (secondary estimands 7, 9, 10, 11, 12, 13, and 14) were repeated to compare tramadol with placebo. The 90% CI and a 1-sided p-value for tramadol were presented.

Disposition of Participants

Of the 793 participants screened for the study, 410 were enrolled and randomized to one of three treatment groups (See FIG. 46). The MR-107A-02 and Tramadol groups each included 137 participants, and the Placebo group included 136 participants. The composition of each analysis set is described in sections below.

3A.6 Efficacy Evaluation

During the in-patient treatment phase, participants received MR-107A-02 (15 mg BID), tramadol (50 mg q6h), or placebo (q6h; see Table 20), and during the out-patient treatment phase, participants received either MR-107A-02 (15 mg BID) or placebo (BID; see Table 21). To simplify the discussions in the section below, the three treatment groups are referenced as follows:

MR-107A-02 group=MR-107A-02 (15 mg BID)→MR-107A-02 (15 mg BID)

Tramadol group=tramadol (50 mg q6h)→placebo.

Placebo group=placebo→placebo

The Safety Analysis Set and FAS were both composed of 410 participants, with 137 participants each in the MR-107A-02 and Tramadol groups and 136 participants in the Placebo group. The mFAS was composed of 407 (99.3%) participants, with 137 participants in the MR-107A-02 group and 135 participants each in the Tramadol and Placebo groups. The PP Analysis Set was composed of 333 (81.2%) participants with 111 participants in each of the three treatment groups. The PK Analysis Set was composed of 197 (48.0%) participants, with 64 participants in the MR-107A-02 group, 66 participants in the Tramadol group, and 67 participants in the Placebo group.

Furthermore, herein is presented by-participant information on inclusion in each analysis set, including the reasons for exclusion of the 77 participants from the PP Analysis Set. As noted below, 8 protocol deviations (3 major and 5 minor) in 5 participants were identified post-database lock. Of the 3 participants with newly identified major protocol deviations, participants 105-041 and 106-107 (both in the Tramadol group) were included in the PP Analysis Set but should have been excluded due to a major protocol deviation. The third participant (107-004 in the Tramadol group) had already been excluded from the PP Analysis Set due to a separate major protocol deviation.

Table 24 summarizes the demographic and baseline characteristics of the FAS. Most participants (85.9% of all participants) were female, and over half of all participants were White (60.0%) and not Hispanic or Latino (68.3%). The mean age was 48.0 years (range 18 to 77 years), and most participants were <65 years of age (89.3%). The mean BMI was 28.7 kg/$m^2$ (range 16 to 40 kg/$m^2$), and the mean baseline NRS-R was 7.3 (range 3 to 10). The mean duration of surgery was 31.9 minutes (range 12 to 92 minutes). The three treatment groups were comparable with respect to demographic and baseline characteristics.

By-participant information on demographic and baseline characteristics and baseline data for efficacy and PK measurements and laboratory tests are included below.

TABLE 24

Demographic and Baseline Characteristics (Full Analysis Set)

| | MR-107A-02 (15 mg BID) → MR-107A-02 (15 mg BID) (N = 137) | Tramadol (50 mg q6h) → Placebo (N = 137) | Placebo → Placebo (N = 136) | Total (N = 410) |
|---|---|---|---|---|
| Age (years) | | | | |
| N | 137 | 137 | 136 | 410 |
| Mean (SD) | 47.8 (13.80) | 49.0 (13.13) | 47.2 (13.36) | 48.0 (13.42) |
| Median | 48.0 | 51.0 | 47.5 | 49.0 |
| Min, Max | 18, 77 | 18, 76 | 18, 74 | 18, 77 |
| Age group, n (%) | | | | |
| <65 years | 122 (89.1) | 122 (89.1) | 122 (89.7) | 366 (89.3) |
| ≥65 years | 15 (10.9) | 15 (10.9) | 14 (10.3) | 44 (10.7) |
| Sex, n (%)[1] | | | | |
| Male | 19 (13.9) | 17 (12.4) | 22 (16.2) | 58 (14.1) |
| Female | 118 (86.1) | 120 (87.6) | 114 (83.8) | 352 (85.9) |
| Race, n (%) | | | | |
| American Indian or Alaskan Native | 0 | 3 (2.2) | 3 (2.2) | 6 (1.5) |
| Asian | 5 (3.6) | 5 (3.6) | 7 (5.1) | 17 (4.1) |
| Black or African American | 43 (31.4) | 36 (26.3) | 53 (39.0) | 132 (32.2) |
| Native Hawaiian or Other Pacific Islander | 0 | 0 | 0 | 0 |
| White | 86 (62.8) | 90 (65.7) | 70 (51.5) | 246 (60.0) |
| Not Reported | 0 | 1 (0.7) | 0 | 1 (0.2) |

TABLE 24-continued

Demographic and Baseline Characteristics (Full Analysis Set)

| | MR-107A-02 (15 mg BID) → MR-107A-02 (15 mg BID) (N = 137) | Tramadol (50 mg q6h) → Placebo (N = 137) | Placebo → Placebo (N = 136) | Total (N = 410) |
|---|---|---|---|---|
| Unknown | 0 | 1 (0.7) | 0 | 1 (0.2) |
| Other | 1 (0.7) | 0 | 1 (0.7) | 2 (0.5) |
| Multiple | 2 (1.5) | 1 (0.7) | 2 (1.5) | 5 (1.2) |
| Ethnicity, n (%)[1] | | | | |
| Hispanic or Latino | 42 (30.7) | 43 (31.4) | 41 (30.1) | 126 (30.7) |
| Not Hispanic or Latino | 93 (67.9) | 93 (67.9) | 94 (69.1) | 280 (68.3) |
| Not Reported | 2 (1.5) | 1 (0.7) | 1 (0.7) | 4 (1.0) |
| Baseline Weight (kg) | | | | |
| N | 137 | 137 | 136 | 410 |
| Mean (SD) | 76.1 (17.21) | 78.5 (17.11) | 78.7 (16.59) | 77.8 (16.97) |
| Median | 72.6 | 75.7 | 76.6 | 75.6 |
| Min, Max | 47, 126 | 45, 126 | 46, 124 | 45, 126 |
| Baseline Height (cm) | | | | |
| N | 137 | 137 | 136 | 410 |
| Mean (SD) | 164.0 (9.55) | 164.1 (8.41) | 165.0 (9.17) | 164.4 (9.04) |
| Median | 162.6 | 163.0 | 163.7 | 163.2 |
| Min, Max | 142, 195 | 146, 186 | 147, 194 | 142, 195 |
| Baseline BMI ($kg/m^2$) | | | | |
| N | 137 | 137 | 136 | 410 |
| Mean (SD) | 28.2 (5.19) | 29.0 (5.38) | 28.8 (5.09) | 28.7 (5.22) |
| Median | 27.9 | 28.4 | 28.0 | 28.3 |
| Min, Max | 18, 40 | 16, 40 | 18, 40 | 16, 40 |
| Duration of surgery (minutes)[2] | | | | |
| N | 137 | 137 | 136 | 410 |
| Mean (SD) | 31.5 (12.06) | 32.5 (13.44) | 31.7 (12.18) | 31.9 (12.55) |
| Median | 32.0 | 32.0 | 32.0 | 32.0 |
| Min, Max | 12, 61 | 12, 92 | 12, 69 | 12, 92 |
| Baseline NRS-R | | | | |
| N | 137 | 135 | 135 | 407 |
| Mean (SD) | 7.2 (1.67) | 7.2 (1.64) | 7.6 (1.73) | 7.3 (1.68) |
| Median | 7.0 | 7.0 | 8.0 | 7.0 |
| Min, Max | 3, 10 | 4, 10 | 4, 10 | 3, 10 |

BID = Twice daily;

BMI = Body mass index;

Max = Maximum;

Min = Minimum;

n = Number of participants;

N = Number of participants per treatment group in the Full Analysis Set;

NRS-R = Numeric Rating Scale at rest;

q6h = Every 6 hours;

SD = Standard deviation

Note:

During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase.

Note:

Percentages were based on the number of participants in the Full Analysis Set, in each treatment group.

Note:

Baseline was defined as the last assessment taken prior to the start of study drug administration.

[1]Demographic and baseline characteristics reported by 0 participants overall are excluded from this table.

[2]Calculated as the time between the start and stop times of the bunionectomy surgery, in minutes.

Participant efficacy data were summarized by treatment group for the entire treatment phase and/or individually for the in-patient and out-patient treatment phases. The groups are referenced using the full treatment sequence (i.e., treatment during the in-patient treatment phase→treatment during the out-patient treatment phase) when the entire treatment phase was analyzed or using the treatment that participants were assigned in that phase of the study (i.e., treatment during the in-patient treatment phase or treatment during the out-patient treatment phase).

During the in-patient treatment phase, participants received MR-107A-02 (15 mg BID), tramadol (50 mg q6h), or placebo (q6h; see Table 20), and during the out-patient treatment phase, participants received either MR-107A-02 (15 mg BID) or placebo (BID; see Table 21). To differentiate the participants who received tramadol (50 mg q6h) or placebo during the in-patient treatment phase, the out-patient treatment phase tables include the Tramadol Placebo and Placebo groups. All participants who received placebo during the out-patient treatment phase, regardless of their treatment during the in-patient treatment phase, are included in the All-Placebo group.

To simplify the discussions, the treatment groups are referenced in text as follows:

MR-107A-02 group=MR-107A-02 (15 mg BID) during the in-patient treatment phase and MR-107A-02 (15 mg BID) during the out-patient treatment phase Tramadol group (referred to as the Tramadol Placebo group in the descriptions of the out-patient treatment phase in sections below)=tramadol (50 mg q6h) during the in-patient treatment phase and placebo during the out-patient treatment phase.

Placebo group=placebo during both the in- and out-patient treatment phases

All Placebo group=placebo during the out-patient treatment phase (includes participants who received either tramadol [50 mg q6h] or placebo during the in-patient treatment phase)

The primary efficacy endpoint was the $SPID_{0-48}$ (based on NRS-R scores), and the analysis used an ANCOVA model to compare the MR-107A-02 and Placebo groups in the FAS. The censoring of NRS-R scores due to rescue medication use was managed by the WLOCF approach, and missing data for NRS-R scores were managed by an MI approach. The FAS included 137 participants each in the MR-107A-02 and Tramadol groups and 136 participants in the Placebo group, which exceeded the minimum treatment group size required to sufficiently power the study for the planned analyses of the primary and secondary estimands.

The primary efficacy endpoint of $SPID_{0-48}$ (NRS-R) was met, and Table 25 presents the results of the primary endpoint analysis in the FAS. The LS means (95% CI) for $SPID_{0-48}$ in the MR-107A-02 and Placebo groups were 183.9 (163.0, 204.7) and 101.2 (80.0, 122.4), respectively; the difference in LS means (95% CI) for MR-107A-02 versus placebo (82.7 [62.0, 103.4]) was statistically significant (p<0.001).

TABLE 25

Primary Endpoint: SPID (NRS-R) Over 0-48 Hours, ANCOVA with MI (Full Analysis Set)

| Variable<br>Statistic | MR-107A-02<br>(15 mg BID)<br>(N = 137) | Placebo<br>(N = 136) |
|---|---|---|
| $SPID_{0-48}$ | | |
| n | 134 | 133 |
| Mean (SD) | 157.9 (100.21) | 85.0 (90.56) |
| Min, Max | −59.5, 387.3 | −102.7, 305.7 |
| LS Mean (SE) | 183.9 (10.64) | 101.2 (10.83) |
| CI[1] | (163.0, 204.7) | (80.0, 122.4) |
| Difference in LS Means (SE) versus Placebo | 82.7 (10.54) | |
| CI for Difference in LS Means[1] | (62.0, 103.4) | |
| p-value for Difference[2] | <0.001 | |

ANCOVA = Analysis of covariance;
APAP = acetaminophen;
BID = Twice daily;
CI = Confidence interval;
LS = Least squares;
Max = Maximum;
MI = Multiple imputation;
Min = Minimum;
n = Number of participants;
N = Number of participants per treatment group in the Full Analysis Set;
NRS-R = Numeric Rating Scale at rest;
q6h = Once every 6 hours;
SAP = Statistical Analysis Plan;
SD = Standard deviation;
SE = Standard error;
SPID = Summed pain intensity difference;
$SPID_{0-48}$ = Summed pain intensity difference from 0-48 hours;
WLOCF = Windowed last observation carried forward Note:
During the in-patient treatment phase, participants received MR-107A-02 (15 mg BID), tramadol (50 mg q6h), or placebo (q6h).

Note:
Missing values due to participants discontinuing early were imputed using an MI approach, taking into account the reasons for discontinuation. For any rescue medication use, a WLOCF approach was used, whereby the last observed pain intensity score prior to taking rescue medication was carried forward to replace the observed pain intensity scores during the period of time following the rescue medication intake. The window for APAP (1st step) rescue medication was 6 hours; the window for oxycodone (2nd step) rescue medication was 4 hours; the window for morphine (3rd step) rescue medication was 2 hours.

Note:
Summary statistics (n, mean, SD, Min, and Max) were based on observed data only (i.e., participants whose SPID values included data imputed by MI were not included in these summary statistics).

Note:
The LS means, differences, CIs, and p-values were based on an ANCOVA model with fixed, categorical effects for treatment (MR-107A-02, Placebo), age group (<65 years, ≥65 years), and study site and baseline pain intensity score as a continuous covariate.

[1]95% CI for MR-107A-02 and Placebo.

[2]2-sided p-value.

FIG. 13 displays the LS mean pain scores (NRS-R) based on the ANCOVA model for the MR-107A-02 and Placebo groups in the FAS over time. Over the period of 0-48 hours, the LS mean pain scores decreased for both groups, but the reductions were larger in the MR-107A-02 group than in the Placebo group.

A sensitivity analysis of the primary estimand was conducted using the same ANCOVA model as the primary estimand, but the Tramadol group was included. Five additional sensitivity analyses were implemented to include the application of additional windows and different censoring approaches following for rescue medication use in place of the WLOCF in the calculation of the primary estimand (i.e., no censoring, a 4-hour APAP window, a 6-hour oxycodone window, alternative censoring, and all values censored). Another sensitivity analysis was implemented using an alternate MI approach based on the pooled data from the MR-107A-02 and Placebo groups only.

All 7 sensitivity analyses resulted in larger $SPID_{0-48}$ in the MR-107A-02 group than in the Placebo group and mirrored the results of the primary analysis of the primary efficacy estimand.

FIG. 14 presents the LS mean pain scores (NRS-R) from 0-48 hours for the FAS based on an ANCOVA model with the Tramadol group included. Over the period of 0-48 hours, the LS mean pain scores decreased with time for all three groups, but the MR-107A-02 group had the largest pain score reductions during this time period.

The LS mean pain scores (NRS-R) over time for the MR-107A-02, Tramadol, and Placebo groups in the FAS based on the ANCOVA model used for the primary efficacy estimand with additional windows for rescue medication use in place of the WLOCF in the calculation of the primary estimand (i.e., no censoring, a 4-hour APAP window, a 6-hour oxycodone window, alternative censoring, and all values censored, respectively) were similar to the primary analysis, the LS mean pain scores decreased with time for all groups, with the MR-107A-02 group showing the largest reductions over the period of 0-48 hours, for all sensitivity analyses. The magnitude of the LS mean pain scores over time was dependent on the analysis method, with the biggest impact on the LS mean pain scores over time in the analysis with all values censored.

The primary efficacy endpoint was the $SPID_{0-48}$, and the supplementary analyses used an ANCOVA model to compare the MR-107A-02 and Placebo groups in the mFAS and PP Analysis Set. Rescue medication use was managed by the WLOCF approach and missing data was managed by an MI approach.

The results of the supplementary analyses of the primary estimand in the mFAS and PP Analysis Set, respectively showed that for the mFAS, the LS means (95% CI) for $SPID_{0-48}$ in the MR-107A-02 and Placebo groups were 184.4 (163.6, 205.2) and 100.7 (79.5, 121.9), respectively; the difference in LS means (95% CI) for MR-107A-02 versus placebo was 83.6 (63.0, 104.3). For the PP Analysis Set, the LS means (95% CI) for $SPID_{0-48}$ in the MR-107A-02 and Placebo groups were 187.0 (164.5, 209.5) and 105.5 (82.9, 128.2), respectively; the difference in LS means (95% CI) for MR-107A-02 versus placebo was 81.5 (58.6, 104.3). The results of the primary efficacy estimand analyses in the mFAS and PP Analysis Set were very similar to those in the FAS and supported the conclusions of the primary analysis.

The LS mean pain scores (NRS-R) over time based on the ANCOVA model used for the primary efficacy estimand analysis with the Tramadol group included in the mFAS and PP Analysis Set, respectively showed that over the period of 0-48 hours for the mFAS and PP Analysis Set, the LS mean pain scores decreased with time for all three treatment groups, but the pain score reductions were largest in the MR-107A-02 group.

The primary efficacy endpoint was the $SPID_{0-48}$, and the analysis used an ANCOVA model to compare the MR-107A-02 and Placebo groups in the FAS. The analysis was repeated for each subgroup including age (<65 years and ≥65 years), sex (female, male) and race (White, Black or African American, and Other Race [included American Indian or Alaska Native, Asian, Multiple, Not reported, Other, and Unknown]). Rescue medication use was managed by the WLOCF approach and missing data was managed by an MI approach.

The results of the primary estimand analysis by age subgroup in the FAS showed that for the <65 years subgroup, the LS means (95% CI) for $SPID_{0-48}$ in the MR-107A-02 and Placebo groups were 170.9 (153.9, 187.9) and 87.3 (69.9, 104.8), respectively; the difference in LS means (95% CI) for MR-107A-02 versus placebo (83.5 [62.1, 105.0]) was nominally statistically significant ($p<0.001$).

For the ≥65 years subgroup, the LS means (95% CI) for $SPID_{0-48}$ in the MR-107A-02 and Placebo groups were 224.3 (151.4, 297.1) and 104.2 (32.6, 175.8), respectively; the difference in LS means (95% CI) for MR-107A-02 versus placebo (120.1 [16.2, 223.9]) was nominally statistically significant ($p=0.026$).

The nominal differences between MR-107A-02 and placebo for $SPID_{0-48}$ in both age subgroups suggest no effect of age on the efficacy of MR-107A-02; however, the clinical meaningfulness of this comparison is limited by the comparatively smaller sample size of the ≥65 years subgroup.

The LS mean pain scores (NRS-R) over time by age subgroup for the FAS based on the ANCOVA model used for the primary efficacy estimand analysis with the Tramadol group included showed that over the period of 0-48 hours, the LS mean pain scores decreased with time for all three treatment groups, but the pain score reductions were largest in the MR-107A-02 group for both age subgroups; in the ≥65 years subgroup, there was more variation in LS mean pain scores (i.e., wider CIs) within each treatment group than in the <65 years subgroup due to the comparatively smaller sample size in the ≥65 years subgroup.

The results of the primary estimand analysis by sex in the FAS showed that for the female subgroup, the LS means (95% CI) for $SPID_{0-48}$ in the MR-107A-02 and Placebo groups were 183.5 (160.1, 206.8) and 96.0 (72.0, 120.1), respectively; the difference in LS means (95% CI) for MR-107A-02 versus placebo (87.5 [64.4, 110.5]) was nominally statistically significant ($p<0.001$).

For the male subgroup, the LS means (95% CI) for $SPID_{0-48}$ in the MR-107A-02 and Placebo groups were 207.8 (157.1, 258.6) and 127.3 (81.4, 173.2), respectively; the difference in LS means (95% CI) for MR-107A-02 versus placebo (80.5 [24.5, 136.5]) was nominally statistically significant ($p=0.007$).

The nominal differences between MR-107A-02 and placebo for $SPID_{0-48}$ in both sexes suggest no effect of sex on the efficacy of MR-107A-02; however, the clinical meaningfulness of this comparison is limited by the relatively smaller sample size of the male subgroup.

The LS mean pain scores (NRS-R) over time by sex for the FAS based on the ANCOVA model used for the primary efficacy estimand analysis with the Tramadol group included showed that over the period of 0-48 hours, the LS mean pain scores decreased with time for all three treatment groups, but the pain score reductions were largest in the MR-107A-02 group for both sexes; in the male subgroup, there was more variation in LS mean pain scores (i.e., larger CIs) within each treatment group than in the female subgroup due to the small sample size in the male subgroup.

The results of the primary estimand analysis by race for the FAS show that for the White subgroup, the LS means (95% CI) for $SPID_{0-48}$ in the MR-107A-02 and Placebo groups were 189.7 (160.7, 218.7) and 110.7 (79.6, 141.7), respectively; the difference in LS means (95% CI) for MR-107A-02 versus placebo (79.0 [49.5, 108.6]) was nominally statistically significant ($p<0.001$).

For the Black or African American subgroup, the LS means (95% CI) for $SPID_{0-48}$ in the MR-107A-02 and Placebo groups were 184.2 (139.3, 229.2) and 100.3 (57.6, 142.9), respectively; the difference in LS means (95% CI) for MR-107A-02 versus placebo (84.0 [50.6, 117.3]) was nominally significant ($p<0.001$).

For the Other Race subgroup, the LS means (95% CI) for $SPID_{0-48}$ in the MR-107A-02 and Placebo groups were 255.9 (108.6, 403.2) and 136.5 (27.9, 245.1), respectively; the difference in LS means (95% CI) for MR-107A-02 versus placebo (119.4 [−0.8, 239.6]) was not statistically significant ($p=0.051$), which may be due to the small sample size in the Other Race subgroup.

The LS mean pain scores (NRS-R) over time by race for the FAS based on the ANCOVA model used for the primary efficacy estimand analysis with the Tramadol group included show that over the period of 0-48 hours, the LS mean pain scores decreased with time for all three treatment groups, but the reductions were largest in the MR-107A-02 group across the race subgroups; in the Other Race subgroup, there was more variation in LS mean pain scores (i.e., larger CIs) within each treatment group than in the White and Black or African American subgroups, due to the small sample size in the Other Race subgroup.

The primary efficacy endpoint was the $SPID_{0-48}$, and other analyses of this endpoint used an ANCOVA model to compare the Tramadol and Placebo groups (with and without MR-107A-02) and the MR-107A-02 and Tramadol groups (with and without Placebo) in the FAS. Rescue medication use was managed by the WLOCF approach, and missing data was managed by an MI approach. Additional details on the analyses are provided below. A discussion of the primary endpoint, $SPID_{0-48}$, comparing the MR-107A-02 and Placebo groups (without Tramadol), is also included herein.

Tramadol Versus Placebo, Excluding MR-107A-02:

The results of the $SPID_{0-48}$ analysis comparing the Tramadol and Placebo groups, excluding MR-107A-02, in the FAS show that the LS means (95% CI) for $SPID_{0-48}$ in the Tramadol and Placebo groups were 156.1 (138.9, 173.2) and 98.0 (77.6, 118.5), respectively; the difference in LS means (95% CI) for tramadol versus placebo (58.0 [40.9, 75.1]) was nominally statistically significant (p<0.001).

Tramadol Versus Placebo, Including MR-107A-02:

The results of the $SPID_{0-48}$ analysis comparing the Tramadol and Placebo groups, including MR-107A-02, in the FAS show that the LS means (95% CI) for $SPID_{0-48}$ in the Tramadol and Placebo groups were 154.9 (139.2, 170.6) and 97.3 (78.5, 116.1), respectively; the difference in LS means (95% CI) for tramadol versus placebo (57.6 [40.4, 74.8]) was nominally statistically significant (p<0.001).

MR-107A-02 Versus Tramadol, Excluding Placebo:

The results of the $SPID_{0-48}$ analysis comparing the MR-107A-02 and Tramadol groups, excluding Placebo, in the FAS show that the LS means (95% CI) for $SPID_{0-48}$ in the MR-107A-02 and Tramadol groups were 174.3 (153.8, 194.7) and 148.1 (130.5, 165.6), respectively; the difference in LS means (95% CI) for MR-107A-02 versus tramadol (26.2 [8.8, 43.6]) was nominally statistically significant (p=0.013) based on a post-hoc analysis.

MR-107A-02 Versus Tramadol, Including Placebo:

The results of the $SPID_{0-48}$ analysis comparing the MR-107A-02 and Tramadol groups, including Placebo, in the FAS show that the LS means (95% CI) for $SPID_{0-48}$ in the MR-107A-02 and Tramadol groups were 180.4 (161.9, 199.0) and 154.9 (139.2, 170.6), respectively; the difference in LS means (95% CI) for MR-107A-02 versus tramadol (25.5 [8.4, 42.6]) was nominally statistically significant (p=0.014) based on a post-hoc analysis.

The key secondary efficacy endpoint was the number of doses of opioid (oxycodone and/or morphine) rescue medication taken during the entire treatment phase, and the analysis used a negative binomial regression model with a log link to compare the MR-107A-02 and Placebo groups in the FAS. Missing data was managed by an MI approach.

Table 26 presents the results of the key secondary estimand analysis for the FAS. The mean (SD) number of doses of opioid (oxycodone and/or morphine) rescue medication during the entire treatment phase for the MR-107A-02 and Placebo groups were 1.3 (2.16) and 2.9 (3.64), respectively. The LS geometric mean number of opioid doses used in the MR-107A-02 group (0.12 doses) over the entire treatment phase was 59% lower than that in the Placebo group (0.29 doses). The ratio of LS geometric means (95% CI) for MR-107A-02 versus placebo (0.41 [0.29, 0.58]) was statistically significant (p<0.001). The results for the number of doses of opioid (oxycodone and/or morphine) rescue medication during other time intervals are discussed below.

TABLE 26

Key Secondary: Number of Doses of Opioid (Oxycodone and/or Morphine) Rescue Medication (Entire Treatment Phase) (Full Analysis Set)

| Variable<br>Statistic | MR-107A-02<br>(15 mg BID)<br>(N = 137) | Placebo<br>(N = 136) |
|---|---|---|
| Number of doses of Opioid (Oxycodone and/or Morphine) | | |
| Rescue Medication | | |
| Mean (SD) | 1.3 (2.16) | 2.9 (3.64) |
| Median | 0 | 2 |
| Min, Max | 0, 10 | 0, 23 |
| Difference in Means | −1.6 | |
| LS Geometric Mean | 0.12 | 0.29 |
| 95% CI | (0.08, 0.18) | (0.20, 0.43) |
| Ratio of LS Geometric Means versus Placebo | 0.41 | |
| 95% CI for Ratio of LS Geometric Means | (0.29, 0.58) | |
| p-value for Ratio | <0.001 | |

BID = Twice daily;
CI = Confidence interval;
LS = Least squares;
MAR = Missing at random;
Max = Maximum;
MI = Multiple imputation;
N = Number of participants per treatment group in the Full Analysis Set;
Min = Minimum;
q6h = Once every 6 hours;
SD = Standard deviation Note:
During the in-patient treatment phase, participants received MR-107A-02 (15 mg BID), tramadol (50 mg q6h), or placebo (q6h), and during the out-patient treatment phase, participants received either MR-107A-02(15 mg BID) or placebo (BID); participants in the Tramadol group received placebo only during the out-patient treatment phase.

Note:
The number of doses of opioid was defined as the number of doses of oxycodone and/or morphine taken.

Note:
For any missing data from participants discontinuing treatment early due to a lack of efficacy or an adverse event, a placebo-based MI approach was used, whereby both the rate before and after withdrawal for such participants was assumed to follow that of the Placebo group. Missing data from participants discontinuing for any other reasons was imputed using a MAR approach.

Note:
The LS geometric means, differences, CIs and 2-sided p-value were based on a negative binomial regression model with a log link with fixed, categorical effects for treatment (MR-107A-02 and placebo), age group (<65 years, ≥65 years), and study site. The LS geometric means (and difference) were estimated using this model and then back transformed to the original scale by exponentiating.

Note:
Summary statistics (mean, median, SD, Min, Max) were based on observed data only.

A sensitivity analysis of the key secondary efficacy estimand was performed to calculate the number of doses of oxycodone only taken during the entire treatment phase; and the analysis used a negative binomial regression model with a log link to compare the MR-107A-02 and Placebo groups in the FAS. Missing data was managed by an MI approach. A second sensitivity analysis for the number of doses of opioid was also performed, with an alternate MI approach using a negative binomial distribution based on the pooled data from the MR-107A-02 and Placebo groups.

The results of the first sensitivity analysis of the key secondary estimand for the FAS show that the mean (SD) number of doses of oxycodone rescue medication for the MR-107A-02 and Placebo groups was 1.3 (2.11) and 2.7

(3.52), respectively, and the ratio of LS geometric means (95% CI) for MR-107A-02 versus placebo was 0.41 (0.29, 0.58).

The results of the second sensitivity analysis of the key secondary estimand for the FAS show that the mean (SD) number of doses of oxycodone rescue medication for the MR-107A-02 and Placebo groups was 1.3 (2.16) and 2.9 (3.64), respectively, and the ratio of LS geometric means (95% CI) for MR-107A-02 versus placebo was 0.41 (0.29, 0.59).

Overall, the results of the sensitivity analyses of the key secondary efficacy estimand were similar to those of the primary analysis discussed below.

The key secondary efficacy endpoint was the number of doses of opioid (oxycodone and/or morphine) rescue medication taken during the entire treatment phase, and the analysis used a negative binomial regression model with a log link to compare the MR-107A-02 and Placebo groups in the FAS. The analysis was repeated for each age (<65 years and ≥65 years), sex (female, male) and race (White, Black or African American, and Other Race) subgroup. Missing data was managed by an MI approach.

The results of the key secondary estimand analysis by age subgroup for the FAS.

For the <65 years subgroup, the mean (SD) number of doses of opioid (oxycodone and/or morphine) rescue medication for the MR-107A-02 and Placebo groups was 1.3 (2.15) and 2.9 (3.65), respectively, and the ratio of LS geometric means (95% CI) for MR-107A-02 versus placebo (0.42 [0.30, 0.60]) was nominally statistically significant ($p<0.001$).

For the ≥65 years subgroup, the mean (SD) number of doses of opioid (oxycodone and/or morphine) rescue medication for the MR-107A-02 and Placebo groups was 1.0 (2.24) and 2.6 (3.67), respectively, and the ratio of LS geometric means (95% CI) for MR-107A-02 versus placebo (0.10 [0.01, 0.89]) was nominally statistically significant ($p=0.039$).

The nominal differences between MR-107A-02 and placebo for the number of doses of opioid (oxycodone and/or morphine) rescue medication during the entire treatment phase in both age subgroups suggest no effect of age on the efficacy of MR-107A-02; however, the limited sample size of the ≥65 years subgroup limits the meaning of this comparison.

The results of the key secondary estimand analysis by sex for the FAS.

For the female subgroup, the mean (SD) number of doses of opioid (oxycodone and/or morphine) rescue medication for the MR-107A-02 and Placebo groups was 1.4 (2.20) and 3.0 (3.83), respectively, and the ratio of LS geometric means (95% CI) for MR-107A-02 versus placebo (0.42 [0.29, 0.61]) was nominally significant ($p<0.001$).

For the male subgroup, the mean (SD) number of doses of opioid (oxycodone and/or morphine) rescue medication for the MR-107A-02 and Placebo groups was 0.9 (1.87) and 2.5 (2.46), and the ratio of LS geometric means (95% CI) for MR-107A-02 versus placebo (0.38 [0.18, 0.80]) was nominally statistically significant ($p=0.010$).

The nominal differences between MR-107A-02 and placebo for the number of doses of opioid (oxycodone and/or morphine) rescue medication during the entire treatment phase in both sexes suggest no effect of sex on the efficacy of MR-107A-02; however, the limited sample size of the male subgroup limits the meaning of this comparison.

The results of the key secondary estimand analysis by race for the FAS.

For the White subgroup, the mean (SD) number of doses of opioid (oxycodone and/or morphine) rescue medication during the entire treatment phase for the MR-107A-02 and Placebo groups was 1.4 (2.25) and 2.8 (4.31), respectively, and the ratio of LS geometric means (95% CI) for MR-107A-02 versus placebo (0.44 [0.26, 0.73]) was nominally statistically significant ($p=0.002$).

For the Black or African American subgroup, the mean (SD) number of doses of opioid (oxycodone and/or morphine) rescue medication during the entire treatment phase for the MR-107A-02 and Placebo groups was 1.4 (2.12) and 3.2 (2.61), respectively, and the ratio of LS geometric means (95% CI) for MR-107A-02 versus placebo (0.430 [0.275, 0.673]) was nominally statistically significant ($p<0.001$).

For the Other Race subgroup, the mean (SD) number of doses of opioid (oxycodone and/or morphine) rescue medication during the entire treatment phase for the MR-107A-02 and Placebo groups was 0.3 (0.71) and 2.1 (3.43), respectively, and the ratio of LS geometric means (95% CI) for MR-107A-02 versus placebo (0.0791 [0.0187, 0.3348]) was nominally statistically significant ($p<0.001$).

The nominal differences between MR-107A-02 and placebo for the number of doses of opioid (oxycodone and/or morphine) rescue medication during the entire treatment phase for all race subgroups suggest no effect of race on the efficacy of MR-107A-02; however, the limited sample size of the Black or African American and Other Race subgroups limits the meaning of this comparison.

The number of doses of opioid (oxycodone and/or morphine) rescue medication taken during the last 24 and 36 hours before discharge, in-patient and out-patient treatment phases, 0-24 hours after randomization, and post-discharge phase (up to 30 days) were other secondary efficacy endpoints and the analysis followed the methods used for the primary analysis of the key secondary endpoint (i.e., a negative binomial regression model with a log link) to compare the MR-107A-02 and Placebo groups in the FAS. Missing data was managed by an MI approach. For the in-patient interval, the Poisson distribution (which can be considered as a simplified case of the negative binomial distribution) was used due to the closeness of the dispersion parameter to zero.

The number of doses of opioid (oxycodone and/or morphine) rescue medication during the last 24 hours before discharge for the FAS shows that the mean (SD) number of doses of opioid (oxycodone and/or morphine) rescue medication during the last 24 hours before discharge for the MR-107A-02 and Placebo groups was 0.1 (0.46) and 0.4 (0.86), respectively, and the ratio of LS geometric means (95% CI) for MR-107A-02 versus placebo (0.2840 [0.1541, 0.5233]) was nominally statistically significant ($p<0.001$).

The number of doses of opioid (oxycodone and/or morphine) rescue medication during the last 36 hours before discharge for the FAS shows that the mean (SD) number of doses of opioid (oxycodone and/or morphine) rescue medication during the last 36 hours before discharge for the MR-107A-02 and Placebo groups was 0.4 (0.79) and 0.9 (1.36), respectively, and the ratio of LS geometric means (95% CI) for MR-107A-02 versus placebo (0.36 [0.23, 0.57]) was nominally statistically significant ($p<0.001$).

In-Patient Treatment Phase (i.e., 0-48 Hours after Randomization):

The number of doses of opioid (oxycodone and/or morphine) rescue medication during the in-patient treatment phase for the FAS shows that the mean (SD) number of doses of opioid (oxycodone and/or morphine) rescue medication during in-patient treatment phase for the MR-107A-

02 and Placebo groups was 0.8 (1.21) and 1.6 (1.93), respectively, and the ratio of LS geometric means (95% CI) for MR-107A-02 versus placebo (0.45 [0.33, 0.62]) was nominally statistically significant (p<0.001).

Out-Patient Treatment Phase (i.e., 5 Days Following Discharge):

The number of doses of opioid (oxycodone and/or morphine) rescue medication during the out-patient treatment phase for the FAS shows that the mean (SD) number of doses of opioid (oxycodone and/or morphine) rescue medication during out-patient treatment phase for the MR-107A-02 and Placebo groups was 0.5 (1.43) and 1.3 (2.43), respectively, and the ratio of LS geometric means (95% CI) for MR-107A-02 versus placebo (0.33 [0.18, 0.59]) was nominally statistically significant (p<0.001).

0-24 Hours after Randomization:

The number of doses of opioid (oxycodone and/or morphine) rescue medication during 0-24 hours after randomization for the FAS shows that the mean (SD) number of doses of opioid (oxycodone and/or morphine) rescue medication during 0-24 hours after randomization for the MR-107A-02 and Placebo groups was 0.6 (0.97) and 1.2 (1.31), respectively, and the ratio of LS geometric means (95% CI) for MR-107A-02 versus placebo (0.51 [0.38, 0.68]) was nominally statistically significant (p<0.001).

Post-Discharge Phase (i.e., Up to 30 Days after Discharge):

The number of doses of opioid (oxycodone and/or morphine) rescue medication during the post-discharge phase, up to 30 days, for the FAS shows that the mean (SD) number of doses of opioid (oxycodone and/or morphine) rescue medication during the post-discharge phase, up to 30 days, for the MR-107A-02 and Placebo groups was 0.7 (1.94) and 1.8 (3.80), respectively, and the ratio of LS geometric means (95% CI) for MR-107A-02 versus placebo (0.370 [0.207, 0.663]) was nominally statistically significant (p<0.001).

The number and proportion of participants who were opioid-free during the entire treatment phase, the last 24 and 36 hours before discharge, the in-patient treatment phase, and the out-patient treatment phase, 0-24 hours after randomization, and post-discharge phase (up to 30 days after discharge) were other secondary efficacy endpoints. The proportion of participants who were opioid-free during any time interval was defined as the proportion of participants who had not taken oxycodone and/or morphine; for any participants who reported taking a rescue medication without reporting the type taken, or if the rescue medication was noted to be Norco/hydrocodone, that rescue medication was counted as an opioid. The proportions were analyzed with the difference in proportions Z-test, and a sensitivity analysis based on the proportion of participants who had not taken oxycodone during the entire treatment phase was performed.

Entire Treatment Phase:

The number and proportion of opioid (oxycodone and/or morphine) free participants during the entire treatment phase for the FAS shows that in the MR-107A-02 and Placebo groups, 78 (56.9%) and 45 (33.1%) participants, respectively, were opioid (oxycodone and/or morphine) free during the entire treatment phase; the MR-107A-02 group had 24% more opioid-free participants than the Placebo group, and the difference in proportions (95% CI) of 23.8% (12.4%, 35.3%) was statistically significant (p<0.001).

The results of the sensitivity analysis of the number and proportion of opioid free participants during the entire treatment phase for the FAS, in which only oxycodone use was analyzed shows that in the MR-107A-02 and Placebo groups, 78 (56.9%) and 46 (33.8%) participants, respectively, were oxycodone free during the entire treatment phase; the difference in proportions (95% CI) of 23.1% (11.6%, 34.6%) was nominally significant (p<0.001). The results of the sensitivity analysis (only oxycodone) were similar to those of the analysis that included both oxycodone and/or morphine Last 24 Hours Before Discharge (i.e., 24-48 Hours after Randomization):

The number and proportion of opioid (oxycodone and/or morphine) free participants during the last 24 hours before discharge for the FAS shows that in the MR-107A-02 and Placebo groups, 122 (89.1%) and 99 (72.8%) participants, respectively, were opioid (oxycodone and/or morphine) free during the last 24 hours before discharge; the difference in proportions (95% CI) of 16.3% (7.1%, 25.4%) was nominally statistically significant (p<0.001).

Last 36 Hours Before Discharge (i.e., 12-48 Hours after Randomization):

The number and proportion of opioid (oxycodone and/or morphine) free participants during the last 36 hours before discharge for the FAS shows that in the MR-107A-02 and Placebo groups, 107 (78.1%) and 78 (57.4%) participants, respectively, were opioid (oxycodone and/or morphine) free during the last 36 hours before discharge; the difference in proportions (95% CI) of 20.7% (9.9%, 31.6%) was nominally statistically significant (p<0.001).

In-patient Treatment Phase (i.e., 0-48 hours after Randomization):

The number and proportion of opioid (oxycodone and/or morphine) free participants during the in-patient treatment phase for the FAS shows that in the MR-107A-02 and Placebo groups, 84 (61.3%) and 53 (39.0%) participants, respectively, were opioid (oxycodone and/or morphine) free during the in-patient treatment phase; the difference in proportions (95% CI) of 22.3% (10.8%, 33.9%) was nominally statistically significant (p<0.001).

Out-Patient Treatment Phase (i.e., 5 Days Following Discharge):

The number and proportion of opioid (oxycodone and/or morphine) free participants during the out-patient treatment phase for the FAS shows that in the MR-107A-02 and Placebo groups, 109 (79.6%) and 87 (64.0%) participants, respectively, were opioid (oxycodone and/or morphine) free during the out-patient treatment phase; the difference in proportions (95% CI) of 15.6% (5.1%, 26.1%) was nominally statistically significant (p=0.004).

This analysis was repeated to compare the MR-107A-02 group with the All-Placebo group and with the Tramadol Placebo group. In the Tramadol Placebo group, 87 (63.5%) participants were opioid (oxycodone and/or morphine) free during the out-patient treatment phase; the difference in proportions (95% CI) for MR-107A-02 versus tramadol of 16.1% (5.5%, 26.6%) was nominally statistically significant (p=0.003). In the All-Placebo group, 174 (63.7%) participants were opioid (oxycodone and/or morphine) free; the difference in proportions (95% CI) for MR-107A-02 versus placebo (all) of 15.8% (7.0%, 24.7%) was nominally statistically significant (p=0.001).

0-24 Hours after Randomization:

The number and proportion of opioid (oxycodone and/or morphine) free participants during 0-24 hours after randomization for the FAS shows that in the MR-107A-02 and Placebo groups, 85 (62.0%) and 55 (40.4%) participants, respectively, were opioid (oxycodone and/or morphine) free during 0-24 hours after randomization; the difference in proportions (95% CI) of 21.6% (10.0%, 33.2%) was nominally statistically significant (p<0.001).

Post-Discharge Phase (i.e., Up to 30 Days after Discharge):

The number and proportion of opioid (oxycodone and/or morphine) free participants during the post-discharge phase, up to 30 days, for the FAS shows that in the MR-107A-02 and Placebo groups, 105 (76.6%) and 84 (61.8%) participants, respectively, were opioid (oxycodone and/or morphine) free during the post-discharge phase, up to 30 days; the difference in proportions (95% CI) of 14.9% (4.1%, 25.7%) was nominally statistically significant (p=0.008).

This analysis was repeated to compare the MR-107A-02 group with the All-Placebo group and with the Tramadol Placebo group. In the Tramadol Placebo group, 85 (62.0%) participants were opioid (oxycodone and/or morphine) free during the post-discharge phase, up to 30 days; the difference in proportions (95% CI) for MR-107A-02 versus tramadol of 14.6% (3.8%, 25.4%) was nominally statistically significant (p=0.009). In the All-Placebo group, 169 (61.9%) participants were opioid (oxycodone and/or morphine) free during the post-discharge phase, up to 30 days; the difference in proportions (95% CI) for MR-107A-02 versus placebo (all) of 14.7% (5.6%, 23.9%) was nominally statistically significant (p=0.003).

Summed Pain Intensity Difference Over Time Following Study Drug Administration

The SPID over 0-4 hours, 0-8 hours, 0-12 hours, 12-24 hours, and 0-24 hours following study drug administration (based on NRS-R scores) were other secondary efficacy endpoints; the analysis was similar to that of the primary estimand.

The SPID over time following study drug administration for the FAS. Overall, the LS means for the SPID in the MR-107A-02, Tramadol, and Placebo groups increased with time through 24 hours post-dose showed that the MR-107A-02 and Tramadol groups both had larger (and nominally statistically significantly different) LS mean SPIDs than the Placebo group at each time interval evaluated (MR-107A-02 versus placebo [p<0.005] and tramadol versus placebo [p<0.042; post-hoc]). The MR-107A-02 group had numerically larger LS mean SPIDs than the Tramadol group at each time interval evaluated. The various analyses of $SPID_{0-48}$ (the primary estimand) are discussed below.

Pain Intensity Differences Over Time Following Study Drug Administration

The PIDs over time following study drug administration (based on NRS-R scores) were other secondary efficacy endpoints and were analyzed using MMRM. Additional details on the analysis are provided below.

The PID (NRS-R) over time following study drug administration for the FAS. The PID at each time point was proportional to the NRS pain score at that time point, such that lower PIDs corresponded to lower NRS pain scores show that the MR-107A-02 and Tramadol groups had lower LS mean PIDs than the Placebo group from 0.5 through 48 hours following study drug administration (i.e., all time points evaluated), and the MR-107A-02 group had numerically lower LS mean PIDs than the Tramadol group from 2 through 12 hours and from 20 through 48 hours following study drug administration.

Time to Perceptible Pain Relief

The time to perceptible pain relief, which was measured by the two-stopwatch technique, was a secondary efficacy endpoint that was analyzed using Kaplan-Meir plots with censoring at the time of first rescue medication. Additional details on the analysis are provided in section herein, and the post-hoc analyses for tramadol versus placebo are noted in sections herein.

The time to perceptible pain relief for the FAS, and FIG. 15 displays the Kaplan-Meier plot for the time to perceptible pain relief for the FAS. The median (95% CI) time to first perceptible pain relief in the MR-107A-02 group (0.7 [0.6, 0.9] hours) was lower than that in the Placebo group (0.9 [0.6, 5.8] hours). The log rank test yielded a nominally statistically significant p-value (p=0.037); the median (CI) time to first perceptible relief of pain was numerically lower in the Tramadol group (0.8 [90% CI: 0.6, 0.9] hours) than that in the Placebo group (0.9 [95% CI: 0.6, 5.8] hours). The log rank test yielded a statistically non-significant p-value (p=0.056; post-hoc). Of the three treatment groups MR-107A-02 had the fastest time to first perceptible pain relief.

Time to Meaningful Pain Relief

The time to meaningful pain relief, which was measured by the two-stopwatch technique, was another secondary efficacy endpoint analyzed using Kaplan-Meir plots with censoring at the time of first rescue medication. Additional details on the analysis are provided herein, and the post-hoc analyses for tramadol versus placebo are noted in sections herein.

The time to meaningful pain relief for the FAS, and FIG. 16 displays the Kaplan-Meier plot for the time to meaningful pain relief for the FAS show that the median (CI) times to meaningful relief of pain in the MR-107A-02 and Tramadol groups (2.4 hours [95% CI: 1.9, 3.0 hours] and 3.4 hours [90% CI: 2.6, 4.9 hours], respectively) were lower than that in the Placebo group (5.1 hours [95% CI: 3.1, not available hours]). The log rank test yielded nominally statistically significant p-values (p=0.012 for MR-107A-02 versus placebo and p=0.046 [post-hoc] for tramadol versus placebo). Of the three treatment groups, MR-107A-02 had the fastest median time to meaningful pain relief.

Proportion of Participants with Overall Pain Reductions from Baseline of ≥30% and ≥50% Over Time Following Study Drug Administration The proportion of participants with an overall pain reduction of ≥30% and ≥50% from baseline within 0-4 hours, 0-8 hours, 0-12 hours, 12-24 hours, 0-24 hours, 24-48 hours, and 0-48 hours after the first dose were other secondary efficacy endpoints that were analyzed using the difference in proportions Z-test. Additional details on the planned analysis are provided herein, and the post-hoc analyses for tramadol versus placebo are noted in sections herein.

Overall Pain Reduction≥30% from Baseline:

The proportion of participants with an overall pain reduction≥30% from baseline, using NRS-R for the FAS show that with increasing time intervals, the proportions of participants with an overall pain reduction≥30% from baseline (i.e., responders) increased within each treatment group; the proportions of responders were higher in the MR-107A-02 and Tramadol groups than in the Placebo group at all intervals (nominal p-values of p≤0.024 for MR-107A-02 versus placebo and p≤0.022 [post-hoc] for tramadol versus placebo). The proportions of responders in the MR-107A-02 and Tramadol groups were numerically similar at all intervals.

Overall Pain Reduction≥50% from Baseline:

The Proportions of participants with an overall pain reduction≥50% from baseline, using NRS-R for the FAS show that as for the proportions of participants with an overall pain reduction≥50% from baseline, the proportions of participants with an overall pain reduction≥50% from baseline (i.e., responders) increased within each treatment group with increasing time intervals; the proportions of responders were higher in the MR-107A-02 and Tramadol groups than in the Placebo group at all intervals (nominal p-values of p≤0.018 for MR-107A-02 versus placebo and p≤0.015 [post-hoc] for tramadol versus placebo). The proportions of responders in the MR-107A-02 and Tramadol groups were numerically similar at all intervals.

Patient's Global Assessment of Pain Control from 0-24 Hours, 24-48 Hours, and on Day 9

The PGA of pain control within 0-24 hours and 24-48 hours after the first dose and at Day 9 were other secondary efficacy endpoints that were analyzed using the difference in proportions Z-test. Additional details on the planned analysis are provided in herein, and the post-hoc analyses are described in sections below.

In-Patient Treatment Phase:

The proportion of participants with "very good" or "excellent" PGA of pain control during the in-patient treatment phase for the FAS show that from 0-24 hours to 24-48 hours, the proportions of participants with "very good" or "excellent" PGA of pain control (i.e., responders) increased within each treatment group; the proportions of responders were higher in the MR-107A-02 and Tramadol groups than in the Placebo group at both intervals (nominal p-values of p<0.001 for both MR-107A-02 versus placebo and tramadol versus placebo [post-hoc]). Of the three treatment groups, MR-107A-02 had the greatest proportion of responders at both measured in-patient intervals.

Out-Patient Treatment Phase:

The proportion of participants with "very good" or "excellent" PGA of pain control during the out-patient treatment phase for the FAS show that the proportions of responders at Day 9 were higher in the MR-107A-02 and Tramadol Placebo groups than in the Placebo group (nominal p-value of p<0.001 for MR-107A-02 versus placebo and p=0.048 [post-hoc] for tramadol versus placebo). Of the three treatment groups, MR-107A-02 had the greatest proportions of responders at Day 9.

Time to First Opioid (Oxycodone and/or Morphine) Rescue Medication Use

The time to first opioid (oxycodone and/or morphine) rescue medication use was another secondary efficacy endpoint that was analyzed using Kaplan-Meir plots. Participants who discontinued early were censored at the time of discontinuation. Additional details on the planned analysis are provided herein, and the changes to the planned analyses and the tramadol versus placebo post-hoc analyses are noted in sections herein.

The time to first opioid (oxycodone and/or morphine) rescue medication use for the FAS, and FIG. 17 displays the Kaplan-Meier plot for the time to first opioid (oxycodone and/or morphine) rescue medication use for the FAS. The median (CI) times to first opioid (oxycodone and/or morphine) rescue medication use in the MR-107A-02 and Tramadol groups were not available (95% CI: 62.5 hours, not available) and 64.7 hours (90% CI: 20.2 hours, not available), respectively. The MR-107A-02 and Tramadol groups had longer times to first opioid use than the Placebo group (10.0 hours [95% CI: 8.2, 14.9 hours]. The log rank test yielded nominal p-values (p<0.001 for MR-107A-02 versus placebo and p=0.007 [post-hoc] for tramadol versus placebo). Of the three treatment groups, the MR-107A-02 group had the largest 25th percentile time (7.4 hours), representing the time beyond which 25% of the participants had the event interest (Q1). Corresponding values of Q1 for the Tramadol and Placebo groups were 7.1 and 3.6 hours, respectively. No median time was calculated for the MR-107A-02 group as <50% of participants had an event.

Rescue Medication Use

APAP was the $1^{st}$ step rescue medication during the entire treatment phase and was allowed at any time (up to 1 g [2×500 mg] q6h, maximum daily dose of 4 g). As shown, the mean (range) amount of APAP used in the MR-107A-02 group (4.39 g [0.5 g, 17.0 g]) was lower than in the Tramadol and Placebo groups (5.25 g [1.0 g, 15.0 g] and 6.94 g [1.0 g, 24.0 g], respectively) over the entire treatment phase.

During the entire treatment phase, participants in the MR-107A-02 group used the lowest amount of $1^{st}$ step rescue medication (i.e., APAP of the three treatment groups.

Of the participants in the MR-107A-02, Tramadol, and Placebo groups that completed study treatment in both the in- and out-patient treatment phases, 26 (21.3%), 10 (8.2%), and 8 (6.9%) participants, respectively, took no rescue medication during the entire treatment phase; the MR-107A-02 group had the highest proportion of participants reporting no rescue medication use during the entire treatment phase of all three treatment groups.

In-Patient Treatment Phase (i.e., 0-48 Hours after Randomization):

As described herein, APAP was the $1^{st}$ step rescue medication during the in-patient treatment phase and was allowed at any time (up to 1 g [2×500 mg] q6h, maximum daily dose of 4 g). As shown, the mean (range) amount of APAP used in the MR-107A-02 group (2.55 g [1.0 g, 6.0 g]) was numerically lower than in the Tramadol and Placebo groups (2.83 g [1.0 g, 7.0 g] and 3.94 g [1.0 g, 7.0 g], respectively) during the in-patient treatment phase.

During the in-patient treatment phase, participants in the MR-107A-02 group used the lowest amount of $1^{st}$ step rescue medication (i.e., APAP) of the three treatment groups.

Of the participants in the MR-107A-02, Tramadol, and Placebo groups that completed study treatment in the in-patient treatment phase, 36 (26.7%), 22 (17.1%), and 11 (8.3%) participants, respectively, took no rescue medication during the in-patient treatment phase; the MR-107A-02 group had the highest proportion of participants reporting no rescue medication use during the in-patient treatment phase of all three treatment groups.

Out-Patient Treatment Phase (i.e., 5 Days Following Discharge):

APAP was the $1^{st}$ step rescue medication during the out-patient treatment phase and was allowed at any time (up to 1 g [2×500 mg] q6h, maximum daily dose of 4 g). As shown, the mean (range) amount of APAP used in the MR-107A-02 group (3.45 g [0.5 g, 11.0 g]) was numerically lower than in the Tramadol Placebo and Placebo groups (3.68 g [0.5 g, 12.0 g] and 4.58 g [1.0 g, 17.0 g], respectively) during the out-patient treatment phase During the out-patient treatment phase, participants in the MR-107A-02 group used the lowest amount of $1^{st}$ step rescue medication (i.e., APAP) of the three treatment groups.

Of the participants in the MR-107A-02, Tramadol Placebo, and Placebo groups that completed study treatment in the out-patient treatment phase, 63 (51.2%), 34 (27.6%), and 38 (32.5%) participants, respectively, took no rescue medication during the out-patient treatment phase; the MR-107A-02 group had the highest proportion of participants reporting no rescue medication use during the out-patient treatment phase of all three treatment groups.

Time to First Rescue Medication Use:

The time to first rescue medication use was another secondary efficacy endpoint that was analyzed using Kaplan-Meir plots with censoring for participants who discontinued early at the time of discontinuation. Additional details on the planned analysis are provided in herein, and the changes to the planned analyses and post-hoc analyses for tramadol versus placebo are noted in sections below.

The time to first rescue medication use for the FAS, and FIG. 18 displays the Kaplan-Meier plot for the time to first rescue medication use for the FAS shows that the median (CI) times to first rescue medication use in the MR-107A-02 and Tramadol groups (4.3 hours [95% CI: 2.8, 5.1 hours] and 3.1 hours [90% CI: 2.4, 3.8 hours], respectively) were both longer than that in the Placebo group (2.2 hours [95% CI: 1.6, 2.6 hours]. The log rank test yielded nominal p-values ($p<0.001$ for MR-107A-02 versus placebo and $p=0.019$ [post-hoc] for tramadol versus placebo). The median time to first rescue medication was numerically larger for the MR-107A-02 group than for the Tramadol group.

Modified Post-Anesthetic Discharge Scoring System at 24 hours, 48 hours, Visit 3, and Early Termination The MPADSS at 24 hours, 48 hours, Visit 3, and ET was a secondary efficacy endpoint whose results were summarized using descriptive statistics. On the MPADSS, a higher score was indicative of increased readiness for successful discharge (Table 21).

A summary of the MPADSS results at 24 hours, 48 hours, Visit 3, and ET for the FAS; the mean MPADSS within each treatment group increased slightly from 24 hours to 48 hours post-dose shows that at 24 hours post-dose, the MR-107A-02 group had the highest mean (SD) MPADSS score of 9.3 (0.91); the mean (SD) for the Tramadol and Placebo groups were 8.9 (1.26) and 8.8 (1.03), respectively. At 48 hours post-dose and Follow-up (Visit 3), the three treatment groups had similar mean (SD) MPADSS (48 hours post-dose: 9.5 [0.91], 9.3 [1.39], and 9.3 [0.94] for MR-107A-02, Tramadol, and Placebo, respectively; Follow-up: 9.6 [1.00], 9.7 [0.74], and 9.6 [0.74], respectively). Few participants provided MPADSS data at ET.

Overall Benefit of Analgesic Score at 24 Hours, 48 Hours, Visit 3, and Early Termination The OBAS at 24 hours, 48 hours, Visit 3, and ET was another secondary efficacy endpoint whose results were summarized using descriptive statistics. On the OBAS, a lower score was indicative of reduced pain intensity and ORAEs and higher patient satisfaction (Table 22).

A summary of the OBAS results at 24 hours, 48 hours, Visit 3, and ET for the FAS; the mean OBAS within each treatment group decreased slightly from 24 hours post-dose to Follow-up (Visit 3) shows that at 24 hours post-dose, 48 hours post-dose, and Follow-up, the mean (SD) OBAS was 4.4 (3.17), 3.0 (2.72), and 2.5 (2.80), respectively, for MR-107A-02; 5.9 (3.74), 4.1 (3.21), and 3.3 (2.99), respectively, for Placebo; and 5.3 (3.00), 4.6 (3.61), and 2.9 (2.37), respectively, for Tramadol. From 24 hours post-dose to Follow-up (Visit 3), the MR-107A-02 group had the lowest mean OBAS of all three treatment groups. Few participants provided OBAS data at ET.

Numeric Rating Scale with Activity at 24 Hours, 48 Hours, Visit 3, and Early Termination The NRS-A at 24 hours, 48 hours, Visit 3, and ET was another secondary efficacy endpoint whose results were summarized using descriptive statistics. On the NRS-A scale, a lower score was indicative of lower pain levels perceived by the participant when seated with the plantar surface of the ball of surgical attended foot touching the floor. NRS-A is an indicator for early mobilization after surgery.

A summary of the NRS-A results at 24 hours, 48 hours, Visit 3, and ET for the FAS; the mean NRS-A within each treatment group decreased from 24 hours post-dose to Follow-up (Visit 3) shows that at 24 hours post-dose, 48 hours post-dose, and Follow-up, the mean (SD) NRS-A was 3.6 (2.62), 2.3 (2.34), and 1.7 (2.02), respectively, for MR-107A-02; 5.6 (2.95), 4.1 (2.92), and 2.3 (2.38), respectively, for Placebo; and 4.2 (2.65), 3.5 (2.66), and 2.1 (2.31), respectively, for Tramadol. From 24 hours post-dose to Follow-up (Visit 3), the MR-107A-02 group had the lowest mean NRS-A of the three treatment groups. Few participants provided data at ET for NRS-A.

Multiple Comparisons/Multiplicity

In order to control Type 1 error, the analyses for the key secondary estimand were considered valid only if the specified primary analysis for the primary estimand showed a statistically significant result ($p<0.05$, based on a 2-sided test). The analyses for additional secondary estimands were considered valid only if the analysis for the key secondary estimand also showed a statistically significant result ($p<0.05$, based on a 2-sided test). The analysis for additional secondary estimands continued using a pre-specified statistical hierarchy. The full statistical hierarchy is described as follows:

1. Primary analysis for the primary estimand (if $p<0.05$ based on a 2-sided test, then continue to 2).
2. Analysis of the key secondary estimand: The number of doses of opioid rescue medication during the entire treatment phase (in-patient and out-patient treatment phases) (if $p<0.05$ based on a 2-sided test, then continue to 3).
3. Proportion of participants using no opioid rescue medication during the entire treatment phase (in-patient and out-patient treatment phases). The proportion for MR-107A-02 and the proportion for placebo was to be compared.

In practice, all analyses were to be performed but if a non-significant p-value (as defined above) at any step occurred, then all p-values following the first non-significant p-value were to be considered nominal only. Regardless of the outcome of the statistical testing strategy for the estimands defined above, all p-values for the remaining secondary estimands (that were subjected to statistical testing) were considered nominal.

Use of an "Efficacy Subset" of Participants

The primary and key secondary analyses were conducted for the FAS, which included all randomized participants who received at least one dose of study drug, including participants who discontinued study treatment or received protocol allowed rescue medication. Supplemental analyses of the primary endpoint were conducted for the mFAS and PP Analysis Set.

Active-Control Studies Intended to Show Equivalence

This study included tramadol as an active control. A sensitivity analysis was conducted for the primary estimand by using the same ANCOVA model described earlier sections, but with the active control included.

Analyses of the primary efficacy variable comparing the efficacy of the active control with the study drug and the active control with placebo were also performed; for more details about these analyses.

Examination of Subgroups

Subgroup analyses were performed for the primary and key secondary estimands and are described herein.

Drug Dose, Drug Concentration, and Relationships to Response

The PK endpoints in this study were designed to measure exposure of MR-107A-02 following bunionectomy surgery using sparse sampling and included $C_{max}$, $T_{max}$, $AUC_{0-4}$, $AUC_{0-24}$, and $AUC_{0-48}$ based on observed data. The meloxicam plasma concentrations will also be utilized for subsequent analysis using Pop PK methods. The PK analyses were conducted for the PK Analysis Set with PK samples taken as described herein. Four participants (101-32, 104-011, 104-076, 111-024) in the PK Analysis Set had insufficient concentration data, and therefore, their PK data were not included in the summary statistics of MR-107A-02 plasma concentrations and PK parameters. However, the meloxicam concentration and PK data for all participants in the PK Analysis Set is available herein and will be included in subsequent PopPK analyses.

The summary statistics and individual plasma MR-107A-02 concentrations through 48 hours after the first dose for participants in the MR-107A-02 group, and FIG. 19 displays the mean meloxicam concentrations through 48 hours after the first dose for the PK Analysis Set (only for participants in the MR-107A-02 group with sufficient concentration data) shows that the mean plasma concentration increased through 1 hour following the first dose with accumulation after the repeat 12-hour dosing. In general, the mean profile, showing rapid meloxicam absorption by 1 hour is in line with previous Phase 1 and Phase 2 study data.

The individual plasma meloxicam concentrations on linear and semi-log scales for participants in the PK Analysis Set as a composite plot, which shows the plasma meloxicam concentrations by participant on a linear and semi-log scale, respectively.

The summary statistics and by-participant PK parameters for participants in the MR-107A-02 group, and Table 27 summarizes the mean PK parameters show that following the first dose of MR-107A-02 (15 mg), the geometric mean values (coefficient of variance [CV %]) for initial $C_{max}$ was 1881.222 (30.060) ng/ml and the corresponding median $T_{max}$ value was 1.090 hours. Repeat dosing of MR-107A-02 (15 mg BID) resulted in accumulation, with increasing mean meloxicam concentration values at the pre-dose timepoints of 12, 24, and 48 hours.

TABLE 27

Pharmacokinetic Parameters following Administration
of MR-107A-02 (15 mg BID) (PK Analysis Set)

| Variable[1]<br>Statistic | MR-107A-02<br>(15 mg BID)<br>(N = 137) |
|---|---|
| $n^2$ | 60 |
| $C_{max}$ (ng/mL) | |
| First dosing period | 1881.222 (30.060) |
| Through 48 hours after first dose | 2532.254 (38.625) |
| $T_{max}$ (h) | |
| First dosing period | 1.090 (0.220, 12.070) |
| Through 48 hours after first dose | 32.030 (0.220, 48.670) |
| $AUC_{0-4}$ (ng*h/mL) | 5072.570 (36.754) |

TABLE 27-continued

Pharmacokinetic Parameters following Administration
of MR-107A-02 (15 mg BID) (PK Analysis Set)

| Variable[1]<br>Statistic | MR-107A-02<br>(15 mg BID)<br>(N = 137) |
|---|---|
| $AUC_{0-24}$ (ng*h/mL) | 30115.952 (22.504) |
| $AUC_{0-48}$ (ng*h/mL) | 81593.999 (29.443) |

AUC = area under the concentration-versus-time curve;
$AUC_{0-4}$ = AUC from time 0 to 4 hours after dosing (first dose);
$AUC_{0-24}$ = AUC from time 0 to 24 hours after dosing (first dose);
$AUC_{0-48}$ = AUC from 0 to 48 hours after dosing (first dose but includes second dose);
BID = twice daily;
$C_{max}$ = maximum plasma concentration;
Max = maximum;
Min = minimum;
N = Number of participants per treatment group in the PK Analysis Set;
PK = pharmacokinetic;
$T_{max}$ = time to maximum plasma concentration;
q6h = Once every 6 hours
Note:
During the in-patient treatment phase, participants received (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase).
[1]$T_{max}$ is presented as median (Min, Max); all other parameters are presented as geometric mean (coefficient of variance).
[2]Participants 101-32, 104-011, 104-076, 111-024 were not included due to insufficient available concentration data.

TABLE 28

Arithmetic Mean (% CV) MR-107A-02
PK Parameters, Bunionectomy Study

| Parameter | MR-107A-02 15 mg BID<br>(n = 60) |
|---|---|
| Cmax, after 1st Dose (ng/ml) | 1964.578 (30.1%) |
| Cmax, overall (ng/ml) | 2660.733 (38.6%) |
| Tmax, after 1st Dose (hr)[1] | 1.090 (0.220-12.070) |
| Tmax, overall (hr)[1] | 32.030 (0.220-48.670) |
| $AUC_{0-4\ h}$ (ng*hr/mL) | 5460.820 (36.8%) |
| $AUC_{0-24\ h}$ (ng*hr/mL) | 30823.688 (22.5%) |
| $AUC_{0-48\ h}$ (ng*hr/mL) | 84752.299 (29.4%) |

[1]Median (Minimum-Maximum)

3A.7 Efficacy Conclusions from Study 3001

The primary objective of the study was to confirm the efficacy of MR-107A-02 in treating acute pain, following bunionectomy surgery. The secondary efficacy objectives were to confirm the opioid-sparing effect associated with the use of MR-107A-02, to further confirm the efficacy of MR-107A-02 in participants following bunionectomy surgery using additional efficacy measures, to confirm the association of clinical benefit with reduced opioid use, to confirm the efficacy of tramadol in the study, and to estimate the difference in efficacy between MR-107A-02 and tramadol. The study also measured the exposure of meloxicam after administration of MR-107A-02 (15 mg BID) in participants following bunionectomy surgery.

Most participants (85.9% of all participants) were female, and over half of all participants were White (60.0%) and not Hispanic or Latino (68.3%). The mean age was 48.0 years (range 18 to 77 years), and most participants were <65 years of age (89.3%). The mean baseline NRS-R was 7.3 (range 3 to 10). The three treatment groups were comparable with respect to demographic and baseline characteristics. The three treatment groups were also comparable with respect to common medical history and use of prior medications.

The FAS included 137 participants in each of the MR-107A-02 and Tramadol groups and 136 participants in the Placebo group, which satisfied (marginally exceeded) the minimum treatment group size required to sufficiently power the study for the planned analyses of the primary and secondary estimands.

The primary efficacy estimand compared the $SPID_{0-48}$ (based on NRS-R scores) for the MR-107A-02 and Placebo groups in the FAS using an ANCOVA model; rescue medication use was managed by the WLOCF approach, and missing data was managed by an MI approach. The study met the primary endpoint, as the difference in LS mean $SPID_{0-48}$ (95% CI) for MR-107A-02 versus placebo (82.7 [62.0, 103.4]) was statistically significant ($p<0.001$). The $SPID_{0-48}$ endpoint captures both the magnitude and duration of the analgesic effect, offering a comprehensive measure of treatment efficacy in acute pain. The statistically significant increase in $SPID_{0-48}$ for MR-107A-02 over placebo suggests that MR-107A-02 provides clinically meaningful pain relief within the critical early time window, when pain is typically most intense and patients are most vulnerable to breakthrough symptoms.

The key secondary efficacy estimand was the number of doses of opioid (oxycodone and/or morphine) rescue medication taken during the entire treatment phase. The analysis used a negative binomial regression model with a log link to compare the MR-107A-02 and Placebo groups in the FAS. Missing data was managed by an MI approach. The study met the key secondary endpoint, as the ratio of LS geometric means of the number of doses of opioid (oxycodone and/or morphine) medication (95% CI) for MR-107A-02 versus placebo (0.41 [0.29, 0.58]) was statistically significant ($p<0.001$). Notably, the LS geometric mean number of opioid doses (i.e., total opioid consumption) used in the MR-107A-02 group (0.12 doses) over the entire treatment phase was 59% lower than that in the Placebo group (0.29 doses). This substantial decrease in opioid use is expected to be clinically significant, given the risks associated with opioids including dependence, tolerance and AEs.

Similarly, participants in the MR-107A-02 group took fewer doses of opioids (oxycodone and/or morphine) than those in the Placebo group during all intervals (i.e., the last 24 and 36 hours before discharge, the in-patient treatment phase, and the out-patient treatment phase, 0-24 hours after randomization, and post-discharge phase [up to 30 days after discharge]; $p<0.001$ [nominal]). These differences suggest that MR-107A-02 effectively reduced the need for rescue opioid analgesia throughout both acute and extended recovery periods.

The proportion of participants who were opioid (oxycodone and/or morphine)-free over various intervals was also evaluated. During the entire treatment phase, the MR-107A-02 group had 23.8% more opioid-free participants than the Placebo group, and the difference in proportions (95% CI) of opioid (oxycodone and/or morphine)-free participants in the MR-107A-02 and Placebo groups of 23.8% (12.4%, 35.3%) was statistically significant ($p<0.001$). For all other intervals (i.e., the last 24 and 36 hours before discharge, the in-patient treatment phase, and the out-patient treatment phase, 0-24 hours after randomization, and post-discharge phase [up to 30 days after discharge]), the MR-107A-02 group had larger proportions of opioid-free participants than the Placebo group ($p<0.008$ [nominal]). This finding indicates that MR-107A-02 was not only effective in reducing moderate to severe pain but also reduced the need for opioid rescue medication to a meaningful degree. Across all pre-defined time intervals, the MR-107A-02 group consistently had higher proportions of opioid-free participants. These consistent observations across all intervals suggest a sustained benefit of MR-107A-02 in limiting opioid exposures throughout the whole recovery phase.

Importantly, regardless of this reduced opioid use, participants in the MR-107A-02 group also took less APAP rescue medication than those in the Placebo group during the entire treatment phase, in-patient treatment phase, and out-patient treatment phase. This finding underscores the robustness of the analgesic effect provided by MR-107A-02 and suggests that the observed reduction in opioid use was not offset by increased use of non-opioid rescue medication. A larger proportion of participants in the MR-107A-02 group also took no rescue medication during the entire treatment phase, in-patient treatment phase, and out-patient treatment phase than in the Placebo group. These results demonstrate that participants treated with MR-107A-02 required less rescue medication (APAP and opioid) than those in the Placebo group; this indicates that a meaningful subset of patients receiving MR-107A-02 achieved adequate pain control without the need for any rescue medication, reflecting both efficacy and convenience from a patient care perspective.

The participants in the MR-107A-02 group experienced faster times to first perceptible and meaningful relief of pain than those in the Placebo group ($p<0.037$ [nominal]). In addition, the time to first use of rescue medication, both overall and specifically for opioid rescue medication, was longer in the MR-107A-02 group than in the Placebo group ($p<0.001$ [nominal]). This indicates that participants receiving MR-107A-02 experienced more sustained analgesic effects and were less reliant on supplementary medication to manage their pain than those in the Placebo group.

The geometric mean (CV %) for initial $C_{max}$ of meloxicam after the first dose of MR-107A-02 was 1881.222 (30.060) ng/ml with a corresponding median $T_{max}$ value of 1.090 hours. Repeat dosing of MR-107A-02 (15 mg BID) resulted in accumulation, with increasing mean meloxicam concentration values at the pre-dose timepoints of 12, 24, and 48 hours. The $T_{max}$ after the first dose of 1.090 hours was in proximity to the median time to first perceptible relief of pain in the MR-107A-02 group of 0.7 hours, and the overall exposure of meloxicam with repeat dosing correlated with the long-term pain control observed in the MR-107A-02 group.

Other efficacy endpoints, including the SPID, PID, and the proportion of participants with overall pain reductions from baseline of ≥30% and ≥50%, indicated that participants in the MR-107A-02 group experienced better pain control over time than those in the Placebo group. These results suggest a robust analgesic effect of MR-107A-02 relative to placebo.

Collectively, these findings provide consistent and complementary evidence of the analgesic effectiveness and opioid-sparing potential of MR-107A-02. The ability to achieve pain relief while reducing overall reliance on both opioid and non-opioid rescue medications enhances the treatment's clinical utility and aligns with current guidelines aimed at minimizing unnecessary medication exposure and associated risks.

Concerning PGA of pain control, the proportion of participants rating their pain control as "very good" or "excellent" increased in all groups from 0-24 hours through Follow-up. Notably, MR-107A-02 showed advantages over placebo, with nominal p-values of $p<0.001$ at both 0-24 hours and 24-48 hours. As PGA includes the overall sense of satisfaction and control which plays a major role in emotional well-being and trust of the patient in the healthcare team, this outcome is clinically relevant.

The OBAS was used to measure both the relief from pain and any side effects of treatment. From 24 hours through Follow-up, MR-107A-02 showed a greater reduction in OBAS than placebo, suggesting better overall benefit with MR-107A-02, including pain relief and fewer side effects, than with placebo.

The NRS-A is an indicator for patient mobilization. Participants who received MR-107A-02 experienced greater relief in movement-related pain (as measured by NRS-A) than those who received placebo. Improvements were noticeable as early as 24 hours after the first dose and continued through Follow-up. Participants in the MR-107A-02 group reported the lowest pain scores during activity from 24 hours post-dose through Follow-up, suggesting better support for early mobilization than placebo.

The MPADSS is used to evaluate whether a patient has recovered sufficiently following surgery to be safely discharged. Although participants in both the MR-107A-02 and Placebo groups reported high MPADSS scores from 24 hours post-dose through Follow-up, at 24 hours the MR-107A-02 group demonstrated a mean (SD) MPADSS score of 9.3 (0.91), while the Placebo group had a mean (SD) score of 8.8 (1.03). The MPADDS defines a score of ≥9 as the threshold for safe discharge readiness. Therefore, with a mean score above this cutoff by 24 hours post-dose, participants in the MR-107A-02 group reached the minimum discharge criteria more reliably and rapidly than those in the Placebo group despite their lower use of both APAP and opioid rescue medications; this shows a direct patient benefit related to reduced opioid analgesic use, such as earlier functional recovery for allowing discharge.

Sensitivity analyses were conducted to assess the robustness of the primary and key secondary efficacy results. These analyses, which included alternative statistical models and assumptions, yielded results that were consistent with those of the primary analyses. This consistency supports the reliability and validity of the primary conclusions drawn from the FAS. To further evaluate the treatment effect, the primary efficacy estimand was analyzed using both the mFAS and the PP Analysis Set. Results from these additional populations closely mirrored those observed in the FAS. This reinforces confidence in the observed treatment effect and indicates that the findings are not sensitive to population selection criteria or protocol adherence.

Subgroup analyses were performed for the primary and key secondary estimands to examine potential differential treatment effects across demographic variables, including age, sex, and race. These analyses did not reveal any consistent or clinically meaningful interactions between treatment efficacy and subgroup membership. The efficacy of MR-107A-02 appeared stable across these subgroups, suggesting that its effect is broadly applicable within the studied population. Collectively, these findings from sensitivity, supplementary, and subgroup analyses support the robustness and generalizability of the primary and key secondary efficacy results.

To show the assay sensitivity, several analyses, including some post-hoc, were conducted to confirm the efficacy of tramadol in the study by comparing the effects of tramadol with placebo. Across endpoints, the efficacy of tramadol was demonstrated; tramadol displayed better pain control than placebo with higher $SPID_{0-48}$ ($p<0.001$ [nominal]), higher SPID over other intervals ($p\leq 0.042$ [nominal; post-hoc]), faster time to meaningful pain relief ($p=0.046$ [nominal; post-hoc]), longer time to first rescue medication, including opioid rescue ($p\leq 0.019$ [nominal; post-hoc]), and larger proportions of participants with overall pain reductions from baseline of ≥30% or ≥50% ($p\leq 0.022$ [nominal; post-hoc]) and with PGA of "very good" or "excellent" ($p<0.048$ [nominal; post-hoc]).

An analysis was also performed to estimate the difference in efficacy between MR-107A-02 and tramadol in treating acute pain following bunionectomy surgery. Results demonstrated that MR-107A-02 was associated with greater pain relief than tramadol as measured by the primary endpoint, $SPID_{0-48}$ ($p=0.013$ [nominal; post-hoc]), indicating an advantage over tramadol. Although no formal comparisons of MR-107A-02 and tramadol were made for other endpoints, participants in the MR-107A-02 group reported similar or better pain control as those in the Tramadol group with numerically larger LS mean SPIDs at each time interval evaluated, consistent numerically lower PIDs from 2 through 12 hours and from 20 through 48 hours following study drug administration, suggesting a more robust and sustained analgesic effect. There were also similar proportions of participants with overall pain reductions from baseline of ≥30% or ≥50% in the MR-107A-02 and the Tramadol groups, suggesting similar pain relief from both treatments. In addition, participants in the MR-107A-02 group achieved perceptible and meaningful pain relief faster than those in the Tramadol group, further supporting the potential of MR-107A-02 to deliver rapid onset of pain relief. The times to first rescue medication (any type) and to first opioid rescue medication were similar or slightly longer in the MR-107A-02 group compared with those in the Tramadol group, consistent with the observed analgesic efficacy. Concerning PGA, the MR-107A-02 group had numerically higher proportions of participants reporting "very good" or "excellent" pain control than the Tramadol group, which suggests that participants experienced more effective results with MR-107A-02 than with tramadol. For MPADSS at 24 hours post-dose, a slightly higher mean (SD) score was observed in the MR-107A-02 group (9.3 [0.91]) than in the Tramadol group (8.9 [1.26]), which suggests that on average, participants in the MR-107A-02 group reached the minimum discharge criteria more reliably and rapidly than those in the Tramadol group. For OBAS, at 24 and 48 hours after the first dose and at Follow-up, participants in the MR-107A-02 group had lower mean OBAS than those in the Tramadol group. This suggests a better overall benefit with MR-107A-02 than with tramadol, including pain relief and fewer side effects. For NRS-A, participants in the MR-107A-02 group reported lower pain scores during activity at 24- and 48-hours post-dose and at Follow-up, suggesting better support for early mobilization than tramadol.

A numerically larger proportion of participants in the MR-107A-02 group than in the Tramadol group took no rescue medication during the in-patient treatment phase, out-patient treatment phase, and entire treatment phase. This suggests that MR-107A-02 may offer better baseline pain control than tramadol, which is consistent with the outcome for $SPID_{0-48}$. This is further supported by the finding that participants in the MR-107A-02 group used numerically less APAP as rescue medication than those in the Tramadol group during the in-patient treatment phase, out-patient treatment phase, and entire treatment phase, suggesting that MR-107A-02 provided pain control with lower use of first step rescue medication.

Overall, MR-107A-02 is more effective in treating acute pain following bunionectomy surgery than placebo and demonstrates pain control that is similar or better than that provided by the active, standard of care option, opioid-comparator, tramadol.

3A.8 Safety Evaluation

Table 29 presents the extent of exposure by treatment phase for the Safety Analysis Set. Overall, the mean duration of exposure was 7.7 days (range 1 to 9 days for all three treatment groups), and the mean total number of doses taken was 17.3 doses (range 2 to 18 doses [MR-107A-02 and Tramadol groups] and 1 to 18 doses [Placebo group]). During the in-patient treatment phase, the mean duration of exposure overall was 2.7 days (range 1 to 3 days for all three treatment groups), and the mean total number of doses taken overall was 7.9 doses (range 2 to 8 doses [MR-107A-02 and Tramadol groups] and 1 to 8 doses [Placebo group]). During the out-patient treatment phase, the mean duration of exposure overall was 5.1 days (range 1 to 6 days [MR-107A-02 and Tramadol groups] and 3 to 6 days [Placebo group]), and the mean total number of doses taken overall was 9.7 doses (range 1 to 10 doses [MR-107A-02 and Tramadol groups] and 3 to 10 doses [Placebo group]). Within each treatment phase and overall, the duration of exposure and total number of doses taken were similar across treatment groups.

TABLE 29

Extent of Exposure (Safety Analysis Set)

| Phase<br>Variable<br>Statistic | MR-107A-02 (15 mg BID) → MR-107A-02 (15 mg BID) (N = 137) | Tramadol (50 mg q6h) → Placebo (N = 137) | Placebo → Placebo (N = 136) | Total (N = 410) |
|---|---|---|---|---|
| In-patient Treatment Phase Duration of exposure (days)[1] | | | | |
| n | 137 | 137 | 136 | 410 |
| Mean (SD) | 2.7 (0.48) | 2.7 (0.50) | 2.6 (0.53) | 2.7 (0.50) |
| Median | 3.0 | 3.0 | 3.0 | 3.0 |
| Min, Max | 1, 3 | 1, 3 | 1, 3 | 1, 3 |
| Total number of doses taken[2] | | | | |
| n | 137 | 137 | 136 | 410 |
| Mean (SD) | 7.9 (0.53) | 7.8 (0.98) | 7.8 (0.99) | 7.9 (0.86) |
| Median | 8.0 | 8.0 | 8.0 | 8.0 |
| Min, Max | 2, 8 | 2, 8 | 1, 8 | 1, 8 |
| Out-patient Treatment Phase Duration of exposure (days)[1] | | | | |
| n | 136 | 130 | 133 | 399 |
| Mean (SD) | 5.1 (0.62) | 5.1 (0.62) | 5.1 (0.50) | 5.1 (0.58) |
| Median | 5.0 | 5.0 | 5.0 | 5.0 |
| Min, Max | 1, 6 | 1, 6 | 3, 6 | 1, 6 |
| Total number of doses taken[2] | | | | |
| n | 136 | 130 | 133 | 399 |
| Mean (SD) | 9.7 (1.24) | 9.8 (1.00) | 9.7 (1.08) | 9.7(1.11) |
| Median | 10.0 | 10.0 | 10.0 | 10.0 |
| Min, Max | 1, 10 | 1, 10 | 3, 10 | 1, 10 |
| Overall Duration of exposure (days)[1] | | | | |
| n | 137 | 137 | 136 | 410 |
| Mean (SD) | 7.8 (1.00) | 7.6 (1.60) | 7.6 (1.26) | 7.7 (1.31) |
| Median | 8.0 | 8.0 | 8.0 | 8.0 |
| Min, Max | 1, 9 | 1, 9 | 1, 9 | 1, 9 |
| Total number of doses taken[2] | | | | |
| n | 137 | 137 | 136 | 410 |
| Mean (SD) | 17.6 (1.83) | 17.1 (3.25) | 17.3 (2.64) | 17.3 (2.64) |
| Median | 18.0 | 18.0 | 18.0 | 18.0 |
| Min, Max | 2, 18 | 2, 18 | 1, 18 | 1, 18 |

BID = Twice daily;
Max = Maximum;
Min = Minimum;
n = Number of participants;
N = Number of participants per treatment group in the Safety Analysis Set;
q6h = Once every 6 hours;
SD = Standard deviation
Note:
During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase.
[1]Defined as: last dose date − first dose date + 1.
[2]Only active doses were counted for the MR-107A-02 and Tramadol groups during the in-patient treatment phase.

Adverse Events

Adverse events were summarized by treatment group for the in-patient and out-patient treatment phases individually; the names of the three treatment groups contain the treatment that participants were assigned in that phase of the study (i.e., treatment during the in-patient treatment phase or treatment during the out-patient treatment phase). During the in-patient treatment phase, participants received MR-107A-02 (15 mg BID), tramadol (50 mg q6h), or placebo (q6h; see Table 20). During the out-patient treatment phase, participants received either MR-107A-02 (15 mg BID) or placebo (BID; see Table 21). To differentiate the participants who received tramadol (50 mg q6h) and placebo during the in-patient treatment phase, the out-patient treatment phase AE summary tables include the Tramadol Placebo and Placebo groups. All participants who received placebo during the out-patient treatment phase, regardless of their treatment during the in-patient treatment phase, are included in the All-Placebo group.

To simplify, the treatment groups are referenced as follows:

MR-107A-02 group=MR-107A-02 (15 mg BID) during the in-patient treatment phase and MR-107A-02 (15 mg BID) during the out-patient treatment phase Tramadol group (referred to as the Tramadol Placebo group in the descriptions of the out-patient treatment phase in section herein)=tramadol (50 mg q6h) during the in-patient treatment phase and placebo during the out-patient treatment phase Placebo group=placebo during both the in- and out-patient treatment phases All Placebo group=placebo during the out-patient treatment phase (includes participants who received either tramadol [50 mg q6h] or placebo during the in-patient treatment phase)

No deaths or TEAEs of special interest were reported at any time during the study.

Table 30 presents an overall summary of TEAEs in the Safety Analysis Set during the in-patient treatment phase. Overall, 165 (40.2%) participants reported 374 TEAEs. The incidence of TEAEs was higher in the Tramadol group (55.5%) than in the MR-107A-02 and Placebo groups (31.4% and 33.8%, respectively). One hundred twenty (29.3%) participants reported 227 TEAEs related to study drug; the incidence of related TEAEs was notably higher in the Tramadol group (45.3%) than in the MR-107A-02 and Placebo groups (20.4% and 22.1%, respectively). One hundred eight (26.3%) participants reported 234 opioid-related TEAEs; the incidence of opioid-related TEAEs was notably higher in the Tramadol group (46.0%) than in the MR-107A-02 and Placebo groups (16.1% and 16.9%, respectively).

No serious TEAEs were reported. Most TEAEs were either mild or moderate in severity, with 2 (0.5%) participants overall reporting 2 severe TEAEs (1 [0.7%] participant each in the Tramadol and Placebo groups). No participant in the MR-107A-02 group reported a severe TEAE. One (0.2%) participant overall, who was in the Tramadol group, reported one TEAE leading to study discontinuation.

TABLE 30

Overview of Treatment-emergent Adverse Events: In-patient (Safety Analysis Set)

| Category, n (%) m | MR-107A-02 (15 mg BID) (N = 137) | Tramadol (50 mg q6h) (N = 137) | Placebo (N = 136) | Total (N = 410) |
|---|---|---|---|---|
| TEAEs | 43 (31.4) 67 | 76 (55.5) 224 | 46 (33.8) 83 | 165 (40.2) 374 |
| Serious TEAEs | 0 | 0 | 0 | 0 |
| Severe TEAEs | 0 | 1 (0.7) 1 | 1 (0.7) 1 | 2 (0.5) 2 |
| TEAEs related to study drug[1] | 28 (20.4) 38 | 62 (45.3) 151 | 30 (22.1) 38 | 120 (29.3) 227 |
| TEAEs leading to study discontinuation | 0 | 1 (0.7) 1 | 0 | 1 (0.2) 1 |
| Opioid-related TEAEs | 22 (16.1) 31 | 63 (46.0) 166 | 23 (16.9) 37 | 108 (26.3) 234 |
| TEAEs of special interest | 0 | 0 | 0 | 0 |
| TEAEs leading to death | 0 | 0 | 0 | 0 |

AE = Adverse event;

BID = Twice daily;

m = number of events;

n = Number of participants;

N = Number of participants per treatment group in the Safety Analysis Set;

q6h = Once every 6 hours;

TEAE = Treatment-emergent adverse event;

Note:

During the in-patient treatment phase, participants received MR-107A-02 (15 mg BID), tramadol (50 mg q6h), or placebo (q6h).

Note:

Percentages were based on the number of participants in the Safety Analysis Set, in each treatment group, for that study phase.

Note:

TEAEs in the in-patient treatment phase were those with an onset date on or after the first dose of study drug administration in the in-patient treatment phase and before the first dose of study drug administration in the out-patient treatment phase.

Note:

TEAEs were summarized according to the last treatment that the participant received prior to the start of that AE.

[1]Related TEAEs were those reported as possibly, probably, or definitely related to study treatment. Missing relationships were considered related.

Out-Patient Treatment Phase:

Table 31 presents an overall summary of TEAEs in the Safety Analysis Set during the out-patient treatment phase. Overall, 167 (41.9%) participants reported 314 TEAEs with similar incidence of TEAEs among the treatment groups. Eighty-three (20.8%) participants reported 125 TEAEs related to study drug. Seventy-six (19.0%) participants reported 103 opioid-related TEAEs, with a similar incidence of opioid-related TEAEs among the treatment groups. Most TEAEs were either mild or moderate in severity, with 2 (0.5%) participants overall reporting 3 severe TEAEs (2 [1.6%] participants in the Tramadol group). Three (0.8%) participants in the Tramadol Placebo group (also counted in the All-Placebo group) reported 4 serious TEAEs. No TEAEs leading to study discontinuation were reported during the out-patient treatment phase.

TABLE 31

Overview of Treatment-emergent Adverse Events: Out-patient (Safety Analysis Set)

| Category, n (%) m | MR-107A-02 (15 mg BID) (N = 138) | Tramadol Placebo (N = 129) | Placebo (N = 132) | All Placebo (N = 261) | Total (N = 399) |
|---|---|---|---|---|---|
| TEAEs | 52 (37.7) 192 | 66 (51.2) 121 | 49 (37.1) 97 | 115 (44.1) 218 | 167 (41.9) 314 |
| Serious TEAEs | 0 | 3 (2.3) 4 | 0 | 3 (1.1) 4 | 3 (0.8) 4 |
| Severe TEAEs | 0 | 2 (1.6) 3 | 0 | 2 (0.8) 3 | 2 (0.5) 3 |
| TEAEs related to study drug[1] | 28 (20.3) 72 | 36 (27.9) 56 | 19 (14.4) 33 | 55 (21.1) 89 | 83 (20.8) 125 |
| TEAEs leading to study discontinuation | 0 | 0 | 0 | 0 | 0 |
| Opioid-related TEAEs | 24 (17.4) 58 | 29 (22.5) 41 | 23 (17.4) 33 | 52 (19.9) 74 | 76 (19.0) 103 |
| TEAEs of special interest | 0 | 0 | 0 | 0 | 0 |
| TEAEs leading to death | 0 | 0 | 0 | 0 | 0 |

AE = Adverse event;
BID = Twice daily;
m = number of events;
n = Number of participants;
N = Number of participants per treatment group in the Safety Analysis Set;
TEAE = Treatment-emergent adverse event Note:
During the out-patient treatment phase, participants received either MR-107A-02 (15 mg BID) or placebo (BID); participants in the Tramadol group received placebo only during the out-patient treatment phase and are labelled as Tramadol Placebo.

Note:
Percentages were based on the number of participants in the Safety Analysis Set, in each treatment group, for that study phase.

Note:
TEAEs in the out-patient treatment phase were those that started on or after the first dose of study drug administration in the out-patient treatment phase.

Note:
TEAEs were summarized according to the last treatment that the participant received prior to the start of that AE.

Note:
The All-Placebo treatment column summarizes participants who were randomized to the Tramadol or Placebo groups and that received placebo during the out-patient treatment phase.

[1]Related TEAEs were those reported as possibly, probably, or definitely related to study treatment. Missing relationships were considered related.

All summary tabulations of AEs are provided herein and by-participant listings of selected categories of AEs are provided in sections below (SAEs, severe AEs, AEs related to study drug, ORAEs, AESIs, AEs leading to study discontinuation, and AEs leading to death).

Analysis of Adverse Events

In-patient Treatment Phase:

TEAEs by SOC and PT reported in the Safety Analysis Set during the in-patient treatment phase. The most common (≥5% of participants overall) SOCs of TEAEs included gastrointestinal disorders (92 [22.4%] participants), nervous system disorders (60 [14.6%] participants), skin and subcutaneous tissue disorders (41 [10.0%] participants), and investigations (21 [5.1%] participants) show that of the most common SOCs of TEAEs, the incidences of gastrointestinal disorders and nervous system disorders were notably higher in the Tramadol group (41.6% and 23.4%, respectively) than in the MR-107A-02 and Placebo groups (gastrointestinal disorders: 10.2% and 15.4%, respectively; and nervous system disorders: 9.5% and 11.0%).

Table 32 displays the most common (≥2% of participants overall) PTs of TEAEs reported during the in-patient treatment phase. The most common PTs included nausea (74 [18.0%] participants), dizziness (38 [9.3%] participants), vomiting (27 [6.6%] participants), headache (24 [5.9%] participants), pruritus (23 [5.6%] participants), constipation (21 [5.1%] participants), and hyperhidrosis and C-reactive protein increased (14 [3.4%] participants each). Of the most common PTs of TEAEs, the incidences of nausea, vomiting, dizziness, and constipation were notably higher in the Tramadol group (38.0%, 16.8%, 18.2%, and 8.8%, respectively) than in the MR-107A-02 and Placebo groups (nausea: 5.8% and 10.3%, respectively; vomiting: 2.9% and 0; dizziness: 2.9% and 6.6%; and constipation: 3.6% and 2.9%).

TABLE 32

Most Common (≥2% of Participants Overall) Treatment-emergent Adverse Events by Preferred Term: In-patient (Safety Analysis Set)

| Preferred Term | MR-107A-02 (15 mg BID) (N = 137) | Tramadol (50 mg q6h) (N = 137) | Placebo (N = 136) | Total (N = 410) |
|---|---|---|---|---|
| Nausea | 8 (5.8) | 52 (38.0) | 14 (10.3) | 74 (18.0) |
| Dizziness | 4 (2.9) | 25 (18.2) | 9 (6.6) | 38 (9.3) |
| Vomiting | 4 (2.9) | 23 (16.8) | 0 | 27 (6.6) |
| Headache | 9 (6.6) | 9 (6.6) | 6 (4.4) | 24 (5.9) |
| Pruritus | 7 (5.1) | 12 (8.8) | 4 (2.9) | 23 (5.6) |
| Constipation | 5 (3.6) | 12 (8.8) | 4 (2.9) | 21 (5.1) |
| Hyperhidrosis | 4 (2.9) | 4 (2.9) | 6 (4.4) | 14 (3.4) |
| C-reactive protein increased | 4 (2.9) | 4 (2.9) | 6 (4.4) | 14 (3.4) |

AE = Adverse event;
BID = Twice daily;
MedDRA = Medical Dictionary for Regulatory Activities;
n = Number of participants;
N = Number of participants per treatment group in the Safety Analysis Set;
q6h = Once every 6 hours;
TEAE = Treatment-emergent adverse event TABLE 32-continued Most Common (≥2% of Participants Overall) Treatment-emergent Adverse Events by Preferred Term: In-patient (Safety Analysis Set)

| Preferred Term | MR-107A-02 (15 mg BID) (N = 137) | Tramadol (50 mg q6h) (N = 137) | Placebo (N = 136) | Total (N = 410) |
|---|---|---|---|---|

Note:
During the in-patient treatment phase, participants received MR-107A-02 (15 mg BID), tramadol (50 mg q6h), or placebo (q6h).
Note:
Percentages were based on the number of participants in the Safety Analysis Set, in each treatment group, for that study phase.
Note:
TEAEs in the in-patient treatment phase were those with an onset date on or after thefirst dose of study drug administration in the in-patient treatment phase and before the first dose of study drug administration in the out-patient treatment phase.
Note:
TEAEs were summarized according to the last treatment that the participant received prior to the start of that AE.
Note:
Participants with multiple events in a preferred term were counted only once for that preferred term.
Note:
All terms were coded using MedDRA Version 26.1 and sorted in descending order of frequency in the Total group for preferred terms.

Out-Patient Treatment Phase:

TEAEs by SOC and PT reported in the Safety Analysis Set during the out-patient treatment phase. The most common (≥5% of participants overall) SOCs of TEAEs included gastrointestinal disorders (74 [18.5%] participants), nervous system disorders (38 [9.5%] participants), skin and subcutaneous tissue disorders (36 [9.0%] participants), general disorders and administration site conditions (29 [7.3%] participants), and investigations (24 [6.0%] participants) show that of the most common SOCs of TEAEs, the incidence of gastrointestinal disorders was notably higher in the Tramadol Placebo group (26.4%) than in the Placebo group (10.6%).

Table 33 displays the most common (≥2% of participants overall) PTs of TEAEs reported during the out-patient treatment phase. The most common PTs included constipation (31 [7.8%] participants), fatigue (23 [5.8%] participants), dizziness and pruritus (20 [5.0%] participants each), nausea (19 [4.8%] participants), diarrhea and C-reactive protein increased (18 [4.5%] participants each), headache (14 [3.5%] participants), rash (12 [3.0%] participants), and abdominal pain (11 [2.8%] participants). Of the most common PTs of TEAEs, the incidence of constipation was notably higher in the Tramadol Placebo group (10.9%) than in the Placebo group (4.5%), and the incidence of pruritus was notably higher in the Tramadol Placebo, Placebo, and All Placebo groups (7.0%, 6.1%, and 6.5%, respectively) than in the MR-107A-02 group (2.2%).

TABLE 33

Most Common (≥2% of Participants Overall) Treatment-emergent Adverse Events by Preferred Term: Out-patient (Safety Analysis Set)

| Preferred Term | MR-107A-02 (15 mg BID) (N = 138) | Tramadol Placebo (N = 129) | Placebo (N = 132) | All Placebo (N = 261) | (N = 399) Total |
|---|---|---|---|---|---|
| Constipation | 11 (8.0) | 14 (10.9) | 6 (4.5) | 20 (7.7) | 31 (7.8) |
| Fatigue | 7 (5.1) | 5 (3.9) | 11 (8.3) | 16 (6.1) | 23 (5.8) |
| Dizziness | 4 (2.9) | 4 (3.1) | 12 (9.1) | 16 (6.1) | 20 (5.0) |
| Pruritus | 3 (2.2) | 9 (7.0) | 8 (6.1) | 17 (6.5) | 20 (5.0) |
| Nausea | 7 (5.1) | 7 (5.4) | 5 (3.8) | 12 (4.6) | 19 (4.8) |

TABLE 33-continued

Most Common (≥2% of Participants Overall) Treatment-emergent Adverse Events by Preferred Term: Out-patient (Safety Analysis Set)

| Preferred Term | MR-107A-02 (15 mg BID) (N = 138) | Tramadol Placebo (N = 129) | Placebo (N = 132) | All Placebo (N = 261) | (N = 399) Total |
|---|---|---|---|---|---|
| Diarrhea | 6 (4.3) | 7 (5.4) | 5 (3.8) | 12 (4.6) | 18 (4.5) |
| C-reactive protein increased | 5 (3.6) | 7 (5.4) | 6 (4.5) | 13 (5.0) | 18 (4.5) |
| Headache | 4 (2.9) | 7 (5.4) | 3 (2.3) | 10 (3.8) | 14 (3.5) |
| Rash | 6 (4.3) | 5 (3.9) | 1 (0.8) | 6 (2.3) | 12 (3.0) |
| Abdominal pain | 4 (2.9) | 3 (2.3) | 4 (3.0) | 7 (2.7) | 11 (2.8) |

AE = Adverse event;
BID = Twice daily;
MedDRA = Medical Dictionary for Regulatory Activities;
n = Number of participants;
N = Number of participants per treatment group in the Safety Analysis Set;
TEAE = Treatment-emergent adverse event
Note:
During the out-patient treatment phase, participants received either MR-107A-02 (15 mg BID) or placebo (BID); participants in the Tramadol group received placebo only during the out-patient treatment phase and are labelled as Tramadol Placebo. See
Note:
Percentages were based on the number of participants in the Safety Analysis Set, in each treatment group, for that study phase.
Note:
TEAEs in the out-patient treatment phase were those that started on or after the first dose of study drug administration in the out-patient treatment phase.
Note:
TEAEs were summarized according to the last treatment that the participant received prior to the start of that AE.
Note:
Participants with multiple events in a preferred term were counted only once for that preferred term.
Note:
All terms were coded using MedDRA Version 26.1 and sorted in descending order of frequency in the Total group for preferred terms.
Note:
The All-Placebo treatment column summarizes participants who were randomized to the Tramadol or Placebo groups and who received placebo during the out-patient treatment phase.

Severe Treatment-emergent Adverse Events

In-patient Treatment Phase:

Severe TEAEs by SOC and PT reported during the in-patient treatment phase for the Safety Analysis Set. Overall, 2 (0.5%) participants reported severe TEAEs, with the PT of hypotension in 1 (0.7%) participant in the Tramadol group and the PT syncope in 1 (0.7%) participant in Placebo group show that no severe TEAEs were reported in the MR-107A-02 group.

Out-Patient Treatment Phase:

Severe TEAEs by SOC and PT reported during the out-patient treatment phase for the Safety Analysis Set. Overall, 2 (0.5%) participants (both in the Tramadol Placebo group [1.6%]; also counted in the All Placebo group [0.8%]) reported severe TEAEs with the PTs of appendicitis and sepsis in 1 (0.8%) participant and intervertebral disc protrusion in the other 1 (0.8%) participant show that no severe TEAEs were reported in the MR-107A-02 or Placebo groups.

In-Patient Treatment Phase:

TEAEs related to study drug by SOC and PT reported during the in-patient treatment phase for the Safety Analysis Set show that overall, 120 (29.3%) participants reported TEAEs related to study drug with a higher proportion of participants reporting related TEAEs in the Tramadol group (45.3%) than in the MR-107A-02 and Placebo groups (20.4% and 22.1%, respectively).

The most common (≥5% of participants overall) SOCs of related TEAEs included gastrointestinal disorders (71

[17.3%] participants), nervous system disorders (34 [8.3%] participants), and skin and subcutaneous tissue disorders (22 [5.4%] participants). Of the most common SOCs of TEAEs, the incidences of gastrointestinal disorders and nervous system disorders were notably higher in the Tramadol group (34.3% and 16.8%, respectively) than in the MR-107A-02 and Placebo groups (gastrointestinal disorders: 8.8% each; and nervous system disorders: 2.9% and 5.1%, respectively), and the incidence of skin and subcutaneous tissue disorders was higher in the MR-107A-02 and Tramadol groups (5.8% and 8.0%, respectively) than in the Placebo group (2.2%).

The most common (≥2% of participants overall) PTs of related TEAEs included nausea (57 [13.9%] participants), dizziness (24 [5.9%] participants), vomiting (21 [5.1%] participants), constipation and C-reactive protein increased (13 [3.2%] participants each), pruritus (12 [2.9%] participants), and headache (10 [2.4%] participants). Of the most common PTs of TEAEs, the incidences of nausea, dizziness, vomiting, and constipation were notably higher in the Tramadol group (30.7%, 13.1%, 13.1%, and 5.1%, respectively) than in the MR-107A-02 and Placebo groups (nausea: 5.1% and 5.9%, respectively; dizziness: 1.5% and 2.9%; vomiting: 2.2% and 0; and constipation: 2.2% each).

Out-Patient Treatment Phase:

TEAEs related to study drug by SOC and PT reported during the out-patient treatment phase for the Safety Analysis Set show that overall, 83 (20.8%) participants reported TEAEs related to study drug.

The most common (≥5% of participants overall) SOCs of related TEAEs included gastrointestinal disorders (39 [9.8%] participants) and investigations (20 [5.0%] participants). The most common (≥2% of participants overall) PTs of related TEAEs during the out-patient treatment phase included C-reactive protein increased (18 [4.5%] participants), constipation (17 [4.3%] participants), nausea (12 [3.0%] participants), fatigue (11 [2.8%] participants), dizziness (10 [2.5%] participants), diarrhea (9 [2.3%] participants), and pruritus (8 [2.0%] participants). The incidences of the most common SOCs and PTs of related TEAEs were numerically higher in the Tramadol Placebo group than in the MR-107A-02 and Placebo groups during the out-patient treatment phase.

No deaths were reported in this study.

Other Serious Adverse Events

In-Patient Treatment Phase:

During the in-patient treatment phase, no serious TEAE was reported.

Out-Patient Treatment Phase:

Table 34 presents a summary of serious TEAEs by SOC and PT reported during the out-patient treatment phase for the Safety Analysis Set, and this example presents a by-participant listing of all SAEs in the study. Overall, 3 (0.8%) participants (all in the Tramadol Placebo group [also counted in the All-Placebo group]) reported at least one serious TEAE with PTs of appendicitis and sepsis in 1 (0.8%) participant, intervertebral disc protrusion in 1 (0.8%) participant, and abortion spontaneous in 1 [0.8%] participant.

TABLE 34

Serious Treatment-emergent Adverse Events, by System Organ Class and Preferred Term: Out-patient (Safety Analysis Set)

| System Organ Class Preferred Term | MR-107A-02 (15 mg BID) (N = 138) | Tramadol Placebo (N = 129) | Placebo (N = 132) | All Placebo (N = 261) | Total (N = 399) |
|---|---|---|---|---|---|
| Any Serious TEAE, n (%) | 0 | 3 (2.3) | 0 | 3 (1.1) | 3 (0.8) |
| Infections and infestations | 0 | 1 (0.8) | 0 | 1 (0.4) | 1 (0.3) |
| Appendicitis | 0 | 1 (0.8) | 0 | 1 (0.4) | 1 (0.3) |
| Sepsis | 0 | 1 (0.8) | 0 | 1 (0.4) | 1 (0.3) |
| Musculoskeletal and connective tissue disorders | 0 | 1 (0.8) | 0 | 1 (0.4) | 1 (0.3) |
| Intervertebral disc protrusion | 0 | 1 (0.8) | 0 | 1 (0.4) | 1 (0.3) |
| Pregnancy, puerperium and perinatal conditions | 0 | 1 (0.8) | 0 | 1 (0.4) | 1 (0.3) |
| Abortion spontaneous | 0 | 1 (0.8) | 0 | 1 (0.4) | 1 (0.3) |

AE = Adverse event;
BID = Twice daily;
MedDRA = Medical Dictionary for Regulatory Activities;
n = Number of participants;
N = Number of participants per treatment group in the Safety Analysis Set;
TEAE = Treatment-emergent adverse event Note:
During the out-patient treatment phase, participants received either MR-107A-02 (15 mg BID) or placebo (BID); participants in the Tramadol group received placebo only during the out-patient treatment phase and are labelled as Tramadol Placebo.

Note:
Percentages were based on the number of participants in the Safety Analysis Set, in each treatment group, for that study phase.

Note:
TEAEs in the out-patient treatment phase were those that started on or after the first dose of study drug administration in the out-patient treatment phase.

Note:
TEAEs were summarized according to the last treatment that the participant received prior to the start of that AE.

Note:
Participants with multiple events in a system organ class/preferred term were counted only once for that system organ class/preferred term.

Note:
All terms were coded using MedDRA Version 26.1 and sorted in descending order of frequency in the Total group for both system organ classes and preferred terms.

Note:
The All-Placebo treatment column summarizes participants who were randomized to the Tramadol or Placebo groups and who received placebo during the out-patient treatment phase.

Other Significant Adverse Events

Adverse Events Leading to Study Discontinuation

In-Patient Treatment Phase:

TEAEs leading to study discontinuation reported during the in-patient treatment phase by SOC and PT for the Safety Analysis Set. Overall, 1 (0.2%) participant (in the Tramadol group) reported at least one TEAE leading to study discontinuation with the PT of vomiting; however, the reported action taken (discontinued study) for the TEAE of vomiting (participant 104-044) was an apparent error show that study drug was withdrawn for this participant due to the TEAE of nausea; an ET visit was recorded, but the participant went on to complete the study.

Out-Patient Treatment Phase:

No TEAE leading to study discontinuation was reported during the out-patient treatment phase.

Adverse Events Leading to Treatment Discontinuation

In-Patient Treatment Phase:

Table 35 presents TEAEs leading to treatment discontinuation reported during the in-patient treatment phase by SOC and PT for the Safety Analysis Set. Overall, 6 (1.5%) participants reported at least one TEAE leading to treatment discontinuation. Reported PTs included nausea, drug hypersensitivity, and urticaria, with an incidence of 2 (0.5%) participants each, and dizziness with an incidence of 1 (0.7%) participant. Events reported in the MR-107A-02 group consisted of urticaria in 1 (0.7%) participant.

TABLE 35

Treatment-emergent Adverse Events Leading to
Treatment Discontinuation, by System Organ Class and
Preferred Term: In-patient (Safety Analysis Set)

| System Organ Class Preferred Term | MR-107A-02 (15 mg BID) (N = 137) | Tramadol (50 mg q6h) (N = 137) | Placebo (N = 136) | Total (N = 410) |
|---|---|---|---|---|
| Any TEAE Leading to Treatment Discontinuation, n (%) | 1 (0.7) | 4 (2.9) | 1 (0.7) | 6 (1.5) |
| Gastrointestinal disorders | 0 | 2 (1.5) | 0 | 2 (0.5) |
| Nausea | 0 | 2 (1.5) | 0 | 2 (0.5) |
| Immune system disorders | 0 | 1 (0.7) | 1 (0.7) | 2 (0.5) |
| Drug hypersensitivity | 0 | 1 (0.7) | 1 (0.7) | 2 (0.5) |
| Skin and subcutaneous tissue disorders | 1 (0.7) | 1 (0.7) | 0 | 2 (0.5) |
| Urticaria | 1 (0.7) | 1 (0.7) | 0 | 2 (0.5) |
| Nervous system disorders | 0 | 1 (0.7) | 0 | 1 (0.2) |
| Dizziness | 0 | 1 (0.7) | 0 | 1 (0.2) |

AE = Adverse event;

BID = Twice daily;

MedDRA = Medical Dictionary for Regulatory Activities;

n = Number of participants;

N = Number of participants per treatment group in the Safety Analysis Set;

q6h = Once every 6 hours;

TEAE = Treatment-emergent adverse event

Note:

During the in-patient treatment phase, participants received MR-107A-02 (15 mg BID), tramadol (50 mg q6h), or placebo (q6h).

Note:

Percentages were based on the number of participants in the Safety Analysis Set, in each treatment group, for that study phase.

Note:

TEAEs in the in-patient treatment phase were those with an onset date on or after the first dose of study drug administration in the in-patient treatment phase and before the first dose of study drug administration in the out-patient treatment phase.

Note:

TEAEs were summarized according to the last treatment that the participant received prior to the start of that AE.

Note:

Participants with multiple events in a system organ class/preferred term were counted only once for that system organ class/preferred term.

Note:

All terms were coded using MedDRA Version 26.1 and sorted in descending order of frequency in the Total group for both system organ classes and preferred terms.

Table 36 presents TEAEs leading to treatment discontinuation reported during the out-patient treatment phase by SOC and PT for the Safety Analysis Set. Overall, 5 (1.3%) participants reported at least one TEAE leading to treatment discontinuation with PTs of abdominal pain, 5 somnolence, pruritus, abortion spontaneous, skin abrasion, rash, chest pain, and appendicitis, each of which had an incidence of 1 (0.3%) participant. The TEAE of abortion spontaneous (participant 113-013) was recorded as a TEAE that led to treatment discontinuation; however, study drug had already been withdrawn due to prior TEAEs, and the participant had completed the study before the start of this event. The events leading to treatment discontinuation in the MR-107A-02 group consisted of rash and chest pain.

TABLE 36

Treatment-emergent Adverse Events Leading to
Treatment Discontinuation, by System Organ Class
and Preferred Term: Out-patient (Safety Analysis Set)

| System Organ Class Preferred Term | MR-107A-02 (15 mg BID) (N = 138) | Tramadol Placebo (N = 129) | Placebo (N = 132) | All Placebo (N = 261) | Total (N = 399) |
|---|---|---|---|---|---|
| Any TEAE Leading to Treatment Discontinuation, n (%) | 2 (1.4) | 2 (1.6) | 1 (0.8) | 3 (1.1) | 5 (1.3) |
| Skin and subcutaneous tissue disorders | 1 (0.7) | 1 (0.8) | 0 | 1 (0.4) | 2 (0.5) |
| Pruritus | 0 | 1 (0.8) | 0 | 1 (0.4) | 1 (0.3) |
| Rash | 1 (0.7) | 0 | 0 | 0 | 1 (0.3) |
| Gastrointestinal disorders | 0 | 1 (0.8) | 0 | 1 (0.4) | 1 (0.3) |
| Abdominal pain | 0 | 1 (0.8) | 0 | 1 (0.4) | 1 (0.3) |
| General disorders and administration site conditions | 1 (0.7) | 0 | 0 | 0 | 1 (0.3) |
| Chest pain | 1 (0.7) | 0 | 0 | 0 | 1 (0.3) |
| Infections and infestations | 0 | 1 (0.8) | 0 | 1 (0.4) | 1 (0.3) |
| Appendicitis | 0 | 1 (0.8) | 0 | 1 (0.4) | 1 (0.3) |
| Injury, poisoning and procedural complications | 0 | 0 | 1 (0.8) | 1 (0.4) | 1 (0.3) |
| Skin abrasion | 0 | 0 | 1 (0.8) | 1 (0.4) | 1 (0.3) |
| Nervous system disorders | 0 | 1 (0.8) | 0 | 1 (0.4) | 1 (0.3) |
| Somnolence | 0 | 1 (0.8) | 0 | 1 (0.4) | 1 (0.3) |
| Pregnancy, puerperium, and perinatal conditions | 0 | 1 (0.8) | 0 | 1 (0.4) | 1 (0.3) |
| Abortion spontaneous | 0 | 1 (0.8) | 0 | 1 (0.4) | 1 (0.3) |

AE = Adverse event;

BID = Twice daily;

MedDRA = Medical Dictionary for Regulatory Activities;

n = Number of participants;

N = Number of participants per treatment group in the Safety Analysis Set;

TEAE = Treatment-emergent adverse event

Note:

During the out-patient treatment phase, participants received either MR-107A-02 (15 mg BID) or placebo (BID); participants in the Tramadol group received placebo only during the out-patient treatment phase and are labelled as Tramadol Placebo.

Note:

Percentages were based on the number of participants in the Safety Analysis Set, in each treatment group, for that study phase.

Note:

TEAEs in the out-patient treatment phase were those that started on or after the first dose of study drug administration in the out-patient treatment phase.

Note:

TEAEs were summarized according to the last treatment that the participant received prior to the start of that AE.

Note:

Participants with multiple events in a system organ class/preferred term were counted only once for that system organ class/preferred term.

Note:

All terms were coded using MedDRA Version 26.1 and sorted in descending order of frequency in the Total group for both system organ classes and preferred terms.

Note:

The All-Placebo treatment column summarizes participants who were randomized to the Tramadol or Placebo groups and who received placebo during the out-patient treatment phase.

Opioid-Related Adverse Events
In-Patient Treatment Phase:

Table 37 presents opioid-related TEAEs reported during the in-patient treatment phase by SOC and PT for the Safety Analysis Set. Overall, 108 (26.3%) participants reported at least one opioid-related TEAE.

The most common (≥2% participants overall) PTs of opioid-related TEAEs included nausea (74 [18.0%] participants), dizziness (38 [9.3%] participants), vomiting (27 [6.6%] participants), pruritus (22 [5.4%] participants), and constipation (21 [5.1%] participants). The incidences of PTs of the most common opioid-related TEAEs were all notably higher in the Tramadol group (38.0%, 18.2%, 16.8%, 8.8%, and 8.8%, respectively) than in the MR-107A-02 and Placebo groups 10 (nausea: 5.8% and 10.3%, respectively;

dizziness: 2.9% and 6.6%; vomiting: 2.9% and 0; pruritus: 4.4% and 2.9%; and constipation: 3.6% and 2.9%).

TABLE 37

Opioid-related Treatment-emergent Adverse Events, by System Organ Class and Preferred Term: In-patient (Safety Analysis Set)

| System Organ Class Preferred Term | MR-107A-02 (15 mg BID) (N = 137) | Tramadol (50 mg q6h) (N = 137) | Placebo (N = 136) | Total (N = 410) |
|---|---|---|---|---|
| Any Opioid-Related TEAE, n (%) | 22 (16.1) | 63 (46.0) | 23 (16.9) | 108 (26.3) |
| Gastrointestinal disorders | 13 (9.5) | 56 (40.9) | 16 (11.8) | 85 (20.7) |
| Nausea | 8 (5.8) | 52 (38.0) | 14 (10.3) | 74 (18.0) |
| Vomiting | 4 (2.9) | 23 (16.8) | 0 | 27 (6.6) |
| Constipation | 5 (3.6) | 12 (8.8) | 4 (2.9) | 21 (5.1) |
| Nervous system disorders | 4 (2.9) | 26 (19.0) | 9 (6.6) | 39 (9.5) |
| Dizziness | 4 (2.9) | 25 (18.2) | 9 (6.6) | 38 (9.3) |
| Somnolence | 0 | 1 (0.7) | 1 (0.7) | 2 (0.5) |
| Presyncope | 0 | 1 (0.7) | 0 | 1 (0.2) |
| Skin and subcutaneous tissue disorders | 7 (5.1) | 12 (8.8) | 4 (2.9) | 23 (5.6) |
| Pruritus | 6 (4.4) | 12 (8.8) | 4 (2.9) | 22 (5.4) |
| Urticaria | 1 (0.7) | 0 | 0 | 1 (0.2) |
| Injury, poisoning and procedural complications | 1 (0.7) | 0 | 1 (0.7) | 2 (0.5) |
| Incision site pruritus | 0 | 0 | 1 (0.7) | 1 (0.2) |
| Vascular access site pruritus | 1 (0.7) | 0 | 0 | 1 (0.2) |
| General disorders and administration site conditions | 0 | 1 (0.7) | 0 | 1 (0.2) |
| Fatigue | 0 | 1 (0.7) | 0 | 1 (0.2) |

AE = Adverse event;
BID = Twice daily;
MedDRA = Medical Dictionary for Regulatory Activities;
n = Number of participants;
N = Number of participants per treatment group in the Safety Analysis Set;
q6h = Once every 6 hours;
TEAE = Treatment-emergent adverse event
Note:
During the in-patient treatment phase, participants received MR-107A-02 (15 mg BID), tramadol (50 mg q6h), or placebo (q6h).
Note:
Percentages were based on the number of participants in the Safety Analysis Set, in each treatment group, for that study phase.
Note:
TEAEs in the in-patient treatment phase were those with an onset date on or after the first dose of study drug administration in the in-patient treatment phase and before the first dose of study drug administration in the out-patient treatment phase.
Note:
TEAEs were summarized according to the last treatment that the participant received prior to the start of that AE.
Note:
Participants with multiple events in a system organ class/preferred term were counted only once for that system organ class/preferred term.
Note:
All terms were coded using MedDRA Version 26.1 and sorted in descending order of frequency in the Total group for both system organ classes and preferred terms.

Table 38 presents opioid-related TEAEs reported during the out-patient treatment phase by SOC and PT for the Safety Analysis Set. Overall, 76 (19.0%) participants reported at least one opioid-related TEAE.

The most common (≥2% participants overall) PTs of opioid-related TEAEs included constipation (31 [7.8%] participants), pruritus (20 [5.0%] participants), and nausea and dizziness (19 [4.8%] participants each). Of the most common opioid-related TEAEs, the incidence of pruritus was notably higher in the Tramadol Placebo, Placebo, and All Placebo groups (7.0%, 6.1%, and 6.5%, respectively) than in the MR-107A-02 group (2.2%).

TABLE 38

Opioid-related Treatment-emergent Adverse Events, by System Organ Class and Preferred Term: Out-patient (Safety Analysis Set)

| System Organ Class Preferred Term | MR-107A-02 (15 mg BID) (N = 138) | Tramadol Placebo (N = 129) | Placebo (N = 132) | All Placebo (N = 261) | Total (N = 399) |
|---|---|---|---|---|---|
| Any Opioid-Related TEAE, n (%) | 24 (17.4) | 29 (22.5) | 23 (17.4) | 52 (19.9) | 76 (19.0) |
| Gastrointestinal disorders | 19 (13.8) | 21 (16.3) | 9 (6.8) | 30 (11.5) | 49 (12.3) |
| Constipation | 11 (8.0) | 14 (10.9) | 6 (4.5) | 20 (7.7) | 31 (7.8) |
| Nausea | 7 (5.1) | 7 (5.4) | 5 (3.8) | 12 (4.6) | 19 (4.8) |
| Vomiting | 3 (2.2) | 2 (1.6) | 0 | 2 (0.8) | 5 (1.3) |
| Nervous system disorders | 5 (3.6) | 6 (4.7) | 11 (8.3) | 17 (6.5) | 22 (5.5) |
| Dizziness | 4 (2.9) | 4 (3.1) | 11 (8.3) | 15 (5.7) | 19 (4.8) |
| Somnolence | 1 (0.7) | 2 (1.6) | 0 | 2 (0.8) | 3 (0.8) |
| Skin and subcutaneous tissue disorders | 3 (2.2) | 9 (7.0) | 8 (6.1) | 17 (6.5) | 20 (5.0) |
| Pruritus | 3 (2.2) | 9 (7.0) | 8 (6.1) | 17 (6.5) | 20 (5.0) |
| General disorders and administration site conditions | 0 | 1 (0.8) | 0 | 1 (0.4) | 1 (0.3) |
| Fatigue | 0 | 1 (0.8) | 0 | 1 (0.4) | 1 (0.3) |

AE = Adverse event;
BID = Twice daily;
MedDRA = Medical Dictionary for Regulatory Activities;
n = Number of participants;
N = Number of participants per treatment group in the Safety Analysis Set;
TEAE = Treatment-emergent adverse event
Note:
During the out-patient treatment phase, participants received either MR-107A-02 (15 mg BID) or placebo (BID); participants in the Tramadol group received placebo only during the out-patient treatment phase and are labelled as Tramadol Placebo.
Note:
Percentages were based on the number of participants in the Safety Analysis Set, in each treatment group, for that study phase.
Note:
TEAEs in the out-patient treatment phase were those that started on or after the first dose of study drug administration in the out-patient treatment phase.
Note:
TEAEs were summarized according to the last treatment that the participant received prior to the start of that AE.
Note:
Participants with multiple events in a system organ class/preferred term were counted only once for that system organ class/preferred term.
Note:
All terms were coded using MedDRA Version 26.1 and sorted in descending order of frequency in the Total group for both system organ classes and preferred terms.
Note:
The All-Placebo treatment column summarizes participants who were randomized to the Tramadol or Placebo groups and who received placebo during the out-patient treatment phase.

Analysis and Discussion of Deaths, Other Serious Adverse Events, and Other In-Patient Treatment Phase:

No serious TEAE was reported, and one TEAE leading to study discontinuation (PT of vomiting) was reported; however, the participant who reported the TEAE leading to study discontinuation did complete the study after discontinuing treatment. Overall, 6 (1.5%) participants reported at least one TEAE leading to treatment discontinuation (PTs of nausea, urticaria, dizziness, and drug hypersensitivity); the TEAEs leading to treatment discontinuation were all considered resolved or resolving at last report. A total of 108 (26.3%) participants overall reported at least one opioid-related TEAE, and the most common (≥2% participants overall) PTs included nausea, dizziness, vomiting, pruritus, and constipation, all of which were reported more frequently in the Tramadol group than in the MR-107A-02 and Placebo groups.

No TEAE leading to study discontinuation was reported during the out-patient treatment phase. Overall, 3 (0.8%)

participants reported at least one serious TEAE (PTs of appendicitis, sepsis, intervertebral disc protrusion, and abortion spontaneously). The serious TEAEs of appendicitis, sepsis, intervertebral disc protrusion, and abortion spontaneous were all considered not related to study drug and had resolved at the time of last report, and all were reported in the Tramadol Placebo group. Overall, 5 (1.3%) participants reported at least one TEAE leading to treatment discontinuation (PTs of abdominal pain, somnolence, pruritus, abortion spontaneous, skin abrasion, rash, chest pain, and appendicitis); the TEAEs leading to treatment discontinuation were all considered resolved or resolving. The TEAE of abortion spontaneous was recorded as a TEAE that led to treatment discontinuation; however, study drug had already been withdrawn due to prior TEAEs, and the participant had completed the study before the start of this event. A total of 76 (19.0%) participants reported at least one opioid-related TEAE, and the most common (≥2% participants overall) PTs included constipation, pruritus, nausea, and dizziness. Pruritus was reported more frequently in the Tramadol Placebo and Placebo groups than in the MR-107A-02 group.

The PTs of opioid-related TEAEs observed during the in- and out-patient treatment phases were expected effects of meloxicam, as most were reported during clinical studies of MOBIC (MOBIC Prescribing Information, 2024).

Safety Conclusions from Study 3001

The safety objective of this study was to confirm the safety and tolerability of MR-107A-02 in participants following bunionectomy surgery. Safety was assessed through the incidence, severity, duration, and outcome of AEs, including ORAEs, as well as changes from baseline in vital signs, laboratory parameters (hematology, chemistry, urinalysis), and 12-lead ECGs.

No deaths or TEAEs of special interest, including AEs related to GI events (particularly bleeding) and those related to cardiovascular events, such as myocardial infarction/unstable angina, stroke/TIA, heart failure, cardiac arrhythmia (atrial and ventricular), were reported at any time during the study, which demonstrates the safety of MR-107A-02 in terms of the risks associated with the NSAID class.

During the in-patient treatment phase, a total of 165 (40.2%) participants overall reported 374 TEAEs. The incidence of TEAEs was higher in the Tramadol group (55.5%) than in the MR-107A-02 and Placebo groups (31.4% and 33.8%, respectively). One hundred twenty (29.3%) participants reported 227 TEAEs considered related to the study drug. The incidence of related TEAEs was notably higher in the Tramadol group (45.3%) than in the MR-107A-02 and Placebo groups (20.4% and 22.1%, respectively). This means that the MR-107A-02 group had an even slightly lower proportion of participants with TEAEs than the Placebo group, possibly due to lower use of rescue medication.

During the in-patient treatment phase, 108 (26.3%) participants reported 234 opioid-related TEAEs. The incidence of opioid-related TEAEs was notably higher in the Tramadol group (46.0%) than in the MR-107A-02 and Placebo groups (16.1% and 16.9%, respectively), and the MR-107A-02 group had the lowest incidence of opioid-related TEAEs of all three treatment groups. The most common (≥2% participants overall) PTs of opioid-related TEAEs included nausea, dizziness, vomiting, pruritus, and constipation, all of which were reported more frequently in the Tramadol group than in the MR-107A-02 and Placebo groups. Most TEAEs were either mild or moderate in severity, with only 2 (0.5%) participants overall reporting 2 severe TEAEs (1 [0.7%] participants each in the Tramadol and Placebo groups). Notably, no participant in the MR-107A-02 group reported a severe TEAE. One (0.2%) participant overall, who was in the Tramadol group, reported one TEAE leading to study discontinuation (PT of vomiting); however, the participant who reported the TEAE leading to study discontinuation did complete the study after discontinuing treatment. No serious TEAEs were reported during the in-patient treatment phase.

A total of 6 (1.5%) participants reported at least one TEAE leading to treatment discontinuation (1 [0.7%] participant in the MR-107A-02 group, 4 [2.9%] participants in the Tramadol group, and 1 [0.7%] participant in the Placebo group); the TEAEs leading to treatment discontinuation were all considered resolved or resolving at the last report. Reported PTs included nausea (2 [1.5%] participants in the Tramadol group), drug hypersensitivity (1 [0.7%] participant each in the Tramadol and Placebo groups), urticaria (1 [0.7%] participant each in the MR-107A-02 and Tramadol groups), and dizziness (1 [0.7%] participant in the Tramadol group).

During the out-patient treatment phase, a total of 167 (41.9%) participants overall reported 314 TEAEs with similar proportions of participants reporting TEAEs among the treatment groups. Eighty-three (20.8%) participants reported 125 TEAEs related to study drug. Seventy-six (19.0%) participants reported 103 opioid-related TEAEs. The most common (≥2% participants overall) PTs of opioid-related TEAEs included constipation, pruritus, nausea, and dizziness; pruritus was reported more frequently in the Tramadol Placebo and Placebo groups than in the MR-107A-02 group.

As with the in-patient treatment phase, most out-patient TEAEs were either mild or moderate in severity, with 2 (0.5%) participants overall reporting 3 severe TEAEs (2 [1.6%] participants in the Tramadol Placebo group). Three (0.8%) participants in the Tramadol Placebo group reported 4 serious TEAEs (PTs of appendicitis, sepsis, intervertebral disc protrusion, and abortion spontaneous), which were all considered not related to study drug and were recovered/resolved at the time of last report. No TEAEs leading to study discontinuation were reported during the out-patient treatment phase. Overall, 5 (1.3%) participants reported at least one TEAE leading to treatment discontinuation (PTs of abdominal pain, somnolence, pruritus, abortion spontaneous, skin abrasion, rash, chest pain, and appendicitis); the TEAEs leading to treatment discontinuation were all considered resolved or recovered at last report. The TEAE of abortion spontaneous was recorded as a TEAE that led to treatment discontinuation; however, the study drug had already been withdrawn due to prior TEAEs, and the participant had completed the study before the start of this event. Treatment-emergent AEs leading to treatment discontinuation in the MR-107A-02 group consisted of rash and chest pain in 1 (0.7%) participant each.

The marked difference in the incidence of opioid-related TEAEs between treatment groups—particularly in the first 48 hours—demonstrates a likely clinically meaningful benefit associated with MR-107A-02. Specifically, 16.1% of participants in the MR-107A-02 group experienced opioid-related TEAEs, compared with 46.0% in the Tramadol group. This represents a 29.9% absolute risk reduction and a relative reduction of approximately 65% of experiencing an ORAE, reflecting a substantial improvement in tolerability.

This lower incidence of ORAEs is particularly important given their known impact on patient comfort, recovery, and clinical resource utilization (Shafi et al., 2018). Common opioid-related effects such as nausea, dizziness, and sedation can impair postoperative function and delay discharge while requiring additional medications and monitoring. By contrast, MR-107A-02 demonstrated a more favorable safety profile, reducing these burdens and aligning with best practices in opioid-sparing multimodal analgesia.

The PTs of opioid-related TEAEs observed during the in- and out-patient treatment phases were expected effects of meloxicam, as most were reported during clinical studies of MOBIC (MOBIC Prescribing Information, 2024).

larger CIs) within each treatment group than in the White and Black or African American subgroups, due to the small sample size in the Other Race subgroup.

The primary efficacy endpoint was the $SPID_{0-48}$, and other analyses of this endpoint used an ANCOVA model to compare the Tramadol and Placebo groups (with and without MR-107A-02) and the MR-107A-02 and Tramadol groups (with and without Placebo) in the FAS. Rescue medication use was managed by the WLOCF approach, and missing data was managed by an MI approach. Additional details on the analyses are provided below. A discussion of the primary endpoint, $SPID_{0-48}$, comparing the MR-107A-02 and Placebo groups (without Tramadol), is also included herein.

Tramadol Versus Placebo, Excluding MR-107A-02:

The results of the $SPID_{0-48}$ analysis comparing the Tramadol and Placebo groups, excluding MR-107A-02, in the FAS show that the LS means (95% CI) for $SPID_{0-48}$ in the Tramadol and Placebo groups were 156.1 (138.9, 173.2) and 98.0 (77.6, 118.5), respectively; the difference in LS means (95% CI) for tramadol versus placebo (58.0 [40.9, 75.1]) was nominally statistically significant (p<0.001).

Tramadol Versus Placebo, Including MR-107A-02:

The results of the $SPID_{0-48}$ analysis comparing the Tramadol and Placebo groups, including MR-107A-02, in the FAS show that the LS means (95% CI) for $SPID_{0-48}$ in the Tramadol and Placebo groups were 154.9 (139.2, 170.6) and 97.3 (78.5, 116.1), respectively; the difference in LS means (95% CI) for tramadol versus placebo (57.6 [40.4, 74.8]) was nominally statistically significant (p<0.001).

MR-107A-02 Versus Tramadol, Excluding Placebo:

The results of the $SPID_{0-48}$ analysis comparing the MR-107A-02 and Tramadol groups, excluding Placebo, in the FAS show that the LS means (95% CI) for $SPID_{0-48}$ in the MR-107A-02 and Tramadol groups were 174.3 (153.8, 194.7) and 148.1 (130.5, 165.6), respectively; the difference in LS means (95% CI) for MR-107A-02 versus tramadol (26.2 [8.8, 43.6]) was nominally statistically significant (p=0.013) based on a post-hoc analysis.

MR-107A-02 Versus Tramadol, Including Placebo:

The results of the $SPID_{0-48}$ analysis comparing the MR-107A-02 and Tramadol groups, including Placebo, in the FAS show that the LS means (95% CI) for $SPID_{0-48}$ in the MR-107A-02 and Tramadol groups were 180.4 (161.9, 199.0) and 154.9 (139.2, 170.6), respectively; the difference in LS means (95% CI) for MR-107A-02 versus tramadol (25.5 [8.4, 42.6]) was nominally statistically significant (p=0.014) based on a post-hoc analysis.

The key secondary efficacy endpoint was the number of doses of opioid (oxycodone and/or morphine) rescue medication taken during the entire treatment phase, and the analysis used a negative binomial regression model with a log link to compare the MR-107A-02 and Placebo groups in the FAS. Missing data was managed by an MI approach.

Table 26 presents the results of the key secondary estimand analysis for the FAS. The mean (SD) number of doses of opioid (oxycodone and/or morphine) rescue medication during the entire treatment phase for the MR-107A-02 and Placebo groups were 1.3 (2.16) and 2.9 (3.64), respectively. The LS geometric mean number of opioid doses used in the MR-107A-02 group (0.12 doses) over the entire treatment phase was 59% lower than that in the Placebo group (0.29 doses). The ratio of LS geometric means (95% CI) for MR-107A-02 versus placebo (0.41 [0.29, 0.58]) was statistically significant (p<0.001). The results for the number of doses of opioid (oxycodone and/or morphine) rescue medication during other time intervals are discussed below.

TABLE 26

Key Secondary: Number of Doses of Opioid (Oxycodone and/or Morphine) Rescue Medication (Entire Treatment Phase) (Full Analysis Set)

| Variable Statistic | MR-107A-02 (15 mg BID) (N = 137) | Placebo (N = 136) |
|---|---|---|
| Number of doses of Opioid (Oxycodone and/or Morphine) Rescue Medication | | |
| Mean (SD) | 1.3 (2.16) | 2.9 (3.64) |
| Median | 0 | 2 |
| Min, Max | 0, 10 | 0, 23 |
| Difference in Means | −1.6 | |
| LS Geometric Mean | 0.12 | 0.29 |
| 95% CI | (0.08, 0.18) | (0.20, 0.43) |
| Ratio of LS Geometric Means versus Placebo | 0.41 | |
| 95% CI for Ratio of LS Geometric Means | (0.29, 0.58) | |
| p-value for Ratio | <0.001 | |

BID = Twice daily;
CI = Confidence interval;
LS = Least squares;
MAR = Missing at random;
Max = Maximum;
MI = Multiple imputation;
N = Number of participants per treatment group in the Full Analysis Set;
Min = Minimum;
q6h = Once every 6 hours;
SD = Standard deviation Note:
During the in-patient treatment phase, participants received MR-107A-02 (15 mg BID), tramadol (50 mg q6h), or placebo (q6h), and during the out-patient treatment phase, participants received either MR-107A-02(15 mg BID) or placebo (BID); participants in the Tramadol group received placebo only during the out-patient treatment phase.

Note:
The number of doses of opioid was defined as the number of doses of oxycodone and/or morphine taken.

Note:
For any missing data from participants discontinuing treatment early due to a lack of efficacy or an adverse event, a placebo-based MI approach was used, whereby both the rate before and after withdrawal for such participants was assumed to follow that of the Placebo group. Missing data from participants discontinuing for any other reasons was imputed using a MAR approach.

Note:
The LS geometric means, differences, CIs and 2-sided p-value were based on a negative binomial regression model with a log link with fixed, categorical effects for treatment (MR-107A-02 and placebo), age group (<65 years, ≥65 years), and study site. The LS geometric means (and difference) were estimated using this model and then back transformed to the original scale by exponentiating.

Note:
Summary statistics (mean, median, SD, Min, Max) were based on observed data only.

A sensitivity analysis of the key secondary efficacy estimand was performed to calculate the number of doses of oxycodone only taken during the entire treatment phase; and the analysis used a negative binomial regression model with a log link to compare the MR-107A-02 and Placebo groups in the FAS. Missing data was managed by an MI approach. A second sensitivity analysis for the number of doses of opioid was also performed, with an alternate MI approach using a negative binomial distribution based on the pooled data from the MR-107A-02 and Placebo groups.

The results of the first sensitivity analysis of the key secondary estimand for the FAS show that the mean (SD) number of doses of oxycodone rescue medication for the MR-107A-02 and Placebo groups was 1.3 (2.11) and 2.7 (3.52), respectively, and the ratio of LS geometric means (95% CI) for MR-107A-02 versus placebo was 0.41 (0.29, 0.58).

The results of the second sensitivity analysis of the key secondary estimand for the FAS show that the mean (SD) number of doses of oxycodone rescue medication for the MR-107A-02 and Placebo groups was 1.3 (2.16) and 2.9 (3.64), respectively, and the ratio of LS geometric means (95% CI) for MR-107A-02 versus placebo was 0.41 (0.29, 0.59).

Overall, the results of the sensitivity analyses of the key secondary efficacy estimand were similar to those of the primary analysis discussed below.

The key secondary efficacy endpoint was the number of doses of opioid (oxycodone and/or morphine) rescue medication taken during the entire treatment phase, and the analysis used a negative binomial regression model with a log link to compare the MR-107A-02 and Placebo groups in the FAS. The analysis was repeated for each age (<65 years and ≥65 years), sex (female, male) and race (White, Black or African American, and Other Race) subgroup. Missing data was managed by an MI approach.

The results of the key secondary estimand analysis by age subgroup for the FAS.

For the <65 years subgroup, the mean (SD) number of doses of opioid (oxycodone and/or morphine) rescue medication for the MR-107A-02 and Placebo groups was 1.3 (2.15) and 2.9 (3.65), respectively, and the ratio of LS geometric means (95% CI) for MR-107A-02 versus placebo (0.42 [0.30, 0.60]) was nominally statistically significant (p<0.001).

For the ≥65 years subgroup, the mean (SD) number of doses of opioid (oxycodone and/or morphine) rescue medication for the MR-107A-02 and Placebo groups was 1.0 (2.24) and 2.6 (3.67), respectively, and the ratio of LS geometric means (95% CI) for MR-107A-02 versus placebo (0.10 [0.01, 0.89]) was nominally statistically significant (p=0.039).

The nominal differences between MR-107A-02 and placebo for the number of doses of opioid (oxycodone and/or morphine) rescue medication during the entire treatment phase in both age subgroups suggest no effect of age on the efficacy of MR-107A-02; however, the limited sample size of the ≥65 years subgroup limits the meaning of this comparison.

The results of the key secondary estimand analysis by sex for the FAS.

For the female subgroup, the mean (SD) number of doses of opioid (oxycodone and/or morphine) rescue medication for the MR-107A-02 and Placebo groups was 1.4 (2.20) and 3.0 (3.83), respectively, and the ratio of LS geometric means (95% CI) for MR-107A-02 versus placebo (0.42 [0.29, 0.61]) was nominally significant (p<0.001).

For the male subgroup, the mean (SD) number of doses of opioid (oxycodone and/or morphine) rescue medication for the MR-107A-02 and Placebo groups was 0.9 (1.87) and 2.5 (2.46), and the ratio of LS geometric means (95% CI) for MR-107A-02 versus placebo (0.38 [0.18, 0.80]) was nominally statistically significant (p=0.010).

The nominal differences between MR-107A-02 and placebo for the number of doses of opioid (oxycodone and/or morphine) rescue medication during the entire treatment phase in both sexes suggest no effect of sex on the efficacy of MR-107A-02; however, the limited sample size of the male subgroup limits the meaning of this comparison.

The results of the key secondary estimand analysis by race for the FAS.

For the White subgroup, the mean (SD) number of doses of opioid (oxycodone and/or morphine) rescue medication during the entire treatment phase for the MR-107A-02 and Placebo groups was 1.4 (2.25) and 2.8 (4.31), respectively, and the ratio of LS geometric means (95% CI) for MR-107A-02 versus placebo (0.44 [0.26, 0.73]) was nominally statistically significant (p=0.002).

For the Black or African American subgroup, the mean (SD) number of doses of opioid (oxycodone and/or morphine) rescue medication during the entire treatment phase for the MR-107A-02 and Placebo groups was 1.4 (2.12) and 3.2 (2.61), respectively, and the ratio of LS geometric means (95% CI) for MR-107A-02 versus placebo (0.430 [0.275, 0.673]) was nominally statistically significant (p<0.001).

For the Other Race subgroup, the mean (SD) number of doses of opioid (oxycodone and/or morphine) rescue medication during the entire treatment phase for the MR-107A-02 and Placebo groups was 0.3 (0.71) and 2.1 (3.43), respectively, and the ratio of LS geometric means (95% CI) for MR-107A-02 versus placebo (0.0791 [0.0187, 0.3348]) was nominally statistically significant (p<0.001).

The nominal differences between MR-107A-02 and placebo for the number of doses of opioid (oxycodone and/or morphine) rescue medication during the entire treatment phase for all race subgroups suggest no effect of race on the efficacy of MR-107A-02; however, the limited sample size of the Black or African American and Other Race subgroups limits the meaning of this comparison.

The number of doses of opioid (oxycodone and/or morphine) rescue medication taken during the last 24 and 36 hours before discharge, in-patient and out-patient treatment phases, 0-24 hours after randomization, and post-discharge phase (up to 30 days) were other secondary efficacy endpoints and the analysis followed the methods used for the primary analysis of the key secondary endpoint (i.e., a negative binomial regression model with a log link) to compare the MR-107A-02 and Placebo groups in the FAS. Missing data was managed by an MI approach. For the in-patient interval, the Poisson distribution (which can be considered as a simplified case of the negative binomial distribution) was used due to the closeness of the dispersion parameter to zero.

The number of doses of opioid (oxycodone and/or morphine) rescue medication during the last 24 hours before discharge for the FAS shows that the mean (SD) number of doses of opioid (oxycodone and/or morphine) rescue medication during the last 24 hours before discharge for the MR-107A-02 and Placebo groups was 0.1 (0.46) and 0.4 (0.86), respectively, and the ratio of LS geometric means (95% CI) for MR-107A-02 versus placebo (0.2840 [0.1541, 0.5233]) was nominally statistically significant (p<0.001).

The number of doses of opioid (oxycodone and/or morphine) rescue medication during the last 36 hours before discharge for the FAS shows that the mean (SD) number of doses of opioid (oxycodone and/or morphine) rescue medication during the last 36 hours before discharge for the MR-107A-02 and Placebo groups was 0.4 (0.79) and 0.9 (1.36), respectively, and the ratio of LS geometric means (95% CI) for MR-107A-02 versus placebo (0.36 [0.23, 0.57]) was nominally statistically significant (p<0.001).

In-Patient Treatment Phase (i.e., 0-48 Hours after Randomization):

The number of doses of opioid (oxycodone and/or morphine) rescue medication during the in-patient treatment phase for the FAS shows that the mean (SD) number of doses of opioid (oxycodone and/or morphine) rescue medication during in-patient treatment phase for the MR-107A-02 and Placebo groups was 0.8 (1.21) and 1.6 (1.93), respectively, and the ratio of LS geometric means (95% CI) for MR-107A-02 versus placebo (0.45 [0.33, 0.62]) was nominally statistically significant ($p<0.001$).

Out-Patient Treatment Phase (i.e., 5 Days Following Discharge):

The number of doses of opioid (oxycodone and/or morphine) rescue medication during the out-patient treatment phase for the FAS shows that the mean (SD) number of doses of opioid (oxycodone and/or morphine) rescue medication during out-patient treatment phase for the MR-107A-02 and Placebo groups was 0.5 (1.43) and 1.3 (2.43), respectively, and the ratio of LS geometric means (95% CI) for MR-107A-02 versus placebo (0.33 [0.18, 0.59]) was nominally statistically significant ($p<0.001$).

0-24 Hours after Randomization:

The number of doses of opioid (oxycodone and/or morphine) rescue medication during 0-24 hours after randomization for the FAS shows that the mean (SD) number of doses of opioid (oxycodone and/or morphine) rescue medication during 0-24 hours after randomization for the MR-107A-02 and Placebo groups was 0.6 (0.97) and 1.2 (1.31), respectively, and the ratio of LS geometric means (95% CI) for MR-107A-02 versus placebo (0.51 [0.38, 0.68]) was nominally statistically significant ($p<0.001$).

Post-Discharge Phase (i.e., Up to 30 Days after Discharge):

The number of doses of opioid (oxycodone and/or morphine) rescue medication during the post-discharge phase, up to 30 days, for the FAS shows that the mean (SD) number of doses of opioid (oxycodone and/or morphine) rescue medication during the post-discharge phase, up to 30 days, for the MR-107A-02 and Placebo groups was 0.7 (1.94) and 1.8 (3.80), respectively, and the ratio of LS geometric means (95% CI) for MR-107A-02 versus placebo (0.370 [0.207, 0.663]) was nominally statistically significant ($p<0.001$).

The number and proportion of participants who were opioid-free during the entire treatment phase, the last 24 and 36 hours before discharge, the in-patient treatment phase, and the out-patient treatment phase, 0-24 hours after randomization, and post-discharge phase (up to 30 days after discharge) were other secondary efficacy endpoints. The proportion of participants who were opioid-free during any time interval was defined as the proportion of participants who had not taken oxycodone and/or morphine; for any participants who reported taking a rescue medication without reporting the type taken, or if the rescue medication was noted to be Norco/hydrocodone, that rescue medication was counted as an opioid. The proportions were analyzed with the difference in proportions Z-test, and a sensitivity analysis based on the proportion of participants who had not taken oxycodone during the entire treatment phase was performed.

Entire Treatment Phase:

The number and proportion of opioid (oxycodone and/or morphine) free participants during the entire treatment phase for the FAS shows that in the MR-107A-02 and Placebo groups, 78 (56.9%) and 45 (33.1%) participants, respectively, were opioid (oxycodone and/or morphine) free during the entire treatment phase; the MR-107A-02 group had 24% more opioid-free participants than the Placebo group, and the difference in proportions (95% CI) of 23.8% (12.4%, 35.3%) was statistically significant ($p<0.001$).

The results of the sensitivity analysis of the number and proportion of opioid free participants during the entire treatment phase for the FAS, in which only oxycodone use was analyzed shows that in the MR-107A-02 and Placebo groups, 78 (56.9%) and 46 (33.8%) participants, respectively, were oxycodone free during the entire treatment phase; the difference in proportions (95% CI) of 23.1% (11.6%, 34.6%) was nominally significant ($p<0.001$). The results of the sensitivity analysis (only oxycodone) were similar to those of the analysis that included both oxycodone and/or morphine Last 24 Hours Before Discharge (i.e., 24-48 Hours after Randomization):

The number and proportion of opioid (oxycodone and/or morphine) free participants during the last 24 hours before discharge for the FAS shows that in the MR-107A-02 and Placebo groups, 122 (89.1%) and 99 (72.8%) participants, respectively, were opioid (oxycodone and/or morphine) free during the last 24 hours before discharge; the difference in proportions (95% CI) of 16.3% (7.1%, 25.4%) was nominally statistically significant ($p<0.001$).

Last 36 Hours Before Discharge (i.e., 12-48 Hours after Randomization):

The number and proportion of opioid (oxycodone and/or morphine) free participants during the last 36 hours before discharge for the FAS shows that in the MR-107A-02 and Placebo groups, 107 (78.1%) and 78 (57.4%) participants, respectively, were opioid (oxycodone and/or morphine) free during the last 36 hours before discharge; the difference in proportions (95% CI) of 20.7% (9.9%, 31.6%) was nominally statistically significant ($p<0.001$).

In-Patient Treatment Phase (i.e., 0-48 Hours after Randomization):

The number and proportion of opioid (oxycodone and/or morphine) free participants during the in-patient treatment phase for the FAS shows that in the MR-107A-02 and Placebo groups, 84 (61.3%) and 53 (39.0%) participants, respectively, were opioid (oxycodone and/or morphine) free during the in-patient treatment phase; the difference in proportions (95% CI) of 22.3% (10.8%, 33.9%) was nominally statistically significant ($p<0.001$).

Out-Patient Treatment Phase (i.e., 5 Days Following Discharge):

The number and proportion of opioid (oxycodone and/or morphine) free participants during the out-patient treatment phase for the FAS shows that in the MR-107A-02 and Placebo groups, 109 (79.6%) and 87 (64.0%) participants, respectively, were opioid (oxycodone and/or morphine) free during the out-patient treatment phase; the difference in proportions (95% CI) of 15.6% (5.1%, 26.1%) was nominally statistically significant ($p=0.004$).

This analysis was repeated to compare the MR-107A-02 group with the All-Placebo group and with the Tramadol Placebo group. In the Tramadol Placebo group, 87 (63.5%) participants were opioid (oxycodone and/or morphine) free during the out-patient treatment phase; the difference in proportions (95% CI) for MR-107A-02 versus tramadol of 16.1% (5.5%, 26.6%) was nominally statistically significant ($p=0.003$). In the All-Placebo group, 174 (63.7%) participants were opioid (oxycodone and/or morphine) free; the difference in proportions (95% CI) for MR-107A-02 versus placebo (all) of 15.8% (7.0%, 24.7%) was nominally statistically significant ($p=0.001$).

0-24 Hours after Randomization:

The number and proportion of opioid (oxycodone and/or morphine) free participants during 0-24 hours after randomization for the FAS shows that in the MR-107A-02 and Placebo groups, 85 (62.0%) and 55 (40.4%) participants, respectively, were opioid (oxycodone and/or morphine) free during 0-24 hours after randomization; the difference in proportions (95% CI) of 21.6% (10.0%, 33.2%) was nominally statistically significant ($p<0.001$).

Post-Discharge Phase (i.e., Up to 30 Days after Discharge):

The number and proportion of opioid (oxycodone and/or morphine) free participants during the post-discharge phase, up to 30 days, for the FAS shows that in the MR-107A-02 and Placebo groups, 105 (76.6%) and 84 (61.8%) participants, respectively, were opioid (oxycodone and/or morphine) free during the post-discharge phase, up to 30 days; the difference in proportions (95% CI) of 14.9% (4.1%, 25.7%) was nominally statistically significant ($p=0.008$).

This analysis was repeated to compare the MR-107A-02 group with the All-Placebo group and with the Tramadol Placebo group. In the Tramadol Placebo group, 85 (62.0%) participants were opioid (oxycodone and/or morphine) free during the post-discharge phase, up to 30 days; the difference in proportions (95% CI) for MR-107A-02 versus tramadol of 14.6% (3.8%, 25.4%) was nominally statistically significant ($p=0.009$). In the All-Placebo group, 169 (61.9%) participants were opioid (oxycodone and/or morphine) free during the post-discharge phase, up to 30 days; the difference in proportions (95% CI) for MR-107A-02 versus placebo (all) of 14.7% (5.6%, 23.9%) was nominally statistically significant ($p=0.003$).

Summed Pain Intensity Difference Over Time Following Study Drug Administration

The SPID over 0-4 hours, 0-8 hours, 0-12 hours, 12-24 hours, and 0-24 hours following study drug administration (based on NRS-R scores) were other secondary efficacy endpoints; the analysis was similar to that of the primary estimand.

The SPID over time following study drug administration for the FAS. Overall, the LS means for the SPID in the MR-107A-02, Tramadol, and Placebo groups increased with time through 24 hours post-dose showed that the MR-107A-02 and Tramadol groups both had larger (and nominally statistically significantly different) LS mean SPIDs than the Placebo group at each time interval evaluated (MR-107A-02 versus placebo [$p<0.005$] and tramadol versus placebo [$p<0.042$; post-hoc]). The MR-107A-02 group had numerically larger LS mean SPIDs than the Tramadol group at each time interval evaluated. The various analyses of $SPID_{0-48}$ (the primary estimand) are discussed below.

Pain Intensity Differences Over Time Following Study Drug Administration

The PIDs over time following study drug administration (based on NRS-R scores) were other secondary efficacy endpoints and were analyzed using MMRM. Additional details on the analysis are provided below.

The PID (NRS-R) over time following study drug administration for the FAS. The PID at each time point was proportional to the NRS pain score at that time point, such that lower PIDs corresponded to lower NRS pain scores show that the MR-107A-02 and Tramadol groups had lower LS mean PIDs than the Placebo group from 0.5 through 48 hours following study drug administration (i.e., all time points evaluated), and the MR-107A-02 group had numerically lower LS mean PIDs than the Tramadol group from 2 through 12 hours and from 20 through 48 hours following study drug administration.

Time to Perceptible Pain Relief

The time to perceptible pain relief, which was measured by the two-stopwatch technique, was a secondary efficacy endpoint that was analyzed using Kaplan-Meir plots with censoring at the time of first rescue medication. Additional details on the analysis are provided in section herein, and the post-hoc analyses for tramadol versus placebo are noted in sections herein.

The time to perceptible pain relief for the FAS, and FIG. 15 displays the Kaplan-Meier plot for the time to perceptible pain relief for the FAS. The median (95% CI) time to first perceptible pain relief in the MR-107A-02 group (0.7 [0.6, 0.9] hours) was lower than that in the Placebo group (0.9 [0.6, 5.8] hours). The log rank test yielded a nominally statistically significant p-value ($p=0.037$); the median (CI) time to first perceptible relief of pain was numerically lower in the Tramadol group (0.8 [90% CI: 0.6, 0.9] hours) than that in the Placebo group (0.9 [95% CI: 0.6, 5.8] hours). The log rank test yielded a statistically non-significant p-value ($p=0.056$; post-hoc). Of the three treatment groups MR-107A-02 had the fastest time to first perceptible pain relief.

Time to Meaningful Pain Relief

The time to meaningful pain relief, which was measured by the two-stopwatch technique, was another secondary efficacy endpoint analyzed using Kaplan-Meir plots with censoring at the time of first rescue medication. Additional details on the analysis are provided herein, and the post-hoc analyses for tramadol versus placebo are noted in sections herein.

The time to meaningful pain relief for the FAS, and FIG. 16 displays the Kaplan-Meier plot for the time to meaningful pain relief for the FAS show that the median (CI) times to meaningful relief of pain in the MR-107A-02 and Tramadol groups (2.4 hours [95% CI: 1.9, 3.0 hours] and 3.4 hours [90% CI: 2.6, 4.9 hours], respectively) were lower than that in the Placebo group (5.1 hours [95% CI: 3.1, not available hours]). The log rank test yielded nominally statistically significant p-values ($p=0.012$ for MR-107A-02 versus placebo and $p=0.046$ [post-hoc] for tramadol versus placebo). Of the three treatment groups, MR-107A-02 had the fastest median time to meaningful pain relief.

Proportion of Participants with Overall Pain Reductions from Baseline of ≥30% and ≥50% Over Time Following Study Drug Administration The proportion of participants with an overall pain reduction of ≥30% and ≥50% from baseline within 0-4 hours, 0-8 hours, 0-12 hours, 12-24 hours, 0-24 hours, 24-48 hours, and 0-48 hours after the first dose were other secondary efficacy endpoints that were analyzed using the difference in proportions Z-test. Additional details on the planned analysis are provided herein, and the post-hoc analyses for tramadol versus placebo are noted in sections herein.

Overall Pain Reduction≥30% from Baseline:

The proportion of participants with an overall pain reduction≥30% from baseline, using NRS-R for the FAS show that with increasing time intervals, the proportions of participants with an overall pain reduction≥30% from baseline (i.e., responders) increased within each treatment group; the proportions of responders were higher in the MR-107A-02 and Tramadol groups than in the Placebo group at all intervals (nominal p-values of $p\leq0.024$ for MR-107A-02 versus placebo and $p\leq0.022$ [post-hoc] for tramadol versus placebo). The proportions of responders in the MR-107A-02 and Tramadol groups were numerically similar at all intervals.

Overall Pain Reduction≥50% from Baseline:

The Proportions of participants with an overall pain reduction≥50% from baseline, using NRS-R for the FAS show that as for the proportions of participants with an overall pain reduction≥50% from baseline, the proportions of participants with an overall pain reduction≥50% from baseline (i.e., responders) increased within each treatment group with increasing time intervals; the proportions of responders were higher in the MR-107A-02 and Tramadol groups than in the Placebo group at all intervals (nominal p-values of p≤0.018 for MR-107A-02 versus placebo and p≤0.015 [post-hoc] for tramadol versus placebo). The proportions of responders in the MR-107A-02 and Tramadol groups were numerically similar at all intervals.

Patient's Global Assessment of Pain Control from 0-24 Hours, 24-48 Hours, and on Day 9

The PGA of pain control within 0-24 hours and 24-48 hours after the first dose and at Day 9 were other secondary efficacy endpoints that were analyzed using the difference in proportions Z-test. Additional details on the planned analysis are provided in herein, and the post-hoc analyses are described in sections below.

In-Patient Treatment Phase:

The proportion of participants with "very good" or "excellent" PGA of pain control during the in-patient treatment phase for the FAS show that from 0-24 hours to 24-48 hours, the proportions of participants with "very good" or "excellent" PGA of pain control (i.e., responders) increased within each treatment group; the proportions of responders were higher in the MR-107A-02 and Tramadol groups than in the Placebo group at both intervals (nominal p-values of p<0.001 for both MR-107A-02 versus placebo and tramadol versus placebo [post-hoc]). Of the three treatment groups, MR-107A-02 had the greatest proportion of responders at both measured in-patient intervals.

Out-Patient Treatment Phase:

The proportion of participants with "very good" or "excellent" PGA of pain control during the out-patient treatment phase for the FAS show that the proportions of responders at Day 9 were higher in the MR-107A-02 and Tramadol Placebo groups than in the Placebo group (nominal p-value of p<0.001 for MR-107A-02 versus placebo and p=0.048 [post-hoc] for tramadol versus placebo). Of the three treatment groups, MR-107A-02 had the greatest proportions of responders at Day 9.

Time to First Opioid (Oxycodone and/or Morphine) Rescue Medication Use

The time to first opioid (oxycodone and/or morphine) rescue medication use was another secondary efficacy endpoint that was analyzed using Kaplan-Meir plots. Participants who discontinued early were censored at the time of discontinuation. Additional details on the planned analysis are provided herein, and the changes to the planned analyses and the tramadol versus placebo post-hoc analyses are noted in sections herein.

The time to first opioid (oxycodone and/or morphine) rescue medication use for the FAS, and FIG. 17 displays the Kaplan-Meier plot for the time to first opioid (oxycodone and/or morphine) rescue medication use for the FAS. The median (CI) times to first opioid (oxycodone and/or morphine) rescue medication use in the MR-107A-02 and Tramadol groups were not available (95% CI: 62.5 hours, not available) and 64.7 hours (90% CI: 20.2 hours, not available), respectively. The MR-107A-02 and Tramadol groups had longer times to first opioid use than the Placebo group (10.0 hours [95% CI: 8.2, 14.9 hours]. The log rank test yielded nominal p-values (p<0.001 for MR-107A-02 versus placebo and p=0.007 [post-hoc] for tramadol versus placebo). Of the three treatment groups, the MR-107A-02 group had the largest 25th percentile time (7.4 hours), representing the time beyond which 25% of the participants had the event interest (Q1). Corresponding values of Q1 for the Tramadol and Placebo groups were 7.1 and 3.6 hours, respectively. No median time was calculated for the MR-107A-02 group as <50% of participants had an event.

Rescue Medication Use

APAP was the 1st step rescue medication during the entire treatment phase and was allowed at any time (up to 1 g [2×500 mg] q6h, maximum daily dose of 4 g). As shown, the mean (range) amount of APAP used in the MR-107A-02 group (4.39 g [0.5 g, 17.0 g]) was lower than in the Tramadol and Placebo groups (5.25 g [1.0 g, 15.0 g] and 6.94 g [1.0 g, 24.0 g], respectively) over the entire treatment phase.

During the entire treatment phase, participants in the MR-107A-02 group used the lowest amount of 1st step rescue medication (i.e., APAP of the three treatment groups.

Of the participants in the MR-107A-02, Tramadol, and Placebo groups that completed study treatment in both the in- and out-patient treatment phases, 26 (21.3%), 10 (8.2%), and 8 (6.9%) participants, respectively, took no rescue medication during the entire treatment phase; the MR-107A-02 group had the highest proportion of participants reporting no rescue medication use during the entire treatment phase of all three treatment groups.

In-Patient Treatment Phase (i.e., 0-48 Hours after Randomization):

As described herein, APAP was the 1st step rescue medication during the in-patient treatment phase and was allowed at any time (up to 1 g [2×500 mg] q6h, maximum daily dose of 4 g). As shown, the mean (range) amount of APAP used in the MR-107A-02 group (2.55 g [1.0 g, 6.0 g]) was numerically lower than in the Tramadol and Placebo groups (2.83 g [1.0 g, 7.0 g] and 3.94 g [1.0 g, 7.0 g], respectively) during the in-patient treatment phase.

During the in-patient treatment phase, participants in the MR-107A-02 group used the lowest amount of 1st step rescue medication (i.e., APAP) of the three treatment groups.

Of the participants in the MR-107A-02, Tramadol, and Placebo groups that completed study treatment in the in-patient treatment phase, 36 (26.7%), 22 (17.1%), and 11 (8.3%) participants, respectively, took no rescue medication during the in-patient treatment phase; the MR-107A-02 group had the highest proportion of participants reporting no rescue medication use during the in-patient treatment phase of all three treatment groups.

Out-Patient Treatment Phase (i.e., 5 Days Following Discharge):

APAP was the 1st step rescue medication during the out-patient treatment phase and was allowed at any time (up to 1 g [2×500 mg] q6h, maximum daily dose of 4 g). As shown, the mean (range) amount of APAP used in the MR-107A-02 group (3.45 g [0.5 g, 11.0 g]) was numerically lower than in the Tramadol Placebo and Placebo groups (3.68 g [0.5 g, 12.0 g] and 4.58 g [1.0 g, 17.0 g], respectively) during the out-patient treatment phase During the out-patient treatment phase, participants in the MR-107A-02 group used the lowest amount of 1st step rescue medication (i.e., APAP) of the three treatment groups.

Of the participants in the MR-107A-02, Tramadol Placebo, and Placebo groups that completed study treatment in the out-patient treatment phase, 63 (51.2%), 34 (27.6%), and 38 (32.5%) participants, respectively, took no rescue medication during the out-patient treatment phase; the MR-107A-02 group had the highest proportion of participants reporting no rescue medication use during the out-patient treatment phase of all three treatment groups.

Time to First Rescue Medication Use:

The time to first rescue medication use was another secondary efficacy endpoint that was analyzed using Kaplan-Meir plots with censoring for participants who discontinued early at the time of discontinuation. Additional details on the planned analysis are provided in herein, and the changes to the planned analyses and post-hoc analyses for tramadol versus placebo are noted in sections below.

The time to first rescue medication use for the FAS, and FIG. 18 displays the Kaplan-Meier plot for the time to first rescue medication use for the FAS shows that the median (CI) times to first rescue medication use in the MR-107A-02 and Tramadol groups (4.3 hours [95% CI: 2.8, 5.1 hours] and 3.1 hours [90% CI: 2.4, 3.8 hours], respectively) were both longer than that in the Placebo group (2.2 hours [95% CI: 1.6, 2.6 hours]. The log rank test yielded nominal p-values ($p<0.001$ for MR-107A-02 versus placebo and $p=0.019$ [post-hoc] for tramadol versus placebo). The median time to first rescue medication was numerically larger for the MR-107A-02 group than for the Tramadol group.

Modified Post-Anesthetic Discharge Scoring System at 24 Hours, 48 Hours, Visit 3, and Early Termination The MPADSS at 24 hours, 48 hours, Visit 3, and ET was a secondary efficacy endpoint whose results were summarized using descriptive statistics. On the MPADSS, a higher score was indicative of increased readiness for successful discharge (Table 21).

A summary of the MPADSS results at 24 hours, 48 hours, Visit 3, and ET for the FAS; the mean MPADSS within each treatment group increased slightly from 24 hours to 48 hours post-dose shows that at 24 hours post-dose, the MR-107A-02 group had the highest mean (SD) MPADSS score of 9.3 (0.91); the mean (SD) for the Tramadol and Placebo groups were 8.9 (1.26) and 8.8 (1.03), respectively. At 48 hours post-dose and Follow-up (Visit 3), the three treatment groups had similar mean (SD) MPADSS (48 hours post-dose: 9.5 [0.91], 9.3 [1.39], and 9.3 [0.94] for MR-107A-02, Tramadol, and Placebo, respectively; Follow-up: 9.6 [1.00], 9.7 [0.74], and 9.6 [0.74], respectively). Few participants provided MPADSS data at ET.

Overall Benefit of Analgesic Score at 24 Hours, 48 Hours, Visit 3, and Early Termination The OBAS at 24 hours, 48 hours, Visit 3, and ET was another secondary efficacy endpoint whose results were summarized using descriptive statistics. On the OBAS, a lower score was indicative of reduced pain intensity and ORAEs and higher patient satisfaction (Table 22).

A summary of the OBAS results at 24 hours, 48 hours, Visit 3, and ET for the FAS; the mean OBAS within each treatment group decreased slightly from 24 hours post-dose to Follow-up (Visit 3) shows that at 24 hours post-dose, 48 hours post-dose, and Follow-up, the mean (SD) OBAS was 4.4 (3.17), 3.0 (2.72), and 2.5 (2.80), respectively, for MR-107A-02; 5.9 (3.74), 4.1 (3.21), and 3.3 (2.99), respectively, for Placebo; and 5.3 (3.00), 4.6 (3.61), and 2.9 (2.37), respectively, for Tramadol. From 24 hours post-dose to Follow-up (Visit 3), the MR-107A-02 group had the lowest mean OBAS of all three treatment groups. Few participants provided OBAS data at ET.

Numeric Rating Scale with Activity at 24 Hours, 48 Hours, Visit 3, and Early Termination The NRS-A at 24 hours, 48 hours, Visit 3, and ET was another secondary efficacy endpoint whose results were summarized using descriptive statistics. On the NRS-A scale, a lower score was indicative of lower pain levels perceived by the participant when seated with the plantar surface of the ball of surgical attended foot touching the floor. NRS-A is an indicator for early mobilization after surgery.

A summary of the NRS-A results at 24 hours, 48 hours, Visit 3, and ET for the FAS; the mean NRS-A within each treatment group decreased from 24 hours post-dose to Follow-up (Visit 3) shows that at 24 hours post-dose, 48 hours post-dose, and Follow-up, the mean (SD) NRS-A was 3.6 (2.62), 2.3 (2.34), and 1.7 (2.02), respectively, for MR-107A-02; 5.6 (2.95), 4.1 (2.92), and 2.3 (2.38), respectively, for Placebo; and 4.2 (2.65), 3.5 (2.66), and 2.1 (2.31), respectively, for Tramadol. From 24 hours post-dose to Follow-up (Visit 3), the MR-107A-02 group had the lowest mean NRS-A of the three treatment groups. Few participants provided data at ET for NRS-A.

Multiple Comparisons/Multiplicity

In order to control Type 1 error, the analyses for the key secondary estimand were considered valid only if the specified primary analysis for the primary estimand showed a statistically significant result ($p<0.05$, based on a 2-sided test). The analyses for additional secondary estimands were considered valid only if the analysis for the key secondary estimand also showed a statistically significant result ($p<0.05$, based on a 2-sided test). The analysis for additional secondary estimands continued using a pre-specified statistical hierarchy. The full statistical hierarchy is described as follows:

1. Primary analysis for the primary estimand (if $p<0.05$ based on a 2-sided test, then continue to 2).
2. Analysis of the key secondary estimand: The number of doses of opioid rescue medication during the entire treatment phase (in-patient and out-patient treatment phases) (if $p<0.05$ based on a 2-sided test, then continue to 3).
3. Proportion of participants using no opioid rescue medication during the entire treatment phase (in-patient and out-patient treatment phases). The proportion for MR-107A-02 and the proportion for placebo was to be compared.

In practice, all analyses were to be performed but if a non-significant p-value (as defined above) at any step occurred, then all p-values following the first non-significant p-value were to be considered nominal only. Regardless of the outcome of the statistical testing strategy for the estimands defined above, all p-values for the remaining secondary estimands (that were subjected to statistical testing) were considered nominal.

Use of an "Efficacy Subset" of Participants

The primary and key secondary analyses were conducted for the FAS, which included all randomized participants who received at least one dose of study drug, including participants who discontinued study treatment or received protocol allowed rescue medication. Supplemental analyses of the primary endpoint were conducted for the mFAS and PP Analysis Set.

Active-Control Studies Intended to Show Equivalence

This study included tramadol as an active control. A sensitivity analysis was conducted for the primary estimand by using the same ANCOVA model described earlier sections, but with the active control included.

Analyses of the primary efficacy variable comparing the efficacy of the active control with the study drug and the active control with placebo were also performed; for more details about these analyses.

Examination of Subgroups

Subgroup analyses were performed for the primary and key secondary estimands and are described herein.

Drug Dose, Drug Concentration, and Relationships to Response

The PK endpoints in this study were designed to measure exposure of MR-107A-02 following bunionectomy surgery using sparse sampling and included $C_{max}$, $T_{max}$, $AUC_{0-4}$, $AUC_{0-24}$, and $AUC_{0-48}$ based on observed data. The meloxicam plasma concentrations will also be utilized for subsequent analysis using Pop PK methods. The PK analyses were conducted for the PK Analysis Set with PK samples taken as described herein. Four participants (101-32, 104-011, 104-076, 111-024) in the PK Analysis Set had insufficient concentration data, and therefore, their PK data were not included in the summary statistics of MR-107A-02 plasma concentrations and PK parameters. However, the meloxicam concentration and PK data for all participants in the PK Analysis Set is available herein and will be included in subsequent PopPK analyses.

The summary statistics and individual plasma MR-107A-02 concentrations through 48 hours after the first dose for participants in the MR-107A-02 group, and FIG. 19 displays the mean meloxicam concentrations through 48 hours after the first dose for the PK Analysis Set (only for participants in the MR-107A-02 group with sufficient concentration data) shows that the mean plasma concentration increased through 1 hour following the first dose with accumulation after the repeat 12-hour dosing. In general, the mean profile, showing rapid meloxicam absorption by 1 hour is in line with previous Phase 1 and Phase 2 study data.

The individual plasma meloxicam concentrations on linear and semi-log scales for participants in the PK Analysis Set as a composite plot, which shows the plasma meloxicam concentrations by participant on a linear and semi-log scale, respectively.

The summary statistics and by-participant PK parameters for participants in the MR-107A-02 group, and Table 27 summarizes the mean PK parameters show that following the first dose of MR-107A-02 (15 mg), the geometric mean values (coefficient of variance [CV %]) for initial $C_{max}$ was 1881.222 (30.060) ng/ml and the corresponding median $T_{max}$ value was 1.090 hours. Repeat dosing of MR-107A-02 (15 mg BID) resulted in accumulation, with increasing mean meloxicam concentration values at the pre-dose timepoints of 12, 24, and 48 hours.

TABLE 27

Pharmacokinetic Parameters following Administration of MR-107A-02 (15 mg BID) (PK Analysis Set)

| Variable[1] Statistic | MR-107A-02 (15 mg BID) (N = 137) |
|---|---|
| n[2] | 60 |
| $C_{max}$ (ng/mL) | |
| First dosing period | 1881.222 (30.060) |
| Through 48 hours after first dose | 2532.254 (38.625) |
| $T_{max}$ (h) | |
| First dosing period | 1.090 (0.220, 12.070) |
| Through 48 hours after first dose | 32.030 (0.220, 48.670) |
| $AUC_{0-4}$ (ng*h/mL) | 5072.570 (36.754) |
| $AUC_{0-24}$ (ng*h/mL) | 30115.952 (22.504) |
| $AUC_{0-48}$ (ng*h/mL) | 81593.999 (29.443) |

AUC = area under the concentration-versus-time curve;
$AUC_{0-4}$ = AUC from time 0 to 4 hours after dosing (first dose);
$AUC_{0-24}$ = AUC from time 0 to 24 hours after dosing (first dose);
$AUC_{0-48}$ = AUC from 0 to 48 hours after dosing (first dose but includes second dose);
BID = twice daily;
$C_{max}$ = maximum plasma concentration;
Max = maximum;
Min = minimum;
N = Number of participants per treatment group in the PK Analysis Set;
PK = pharmacokinetic;
$T_{max}$ = time to maximum plasma concentration;
q6h = Once every 6 hours
Note:
During the in-patient treatment phase, participants received (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase).

TABLE 27-continued

Pharmacokinetic Parameters following Administration of MR-107A-02 (15 mg BID) (PK Analysis Set)

| Variable[1] Statistic | MR-107A-02 (15 mg BID) (N = 137) |
|---|---|

[1]Tmax is presented as median (Min, Max); all other parameters are presented as geometric mean (coefficient of variance).
[2]Participants 101-32, 104-011, 104-076, 111-024 were not included due to insufficient available concentration data.

Table 28 shows the same pK parameters as Table 27, with arithmetic mean instead of geometric mean calculations.

TABLE 28

Arithmetic Mean (% CV) MR-107A-02 PK Parameters, Bunionectomy Study

| Parameter | MR-107A-02 15 mg BID (n = 60) |
|---|---|
| Cmax, after 1st Dose (ng/mL) | 1964.578 (30.1%) |
| Cmax, overall (ng/ml) | 2660.733 (38.6%) |
| Tmax, after 1st Dose (hr)[1] | 1.090 (0.220-12.070) |
| Tmax, overall (hr)[1] | 32.030 (0.220-48.670) |
| $AUC_{0-4\ h}$ (ng*hr/mL) | 5460.820 (36.8%) |
| $AUC_{0-24\ h}$ (ng*hr/mL) | 30823.688 (22.5%) |
| $AUC_{0-48\ h}$ (ng*hr/mL) | 84752.299 (29.4%) |

[1]Median (Minimum-Maximum)

3A.7 Efficacy Conclusions from Study 3001

The primary objective of the study was to confirm the efficacy of MR-107A-02 in treating acute pain, following bunionectomy surgery. The secondary efficacy objectives were to confirm the opioid-sparing effect associated with the use of MR-107A-02, to further confirm the efficacy of MR-107A-02 in participants following bunionectomy surgery using additional efficacy measures, to confirm the association of clinical benefit with reduced opioid use, to confirm the efficacy of tramadol in the study, and to estimate the difference in efficacy between MR-107A-02 and tramadol. The study also measured the exposure of meloxicam after administration of MR-107A-02 (15 mg BID) in participants following bunionectomy surgery.

Most participants (85.9% of all participants) were female, and over half of all participants were White (60.0%) and not Hispanic or Latino (68.3%). The mean age was 48.0 years (range 18 to 77 years), and most participants were <65 years of age (89.3%). The mean baseline NRS-R was 7.3 (range 3 to 10). The three treatment groups were comparable with respect to demographic and baseline characteristics. The three treatment groups were also comparable with respect to common medical history and use of prior medications.

The FAS included 137 participants in each of the MR-107A-02 and Tramadol groups and 136 participants in the Placebo group, which satisfied (marginally exceeded) the minimum treatment group size required to sufficiently power the study for the planned analyses of the primary and secondary estimands.

The primary efficacy estimand compared the $SPID_{0-48}$ (based on NRS-R scores) for the MR-107A-02 and Placebo groups in the FAS using an ANCOVA model; rescue medication use was managed by the WLOCF approach, and missing data was managed by an MI approach. The study met the primary endpoint, as the difference in LS mean $SPID_{0-48}$ (95% CI) for MR-107A-02 versus placebo (82.7 [62.0, 103.4]) was statistically significant ($p<0.001$). The $SPID_{0-48}$ endpoint captures both the magnitude and duration of the analgesic effect, offering a comprehensive measure of treatment efficacy in acute pain. The statistically significant increase in $SPID_{0-48}$ for MR-107A-02 over placebo suggests that MR-107A-02 provides clinically meaningful pain relief within the critical early time window, when pain is typically most intense and patients are most vulnerable to breakthrough symptoms.

The key secondary efficacy estimand was the number of doses of opioid (oxycodone and/or morphine) rescue medication taken during the entire treatment phase. The analysis used a negative binomial regression model with a log link to compare the MR-107A-02 and Placebo groups in the FAS. Missing data was managed by an MI approach. The study met the key secondary endpoint, as the ratio of LS geometric means of the number of doses of opioid (oxycodone and/or morphine) medication (95% CI) for MR-107A-02 versus placebo (0.41 [0.29, 0.58]) was statistically significant ($p<0.001$). Notably, the LS geometric mean number of opioid doses (i.e., total opioid consumption) used in the MR-107A-02 group (0.12 doses) over the entire treatment phase was 59% lower than that in the Placebo group (0.29 doses). This substantial decrease in opioid use is expected to be clinically significant, given the risks associated with opioids including dependence, tolerance and AEs.

Similarly, participants in the MR-107A-02 group took fewer doses of opioids (oxycodone and/or morphine) than those in the Placebo group during all intervals (i.e., the last 24 and 36 hours before discharge, the in-patient treatment phase, and the out-patient treatment phase, 0-24 hours after randomization, and post-discharge phase [up to 30 days after discharge]; $p<0.001$ [nominal]). These differences suggest that MR-107A-02 effectively reduced the need for rescue opioid analgesia throughout both acute and extended recovery periods.

The proportion of participants who were opioid (oxycodone and/or morphine)-free over various intervals was also evaluated. During the entire treatment phase, the MR-107A-02 group had 23.8% more opioid-free participants than the Placebo group, and the difference in proportions (95% CI) of opioid (oxycodone and/or morphine)-free participants in the MR-107A-02 and Placebo groups of 23.8% (12.4%, 35.3%) was statistically significant ($p<0.001$). For all other intervals (i.e., the last 24 and 36 hours before discharge, the in-patient treatment phase, and the out-patient treatment phase, 0-24 hours after randomization, and post-discharge phase [up to 30 days after discharge]), the MR-107A-02 group had larger proportions of opioid-free participants than the Placebo group ($p<0.008$ [nominal]). This finding indicates that MR-107A-02 was not only effective in reducing moderate to severe pain but also reduced the need for opioid rescue medication to a meaningful degree. Across all pre-defined time intervals, the MR-107A-02 group consistently had higher proportions of opioid-free participants. These consistent observations across all intervals suggest a sustained benefit of MR-107A-02 in limiting opioid exposures throughout the whole recovery phase.

Importantly, regardless of this reduced opioid use, participants in the MR-107A-02 group also took less APAP rescue medication than those in the Placebo group during the entire treatment phase, in-patient treatment phase, and out-patient treatment phase. This finding underscores the robustness of the analgesic effect provided by MR-107A-02 and suggests that the observed reduction in opioid use was not offset by increased use of non-opioid rescue medication. A larger proportion of participants in the MR-107A-02 group also took no rescue medication during the entire treatment phase, in-patient treatment phase, and out-patient treatment phase than in the Placebo group. These results demonstrate that participants treated with MR-107A-02 required less rescue medication (APAP and opioid) than those in the Placebo group; this indicates that a meaningful subset of patients receiving MR-107A-02 achieved adequate pain control without the need for any rescue medication, reflecting both efficacy and convenience from a patient care perspective.

The participants in the MR-107A-02 group experienced faster times to first perceptible and meaningful relief of pain than those in the Placebo group ($p<0.037$ [nominal]). In addition, the time to first use of rescue medication, both overall and specifically for opioid rescue medication, was longer in the MR-107A-02 group than in the Placebo group ($p<0.001$ [nominal]). This indicates that participants receiving MR-107A-02 experienced more sustained analgesic effects and were less reliant on supplementary medication to manage their pain than those in the Placebo group.

The geometric mean (CV %) for initial $C_{max}$ of meloxicam after the first dose of MR-107A-02 was 1881.222 (30.060) ng/ml with a corresponding median $T_{max}$ value of 1.090 hours. Repeat dosing of MR-107A-02 (15 mg BID) resulted in accumulation, with increasing mean meloxicam concentration values at the pre-dose timepoints of 12, 24, and 48 hours. The $T_{max}$ after the first dose of 1.090 hours was in proximity to the median time to first perceptible relief of pain in the MR-107A-02 group of 0.7 hours, and the overall exposure of meloxicam with repeat dosing correlated with the long-term pain control observed in the MR-107A-02 group.

Other efficacy endpoints, including the SPID, PID, and the proportion of participants with overall pain reductions from baseline of ≥30% and ≥50%, indicated that participants in the MR-107A-02 group experienced better pain control over time than those in the Placebo group. These results suggest a robust analgesic effect of MR-107A-02 relative to placebo.

Collectively, these findings provide consistent and complementary evidence of the analgesic effectiveness and opioid-sparing potential of MR-107A-02. The ability to achieve pain relief while reducing overall reliance on both opioid and non-opioid rescue medications enhances the treatment's clinical utility and aligns with current guidelines aimed at minimizing unnecessary medication exposure and associated risks.

Concerning PGA of pain control, the proportion of participants rating their pain control as "very good" or "excellent" increased in all groups from 0-24 hours through Follow-up. Notably, MR-107A-02 showed advantages over placebo, with nominal p-values of $p<0.001$ at both 0-24 hours and 24-48 hours. As PGA includes the overall sense of satisfaction and control which plays a major role in emotional well-being and trust of the patient in the healthcare team, this outcome is clinically relevant.

The OBAS was used to measure both the relief from pain and any side effects of treatment. From 24 hours through Follow-up, MR-107A-02 showed a greater reduction in OBAS than placebo, suggesting better overall benefit with MR-107A-02, including pain relief and fewer side effects, than with placebo.

The NRS-A is an indicator for patient mobilization. Participants who received MR-107A-02 experienced greater relief in movement-related pain (as measured by NRS-A) than those who received placebo. Improvements were noticeable as early as 24 hours after the first dose and continued through Follow-up. Participants in the MR-107A-02 group reported the lowest pain scores during activity from 24 hours post-dose through Follow-up, suggesting better support for early mobilization than placebo.

The MPADSS is used to evaluate whether a patient has recovered sufficiently following surgery to be safely discharged. Although participants in both the MR-107A-02 and Placebo groups reported high MPADSS scores from 24 hours post-dose through Follow-up, at 24 hours the MR-107A-02 group demonstrated a mean (SD) MPADSS score of 9.3 (0.91), while the Placebo group had a mean (SD) score of 8.8 (1.03). The MPADDS defines a score of ≥9 as the threshold for safe discharge readiness. Therefore, with a mean score above this cutoff by 24 hours post-dose, participants in the MR-107A-02 group reached the minimum discharge criteria more reliably and rapidly than those in the Placebo group despite their lower use of both APAP and opioid rescue medications; this shows a direct patient benefit related to reduced opioid analgesic use, such as earlier functional recovery for allowing discharge.

Sensitivity analyses were conducted to assess the robustness of the primary and key secondary efficacy results. These analyses, which included alternative statistical models and assumptions, yielded results that were consistent with those of the primary analyses. This consistency supports the reliability and validity of the primary conclusions drawn from the FAS. To further evaluate the treatment effect, the primary efficacy estimand was analyzed using both the mFAS and the PP Analysis Set. Results from these additional populations closely mirrored those observed in the FAS. This reinforces confidence in the observed treatment effect and indicates that the findings are not sensitive to population selection criteria or protocol adherence.

Subgroup analyses were performed for the primary and key secondary estimands to examine potential differential treatment effects across demographic variables, including age, sex, and race. These analyses did not reveal any consistent or clinically meaningful interactions between treatment efficacy and subgroup membership. The efficacy of MR-107A-02 appeared stable across these subgroups, suggesting that its effect is broadly applicable within the studied population.

Collectively, these findings from sensitivity, supplementary, and subgroup analyses support the robustness and generalizability of the primary and key secondary efficacy results.

To show the assay sensitivity, several analyses, including some post-hoc, were conducted to confirm the efficacy of tramadol in the study by comparing the effects of tramadol with placebo. Across endpoints, the efficacy of tramadol was demonstrated; tramadol displayed better pain control than placebo with higher $SPID_{0-48}$ ($p<0.001$ [nominal]), higher SPID over other intervals ($p\leq 0.042$ [nominal; post-hoc]), faster time to meaningful pain relief ($p=0.046$ [nominal; post-hoc]), longer time to first rescue medication, including opioid rescue ($p\leq 0.019$ [nominal; post-hoc]), and larger proportions of participants with overall pain reductions from baseline of ≥30% or ≥50% ($p\leq 0.022$ [nominal; post-hoc]) and with PGA of "very good" or "excellent" ($p\leq 0.048$ [nominal; post-hoc]).

An analysis was also performed to estimate the difference in efficacy between MR-107A-02 and tramadol in treating acute pain following bunionectomy surgery. Results demonstrated that MR-107A-02 was associated with greater pain relief than tramadol as measured by the primary endpoint, $SPID_{0-48}$ ($p=0.013$ [nominal; post-hoc]), indicating an advantage over tramadol. Although no formal comparisons of MR-107A-02 and tramadol were made for other endpoints, participants in the MR-107A-02 group reported similar or better pain control as those in the Tramadol group with numerically larger LS mean SPIDs at each time interval evaluated, consistent numerically lower PIDs from 2 through 12 hours and from 20 through 48 hours following study drug administration, suggesting a more robust and sustained analgesic effect. There were also similar proportions of participants with overall pain reductions from baseline of ≥30% or ≥50% in the MR-107A-02 and the Tramadol groups, suggesting similar pain relief from both treatments. In addition, participants in the MR-107A-02 group achieved perceptible and meaningful pain relief faster than those in the Tramadol group, further supporting the potential of MR-107A-02 to deliver rapid onset of pain relief. The times to first rescue medication (any type) and to first opioid rescue medication were similar or slightly longer in the MR-107A-02 group compared with those in the Tramadol group, consistent with the observed analgesic efficacy. Concerning PGA, the MR-107A-02 group had numerically higher proportions of participants reporting "very good" or "excellent" pain control than the Tramadol group, which suggests that participants experienced more effective results with MR-107A-02 than with tramadol. For MPADSS at 24 hours post-dose, a slightly higher mean (SD) score was observed in the MR-107A-02 group (9.3 [0.91]) than in the Tramadol group (8.9 [1.26]), which suggests that on average, participants in the MR-107A-02 group reached the minimum discharge criteria more reliably and rapidly than those in the Tramadol group. For OBAS, at 24 and 48 hours after the first dose and at Follow-up, participants in the MR-107A-02 group had lower mean OBAS than those in the Tramadol group. This suggests a better overall benefit with MR-107A-02 than with tramadol, including pain relief and fewer side effects. For NRS-A, participants in the MR-107A-02 group reported lower pain scores during activity at 24- and 48-hours post-dose and at Follow-up, suggesting better support for early mobilization than tramadol.

A numerically larger proportion of participants in the MR-107A-02 group than in the Tramadol group took no rescue medication during the in-patient treatment phase, out-patient treatment phase, and entire treatment phase. This suggests that MR-107A-02 may offer better baseline pain control than tramadol, which is consistent with the outcome for $SPID_{0-48}$. This is further supported by the finding that participants in the MR-107A-02 group used numerically less APAP as rescue medication than those in the Tramadol group during the in-patient treatment phase, out-patient treatment phase, and entire treatment phase, suggesting that MR-107A-02 provided pain control with lower use of first step rescue medication.

Overall, MR-107A-02 is more effective in treating acute pain following bunionectomy surgery than placebo and demonstrates pain control that is similar or better than that provided by the active, standard of care option, opioid-comparator, tramadol.

3A.8 Safety Evaluation

Table 29 presents the extent of exposure by treatment phase for the Safety Analysis Set. Overall, the mean duration of exposure was 7.7 days (range 1 to 9 days for all three treatment groups), and the mean total number of doses taken was 17.3 doses (range 2 to 18 doses [MR-107A-02 and Tramadol groups] and 1 to 18 doses [Placebo group]). During the in-patient treatment phase, the mean duration of exposure overall was 2.7 days (range 1 to 3 days for all three treatment groups), and the mean total number of doses taken overall was 7.9 doses (range 2 to 8 doses [MR-107A-02 and Tramadol groups] and 1 to 8 doses [Placebo group]). During the out-patient treatment phase, the mean duration of exposure overall was 5.1 days (range 1 to 6 days [MR-107A-02 and Tramadol groups] and 3 to 6 days [Placebo group]), and the mean total number of doses taken overall was 9.7 doses (range 1 to 10 doses [MR-107A-02 and Tramadol groups] and 3 to 10 doses [Placebo group]). Within each treatment phase and overall, the duration of exposure and total number of doses taken were similar across treatment groups.

TABLE 29

Extent of Exposure (Safety Analysis Set)

| Phase Variable Statistic | MR-107A-02 (15 mg BID) → MR-107A-02 (15 mg BID) (N = 137) | Tramadol (50 mg q6h) → Placebo (N = 137) | Placebo → Placebo (N = 136) | Total (N = 410) |
|---|---|---|---|---|
| In-patient Treatment Phase | | | | |
| Duration of exposure (days)[1] | | | | |
| n | 137 | 137 | 136 | 410 |
| Mean (SD) | 2.7 (0.48) | 2.7 (0.50) | 2.6 (0.53) | 2.7 (0.50) |
| Median | 3.0 | 3.0 | 3.0 | 3.0 |
| Min, Max | 1, 3 | 1, 3 | 1, 3 | 1, 3 |
| Total number of doses taken[2] | | | | |
| n | 137 | 137 | 136 | 410 |
| Mean (SD) | 7.9 (0.53) | 7.8 (0.98) | 7.8 (0.99) | 7.9 (0.86) |
| Median | 8.0 | 8.0 | 8.0 | 8.0 |
| Min, Max | 2, 8 | 2, 8 | 1, 8 | 1, 8 |
| Out-patient Treatment Phase | | | | |
| Duration of exposure (days)[1] | | | | |
| n | 136 | 130 | 133 | 399 |
| Mean (SD) | 5.1 (0.62) | 5.1 (0.62) | 5.1 (0.50) | 5.1 (0.58) |
| Median | 5.0 | 5.0 | 5.0 | 5.0 |
| Min, Max | 1, 6 | 1, 6 | 3, 6 | 1, 6 |
| Total number of doses taken[2] | | | | |
| n | 136 | 130 | 133 | 399 |
| Mean (SD) | 9.7 (1.24) | 9.8 (1.00) | 9.7 (1.08) | 9.7(1.11) |
| Median | 10.0 | 10.0 | 10.0 | 10.0 |
| Min, Max | 1, 10 | 1, 10 | 3, 10 | 1, 10 |
| Overall | | | | |
| Duration of exposure (days)[1] | | | | |
| n | 137 | 137 | 136 | 410 |
| Mean (SD) | 7.8 (1.00) | 7.6 (1.60) | 7.6 (1.26) | 7.7 (1.31) |
| Median | 8.0 | 8.0 | 8.0 | 8.0 |
| Min, Max | 1, 9 | 1, 9 | 1, 9 | 1, 9 |
| Total number of doses taken[2] | | | | |
| n | 137 | 137 | 136 | 410 |
| Mean (SD) | 17.6 (1.83) | 17.1 (3.25) | 17.3 (2.64) | 17.3 (2.64) |
| Median | 18.0 | 18.0 | 18.0 | 18.0 |
| Min, Max | 2, 18 | 2, 18 | 1, 18 | 1, 18 |

BID = Twice daily;
Max = Maximum;
Min = Minimum;
n = Number of participants;
N = Number of participants per treatment group in the Safety Analysis Set;
q6h = Once every 6 hours;
SD = Standard deviation
Note:

TABLE 29-continued

Extent of Exposure (Safety Analysis Set)

| Phase Variable Statistic | MR-107A-02 (15 mg BID) → MR-107A-02 (15 mg BID) (N = 137) | Tramadol (50 mg q6h) → Placebo (N = 137) | Placebo → Placebo (N = 136) | Total (N = 410) |
|---|---|---|---|---|

During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase.
[1]Defined as: last dose date − first dose date + 1.
[2]Only active doses were counted for the MR-107A-02 and Tramadol groups during the in-patient treatment phase.

Adverse Events

Adverse events were summarized by treatment group for the in-patient and out-patient treatment phases individually; the names of the three treatment groups contain the treatment that participants were assigned in that phase of the study (i.e., treatment during the in-patient treatment phase or treatment during the out-patient treatment phase). During the in-patient treatment phase, participants received MR-107A-02 (15 mg BID), tramadol (50 mg q6h), or placebo (q6h; see Table 20). During the out-patient treatment phase, participants received either MR-107A-02 (15 mg BID) or placebo (BID; see Table 21). To differentiate the participants who received tramadol (50 mg q6h) and placebo during the in-patient treatment phase, the out-patient treatment phase AE summary tables include the Tramadol Placebo and Placebo groups. All participants who received placebo during the out-patient treatment phase, regardless of their treatment during the in-patient treatment phase, are included in the All-Placebo group.

To simplify, the treatment groups are referenced as follows:

MR-107A-02 group=MR-107A-02 (15 mg BID) during the in-patient treatment phase and MR-107A-02 (15 mg BID) during the out-patient treatment phase Tramadol group (referred to as the Tramadol Placebo group in the descriptions of the out-patient treatment phase in section herein)=tramadol (50 mg q6h) during the in-patient treatment phase and placebo during the out-patient treatment phase Placebo group=placebo during both the in- and out-patient treatment phases All Placebo group=placebo during the out-patient treatment phase (includes participants who received either tramadol [50 mg q6h] or placebo during the in-patient treatment phase)

No deaths or TEAEs of special interest were reported at any time during the study.

Table 30 presents an overall summary of TEAEs in the Safety Analysis Set during the in-patient treatment phase. Overall, 165 (40.2%) participants reported 374 TEAEs. The incidence of TEAEs was higher in the Tramadol group (55.5%) than in the MR-107A-02 and Placebo groups (31.4% and 33.8%, respectively). One hundred twenty (29.3%) participants reported 227 TEAEs related to study drug; the incidence of related TEAEs was notably higher in the Tramadol group (45.3%) than in the MR-107A-02 and Placebo groups (20.4% and 22.1%, respectively). One hundred eight (26.3%) participants reported 234 opioid-related TEAEs; the incidence of opioid-related TEAEs was notably higher in the Tramadol group (46.0%) than in the MR-107A-02 and Placebo groups (16.1% and 16.9%, respectively).

No serious TEAEs were reported. Most TEAEs were either mild or moderate in severity, with 2 (0.5%) participants overall reporting 2 severe TEAEs (1 [0.7%] participant each in the Tramadol and Placebo groups). No participant in the MR-107A-02 group reported a severe TEAE. One (0.2%) participant overall, who was in the Tramadol group, reported one TEAE leading to study discontinuation.

TABLE 30

Overview of Treatment-emergent Adverse Events: In-patient (Safety Analysis Set)

| Category, n (%) m | MR-107A-02 (15 mg BID) (N = 137) | Tramadol (50 mg q6h) (N = 137) | Placebo (N = 136) | Total (N = 410) |
|---|---|---|---|---|
| TEAEs | 43 (31.4) 67 | 76 (55.5) 224 | 46 (33.8) 83 | 165 (40.2) 374 |
| Serious TEAEs | 0 | 0 | 0 | 0 |
| Severe TEAEs | 0 | 1 (0.7) 1 | 1 (0.7) 1 | 2 (0.5) 2 |
| TEAEs related to study drug[1] | 28 (20.4) 38 | 62 (45.3) 151 | 30 (22.1) 38 | 120 (29.3) 227 |
| TEAEs leading to study discontinuation | 0 | 1 (0.7) 1 | 0 | 1 (0.2) 1 |
| Opioid-related TEAEs | 22 (16.1) 31 | 63 (46.0) 166 | 23 (16.9) 37 | 108 (26.3) 234 |
| TEAEs of special interest | 0 | 0 | 0 | 0 |
| TEAEs leading to death | 0 | 0 | 0 | 0 |

AE = Adverse event;
BID = Twice daily;
m = number of events;
n = Number of participants;
N = Number of participants per treatment group in the Safety Analysis Set;
q6h = Once every 6 hours;
TEAE = Treatment-emergent adverse event;
Note:
During the in-patient treatment phase, participants received MR-107A-02 (15 mg BID), tramadol (50 mg q6h), or placebo (q6h).
Note:
Percentages were based on the number of participants in the Safety Analysis Set, in each treatment group, for that study phase.
Note:
TEAEs in the in-patient treatment phase were those with an onset date on or after the first dose of study drug administration in the in-patient treatment phase and before the first dose of study drug administration in the out-patient treatment phase.
Note:
TEAEs were summarized according to the last treatment that the participant received prior to the start of that AE.
[1]Related TEAEs were those reported as possibly, probably, or definitely related to study treatment. Missing relationships were considered related.

Table 31 presents an overall summary of TEAEs in the Safety Analysis Set during the out-patient treatment phase. Overall, 167 (41.9%) participants reported 314 TEAEs with similar incidence of TEAEs among the treatment groups. Eighty-three (20.8%) participants reported 125 TEAEs related to study drug. Seventy-six (19.0%) participants reported 103 opioid-related TEAEs, with a similar incidence of opioid-related TEAEs among the treatment groups. Most TEAEs were either mild or moderate in severity, with 2 (0.5%) participants overall reporting 3 severe TEAEs (2 [1.6%] participants in the Tramadol group). Three (0.8%) participants in the Tramadol Placebo group (also counted in the All-Placebo group) reported 4 serious TEAEs. No TEAEs leading to study discontinuation were reported during the out-patient treatment phase.

TABLE 31

Overview of Treatment-emergent Adverse Events: Out-patient (Safety Analysis Set)

| Category, n (%) m | MR-107A-02 (15 mg BID) (N = 138) | Tramadol Placebo (N = 129) | Placebo (N = 132) | All Placebo (N = 261) | Total (N = 399) |
|---|---|---|---|---|---|
| TEAEs | 52 (37.7) 192 | 66 (51.2) 121 | 49 (37.1) 97 | 115 (44.1) 218 | 167 (41.9) 314 |
| Serious TEAEs | 0 | 3 (2.3) 4 | 0 | 3 (1.1) 4 | 3 (0.8) 4 |
| Severe TEAEs | 0 | 2 (1.6) 3 | 0 | 2 (0.8) 3 | 2 (0.5) 3 |
| TEAEs related to study drug[1] | 28 (20.3) 72 | 36 (27.9) 56 | 19 (14.4) 33 | 55 (21.1) 89 | 83 (20.8) 125 |
| TEAEs leading to study discontinuation | 0 | 0 | 0 | 0 | 0 |
| Opioid-related TEAEs | 24 (17.4) 58 | 29 (22.5) 41 | 23 (17.4) 33 | 52 (19.9) 74 | 76 (19.0) 103 |
| TEAEs of special interest | 0 | 0 | 0 | 0 | 0 |
| TEAEs leading to death | 0 | 0 | 0 | 0 | 0 |

AE = Adverse event;
BID = Twice daily;
m = number of events;
n = Number of participants;
N = Number of participants per treatment group in the Safety Analysis Set;
TEAE = Treatment-emergent adverse event
Note:
During the out-patient treatment phase, participants received either MR-107A-02 (15 mg BID) or placebo (BID); participants in the Tramadol group received placebo only during the out-patient treatment phase and are labelled as Tramadol Placebo.
Note:
Percentages were based on the number of participants in the Safety Analysis Set, in each treatment group, for that study phase.
Note:
TEAEs in the out-patient treatment phase were those that started on or after the first dose of study drug administration in the out-patient treatment phase.
Note:
TEAEs were summarized according to the last treatment that the participant received prior to the start of that AE.
Note:
The All-Placebo treatment column summarizes participants who were randomized to the Tramadol or Placebo groups and that received placebo during the out-patient treatment phase.
[1]Related TEAEs were those reported as possibly, probably, or definitely related to study treatment. Missing relationships were considered related.

All summary tabulations of AEs are provided herein and by-participant listings of selected categories of AEs are provided in sections below (SAEs, severe AEs, AEs related to study drug, ORAEs, AESIs, AEs leading to study discontinuation, and AEs leading to death).

Analysis of Adverse Events

In-Patient Treatment Phase:

TEAEs by SOC and PT reported in the Safety Analysis Set during the in-patient treatment phase. The most common (≥5% of participants overall) SOCs of TEAEs included gastrointestinal disorders (92 [22.4%] participants), nervous system disorders (60 [14.6%] participants), skin and subcutaneous tissue disorders (41 [10.0%] participants), and investigations (21 [5.1%] participants) show that of the most common SOCs of TEAEs, the incidences of gastrointestinal disorders and nervous system disorders were notably higher in the Tramadol group (41.6% and 23.4%, respectively) than in the MR-107A-02 and Placebo groups (gastrointestinal disorders: 10.2% and 15.4%, respectively; and nervous system disorders: 9.5% and 11.0%).

Table 32 displays the most common (≥2% of participants overall) PTs of TEAEs reported during the in-patient treatment phase. The most common PTs included nausea (74 [18.0%] participants), dizziness (38 [9.3%] participants), vomiting (27 [6.6%] participants), headache (24 [5.9%] participants), pruritus (23 [5.6%] participants), constipation (21 [5.1%] participants), and hyperhidrosis and C-reactive protein increased (14 [3.4%] participants each). Of the most common PTs of TEAEs, the incidences of nausea, vomiting, dizziness, and constipation were notably higher in the Tramadol group (38.0%, 16.8%, 18.2%, and 8.8%, respectively) than in the MR-107A-02 and Placebo groups (nausea: 5.8% and 10.3%, respectively; vomiting: 2.9% and 0; dizziness: 2.9% and 6.6%; and constipation: 3.6% and 2.9%).

TABLE 32

Most Common (≥2% of Participants Overall) Treatment-emergent Adverse Events by Preferred Term: In-patient (Safety Analysis Set)

| Preferred Term | MR-107A-02 (15 mg BID) (N = 137) | Tramadol (50 mg q6h) (N = 137) | Placebo (N = 136) | Total (N = 410) |
|---|---|---|---|---|
| Nausea | 8 (5.8) | 52 (38.0) | 14 (10.3) | 74 (18.0) |
| Dizziness | 4 (2.9) | 25 (18.2) | 9 (6.6) | 38 (9.3) |
| Vomiting | 4 (2.9) | 23 (16.8) | 0 | 27 (6.6) |
| Headache | 9 (6.6) | 9 (6.6) | 6 (4.4) | 24 (5.9) |
| Pruritus | 7 (5.1) | 12 (8.8) | 4 (2.9) | 23 (5.6) |
| Constipation | 5 (3.6) | 12 (8.8) | 4 (2.9) | 21 (5.1) |
| Hyperhidrosis | 4 (2.9) | 4 (2.9) | 6 (4.4) | 14 (3.4) |
| C-reactive protein increased | 4 (2.9) | 4 (2.9) | 6 (4.4) | 14 (3.4) |

AE = Adverse event;
BID = Twice daily;
MedDRA = Medical Dictionary for Regulatory Activities;
n = Number of participants;
N = Number of participants per treatment group in the Safety Analysis Set;
q6h = Once every 6 hours;
TEAE = Treatment-emergent adverse event
Note:
During the in-patient treatment phase, participants received MR-107A-02 (15 mg BID), tramadol (50 mg q6h), or placebo (q6h).
Note:
Percentages were based on the number of participants in the Safety Analysis Set, in each treatment group, for that study phase.
Note:
TEAEs in the in-patient treatment phase were those with an onset date on or after the first dose of study drug administration in the in-patient treatment phase and before the first dose of study drug administration in the out-patient treatment phase.
Note:
TEAEs were summarized according to the last treatment that the participant received prior to the start of that AE.
Note:
Participants with multiple events in a preferred term were counted only once for that preferred term.
Note:
All terms were coded using MedDRA Version 26.1 and sorted in descending order of frequency in the Total group for preferred terms.

Out-Patient Treatment Phase:

TEAEs by SOC and PT reported in the Safety Analysis Set during the out-patient treatment phase. The most common (≥5% of participants overall) SOCs of TEAEs included gastrointestinal disorders (74 [18.5%] participants), nervous system disorders (38 [9.5%] participants), skin and subcutaneous tissue disorders (36 [9.0%] participants), general disorders and administration site conditions (29 [7.3%] participants), and investigations (24 [6.0%] participants) show that of the most common SOCs of TEAEs, the incidence of gastrointestinal disorders was notably higher in the Tramadol Placebo group (26.4%) than in the Placebo group (10.6%).

Table 33 displays the most common (≥2% of participants overall) PTs of TEAEs reported during the out-patient treatment phase. The most common PTs included constipation (31 [7.8%] participants), fatigue (23 [5.8%] participants), dizziness and pruritus (20 [5.0%] participants each), nausea (19 [4.8%] participants), diarrhea and C-reactive protein increased (18 [4.5%] participants each), headache (14 [3.5%] participants), rash (12 [3.0%] participants), and abdominal pain (11 [2.8%] participants). Of the most common PTs of TEAEs, the incidence of constipation was notably higher in the Tramadol Placebo group (10.9%) than in the Placebo group (4.5%), and the incidence of pruritus was notably higher in the Tramadol Placebo, Placebo, and All Placebo groups (7.0%, 6.1%, and 6.5%, respectively) than in the MR-107A-02 group (2.2%).

TABLE 33

Most Common (≥2% of Participants Overall) Treatment-emergent Adverse Events by Preferred Term: Out-patient (Safety Analysis Set)

| Preferred Term | MR-107A-02 (15 mg BID) (N = 138) | Tramadol Placebo (N = 129) | Placebo (N = 132) | All Placebo (N = 261) | Total (N = 399) |
|---|---|---|---|---|---|
| Constipation | 11 (8.0) | 14 (10.9) | 6 (4.5) | 20 (7.7) | 31 (7.8) |
| Fatigue | 7 (5.1) | 5 (3.9) | 11 (8.3) | 16 (6.1) | 23 (5.8) |
| Dizziness | 4 (2.9) | 4 (3.1) | 12 (9.1) | 16 (6.1) | 20 (5.0) |
| Pruritus | 3 (2.2) | 9 (7.0) | 8 (6.1) | 17 (6.5) | 20 (5.0) |
| Nausea | 7 (5.1) | 7 (5.4) | 5 (3.8) | 12 (4.6) | 19 (4.8) |
| Diarrhea | 6 (4.3) | 7 (5.4) | 5 (3.8) | 12 (4.6) | 18 (4.5) |
| C-reactive protein increased | 5 (3.6) | 7 (5.4) | 6 (4.5) | 13 (5.0) | 18 (4.5) |
| Headache | 4 (2.9) | 7 (5.4) | 3 (2.3) | 10 (3.8) | 14 (3.5) |
| Rash | 6 (4.3) | 5 (3.9) | 1 (0.8) | 6 (2.3) | 12 (3.0) |
| Abdominal pain | 4 (2.9) | 3 (2.3) | 4 (3.0) | 7 (2.7) | 11 (2.8) |

AE = Adverse event;
BID = Twice daily;
MedDRA = Medical Dictionary for Regulatory Activities;
n = Number of participants;
N = Number of participants per treatment group in the Safety Analysis Set;
TEAE = Treatment-emergent adverse event
Note:
During the out-patient treatment phase, participants received either MR-107A-02 (15 mg BID) or placebo (BID); participants in the Tramadol group received placebo only during the out-patient treatment phase and are labelled as Tramadol Placebo. See
Note:
Percentages were based on the number of participants in the Safety Analysis Set, in each treatment group, for that study phase.
Note:
TEAEs in the out-patient treatment phase were those that started on or after the first dose of study drug administration in the out-patient treatment phase.
Note:
TEAEs were summarized according to the last treatment that the participant received prior to the start of that AE.
Note:
Participants with multiple events in a preferred term were counted only once for that preferred term.
Note:
All terms were coded using MedDRA Version 26.1 and sorted in descending order of frequency in the Total group for preferred terms.
Note:
The All-Placebo treatment column summarizes participants who were randomized to the Tramadol or Placebo groups and who received placebo during the out-patient treatment phase.

Severe Treatment-Emergent Adverse Events

In-Patient Treatment Phase:

Severe TEAEs by SOC and PT reported during the in-patient treatment phase for the Safety Analysis Set. Overall, 2 (0.5%) participants reported severe TEAEs, with the PT of hypotension in 1 (0.7%) participant in the Tramadol group and the PT syncope in 1 (0.7%) participant in Placebo group show that no severe TEAEs were reported in the MR-107A-02 group.

Out-Patient Treatment Phase:

Severe TEAEs by SOC and PT reported during the out-patient treatment phase for the Safety Analysis Set. Overall, 2 (0.5%) participants (both in the Tramadol Placebo group [1.6%]; also counted in the All Placebo group [0.8%]) reported severe TEAEs with the PTs of appendicitis and sepsis in 1 (0.8%) participant and intervertebral disc protrusion in the other 1 (0.8%) participant show that no severe TEAEs were reported in the MR-107A-02 or Placebo groups.

In-Patient Treatment Phase:

TEAEs related to study drug by SOC and PT reported during the in-patient treatment phase for the Safety Analysis Set show that overall, 120 (29.3%) participants reported TEAEs related to study drug with a higher proportion of participants reporting related TEAEs in the Tramadol group (45.3%) than in the MR-107A-02 and Placebo groups (20.4% and 22.1%, respectively).

The most common (≥5% of participants overall) SOCs of related TEAEs included gastrointestinal disorders (71 [17.3%] participants), nervous system disorders (34 [8.3%] participants), and skin and subcutaneous tissue disorders (22 [5.4%] participants). Of the most common SOCs of TEAEs, the incidences of gastrointestinal disorders and nervous system disorders were notably higher in the Tramadol group (34.3% and 16.8%, respectively) than in the MR-107A-02 and Placebo groups (gastrointestinal disorders: 8.8% each; and nervous system disorders: 2.9% and 5.1%, respectively), and the incidence of skin and subcutaneous tissue disorders was higher in the MR-107A-02 and Tramadol groups (5.8% and 8.0%, respectively) than in the Placebo group (2.2%).

The most common (≥2% of participants overall) PTs of related TEAEs included nausea (57 [13.9%] participants), dizziness (24 [5.9%] participants), vomiting (21 [5.1%] participants), constipation and C-reactive protein increased (13 [3.2%] participants each), pruritus (12 [2.9%] participants), and headache (10 [2.4%] participants). Of the most common PTs of TEAEs, the incidences of nausea, dizziness, vomiting, and constipation were notably higher in the Tramadol group (30.7%, 13.1%, 13.1%, and 5.1%, respectively) than in the MR-107A-02 and Placebo groups (nausea: 5.1% and 5.9%, respectively; dizziness: 1.5% and 2.9%; vomiting: 2.2% and 0; and constipation: 2.2% each).

Out-Patient Treatment Phase:

TEAEs related to study drug by SOC and PT reported during the out-patient treatment phase for the Safety Analysis Set show that overall, 83 (20.8%) participants reported TEAEs related to study drug.

The most common (≥5% of participants overall) SOCs of related TEAEs included gastrointestinal disorders (39 [9.8%] participants) and investigations (20 [5.0%] participants). The most common (≥2% of participants overall) PTs of related TEAEs during the out-patient treatment phase included C-reactive protein increased (18 [4.5%] participants), constipation (17 [4.3%] participants), nausea (12 [3.0%] participants), fatigue (11 [2.8%] participants), dizziness (10 [2.5%] participants), diarrhea (9 [2.3%] participants), and pruritus (8 [2.0%] participants). The incidences of the most common SOCs and PTs of related TEAEs were numerically higher in the Tramadol Placebo group than in the MR-107A-02 and Placebo groups during the out-patient treatment phase.

No deaths were reported in this study.

Other Serious Adverse Events

In-Patient Treatment Phase:

During the in-patient treatment phase, no serious TEAE was reported.

Out-Patient Treatment Phase:

Table 34 presents a summary of serious TEAEs by SOC and PT reported during the out-patient treatment phase for the Safety Analysis Set, and this example presents a by-participant listing of all SAEs in the study. Overall, 3 (0.8%) participants (all in the Tramadol Placebo group [also counted in the All-Placebo group]) reported at least one serious TEAE with PTs of appendicitis and sepsis in 1 (0.8%) participant, intervertebral disc protrusion in 1 (0.8%) participant, and abortion spontaneous in 1 [0.8%] participant.

TABLE 34

Serious Treatment-emergent Adverse Events, by System Organ Class and Preferred Term: Out-patient (Safety Analysis Set)

| System Organ Class Preferred Term | MR-107A-02 (15 mg BID) (N = 138) | Tramadol Placebo (N = 129) | Placebo (N = 132) | All Placebo (N = 261) | Total (N = 399) |
|---|---|---|---|---|---|
| Any Serious TEAE, n (%) | 0 | 3 (2.3) | 0 | 3 (1.1) | 3 (0.8) |
| Infections and infestations | 0 | 1 (0.8) | 0 | 1 (0.4) | 1 (0.3) |
| Appendicitis | 0 | 1 (0.8) | 0 | 1 (0.4) | 1 (0.3) |
| Sepsis | 0 | 1 (0.8) | 0 | 1 (0.4) | 1 (0.3) |
| Musculoskeletal and connective tissue disorders | 0 | 1 (0.8) | 0 | 1 (0.4) | 1 (0.3) |
| Intervertebral disc protrusion | 0 | 1 (0.8) | 0 | 1 (0.4) | 1 (0.3) |
| Pregnancy, puerperium and perinatal conditions | 0 | 1 (0.8) | 0 | 1 (0.4) | 1 (0.3) |
| Abortion spontaneous | 0 | 1 (0.8) | 0 | 1 (0.4) | 1 (0.3) |

AE = Adverse event;
BID = Twice daily;
MedDRA = Medical Dictionary for Regulatory Activities;
n = Number of participants;
N = Number of participants per treatment group in the Safety Analysis Set;
TEAE = Treatment-emergent adverse event
Note:
During the out-patient treatment phase, participants received either MR-107A-02 (15 mg BID) or placebo (BID); participants in the Tramadol group received placebo only during the out-patient treatment phase and are labelled as Tramadol Placebo.
Note:
Percentages were based on the number of participants in the Safety Analysis Set, in each treatment group, for that study phase.
Note:
TEAEs in the out-patient treatment phase were those that started on or after the first dose of study drug administration in the out-patient treatment phase.
Note:
TEAEs were summarized according to the last treatment that the participant received prior to the start of that AE.
Note:
Participants with multiple events in a system organ class/preferred term were counted only once for that system organ class/preferred term.
Note:
All terms were coded using MedDRA Version 26.1 and sorted in descending order of frequency in the Total group for both system organ classes and preferred terms.
Note:
The All-Placebo treatment column summarizes participants who were randomized to the Tramadol or Placebo groups and who received placebo during the out-patient treatment phase.

Other Significant Adverse Events

Adverse Events Leading to Study Discontinuation

In-Patient Treatment Phase:

TEAEs leading to study discontinuation reported during the in-patient treatment phase by SOC and PT for the Safety Analysis Set. Overall, 1 (0.2%) participant (in the Tramadol group) reported at least one TEAE leading to study discontinuation with the PT of vomiting; however, the reported action taken (discontinued study) for the TEAE of vomiting (participant 104-044) was an apparent error show that study drug was withdrawn for this participant due to the TEAE of nausea; an ET visit was recorded, but the participant went on to complete the study.

Out-Patient Treatment Phase:

No TEAE leading to study discontinuation was reported during the out-patient treatment phase.

Adverse Events Leading to Treatment Discontinuation

In-Patient Treatment Phase:

Table 35 presents TEAEs leading to treatment discontinuation reported during the in-patient treatment phase by SOC and PT for the Safety Analysis Set. Overall, 6 (1.5%)

participants reported at least one TEAE leading to treatment discontinuation. Reported PTs included nausea, drug hypersensitivity, and urticaria, with an incidence of 2 (0.5%) participants each, and dizziness with an incidence of 1 (0.7%) participant. Events reported in the MR-107A-02 group consisted of urticaria in 1 (0.7%) participant.

TABLE 35

Treatment-emergent Adverse Events Leading to Treatment Discontinuation, by System Organ Class and Preferred Term: In-patient (Safety Analysis Set)

| System Organ Class Preferred Term | MR-107A-02 (15 mg BID) (N = 137) | Tramadol (50 mg q6h) (N = 137) | Placebo (N = 136) | Total (N = 410) |
|---|---|---|---|---|
| Any TEAE Leading to Treatment Discontinuation, n (%) | 1 (0.7) | 4 (2.9) | 1 (0.7) | 6 (1.5) |
| Gastrointestinal disorders | 0 | 2 (1.5) | 0 | 2 (0.5) |
| Nausea | 0 | 2 (1.5) | 0 | 2 (0.5) |
| Immune system disorders | 0 | 1 (0.7) | 1 (0.7) | 2 (0.5) |
| Drug hypersensitivity | 0 | 1 (0.7) | 1 (0.7) | 2 (0.5) |
| Skin and subcutaneous tissue disorders | 1 (0.7) | 1 (0.7) | 0 | 2 (0.5) |
| Urticaria | 1 (0.7) | 1 (0.7) | 0 | 2 (0.5) |
| Nervous system disorders | 0 | 1 (0.7) | 0 | 1 (0.2) |
| Dizziness | 0 | 1 (0.7) | 0 | 1 (0.2) |

AE = Adverse event;
BID = Twice daily;
MedDRA = Medical Dictionary for Regulatory Activities;
n = Number of participants;
N = Number of participants per treatment group in the Safety Analysis Set;
q6h = Once every 6 hours;
TEAE = Treatment-emergent adverse event
Note:
During the in-patient treatment phase, participants received MR-107A-02 (15 mg BID), tramadol (50 mg q6h), or placebo (q6h).
Note:
Percentages were based on the number of participants in the Safety Analysis Set, in each treatment group, for that study phase.
Note:
TEAEs in the in-patient treatment phase were those with an onset date on or after the first dose of study drug administration in the in-patient treatment phase and before the first dose of study drug administration in the out-patient treatment phase.
Note:
TEAEs were summarized according to the last treatment that the participant received prior to the start of that AE.
Note:
Participants with multiple events in a system organ class/preferred term were counted only once for that system organ class/preferred term.
Note:
All terms were coded using MedDRA Version 26.1 and sorted in descending order of frequency in the Total group for both system organ classes and preferred terms.

Table 36 presents TEAEs leading to treatment discontinuation reported during the out-patient treatment phase by SOC and PT for the Safety Analysis Set. Overall, 5 (1.3%) participants reported at least one TEAE leading to treatment discontinuation with PTs of abdominal pain, somnolence, pruritus, abortion spontaneous, skin abrasion, rash, chest pain, and appendicitis, each of which had an incidence of 1 (0.3%) participant. The TEAE of abortion spontaneous (participant 113-013) was recorded as a TEAE that led to treatment discontinuation; however, study drug had already been withdrawn due to prior TEAEs, and the participant had completed the study before the start of this event. The events leading to treatment discontinuation in the MR-107A-02 group consisted of rash and chest pain.

TABLE 36

Treatment-emergent Adverse Events Leading to Treatment Discontinuation, by System Organ Class and Preferred Term: Out-patient (Safety Analysis Set)

| System Organ Class Preferred Term | MR-107A-02 (15 mg BID) (N = 138) | Tramadol Placebo (N = 129) | Placebo (N = 132) | Placebo (N = 261) | Total (N = 399) |
|---|---|---|---|---|---|
| Any TEAE Leading to Treatment Discontinuation, n (%) | 2 (1.4) | 2 (1.6) | 1 (0.8) | 3 (1.1) | 5 (1.3) |
| Skin and subcutaneous tissue disorders | 1 (0.7) | 1 (0.8) | 0 | 1 (0.4) | 2 (0.5) |
| Pruritus | 0 | 1 (0.8) | 0 | 1 (0.4) | 1 (0.3) |
| Rash | 1 (0.7) | 0 | 0 | 0 | 1 (0.3) |
| Gastrointestinal disorders | 0 | 1 (0.8) | 0 | 1 (0.4) | 1 (0.3) |
| Abdominal pain | 0 | 1 (0.8) | 0 | 1 (0.4) | 1 (0.3) |
| General disorders and administration site conditions | 1 (0.7) | 0 | 0 | 0 | 1 (0.3) |
| Chest pain | 1 (0.7) | 0 | 0 | 0 | 1 (0.3) |
| Infections and infestations | 0 | 1 (0.8) | 0 | 1 (0.4) | 1 (0.3) |
| Appendicitis | 0 | 1 (0.8) | 0 | 1 (0.4) | 1 (0.3) |
| Injury, poisoning and procedural complications | 0 | 0 | 1 (0.8) | 1 (0.4) | 1 (0.3) |
| Skin abrasion | 0 | 0 | 1 (0.8) | 1 (0.4) | 1 (0.3) |
| Nervous system disorders | 0 | 1 (0.8) | 0 | 1 (0.4) | 1 (0.3) |
| Somnolence | 0 | 1 (0.8) | 0 | 1 (0.4) | 1 (0.3) |
| Pregnancy, puerperium, and perinatal conditions | 0 | 1 (0.8) | 0 | 1 (0.4) | 1 (0.3) |
| Abortion spontaneous | 0 | 1 (0.8) | 0 | 1 (0.4) | 1 (0.3) |

AE = Adverse event;
BID = Twice daily;
MedDRA = Medical Dictionary for Regulatory Activities;
n = Number of participants;
N = Number of participants per treatment group in the Safety Analysis Set;
TEAE = Treatment-emergent adverse event
Note:
During the out-patient treatment phase, participants received either MR-107A-02 (15 mg BID) or placebo (BID); participants in the Tramadol group received placebo only during the out-patient treatment phase and are labelled as Tramadol Placebo.
Note:
Percentages were based on the number of participants in the Safety Analysis Set, in each treatment group, for that study phase.
Note:
TEAEs in the out-patient treatment phase were those that started on or after the first dose of study drug administration in the out-patient treatment phase.
Note:
TEAEs were summarized according to the last treatment that the participant received prior to the start of that AE.
Note:
Participants with multiple events in a system organ class/preferred term were counted only once for that system organ class/preferred term.
Note:
All terms were coded using MedDRA Version 26.1 and sorted in descending order of frequency in the Total group for both system organ classes and preferred terms.
Note:
The All-Placebo treatment column summarizes participants who were randomized to the Tramadol or Placebo groups and who received placebo during the out-patient treatment phase.

Opioid-Related Adverse Events

In-Patient Treatment Phase:

Table 37 presents opioid-related TEAEs reported during the in-patient treatment phase by SOC and PT for the Safety Analysis Set. Overall, 108 (26.3%) participants reported at least one opioid-related TEAE.

The most common (≥2% participants overall) PTs of opioid-related TEAEs included nausea (74 [18.0%] participants), dizziness (38 [9.3%] participants), vomiting (27 [6.6%] participants), pruritus (22 [5.4%] participants), and constipation (21 [5.1%] participants). The incidences of PTs of the most common opioid-related TEAEs were all notably higher in the Tramadol group (38.0%, 18.2%, 16.8%, 8.8%, and 8.8%, respectively) than in the MR-107A-02 and Placebo groups (nausea: 5.8% and 10.3%, respectively; dizziness: 2.9% and 6.6%; vomiting: 2.9% and 0; pruritus: 4.4% and 2.9%; and constipation: 3.6% and 2.9%).

TABLE 37

Opioid-related Treatment-emergent Adverse Events, by System Organ Class and Preferred Term: In-patient (Safety Analysis Set)

| System Organ Class Preferred Term | MR-107A-02 (15 mg BID) (N = 137) | Tramadol (50 mg q6h) (N = 137) | Placebo (N = 136) | Total (N = 410) |
|---|---|---|---|---|
| Any Opioid-Related TEAE, n (%) | 22 (16.1) | 63 (46.0) | 23 (16.9) | 108 (26.3) |
| Gastrointestinal disorders | 13 (9.5) | 56 (40.9) | 16 (11.8) | 85 (20.7) |
| Nausea | 8 (5.8) | 52 (38.0) | 14 (10.3) | 74 (18.0) |
| Vomiting | 4 (2.9) | 23 (16.8) | 0 | 27 (6.6) |
| Constipation | 5 (3.6) | 12 (8.8) | 4 (2.9) | 21 (5.1) |
| Nervous system disorders | 4 (2.9) | 26 (19.0) | 9 (6.6) | 39 (9.5) |
| Dizziness | 4 (2.9) | 25 (18.2) | 9 (6.6) | 38 (9.3) |
| Somnolence | 0 | 1 (0.7) | 1 (0.7) | 2 (0.5) |
| Presyncope | 0 | 1 (0.7) | 0 | 1 (0.2) |
| Skin and subcutaneous tissue disorders | 7 (5.1) | 12 (8.8) | 4 (2.9) | 23 (5.6) |
| Pruritus | 6 (4.4) | 12 (8.8) | 4 (2.9) | 22 (5.4) |
| Urticaria | 1 (0.7) | 0 | 0 | 1 (0.2) |
| Injury, poisoning and procedural complications | 1 (0.7) | 0 | 1 (0.7) | 2 (0.5) |
| Incision site pruritus | 0 | 0 | 1 (0.7) | 1 (0.2) |
| Vascular access site pruritus | 1 (0.7) | 0 | 0 | 1 (0.2) |
| General disorders and administration site conditions | 0 | 1 (0.7) | 0 | 1 (0.2) |
| Fatigue | 0 | 1 (0.7) | 0 | 1 (0.2) |

AE = Adverse event;
BID = Twice daily;
MedDRA = Medical Dictionary for Regulatory Activities;
n = Number of participants;
N = Number of participants per treatment group in the Safety Analysis Set;
q6h = Once every 6 hours;
TEAE = Treatment-emergent adverse event
Note:
During the in-patient treatment phase, participants received MR-107A-02 (15 mg BID), tramadol (50 mg q6h), or placebo (q6h).
Note:
Percentages were based on the number of participants in the Safety Analysis Set, in each treatment group, for that study phase.
Note:
TEAEs in the in-patient treatment phase were those with an onset date on or after the first dose of study drug administration in the in-patient treatment phase and before the first dose of study drug administration in the out-patient treatment phase.
Note:
TEAEs were summarized according to the last treatment that the participant received prior to the start of that AE.
Note:
Participants with multiple events in a system organ class/preferred term were counted only once for that system organ class/preferred term.
Note:
All terms were coded using MedDRA Version 26.1 and sorted in descending order of frequency in the Total group for both system organ classes and preferred terms.

Table 38 presents opioid-related TEAEs reported during the out-patient treatment phase by SOC and PT for the Safety Analysis Set. Overall, 76 (19.0%) participants reported at least one opioid-related TEAE.

The most common (≥2% participants overall) PTs of opioid-related TEAEs included constipation (31 [7.8%] participants), pruritus (20 [5.0%] participants), and nausea and dizziness (19 [4.8%] participants each). Of the most common opioid-related TEAEs, the incidence of pruritus was notably higher in the Tramadol Placebo, Placebo, and All Placebo groups (7.0%, 6.1%, and 6.5%, respectively) than in the MR-107A-02 group (2.2%).

TABLE 38

Opioid-related Treatment-emergent Adverse Events, by System Organ Class and Preferred Term: Out-patient (Safety Analysis Set)

| System Organ Class Preferred Term | MR-107A-02 (15 mg BID) (N = 138) | Tramadol Placebo (N = 129) | Placebo (N = 132) | All Placebo (N = 261) | Total (N = 399) |
|---|---|---|---|---|---|
| Any Opioid-Related TEAE, n (%) | 24 (17.4) | 29 (22.5) | 23 (17.4) | 52 (19.9) | 76 (19.0) |
| Gastrointestinal disorders | 19 (13.8) | 21 (16.3) | 9 (6.8) | 30 (11.5) | 49 (12.3) |
| Constipation | 11 (8.0) | 14 (10.9) | 6 (4.5) | 20 (7.7) | 31 (7.8) |
| Nausea | 7 (5.1) | 7 (5.4) | 5 (3.8) | 12 (4.6) | 19 (4.8) |
| Vomiting | 3 (2.2) | 2 (1.6) | 0 | 2 (0.8) | 5 (1.3) |
| Nervous system disorders | 5 (3.6) | 6 (4.7) | 11 (8.3) | 17 (6.5) | 22 (5.5) |
| Dizziness | 4 (2.9) | 4 (3.1) | 11 (8.3) | 15 (5.7) | 19 (4.8) |
| Somnolence | 1 (0.7) | 2 (1.6) | 0 | 2 (0.8) | 3 (0.8) |
| Skin and subcutaneous tissue disorders | 3 (2.2) | 9 (7.0) | 8 (6.1) | 17 (6.5) | 20 (5.0) |
| Pruritus | 3 (2.2) | 9 (7.0) | 8 (6.1) | 17 (6.5) | 20 (5.0) |
| General disorders and administration site conditions | 0 | 1 (0.8) | 0 | 1 (0.4) | 1 (0.3) |
| Fatigue | 0 | 1 (0.8) | 0 | 1 (0.4) | 1 (0.3) |

AE = Adverse event;
BID = Twice daily;
MedDRA = Medical Dictionary for Regulatory Activities;
n = Number of participants;
N = Number of participants per treatment group in the Safety Analysis Set;
TEAE = Treatment-emergent adverse event
Note:
During the out-patient treatment phase, participants received either MR-107A-02 (15 mg BID) or placebo (BID); participants in the Tramadol group received placebo only during the out-patient treatment phase and are labelled as Tramadol Placebo.
Note:
Percentages were based on the number of participants in the Safety Analysis Set, in each treatment group, for that study phase.
Note:
TEAEs in the out-patient treatment phase were those that started on or after the first dose of study drug administration in the out-patient treatment phase.
Note:
TEAEs were summarized according to the last treatment that the participant received prior to the start of that AE.
Note:
Participants with multiple events in a system organ class/preferred term were counted only once for that system organ class/preferred term.
Note:
All terms were coded using MedDRA Version 26.1 and sorted in descending order of frequency in the Total group for both system organ classes and preferred terms.
Note:
The All-Placebo treatment column summarizes participants who were randomized to the Tramadol or Placebo groups and who received placebo during the out-patient treatment phase.

Analysis and Discussion of Deaths, Other Serious Adverse Events, and Other

In-Patient Treatment Phase:

No serious TEAE was reported, and one TEAE leading to study discontinuation (PT of vomiting) was reported; however, the participant who reported the TEAE leading to study discontinuation did complete the study after discontinuing treatment. Overall, 6 (1.5%) participants reported at least one TEAE leading to treatment discontinuation (PTs of nausea, urticaria, dizziness, and drug hypersensitivity); the TEAEs leading to treatment discontinuation were all considered resolved or resolving at last report. A total of 108 (26.3%) participants overall reported at least one opioid-related TEAE, and the most common (≥2% participants overall) PTs included nausea, dizziness, vomiting, pruritus, and constipation, all of which were reported more frequently in the Tramadol group than in the MR-107A-02 and Placebo groups.

No TEAE leading to study discontinuation was reported during the out-patient treatment phase. Overall, 3 (0.8%)

participants reported at least one serious TEAE (PTs of appendicitis, sepsis, intervertebral disc protrusion, and abortion spontaneously). The serious TEAEs of appendicitis, sepsis, intervertebral disc protrusion, and abortion spontaneous were all considered not related to study drug and had resolved at the time of last report, and all were reported in the Tramadol Placebo group. Overall, 5 (1.3%) participants reported at least one TEAE leading to treatment discontinuation (PTs of abdominal pain, somnolence, pruritus, abortion spontaneous, skin abrasion, rash, chest pain, and appendicitis); the TEAEs leading to treatment discontinuation were all considered resolved or resolving. The TEAE of abortion spontaneous was recorded as a TEAE that led to treatment discontinuation; however, study drug had already been withdrawn due to prior TEAEs, and the participant had completed the study before the start of this event. A total of 76 (19.0%) participants reported at least one opioid-related TEAE, and the most common (≥2% participants overall) PTs included constipation, pruritus, nausea, and dizziness. Pruritus was reported more frequently in the Tramadol Placebo and Placebo groups than in the MR-107A-02 group.

The PTs of opioid-related TEAEs observed during the in- and out-patient treatment phases were expected effects of meloxicam, as most were reported during clinical studies of MOBIC (MOBIC Prescribing Information, 2024).

Safety Conclusions from Study 3001

The safety objective of this study was to confirm the safety and tolerability of MR-107A-02 in participants following bunionectomy surgery. Safety was assessed through the incidence, severity, duration, and outcome of AEs, including ORAEs, as well as changes from baseline in vital signs, laboratory parameters (hematology, chemistry, urinalysis), and 12-lead ECGs.

No deaths or TEAEs of special interest, including AEs related to GI events (particularly bleeding) and those related to cardiovascular events, such as myocardial infarction/unstable angina, stroke/TIA, heart failure, cardiac arrhythmia (atrial and ventricular), were reported at any time during the study, which demonstrates the safety of MR-107A-02 in terms of the risks associated with the NSAID class.

During the in-patient treatment phase, a total of 165 (40.2%) participants overall reported 374 TEAEs. The incidence of TEAEs was higher in the Tramadol group (55.5%) than in the MR-107A-02 and Placebo groups (31.4% and 33.8%, respectively). One hundred twenty (29.3%) participants reported 227 TEAEs considered related to the study drug. The incidence of related TEAEs was notably higher in the Tramadol group (45.3%) than in the MR-107A-02 and Placebo groups (20.4% and 22.1%, respectively). This means that the MR-107A-02 group had an even slightly lower proportion of participants with TEAEs than the Placebo group, possibly due to lower use of rescue medication.

During the in-patient treatment phase, 108 (26.3%) participants reported 234 opioid-related TEAEs. The incidence of opioid-related TEAEs was notably higher in the Tramadol group (46.0%) than in the MR-107A-02 and Placebo groups (16.1% and 16.9%, respectively), and the MR-107A-02 group had the lowest incidence of opioid-related TEAEs of all three treatment groups. The most common (≥2% participants overall) PTs of opioid-related TEAEs included nausea, dizziness, vomiting, pruritus, and constipation, all of which were reported more frequently in the Tramadol group than in the MR-107A-02 and Placebo groups. Most TEAEs were either mild or moderate in severity, with only 2 (0.5%) participants overall reporting 2 severe TEAEs (1 [0.7%] participants each in the Tramadol and Placebo groups). Notably, no participant in the MR-107A-02 group reported a severe TEAE. One (0.2%) participant overall, who was in the Tramadol group, reported one TEAE leading to study discontinuation (PT of vomiting); however, the participant who reported the TEAE leading to study discontinuation did complete the study after discontinuing treatment. No serious TEAEs were reported during the in-patient treatment phase.

A total of 6 (1.5%) participants reported at least one TEAE leading to treatment discontinuation (1 [0.7%] participant in the MR-107A-02 group, 4 [2.9%] participants in the Tramadol group, and 1 [0.7%] participant in the Placebo group); the TEAEs leading to treatment discontinuation were all considered resolved or resolving at the last report. Reported PTs included nausea (2 [1.5%] participants in the Tramadol group), drug hypersensitivity (1 [0.7%] participant each in the Tramadol and Placebo groups), urticaria (1 [0.7%] participant each in the MR-107A-02 and Tramadol groups), and dizziness (1 [0.7%] participant in the Tramadol group). During the out-patient treatment phase, a total of 167 (41.9%) participants overall reported 314 TEAEs with similar proportions of participants reporting TEAEs among the treatment groups. Eighty-three (20.8%) participants reported 125 TEAEs related to study drug. Seventy-six (19.0%) participants reported 103 opioid-related TEAEs. The most common (≥2% participants overall) PTs of opioid-related TEAEs included constipation, pruritus, nausea, and dizziness; pruritus was reported more frequently in the Tramadol Placebo and Placebo groups than in the MR-107A-02 group.

As with the in-patient treatment phase, most out-patient TEAEs were either mild or moderate in severity, with 2 (0.5%) participants overall reporting 3 severe TEAEs (2 [1.6%] participants in the Tramadol Placebo group). Three (0.8%) participants in the Tramadol Placebo group reported 4 serious TEAEs (PTs of appendicitis, sepsis, intervertebral disc protrusion, and abortion spontaneous), which were all considered not related to study drug and were recovered/resolved at the time of last report. No TEAEs leading to study discontinuation were reported during the out-patient treatment phase. Overall, 5 (1.3%) participants reported at least one TEAE leading to treatment discontinuation (PTs of abdominal pain, somnolence, pruritus, abortion spontaneous, skin abrasion, rash, chest pain, and appendicitis); the TEAEs leading to treatment discontinuation were all considered resolved or recovered at last report. The TEAE of abortion spontaneous was recorded as a TEAE that led to treatment discontinuation; however, the study drug had already been withdrawn due to prior TEAEs, and the participant had completed the study before the start of this event. Treatment-emergent AEs leading to treatment discontinuation in the MR-107A-02 group consisted of rash and chest pain in 1 (0.7%) participant each.

The marked difference in the incidence of opioid-related TEAEs between treatment groups-particularly in the first 48 hours-demonstrates a likely clinically meaningful benefit associated with MR-107A-02. Specifically, 16.1% of participants in the MR-107A-02 group experienced opioid-related TEAEs, compared with 46.0% in the Tramadol group. This represents a 29.9% absolute risk reduction and a relative reduction of approximately 65% of experiencing an ORAE, reflecting a substantial improvement in tolerability.

This lower incidence of ORAEs is particularly important given their known impact on patient comfort, recovery, and clinical resource utilization (Shafi et al., 2018). Common opioid-related effects such as nausea, dizziness, and sedation can impair postoperative function and delay discharge while requiring additional medications and monitoring. By contrast, MR-107A-02 demonstrated a more favorable safety profile, reducing these burdens and aligning with best practices in opioid-sparing multimodal analgesia.

The PTs of opioid-related TEAEs observed during the in- and out-patient treatment phases were expected effects of meloxicam, as most were reported during clinical studies of MOBIC (MOBIC Prescribing Information, 2024).

No renal toxicity or hepatotoxicity concerns were identified, and no clinically relevant trends over time or treatment group differences in vital signs, laboratory parameters, or ECGs were observed. These findings further support the safety of MR-107A-02.

Overall, MR-107A-02 15 mg BID was well tolerated and demonstrated a favorable safety profile. The MR-107A-02 group reported no serious TEAEs, severe TEAEs, or TEAEs leading to study discontinuation, and the incidence of TEAEs and opioid-related TEAEs in the MR-107A-02 group was similar to that of the Placebo group.

3A.9 Discussion and Overall Conclusions from Study 3001

Study Design for Acute Pain Indication

This randomized, placebo- and active-controlled study evaluated the efficacy, opioid-sparing capacity, and safety of MR-107A-02 (15 mg BID), a novel oral formulation of meloxicam designed for faster absorption than approved oral meloxicam formulations. As one of two studies in the Sponsor's Phase 3 program supporting the indication of treatment of acute pain per the US FDA draft guidance *Development of Non-Opioid Analgesics for Acute Pain* (FDA, 2022), this study evaluated post-operative pain following bunionectomy.

In alignment with the study design considerations outlined in the US FDA draft guidance *Development of Nonopioid Analgesics for Acute Pain* (FDA, 2022), this was a randomized, double-blind, repeat-dose, placebo and active controlled superiority (versus placebo) study of MR-107A-02. The primary objective was to confirm the efficacy of MR-107A-02 (versus placebo) in treating acute pain following bunionectomy surgery. This was evaluated with a recommended endpoint, i.e., $SPID_{0-48}$ based on NRS-R scores. Safety data were collected through 30 days following last administration of the study drug. Rescue medications (APAP and opioids) were pre-defined in the protocol and a stepwise approach for their use was described in case of inadequate pain control during each phase of the study. The pre-specified analyses for this study incorporated FDA feedback and were aligned with the recommendations for outcome measures to obtain an acute pain analgesic indication included in the US FDA draft guidance *Development of Non-Opioid Analgesics for Acute Pain* (FDA, 2022). A post-hoc analysis to compare MR-107A-02 with tramadol for $SPID_{0-48}$, and analyses to compare tramadol with placebo for some of the secondary efficacy estimands were added to this report; however, the results of post-hoc analyses are considered exploratory in nature as they were conducted after unblinding activities were completed.

This study was placebo-(double-dummy) and active-controlled (with tramadol used as an active comparator during the in-patient treatment phase). The rationale for the inclusion of the active comparator, tramadol, in this study was twofold: (1) to confirm the sensitivity of the study with a comparison of the tramadol and placebo treatment groups based on the primary endpoint and (2) to estimate the effect of MR-107A-02 versus that of tramadol using the primary endpoint. Tramadol is an opioid analgesic approved for the management of moderate to moderately severe pain in adults, and the pain level expected for bunionectomy pain studies (mean baseline level is expected to be between NRS 6.7-7.7) aligns with this indication (Daniels et al., 2010; Gottlieb et al., 2018; Pollak et al., 2018; Riff et al., 2009; Singla et al., 2020; Viscusi et al., 2023).

The tramadol formulation included as the active comparator in this study (i.e., 50 mg IR) is well characterized based on historical use with respect to its efficacy, safety, and PK and is routinely used for postoperative pain management following surgical procedures. Tramadol is also recognized by the CDC as one of the most commonly prescribed opioids in the US, and it appears in regional and institutional prescribing guidelines. Its use in foot and ankle surgery is particularly well established. It ranks among the top three opioids prescribed for postoperative pain (Tan et al., 2018) and is one of the four most frequently prescribed opioids at discharge following foot surgery (Kvarda et al., 2019). In conclusion, tramadol (50 mg IR) was selected as the active control in this study based on its regulatory status, demonstrated efficacy in the bunionectomy model, routine clinical use, and compatibility with the study's rescue medication strategy. Its parallel use as a comparator in the second Phase 3 study (herniorrhaphy) reinforces its usefulness in supporting the MR-107A-02 clinical development program.

In this study, APAP was used as the first-step rescue medication. Tramadol's availability as a single-agent opioid enables first step rescue medication APAP. In contrast, hydrocodone—available only in fixed-dose combination with APAP—was not suitable for use as an active comparator in this study, as its use could have resulted in exceeding the maximum daily dose of APAP. Moreover, if escalation to stronger rescue analgesia was required, oxycodone as second step rescue medication was available. Oxycodone is a preferred opioid rescue medication due to its rapid onset of action and reliable analgesic efficacy in postoperative settings.

Study Participants

A total of 410 participants were randomized and received treatment in this study, and 397 (96.8%) participants overall completed the study, with 7 (1.7%) and 6 (1.5%) participants discontinuing the study during the in-patient treatment phase and out-patient treatment phase, respectively. A total of 390 (95.1%) participants overall completed treatment, and 11 (2.7%) and 9 (2.2%) participants discontinued treatment during the in-patient treatment phase and out-patient treatment phase, respectively. The three treatment groups were generally comparable with respect to participant disposition, except the incidence of treatment discontinuation during the in-patient treatment phase, which was higher in the Tramadol group (7 [5.1%] participants) than in the MR-107A-02 and Placebo groups (1 [0.7%] and 3 [2.2%] participants, respectively). The high completion rates for both the study overall and treatment indicate that sufficient data was collected for a robust analysis of the efficacy, opioid-sparing capacity, and safety of MR-107A-02 following bunionectomy.

Most participants (85.9% of all participants) were female, and over half of all participants were White (60.0%) and not Hispanic or Latino (68.3%). The mean age was 48.0 years (range 18 to 77 years), and most participants were <65 years of age (89.3%). The mean BMI was 28.7 $kg/m^2$ (range 16 to 40 $kg/m^2$), and the mean baseline NRS-R was 7.3 (range 3 to 10). The mean duration of surgery was 31.9 minutes (range 12 to 92 minutes). The baseline pain level for participants enrolled in this study aligned with what was expected for bunionectomy pain studies of NRS 6.7-7.7 (Daniels et al., 2010; Gottlieb et al., 2018; Pollak et al., 2018; Riff et al., 2009; Singla et al., 2020; Viscusi et al., 2023). The three treatment groups were comparable with respect to demographic and baseline characteristics and also with respect to common medical history and use of prior medications. The well-balanced background characteristics across the treatment groups demonstrated uniformity in the three groups included in the study and limited the effects of underlying demographic and medical characteristics on the results of the study.

The FAS included 137 participants in each of the MR-107A-02 and Tramadol groups and 136 participants in the Placebo group, which satisfied (marginally exceeded) the minimum treatment group size required to sufficiently power the study for the planned analysis of the primary and secondary estimands.

The overall mean compliance was 97.7% (range 50% to 100% [MR-107A-02 and Tramadol groups] and 25% to 100% [Placebo group]). Within each treatment phase and overall, the mean and median expected number of doses, actual number of doses, compliance, the duration of exposure, and total number of doses taken were similar across treatment groups. The high compliance rates demonstrated that most participants administered study drug as planned, which indicates potential for high patient compliance in a clinical setting.

MR-107A-02 for the Treatment of Acute Pain

The primary efficacy estimand compared the $SPID_{0-48}$ (based on NRS-R scores) for the MR-107A-02 and Placebo groups in the FAS using an ANCOVA model; rescue medication use was managed by the WLOCF approach, and missing data was managed by an MI approach. The study met the primary endpoint, as the difference in LS means $SPID_{0-48}$ (95% CI) for MR-107A-02 versus placebo (82.7 [62.0, 103.4]) was statistically significant ($p<0.001$). The $SPID_{0-48}$ endpoint captures both the magnitude and duration of the analgesic effect, offering a comprehensive measure of treatment efficacy in acute pain. The results of primary efficacy estimand analysis demonstrated that MR-107A-02 provided statistically significant pain relief compared to placebo within the critical early time window; as this is when pain is typically most intense and when patients are most vulnerable to breakthrough symptoms, the improved pain relief is expected to be clinically meaningful. This confirmed that MR-107A-02 is an effective oral analgesic for managing moderate to severe acute pain.

The participants in the MR-107A-02 group experienced faster times to first perceptible and meaningful relief of pain than those in the Placebo group ($p<0.037$ [nominal]). In addition, the time to first use of rescue medication, both overall and specifically for opioid rescue medication, was longer in the MR-107A-02 group than in the Placebo group ($p<0.001$ [nominal]). This indicates that participants receiving MR-107A-02 experienced more sustained analgesic effects and were less reliant on supplementary medication to manage their pain than those in the Placebo group.

The geometric mean $C_{max}$ of meloxicam after the first dose was 1881.222 (30.060) ng/ml with a corresponding median $T_{max}$ value of 1.090 hours. Repeat dosing of MR-107A-02 (15 mg BID) resulted in accumulation, with increasing mean meloxicam concentration values at the pre-dose timepoints of 12, 24, and 48 hours. The $T_{max}$ after the first dose of 1.090 hours was in proximity to the median time to first perceptible relief of pain in the MR-107A-02 group of 0.7 hours, and the overall exposure of meloxicam with repeat dosing correlated with the long-term pain control observed in the MR-107A-02 group.

Other efficacy endpoints, including the SPID, PID, and the proportion of participants with overall pain reductions from baseline of ≥30% and ≥50%, indicated that participants in the MR-107A-02 group experienced better pain control over time than those in the Placebo group. These results suggest a robust analgesic effect of MR-107A-02 relative to placebo.

Reducing or Eliminating Opioid Use:

The key secondary efficacy estimand was the number of doses of opioid rescue medication (oxycodone and/or morphine) taken during the entire treatment phase (in-patient and out-patient treatment phases). The analysis used a negative binomial regression model with a log link to compare the MR-107A-02 and Placebo groups in the FAS. Missing data was managed by an MI approach. The study met the key secondary endpoint, as the ratio of LS geometric means of the number of doses of opioid (oxycodone and/or morphine) medication (95% CI) for MR-107A-02 versus placebo (0.41 [0.29, 0.58]) was statistically significant ($p<0.001$). Notably, the LS geometric mean number of opioid doses (i.e., total opioid consumption) was 59% lower in the MR-107A-02 group (0.12 doses) than in the Placebo group (0.29 doses)). This substantial decrease in opioid use is expected to be clinically significant, given the risks associated with opioid medications, such as dependence, tolerance, and AEs. Similarly, participants in the MR-107A-02 group took fewer doses of opioid (oxycodone and/or morphine) than those in the Placebo group during all other intervals evaluated (i.e., the last 24 and 36 hours before discharge, the in-patient treatment phase, the out-patient treatment phase, 0-24 hours after randomization, and post-discharge phase [up to 30 days after discharge]; $p<0.001$ [nominal]). These differences suggest that MR-107A-02 effectively reduced the need for rescue opioid analgesia throughout both acute and extended recovery periods.

During the entire treatment phase, the MR-107A-02 group had 23.8% more opioid-free participants than the Placebo group, and the difference in proportions (95% CI) of opioid (oxycodone and/or morphine)-free participants in the MR-107A-02 and Placebo groups of 23.8% (12.4%, 35.3%) was statistically significant ($p<0.001$). For all other intervals (i.e., the last 24 and 36 hours before discharge, the inpatient treatment phase, the out-patient treatment phase, 0-24 hours after randomization, and post discharge phase [up to 30 days after discharge]), the MR-107A-02 group had larger proportions of opioid free participants than the Placebo group ($p\leq 0.008$ [nominal]). These results were reflective of adequate pain control from MR-107A-02 without supplemental opioids, and this reduction in opioid exposure is clinically important, especially in the context of enhanced recovery pathways and current guidelines that emphasize opioid minimization after surgery.

Importantly, regardless of this reduced opioid use, participants in the MR-107A-02 group also took less APAP rescue medication than those in the Placebo group during the entire treatment phase, in-patient treatment phase, and out-patient treatment phase. This finding highlights the strength of the analgesic effect provided by MR-107A-02 and suggests that the observed reduction in opioid use was not compensated by increased use of non-opioid rescue medication. A larger proportion of participants in the MR-107A-02 group also took no rescue medication during the entire treatment phase, in-patient treatment phase, and out-patient treatment phase than in the Placebo group. These results demonstrate that participants treated with MR-107A-02 required less rescue medication (APAP and opioid) than those in the Placebo group; this indicates that a meaningful proportion of patients receiving MR-107A-02 achieved adequate pain control without the need for any rescue medication, reflecting both efficacy and convenience from a patient care perspective.

Sensitivity analyses were conducted to assess the robustness of the primary and key secondary efficacy results. These analyses, which included alternative statistical models and assumptions, yielded results that were consistent with those of the primary analyses. This consistency supports the reliability and validity of the primary conclusions drawn from the FAS. To further evaluate the treatment effect, the primary efficacy estimand was analyzed using both the mFAS and the PP Analysis Set. Results from these additional populations closely mirrored those observed in the FAS. This reinforces confidence in the observed treatment effect and indicates that the findings are not particularly sensitive to population selection criteria or protocol adherence.

Subgroup analyses were performed for the primary and key secondary estimands to examine potential differential treatment effects across demographic variables, including age, sex, and race. These analyses did not reveal any consistent or clinically meaningful interactions between treatment efficacy and subgroups. The efficacy of MR-107A-02 appeared stable across these subgroups, suggesting that its effect is broadly applicable across the studied subpopulations. Collectively, these findings from sensitivity, supplementary, and subgroup analyses support the robustness and generalizability of the primary and key secondary efficacy results.

Comparison of Tramadol with Placebo for Assay Sensitivity

To demonstrate the assay sensitivity, several analyses, including some post-hoc, were conducted to confirm the efficacy of tramadol in the study by comparing the effects of tramadol with placebo. Across endpoints, the efficacy of tramadol was demonstrated; tramadol displayed better pain control than placebo with higher $SPID_{0-48}$ ($p<0.001$ [nominal]), higher SPID over other intervals ($p\leq0.042$ [nominal; post-hoc]), faster time to meaningful pain relief ($p=0.046$ [nominal; post-hoc]), longer time to first rescue medication, including opioid rescue ($p\leq0.019$ [nominal; post-hoc]), and larger proportions of participants with overall pain reductions from baseline of ≥30% or ≥50% ($p\leq0.022$ [nominal; post-hoc]) and with PGA of "very good" or "excellent" ($p\leq0.048$ [nominal; post-hoc]).

Comparison of MR-107A-02 with Standard of Care (Tramadol) for the Treatment of Acute Pain:

An analysis was also performed to estimate the difference in efficacy between MR-107A-02 and tramadol in treating acute pain following bunionectomy surgery. The results demonstrated that MR-107A-02 provided significantly greater pain relief than tramadol, as measured by the primary exploratory endpoint, $SPID_{0-48}$, ($p=0.013$ [nominal; post hoc]), indicating an advantage over tramadol.

Although no formal comparisons were made between MR-107A-02 and tramadol for other endpoints, participants in the MR-107A-02 group reported similar or better pain control as those in the Tramadol group with numerically larger LS mean SPIDs at each time interval evaluated, consistent numerically lower PIDs from 2 through 12 hours and from 20 through 48 hours following study drug administration, suggesting a more robust and sustained analgesic effect.

The proportions of participants experiencing overall pain reductions from baseline of ≥30% or ≥50% were similar in the MR-107A-02 and the Tramadol groups, indicating comparable pain relief from both treatments. In addition, participants in the MR-107A-02 group achieved perceptible and meaningful pain relief faster than those in the Tramadol group, further supporting the potential of MR-107A-02 to deliver rapid onset of pain relief. The time to first rescue medication, including opioid rescue, was similar or slightly longer in the MR-107A-02 group, consistent with the observed analgesic efficacy.

Regarding PGA, a numerically higher proportion of participants in the MR-107A-02 group reported "very good" or "excellent" pain control than in the Tramadol group, which suggests that participants experienced more effective results with MR-107A-02 than with tramadol.

For MPADSS at 24 hours post-dose, a slightly higher mean (SD) score was observed in the MR-107A-02 group (9.3 [0.91]) than in the Tramadol group (8.9 [1.26]), which suggests that on average, participants in the MR-107A-02 group reached the minimum discharge criteria more reliably and rapidly than those in the Tramadol group.

For OBAS at 24 and 48 hours after the first dose and at Follow-up, participants in the MR-107A-02 group had lower mean OBAS than those in the Tramadol group. This suggests a better overall benefit with MR-107A-02 than with tramadol, including pain relief and fewer side effects.

For NRS-A, participants in the MR-107A-02 group reported lower pain scores during activity at 24- and 48-hours post-dose and at Follow-up, suggesting better support for early mobilization than tramadol.

A numerically larger proportion of participants in the MR-107A-02 group than in the Tramadol group took no rescue medication during the in-patient treatment phase, out-patient treatment phase, and entire treatment phase. This implies that MR-107A-02 may provide better pain control on its own than tramadol, consistent with the outcome for $SPID_{0-48}$. This is further supported by the finding that participants in the MR-107A-02 group used numerically less APAP as rescue medication than those in the Tramadol group across all treatment phases and waited longer to take their first rescue medication than those in the Tramadol group.

Improved Patient-Centered Outcomes:

MR-107A-02 consistently outperformed placebo and tramadol in key patient-reported outcome measures, which reflect the real-world impact of analgesic interventions on recovery and comfort. Participants in the MR-107A-02 group reported consistently lower NRS-A pain and OBAS scores than those in the Tramadol and Placebo groups across timepoints, which reflected improved analgesic benefit with fewer side effects. At 24 hours post-dose, the MR-107A-02 group had the highest MPADSS of the three treatment groups, suggesting that those in the MR-107A-02 group reached the minimum discharge criteria more reliably and more rapidly than those in the Tramadol and Placebo groups, despite their lower use of both APAP and opioid rescue medications; this shows a direct patient benefit related to reduced opioid analgesic use, such as earlier functional recovery for allowing discharge.

These findings collectively support the conclusion that MR-107A-02 not only manages pain effectively but also enhances the overall recovery experience by improving comfort and reducing the need for supportive medications.

Favorable Safety and Tolerability Profile:

MR-107A-02 was well tolerated in this study. No deaths or TEAEs of special interest, such as GI events (e.g., bleeding), and those related to cardiovascular events (e.g., myocardial infarction/unstable angina, stroke/TIA, heart failure, cardiac arrhythmia [atrial and ventricular]), were reported at any time during the study, which demonstrates the safety of MR-107A-02 in terms of the risks associated with the NSAID class. No serious or severe TEAEs were reported in the MR-107A-02 group at any time during the study.

During the in-patient treatment phase, a total of 165 (40.2%) participants overall reported 374 TEAEs. The incidence of TEAEs was higher in the Tramadol group (55.5%) than in the MR-107A-02 and Placebo groups (31.4% and 33.8%, respectively). One hundred twenty (29.3%) participants reported 227 TEAEs considered related to the study drug. The incidence of related TEAEs was notably higher in the Tramadol group (45.3%) than in the MR-107A-02 and Placebo groups (20.4% and 22.1%, respectively). One hundred eight (26.3%) participants reported 234 opioid-related TEAEs during the in-patient treatment phase. The incidence of opioid-related TEAEs was notably higher in the Tramadol group (46.0%) than in the MR-107A-02 and Placebo groups (16.1% and 16.9%, respectively), and the MR-107A-02 group had the lowest incidence of opioid-related TEAEs of all three treatment groups. Most TEAEs were either mild or moderate in severity, with only 2 (0.5%) participants overall reporting 2 severe TEAEs (1 [0.7%] participant each in the Tramadol and Placebo groups). Notably, no participant in the MR-107A-02 group reported a severe TEAE.

One (0.2%) participant overall, who was in the Tramadol group, reported one TEAE leading to study discontinuation (PT of vomiting); however, that participant did eventually complete the study after discontinuing treatment. No serious TEAEs were reported during the in-patient treatment phase. A total of 6 (1.5%) participants (1 [0.7%] participant in the MR-107A-02 group, 4 [2.9%] participants in the Tramadol group, and 1 [0.7%] participant in the Placebo group) reported at least one TEAE leading to treatment discontinuation, all of which were considered resolved or resolving at last report. Reported PTs included nausea (2 [1.5%] participants in the Tramadol group), drug hypersensitivity (1 [0.7%] participant each in the Tramadol and Placebo groups), urticaria (1 [0.7%] participant each in the MR-107A-02 and Tramadol groups), and dizziness (1 [0.7%] participant in the Tramadol group). Participants in the MR-107A-02 group reported fewer TEAEs related to study drug during the in-patient treatment phase (20.4%) than the Tramadol group (45.3%) and even slightly fewer TEAEs compared to the Placebo group (22.1%).

There was a lower incidence of ORAEs during inpatient treatment period in the MR-107A-02 group (16.1%) than in the Tramadol group (46.0%)—an absolute reduction of 29.9 percentage points and a relative reduction of approximately 65% of experiencing an ORAE. The incidence of ORAEs in the MR-107A-02 group was even slightly lower than that in the Placebo group (16.9%).

During the out-patient treatment phase, a total of 167 (41.9%) participants overall reported 314 TEAEs with similar proportions of participants reporting TEAEs among the treatment groups. Eighty-three (20.8%) participants reported 125 TEAEs related to study drug. Seventy-six (19.0%) participants reported 103 opioid-related TEAEs. Most TEAEs were either mild or moderate in severity, with 2 (0.5%) participants overall reporting 3 severe TEAEs (2 [1.6%] participants in the Tramadol group). Three (0.8%) participants in the Tramadol Placebo group reported 4 serious TEAEs. No TEAEs leading to study discontinuation were reported during the out-patient treatment phase. Overall, 5 (1.3%) participants reported at least one TEAE leading to treatment discontinuation, all of which were considered resolved or recovered at the last report. Treatment-emergent AEs leading to treatment discontinuation in the MR-107A-02 group consisted of rash and chest pain in 1 (0.7%) participant each.

No renal toxicity or hepatotoxicity concerns were identified, and no clinically relevant trends over time or treatment group differences in vital signs, laboratory parameters, or ECGs were observed.

Benefit-Risk Profile of MR-107A-02 in the Context of the Opioid Crisis:

In comparison to tramadol, MR-107A-02 demonstrated similar or superior pain relief as shown in post-hoc analysis, reinforcing the effectiveness of MR-107A-02 as a non-opioid alternative for moderate to severe acute pain. The clinical significance of this finding is underscored by the ability of MR-107A-02 to achieve efficacy with a reduced burden of side effects typically encountered with opioids. While Tramadol demonstrated analgesic efficacy, it was associated with a substantially higher rate of ORAEs and greater overall treatment burden (e.g., higher rates of treatment discontinuation during the in-patient treatment phase). Specifically: 46.0% of participants in the Tramadol group experienced ORAEs during the in-patient treatment phase, compared with 16.1% in the MR-107A-02 group—a 29.9% absolute reduction and a relative reduction of approximately 65% of experiencing an ORAE. Tramadol was also linked to a higher rate of study drug-related TEAEs during the in-patient treatment phase (45.3%) than MR-107A-02 (20.4%). On the contrary, MR-107A-02 was associated with less sedation, nausea, and dizziness than placebo and tramadol-factors that are common barriers to recovery and discharge in post-surgical care. These findings underscore therapeutic advantage of MR-107A-02 in providing effective pain relief while minimizing the risks associated with opioid analgesics.

Example III B. MR-107A-02 Following Herniorrhaphy Surgery (Study 3002)

A post-operative study following herniorrhaphy surgery was also conducted to assess MR-107A-02 in treating acute soft tissue pain (as opposed to acute pain from bone fracture as with bunionectomy). This study included 579 human subjects (n=579), both male and female, ages≥18 years. Subject disposition during the course of this study is depicted in FIG. 38 and FIG. 47.

Demographics and baseline characteristics of the subjects are shown in Table 39.

TABLE 39

Subject Demographics and Baseline Characteristics: Herniorrhaphy Study

| Characteristics | MELO 15 mg BID | Tramadol 50 mg q6h | Placebo | Total |
|---|---|---|---|---|
| N | 232 | 116 | 231 | 579 |
| Age, years | | | | |
| Mean (SD), | 48.8 (12.45) | 49.8 (11.40) | 49.1 (12.39) | 49.1 (12.21) |
| Range (Min, Max) | 22, 76 | 18, 74 | 18, 80 | 18, 80 |
| Age group, n (%) | | | | |
| <65 years | 213 (92.6) | 109 (94.8) | 212 (93.4) | 534 (93.4) |
| ≥65 years | 17 (7.4) | 6 (5.2) | 15 (6.6) | 38 (6.6) |
| Sex, n (%) | | | | |
| Male | 222 (96.5) | 113 (98.3) | 216 (95.2) | 551 (96.3) |
| Female | 8 (3.5) | 2 (1.7) | 11 (4.8) | 21 (3.7) |

TABLE 39-continued

| | Subject Demographics and Baseline Characteristics: Herniorrhaphy Study | | | |
|---|---|---|---|---|
| Characteristics | MELO 15 mg BID | Tramadol 50 mg q6h | Placebo | Total |
| Baseline NRS | | | | |
| NRS-R Mean (SD) | 7.0 (1.70) | 6.9 (1.74) | 6.9 (1.81) | 6.9 (1.75) |
| NRS-A Mean (SD) | 7.8 (1.66) | 7.8 (1.57) | 7.7 (1.68) | 7.8 (1.65) |

Assumption ≈20% ≥65 years
Assumption ≈90% male
Assumption baseline NRS in moderate to serve range.
Assumption difference between NRS-R Patients experiencing the requisite level of pain (score≥4 on an 11-point numeric rating scale-activity [NRS-A] from 0=no pain to 10=worst possible pain) after herniorrhaphy were randomized to receive MR-107A-02 15 mg meloxicam (BID), placebo or tramadol 50 mg (QID) in 2:2:1 ratio. The primary endpoint was the summed pain intensity difference over 0-48 hours ($SPID_{0-48}$) based on NRS-A for MR-107A-02 versus placebo. The times to perceptible and meaningful pain relief were measured using the double-stopwatch technique after the first dose to quantify the onset of pain relief.

In-patient Treatment Phase: Patients were dosed every six (6) hours over 48 hours for a total of eight (8) doses. The in-patient phase included MR-107A-02, tramadol and placebo. (To maintain the blind, subjects in the MR-107A-02 group received meloxicam active and meloxicam placebo alternately to allow for a q6h dosing of all subjects during the subject in-patient treatment phase.)

Out-patient Treatment Phase: Patients were dosed for five (5) days. Dosing was twice daily for a total of 10 doses. The out-patient phase included just MR-107A-02 and placebo. The tramadol subjects from the in-patient phase were given placebo for the out-patient phase.

Certain efficacy results are depicted in FIG. 20. As shown in FIG. 20, the group given MR-107A-02 BID showed the lowest NRS-A scores (Numeric Rating Scale scores with activity) among all treatment groups over the whole in-patient treatment phase and over the population full analysis set. FIG. 21 shows the NRS-A scores truncated to 12 hours. With exception of the first hour, MR-107A-02 BID group showed the lowest NRS-A scores among all treatment groups at each timepoint during the whole in-patient treatment.

Details of the assessment of the efficacy of MR-107A-02 versus placebo are given in Table 40.

TABLE 40

| | MR-107A-02 Tablets vs. Placebo: SPID (NRS-A) Over 0-48 Hours, ANCOVA with MI (Multiple Imputation) Primary Endpoint: SPID (NRS-A) Over 0-48 Hours, ANCOVA with MI Population: Full Analysis Set | |
|---|---|---|
| Variable Statistic | Meloxicam 15 mg BID (N = 230) | Placebo (N = 227) |
| $SPID_{0-48}$ | | |
| n | 222 | 219 |
| Mean (SD) | 161.8 (87.45) | 112.5 (86.34) |
| Min, Max | −55.9, 392.6 | −102.5, 363.4 |
| LS Mean (SE) | 163.1 (8.99) | 113.0 (9.16) |

TABLE 40-continued

| | MR-107A-02 Tablets vs. Placebo: SPID (NRS-A) Over 0-48 Hours, ANCOVA with MI (Multiple Imputation) Primary Endpoint: SPID (NRS-A) Over 0-48 Hours, ANCOVA with MI Population: Full Analysis Set | |
|---|---|---|
| Variable Statistic | Meloxicam 15 mg BID (N = 230) | Placebo (N = 227) |
| CI [1] | (145.5, 180.7) | (95.0, 131.0) |
| Difference in LS Mean (SE) versus Placebo | 50.1 (7.48) | |
| CI for Difference in LS Means [1] | (35.4, 64.8) | |
| p-value for Difference [2] | <0.001 | |

[1] 95% CI for MR-107A-02 and Placebo.
[2] 2-sided p-value.

Table 41 shows analysis of tramadol efficacy versus placebo in Study 3002, demonstrating assay sensitivity.

TABLE 41

| | Tramadol vs. Placebo: SPID (NRS-A) Over 0-48 Hours, ANCOVA with MI (Multiple Imputation) SPID (NRS-A) Over 0-48 Hours, ANCOVA (Tramadol versus Placebo, Excluding Meloxicam) with MI Population: Full Analysis Set | |
|---|---|---|
| Variable Statistic | Tramadol 50 mg q6h (N = 115) | Placebo (N = 227) |
| $SPID_{0-48}$ | | |
| n | 110 | 219 |
| Mean (SD) | 138.9 (82.34) | 112.5 (86.34) |
| Min, Max | −46.9, 352.5 | −102.5, 363.4 |
| LS Mean (SE) | 160.0 (12.20) | 130.5 (11.53) |
| CI [1] | (140.0, 180.1) | (107.9, 153.1) |
| Difference in LS Mean (SE) versus Placebo | 29.5 (9.00) | |
| CI for Difference in LS Means [1] | (14.7, 44.3) | |
| p-value for Difference [2] | <0.001 | |

[1] 95% CI for Placebo. 90% CI for Tramadol.
[2] 1-sided p-value for Tramadol.

Table 42 shows analysis of MR-107A-02 efficacy versus tramadol efficacy. MR-107A-02 $SPID_{0-48}$h (162.2) was significantly higher than tramadol $SPID_{0-48}$h (141.3).

TABLE 42

| | MR-107A-02 Tablets ("Meloxicam 15 mg") vs. Tramadol: SPID (NRS-A) Over 0-48 Hours, ANCOVA with MI (Multiple Imputation) SPID (NRS-A) Over 0-48 Hours, ANCOVA with MI (Meloxicam versus Tramadol, excluding Placebo) Population: Full Analysis Set | |
|---|---|---|
| Variable Statistic | Meloxicam 15 mg BID (N = 230) | Tramadol 50 mg q6h (N = 115) |
| $SPID_{0-48}$ | | |
| n | 222 | 110 |
| Mean (SD) | 161.8 (87.45) | 138.9 (82.34) |
| Min, Max | −55.9, 392.6 | −46.9, 352.5 |
| LS Mean (SE) | 162.2 (11.05) | 141.3 (12.16) |
| CI [1] | (140.5, 183.8) | (121.3, 161.2) |
| Difference in LS Means (SE) versus Tramadol | 20.9 (9.34) | |
| 90% CI for Difference in LS Means | (5.6, 36.3) | |
| p-value for Difference [2] | 0.025 | |

[1] 95% CI for Meloxicam. 90% CI for Tramadol.
[2] 2-sided p-value.

The mean numbers of rescue opioid (oxycodone and/or morphine) doses over the entire treatment period for herniorrhaphy study are shown in Table 43.

TABLE 43

Number of Doses of Opioid (Oxycodone and/or Morphine) Rescue Medication (Entire Treatment Phase)
Key Secondary: Number of Doses of Opioid (Oxycodone and/or Morphine) Rescue Medication (entire treatment phase) with MI
Population: Full Analysis Set

| Variable Statistic | Meloxicam 15 mg BID (N = 230) | Placebo (N = 227) |
|---|---|---|
| Number of doses of Opioid (Oxycodone and/or Morphine) | | |
| N | 230 | 227 |
| Mean (SD) | 0.89 (2.17) | 1.25 (2.14) |
| Median | 0 | 0 |
| Min, Max | 0, 17 | 0, 12 |
| Difference in Means | −0.36 | |
| LS Geometric Mean | 0.003 | 0.004 |
| 95% CI | (0.000, NC) | (0.000, NC) |
| Ratio of LS Geometric Means versus Placebo | 0.654 | |
| 95% CI for Ratio of LS Geometric Means | (0.437, 0.980) | |
| p-value for Ratio | 0.039 | |

The group given MR-107A-02 had a 35% lower (based on ratio of LS means) opioid use versus the placebo group (0.89 doses vs. 1.25 dose) over the entire treatment period (including both in-patient and out-patient treatment phase). Table 44 details the number of opioid-free patients over the entire treatment period. The MR-107A-02 group had 14% more opioid-free patients versus the placebo group (75% vs. 59%).

TABLE 44

Number and Proportion of Opioid (Oxycodone and/or Morphine) Free Subjects (Entire Treatment Phase)
Secondary: Number and Proportion of Opioid (Oxycodone and/or Morphine) Free Subjects (entire treatment phase)
Population: Full Analysis Set

| | Meloxicam 15 mg BID (N = 230) | Placebo (N = 227) |
|---|---|---|
| Opioid (Oxycodone and/or Morphin) Free | 167 (72.6) | 133 (58.6) |
| Not Opioid (Oxycodone and/or Morphin) Free | 63 (27.4) | 94 (41.4) |
| Difference in proportions (95% CI) versus Placebo | 14.0% (5.4%, 22.6%) | |
| p-value | 0.002 | |

Table 45 below details the analysis of time to perceptible pain relief in Study 3002. The MR-107A-02 group had a shorter time to perceptible pain relief versus the placebo group. The MR-107A-02 group had a comparable time to perceptible pain relief versus the tramadol group.

TABLE 45

Time to Perceptible Pain Relief-Herniorrhapy Study Relief
Time to Perceptible Pain Relief
Population: Full Analysis Set

| | Meloxicam 15 mg BID (N = 230) | Tramadol 50 mg q6h (N = 115) | Placebo (N = 227) |
|---|---|---|---|
| Subjects with event, n (%) | 158 (68.7) | 75 (65.2) | 126 (55.5) |
| Subjects censored, n (%) | 72 (31.3) | 40 (34.8) | 101 (44.5) |
| Time to event (hours) | | | |
| Q1 | 0.4 | 0.5 | 0.4 |
| Median (CI) [1] | 0.9 (0.8, 1.0) | 0.9 (0.7, 1.5) | 1.1 (0.9, 2.1) |
| Q3 | 2.1 | 2.9 | NA |
| p-value (versus Placebo) [2] | 0.014 | 0.035 | |

Table 46 details the analysis of time to meaningful pain relief across the FAS of patients. The MR-107A-02 group had a shorter time to meaningful pain relief than the placebo group. The MR-107A-02 group also had a shorter time to meaningful pain relief versus the tramadol group.

TABLE 46

Time to Meaningful Pain Relief-Herniorrhaphy Study
Relief-Herniorrhaphy Study
Time to Meaningful Pain Relief
Population: Full Analysis Set

| | Meloxicam 15 mg BID (N = 230) | Tramadol 50 mg q6h (N = 115) | Placebo (N = 227) |
|---|---|---|---|
| Subjects with event, n (%) | 99 (43.0) | 45 (39.1) | 70 (30.8) |
| Subjects censored, n (%) | 131 (57.0) | 70 (60.9) | 157 (69.2) |
| Time to event (hours) | | | |
| Q1 | 1.5 | 1.6 | 1.8 |
| Median (CI) [1] | 3.7 (2.9, 5.3) | 5.0 (3.0, NA) | NA (4.1, NA) |
| Q3 | NA | NA | NA |
| p-value (versus Placebo) [2] | 0.025 | 0.058 | |

[1] 95% CI for MR-107A-02 ("Meloxicam") and placebo. 90% CI for tramadol.
[2] 2-sided p-value for meloxicam. 1-sided p-value for tramadol.

Table 47 shows an analysis of the time to first opioid (oxycodone and/or morphine) rescue medication use. The group given MR-107A-02 had a longer time to first opioid rescue medication use versus the placebo group. Also, less patients took opioid rescue medication in the MR-107A-02 group (28%) than in the tramadol group (31%) and the placebo group (41%).

TABLE 47

Time to First Opioid (Oxycodone and/or Morphine) Rescue Medication Use-Herniorrhaphy Study
Time to First Opioid (Oxycodone and/or Morphine) Rescue Medication Use Population: Full Analysis Set

| | Meloxicam 15 mg BID (N = 230) | Tramadol 50 mg q6h (N = 115) | Placebo (N = 227) |
|---|---|---|---|
| Subjects with event, n (%) | 65 (28.3) | 36 (31.3) | 93 (41.0) |
| Subjects censored, n (%) | 165 (71.7) | 79 (68.7) | 134 (59.0) |

TABLE 47-continued

Time to First Opioid (Oxycodone and/or Morphine) Rescue Medication Use-Herniorrhaphy Study
Time to First Opioid (Oxycodone and/or Morphine) Rescue Medication Use Population: Full Analysis Set

| | Meloxicam 15 mg BID (N = 230) | Tramadol 50 mg q6h (N = 115) | Placebo (N = 227) |
|---|---|---|---|
| Time to event (hours) | | | |
| Q1 | 58.9 | 80.2 | 9.0 |
| Median (CI) [1] | NA (NA, NA) | NA (NA, NA) | NA (NA, NA) |
| Q3 | NA | NA | NA |
| p-value (versus Placebo) [2] | 0.006 | 0.015 | |

[1] 95% CI for MR-107A-02 ("Meloxicam") and placebo. 90% CI for tramadol.
[2] 2-sided p-value for meloxicam. 1-sided p-value for tramadol.

Table 48 shows an analysis of the time to first rescue medication use. The group that took MR-107A-02 had a longer time to first rescue medication use versus the group that took placebo. Less patients took any rescue medication in the MR-107A-02 group (56%) than in the tramadol group (66%) and the placebo group (76.2%).

TABLE 48

Time to First Rescue Medication Use-Herniorrhaphy Study
Time to First Rescue Medication Use
Population: Full Analysis Set

| | Meloxicam 15 mg BID (N = 230) | Tramadol 50 mg q6h (N = 115) | Placebo (N = 227) |
|---|---|---|---|
| Subjects with event, n (%) | 128 (55.7) | 76 (66.1) | 173 (76.2) |
| Subjects censored, n (%) | 102 (44.3) | 39 (33.9) | 54 (23.8) |
| Time to event (hours) | | | |
| Q1 | 1.7 | 1.6 | 1.4 |
| Median (CI) [1] | 49.5 (7.1, NA) | 5.5 (3.4, 50.1) | 3.6 (2.4, 5.2) |
| Q3 | NA | NA | 145.2 |
| p-value (versus Placebo) [2] | <0.001 | 0.004 | |

[1] 95% CI for MR-107A-02 ("Meloxicam") and placebo. 90% CI for tramadol.
[2] 2-sided p-value for meloxicam. 1-sided p-value for tramadol.

With regard to Study 3002, MR-107A-02 BID demonstrated efficacy in treating acute pain following herniorrhaphy. The assay sensitivity was shown as tramadol efficacy versus placebo was shown (p-value difference<0.001). MR-107A-02 $SPID_{0-48}$ h SES (0.36) [powered for SES=0.3] was numerically higher than tramadol $SPID_{0-48}$ h SES (0.23). The MR-107A-02 group had 35% lower (based on ratio of LS means) opioid use versus placebo group (0.89 doses vs. 1.25 dose) over the entire treatment period (in-patient plus out-patient treatment phases). The MR-107A-02 group had 14% more opioid-free patients versus the placebo group (73% versus 59%). Less patients took opioid rescue medication in the MR-107A-02 group than in the tramadol group (28% vs. 41%). The MR-107A-02 group had the longest median time to first rescue use and the longest Q1 time to first opioid rescue use among all groups. The MR-107A-02 group had a shorter time to perceptible pain relief versus placebo (p-value 0.014). The MR-107A-02 group had a shorter time to meaningful pain relief versus placebo (p-value 0.024). The MR-107A-02 group had a comparable time to perceptible and shorter time to meaningful pain relief versus tramadol.

Note, SES equals Standardized Effect Size, the Difference in LS Means/SD from ANCOVA.

Of 579 randomized participants in Study 3002 (232 MR-107A-02, 231 placebo, 116 tramadol; 96.3% males; 84% whites; mean [SD] age, 49.1 [12.21] years; weight range, 44-152 kg), 551 participants completed the study. The baseline NRS-A scores (mean [SD]) were similar across all three groups (7.8 [1.66] MR-107A-02, 7.7 (1.68) placebo, 7.8 [1.57] tramadol).

The primary endpoint $SPID_{0-48}$ (NRS-A), for MR-107A-02 versus placebo, was met. The least squares mean (SE) [95% CI] of $SPID_{0-48}$ (NRS-A) for MR-107A-02 was 163.1 (8.99) [145.5, 180.7] vs. 113.0 (9.16) [95.0, 131.0] for placebo, with treatment difference of 50.1 (7.48) [35.4, 64.8], p<0.001. Assay sensitivity was demonstrated with tramadol versus placebo, showing a treatment difference of 29.5 (9.0) [14.7, 44.3]; p<0.001.

In post-hoc analysis, MR-107A-02 showed a higher $SPID_{0-48}$ compared to tramadol: 162.2 (11.05) [140.5, 183.8] vs. 141.3 (12.16) [121.3, 161.2], with a treatment difference of 20.9 (9.34) [5.6, 36.3], p=0.025.

MR-107A-02 demonstrated a shorter time to perceptible pain relief compared to placebo (median [CI], hours) (0.9 [0.8, 1.0] vs 1.1 [0.9, 2.1]; p=0.014) and was comparable to tramadol (0.9 [0.7, 1.5]).

Time to meaningful pain relief was also shorter for MR-107A-02 compared to placebo (median [CI], hours) (3.7 [2.9, 5.3] vs NA [4.1, NA]; p=0.025) and tramadol (5.0 [3.0, NA]). Both the endpoints demonstrated a significantly faster onset of action for MR-107A-02 compared to placebo.

Overall, MR-107A-02 was well-tolerated with the fewest treatment emergent adverse events (TEAEs) among all groups during the in-patient phase. The number of severe or serious TEAEs was lower in MR-107A-02 and comparable to placebo. During the in-patient treatment period, the most common adverse events (AEs) in the MR-107A-02 group were constipation (17.0%, MR-107A-02; 14.1%, placebo; 20.9%, tramadol), dizziness (5.7%, 5.3%, 11.3%), headache (5.2%, 7.9%, 4.3%), and hyperhidrosis (6.5%, 6.6%, 7.0%).

MR-107A-02 (15 mg meloxicam BID) was effective in reducing the acute, moderate-to-severe pain following herniorrhaphy, as demonstrated by $SPID_{0-48}$ values compared with placebo, and with a superior efficacy profile to its opioid comparator. The twice daily dose of MR-107A-02 produced a rapid onset of analgesia, as evidenced by the shorter time taken to achieve meaningful pain relief compared to placebo, with a well-tolerated safety profile.

In Study 3002, the MR-107A-02 group had 14% more opioid-free patients compared to placebo (167 [72.6%] vs. 133 [58.6%]) with a significant difference in proportions (95% [CI]) (14.04% [5.4, 22.6], p=0.002). The MR-107A-02 group showed a 35% lower opioid use vs. placebo (mean [SD]) (0.89 [2.17] vs. 1.25 [2.14] doses) with the ratio of LS geometric mean (95% [CI]) (0.654 [0.437, 0.980], p=0.039). The MR-107A-02 also had fewer patients requiring opioid rescue (65 [28.3%] MR-107A-02, 93 [41.0%] placebo, 36 [31.3%] tramadol) or any rescue medication (128 [55.7%] MR-107A-02, 173 [76.2%] placebo, 76 [66.1%] tramadol) and the longest median time (hours) to first rescue medication compared to placebo and tramadol groups.

To recapitulate, the disclosed independent Phase 3, multicenter, randomized, double-blind, placebo- and active-controlled (double-dummy), parallel-group study conducted to evaluate the efficacy and safety of MR-107A-02 for the treatment of acute postoperative pain was carried out in patients undergoing herniorrhaphy. The investigational drug, MR-107A-02 (15 mg BID), was compared with an active control (tramadol 50 mg every 6 hours) and a placebo arm using a double-dummy design.

Five hundred and seventy-nine (579) subjects were randomized (232:116:231; MELO:TRAM:PBO), and 572 subjects were treated in 3 study arms, with 551 completing the study.

The median time to 2-point reduction (in minutes) in the NRS-A (95% CI) was 180.5 (92.0, 242.0) and 476.0 (274.0, 577.0) for Meloxicam and placebo, respectively. The Meloxicam arm was statistically separated from placebo at $p<0.001$ (post-hoc). For Tramadol, the median time to 2-point reduction in the NRS-A (90% CI) was 181.0 (91.0, 470.0), with the median time comparable to that of the Meloxicam group. See FIG. 23.

The median time to 2-point reduction (in minutes) in the NRS-A (95% CI) was 120.5 (91.0, 177.0) and 182.0 (173.0, 241.0) for Meloxicam and placebo, respectively. The Meloxicam arm was statistically separated from placebo at $p=0.001$ (post-hoc). For Tramadol, the median time to 2-point reduction in the NRS-A (90% CI) was 121.0 (91.0, 172.0), which was comparable to the Meloxicam group. See FIG. 24. A comparison is shown in Table 49.

TABLE 49

Comparison of Censoring Methods for time to 2-point NRS-A Reduction

| WLOCF rescue censoring | Meloxicam | Tramadol | Placebo |
|---|---|---|---|
| Subjects with/without 2-point reduction | 225/5 | 111/4 | 212/15 |
| Median time (minutes) | 180.5 | 181 | 476 |
| p-value (versus placebo) | <0.001[a] | <0.001[b] | |
| **No rescue censoring** | **Meloxicam** | **Tramadol** | **Placebo** |
| Subjects with/without 2-point reduction | 225/5 | 112/3 | 216/11 |
| Median time (minutes) | 120.5 | 121 | 182 |
| p-value (versus placebo) | 0.001[a] | 0.006[b] | |

[a]2-sided p-value;
[b]1-sided p-value; all tests are post-hoc and exploratory

To show the opioid sparing effect of MR-107A-02 with this study and descriptively compare the efficacy of MR-107A-02 against an opioid comparator, an active control group [tramadol 50 mg immediate release (IR) once every 6 hours (q6h)] for the in-patient treatment phase was included. In accordance with clinical standards to limit duration of opioid exposure to the shortest possible duration, the fixed opioid dose regimen was limited to the in-patient treatment phase. Following discharge, the participants in the opioid group received placebo.

The clinical trial will be discussed in more detail below.

The primary objective of the study was to confirm the efficacy of MR-107A-02 as acute analgesic in participants following unilateral open inguinal herniorrhaphy surgery.

The secondary objectives of the study with respect to efficacy, safety and pharmacokinetics were essentially the same as for the study in Example IIIA (Study 3001).

The study endpoints for this study also were essentially the same as for Study 3001.

3B.1 Overall Study Design and Plan

This was a multi-center, randomized, double-blind, placebo (double-dummy)- and active-controlled, parallel-group study, randomizing and dosing 579 male and female participants (approximately 570 planned) following an open inguinal mesh herniorrhaphy. Participants received doses of study drug on Day 1 until Day 3 during the in-patient treatment phase (8 doses of study drug) as well as on the 5 consecutive days following discharge during the out-patient treatment phase (10 doses of study drug).

During the in-patient treatment phase (Day 1 to Day 3), all participants received either MR-107A-02, tramadol, or placebo.

During the out-patient treatment phase (Day 3 to Day 7/8), participants received either MR-107A-02 or placebo. Participants who received tramadol during the in-patient treatment phase received placebo during the out-patient treatment phase.

Participants had the inguinal herniorrhaphy performed on Day 1 (Visit 2) under general anesthesia and administration of IV fentanyl (up to 4 μg/kg) was to be permitted for intra-operative pain control. Just prior to the end of surgery, all participants received an additional 50 μg IV fentanyl to decrease inherent variability in pain control on post-operative pain perception. A field block using 15-30 mL of 1% lidocaine without epinephrine was performed by the surgeon prior to wound closure. Permitted peri-operative medications included propofol (IV), anesthetic gas (such as sevoflurane) as well as myorelaxants (such as rocuronium) as required based on clinical situation. Epidural, spinal, or other regional anesthesia techniques were not permitted.

Peri-operative administration of other opioids or any other analgesics (including ketamine), local anesthetics, anxiolytics, or anti-inflammatory agents (except as specified by the protocol) were prohibited, unless needed to treat an AE that occurred after signing the ICF, for pre-treatment prior to a needle placement, or to decrease venous irritation (e.g., caused by propofol, in which case no more than a single administration of lidocaine 1%, 20 mg IV was administered).

Blood samples (1×4 mL) for PK analysis were to be collected for a subset of 50% of the participants per treatment group at pre-dose (post-randomization) and 15 minutes and 1, 2, 4, 12, 24, 30-34 (one sample collected freely during the interval), and 48 hours post-dose, relative to the first dose at Day 1. The samples at 12, 24, and 48 hours were collected prior to administration of the scheduled dose.

The End of Study (EOS) was considered to be the date of last participant's last visit (telephonic) or the date of ET of the study, whichever was the later.

Visits and procedures were conducted as presented in the study design in FIG. 48.

This study was placebo-(double-dummy) and active-controlled (with tramadol, used as an active comparator during the in-patient treatment phase). The rationale for the inclusion of the active comparator, tramadol, in this study was twofold: (1) to confirm the sensitivity of the study with a comparison of the tramadol and placebo treatment groups based on the primary endpoint and (2) to estimate the effect of MR-107A-02 versus that of tramadol using the primary endpoint. Tramadol is an opioid analgesic approved for the management of moderate to moderately severe pain in adults, and the pain level expected for herniorrhaphy surgeries (NRS 4-10 following surgery in approximately 30% of patients) aligns with this indication (HerniaSurge, 2018; Mentes and Bagci, 2009; Bugada et al., 2015). For further information on specifics of the study design please refer to the discussion of the design for Study 3001 described herein.

Approximately 800,000 inguinal hernia repairs are performed annually in the US. Open inguinal hernia repair is thought to cause worse post-operative pain than minimally invasive surgery, and thus patients are often prescribed more opioids at discharge than actually taken (Knight et al., 2019). Investigations about the opioid use in hernia patients revealed that a high percentage of herniorrhaphy patients receive an opioid prescription at discharge. A study of 79 patients undergoing open inguinal hernia repair showed that the median number of opioid doses prescribed was 30 (with one dose equivalent to 5 mg oxycodone), while the number of opioid doses expected to fully supply the needs of 80% of patients undergoing open inguinal hernia repair was 15 doses (Hill et al., 2017), suggesting that a considerable proportion of patients typically require opioid-treatment following herniorrhaphy. A retrospective study revealed that 1.5% of the opioid-naïve patients developed new persistent opioid use following inguinal hernia repair (Howard et al., 2022).

Therefore, herniorrhaphy can be regarded as settings in which opioids are routinely required for adequate pain control, and that this model can be considered as adequate to demonstrate opioid reducing capacities of a pain medication such as MR-107A-02. The concept of multimodal analgesia is addressed with the stepwise approach of rescue medication during the in-patient phase ($1^{st}$ step APAP, $2^{nd}$ step oxycodone and for the first 4 hours following intake of first dose of study medication $3^{rd}$ step rescue morphine) as well as during the first 5 days after discharge ($1^{st}$ step APAP, $2^{nd}$ step oxycodone).

Selection of Study Population

Inclusion Criteria

Similar criteria were used as for Study 3001. Criteria for inclusion in this Study 3002 included: requirement for unilateral open inguinal herniorrhaphy with mesh under general anesthesia.

1. Pain intensity (using NRS-R)≥4 at any given timepoint during the 5 hours following end of surgery in the eligibility assessment as well as in the baseline assessment (NRS-R and NRS-A) immediately pre-dosing.
2. Rating of moderate or severe pain on a 4-point categorical pain rating scale (i.e., none, mild, moderate, severe) during the 5 hours following end of surgery.

Exclusion Criteria

Participant candidates were not enrolled in the study if they met essentially the same criteria as mentioned above in Example 3A, in addition to any of the following criteria:

1. Had any prior inguinal hernia repair in the past 24 months. Re-do repairs of inguinal hernia were allowed if the prior surgery was >2 years prior to enrollment.
2. Had a planned concurrent surgical procedure (e.g., bilateral herniorrhaphy).
3. Had a pre-existing concurrent acute or chronic painful physical/restrictive condition expected to require analgesic treatment in the post-operative period for pain that was not strictly related to the herniorrhaphy, and which may have confounded the post-operative assessments.

3B.2 Study Treatments

In-Patient Treatment Phase:

Treatments administered during the study included one of the following during the in-patient treatment phase:

4. MR-107A-02 (15 mg twice daily [BID])
5. Tramadol (50 mg q6h)
6. Placebo (q6h)

During the in-patient treatment phase, study drugs were administered orally following randomization and approximately 6 hours following the previous doses (8 doses in total). MR-107A-02 was administered BID and tramadol was administered q6h. To maintain the blind, participants in the MR-107A-02 group received MR-107A-02 active and MR-107A-02 placebo alternately starting with MR-107A-02 active to allow for a q6h dosing of all participants during the in-patient treatment phase. See Table 50, for the allowed window for study drug intake during the in-patient treatment phase. The participants received one tablet and one over-encapsulated tablet of study drug each 6 hours (double-blind, double-dummy); the dosing scheme is summarized for the three treatment groups in Table 51.

TABLE 50

Dosing Scheme of Study Medication During In-patient Treatment Phase

| Group | Dose 1 (T0) | Dose 2 (T6) | Dose 3 (T12) | Dose 4 (T18) | Dose 5 (T24) | Dose 6 (T30) | Dose 7 (T36) | Dose 8 (T42) |
|---|---|---|---|---|---|---|---|---|
| MELO; N = 232 | MELO-Active | MELO-PLA | MELO-Active | MELO-PLA | MELO-Active | MELO-PLA | MELO-Active | MELO-PLA |
| | TRAM-PLA | TRAM-PLA | TRAM-PLA | TRAM-PLA | TRAM-PLA | TRAM-PLA | TRAM-PLA | TRAM-PLA |
| PLA; N = 231 | MELO-PLA | MELO-PLA | MELO-PLA | MELO-PLA | MELO-PLA | MELO-PLA | MELO-PLA | MELO-PLA |
| | TRAM-PLA | TRAM-PLA | TRAM-PLA | TRAM-PLA | TRAM-PLA | TRAM-PLA | TRAM-PLA | TRAM-PLA |

TABLE 50-continued

Dosing Scheme of Study Medication During In-patient Treatment Phase

| Group | Dose 1 (T0) | Dose 2 (T6) | Dose 3 (T12) | Dose 4 (T18) | Dose 5 (T24) | Dose 6 (T30) | Dose 7 (T36) | Dose 8 (T42) |
|---|---|---|---|---|---|---|---|---|
| TRAM; N = 116 | MELO-PLA TRAM-Active | MELO-PL.A. TRAM-Active | MELO-PLA TRAM-Active | MELO-PLA TRAM-Active | MELO-PLA TRAM-Active | MELO-PLA TRAM-Active | MELO-PLA TRAM-Active | MELO-PLA TRAM-Active |

MELO = MR-107A-02 (15 mg);
PLA = Placebo;
TRAM = Tramadol (50 mg);
T0 = Time of first intake of study drug;
T6 = 6 hours following first intake of study drug;
T12 = 12 hours following first intake of study drug;
T18 = 18 hours following first intake of study drug;
T24 = 24 hours following first intake of study drug;
T30 = 30 hours following first intake of study drug;
T36 = 36 hours following first intake of study drug;
T42 = 42 hours following first intake of study drug.

During the out-patient treatment phase, participants in the MR-107A-02 and placebo groups received MR-107A-02 or placebo as assigned during the in-patient treatment phase. Tramadol active and tramadol placebo were discontinued during the out-patient treatment phase. Participants in the Tramadol group received placebo during the out-patient treatment phase. Dosing was BID (10 doses in total). See Table 50, for the allowed window for study drug intake during out-patient treatment phase. The dosing scheme is summarized for the three treatment groups in Table 51.

The first dose of study drug during the out-patient treatment phase occurred in the clinic/hospital/research unit immediately after completion of all 48-hour procedures on Day 3.

TABLE 51

Dosing Scheme of Study Medication During Out-patient Treatment Phase

| Group | Dose 9-Dose 18 (BID) |
|---|---|
| MELO [N = 232] | MELO-Active |
| PLA [N = 231] | MELO-PLA |
| TRAM [N = 116] | MELO-PLA |

BID = Twice daily;
MELO = MR-107A-02 (15 mg);
PLA = Placebo;
TRAM = Tramadol

Identity of Investigational Product

To maintain blinding of the study treatment, the following active and double-dummy tablets/over-encapsulated tablets were administered during the study:

- MR-107A-02 15 mg (MELO-Active), supplied as tablet.
- Tramadol, 50 mg (TRAM-Active), supplied as over-encapsulated 50 mg tablet.
- MR-107A-02 placebo (MELO-PLA), supplied as tablet.
- Tramadol placebo (TRAM-PLA), supplied as over-encapsulated placebo tablet.

The Sponsor supplied MR-107A-02 and tramadol (and corresponding placebos for each active drug). The investigator site supplied:

- Medication required for sedation and anesthesia during the surgery.
- Rescue medication for pain relief following randomization for the in-patient treatment phase, oral APAP (500 mg tablets), IR oral oxycodone (5 mg), and IV morphine sulfate.
- Rescue medication for the out-patient treatment phase, oral APAP (500 mg tablets) or prescription therefore in case the site couldn't provide APAP and prescription for oral oxycodone (5 mg, IR).
- All materials associated with the surgical procedure.
- Naloxone in case of respiratory depression.

Selection and Timing of Dose for Each Participant

As discussed above, tramadol 50 mg q6h and MR-107A-02 15 mg BID were selected as the dosages for the active comparator and study treatment, respectively; the procedure for randomization of participants among the three treatments is discussed above.

In-Patient and Out-Patient Treatment Phase:

Same as above for Example 3A.

Blinding

Same as above for Example 3A.

Prior and Concomitant Therapy

All medications taken during the study (from signing informed consent to post-study follow-up) were recorded with indication, daily dose, and start and stop dates of administration in the CRF. All participants were questioned about concomitant medication at each clinic visit and at follow-up.

Medications taken prior to dosing with study drug were documented as a prior medication. Medications taken after dosing with study drug were documented as concomitant medications or rescue medications, which are described below.

Participants were to abstain from all prohibited medications as described below. Use of prohibited medication during the study was deemed a protocol deviation and such participants were assessed by the Sponsor or designee regarding potential need to early terminate study drug (e.g., for safety reasons). Exclusion criterion 23 indicated the start point for the period of prohibited medication per substance. The endpoint for the period of prohibited medication period was Visit 3 (Day 9).

Rescue Medication

Same as in Example 3A above.

3B.3 Efficacy Assessments

The following parameters were evaluated to assess the efficacy:

Pain Intensity Assessment (Numeric Rating Scale)

Pain intensity scores were assessed using an 11-point NRS (0-10) where 0 represented "no pain" and 10 represented "worst pain imaginable" (Breivik et al., 2008). NRS scores were recorded first at rest (NRS-R) and then with activity (NRS-A).

NRS-R: Participants were to be in supine position. Measurements were to be obtained after the participant was in the resting position for at least 5 minutes.

NRS-A: Participants were to be in supine position and instructed to sit up. Measurements were to be obtained as soon as the participant sat up from the resting position.

For additional details refer to Example 3A above.

Categorical Pain Rating, Rescue Medication Us, Time to First Perceptible Pain Relief, Time to Meaningful Pain Relief, Patient Global Assessment of Pain Control, Modified Post-Anesthetic Discharge Scoring System, and Overall Benefit of Analgesic Score Same as in Example 3A above Safety Assessments The following parameters were evaluated to assess safety:

Primary Efficacy Variable(s)

The primary efficacy variable was the $SPID_{0-48}$.

Drug Concentration Measurements and Prior and Concomitant Medications

Same as in Example 3A above 3B.4 Efficacy Analyses

Primary Efficacy Estimand, Computation of the Primary Estimand, Primary Analysis of the Primary Estimand, Sensitivity Analysis of the Primary Estimand, Supplementary Analysis of the Primary Estimand, Subgroup Analyses for the Primary Estimand, and Key Secondary Estimand Same as in Example 3A above Other Secondary Efficacy Endpoints Number and Proportion of Opioid Free Participants (Entire Treatment Phase):

Essentially the same as described above in Example 3A. Furthermore, the Subgroup Analyses for the Number and Proportion of Opioid Free Participants (Entire Treatment Phase):

No subgroup analyses were planned for this estimand; however, post-hoc subgroup analyses were performed as described below.

Additional details about these analyses are provided in Version 4.0 of the SAP.

Time-to-Event Outcomes, Proportion of Participants with Overall Pain Reductions and PGA of Pain Control, Rescue Medication Use, Pharmacokinetic Analyses, Extent of Exposure, and Analysis of Adverse Events Same as in Example 3A above Disposition of Participants Of the 1192 participants screened for the study, 579 participants were enrolled and randomized to one of three treatment groups (FIG. 49). The MR-107A-02, Tramadol, and Placebo groups included 232 participants, 116 participants, and 231 participants, respectively; 7 participants (2 participants in the MR-107A-02 group, 1 participant in the Tramadol group, and 4 participants in the Placebo group) were randomized in error and not dosed due to failure to meet inclusion and/or exclusion criteria, as described in FIG. 49.

3B.5 Efficacy Evaluation

Participant inclusion in the analysis sets, demographics and other baseline characteristics, and treatment compliance were summarized by treatment group for the study overall and/or individually for the in-patient/out-patient treatment phases; the names of the three treatment groups contain the full treatment sequence that participants were assigned (i.e., treatment during the in-patient treatment phase→treatment during the out-patient treatment phase). During the in-patient treatment phase, participants received MR-107A-02 (15 mg BID), tramadol (50 mg q6h), or placebo (q6h; see Table 50), and during the out-patient treatment phase, participants received either MR-107A-02 (15 mg BID) or placebo (BID; see Table 50). To simplify, the three treatment groups are referenced as follows:

MR-107A-02 group=MR-107A-02 (15 mg BID)→MR-107A-02 (15 mg BID)

Tramadol group=tramadol (50 mg q6h)→placebo

Placebo group=placebo→placebo

Data Sets Analyzed

The Safety Analysis Set and FAS were both composed of 572 participants, with 230, 115, and 227 participants in the MR-107A-02, Tramadol, and Placebo groups, respectively. The mFAS was composed of 571 (98.6%) participants, with 229, 115, and 227 participants in the MR-107A-02, Tramadol, and Placebo groups, respectively. The PP Analysis Set was composed of 457 (78.9%) participants, with 188, 90, and 179 participants in the MR-107A-02, Tramadol, and Placebo groups, respectively. The PK Analysis Set was composed of 287 (49.6%) participants, with 123, 59, and 105 participants in the MR-107A-02, Tramadol, and Placebo groups, respectively.

Demographics and Baseline Characteristics

Table 52 summarizes the demographic and baseline characteristics of the FAS. Most participants (96.3% of all participants) were male, and most participants were White (84.3%) and not Hispanic or Latino (66.3%). The mean age was 49.1 years (range 18 to 80 years), and most participants were <65 years of age (93.4%). The mean BMI was 28.0 kg/m$^2$ (range 17 to 40 kg/m$^2$). The mean baseline NRS-R was 6.9 (range 3 to 10), and the mean baseline NRS-A was 7.8 (range 3 to 10). The mean duration of surgery was 50.0 minutes (range 12 to 152 minutes). The three treatment groups were comparable with respect to demographic and baseline characteristics.

TABLE 52

Demographic and Baseline Characteristics (Full Analysis Set)

| | MR-107A-02 (15 mg BID) → MR-107A-02 (15 mg BID) (N = 230) | Tramadol (50 mg q6h) → Placebo (N = 115) | Placebo → Placebo (N = 227) | Total (N = 572) |
|---|---|---|---|---|
| Age (years) | | | | |
| N | 230 | 115 | 227 | 572 |
| Mean (SD) | 48.8 (12.45) | 49.8 (11.40) | 49.1 (12.39) | 49.1 (12.21) |
| Median | 49.0 | 52.0 | 51.0 | 51.0 |
| Min, Max | 22, 76 | 18, 74 | 18,80 | 18, 80 |
| Age group, n (%) | | | | |
| <65 years | 213 (92.6) | 109 (94.8) | 212 (93.4) | 534 (93.4) |
| ≥65 years | 17 (7.4) | 6 (5.2) | 15 (6.6) | 38 (6.6) |
| Sex, n (%) | | | | |
| Male | 222 (96.5) | 113 (98.3) | 216 (95.2) | 551 (96.3) |
| Female | 8 (3.5) | 2 (1.7) | 11 (4.8) | 21 (3.7) |

TABLE 52-continued

Demographic and Baseline Characteristics (Full Analysis Set)

| | MR-107A-02 (15 mg BID) → MR-107A-02 (15 mg BID) (N = 230) | Tramadol (50 mg q6h) → Placebo (N = 115) | Placebo → Placebo (N = 227) | Total (N = 572) |
|---|---|---|---|---|
| Race, n (%)[1] | | | | |
| American Indian or Alaskan Native | 1 (0.4) | 0 | 1 (0.4) | 2 (0.3) |
| Asian | 2 (0.9) | 0 | 0 | 2 (0.3) |
| Black or African American | 29 (12.6) | 12 (10.4) | 28 (12.3) | 69 (12.1) |
| White | 194 (84.3) | 98 (85.2) | 190 (83.7) | 482 (84.3) |
| Not Reported | 0 | 1 (0.9) | 2 (0.9) | 3 (0.5) |
| Unknown | 0 | 3 (2.6) | 0 | 3 (0.5) |
| Other | 3 (1.3) | 1 (0.9) | 4 (1.8) | 8 (1.4) |
| Multiple | 1 (0.4) | 0 | 2 (0.9) | 3 (0.5) |
| Ethnicity, n (%) | | | | |
| Hispanic or Latino | 74 (32.2) | 41 (35.7) | 73 (32.2) | 188 (32.9) |
| Not Hispanic or Latino | 154 (67.0) | 73 (63.5) | 152 (67.0) | 379 (66.3) |
| Not Reported | 2 (0.9) | 1 (0.9) | 1 (0.4) | 4 (0.7) |
| Unknown | 0 | 0 | 1 (0.4) | 1 (0.2) |
| Baseline Weight (kg) | | | | |
| N | 230 | 115 | 227 | 572 |
| Mean (SD) | 86.6 (15.84) | 85.2 (15.46) | 85.9 (16.22) | 86.0 (15.90) |
| Median | 85.1 | 82.5 | 83.9 | 84.1 |
| Min, Max | 51, 129 | 45, 127 | 44, 152 | 44, 152 |
| Baseline Height (cm) | | | | |
| N | 230 | 115 | 227 | 572 |
| Mean (SD) | 175.3 (8.46) | 175.0 (8.11) | 175.2 (8.06) | 175.2 (8.22) |
| Median | 175.5 | 175.0 | 175.0 | 175.2 |
| Min, Max | 149, 196 | 150, 191 | 151, 201 | 149, 201 |
| Baseline BMI ($kg/m^2$) | | | | |
| N | 230 | 115 | 227 | 572 |
| Mean (SD) | 28.1 (4.37) | 27.8 (4.39) | 27.9 (4.34) | 28.0 (4.35) |
| Median | 27.7 | 27.3 | 27.6 | 27.6 |
| Min, Max | 18, 40 | 17, 38 | 17, 40 | 17, 40 |
| Duration of surgery (minutes)[2] | | | | |
| N | 230 | 115 | 227 | 572 |
| Mean (SD) | 50.2 (22.12) | 50.4 (22.00) | 49.7 (22.80) | 50.0 (22.33) |
| Median | 45.5 | 44.0 | 44.0 | 44.5 |
| Min, Max | 12, 146 | 13, 135 | 16, 152 | 12, 152 |
| Baseline NRS-R | | | | |
| N | 230 | 115 | 227 | 572 |
| Mean (SD) | 7.0 (1.70) | 6.9 (1.74) | 6.9 (1.81) | 6.9 (1.75) |
| Median | 7.0 | 7.0 | 7.0 | 7.0 |
| Min, Max | 4,10 | 3, 10 | 4, 10 | 3, 10 |

TABLE 52-continued

Demographic and Baseline Characteristics (Full Analysis Set)

| | MR-107A-02 (15 mg BID) → MR-107A-02 (15 mg BID) (N = 230) | Tramadol (50 mg q6h) → Placebo (N = 115) | Placebo → Placebo (N = 227) | Total (N = 572) |
|---|---|---|---|---|
| Baseline NRS-A[3] | | | | |
| N | 229 | 115 | 227 | 571 |
| Mean (SD) | 7.8 (1.66) | 7.8 (1.57) | 7.7 (1.68) | 7.8 (1.65) |
| Median | 8.0 | 8.0 | 8.0 | 8.0 |
| Min, Max | 3, 10 | 4, 10 | 4, 10 | 3, 10 |

BID = Twice daily;
BMI = Body mass index;
Max = Maximum;
Min = Minimum;
n = Number of participants;
N = Number of participants per treatment group in the Full Analysis Set;
NRS-A = Numeric Rating Scale active;
NRS-R = Numeric Rating Scale at rest;
q6h = Every 6 hours;
SD = Standard deviation Note:
During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase.

Note:
Percentages were based on the number of participants in the Full Analysis Set, in each treatment group.

Note:
Baseline was defined as the last assessment taken prior to the start of study drug administration.

[1]Demographic and baseline characteristics reported by 0 participants overall are excluded from this table.

[2]Calculated as the time between the start and stop times of the herniorrhaphy surgery, in minutes.

[3]One participant (Participant 201-038) did not have a baseline NRS-A score and was dosed without the NRS-A value; a major protocol deviation was recorded for this event

Analysis of Efficacy

Same as in Example 3A above.

Primary Efficacy Estimand

The primary efficacy endpoint was the $SPID_{0-48}$ (based on NRS-A scores), and the analyses used an ANCOVA model to compare the MR-107A-02 and Placebo groups in the FAS. The censoring of NRS-A scores due to rescue medication use was managed by the WLOCF approach, and missing data for NRS-A scores were managed by an MI approach. The FAS included 230, 115, and 227 participants in the MR-107A-02, Tramadol, and Placebo groups, respectively, which satisfied (marginally exceeded) the minimum treatment group size required to sufficiently power the study for the planned analyses of the primary and secondary estimands.

The primary efficacy endpoint of $SPID_{0-48}$ (NRS-A) was met, and Table 53 presents the results of the primary endpoint analysis in the FAS. The LS means (95% CI) for $SPID_{0-48}$ in the MR-107A-02 and Placebo groups were 163.1 (145.5, 180.7) and 113.0 (95.0, 131.0), respectively; the difference in LS means (95% CI) for MR-107A-02 versus placebo (50.1 [35.4, 64.8]) was statistically significant ($p<0.001$). The analysis of $SPID_{0-48}$ (based on NRS-R) is discussed below. The SPIDs (NRS-A and NRS-R) for other time intervals are discussed below.

TABLE 53

Primary Endpoint: SPID (NRS-A) Over 0-48 Hours, ANCOVA with MI (Full Analysis Set)

| Variable<br>Statistic | MR-107A-02<br>(15 mg BID)<br>(N = 230) | (N = 227) |
|---|---|---|
| $SPID_{0-48}$ | | |
| n | 222 | 219 |
| Mean (SD) | 161.8 (87.45) | 112.5 (86.34) |
| Min, Max | −55.9, 392.6 | −102.5, 363.4 |
| LS Mean (SE) | 163.1 (8.99) | 113.0 (9.16) |
| CI[1] | (145.5, 180.7) | (95.0, 131.0) |
| Difference in LS Means (SE) versus Placebo | 50.1 (7.48) | |
| CI for Difference in LS Means[1] | (35.4, 64.8) | |
| p-value for Difference[2] | <0.001 | |

ANCOVA = Analysis of covariance;
APAP = acetaminophen;
BID = Twice daily;
CI = Confidence interval;
LS = Least squares;
Max = Maximum;
MI = Multiple imputation;
Min = Minimum;
n = Number of participants;
N = Number of participants per treatment group in the Full Analysis Set;
NRS-A = Numeric Rating Scale with activity;
q6h = Once every 6 hours;
SAP = Statistical Analysis Plan;
SD = Standard deviation;
SE = Standard error;
SPID = Summed pain intensity difference;
$SPID_{0-48}$ = Summed pain intensity difference from 0-48 hours;
WLOCF = Windowed last observation carried forward Note:
During the in-patient treatment phase, participants received MR-107A-02 (15 mg BID), tramadol (50 mg q6h), or placebo (q6h).

Note:
Missing values due to participants discontinuing early were imputed using an MI approach, taking into account the reasons for discontinuation. For any rescue medication use, a WLOCF approach was used, whereby the last observed pain intensity score prior to taking rescue medication was carried forward to replace the observed pain intensity scores during the period of time following the rescue medication intake. The window for APAP (1$^{st}$ step) rescue medication was 6 hours; the window for oxycodone (2$^{nd}$ step) rescue medication was 4 hours; the window for morphine (3$^{rd}$ step) rescue medication was 2 hours.

Note:
Summary statistics (n, mean, SD, Min, and Max) were based on observed data only (i.e. participants whose SPID values included data imputed by MI were not included in these summary statistics).

Note:
The LS means, differences, CIs, and p-values were based on an ANCOVA model with fixed, categorical effects for treatment (MR-107A-02, Placebo), age group (<65 years, ≥65 years), and study site and baseline pain intensity score as a continuous covariate.

[1]95% CI for MR-107A-02 and Placebo.

[2]2-sided p-value.

FIG. 25 displays the LS mean pain scores (NRS-A) based on the ANCOVA model for the MR-107A-02 and Placebo groups in the FAS over time. Over the period of 0-48 hours, the LS mean pain scores decreased for both groups, but the reductions were larger in the MR-107A-02 group than in the Placebo group.

Sensitivity Analyses of the Primary Efficacy Estimand

A sensitivity analysis of the primary estimand was conducted using the same ANCOVA model as the primary estimand, but the Tramadol group was included. Five additional sensitivity analyses were implemented to include the application of additional windows and different censoring approaches following for rescue medication use in place of the WLOCF in the calculation of the primary estimand (i.e., no censoring, a 4-hour APAP window, a 6-hour oxycodone window, alternative censoring, and all values censored). Another sensitivity analysis was implemented using an alternate MI approach based on the pooled data from the MR-107A-02 and Placebo groups only.

The results of sensitivity analyses of the primary efficacy estimand show that all sensitivity analyses resulted in larger $SPID_{0-48}$ in the MR-107A-02 group than in the Placebo group and mirrored the results of the primary analysis of the primary efficacy estimand.

FIG. 26 presents the LS mean pain scores (NRS-A) from 0-12 hours. Over the period of 0-48 hours, the LS mean pain scores decreased with time for all three groups, but the MR-107A-02 group had the largest pain score reductions during this time period.

The LS mean pain scores (NRS-A) over time for the MR-107A-02, Tramadol, and Placebo groups in the FAS based on the ANCOVA model used for the primary efficacy estimand with additional windows for rescue medication use in place of the WLOCF in the calculation of the primary estimand (i.e., no censoring, a 4-hour APAP window, a 6-hour oxycodone window, alternative censoring, and all values censored, respectively) show that similar to the primary analysis (FIG. 25), the LS mean pain scores decreased with time for all groups, with the MR-107A-02 group showing the largest reductions over the period of 0-48 hours, for all sensitivity analyses. The magnitude of the LS mean pain scores over time was dependent on the analysis method, with the biggest impact on the LS mean pain scores over time in the analysis with all values censored.

Supplementary Analyses of the Primary Efficacy Endpoint

The primary efficacy endpoint was the $SPID_{0-48}$, and the supplementary analyses used an ANCOVA model to compare the MR-107A-02 and Placebo groups in the mFAS and PP Analysis Set. Rescue medication use was managed by the WLOCF approach and missing data was managed by an MI approach.

The results of the supplementary analyses of the primary estimand in the mFAS and PP Analysis Set, respectively show that for the mFAS, the LS means (95% CI) for $SPID_{0-48}$ in the MR-107A-02 and Placebo groups were 163.2 (145.6, 180.9) and 112.9 (95.0, 130.9), respectively; the difference in LS means (95% CI) for MR-107A-02 versus placebo was 50.3 (35.6, 65.0). For the PP Analysis Set, the LS means (95% CI) for $SPID_{0-48}$ in the MR-107A-02 and Placebo groups were 155.7 (136.2, 175.2) and 102.8 (82.3, 123.4), respectively; the difference in LS means (95% CI) for MR-107A-02 versus placebo was 52.8 (36.6, 69.1). The results of the primary efficacy estimand analyses in the mFAS and PP Analysis Set were very similar to those in the FAS and supported the conclusions of the primary analysis.

The LS mean pain scores (NRS-A) over time based on the ANCOVA model used for the primary efficacy estimand analysis with the Tramadol group included in the mFAS and PP Analysis Set, respectively show that over the period of 0-48 hours for the mFAS and PP Analysis Set, the LS mean pain scores decreased with time for all three treatment groups, but the pain score reductions were largest in the MR-107A-02 group.

Subgroup Analyses of the Primary Efficacy Estimand

Same as in Example 3A above

Age Subgroup:

For the <65 years subgroup, the LS means (95% CI) for $SPID_{0-48}$ in the MR-107A-02 and Placebo groups were 162.5 (146.7, 178.3) and 109.7 (93.6, 125.8), respectively; the difference in LS means (95% CI) for MR-107A-02 versus placebo (52.8 [37.7, 68.0]) was nominally statistically significant (p<0.001).

For the ≥65 years subgroup, the LS means (95% CI) for $SPID_{0-48}$ in the MR-107A-02 and Placebo groups were 138.3 (89.2, 187.5) and 136.7 (78.3, 195.0), respectively; the difference in LS means (95% CI) for MR-107A-02 versus placebo (1.7 [−80.7, 84.0]) was not statistically significant (p=0.996), which may be due to the small sample size in the ≥65 years subgroup.

The LS mean pain scores (NRS-A) over time by age subgroup for the FAS based on the ANCOVA model used for the primary efficacy estimand analysis with the Tramadol group included show that over the period of 0-48 hours, the LS mean pain scores decreased with time for all three treatment groups, but the pain score reductions were largest in the MR-107A-02 group for the <65 age subgroup; in the ≥65 years subgroup, the pain score reductions were largest in the placebo group and there was more variation in LS mean pain scores (i.e., wider CIs) within each treatment group than in the <65 years subgroup due to the comparatively smaller sample size in the ≥65 years subgroup.

Sex:

The results of the primary estimand analysis by sex in the FAS.

For the male subgroup, the LS means (95% CI) for $SPID_{0-48}$ in the MR-107A-02 and Placebo groups were 162.6 (144.8, 180.4) and 113.4 (95.2, 131.6), respectively; the difference in LS means (95% CI) for MR-107A-02 versus placebo (49.2 [34.0, 64.3]) was nominally statistically significant (p<0.001).

For the female subgroup, the LS means (95% CI) for $SPID_{0-48}$ in the MR-107A-02 and Placebo groups were 178.0 (112.9, 243.2) and 66.9 (−9.7, 143.6), respectively; the difference in LS means (95% CI) for MR-107A-02 versus placebo (111.1 [−2.8, 224.9]) was not statistically significant (p=0.055), which may be due to the small sample size in the female subgroup. The LS mean pain scores (NRS-A) over time by sex for the FAS based on the ANCOVA model used for the primary efficacy estimand analysis with the Tramadol group included show that over the period of 0-48 hours, the LS mean pain scores decreased with time for all three treatment groups, but the pain score reductions were largest in the MR-107A-02 group for both sexes; in the female subgroup, there was more variation in LS mean pain scores (i.e., larger CIs) within each treatment group than in the male subgroup due to the small sample size in the female subgroup.

Race:

For the White subgroup, the LS means (95% CI) for $SPID_{0-48}$ in the MR-107A-02 and Placebo groups were 152.9 (133.8, 172.0) and 105.4 (86.1, 124.7), respectively; the difference in LS means (95% CI) for MR-107A-02 versus placebo (47.5 [31.6, 63.4]) was nominally statistically significant (p<0.001).

For the Black or African American subgroup, the LS means (95% CI) for $SPID_{0-48}$ in the MR-107A-02 and Placebo groups were 237.8 (185.8, 289.8) and 162.5 (111.5, 213.5), respectively; the difference in LS means (95% CI) for MR-107A-02 versus placebo (75.3 [25.7, 124.9]) was nominally statistically significant (p=0.003).

For the Other Race subgroup, the LS means (95% CI) for $SPID_{0-48}$ in the MR-107A-02 and Placebo groups were 175.8 (89.7, 261.9) and 53.2 (−23.5, 129.9), respectively; the difference in LS means (95% CI) for MR-107A-02 versus placebo (122.6 [−3.0, 248.3]) was not statistically significant (p=0.056), which may be due to the small sample size in the Other Race subgroup.

LS mean pain scores (NRS-A) over time by race for the FAS based on the ANCOVA model used for the primary efficacy estimand analysis with the Tramadol group included show that over the period of 0-48 hours, the LS mean pain scores decreased with time for all three treatment groups, but the reductions were generally the largest in the MR-107A-02 group across all the race subgroups; in the Other Race subgroup, there was more variation in LS mean pain scores (i.e., larger CIs) within each treatment group than in the White and Black or African American subgroups, due to the small sample size in the Other Race subgroup.

Other Analyses of the Primary Efficacy Endpoint (NRS-A)

The primary efficacy endpoint was the $SPID_{0-48}$, and other analyses of this endpoint used an ANCOVA model to compare the Tramadol and Placebo groups (with and without MR-107A-02) and the MR-107A-02 and Tramadol groups (with and without Placebo) in the FAS. Rescue medication use was managed by the WLOCF approach, and missing data was managed by an MI approach. A discussion of the primary endpoint, $SPID_{0-48}$, comparing the MR-107A-02 and Placebo groups (without Tramadol), is included below.

Tramadol Versus Placebo, Excluding MR-107A-02:

The results of the $SPID_{0-48}$ (NRS-A) analysis comparing the Tramadol and Placebo groups, excluding MR-107A-02, in the FAS shows that the LS means (95% CI) for $SPID_{0-48}$ in the Tramadol and Placebo groups were 160.0 (140.0, 180.1) and 130.5 (107.9, 153.1), respectively; the difference in LS means (95% CI) for tramadol versus placebo (29.5 [14.7, 44.3]) was nominally statistically significant (p<0.001).

Tramadol Versus Placebo, Including MR-107A-02:

The results of the $SPID_{0-48}$ (NRS-A) analysis comparing the Tramadol and Placebo groups, including MR-107A-02, in the FAS shows that the LS means (95% CI) for $SPID_{0-48}$ in the Tramadol and Placebo groups were 149.8 (132.3, 167.3) and 120.4 (101.5, 139.3), respectively; the difference in LS means (95% CI) for tramadol versus placebo (29.4 [14.4, 44.4]) was nominally statistically significant (p<0.001).

MR-107A-02 Versus Tramadol, Excluding Placebo:

The results of the $SPID_{0-48}$ (NRS-A) analysis comparing the MR-107A-02 and Tramadol groups, excluding Placebo, in the FAS shows that the LS means (95% CI) for $SPID_{0-48}$ in the MR-107A-02 and Tramadol groups were 162.2 (140.5, 183.8) and 141.3 (121.3, 161.2), respectively; the difference in LS means (95% CI) for MR-107A-02 versus tramadol (20.9 [5.6, 36.3]) was nominally statistically significant (p=0.025) based on a post-hoc analysis.

MR-107A-02 Versus Tramadol, Including Placebo:

The results of the $SPID_{0-48}$ analysis comparing the MR-107A-02 and Tramadol groups, including Placebo, in the FAS shows that the LS means (95% CI) for $SPID_{0-48}$ in the MR-107A-02 and Tramadol groups were 170.4 (151.8, 189.1) and 149.8 (132.3, 167.3), respectively; the difference in LS means (95% CI) for MR-107A-02 versus tramadol (20.6 [5.6, 35.6]) was nominally statistically significant (p=0.023) based on a post-hoc analysis.

Other Analyses of the Primary Efficacy Endpoint (NRS-R)

MR-107A-02 Versus Placebo, Excluding Tramadol:

The results of the $SPID_{0-48}$ (NRS-R) analysis comparing the MR-107A-02 and Placebo groups, excluding Tramadol, in the FAS shows that the LS means (95% CI) for $SPID_{0-48}$ in the MR-107A-02 and Placebo groups were 193.8 (176.7, 210.9) and 151.2 (133.8, 168.6), respectively; the difference in LS means (95% CI) for MR-107A-02 versus placebo (42.6 [28.3, 56.9]) was nominally statistically significant (p<0.001).

MR-107A-02 Versus Placebo, Including Tramadol:

The results of the $SPID_{0-48}$ (NRS-R) analysis comparing the MR-107A-02 and Placebo groups, including Tramadol, in the FAS shows that the LS means (95% CI) for $SPID_{0-48}$ in the MR-107A-02 and Placebo groups were 198.6 (180.4, 216.8) and 156.5 (138.2, 174.9), respectively; the difference in LS means (95% CI) for tramadol versus placebo (42.1 [27.8, 56.3]) was nominally statistically significant (p<0.001).

Tramadol Versus Placebo, Excluding MR-107A-02:

The results of the $SPID_{0-48}$ (NRS-R) analysis comparing the Tramadol and Placebo groups, excluding MR-107A-02, in the FAS shows that the LS means (95% CI) for $SPID_{0-48}$ in the Tramadol and Placebo groups were 200.7 (181.1, 220.2) and 168.5 (146.6, 190.4), respectively; the difference in LS means (95% CI) for tramadol versus placebo (32.1 [17.6, 46.7]) was nominally statistically significant (p<0.001).

Tramadol Versus Placebo, Including MR-107A-02:

The results of the $SPID_{0-48}$ (NRS-R) analysis comparing the Tramadol and Placebo groups, including MR-107A-02, in the FAS show that the LS means (95% CI) for $SPID_{0-48}$ in the Tramadol and Placebo groups were 189.0 (172.0, 206.0) and 156.5 (138.2, 174.9), respectively; the difference in LS means (95% CI) for tramadol versus placebo (32.5 [17.8, 47.2]) was nominally statistically significant (p<0.001).

MR-107A-02 Versus Tramadol, Excluding Placebo:

The results of the $SPID_{0-48}$ (NRS-R) analysis comparing the MR-107A-02 and Tramadol groups, excluding Placebo, in the FAS show that the LS means (95% CI) for $SPID_{0-48}$ in the MR-107A-02 and Tramadol groups were 189.0 (168.2, 209.8) and 179.8 (160.6, 199.0), respectively; the difference in LS means (95% CI) for tramadol versus placebo (9.2 [−5.7, 24.1]) was not statistically significant (p=0.309).

MR-107A-02 Versus Tramadol, Including Placebo:

The results of the $SPID_{0-48}$ (NRS-R) analysis comparing the MR-107A-02 and Tramadol groups, including Placebo, in the FAS show that the LS means (95% CI) for $SPID_{0-48}$ in the MR-107A-02 and Placebo groups were 198.6 (180.4, 216.8) and 189.0 (172.0, 206.0), respectively; the difference in LS means (95% CI) for tramadol versus placebo (9.6 [−5.1, 24.2]) was not statistically significant (p=0.282).

Key Secondary Efficacy Estimand

The key secondary efficacy endpoint was the number of doses of opioid (oxycodone and/or morphine) rescue medication taken during the entire treatment phase, and the analysis used a negative binomial regression model with a log link to compare the MR-107A-02 and Placebo groups in the FAS. Missing data was managed by an MI approach. Additional details on the analysis are provided below, and the changes to the planned analyses are described below.

Table 54 presents the results of the key secondary estimand analysis for the FAS. The mean (SD) number of doses of opioid (oxycodone and/or morphine) rescue medication during the entire treatment phase for the MR-107A-02 and Placebo groups was 0.87 (2.16) and 1.25 (2.14), respectively. The LS geometric mean number of opioid doses used in the MR-107A-02 group (0.002 doses) over the entire treatment phase was 50% lower than that in the Placebo group (0.004 doses). The ratio of LS geometric means (95% CI) for MR-107A-02 versus placebo (0.627 [0.419, 0.939]) was statistically significant (p=0.023). The results for the number of doses of opioid (oxycodone and/or morphine) rescue medication during other time intervals are discussed below.

TABLE 54

Key Secondary: Number of Doses of Opioid (Oxycodone and/or Morphine) Rescue Medication (Entire Treatment Phase) with MI (Full Analysis Set)

| Variable<br>Statistic | MR-107A-02<br>(15 mg BID)<br>(N = 230) | Placebo<br>(N = 227) |
|---|---|---|
| Number of doses of Opioid (Oxycodone and/or Morphine) Rescue Medication | | |
| Mean (SD) | 0.87 (2.16) | 1.25 (2.14) |
| Median | 0 | 0 |
| Min, Max | 0, 17 | 0, 12 |
| Difference in Means | −0.38 | |
| LS Geometric Mean | 0.002 | 0.004 |
| 95% CI | (0.000, NC) | (0.000, NC) |
| Ratio of LS Geometric Means versus Placebo | 0.627 | |
| 95% CI for Ratio of LS Geometric Means | (0.419, 0.939) | |
| p-value for Ratio | 0.023 | |

BID = Twice daily;
CI = Confidence interval;
LS = Least squares;
MAR = Missing at random;
Max = Maximum;
MI = Multiple imputation;
Min = Minimum;
N = Number of participants per treatment group in the Full Analysis Set;
NC = non-calculable;
q6h = Once every 6 hours;
SD = Standard deviation Note:
During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase.

Note:
The number of doses of opioid was defined as the number of doses of oxycodone and/or morphine taken.

Note:
For any missing data from participants discontinuing treatment early due to a lack of efficacy or an adverse event, a placebo-based MI approach was used, whereby both the rate before and after withdrawal for such participants was assumed to follow that of the Placebo group. Missing data from participants discontinuing for any other reasons was imputed using a MAR approach.

Note:
The LS geometric means, differences, CIs, and 2-sided p-value were based on a negative binomial regression model with a log link with fixed, categorical effects for treatment (MR-107A-02 and placebo), age group (<65 years, ≥65 years), and study site. The LS geometric means (and difference) were estimated using this model and then back transformed to the original scale by exponentiating.

Note:
Summary statistics (mean, median, SD, Min, Max) were based on observed data only.

Sensitivity Analyses of the Key Secondary Efficacy Estimand

A sensitivity analysis of the key secondary efficacy estimand was performed to calculate the number of doses of oxycodone only taken during the entire treatment phase; and the analysis used a negative binomial regression model with a log link to compare the MR-107A-02 and Placebo groups in the FAS. Missing data was managed by an MI approach. A second sensitivity analysis for the number of doses of opioid was also performed, with an alternate MI approach using a negative binomial distribution based on the pooled data from the MR-107A-02 and Placebo groups. Additional details on the analyses are provided below.

The results of the first sensitivity analysis of the key secondary estimand for the FAS shows that the mean (SD) number of doses of oxycodone rescue medication for the MR-107A-02 and Placebo groups was 0.87 (2.16) and 1.21 (2.09), respectively, and the ratio of LS geometric means (95% CI) for MR-107A-02 versus placebo was 0.621 (0.417, 0.926).

The results of the second sensitivity analysis of the key secondary estimand for the FAS show that the mean (SD)

number of doses of oxycodone rescue medication for the MR-107A-02 and Placebo groups was 0.87 (2.16) and 1.25 (2.14), respectively, and the ratio of LS geometric means (95% CI) for MR-107A-02 versus placebo was 0.628 (0.420, 0.940).

Overall, the results of the sensitivity analyses of the key secondary efficacy estimand were similar to those of the primary analysis discussed below.

Subgroup Analyses of the Key Secondary Efficacy Estimand

The key secondary efficacy endpoint was the number of doses of opioid (oxycodone and/or morphine) rescue medication taken during the entire treatment phase, and the analysis used a negative binomial regression model with a log link to compare the MR-107A-02 and Placebo groups in the FAS. The analysis was repeated for each age (<65 years and ≥65 years), sex (female, male) and race (White, Black or African American, and Other Race) subgroup. Missing data was managed by an MI approach.

Age Subgroup:

The analysis for the ≥65 years subgroup to determine the mean (SD) number of doses of opioid (oxycodone and/or morphine) rescue medication for the MR-107A-02 and Placebo could not be completed due to the small sample size. As such, no results for this analysis are included herein. Since this analysis could not be completed, the effect of age on the efficacy of MR-107A-02 with respect to this endpoint could not be determined.

Sex:

For the male subgroup, the mean (SD) number of doses of opioid (oxycodone and/or morphine) rescue medication for the MR-107A-02 and Placebo groups was 0.88 (2.19) and 1.26 (2.17), respectively, and the ratio of LS geometric means (95% CI) for MR-107A-02 versus placebo (0.620 [0.410, 0.937]) was nominally statistically significant (p=0.023).

For the female subgroup, the mean (SD) number of doses of opioid (oxycodone and/or morphine) rescue medication for the MR-107A-02 and Placebo groups was 0.63 (1.19) and 1.09 (1.51), respectively, and the ratio of LS geometric means (95% CI) for MR-107A-02 versus placebo (0.644 [0.091, 4.579]) was not statistically significant (p=0.660), which may be due to the small sample size in the female subgroup.

Race:

For the White subgroup, the mean (SD) number of doses of opioid (oxycodone and/or morphine) rescue medication during the entire treatment phase for the MR-107A-02 and Placebo groups was 0.85 (2.15) and 1.19 (2.13), respectively, and the ratio of LS geometric means (95% CI) for MR-107A-02 versus placebo (0.618 [0.391, 0.978]) was nominally statistically significant (p=0.040).

For the Black or African American subgroup, the mean (SD) number of doses of opioid (oxycodone and/or morphine) rescue medication during the entire treatment phase for the MR-107A-02 and Placebo groups was 1.10 (2.47) and 1.18 (1.74), respectively, and the ratio of LS geometric means (95% CI) for MR-107A-02 versus placebo (0.713 [0.300, 1.698]) was not statistically significant (p=0.445), which may be due to the small sample size in the Black or African American subgroup.

For the Other Race subgroup, the mean (SD) number of doses of opioid (oxycodone and/or morphine) rescue medication during the entire treatment phase for the MR-107A-02 and Placebo groups was 0.57 (0.79) and 2.78 (3.11), respectively, and the ratio of LS geometric means (95% CI) for MR-107A-02 versus placebo (0.803 [0.215, 3.001]) was not statistically significant (p=0.744), which may be due to the small sample size in the Other Race subgroup.

Other Secondary Efficacy Endpoints

Number of Doses of Opioid (Oxycodone and/or Morphine) Rescue Medication

The number of doses of opioid (oxycodone and/or morphine) rescue medication taken during the last 24 and 36 hours before discharge, in-patient and out-patient treatment phases, 0-24 hours after randomization, and post-discharge phase (up to 30 days) were other secondary efficacy endpoints and the analysis followed the methods used for the primary analysis of the key secondary endpoint (i.e., a negative binomial regression model with a log link) to compare the MR-107A-02 and Placebo groups in the FAS. Missing data was managed by an MI approach. Additional details on the planned analysis are provided below, and the changes to the planned analyses are described below.

Last 24 Hours Before Discharge (i.e., 24-48 Hours after Randomization):

The number of doses of opioid (oxycodone and/or morphine) rescue medication during the last 24 hours before discharge for the FAS shows that the mean (SD) number of doses of opioid (oxycodone and/or morphine) rescue medication during the last 24 hours before discharge for the MR-107A-02 and Placebo groups was 0.09 (0.43) and 0.14 (0.51), respectively, and the ratio of LS geometric means (95% CI) for MR-107A-02 versus placebo (0.827 [0.378, 1.809]) was not statistically significant (p=0.634).

Last 36 Hours Before Discharge (i.e., 12-48 Hours after Randomization):

The number of doses of opioid (oxycodone and/or morphine) rescue medication during the last 36 hours before discharge for the FAS shows that the mean (SD) number of doses of opioid (oxycodone and/or morphine) rescue medication during the last 36 hours before discharge for the MR-107A-02 and Placebo groups was 0.14 (0.61) and 0.27 (0.71), respectively, and the ratio of LS geometric means (95% CI) for MR-107A-02 versus placebo (0.602 [0.322, 1.126]) was not statistically significant (p=0.112).

In-Patient Treatment Phase (i.e., 0-48 Hours after Randomization):

The number of doses of opioid (oxycodone and/or morphine) rescue medication during the in-patient treatment phase for the FAS shows that the mean (SD) number of doses of opioid (oxycodone and/or morphine) rescue medication during in-patient treatment phase for the MR-107A-02 and Placebo groups was 0.39 (0.96) and 0.61 (1.09), respectively, and the ratio of LS geometric means (95% CI) for MR-107A-02 versus placebo (0.683 [0.468, 0.998]) was nominally statistically significant (p=0.049).

Out-Patient Treatment Phase (i.e., 5 Days Following Discharge):

The number of doses of opioid (oxycodone and/or morphine) rescue medication during the out-patient treatment phase for the FAS shows that the mean (SD) number of doses of opioid (oxycodone and/or morphine) rescue medication during out-patient treatment phase for the MR-107A-02 and Placebo groups was 0.49 (1.55) and 0.66 (1.62), respectively, and the ratio of LS geometric means (95% CI) for MR-107A-02 versus placebo (0.547 [0.283, 1.059]) was not statistically significant (p=0.073).

0-24 Hours after Randomization:

The number of doses of opioid (oxycodone and/or morphine) rescue medication during 0-24 hours after randomization for the FAS shows that the mean (SD) number of doses of opioid (oxycodone and/or morphine) rescue medication during 0-24 hours after randomization for the MR-107A-02 and Placebo groups was 0.30 (0.67) and 0.48 (0.84), respectively, and the ratio of LS geometric means (95% CI) for MR-107A-02 versus placebo (0.654 [0.456, 0.938]) was nominally statistically significant (p=0.021).

Post-Discharge Phase (i.e., Up to 30 Days after Discharge):

The number of doses of opioid (oxycodone and/or morphine) rescue medication during the post-discharge phase, up to 30 days, for the FAS shows that the mean (SD) number of doses of opioid (oxycodone and/or morphine) rescue medication during the post-discharge phase, up to 30 days, for the MR-107A-02 and Placebo groups was 0.61 (1.85) and 0.75 (1.80), respectively, and the ratio of LS geometric means (95% CI) for MR-107A-02 versus placebo (0.684 [0.365, 1.280]) was not statistically significant (p=0.234).

3B.6 Number and Proportion of Opioid (Oxycodone and/or Morphine) Free Participants The number and proportion of participants who were opioid-free during the entire treatment phase, the last 24 and 36 hours before discharge, the in-patient treatment phase, and the out-patient treatment phase, 0-24 hours after randomization, and post-discharge phase (up to 30 days after discharge) were other secondary efficacy endpoints. The proportion of participants who were opioid-free during any time interval was defined as the proportion of participants who had not taken oxycodone and/or morphine; for any participants who reported taking a rescue medication without reporting the type taken, or if the rescue medication was noted to be an opioid, that rescue medication was counted as an opioid. The proportions were analyzed with the difference in proportions Z-test, and a sensitivity analysis based on the proportion of participants who had not taken oxycodone during the entire treatment phase was performed.

Entire Treatment Phase:

The number and proportion of opioid (oxycodone and/or morphine) free participants during the entire treatment phase for the FAS shows that in the MR-107A-02 and Placebo groups, 168 (73.0%) and 133 (58.6%) participants, respectively, were opioid (oxycodone and/or morphine) free during the entire treatment phase; the MR-107A-02 group had 14.4% more opioid-free participants than the Placebo group, and the difference in proportions (95% CI) of 14.5% (5.9%, 23.1%) was statistically significant (p=0.001).

The results of the sensitivity analysis of the number and proportion of opioid free participants during the entire treatment phase for the FAS, in which only oxycodone use was analyzed shows that in the MR-107A-02 and Placebo groups, 168 (73.0%) and 133 (58.6%) participants, respectively, were oxycodone free during the entire treatment phase; difference in proportions (95% CI) of 14.5% (5.9%, 23.1%) was nominally statistically significant (p=0.001). The results of the sensitivity analysis (only oxycodone) were the same as the analysis that included both oxycodone and/or morphine.

The analysis for the entire treatment phase was repeated for each age (<65 years and ≥65 years), sex (female, male) and race (White, Black or African American, and Other Race) subgroup and were added post hoc.

Age Subgroup:

The results of the analysis show the number and proportion of opioid (oxycodone and/or morphine) free participants during the entire treatment phase by age subgroup for the FAS.

For the <65 years subgroup, the number and proportion of opioid (oxycodone and/or morphine) free participants for the MR-107A-02 and Placebo groups was 152 (71.4%) and 122 (57.5%), respectively, and the difference in proportions (95% CI) of 13.8% (4.8%, 22.8%) was nominally statistically significant (p=0.003).

For the ≥65 years subgroup, the number and proportion of opioid (oxycodone and/or morphine) free participants for the MR-107A-02 and Placebo groups was 16 (94.1%) and 11 (73.3%), respectively, and the difference in proportions (95% CI) of 20.8% (−4.2%, 45.8%) was not statistically significant (p=0.106), which may be due to the small sample size in the ≥65 years subgroup.

Sex Subgroup:

The results of the analysis of the number and proportion of opioid (oxycodone and/or morphine) show free participants during the entire treatment phase by sex for the FAS.

For the female subgroup, the number and proportion of opioid (oxycodone and/or morphine) free participants for the MR-107A-02 and Placebo groups was 6 (75.0%) and 5 (45.5%), respectively, and the difference in proportions (95% CI) of 29.5% (−12.5%, 71.6%) was not statistically significant (p=0.198), which may be due to the small sample size in the female subgroup.

For the male subgroup, the number and proportion of opioid (oxycodone and/or morphine) free participants for the MR-107A-02 and Placebo groups was 162 (73%) and 128 (59.3%), respectively, and the difference in proportions (95% CI) of 13.7% (4.9%, 22.5%) was nominally statistically significant (p=0.002).

Race Subgroup:

For the White subgroup, the number and proportion of opioid (oxycodone and/or morphine) free participants for the MR-107A-02 and Placebo groups was 145 (74.7%) and 116 (61.1%), respectively, and the difference in proportions (95% CI) of 13.7% (4.4%, 22.9%) was nominally statistically significant (p=0.004).

For the Black of African American subgroup, the number and proportion of opioid (oxycodone and/or morphine) free participants for the MR-107A-02 and Placebo groups was 19 (65.5%) and 14 (50.0%), respectively, and the difference in proportions (95% CI) of 15.5% (−9.8%, 40.9%) was not statistically significant (p=0.236), which may be due to the small sample size in the Black of African American subgroup.

For the Other Race subgroup, the number and proportion of opioid (oxycodone and/or morphine) free participants for the MR-107A-02 and Placebo groups was 4 (57.1%) and 3 (33.3%), respectively, and the difference in proportions (95% CI) of 23.8% (−24.1%, 71.7%) was not statistically significant (p=0.341), which may be due to the small sample size in the Other Race subgroup.

Last 24 Hours Before Discharge (i.e., 24-48 Hours after Randomization):

The number and proportion of opioid (oxycodone and/or morphine) free participants during the last 24 hours before discharge for the FAS shows that in the MR-107A-02 and Placebo groups, 215 (93.5%) and 203 (89.4%) participants, respectively, were opioid (oxycodone and/or morphine) free during the last 24 hours before discharge; the difference in proportions (95% CI) of 4.1% (−1.1%, 9.2%) was not statistically significant (p=0.121).

Last 36 Hours Before Discharge (i.e., 12-48 Hours after Randomization):

The number and proportion of opioid (oxycodone and/or morphine) free participants during the last 36 hours before discharge for the FAS shows that in the MR-107A-02 and Placebo groups, 211 (91.7%) and 188 (82.8%) participants, respectively, were opioid (oxycodone and/or morphine) free during the last 36 hours before discharge; the difference in proportions (95% CI) of 8.9% (2.9%, 15.0%) was nominally statistically significant (p=0.004).

In-Patient Treatment Phase (i.e., 0-48 Hours after Randomization):

The number and proportion of opioid (oxycodone and/or morphine) free participants during the in-patient treatment phase for the FAS shows that in the MR-107A-02 and Placebo groups, 179 (77.8%) and 152 (67.0%) participants, respectively, were opioid (oxycodone and/or morphine) free during the in-patient treatment phase; the difference in proportions (95% CI) of 10.9% (2.7%, 19.0%) was nominally statistically significant (p=0.009).

Out-Patient Treatment Phase (i.e., 5 Days Following Discharge):

The number and proportion of opioid (oxycodone and/or morphine) free participants during the out-patient treatment phase for the FAS shows that in the MR-107A-02 and Placebo groups, 197 (85.7%) and 176 (77.5%) participants, respectively, were opioid (oxycodone and/or morphine) free during the out-patient treatment phase; the difference in proportions (95% CI) of 8.1% (1.0%, 15.2%) was nominally statistically significant (p=0.025).

This analysis was repeated to compare the MR-107A-02 group with the All-Placebo group and with the Tramadol Placebo group. In the Tramadol Placebo group, 92 (80.0%) participants were opioid (oxycodone and/or morphine) free during the out-patient treatment phase; the difference in proportions (95% CI) for MR-107A-02 versus tramadol of 5.7% (−2.9%, 14.3%) was not statistically significant (p=0.180). In the All-Placebo group, 268 (78.4%) participants were opioid (oxycodone and/or morphine) free; the difference in proportions (95% CI) for MR-107A-02 versus placebo (all) of 7.3% (1.0%, 13.6%) was nominally statistically significant (p=0.028).

0-24 Hours after Randomization:

The number and proportion of opioid (oxycodone and/or morphine) free participants during 0-24 hours after randomization for the FAS show that in the MR-107A-02 and Placebo groups, 182 (79.1%) and 155 (68.3%) participants, respectively, were opioid (oxycodone and/or morphine) free during the 0-24 hours after randomization; the difference in proportions (95% CI) of 10.8% (2.8%, 18.9%) was nominally statistically significant (p=0.008).

Post-Discharge Phase (i.e., Up to 30 Days after Discharge):

The number and proportion of opioid (oxycodone and/or morphine) free participants during the post-discharge phase, up to 30 days, for the FAS shows that in the MR-107A-02 and Placebo groups, 194 (84.3%) and 175 (77.1%) participants, respectively, were opioid (oxycodone and/or morphine) free during the post-discharge phase, up to 30 days; the difference in proportions (95% CI) of 7.3% (0.0%, 14.5%) was nominally statistically significant (p=0.049).

This analysis was repeated to compare the MR-107A-02 group with the All-Placebo group and with the Tramadol Placebo group. In the Tramadol Placebo group, 90 (78.3%) participants were opioid (oxycodone and/or morphine) free during the post-discharge phase, up to 30 days; the difference in proportions (95% CI) for MR-107A-02 versus Tramadol of 6.1% (−2.8%, 15.0%) was not statistically significant (p=0.162). In the All-Placebo group, 265 (77.5%) participants were opioid (oxycodone and/or morphine) free during the post-discharge phase, up to 30 days; the difference in proportions (95% CI) for MR-107A-02 versus placebo (all) of 6.9% (0.4%, 13.3%) was nominally statistically significant (p=0.043).

Summed Pain Intensity Difference Over Time Following Study Drug Administration

The SPID over 0-4 hours, 0-8 hours, 0-12 hours, 12-24 hours, and 0-24 hours following study drug administration (based on NRS-A scores and NRS-R scores) were other secondary efficacy endpoints; the analysis was similar to that of the primary estimand. Additional details on the planned analysis are provided below, and the changes to the planned analyses and post-hoc analyses are described below The SPID (NRS-A) and SPID (NRS-R), respectively, over time following study drug administration for the FAS show that overall, the LS means for the SPID (NRS-A and NRS-R) in the MR-107A-02, Tramadol, and Placebo groups increased with time through 24 hours post-dose. The MR-107A-02 and Tramadol groups both had larger (and nominally statistically significantly different) LS mean SPIDs (NRS-A and NRS-R) than the Placebo group at each time interval evaluated (MR-107A-02 versus placebo [$p<0.001$] and tramadol versus placebo [$p\leq 0.028$; post-hoc]). The MR-107A-02 group had numerically larger LS mean SPIDs (NRS-A and NRS-R) than the Tramadol group at each time interval evaluated. The various analyses of $SPID_{0-48}$ (the primary estimand) are discussed below.

Pain Intensity Differences Over Time Following Study Drug Administration

The PIDs over time following study drug administration (based on NRS-A scores [FIG. 26] and NRS-R scores) were other secondary efficacy endpoints and were analyzed using MMRM.

NRS-A:

The PID (NRS-A) over time following study drug administration for the FAS. The PID at each time point was proportional to the NRS-A pain score at that time point, such that lower PIDs corresponded to lower NRS-A pain scores shows that the three treatment groups all had the same LS mean PID at 0.5 hours following study drug administration, and the MR-107A-02 group had a slightly higher LS mean PID than the Tramadol and Placebo groups at 1 hour. The MR-107A-02 and Tramadol groups had lower LS mean PIDs than the Placebo group from 1.5 hours to 48 hours, and the MR-107A-02 group had numerically lower LS mean PIDs than the Tramadol group from 2 through 48 hours following study drug administration.

NRS-R:

The PID (NRS-R) over time following study drug administration for the FAS shows that the PID at each time point was proportional to the NRS-R pain score at that time point, such that lower PIDs corresponded to lower NRS-R pain scores. The MR-107A-02 and Tramadol groups had lower LS mean PIDs than the Placebo group from 0.5 through 48 hours following study drug administration (i.e., all time points evaluated), and the MR-107A-02 group had numerically lower LS mean PIDs than the Tramadol group from 2 through 48 hours following study drug administration.

Time to Perceptible Pain Relief

The time to perceptible pain relief, which was measured by the two-stopwatch technique, was a secondary efficacy endpoint that was analyzed using Kaplan-Meir plots with censoring at the time of first rescue medication. Additional details on the analysis are provided below, and the post-hoc analyses for tramadol versus placebo are noted below.

FIG. 27 displays the Kaplan-Meier plot for the time to perceptible pain relief for the FAS. The median (95% CI) time to first perceptible pain relief in the MR-107A-02 group (0.9 [0.8, 1.0] hours) was lower than that in the Placebo group (1.1 [0.9, 2.1] hours). The log rank test yielded a nominally statistically significant p-value (p=0.014). The median (90% CI) time to first perceptible pain relief in the Tramadol group (0.9 [0.7, 1.5] hours) was also lower than that in the Placebo group. The log rank test yielded a nominally statistically significant p-value (p=0.035; post-hoc). Of the three treatment groups MR-107A-02 had the fastest time to first perceptible pain relief.

Time to Meaningful Pain Relief

The time to meaningful pain relief, which was measured by the two-stopwatch technique, was another secondary efficacy endpoint analyzed using Kaplan-Meir plots with censoring at the time of first rescue medication. Additional details on the analysis are provided below, and the post-hoc analyses for tramadol versus placebo are noted below.

FIG. 27 displays the Kaplan-Meier plot for the time to meaningful pain relief for the FAS. The median (CI) times to meaningful relief of pain was lower in the MR-107A-02 (3.7 hours [95% CI: 2.9, 5.3 hours]) than in the Tramadol group (5.0 hours [90% CI; 3.0, not available hours]). No median time was calculated for the Placebo group as <50% of participants had an event. The log rank test yielded a nominally statistically significant p-value (p=0.025 for MR-107A-02 versus placebo) but was not statistically significant for tramadol versus placebo (p=0.058; post-hoc).

Proportion of Participants with Overall Pain Reductions from Baseline of ≥30% and >50% Over Time Following Study Drug Administration The proportion of participants with an overall pain reduction of ≥30% and ≥50% from baseline within 0-4 hours, 0-8 hours, 0-12 hours, 12-24 hours, 0-24 hours, 24-48 hours, and 0-48 hours after the first dose were other secondary efficacy endpoints that were analyzed using the difference in proportions Z-test. Additional details on the planned analysis are provided below, and the post-hoc analyses for tramadol versus placebo are noted below.

Overall Pain Reduction≥30% from Baseline (NRS-A and NRS-R):

Proportion of participants with an overall pain reduction≥30% from baseline, using NRS-A for the FAS show that with increasing time intervals, the proportions of participants with an overall pain reduction≥30% from baseline (i.e., responders) increased within each treatment group; the proportions of responders were higher in the MR-107A-02 group than in the Placebo groups at all intervals (nominal p-values of p≤0.018). The proportions of responders were also higher in the Tramadol group than in the Placebo group for all intervals through 24 hours (nominal p-values of p≤0.049 [post-hoc]). For the interval of 0-48 hours, the proportion of participants with an overall pain reduction≥30% from baseline was similar between the Tramadol and Placebo groups (nominal p-values of p=0.184 [post-hoc]). The proportions of responders in the MR-107A-02 group were numerically larger than in the Tramadol group at all intervals.

Proportion of participants with an overall pain reduction≥30% from baseline, using NRS-R for the FAS show that with increasing time intervals, the proportions of participants with an overall pain reduction≥30% from baseline (i.e., responders) increased within each treatment group; the proportions of responders were higher in the MR-107A-02 and Tramadol groups than in the Placebo group at all intervals through 12 hours (nominal p-values of p≤0.004 for MR-107A-02 versus placebo and p≤0.012 [post-hoc] for tramadol versus placebo). The proportions of participants with an overall pain reduction≥30% from baseline, using NRS-R, was similar among the three groups at 0-48 hours (nominal p-values of p=0.230 for MR-107A-02 versus placebo and p=0.127 [post-hoc] for tramadol versus placebo). The proportions of responders in the MR-107A-02 group were numerically larger than in the Tramadol group for all intervals through 24 hours; for the interval of 0-48 hours, the proportion of responders in the MR-107A-02 and Tramadol groups were numerically similar.

Overall Pain Reduction≥50% from Baseline (NRS-A and NRS-R):

Proportions of participants with an overall pain reduction≥50% from baseline, using NRS-A for the FAS show that as for the proportions of participants with an overall pain reduction≥30% from baseline, the proportions of participants with an overall pain reduction≥50% from baseline (i.e., responders) increased within each treatment group with increasing time intervals; the proportions of responders were higher in the MR-107A-02 group than in the Placebo group at all intervals (nominal p-values of p≤0.036). The proportions of responders were also higher in the Tramadol group than the Placebo group at time intervals of 0-12 hours and 0-24 hours (nominal p-values of p≤0.043 [post-hoc]). For the intervals of 0-4 hours, 0-8 hours, and 0-48 hours, the proportions of participants with an overall pain reduction≥50% from baseline were similar between the Tramadol and Placebo groups (nominal p-values of p≤0.221 [post-hoc]). The proportions of responders in the MR-107A-02 group were numerically larger than in the Tramadol group at all intervals.

Proportions of participants with an overall pain reduction≥50% from baseline, using NRS-R for the FAS show that as for the proportions of participants with an overall pain reduction≥30% from baseline, the proportions of participants with an overall pain reduction≥50% from baseline (i.e., responders) increased within each treatment group with increasing time intervals; the proportions of responders were higher in the MR-107A-02 group than in the Placebo group at all intervals (nominal p-values of p<0.023). The proportions of responders were also higher in the Tramadol group than the Placebo group at time intervals of 0-4 hours, 0-12 hours, and 0-24 hours (nominal p-values of p≤0.029 [post-hoc]). For the intervals of 0-8 hours and 0-48 hours, the proportions of participants with an overall pain reduction≥50% from baseline were similar between the Tramadol and Placebo groups (nominal p-values of p≤0.097 [post-hoc]). The proportions of responders in the MR-107A-02 group were numerically larger than in the Tramadol group at all intervals.

Patient's Global Assessment of Pain Control from 0-24 Hours, 24-48 Hours, and on Day 9

The PGA of pain control within 0-24 hours and 24-48 hours after the first dose and at Day 9 were other secondary efficacy endpoints that were analyzed using the difference in proportions Z-test. Additional details on the planned analysis are provided below, and the post-hoc analyses are described below as well.

In-patient Treatment Phase:

The proportion of participants with "very good" or "excellent" PGA of pain control during the in-patient treatment phase for the FAS shows that from 0-24 hours to 24-48 hours, the proportions of participants with "very good" or "excellent" PGA of pain control (i.e., responders) increased within each treatment group. The proportions of responders was higher in the MR-107A-02 and Tramadol groups than in the Placebo group at both intervals (0-24 hours: nominal p-values of p=0.006 for MR-107A-02 versus placebo and p=0.008 for tramadol versus placebo [post-hoc] and 24-28 hours: nominal p-values of p<0.001 for MR-107A-02 versus placebo and p=0.007 for tramadol versus placebo [post-hoc]). Of the three treatment groups, MR-107A-02 had the greatest proportion of responders at the 24-48 hours interval.

Out-Patient Treatment Phase:

The proportion of participants with "very good" or "excellent" PGA of pain control during the out-patient treatment phase for the FAS shows that the proportions of responders at Day 9 in the MR-107A-02 and Tramadol Placebo groups was higher than in the Placebo group (nominal p-value of p=0.002 for MR-107A-02 versus placebo and p=0.021 for tramadol versus placebo [post-hoc]). Of the three treatment groups, MR-107A-02 had the greatest proportion of responders at Day 9.

Time to First Opioid (Oxycodone and/or Morphine) Rescue Medication Use

The time to first opioid (oxycodone and/or morphine) rescue medication use was another secondary efficacy endpoint that was analyzed using Kaplan-Meir plots. Participants who discontinued early were censored at the time of discontinuation. Additional details on the planned analysis are provided below, and the changes to the planned analyses and the tramadol versus placebo post-hoc analyses are noted below.

FIG. 29 displays the Kaplan-Meier plot for the time to first opioid (oxycodone and/or morphine) rescue medication use for the FAS. The median (CI) times to first opioid (oxycodone and/or morphine) rescue medication use in the MR-107A-02, Tramadol, and Placebo groups were not available as <50% of participants had an event. The log rank test yielded nominal p-values (p=0.006 for MR-107A-02 versus placebo and p=0.015 [post-hoc] for tramadol versus placebo). Of the three treatment groups, the Tramadol group had the largest 25th percentile time (80.2 hours), representing the time beyond which 25% of the participants had the event of interest (Q1). Corresponding values of Q1 for the MR-107A-02 and Placebo groups were 58.9 and 9.0 hours, respectively.

The Kaplan-Meier plot for the time to first opioid (oxycodone and/or morphine) rescue medication use for the FAS truncated to 200 hours after study drug administration.

Rescue Medication Use

Entire Treatment Phase:

APAP was the 1$^{st}$ step rescue medication during the entire treatment phase and was allowed at any time (up to 1 g [2×500 mg] q6h, maximum daily dose of 4 g) and shows that the mean (range) amount of APAP used in the MR-107A-02 group (3.61 g [0.5 g, 21.0 g]) was lower than in the Tramadol and Placebo groups (3.95 g [0.5 g, 22.0 g] and 4.52 g [1.0 g, 16.0 g], respectively) over the entire treatment phase.

During the entire treatment phase, participants in the MR-107A-02 group used the lowest amount of 1$^{st}$ step rescue medication (i.e., APAP) of the three treatment groups.

Of the participants in the MR-107A-02, Tramadol, and Placebo groups that completed study treatment in both the in- and out-patient treatment phases, 107 (48.0%), 40 (36.7%), and 54 (24.3%) participants, respectively, took no rescue medication during the entire treatment phase; the MR-107A-02 group had the highest proportion of participants reporting no rescue medication use during the entire treatment phase of all three treatment groups.

In-Patient Treatment Phase (i.e., 0-48 Hours after Randomization):

APAP was the 1$^{st}$ step rescue medication during the in-patient treatment phase and was allowed at any time (up to 1 g [2×500 mg] q6h, maximum daily dose of 4 g) and shows that the mean (range) amount of APAP used in the MR-107A-02 group (2.09 g [0.5 g, 6.0 g]) was numerically lower than in the Tramadol and Placebo groups (2.20 g [0.5 g, 6.0 g] and 2.77 g [1.0 g, 8.0 g], respectively) during the in-patient treatment phase.

During the in-patient treatment phase, participants in the MR-107A-02 group used the lowest amount of 1$^{st}$ step rescue medication (i.e., APAP) of the three treatment groups.

Of the participants in the MR-107A-02, Tramadol, and Placebo groups that completed study treatment in the in-patient treatment phase, 116 (51.3%), 49 (43.8%), and 70 (31.5%) participants, respectively, took no rescue medication during the in-patient treatment phase; the MR-107A-02 group had the highest proportion of participants reporting no rescue medication use during the in-patient treatment phase of all three treatment groups.

Out-Patient Treatment Phase (i.e., 5 Days Following Discharge):

APAP was the 1$^{st}$ step rescue medication during the in-patient treatment phase and was allowed at any time (up to 1 g [2×500 mg] q6h, maximum daily dose of 4 g) and shows that the mean (range) amount of APAP used in the MR-107A-02 group (3.69 g [0.5 g, 18.0 g]) was numerically higher than in the Tramadol Placebo and Placebo groups (3.27 g [0.7 g, 18.0 g] and 3.46 g [0.5 g, 12.0 g], respectively) during the out-patient treatment phase During the out-patient treatment phase, participants in the Tramadol Placebo group used the lowest amount of 1$^{st}$ step rescue medication (i.e., APAP) of the three treatment groups.

Of the participants in the MR-107A-02, Tramadol Placebo, and Placebo groups that completed study treatment in the out-patient treatment phase, 164 (73.2%), 60 (54.5%), and 115 (51.6%) participants, respectively, took no rescue medication during the out-patient treatment phase; the MR-107A-02 group had the highest proportion of participants reporting no rescue medication use during the out-patient treatment phase of all three treatment groups.

Time to First Rescue Medication Use:

The time to first rescue medication use was another secondary efficacy endpoint that was analyzed using Kaplan-Meir plots with censoring for participants who discontinued early at the time of discontinuation. Additional details on the planned analysis are provided below, and the changes to the planned analyses and post-hoc analyses for Tramadol versus placebo are noted below FIG. 30 displays the Kaplan-Meier plot for the time to first rescue medication use for the FAS. The median (CI) times to first rescue medication use in the MR-107A-02 and Tramadol groups (49.5 hours [95% CI: 7.1, not available hours] and 5.5 hours [90% CI: 3.4, 50.1 hours], respectively) were both longer than that in the Placebo group (3.6 hours [95% CI: 2.4, 5.2 hours]. The log rank test yielded nominal p-values (p<0.001 for MR-107A-02 versus placebo and p=0.004 [post-hoc] for tramadol versus placebo). The median time to first rescue medication was numerically larger for the MR-107A-02 group than for the Tramadol group.

The Kaplan-Meier plot for the time to first rescue medication use for the FAS truncated to 200 hours after study drug administration.

A summary of the MPADSS results at 24 hours, 48 hours, Visit 3, and ET for the FAS; the mean MPADSS within each treatment group increased slightly from 24 hours to 48 hours post-dose show that at 24 hours post-dose, the MR-107A-02 and Tramadol groups had similar mean (SD) MPADSS scores of 9.3 (1.08) and 9.4 (0.86), respectively, while the Placebo group score was 9.0 (1.22). At 48 hours post-dose and Follow-up (Visit 3), the three treatment groups had similar mean (SD) MPADSS (48 hours post-dose: 9.5 [1.14], 9.5 [0.94], and 9.5 [0.81] for the MR-107A-02, Tramadol, and Placebo groups, respectively; Follow-up: 9.7 [0.92], 9.5 [1.40], and 9.7 [0.88], respectively). Few participants provided MPADSS data at ET.

Overall Benefit of Analgesic Score at 24 Hours, 48 Hours, Visit 3 and Early Termination The OBAS at 24 hours, 48 hours, Visit 3, and ET was another secondary efficacy endpoint whose results were summarized using descriptive statistics. On the OBAS, a lower score was indicative of reduced pain intensity and ORAEs and higher patient satisfaction (Table 52).

A summary of the OBAS results at 24 hours, 48 hours, Visit 3, and ET for the FAS; the mean OBAS within each treatment group decreased slightly from 24 hours post-dose to Follow-up (Visit 3) shows that at 24 hours post-dose, 48 hours post-dose, and Follow-up, the mean (SD) OBAS was 3.6 (2.59), 2.6 (2.36), and 2.1 (2.46), respectively, for MR-107A-02; 4.5 (3.26), 3.0 (2.49), and 2.2 (1.98), respectively, for Placebo; and 4.1 (2.91), 3.3 (2.93), and 2.2 (2.20), respectively, for Tramadol. From 24 hours post-dose to Follow-up (Visit 3), the MR-107A-02 group had the lowest mean OBAS of all three treatment groups. Few participants provided OBAS data at ET.

Numeric Rating Scale with Activity at 24 Hours, 48 Hours, Visit 3 and Early Termination The NRS-A at 24 hours, 48 hours, Visit 3, and ET was another secondary efficacy endpoint whose results were summarized using descriptive statistics. On the NRS-A scale, a lower score was indicative of lower pain levels perceived by the participant when in a supine position and instructed to sit up. Measurements were obtained as soon as the participant sat up from the resting position.

A summary of the NRS-A results at 24 hours, 48 hours, Visit 3, and ET for the FAS; the mean NRS-A within each treatment group decreased from 24 hours post-dose to Follow-up (Visit 3) show that at 24 hours post-dose, 48 hours post-dose, and Follow-up, the mean (SD) NRS-A was 4.1 (2.47), 2.9 (2.18), and 1.6 (1.89), respectively, for MR-107A-02; 5.0 (2.38), 3.7 (2.29), and 1.6 (1.43), respectively, for Placebo; and 4.3 (2.26), 3.3 (2.29), and 1.9 (2.26), respectively, for Tramadol. From 24 to 48 hours post-dose, the MR-107A-02 group had the lowest mean NRS-A of the three treatment groups. Few participants provided data at ET for NRS-A.

Multicenter Studies

Study participants were recruited from 19 sites in the US; however, only 18 sites enrolled participants into the study. To take into account site effects, study site was considered as a fixed class effect during the analysis of the primary estimand and the analysis of the key secondary estimand. Small sites (sites which randomized less than 10 participants) were planned to be grouped for analysis.

Multiple Comparisons/Multiplicity, the Use of an "Efficacy Subset" of Participants, and Active-Control Studies Intended to Show Equivalence Same as in Example 3A above Drug Dose, Drug Concentration, and Relationships to Response The PK endpoints in this study were designed to measure exposure of MR-107A-02 following herniorrhaphy using sparse sampling and included $C_{max}$, $T_{max}$, $AUC_{0-4}$, $AUC_{0-24}$, and $AUC_{0-48}$ based on observed data. The meloxicam plasma concentrations were also utilized for subsequent analysis using Pop PK methods. The PK analyses were conducted for the PK Analysis Set with PK samples taken as described previously. Two participants (201-100 and 204-007) in the PK Analysis Set had insufficient concentration data and one participant (212-121) had a pre-dose concentration at Time 0 greater than $C_{max}$; therefore, PK data for these three participants were not included in the summary statistics of MR-107A-02 plasma concentrations and PK parameters FIG. 31 displays the mean meloxicam concentrations through 48 hours after the first dose for the PK Analysis Set (only for participants in the MR-107A-02 group with sufficient concentration data and with Time 0 pre-dose concentrations less than $C_{max}$). The mean plasma concentration increased through 4 hours after first dose with accumulation after the repeat 12-hour dosing. In general, the mean profile, showing rapid meloxicam absorption within 4 hours is in line with previous Phase 1 and Phase 2 study data.

Table 55 summarizes the mean PK parameters. Following the first dose of MR-107A-02 (15 mg), the geometric mean values (coefficient of variance [CV %]) for initial $C_{max}$ was 1254.225 (32.265) ng/mL and the corresponding median $T_{max}$ value was 2.170 hours. Repeat dosing of MR-107A-02 (15 mg BID) resulted in accumulation, with increasing mean meloxicam concentration values at the pre-dose timepoints of 12, 24, and 48 hours.

TABLE 55

Pharmacokinetic Parameters following Administration of MR-107A-02 (15 mg BID) (PK Analysis Set)

| Variable[1] Statistic | MR-107A-02 (15 mg BID) (N = 123) |
|---|---|
| n[2] | 120 |
| $C_{max}$ (ng/mL) | |
| First dosing period | 1254.225 (32.265) |
| Through 48 hours after first dose | 1977.135 (30.506) |
| $T_{max}$ (h) | |
| First dosing period | 2.170 (0.230, 12.370) |
| Through 48 hours after first dose | 46.785 (0.230, 48.500) |
| $AUC_{0-4}$ | 2826.690 (50.382) |
| $AUC_{0-24}$ | 22965.549 (25.393) |
| $AUC_{0-48}$ | 64193.226 (28.249) |

AUC = area under the concentration-versus-time curve;
$AUC_{0-4}$ = AUC from time 0 to 4 hours after dosing (first dose);
$AUC_{0-24}$ = AUC from time 0 to 24 hours after dosing (first dose);
$AUC_{0-48}$ = AUC from 0 to 48 hours after dosing (first dose but includes second dose);
BID = twice daily;
$C_{max}$ = maximum plasma concentration;
Max = maximum;
Min = minimum;
N = Number of participants per treatment group in the PK Analysis Set;
PK = pharmacokinetic;
$T_{max}$ = time to maximum plasma concentration;
q6h = Once every 6 hours
Note:
During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase).
[1]$T_{max}$ is presented as median (Min, Max); all other parameters are presented as geometric mean (coefficient of variance).
[2]Participants 201-100 and 204-007 were not included in the summary tables due to insufficient available concentration data and participant 212-121 was not included due to Time 0 pre-dose concentration greater than $C_{max}$. For $AUC_{0-48}$, n = 119.

Table 56 shows the same pK parameters as Table 55, with arithmetic mean instead of geometric mean calculations.

TABLE 56

Arithmetic Mean (% CV) MR-107A-02 PK Parameters, Herniorrhaphy

| Parameter | MR-107A-02 15 mg BID (n = 120) |
|---|---|
| Cmax, after 1$^{st}$ Dose (ng/ml) | 1317.608 (32.3%) |
| Cmax, overall (ng/mL) | 2064.250 (30.5%) |

TABLE 56-continued

Arithmetic Mean (% CV) MR-107A-02 PK Parameters, Herniorrhaphy

| Parameter | MR-107A-02 15 mg BID (n = 120) |
|---|---|
| Tmax, after 1st Dose (hr)[1] | 2.170 (0.230-12.370) |
| Tmax, overall (hr)1 | 46.785 (0.230-48.500) |
| $AUC_{0-4h}$ (ng*hr/mL) | 3265.689 (50.4%) |
| $AUC_{0-24h}$ (ng*hr/mL) | 23684.770 (25.4%) |
| $AUC_{0-48h}$ (ng*hr/mL) | 66664.373 (28.2%) |

[1]Median (Minimum-Maximum)

3B.7 Efficacy Conclusions from Study 3002

The primary objective of the study was to confirm the efficacy of MR-107A-02 in treating acute pain, following herniorrhaphy. The secondary efficacy objectives were to confirm the opioid-sparing effect associated with the use of MR-107A-02, to further confirm the efficacy of MR-107A-02 in participants following herniorrhaphy using additional efficacy measures, to confirm the association of clinical benefit with reduced opioid use, to confirm the efficacy of tramadol in the study, and to estimate the difference in efficacy between MR-107A-02 and tramadol. The study also measured the exposure of meloxicam after administration of MR-107A-02 (15 mg BID) in participants following herniorrhaphy.

Most participants (96.3% of all participants) were male, White (84.3%), and not Hispanic or Latino (66.3%). The mean age was 49.1 years (range 18 to 80 years), and most participants were <65 years of age (93.4%). The mean baseline NRS-R was 6.9 (range 3 to 10), and the mean baseline NRS-A was 7.8 (range 3 to 10). The three treatment groups were comparable with respect to demographic and baseline characteristics. The three treatment groups were also comparable with respect to common medical history and use of prior medications.

The FAS included 230, 115, and 227 participants in the MR-107A-02, Tramadol, and Placebo groups, respectively, which satisfied (marginally exceeded) the minimum treatment group size required to sufficiently power the study for the planned analyses of the primary and secondary estimands.

The primary efficacy estimand compared the $SPID_{0-48}$ (based on NRS-A scores) for the MR-107A-02 and Placebo group in the FAS using an ANCOVA model; rescue medication use was managed by the WLOCF approach, and missing data was managed by an MI approach. The study met the primary endpoint, as the difference in LS mean $SPID_{0-48}$ (95% CI) for MR-107A-02 versus placebo (50.1 [35.4, 64.8]) was statistically significant (p<0.001). The $SPID_{0-48}$ endpoint captures both the magnitude and duration of the analgesic effect, offering a comprehensive measure of treatment efficacy in acute pain. The statistically significant increase in $SPID_{0-48}$ for MR-107A-02 over placebo suggests that MR-107A-02 provides clinically meaningful pain relief within the critical early time window, when pain is typically most intense and patients are most vulnerable to breakthrough symptoms.

The key secondary efficacy estimand was the number of doses of opioid (oxycodone and/or morphine) rescue medication taken during the entire treatment phase. The analysis used a negative binomial regression model with a log link to compare the MR-107A-02 and Placebo groups in the FAS. Missing data was managed by an MI approach. The study met the key secondary endpoint, as the ratio of LS geometric means of the number of doses of opioid (oxycodone and/or morphine) medication (95% CI) for MR-107A-02 versus placebo (0.627 [0.419, 0.939]) was statistically significant (p=0.023). Notably, the LS geometric mean number of opioid doses (i.e., total opioid consumption) used in the MR-107A-02 group (0.002 doses) over the entire treatment phase was 50% lower than that in the Placebo group (0.004 doses). This substantial decrease in opioid use is expected to be clinically significant, given the risks associated with opioids including dependence, tolerance, and AEs.

Similarly, participants in the MR-107A-02 group took numerically fewer doses of opioids (oxycodone and/or morphine) than those in the Placebo group during all intervals (i.e., the last 24 and 36 hours before discharge, the in-patient treatment phase, and the out-patient treatment phase, 0-24 hours after randomization, and post-discharge phase [up to 30 days after discharge]). The differences were nominally statistically significant for the in-patient treatment phase (p=0.049 [nominal]); 0-24 hours after randomization (p=0.021 [nominal]) but were not statistically significant for all other intervals (p>0.05). These trends suggest that MR-107A-02 reduced the need for rescue opioid analgesia throughout both acute and extended recovery periods.

The proportion of participants who were opioid (oxycodone and/or morphine)-free over various intervals was also evaluated. During the entire treatment phase, 73% of participants in the MR-107A-02 group were opioid free. The MR-107A-02 group had 14.4% more opioid-free participants than the Placebo group, and the difference in proportions (95% CI) of opioid (oxycodone and/or morphine)-free participants in the MR-107A-02 and Placebo groups of 14.5% (5.9%, 23.1%) was statistically significant (p=0.001). During the last 24 hours before discharge, the MR-107A-02 group had a numerically larger proportion of opioid-free participants than the Placebo group (p=0.121 [nominal]). For all other intervals (i.e. the last 36 hours before discharge, the in-patient treatment phase, and the out-patient treatment phase, 0-24 hours after randomization, and post-discharge phase [up to 30 days after discharge]), the MR-107A-02 group had larger proportions of opioid-free participants than the Placebo group (p<0.049 [nominal]). This finding indicates that MR-107A-02 was not only effective in reducing moderate to severe pain but also generally reduced the need for opioid rescue medication to a meaningful degree. Across all pre-defined time intervals, the MR-107A-02 group consistently had higher proportions of opioid-free participants. These consistent observations across all intervals suggest a sustained benefit of MR-107A-02 in limiting opioid exposures throughout the whole recovery phase.

Importantly, regardless of this reduced opioid use, participants in the MR-107A-02 group also took less APAP rescue medication than those in the Placebo group during the entire treatment phase and during the in-patient treatment phase. This finding underscores the robustness of the analgesic effect provided by MR-107A-02 and suggests that the observed reduction in opioid use was not offset by increased use of non-opioid rescue medication during the entire treatment phase. A larger proportion of participants in the MR-107A-02 group also took no rescue medication during the entire treatment phase, in-patient treatment phase, and out-patient treatment phase than in the Placebo group. These results demonstrate that participants treated with MR-107A-02 required less rescue medication (APAP and opioid) than those in the Placebo group; this indicates that a meaningful subset of patients receiving MR-107A-02 achieved adequate pain control without the need for any rescue medication, reflecting both efficacy and convenience from a patient care perspective.

The participants in the MR-107A-02 group experienced faster times to first perceptible and meaningful relief of pain than those in the Placebo group ($p<0.025$ [nominal]). In addition, the time to first use of rescue medication, both overall and specifically for opioid rescue medication, was longer in the MR-107A-02 group than in the Placebo group ($p=0.006$ [nominal]). This indicates that participants receiving MR-107A-02 experienced more sustained analgesic effects and were less reliant on supplementary medication to manage their pain than those in the Placebo group.

The geometric mean (CV %) for initial $C_{max}$ of meloxicam after the first dose of MR-107A-02 was 1254.225 (32.265) ng/mL with a corresponding median $T_{max}$ value of 2.170 hours. Repeat dosing of MR-107A-02 (15 mg BID) resulted in accumulation, with increasing mean meloxicam concentration values at the pre-dose timepoints of 12, 24, and 48 hours. The $T_{max}$ after the first dose of 2.170 hours was in proximity to the median time to first perceptible relief of pain in the MR-107A-02 group of 0.9 hours, and the overall exposure of meloxicam with repeat dosing correlated with the long-term pain control observed in the MR-107A-02 group.

Other efficacy endpoints, including the SPID (based on NRS-A and NRS-R), PID (based on NRS-A and NRS-R), and the proportion of participants with overall pain reductions from baseline of ≥30% and ≥50%, indicated that participants in the MR-107A-02 group experienced better pain control over time than those in the Placebo group. These results suggest a robust analgesic effect of MR-107A-02 relative to placebo.

Collectively, these findings provide consistent and complementary evidence of the analgesic effectiveness and opioid-sparing potential of MR-107A-02. The ability to achieve pain relief while reducing overall reliance on both opioid and non-opioid rescue medications enhances the treatment's clinical utility and aligns with current guidelines aimed at minimizing unnecessary medication exposure and associated risks.

Concerning PGA of pain control, the proportion of participants rating their pain control as "very good" or "excellent" increased in all groups from 0-24 hours through Follow-up. Notably, MR-107A-02 showed advantages over placebo, with nominal p-values of $p\leq0.006$ at both 0-24 hours and 24-48 hours. Similarly, MR-107A-02 showed advantages over placebo from 0-48 hours (the out-patient treatment phase; $p=0.002$). As PGA includes the overall sense of satisfaction and control which plays a major role in emotional well-being and trust of the patient in the healthcare team, this outcome is clinically relevant.

The OBAS was used to measure both the relief from pain and any side effects of treatment. From 24 hours through Follow-up, MR-107A-02 showed a greater reduction in OBAS than placebo, suggesting better overall benefit with MR-107A-02, including pain relief and fewer side effects, than with placebo.

The NRS-A is an indicator for patient mobilization. Participants who received MR-107A-02 experienced greater relief in movement-related pain (as measured by NRS-A) than those who received placebo. Improvements were noticeable as early as 24 hours after the first dose and continued through 48 hours post-dose. Participants in the MR-107A-02 group reported the lowest average pain scores during activity from 24 hours post-dose through 48 hours post-dose, suggesting better support for early mobilization than placebo. The MPADSS is used to evaluate whether a patient has recovered sufficiently following surgery to be safely discharged. Although participants in both the MR-107A-02 and Placebo groups reported high MPADSS scores from 24 hours post-dose through Follow-up, at 24 hours the MR-107A-02 group demonstrated a mean (SD) MPADSS score of 9.3 (1.08), while the Placebo group had a mean (SD) score of 9.0 (1.22). The MPADDS defines a score of ≥9 as the threshold for safe discharge readiness. Therefore, with a higher mean score by 24 hours post-dose, participants in the MR-107A-02 group reached the minimum discharge criteria more reliably than those in the Placebo group despite their lower use of both APAP and opioid rescue medications; this shows a direct patient benefit related to reduced opioid analgesic use, such as reliable functional recovery for allowing discharge.

Sensitivity analyses were conducted to assess the robustness of the primary and key secondary efficacy results. These analyses, which included alternative statistical models and assumptions, yielded results that were consistent with those of the primary analyses. This consistency supports the reliability and validity of the primary conclusions drawn from the FAS. To further evaluate the treatment effect, the primary efficacy estimand was analyzed using both the mFAS and the PP Analysis Set. Results from these additional populations closely mirrored those observed in the FAS. This reinforces confidence in the observed treatment effect and indicates that the findings are not sensitive to population selection criteria or protocol adherence.

Subgroup analyses were performed for the primary and key secondary estimands as well as for the number and proportion of participants who were opioid (oxycodone and/or morphine) free during the entire treatment phase to examine potential differential treatment effects across demographic variables, including age, sex, and race. These analyses did not reveal any consistent or clinically meaningful interactions between treatment efficacy and subgroup membership; several subgroups had few participants, which limited the interpretation of these results. The efficacy of MR-107A-02 appeared generally stable across these subgroups of sufficient size (at least 20 participants), suggesting that its effect is broadly applicable within the studied population. Collectively, these findings from sensitivity, supplementary, and subgroup analyses support the robustness and generalizability of the primary and key secondary efficacy results.

To show the assay sensitivity, several analyses, including some post-hoc, were conducted to confirm the efficacy of tramadol in the study by comparing the effects of tramadol with placebo. Across endpoints, the efficacy of tramadol was demonstrated; tramadol displayed better pain control than placebo with higher $SPID_{0-48}$ ($p<0.001$ [nominal] for both NRS-A and NRS-R), higher SPID over other intervals ($p\leq0.028$ [nominal; post-hoc] for both NRS-A and NRS-R), faster time to perceptible pain relief ($p=0.035$ [nominal; post-hoc]), faster time to meaningful pain relief ($p=0.058$ [nominal; post-hoc]), longer time to first rescue medication, including opioid rescue ($p\leq0.015$ [nominal; post-hoc]), and with PGA of "very good" or "excellent" ($p\leq0.021$ [nominal; post-hoc]).

An analysis was also performed to estimate the difference in efficacy between MR-107A-02 and tramadol in treating acute pain following herniorrhaphy. Results demonstrated that MR-107A-02 was associated with greater pain relief than tramadol as measured by the primary endpoint, $SPID_{0-48}$ based on NRS-A ($p=0.025$ [nominal; post-hoc]), indicating an advantage over tramadol. Although no formal comparisons of MR-107A-02 and tramadol were made for other endpoints, participants in the MR-107A-02 group reported similar or better pain control as those in the Tramadol group with numerically larger LS mean SPIDs at each time interval evaluated, consistent numerically lower PIDs from 2 through 48 hours following study drug administration, suggesting a more robust and sustained analgesic effect. There were also similar proportions of participants with overall pain reductions from baseline of ≥30% or ≥50% in the MR-107A-02 and the Tramadol groups, suggesting similar pain relief from both treatments. In addition, participants in the MR-107A-02 group achieved perceptible and meaningful pain relief faster than those in the Tramadol group, further supporting the potential of MR-107A-02 to deliver rapid onset of pain relief. The time to first rescue medication (any type) was longer in the MR-107A-02 group, compared with those in the Tramadol group, consistent with the observed analgesic efficacy. Concerning PGA, the MR-107A-02 group had numerically higher proportions of participants reporting "very good" or "excellent" pain control than the Tramadol group at 24-48 hours post-dose and at Day 9, which suggests that participants experienced more effective results with MR-107A-02 than with tramadol at these timepoints. For MPADSS at 24 hours post-dose, a similar mean (SD) score was observed in the MR-107A-02 group (9.3 [1.08]) as in the Tramadol group (9.4 [0.86]), which suggests that on average, participants in the MR-107A-02 group reached the minimum discharge criteria as reliably and rapidly as those in the Tramadol group. For OBAS, at 24 and 48 hours after the first dose and at Follow-up, participants in the MR-107A-02 group had lower mean OBAS than those in the Tramadol group. This suggests a better overall benefit with MR-107A-02 than with tramadol, including pain relief and fewer side effects. For NRS-A, participants in the MR-107A-02 group reported lower pain scores during activity at 24- and 48-hours post-dose, suggesting better support for early mobilization than tramadol.

A numerically larger proportion of participants in the MR-107A-02 group than in the Tramadol group took no rescue medication during the in-patient treatment phase, out-patient treatment phase, and entire treatment phase. This suggests that MR-107A-02 may offer better baseline pain control than tramadol, which is consistent with the outcome for $SPID_{0-48}$. This is further supported by the finding that participants in the MR-107A-02 group used numerically less APAP as rescue medication than those in the Tramadol group during the in-patient treatment phase and entire treatment phase, suggesting that MR-107A-02 provided pain control with lower use of first step rescue medication.

Overall, MR-107A-02 is more effective in treating acute pain following herniorrhaphy than placebo and demonstrates pain control that is similar or better than that provided by the active, standard of care option, opioid-comparator, tramadol.

3B.8 Safety Evaluation

Extent of Exposure

Table 57 presents the extent of exposure by treatment phase for the Safety Analysis Set. Overall, the mean duration of exposure was 8.4 days (range 1 to 9 days [MR-107A-02 and Tramadol groups] and 1 to 10 days [Placebo group]), and the mean total number of doses taken was 17.4 doses (range 1 to 18 doses for all three treatment groups). During the in-patient treatment phase, the mean duration of exposure overall was 3.0 days (range 1 to 3 days for all three treatment groups), and the mean total number of doses taken overall was 7.9 doses (range 1 to 8 doses for all three treatment groups). During the out-patient treatment phase, the mean duration of exposure overall was 5.5 days (range 2 to 6 days [MR-107A-02], 1 to 6 days [Tramadol groups], and 1 to 7 days [Placebo group]), and the mean total number of doses taken overall was 9.7 doses (range 3 to 10 doses [MR-107A-02] and 1 to 10 doses [Tramadol and Placebo groups]). Within each treatment phase and overall, the duration of exposure and total number of doses taken were similar across treatment groups.

TABLE 57

Extent of Exposure (Safety Analysis Set)

| Phase<br>Variable<br>Statistic | MR-107A-02 (15 mg BID) → MR-107A-02 (15 mg BID) (N = 230) | Tramadol (50 mg q6h) → Placebo (N = 115) | Placebo → Placebo (N = 227) | (N = 572) Total |
|---|---|---|---|---|
| In-patient phase | | | | |
| Duration of exposure (days)[1] | | | | |
| n | 230 | 115 | 227 | 572 |
| Mean (SD) | 3.0 (0.20) | 3.0 (0.26) | 3.0 (0.20) | 3.0 (0.21) |
| Median | 3.0 | 3.0 | 3.0 | 3.0 |
| Min, Max | 1, 3 | 1, 3 | 1, 3 | 1, 3 |
| Total number of doses taken[2] | | | | |
| n | 230 | 115 | 227 | 572 |
| Mean (SD) | 7.9 (0.63) | 7.9 (0.86) | 7.9 (0.67) | 7.9 (0.69) |
| Median | 8.0 | 8.0 | 8.0 | 8.0 |
| Min, Max | 1, 8 | 1, 8 | 1, 8 | 1, 8 |
| Out-patient phase | | | | |
| Duration of exposure (days)[1] | | | | |
| n | 224 | 110 | 223 | 557 |
| Mean (SD) | 5.6 (0.63) | 5.4 (0.92) | 5.6 (0.64) | 5.5 (0.70) |
| Median | 6.0 | 6.0 | 6.0 | 6.0 |
| Min, Max | 2, 6 | 1, 6 | 1, 7 | 1, 7 |
| Total number of doses taken[2] | | | | |
| n | 224 | 110 | 223 | 557 |
| Mean (SD) | 9.8 (0.92) | 9.4 (1.67) | 9.9 (0.83) | 9.7 (1.09) |
| Median | 10.0 | 10.0 | 10.0 | 10.0 |
| Min, Max | 3, 10 | 1, 10 | 1, 10 | 1, 10 |
| Overall | | | | |
| Duration of exposure (days)[1] | | | | |
| n | 230 | 115 | 227 | 572 |
| Mean (SD) | 8.4 (1.21) | 8.1 (1.56) | 8.5 (1.11) | 8.4 (1.26) |
| Median | 9.0 | 8.0 | 9.0 | 9.0 |
| Min, Max | 1, 9 | 1, 9 | 1, 10 | 1, 10 |
| Total number of doses taken[2] | | | | |
| n | 230 | 115 | 227 | 572 |
| Mean (SD) | 17.4 (2.23) | 16.9 (3.03) | 17.6 (2.09) | 17.4 (2.37) |
| Median | 18.0 | 18.0 | 18.0 | 18.0 |
| Min, Max | 1, 18 | 1, 18 | 1, 18 | 1, 18 |

BID = Twice daily;
Max = Maximum;
Min = Minimum;
n = Number of participants;
N = Number of participants per treatment group in the Safety Analysis Set;
q6h = Once every 6 hours;
SD = Standard deviation
Note:
During the in-patient treatment phase, participants received MR-107A-02 (15 mg BID), tramadol (50 mg q6h), or placebo (q6h), and during the out-patient treatment phase, participants received either MR-107A-02 (15 mg BID) or placebo (BID); participants in the Tramadol group received placebo only during the out-patient treatment phase.
[1]Defined as: last dose date − first dose date + 1.

Adverse Events

Adverse events were summarized by treatment group for the in-patient and out-patient treatment phases individually; i the names of the three treatment groups contain the treatment that participants were assigned in that phase of the study (i.e., treatment during the in-patient treatment phase or treatment during the out-patient treatment phase). During the in-patient treatment phase, participants received MR-107A-02 (15 mg BID), tramadol (50 mg q6h), or placebo (q6h). During the out-patient treatment phase, participants received either MR-107A-02 (15 mg BID) or placebo (BID; see Table 52). To differentiate the participants who received tramadol (50 mg q6h) and placebo during the in-patient treatment phase, the out-patient treatment phase AE summary tables include the Tramadol Placebo and Placebo groups. All participants who received placebo during the out-patient treatment phase, regardless of their treatment during the in-patient treatment phase, are included in the All-Placebo group.

To simplify the discussion, the treatment groups are referenced as follows:

- MR-107A-02 group=MR-107A-02 (15 mg BID) during the in-patient treatment phase and MR-107A-02 (15 mg BID) during the out-patient treatment phase
- Tramadol group (referred to as the Tramadol Placebo group in tables and in the descriptions of the out-patient treatment phase=tramadol (50 mg q6h) during the in-patient treatment phase and placebo during the out-patient treatment phase
- Placebo group=placebo during both the in- and out-patient treatment phases
- All Placebo group=placebo during the out-patient treatment phase (includes participants who received either tramadol [50 mg q6h] or placebo during the in-patient treatment phase)

Brief Summary of Adverse Events

No deaths were reported at any time during the study.

In-Patient Treatment Phase:

Table 57 presents an overall summary of TEAEs in the Safety Analysis Set during the in-patient treatment phase. Overall, 237 (41.4%) participants reported 443 TEAEs. The incidence of TEAEs was higher in the Tramadol and Placebo groups (45.2% and 45.8%, respectively) than in the MR-107A-02 group (35.2%). One hundred seven (18.7%) participants reported 181 TEAEs related to study drug; the incidence of related TEAEs was similar in all three treatment groups. One hundred forty-two (24.8%) participants reported 202 opioid-related TEAEs; the incidence of opioid-related TEAEs was numerically higher in the Tramadol group (33.9%) than in the MR-107A-02 and Placebo groups (19.1% and 26.0%, respectively).

One serious TEAE was reported in the Placebo group. Most TEAEs were either mild or moderate in severity, with 4 (0.7%) participants overall reporting 7 severe TEAEs; all participants reporting severe TEAEs were in the Placebo group. No participant in the MR-107A-02 or Tramadol groups reported a severe TEAE. Two (0.3%) participants overall reported TEAEs of special interest (1 [0.4%] in MR-107A-02 group and 1 [0.9%] in the Tramadol group). Two (0.3%) participants overall reported one TEAE each leading to study discontinuation (1 [0.9%] participant in the Tramadol group and 1 [0.4%] participant in the Placebo group).

TABLE 57

Overview of Treatment-emergent Adverse Events: In-patient (Safety Analysis Set)

| Category, n (%) m | MR-107A-02 BID) (15 mg (N = 230) | Tramadol (50 mg q6h) (N = 115) | Placebo (N = 227) | Total (N = 572) |
|---|---|---|---|---|
| TEAEs | 81 (35.2) 131 | 52 (45.2) 107 | 104 (45.8) 205 | 237 (41.4) 443 |
| Serious TEAEs | 0 | 0 | 1 (0.4) 1 | 1 (0.2) 1 |
| Severe TEAEs | 0 | 0 | 4 (1.8) 7 | 4 (0.7) 7 |
| TEAEs related to study drug[1] | 42 (18.3) 63 | 24 (20.9) 47 | 41 (18.1) 71 | 107 (18.7) 181 |
| TEAEs leading to study discontinuation | 0 | 1 (0.9) 1 | 1 (0.4) 1 | 2 (0.3) 2 |
| Opioid related TEAEs | 44 (19.1) 58 | 39 (33.9) 65 | 59 (26.0) 79 | 142 (24.8) 202 |
| TEAEs of special interest | 1 (0.4) 1 | 1 (0.9) 1 | 0 | 2 (0.3) 2 |
| TEAEs leading to death | 0 | 0 | 0 | 0 |

AE = Adverse event;
BID = Twice daily;
m = number of events;
n = Number of participants;
N = Number of participants per treatment group in the Safety Analysis Set;
q6h = Once every 6 hours;
TEAE = Treatment-emergent adverse event;
Note:
During the in-patient treatment phase, participants received MR-107A-02 (15 mg BID), tramadol (50 mg q6h), or placebo (q6h).
Note:
Percentages were based on the number of participants in the Safety Analysis Set, in each treatment group, for that study phase.
Note:
TEAEs in the in-patient treatment phase were those with an onset date on or after the first dose of study drug administration in the in-patient treatment phase and before the first dose of study drug administration in the out-patient treatment phase.
Note:
TEAEs were summarized according to the last treatment that the participant received prior to the start of that AE.
[1]Related TEAEs were those reported as possibly, probably, or definitely related to study treatment. Missing relationships were considered related.
Note:
Study phase was defined as follows; AEs during the in-patient treatment phase occurred after the first dose of study drug administration in the in-patient treatment phase and before the first dose of study drug administration in the out-patient treatment phase. Adverse events during the out-patient treatment phase occurred after the first dose of study drug administration in the out-patient treatment phase. Adverse events occurring prior to study drug administration did not have a study phase assigned.

Out-Patient Treatment Phase:

Table 58 presents an overall summary of TEAEs in the Safety Analysis Set during the out-patient treatment phase. Overall, 198 (35.5%) participants reported 419 TEAEs with similar incidence of TEAEs among the treatment groups. Sixty-three (11.3%) participants reported 101 TEAEs related to study drug. Ninety-one (16.3%) participants reported 115 opioid-related TEAEs, with a similar incidence of opioid-related TEAEs among the treatment groups. Most TEAEs were either mild or moderate in severity, with 4 (0.7%) participants overall reporting 5 severe TEAEs (3 [1.3%] participants in the MR-107A-02 group and 1 [0.4%] participant in the Tramadol Placebo group (also counted in the All-Placebo group). Four (0.7%) participants reported 4 serious TEAEs (3 [1.3%] in the MR-107A-02 group and 1 [0.4%] in the Placebo group (also counted in the All-Placebo group). Four (0.7%) participants reported 4 TEAEs of special interest (2 [0.9%] participants in the MR-107A-02 group, 1 [0.9%] in the Tramadol Placebo group, and 1 [0.4%] in the Placebo Group). One (0.4%) participant in the Placebo group reported 1 TEAE leading to study discontinuation during the out-patient treatment phase.

TABLE 58

Overview of Treatment-emergent Adverse Events: Out-patient (Safety Analysis Set)

| Category, n (%) m | MR-107A-02 (15 mg BID) (N = 224) | Tramadol Placebo (N = 110) | Placebo (N = 223) | All Placebo (N = 333) | Total (N = 557) |
|---|---|---|---|---|---|
| TEAEs | 80 (35.7) 179 | 41 (37.3) 102 | 77 (34.5) 138 | 118 (35.4) 240 | 198 (35.5) 419 |
| Serious TEAEs | 3 (1.3) 3 | 0 | 1 (0.4) 1 | 1 (0.3) 1 | 4 (0.7) 4 |
| Severe TEAEs | 3 (1.3) 4 | 0 | 1 (0.4) 1 | 1 (0.3) 1 | 4 (0.7) 5 |
| TEAEs related to study drug[1] | 26 (11.6) 47 | 15 (13.6) 25 | 22 (9.9) 29 | 37 (11.1) 54 | 63 (11.3) 101 |
| TEAEs leading to study discontinuation | 0 | 0 | 1 (0.4) 1 | 1 (0.3) 1 | 1 (0.2) 1 |
| Opioid related TEAEs | 35 (15.6) 45 | 23 (20.9) 30 | 33 (14.8) 40 | 56 (16.8) 70 | 91 (16.3) 115 |
| TEAEs of special interest | 2 (0.9) 2 | 1 (0.9) 1 | 1 (0.4) 1 | 2 (0.6) 2 | 4 (0.7) 4 |
| TEAEs leading to death | 0 | 0 | 0 | 0 | 0 |

AE = Adverse event;
BID = Twice daily;
m = number of events;
n = Number of participants;
N = Number of participants per treatment group in the Safety Analysis Set;
TEAE = Treatment-emergent adverse event
Note:
During the out-patient treatment phase, participants received either MR-107A-02 (15 mg BID) or placebo (BID); participants in the Tramadol group received placebo only during the out-patient treatment phase and are labelled as Tramadol Placebo.
Note:
Percentages were based on the number of participants in the Safety Analysis Set, in each treatment group, for that study phase.
Note:
TEAEs in the out-patient treatment phase were those that started on or after the first dose of study drug administration in the out-patient treatment phase.
Note:
TEAEs were summarized according to the last treatment that the participant received prior to the start of that AE.
Note:
The All-Placebo treatment column summarizes participants who were randomized to the Tramadol or Placebo groups and that received placebo during the out-patient treatment phase.
[1]Related TEAEs were those reported as possibly, probably, or definitely related to study treatment. Missing relationships were considered related.
Note:
Study phase was defined as follows; AEs during the in-patient treatment phase occurred after the first dose of study drug administration in the in-patient treatment phase and before the first dose of study drug administration in the out-patient treatment phase. Adverse events during the out-patient treatment phase occurred after the first dose of study drug administration in the out-patient treatment phase. Adverse events occurring prior to study drug administration did not have a study phase assigned.

Display of Adverse Events

All summary tabulations of AEs are provided in sections further below (all AEs) and by-participant listings of selected categories of AEs are provided in sections below (SAEs, severe AEs, AEs related to study drug, ORAEs, AESIs, AEs leading to study discontinuation, and AEs leading to death).

Analysis of Adverse Events

Common Treatment-Emergent Adverse Events

In-Patient Treatment Phase:

TEAEs by SOC and PT reported in the Safety Analysis Set during the out-patient treatment phase. The most common (≥5% of participants overall) SOCs of TEAEs included gastrointestinal disorders (134 [23.4%] participants), nervous system disorders (73 [12.8%] participants), and skin and subcutaneous tissue disorders (56 [9.8%] participants) show that of the most common SOC of TEAEs, the incidence of gastrointestinal disorders was numerically higher in the Tramadol group (33.0%) than in the MR-107A-02 and Placebo groups (17.0% and 25.1%, respectively).

Table 59 displays the most common (≥2% of participants overall) PTs of TEAEs reported during the in-patient treatment phase. The most common PTs included constipation (72 [12.6%] participants), nausea (50 [8.7%] participants), dizziness and hyperhidrosis (both 38 [6.6%] participants), headache (35 [6.1%]), pruritus (20 [3.5%]), and vomiting (12 [2.1%]). Of the most common PTs of TEAEs, the incidences of constipation, dizziness, and vomiting were numerically higher in the Tramadol group (20.9%, 11.3%, and 5.2% respectively) than in the MR-107A-02 and Placebo groups (constipation: 7.0% and 14.1%, respectively; dizziness: 5.7% and 5.3%; and vomiting: 1.7% and 0.9%).

TABLE 59

Most Common (≥2% of Participants Overall) Treatment-emergent Adverse Events by Preferred Term: In-patient (Safety Analysis Set)

| Preferred Term | MR-107A-02 (15 mg BID) (N = 230) | Tramadol (50 mg q6h) (N = 115) | Placebo (N = 227) | Total (N = 572) |
|---|---|---|---|---|
| Constipation | 16 (7.0) | 24 (20.9) | 32 (14.1) | 72 (12.6) |
| Nausea | 16 (7.0) | 15 (13.0) | 19 (8.4) | 50 (8.7) |
| Dizziness | 13 (5.7) | 13 (11.3) | 12 (5.3) | 38 (6.6) |
| Hyperhidrosis | 15 (6.5) | 8 (7.0) | 15 (6.6) | 38 (6.6) |
| Headache | 12 (5.2) | 5 (4.3) | 18 (7.9) | 35 (6.1) |

TABLE 59-continued

Most Common (≥2% of Participants Overall) Treatment-emergent Adverse Events by Preferred Term: In-patient (Safety Analysis Set)

| Preferred Term | MR-107A-02 (15 mg BID) (N = 230) | Tramadol (50 mg q6h) (N = 115) | Placebo (N = 227) | Total (N = 572) |
|---|---|---|---|---|
| Pruritus | 7 (3.0) | 5 (4.3) | 8 (3.5) | 20 (3.5) |
| Vomiting | 4 (1.7) | 6 (5.2) | 2 (0.9) | 12 (2.1) |

AE = Adverse event;
BID = Twice daily;
MedDRA = Medical Dictionary for Regulatory Activities;
n = Number of participants;
N = Number of participants per treatment group in the Safety Analysis Set;
q6h = Once every 6 hours;
TEAE = Treatment-emergent adverse event
Note:
During the in-patient treatment phase, participants received MR-107A-02 (15 mg BID), tramadol (50 mg q6h), or placebo (q6h).
Note:
Percentages were based on the number of participants in the Safety Analysis Set, in each treatment group, for that study phase.
Note:
TEAEs in the in-patient treatment phase were those with an onset date on or after the first dose of study drug administration in the in-patient treatment phase and before the first dose of study drug administration in the out-patient treatment phase.
Note:
TEAEs were summarized according to the last treatment that the participant received prior to the start of that AE.
Note:
Participants with multiple events in a preferred term were counted only once for that preferred term.
Note:
All terms were coded using MedDRA Version 26.1 and sorted in descending order of frequency in the Total group for preferred terms.
Note:
Study phase was defined as follows; AEs during the in-patient treatment phase occurred after the first dose of study drug administration in the in-patient treatment phase and before the first dose of study drug administration in the out-patient treatment phase. Adverse events during the out-patient treatment phase occurred after the first dose of study drug administration in the out-patient treatment phase. Adverse events occurring prior to study drug administration did not have a study phase assigned.

Out-Patient Treatment Phase:

TEAEs by SOC and PT reported in the Safety Analysis Set during the out-patient treatment phase show that the most common (≥5% of participants overall) SOCs of TEAEs included gastrointestinal disorders (108 [19.4%] participants), general disorders and administration site conditions (38 [6.8%] participants), skin and subcutaneous tissue disorders (35 [6.3%] participants), and nervous system disorders (33 [5.9%] participants). Incidence of the most common SOC of TEAEs were generally similar between the treatment groups.

Table 60 displays the most common (≥2% of participants overall) PTs of TEAEs reported during the out-patient treatment phase. The most common PTs included constipation (56 [10.1%] participants), diarrhea (24 [4.3%] participants), nausea (20 [3.6%] participants), fatigue (19 [3.4%] participants), dyspepsia (16 [2.9%] participants), rash and dizziness (15 [2.7%] participants each), abdominal pain, pruritus, and headache (13 [2.3%] participants each). Incidence of the most common PTs of TEAEs was generally similar between treatment groups.

TABLE 60

Most Common (≥2% of Participants Overall) Treatment-emergent Adverse Events, Preferred Term: Out-patient (Safety Analysis Set)

| Preferred Term | MR-107A-02 (15 mg BID) (N = 224) | Tramadol Placebo (N = 110) | Placebo (N = 223) | All Placebo (N = 333) | Total (N = 557) |
|---|---|---|---|---|---|
| Constipation | 21 (9.4) | 16 (14.5) | 19 (8.5) | 35 (10.5) | 56 (10.1) |
| Diarrhea | 11 (4.9) | 5 (4.5) | 8 (3.6) | 13 (3.9) | 24 (4.3) |
| Nausea | 8 (3.6) | 7 (6.4) | 5 (2.2) | 12 (3.6) | 20 (3.6) |

TABLE 60-continued

Most Common (≥2% of Participants Overall) Treatment-emergent Adverse Events, Preferred Term: Out-patient (Safety Analysis Set)

| Preferred Term | MR-107A-02 (15 mg BID) (N = 224) | Tramadol Placebo (N = 110) | Placebo (N = 223) | All Placebo (N = 333) | Total (N = 557) |
|---|---|---|---|---|---|
| Fatigue | 8 (3.6) | 6 (5.5) | 5 (2.2) | 11 (3.3) | 19 (3.4) |
| Dyspepsia | 9 (4.0) | 3 (2.7) | 4 (1.8) | 7 (2.1) | 16 (2.9) |
| Rash | 8 (3.6) | 4 (3.6) | 3 (1.3) | 7 (2.1) | 15 (2.7) |
| Dizziness | 5 (2.2) | 4 (3.6) | 6 (2.7) | 10 (3.0) | 15 (2.7) |
| Abdominal pain | 8 (3.6) | 3 (2.7) | 2 (0.9) | 5 (1.5) | 13 (2.3) |
| Pruritus | 5 (2.2) | 2 (1.8) | 6 (2.7) | 8 (2.4) | 13 (2.3) |
| Headache | 2 (0.9) | 4 (3.6) | 7 (3.1) | 11 (3.3) | 13 (2.3) |

AE = Adverse event; BID = Twice daily; MedDRA = Medical Dictionary for Regulatory Activities; n = Number of participants; N = Number of participants per treatment group in the Safety Analysis Set; TEAE = Treatment-emergent adverse event
Note:
During the out-patient treatment phase, participants received either MR-107A-02 (15 mg BID) or placebo (BID); participants in the Tramadol group received placebo only during the out-patient treatment phase and are labelled as Tramadol Placebo.
Note:
Percentages were based on the number of participants in the Safety Analysis Set, in each treatment group, for that study phase.
Note:
TEAEs in the out-patient treatment phase were those that started on or after the first dose of study drug administration in the out-patient treatment phase.
Note:
TEAEs were summarized according to the last treatment that the participant received prior to the start of that AE.
Note:
Participants with multiple events in a preferred term were counted only once for that preferred term.
Note:
All terms were coded using MedDRA Version 26.1 and sorted in descending order of frequency in the Total group for preferred terms.
Note:
The All-Placebo treatment column summarizes participants who were randomized to the Tramadol or Placebo groups and who received placebo during the out-patient treatment phase.
Note:
Study phase was defined as follows; AEs during the in-patient treatment phase occurred after the first dose of study drug administration in the in-patient treatment phase and before the first dose of study drug administration in the out-patient treatment phase. Adverse events during the out-patient treatment phase occurred after the first dose of study drug administration in the out-patient treatment phase. Adverse events occurring prior to study drug administration did not have a study phase assigned.

Severity of Treatment-Emergent Adverse Events

In-Patient Treatment Phase:

TEAEs by SOC and PT reported during the in-patient treatment phase for the Safety Analysis Set show that overall, 4 (0.7%) participants (all in the Placebo group [1.8%]) reported severe TEAEs, with the PTs of headache and hypertension each in 1 (0.2%) participant; the PTs of ileus, abdominal pain, and nausea in another 1 (0.2%) participant; and the PTs of hypotension and bradycardia in the other 1 (0.2%) participant. No severe TEAEs were reported in the MR-107A-02 or Tramadol groups.

Out-Patient Treatment Phase:

TEAEs by SOC and PT reported during the out-patient treatment phase for the Safety Analysis Set show that overall, 4 (0.7%) participants reported severe TEAEs with the PTs of groin abscess and postoperative wound infection each in 1 (0.4%) participant in the MR-107A-02 group; the PTs of peptic ulcer haemorrhage and anaemia postoperative in the other 1 (0.4%) participant in the MR-107A-02 group; and the PT of acute kidney injury in 1 (0.4%) participant in the Placebo group (also counted in the All Placebo group [0.3%]). No severe TEAEs were reported in the Tramadol Placebo group.

Relationship of Treatment-Emergent Adverse Events to Study Drug

In-Patient Treatment Phase:

TEAEs related to study drug by SOC and PT reported during the in-patient treatment phase for the Safety Analysis Set show that overall, 107 (18.7%) participants reported TEAEs related to study drug. The most common (≥5% of participants overall) SOCs of related TEAEs included gastrointestinal disorders (67 [11.7%] participants) and nervous system disorders (30 [5.2%] participants). The most common (≥2% of participants overall) PTs of related TEAEs included constipation (36 [6.3%] participants), nausea (31 [5.4%] participants), dizziness (17 [3.0%] participants), headache and hyperhidrosis (13 [2.3%] participants each), and pruritus (12 [2.1%] participants). The incidences of the most common SOCs and PTs of related TEAEs, except the SOC of nervous system disorders and the PT of headache, were numerically higher in the Tramadol group than in the MR-107A-02 and Placebo groups during the in-patient treatment phase.

Out-Patient Treatment Phase:

TEAEs related to study drug by SOC and PT reported during the out-patient treatment phase for the Safety Analysis Set show that overall, 63 (11.3%) participants reported TEAEs related to study drug. The most common (≥5% of participants overall) SOCs of related TEAEs included gastrointestinal disorders (43 [7.7%] participants). The most common (≥2% of participants overall) PTs of related TEAEs included constipation (19 [3.4%] participants). The incidences of the most common SOCs and PTs were numerically higher in the Tramadol Placebo group than in the MR-107A-02 and Placebo groups during the out-patient treatment phase.

Deaths, Other Serious Adverse Events, and Other Significant Adverse Events Listing of Deaths, Other Serious Adverse Events, and Other Significant Adverse Events Deaths No deaths were reported in this study Other Serious Adverse Events In-Patient Treatment Phase:

TEAEs by SOC and PT reported during the in-patient treatment phase for the Safety Analysis Set show that overall, 1 (0.2%) participant (in the Placebo group [0.4%]) reported a serious TEAE with the PT of ileus. No serious TEAEs were reported in the MR-107A-02 or Tramadol groups.

Out-Patient Treatment Phase:

Table 61 presents a summary of serious TEAEs by SOC and PT reported during the out-patient treatment phase for the Safety Analysis Set. Overall, 4 (0.7%) participants (3 [1.3%] participants in the MR-107A-02 group and 1 [0.4%] participant in the Placebo group; also counted in the All Placebo group [0.3%]) reported at least one serious TEAE with PTs of groin abscess, postoperative wound infection, and peptic ulcer hemorrhage (1 [0.4%] participant each in the MR-107A-02 group), and acute kidney injury (1 [0.4%] participant in the Placebo group).

TABLE 61

Serious Treatment-emergent Adverse Events, by System Organ Class and Preferred Term: Out-patient (Safety Analysis Set)

| System Organ Class Preferred Term | MR-107A-02 (15 mg BID) (N = 224) | Tramadol Placebo (N = 110) | Placebo (N = 223) | All Placebo (N = 333) | Total (N = 557) |
|---|---|---|---|---|---|
| Any Serious TEAE, n (%) | 3 (1.3) | 0 | 1 (0.4) | 1 (0.3) | 4 (0.7) |
| Infections and infestations | 2 (0.9) | 0 | 0 | 0 | 2 (0.4) |
| Groin abscess | 1 (0.4) | 0 | 0 | 0 | 1 (0.2) |
| Postoperative wound infection | 1 (0.4) | 0 | 0 | 0 | 1 (0.2) |
| Gastrointestinal disorders | 1 (0.4) | 0 | 0 | 0 | 1 (0.2) |
| Peptic ulcer hemorrhage | 1 (0.4) | 0 | 0 | 0 | 1 (0.2) |
| Renal and urinary disorders | 0 | 0 | 1 (0.4) | 1 (0.3) | 1 (0.2) |
| Acute kidney injury | 0 | 0 | 1 (0.4) | 1 (0.3) | 1 (0.2) |

AE = Adverse event; BID = Twice daily; MedDRA = Medical Dictionary for Regulatory Activities; n = Number of participants; N = Number of participants per treatment group in the Safety Analysis Set; TEAE = Treatment-emergent adverse event Note:

During the out-patient treatment phase, participants received either MR-107A-02 (15 mg BID) or placebo (BID); participants in the Tramadol group received placebo only during the out-patient treatment phase and are labelled as Tramadol Placebo.

Note:

Percentages were based on the number of participants in the Safety Analysis Set, in each treatment group, for that study phase.

Note:

TEAEs in the out-patient treatment phase were those that started on or after the first dose of study drug administration in the out-patient treatment phase.

Note:

TEAEs were summarized according to the last treatment that the participant received prior to the start of that AE.

Note:

Participants with multiple events in a system organ class/preferred term were counted only once for that system organ class/preferred term.

Note:

All terms were coded using MedDRA Version 26.1 and sorted in descending order of frequency in the Total group for both system organ classes and preferred terms.

Note:

The All-Placebo treatment column summarizes participants who were randomized to the Tramadol or Placebo groups and who received placebo during the out-patient treatment phase.

TABLE 61-continued

Serious Treatment-emergent Adverse Events, by System Organ Class and Preferred Term: Out-patient (Safety Analysis Set)

| System Organ Class Preferred Term | MR-107A-02 (15 mg BID) (N = 224) | Tramadol Placebo (N = 110) | Placebo (N = 223) | All Placebo (N = 333) | Total (N = 557) |
|---|---|---|---|---|---|

Note:

Study phase was defined as follows; AEs during the in-patient treatment phase occurred after the first dose of study drug administration in the in-patient treatment phase and before the first dose of study drug administration in the out-patient treatment phase. Adverse events during the out-patient treatment phase occurred after the first dose of study drug administration in the out-patient treatment phase. Adverse events occurring prior to study drug administration did not have a study phase assigned.

Other Significant Adverse Events-Adverse Events Leading to Study Discontinuation In-Patient Treatment Phase:

TEAEs leading to study discontinuation reported during the in-patient treatment phase by SOC and PT for the Safety Analysis Set shows that overall, 2 (0.3%) participants reported at least one TEAE leading to study discontinuation with the PTs of constipation (1 [0.9%] participant in the Tramadol group) and ileus (1 [0.4%] participant in the Placebo group).

Out-Patient Treatment Phase:

TEAEs leading to study discontinuation reported during the out-patient treatment phase by SOC and PT for the Safety Analysis Set shows that overall, 1 (0.2%) participant reported at least one TEAE leading to study discontinuation with the PT of gout (1 [0.4%] participant in the Placebo group; also counted in the All-Placebo group [0.3%]).

Adverse Events Leading to Treatment Discontinuation

In-Patient Treatment Phase:

Table 62 presents TEAEs leading to treatment discontinuation reported during the in-patient treatment phase by SOC and PT for the Safety Analysis Set. Overall, 5 (0.9%) participants reported at least one TEAE leading to treatment discontinuation. Reported PTs included constipation with an incidence of 2 (0.3%) participants, and alanine aminotransferase increased, aspartate aminotransferase increased, dizziness, abdominal pain, ileus, and dehydration, with an incidence of 1 (0.2%) participant each. Events reported in the MR-107A-02 group consisted of constipation in 1 (0.4%) participant.

The events of constipation and ileus reported by 1 participant in the Tramadol group (0.9%) and Placebo (0.4%) group, respectively, also led to study discontinuation.

TABLE 62

Treatment-emergent Adverse Events Leading to Treatment Discontinuation, by System Organ Class and Preferred Term: In-patient (Safety Analysis Set)

| System Organ Class Preferred Term | MR-107A-02 (15 mg BID) (N = 230) | Tramadol (50 mg q6h) (N = 115) | Placebo (N = 227) | Total (N = 572) |
|---|---|---|---|---|
| Any TEAE Leading to Treatment Discontinuation, n (%) | 1 (0.4) | 3 (2.6) | 1 (0.4) | 5 (0.9) |
| Gastrointestinal disorders | 1 (0.4) | 1 (0.9) | 1 (0.4) | 3 (0.5) |
| Constipation | 1 (0.4) | 1 (0.9) | 0 | 2 (0.3) |
| Abdominal pain | 0 | 0 | 1 (0.4) | 1 (0.2) |
| Ileus | 0 | 0 | 1 (0.4) | 1 (0.2) |
| Investigations | 0 | 1 (0.9) | 0 | 1 (0.2) |
| Alanine aminotransferase increased | 0 | 1 (0.9) | 0 | 1 (0.2) |
| Aspartate aminotransferase increased | 0 | 1 (0.9) | 0 | 1 (0.2) |
| Metabolism and nutrition disorders | 0 | 0 | 1 (0.4) | 1 (0.2) |
| Dehydration | 0 | 0 | 1 (0.4) | 1 (0.2) |
| Nervous system disorders | 0 | 1 (0.9) | 0 | 1 (0.2) |
| Dizziness | 0 | 1 (0.9) | 0 | 1 (0.2) |

AE = Adverse event; BID = Twice daily; MedDRA = Medical Dictionary for Regulatory Activities; n = Number of participants; N = Number of participants per treatment group in the Safety Analysis Set; TEAE = Treatment-emergent adverse event Note:

During the out-patient treatment phase, participants received either MR-107A-02 (15 mg BID) or placebo (BID); participants in the Tramadol group received placebo only during the out-patient treatment phase and are labelled as Tramadol Placebo.

Note:

Percentages were based on the number of participants in the Safety Analysis Set, in each treatment group, for that study phase.

Note:

TEAEs in the out-patient treatment phase were those that started on or after the first dose of study drug administration in the out-patient treatment phase.

Note:

TEAEs were summarized according to the last treatment that the participant received prior to the start of that AE.

TABLE 62-continued

Treatment-emergent Adverse Events Leading to Treatment Discontinuation, by System Organ Class and Preferred Term: In-patient (Safety Analysis Set)

| System Organ Class Preferred Term | MR-107A-02 (15 mg BID) (N = 230) | Tramadol (50 mg q6h) (N = 115) | Placebo (N = 227) | Total (N = 572) |
|---|---|---|---|---|

Note:
Participants with multiple events in a system organ class/preferred term were counted only once for that system organ class/preferred term.
Note:
All terms were coded using MedDRA Version 26.1 and sorted in descending order of frequency in the Total group for both system organ classes and preferred terms.
Note:
The All-Placebo treatment column summarizes participants who were randomized to the Tramadol or Placebo groups and who received placebo during the out-patient treatment phase.
Note:
Study phase was defined as follows; AEs during the in-patient treatment phase occurred after the first dose of study drug administration in the in-patient treatment phase and before the first dose of study drug administration in the out-patient treatment phase. Adverse events during the out-patient treatment phase occurred after the first dose of study drug administration in the out-patient treatment phase. Adverse events occurring prior to study drug administration did not have a study phase assigned.

Out-Patient Treatment Phase:

Table 63 presents TEAEs leading to treatment discontinuation reported during the out-patient treatment phase by SOC and PT for the Safety Analysis Set. Overall, 6 (1.1%) participants reported at least one TEAE leading to treatment discontinuation. Reported PTs included nausea with an incidence of 2 (0.4%) participants, and diarrhea, mouth swelling, peptic ulcer hemorrhage, fatigue, anemia postoperative, gout, dyspnea, and pallor, with an incidence of 1 (0.2%) participant each. The events leading to treatment discontinuation in the MR-107A-02 group consisted of nausea, mouth swelling, peptic ulcer hemorrhage, anemia postoperative, and dyspnea.

The event of gout that was reported by 1 (0.4%) participant in the Placebo group (also counted in the All-Placebo group [0.3%]) also led to study discontinuation.

TABLE 63

Treatment-emergent Adverse Events Leading to Treatment Discontinuation, by System Organ Class and Preferred Term: Out-patient (Safety Analysis Set)

| System Organ Class Preferred Term | MR- 107A-02 (15 mg BID) (N = 224) | Tramadol Placebo (N = 110) | Placebo (N = 223) | All Placebo (N = 333) | Total (N = 557) |
|---|---|---|---|---|---|
| Any TEAE Leading to Treatment Discontinuation, n (%) | 3 (1.3) | 2 (1.8) | 1 (0.4) | 3 (0.9) | 6 (1.1) |
| Gastrointestinal disorders | 3 (1.3) | 1 (0.9) | 0 | 1 (0.3) | 4 (0.7) |
| Nausea | 1 (0.4) | 1 (0.9) | 0 | 1 (0.3) | 2 (0.4) |
| Diarrhea | 0 | 1 (0.9) | 0 | 1 (0.3) | 1 (0.2) |
| Mouth swelling | 1 (0.4) | 0 | 0 | 0 | 1 (0.2) |
| Peptic ulcer hemorrhage | 1 (0.4) | 0 | 0 | 0 | 1 (0.2) |
| General disorders and administration site conditions | 0 | 1 (0.9) | 0 | 1 (0.3) | 1 (0.2) |
| Fatigue | 0 | 1 (0.9) | 0 | 1 (0.3) | 1 (0.2) |
| Injury, poisoning and procedural complications | 1 (0.4) | 0 | 0 | 0 | 1 (0.2) |
| Anemia postoperative | 1 (0.4) | 0 | 0 | 0 | 1 (0.2) |
| Metabolism and nutritional disorders | 0 | 0 | 1 (0.4) | 1 (0.3) | 1 (0.2) |
| Gout | 0 | 0 | 1 (0.4) | 1 (0.3) | 1 (0.2) |
| Respiratory, thoracic and mediastinal disorders | 1 (0.4) | 0 | 0 | 0 | 1 (0.2) |
| Dyspnea | 1 (0.4) | 0 | 0 | 0 | 1 (0.2) |
| Vascular disorders | 0 | 1 (0.9) | 0 | 1 (0.3) | 1 (0.2) |
| Pallor | 0 | 1 (0.9) | 0 | 1 (0.3) | 1 (0.2) |

AE = Adverse event; BID = Twice daily; MedDRA = Medical Dictionary for Regulatory Activities; n = Number of participants; N = Number of participants per treatment group in the Safety Analysis Set; TEAE = Treatment-emergent adverse event
Note:
During the out-patient treatment phase, participants received either MR-107A-02 (15 mg BID) or placebo (BID); participants in the Tramadol group received placebo only during the out-patient treatment phase and are labelled as Tramadol Placebo.
Note:
Percentages were based on the number of participants in the Safety Analysis Set, in each treatment group, for that study phase.
Note:
TEAEs in the out-patient treatment phase were those that started on or after the first dose of study drug administration in the out-patient treatment phase.
Note:
TEAEs were summarized according to the last treatment that the participant received prior to the start of that AE.
Note:
Participants with multiple events in a system organ class/preferred term were counted only once for that system organ class/preferred term.
Note:
All terms were coded using MedDRA Version 26.1 and sorted in descending order of frequency in the Total group for both system organ classes and preferred terms.

TABLE 63-continued

Treatment-emergent Adverse Events Leading to Treatment Discontinuation, by System Organ Class and Preferred Term: Out-patient (Safety Analysis Set)

| System Organ Class<br>Preferred Term | MR- 107A-02<br>(15 mg BID)<br>(N = 224) | Tramadol<br>Placebo<br>(N = 110) | Placebo<br>(N = 223) | All<br>Placebo<br>(N = 333) | Total<br>(N = 557) |
|---|---|---|---|---|---|

Note:
The All-Placebo treatment column summarizes participants who were randomized to the Tramadol or Placebo groups and who received placebo during the out-patient treatment phase.
Note:
Study phase was defined as follows; AEs during the in-patient treatment phase occurred after the first dose of study drug administration in the in-patient treatment phase and before the first dose of study drug administration in the out-patient treatment phase. Adverse events during the out-patient treatment phase occurred after the first dose of study drug administration in the out-patient treatment phase. Adverse events occurring prior to study drug administration did not have a study phase assigned.

Opioid-Related Adverse Events

In-Patient Treatment Phase:

Table 64 presents opioid-related TEAEs reported during the in-patient treatment phase by SOC and PT for the Safety Analysis Set. Overall, 142 (24.8%) participants reported at least one opioid-related TEAE.

The most common (≥2% participants overall) PTs of opioid-related TEAEs included constipation (72 [12.6%] participants), nausea (50 [8.7%] participants), dizziness (34 [5.9%] participants), pruritus (20 [3.5%] participants), and vomiting (12 [2.1%] participants). The incidences of PTs of the most common opioid-related TEAEs were all numerically higher in the Tramadol group (20.9%, 13.0%, 9.6%, 4.3%, and 5.2%, respectively) than in the MR-107A-02 and Placebo groups (constipation: 7.0% and 14.1%, respectively; nausea: 7.0% and 8.4%; dizziness: 5.7% and 4.4%; pruritus: 3.0% and 3.5%; and vomiting: 1.7% and 0.9%).

TABLE 64

Opioid-related Treatment-emergent Adverse Events, by System Organ Class and Preferred Term: In-patient (Safety Analysis Set)

| System Organ Class<br>Preferred Term | MR-107A-02<br>(15 mg BID)<br>(N = 230) | Tramadol<br>(50 mg q6h)<br>(N = 115) | Placebo<br>(N = 227) | Total<br>(N = 572) |
|---|---|---|---|---|
| Any Opioid-related TEAE, n (%) | 44 (19.1) | 39 (33.9) | 59 (26.0) | 142 (24.8) |
| Gastrointestinal disorders | 33 (14.3) | 36 (31.3) | 46 (20.3) | 115 (20.1) |
| Constipation | 16 (7.0) | 24 (20.9) | 32 (14.1) | 72 (12.6) |
| Nausea | 16 (7.0) | 15 (13.0) | 19 (8.4) | 50 (8.7) |
| Vomiting | 4 (1.7) | 6 (5.2) | 2 (0.9) | 12 (2.1) |
| Ileus | 0 | 0 | 1 (0.4) | 1 (0.2) |
| Nervous system disorders | 13 (5.7) | 11 (9.6) | 10 (4.4) | 34 (5.9) |
| Dizziness | 13 (5.7) | 11 (9.6) | 10 (4.4) | 34 (5.9) |
| Skin and subcutaneous tissue disorders | 7 (3.0) | 5 (4.3) | 8 (3.5) | 20 (3.5) |
| Pruritus | 7 (3.0) | 5 (4.3) | 8 (3.5) | 20 (3.5) |
| Injury, poisoning and procedural complications | 1 (0.4) | 1 (0.9) | 1 (0.4) | 3 (0.5) |
| Fall | 0 | 1 (0.9) | 1 (0.4) | 2 (0.3) |
| Incision site pruritus | 1 (0.4) | 0 | 0 | 1 (0.2) |
| Renal and urinary disorders | 0 | 0 | 2 (0.9) | 2 (0.3) |

TABLE 64-continued

Opioid-related Treatment-emergent Adverse Events, by System Organ Class and Preferred Term: In-patient (Safety Analysis Set)

| System Organ Class<br>Preferred Term | MR-107A-02<br>(15 mg BID)<br>(N = 230) | Tramadol<br>(50 mg q6h)<br>(N = 115) | Placebo<br>(N = 227) | Total<br>(N = 572) |
|---|---|---|---|---|
| Urinary retention | 0 | 0 | 2 (0.9) | 2 (0.3) |
| Eye disorders | 0 | 0 | 1 (0.4) | 1 (0.2) |
| Eye pruritus | 0 | 0 | 1 (0.4) | 1 (0.2) |

AE = Adverse event; BID = Twice daily; MedDRA = Medical Dictionary for Regulatory Activities; n = Number of participants; N = Number of participants per treatment group in the Safety Analysis Set; TEAE = Treatment-emergent adverse event
Note:
During the out-patient treatment phase, participants received either MR-107A-02 (15 mg BID) or placebo (BID); participants in the Tramadol group received placebo only during the out-patient treatment phase and are labelled as Tramadol Placebo.
Note:
Percentages were based on the number of participants in the Safety Analysis Set, in each treatment group, for that study phase.
Note:
TEAEs in the out-patient treatment phase were those that started on or after the first dose of study drug administration in the out-patient treatment phase.
Note:
TEAEs were summarized according to the last treatment that the participant received prior to the start of that AE.
Note:
Participants with multiple events in a system organ class/preferred term were counted only once for that system organ class/preferred term.
Note:
All terms were coded using MedDRA Version 26.1 and sorted in descending order of frequency in the Total group for both system organ classes and preferred terms.
Note:
The All-Placebo treatment column summarizes participants who were randomized to the Tramadol or Placebo groups and who received placebo during the out-patient treatment phase.
Note:
Study phase was defined as follows; AEs during the in-patient treatment phase occurred after the first dose of study drug administration in the in-patient treatment phase and before the first dose of study drug administration in the out-patient treatment phase. Adverse events during the out-patient treatment phase occurred after the first dose of study drug administration in the out-patient treatment phase. Adverse events occurring prior to study drug administration did not have a study phase assigned.

Out-Patient Treatment Phase:

Table 65 presents opioid-related TEAEs reported during the out-patient treatment phase by SOC and PT for the Safety Analysis Set. Overall, 91 (16.3%) participants reported at least one opioid-related TEAE.

The incidence of opioid-related TEAEs during the out-patient treatment phase was similar in all three treatment groups. The most common (≥2% participants overall) PTs of opioid-related TEAEs included constipation (56 [10.1%] participants), nausea (20 [3.6%] participants), dizziness (15 [2.7%]), and pruritus (13 [2.3%]). Of the most common opioid-related TEAEs, the incidences of constipation, nausea, and dizziness were numerically higher in the Tramadol group (14.5%, 6.4%, 3.6% respectively) than in the MR-107A-02 and Placebo groups (constipation: 9.4% and 8.5%, respectively; nausea: 3.6% and 2.2%; and dizziness: 2.2% and 2.7%).

TABLE 65

Opioid-related Treatment-emergent Adverse Events, by System Organ Class and Preferred Term: Out-patient (Safety Analysis Set)

| System Organ Class Preferred Term | MR-107A-02 (15 mg BID) (N = 224) | Tramadol Placebo (N = 110) | Placebo (N = 223) | All Placebo (N = 333) | Total (N = 557) |
|---|---|---|---|---|---|
| Any Opioid-related TEAE, n (%) | 35 (15.6) | 23 (20.9) | 33 (14.8) | 56 (16.8) | 91 (16.3) |
| Gastrointestinal disorders | 29 (12.9) | 21 (19.1) | 25 (11.2) | 46 (13.8) | 75 (13.5) |
| Constipation | 21 (9.4) | 16 (14.5) | 19 (8.5) | 35 (10.5) | 56 (10.1) |
| Nausea | 8 (3.6) | 7 (6.4) | 5 (2.2) | 12 (3.6) | 20 (3.6) |
| Vomiting | 2 (0.9) | 0 | 3 (1.3) | 3 (0.9) | 5 (0.9) |
| Nervous system disorders | 5 (2.2) | 4 (3.6) | 6 (2.7) | 10 (3.0) | 15 (2.7) |
| Dizziness | 5 (2.2) | 4 (3.6) | 6 (2.7) | 10 (3.0) | 15 (2.7) |
| Skin and subcutaneous tissue disorders | 5 (2.2) | 2 (1.8) | 6 (2.7) | 8 (2.4) | 13 (2.3) |
| Pruritus | 5 (2.2) | 2 (1.8) | 6 (2.7) | 8 (2.4) | 13 (2.3) |
| Injury, poisoning and procedural complications | 3 (1.3) | 1 (0.9) | 0 | 1 (0.3) | 4 (0.7) |
| Incision site pruritus | 3 (1.3) | 1 (0.9) | 0 | 1 (0.3) | 4 (0.7) |
| Respiratory, thoracic and mediastinal disorders | 0 | 0 | 1 (0.4) | 1 (0.3) | 1 (0.2) |
| Throat irritation | 0 | 0 | 1 (0.4) | 1 (0.3) | 1 (0.2) |

AE = Adverse event; BID = Twice daily; MedDRA = Medical Dictionary for Regulatory Activities; n = Number of participants; N = Number of participants per treatment group in the Safety Analysis Set; TEAE = Treatment-emergent adverse event Note:

During the out-patient treatment phase, participants received either MR-107A-02 (15 mg BID) or placebo (BID); participants in the Tramadol group received placebo only during the out-patient treatment phase and are labelled as Tramadol Placebo.

Note:

Percentages were based on the number of participants in the Safety Analysis Set, in each treatment group, for that study phase.

Note:

TEAEs in the out-patient treatment phase were those that started on or after the first dose of study drug administration in the out-patient treatment phase.

Note:

TEAEs were summarized according to the last treatment that the participant received prior to the start of that AE.

Note:

Participants with multiple events in a system organ class/preferred term were counted only once for that system organ class/preferred term.

Note:

All terms were coded using MedDRA Version 26.1 and sorted in descending order of frequency in the Total group for both system organ classes and preferred terms.

Note:

The All-Placebo treatment column summarizes participants who were randomized to the Tramadol or Placebo groups and who received placebo during the out-patient treatment phase.

Note:

Study phase was defined as follows; AEs during the in-patient treatment phase occurred after the first dose of study drug administration in the in-patient treatment phase and before the first dose of study drug administration in the out-patient treatment phase. Adverse events during the out-patient treatment phase occurred after the first dose of study drug administration in the out-patient treatment phase. Adverse events occurring prior to study drug administration did not have a study phase assigned.

Adverse Events of Special Interest

AESIs included AEs related to GI events, particularly bleeds, and those related to cardiovascular events (myocardial infarction/unstable angina, stroke/TIA, heart failure, and cardiac arrhythmia [atrial and ventricular]).

In-Patient Treatment Phase

TEAEs of special interest reported during the in-patient treatment phase by SOC and PT for the Safety Analysis Set shows that overall, 2 (0.3%) participants reported at least one TEAE of special interest with PTs of supraventricular tachycardia (1 [0.9%] participant in the Tramadol group) and ventricular extrasystoles (1 [0.4%] participant in the MR-107A-02 group). No TEAE of special interest reported during the in-patient treatment phase led to study or treatment discontinuation.

Out-Patient Treatment Phase

Table 66 presents TEAEs of special interest reported during the out-patient treatment phase by SOC and PT for the Safety Analysis Set. Overall, 4 (0.7%) participants reported at least one TEAE of special interest with PTs of hemorrhoidal hemorrhage (1 [0.4%] participant in the MR-107A-02 and Placebo group each [also counted in the All Placebo group [0.3%]), anal fissure (1 [0.9%] participant in the Tramadol Placebo group [also counted in the All Placebo group [0.3%]), and peptic ulcer hemorrhage (1 [0.4%] participant in the MR-107A-02 group). No TEAEs of special interest reported during the out-patient treatment phase led to study discontinuation. The TEAE of peptic ulcer hemorrhage reported by 1 (0.4%) participant in the MR-107A-02 group led to treatment discontinuation.

TABLE 66

Treatment-emergent Adverse Events of Special Interest, by System Organ Class and Preferred Term: Out-patient (Safety Analysis Set)

| System Organ Class Preferred Term | MR-107A-02 (15 mg BID) (N = 224) | Tramadol Placebo (N = 110) | Placebo (N = 223) | All Placebo (N = 333) | Total (N = 557) |
|---|---|---|---|---|---|
| Any TEAE of Special Interest, n (%) | 2 (0.9) | 1 (0.9) | 1 (0.4) | 2 (0.6) | 4 (0.7) |
| Gastrointestinal disorders | 2 (0.9) | 1 (0.9) | 1 (0.4) | 2 (0.6) | 4 (0.7) |
| Hemorrhoidal hemorrhage | 1 (0.4) | 0 | 1 (0.4) | 1 (0.3) | 2 (0.4) |
| Anal fissure | 0 | 1 (0.9) | 0 | 1 (0.3) | 1 (0.2) |
| Peptic ulcer hemorrhage | 1 (0.4) | 0 | 0 | 0 | 1 (0.2) |

AE = Adverse event; BID = Twice daily; MedDRA = Medical Dictionary for Regulatory Activities; n = Number of participants; N = Number of participants per treatment group in the Safety Analysis Set; TEAE = Treatment-emergent adverse event Note:

During the out-patient treatment phase, participants received either MR-107A-02 (15 mg BID) or placebo (BID); participants in the Tramadol group received placebo only during the out-patient treatment phase and are labelled as Tramadol Placebo.

Note:

Percentages were based on the number of participants in the Safety Analysis Set, in each treatment group, for that study phase.

Note:

TEAEs in the out-patient treatment phase were those that started on or after the first dose of study drug administration in the out-patient treatment phase.

Note:

TEAEs were summarized according to the last treatment that the participant received prior to the start of that AE.

Note:

Participants with multiple events in a system organ class/preferred term were counted only once for that system organ class/preferred term.

Note:

All terms were coded using MedDRA Version 26.1 and sorted in descending order of frequency in the Total group for both system organ classes and preferred terms.

Note:

The All-Placebo treatment column summarizes participants who were randomized to the Tramadol or Placebo groups and who received placebo during the out-patient treatment phase.

Note:

Study phase was defined as follows; AEs during the in-patient treatment phase occurred after the first dose of study drug administration in the in-patient treatment phase and before the first dose of study drug administration in the out-patient treatment phase. Adverse events during the out-patient treatment phase occurred after the first dose of study drug administration in the out-patient treatment phase. Adverse events occurring prior to study drug administration did not have a study phase assigned.

Analysis and Discussion of Deaths, Other Serious Adverse Events, and Other Significant Adverse Events No death was reported in this study.

In-Patient Treatment Phase:

One serious TEAE (PT of ileus) was reported in the Placebo group; the event was considered possibly related to study drug and had resolved at the time of last report. Overall, 2 (0.3%) participants reported TEAEs leading to study discontinuation (PTs of constipation and ileus), and 5 (0.9%) participants reported at least one TEAE leading to treatment discontinuation (PTs of constipation, abdominal pain, ileus, alanine aminotransferase increased, aspartate aminotransferase increased, dehydration, and dizziness). The TEAEs leading to study and treatment discontinuation were all considered resolved at the time of last report. A total of 142 (24.8%) participants overall reported at least one opioid-related TEAE, and the most common (≥2% participants overall) PTs included constipation, nausea, dizziness, pruritus, and vomiting, all of which were reported more frequently in the Tramadol group than in the MR-107A-02 and Placebo groups. Two (0.3%) participants overall reported at least one TEAE of special interest (PTs of supraventricular tachycardia and ventricular extrasystoles); the event of supraventricular tachycardia reported in the Tramadol group was considered resolved at the time of last report. The event of ventricular extrasystoles reported in the MR-107A-02 group was considered not resolved at the time of last report; the participant was observed to have had pre-existing PVC at Screening and had reported symptoms of PVC months prior to study enrollment, which may have also contributed to the event. No TEAEs of special interest led to study or treatment discontinuation.

Out-Patient Treatment Phase:

Overall, 4 (0.7%) participants reported at least one serious TEAE (PTs of groin abscess, postoperative wound infection, peptic ulcer haemorrhage, and acute kidney injury). The serious TEAEs of groin abscess, postoperative wound infection, peptic ulcer haemorrhage, and acute kidney injury were all considered not related or unlikely related to study drug, except one incident of peptic ulcer haemorrhage in a patient, which was considered possibly related to study drug. The serious TEAEs had all resolved at the time of last report and were reported in the MR-107A-02 and Placebo groups. Overall, 1 (0.2%) participant reported a TEAE leading to study discontinuation (PT of gout), and 6 (1.1%) participants overall reported at least one TEAE leading to treatment discontinuation (PTs of nausea, diarrhea, mouth swelling, peptic ulcer haemorrhage, fatigue, anaemia postoperative, gout, dyspnea, and pallor). The TEAEs leading to study and treatment discontinuation were all considered resolved or resolving in the last report. A total of 91 (16.3%) participants reported at least one opioid-related TEAE, and the most common (≥2% participants overall) PTs included constipation, nausea, dizziness, and pruritus. Constipation, nausea, and dizziness were reported more frequently in the Tramadol Placebo group than in the MR-107A-02 and Placebo groups. Four (0.7%) participants overall reported TEAEs of special interest (PTs of hemorrhoidal hemorrhage, anal fissure, and peptic ulcer hemorrhage); the TEAEs of special interest were all considered resolved at the time of last report. No TEAEs of special interest led to study discontinuation, and the TEAEs of hemorrhoidal hemorrhage and anal fissure did not lead to treatment discontinuation. The TEAE of peptic ulcer hemorrhage reported in the MR-107A-02 group led to treatment discontinuation.

The PTs of opioid-related TEAEs observed during the in- and out-patient treatment phases were expected effects of meloxicam, as most were reported during clinical studies of MOBIC (MOBIC Prescribing Information, 2024).

Safety Conclusions

The safety objective of this study was to confirm the safety and tolerability of MR-107A-02 in participants following herniorrhaphy. Safety was assessed through the incidence, severity, duration, and outcome of AEs, including ORAEs, as well as changes from baseline in vital signs, laboratory parameters (hematology, chemistry, urinalysis), and 12-lead ECGs.

No deaths were reported at any time during the study. Two participants in the in-patient treatment phase and 4 participants in the out-patient treatment phase reported TEAEs of special interest. The TEAEs of special interest reported in the MR-107A-02 group were ventricular extrasystoles (1 participant; in-patient treatment phase), hemorrhoidal hemorrhage, and peptic ulcer hemorrhage (1 participant each; out-patient treatment phase). The events of hemorrhoidal hemorrhage and peptic ulcer hemorrhage were resolved. The low incidence of TEAEs of special interest (0.3% overall in-patient treatment phase; 0.7% overall out-patient treatment phase) demonstrates the safety of MR-107A-02 in terms of the risks associated with the NSAID class.

During the in-patient treatment phase, a total of 237 (41.4%) participants reported 443 TEAEs. The incidence of TEAEs was higher in the Tramadol and Placebo groups (45.2% and 45.8%, respectively) than in the MR-107A-02 group (35.2%). One hundred seven (18.7%) participants reported 181 TEAEs related to study drug; the incidence of related TEAEs was similar in all three treatment groups. This means that the MR-107A-02 group had an even slightly lower proportion of participants with TEAEs than the Placebo group, possibly due to lower use of rescue medication.

During the in-patient treatment phase, 142 (24.8%) participants reported 202 opioid-related TEAEs and the incidence of opioid-related TEAEs was numerically higher in the Tramadol group (33.9%) than in the MR-107A-02 and Placebo groups (19.1% and 26.0%, respectively). The most common (≥2% participants overall) PTs of opioid-related TEAEs included constipation, nausea, dizziness, pruritus, and vomiting. Most TEAEs were either mild or moderate in severity with only 4 (0.7%) participants overall reporting severe TEAEs. Notably, all severe TEAEs were reported in the Placebo group, and no severe TEAEs were reported in the MR-107A-02 group. Two (0.3%) participants overall (1 each in the Placebo and Tramadol groups) reported one TEAE leading to study discontinuation (PTs of constipation and ileus). One (0.2% overall) participant in the Placebo group reported the serious TEAE of ileus. No serious TEAEs were reported in the MR-107A-02 group during the in-patient treatment phase.

During the in-patient treatment phase, a total of 5 (0.9%) participants reported at least one TEAE leading to treatment discontinuation (1 [0.4%] participant in the MR-107A-02 group, 3 [2.6%] participants in the Tramadol group, and 1 [0.4%] participant in the Placebo group). Reported PTs included constipation (1 [0.4%] and 1 [0.9%] participant in the MR-107A-02 and Tramadol group, respectively), abdominal pain, ileus, and dehydration (1 [0.4%] participant each in the Placebo group), alanine aminotransferase increased, aspartate aminotransferase increased, and dizziness (1 [0.9%] participant each in the Tramadol group).

During the out-patient treatment phase, a total of 198 (35.5%) participants reported 419 TEAEs with similar incidence of TEAEs among the treatment groups. Sixty-three (11.3%) participants reported 101 TEAEs related to study drug. Ninety-one (16.3%) participants reported 115 opioid-related TEAEs. The most common (≥2% participants overall) PTs of opioid-related TEAEs included constipation, nausea, dizziness, and pruritus; the incidences of constipation, nausea, and dizziness were numerically higher in the Tramadol group than in the MR-107A-02 and Placebo groups.

As with the in-patient treatment phase, most out-patient TEAEs were either mild or moderate in severity, with 4 (0.7%) participants overall reporting 5 severe TEAEs (3 [1.3%] participants in the MR-107A-02 group and 1 [0.4%] participant in the Tramadol Placebo group (also counted in the All-Placebo group). The PTs of severe TEAEs included groin abscess, postoperative wound infection, peptic ulcer hemorrhage, anemia postoperative, and acute kidney injury, which were all recovered/resolved at the time of last report. Overall, 4 (0.7%) participants reported 4 serious TEAEs (3 [1.3%] participants in the MR-107A-02 group and 1 [0.4%] participant in the Placebo group; also counted in the All Placebo group) with PTs of groin abscess, postoperative wound infection, and peptic ulcer hemorrhage (1 [0.4%] participant each in the MR-107A-02 group), and acute kidney injury (1 [0.4%] participant in the Placebo group). One TEAE that led to study discontinuation was reported in the Placebo group (PT of gout). Six (1.1%) participants overall reported at least one TEAE leading to treatment discontinuation with PTs of nausea, diarrhea, mouth swelling, peptic ulcer hemorrhage, fatigue, anemia postoperative, gout, dyspnea, and pallor. Treatment-emergent AEs leading to treatment discontinuation in the MR-107A-02 group consisted of nausea, mouth swelling, peptic ulcer hemorrhage, anemia postoperative, and dyspnea in 1 (0.4%) participant each.

The marked difference in the incidence of opioid-related TEAEs between treatment groups-particularly in the first 48 hours-demonstrates a likely clinically meaningful benefit associated with MR-107A-02. Specifically, 19.1% participants in the MR-107A-02 group experienced opioid-related TEAEs, compared with 33.9% in the Tramadol group. This represents a 14.8% absolute risk reduction and a relative reduction of approximately 44% of experiencing an ORAE, reflecting a substantial improvement in tolerability.

This lower incidence of ORAEs is particularly important given their known impact on patient comfort, recovery, and clinical resource utilization (Shafi et al., 2018). Common opioid-related effects such as nausea, dizziness, and sedation can impair postoperative function and delay discharge while requiring additional medications and monitoring. By contrast, MR-107A-02 demonstrated a more favorable safety profile, reducing these burdens and aligning with best practices in opioid-sparing multimodal analgesia.

The PTs of opioid-related TEAEs observed during the in- and out-patient treatment phases were expected effects of meloxicam, as most were reported during clinical studies of MOBIC (MOBIC Prescribing Information, 2024).

No renal toxicity or hepatotoxicity concerns were identified, and no clinically relevant trends over time or treatment group differences in vital signs, laboratory parameters, or ECGs were observed. These findings further support the safety of MR-107A-02.

Overall, MR-107A-02 15 mg BID was well tolerated and demonstrated a favorable safety profile. The incidence of serious TEAEs, severe TEAEs, and TEAEs leading to study discontinuation was low in the MR-107A-02 group. The incidence of TEAEs and opioid-related TEAEs in the MR-107A-02 group was similar to that of the Placebo group.

3B.9 Discussion and Overall Conclusions from 3002 Study

Study Design for Acute Pain Indication

This randomized, placebo- and active-controlled study evaluated the efficacy, opioid-sparing capacity, and safety of MR-107A-02 (15 mg BID), a novel oral formulation of meloxicam designed for faster absorption than approved oral meloxicam formulations. As one of two studies in the Sponsor's Phase 3 program supporting the indication of treatment of acute pain per the US FDA draft guidance *Development of Non-Opioid Analgesics for Acute Pain* (FDA, 2022), this study evaluated post-operative pain following herniorrhaphy. The herniorrhaphy surgical model is considered a suitable model of acute post-surgical soft tissue pain and is a well-established and accepted model for evaluating novel NSAIDs for the treatment of moderate to severe acute pain and is likewise suitable to show opioid-reducing capacities. The herniorrhaphy model has demonstrated the efficacy of analgesic medications across a range of different pharmacological treatments, including opioids and NSAIDs such as an IV formulation of meloxicam.

In alignment with the study design considerations outlined in the US FDA draft guidance *Development of Non-Opioid Analgesics for Acute Pain* (FDA, 2022), this was a randomized, double-blind, repeat-dose, placebo and active controlled superiority (versus placebo) study of MR-107A-02. The primary objective was to confirm the efficacy of MR-107A-02 (versus placebo) in treating acute pain following hernia repair surgery. This was evaluated with a recommended endpoint, i.e., $SPID_{0-48}$ based on NRS-A scores. Safety data were collected over 30 days following last administration of the study drug. Rescue medications (APAP and opioids) were pre-defined in the protocol and a stepwise approach for their use was described in case of inadequate pain control during each phase of the study. The pre-specified analyses for this study incorporated FDA feedback and were aligned with the recommendations for outcome measures to obtain an acute pain analgesic indication included in the US FDA draft guidance *Development of Non-Opioid Analgesics for Acute Pain* (FDA, 2022). A post-hoc analysis to compare MR-107A-02 with tramadol for $SPID_{0-48}$, and analyses to compare tramadol with placebo for some of the secondary efficacy estimands were added to this report; however, the results of post-hoc analyses are considered exploratory in nature as they were conducted after unblinding activities were completed.

This study was placebo-(double-dummy) and active-controlled (with tramadol used as an active comparator during the in-patient treatment phase). The rationale for the inclusion of the active comparator, tramadol, in this study was twofold: (1) to confirm the sensitivity of the study with a comparison of the tramadol and placebo treatment groups based on the primary endpoint and (2) to estimate the effect of MR-107A-02 versus that of tramadol using the primary endpoint. Tramadol is an opioid analgesic approved for the management of moderate to moderately severe pain in adults, and the pain level expected for herniorrhaphy surgeries (NRS 4-10 following surgery in approximately 30% of patients) aligns with this indication (HerniaSurge, 2018; Mentes and Bagci, 2009; Bugada et al., 2015).

The tramadol formulation included as the active comparator in this study (i.e., 50 mg IR) is well characterized based on historical use with respect to its efficacy, safety, and PK and is routinely used for postoperative pain management following surgical procedures. Tramadol is also recognized by the CDC as one of the most commonly prescribed opioids in the US, and it appears in regional and institutional prescribing guidelines. Its use after surgery is particularly well established. It ranks among the top three opioids prescribed for postoperative pain (Tan et al., 2018), including those prescribed following herniorrhaphy (Knight et al., 2019). In conclusion, tramadol (50 mg IR) was selected as the active control in this study based on its regulatory status, demonstrated efficacy in the herniorrhaphy model, routine clinical use, and compatibility with the study's rescue medication strategy. Its parallel use as a comparator in the second Phase 3 study (bunionectomy) reinforces its usefulness in supporting the MR-107A-02 clinical development program.

In this study, APAP was used as the first-step rescue medication. Tramadol's availability as a single-agent opioid enables first step rescue medication APAP. In contrast, hydrocodone—available only in fixed-dose combination with APAP—was not suitable for use as an active comparator in this study, as its use could have resulted in exceeding the maximum daily dose of APAP. Moreover, if escalation to stronger rescue analgesia was required, oxycodone as second step rescue medication was available. Oxycodone is a preferred opioid rescue medication due to its rapid onset of action and reliable analgesic efficacy in postoperative settings.

Study Participants

A total of 579 participants were enrolled and randomized to one of the three treatment groups. The MR-107A-02, Tramadol, and Placebo groups included 232 participants, 116 participants, 231 participants, respectively; 7 participants (2 participants in the MR-107A-02 group, 1 participant in the Tramadol group, and 4 participants in the Placebo group) were randomized in error and not dosed due to failure to meet inclusion and/or exclusion criteria. Overall, 551 (95.2%) participants completed the study, with 17 (2.9%) and 11 (1.9%) participants discontinuing the study during the in-patient treatment phase and out-patient treatment phase, respectively. A total of 547 (94.5%) participants overall completed treatment, and 14 (2.4%) and 11 (1.9%) participants discontinued treatment during the in-patient treatment phase and out-patient treatment phase, respectively. The three treatment groups were generally comparable with respect to participant disposition. The high completion rates for both the study overall and treatment indicate that sufficient data was collected for a robust analysis of the efficacy, opioid-sparing capacity, and safety of MR-107A-02 following herniorrhaphy.

Most participants (96.3% of all participants) were male, White (84.3%), and not Hispanic or Latino (66.3%). The mean age was 49.1 years (range 18 to 80 years), and most participants were <65 years of age (93.4%). The mean BMI was 28.0 kg/m$^2$ (range 17 to 40 kg/m$^2$), and the mean baseline NRS-A was 7.8 (range 3 to 10). The mean duration of surgery was 50.0 minutes (range 12 to 152 minutes). The baseline pain level for participants enrolled in this study aligned with what was expected for herniorrhaphy pain studies of NRS 4-10 (HerniaSurge, 2018; Mentes and Bagci, 2009; Bugada et al., 2015). The three treatment groups were comparable with respect to demographic and baseline characteristics and also with respect to common medical history and use of prior medications. The well-balanced background characteristics across the treatment groups demonstrated uniformity in the three groups included in the study and limited the effects of underlying demographic and medical characteristics on the results of the study.

The FAS included 230 participants in the MR-107A-02 group, 115 participants in the Tramadol group, and 227 participants in the Placebo group, which satisfied (marginally exceeded) the minimum treatment group size required to sufficiently power the study for the planned analysis of the primary and secondary estimands.

The overall mean compliance was 98.2% (range 25% to 100%). Within each treatment phase and overall, the mean and median expected number of doses, actual number of doses, compliance, the duration of exposure, and total number of doses taken were similar across treatment groups. The high compliance rates demonstrated that most participants administered study drug as planned, which indicates potential for high patient compliance in a clinical setting.

MR-107A-02 for the Treatment of Acute Pain

The primary efficacy estimand compared the $SPID_{0-48}$ (based on NRS-A scores) for the MR-107A-02 and Placebo groups in the FAS using an ANCOVA model; rescue medication use was managed by the WLOCF approach, and missing data was managed by an MI approach. The study met the primary endpoint, as the difference in LS means $SPID_{0-48}$ (95% CI) for MR-107A-02 versus placebo (50.1 [35.4, 64.8]) was statistically significant ($p<0.001$). The $SPID_{0-48}$ endpoint captures both the magnitude and duration of the analgesic effect, offering a comprehensive measure of treatment efficacy in acute pain. The results of the primary efficacy estimand analysis demonstrated that MR-107A-02 provided statistically significant pain relief compared to placebo within the critical early time window; as this is when pain is typically most intense and when patients are most vulnerable to breakthrough symptoms, the improved pain relief is expected to be clinically meaningful. This confirmed that MR-107A-02 is an effective oral analgesic for managing moderate to severe acute pain.

The participants in the MR-107A-02 group experienced faster times to first perceptible and meaningful relief of pain than those in the Placebo group ($p\leq0.025$ [nominal]). In addition, the time to first use of rescue medication, both overall and specifically for opioid rescue medication, was longer in the MR-107A-02 group than in the Placebo group ($p\leq0.006$ [nominal]). This indicates that participants receiving MR-107A-02 experienced more sustained analgesic effects and were less reliant on supplementary medication to manage their pain than those in the Placebo group.

The geometric mean (CV %) $C_{max}$ of meloxicam after the first dose was 1254.225 (32.265) ng/mL with a corresponding median $T_{max}$ value of 2.170 hours. Repeat dosing of MR-107A-02 (15 mg BID) resulted in accumulation, with increasing mean meloxicam concentration values at the pre-dose timepoints of 12, 24, and 48 hours. The $T_{max}$ after the first dose of 2.170 hours was in proximity to the median time to first perceptible relief of pain in the MR-107A-02 group of 0.9 hours, and the overall exposure of meloxicam with repeat dosing correlated with the long-term pain control observed in the MR-107A-02 group.

Other efficacy endpoints, including the SPID, PID, and the proportion of participants with overall pain reductions from baseline of ≥30% and ≥50%, indicated that participants in the MR-107A-02 group experienced better pain control over time than those in the Placebo group. These results suggest a robust analgesic effect of MR-107A-02 relative to placebo.

Reducing or Eliminating Opioid Use:

The key secondary efficacy estimand was the number of doses of opioid rescue medication (oxycodone and/or morphine) taken during the entire treatment phase (in-patient and out-patient treatment phases). The analysis used a negative binomial regression model with a log link to compare the MR-107A-02 and Placebo groups in the FAS. Missing data was managed by an MI approach. The study met the key secondary endpoint, as the ratio of LS geometric means of the number of doses of opioid (oxycodone and/or morphine) medication (95% CI) for MR-107A-02 versus placebo (0.627 [0.419, 0.939]) was statistically significant ($p=0.023$). Notably, the LS geometric mean number of opioid doses (i.e., total opioid consumption) was 50% lower in the MR-107A-02 group (0.002 doses) than in the Placebo group (0.004 doses). This substantial decrease in opioid use is expected to be clinically significant, given the risks associated with opioid medications, such as dependence, tolerance, and AEs. Similarly, participants in the MR-107A-02 group took numerically fewer doses of opioid (oxycodone and/or morphine) than those in the Placebo group during all other intervals evaluated (i.e., the last 24 and 36 hours before discharge, the in-patient treatment phase, the out-patient treatment phase, 0-24 hours after randomization, and post-discharge phase [up to 30 days after discharge]). These differences suggest that MR-107A-02 effectively reduced the need for rescue opioid analgesia throughout both acute and extended recovery periods.

During the entire treatment phase, 73% of participants in the MR-107A-02 group were opioid free. The MR-107A-02 group had 14.4% more opioid-free participants than the Placebo group, and the difference in proportions (95% CI) of opioid (oxycodone and/or morphine)-free participants in the MR-107A-02 and Placebo groups of 14.5% (5.9%, 23.1%) was statistically significant ($p=0.001$). For all other intervals (i.e., the last 24 and 36 hours before discharge, the inpatient treatment phase, the out-patient treatment phase, 0-24 hours after randomization, and post discharge phase [up to 30 days after discharge]), the MR-107A-02 group had larger proportions of opioid free participants than the Placebo group. These results were reflective of adequate pain control from MR-107A-02 without supplemental opioids, and this reduction in opioid exposure is clinically important, especially in the context of enhanced recovery pathways and current guidelines that emphasize opioid minimization after surgery.

Importantly, regardless of this reduced opioid use, participants in the MR-107A-02 group also took less APAP rescue medication than those in the Placebo group during the entire treatment phase and in-patient treatment phase. This finding highlights the strength of the analgesic effect provided by MR-107A-02 and suggests that the observed reduction in opioid use was not compensated by increased use of non-opioid rescue medication during the entire treatment phase and in-patient treatment phase. A larger proportion of participants in the MR-107A-02 group also took no rescue medication during the entire treatment phase, in-patient treatment phase, and out-patient treatment phase than in the Placebo group. These results demonstrate that participants treated with MR-107A-02 required less rescue medication (APAP and opioid) than those in the Placebo group; this indicates that a meaningful proportion of patients receiving MR-107A-02 achieved adequate pain control without the need for any rescue medication, reflecting both efficacy and convenience from a patient care perspective.

Sensitivity analyses were conducted to assess the robustness of the primary and key secondary efficacy results. These analyses, which included alternative statistical models and assumptions, yielded results that were consistent with those of the primary analyses. This consistency supports the reliability and validity of the primary conclusions drawn from the FAS. To further evaluate the treatment effect, the primary efficacy estimand was analyzed using both the mFAS and the PP Analysis Set. Results from these additional populations closely mirrored those observed in the FAS. This reinforces confidence in the observed treatment effect and indicates that the findings are not particularly sensitive to population selection criteria or protocol adherence.

Subgroup analyses were performed for the primary and key secondary estimands as well as for the number and proportion of participants who were opioid (oxycodone and/or morphine) free during the entire treatment phase to examine potential differential treatment effects across demographic variables, including age, sex, and race. These analyses did not reveal any consistent or clinically meaningful interactions between treatment efficacy and subgroup membership; several subgroups had few participants, which limited the interpretation of these results. The efficacy of MR-107A-02 appeared generally stable across these subgroups of sufficient size (at least 20 participants), suggesting that its effect is broadly applicable within the studied population. Collectively, these findings from sensitivity, supplementary, and subgroup analyses support the robustness and generalizability of the primary and key secondary efficacy results.

Comparison of Tramadol with Placebo for Assay Sensitivity

To demonstrate the assay sensitivity, several analyses, including some post-hoc, were conducted to confirm the efficacy of tramadol in the study by comparing the effects of tramadol with placebo. Across endpoints, the efficacy of tramadol was demonstrated; tramadol displayed better pain control than placebo with higher $SPID_{0-48}$ ($p<0.001$ [nominal]), higher SPID over other intervals ($p\leq0.028$ [nominal; post-hoc]), faster time to perceptible pain relief ($p=0.035$ [nominal; post-hoc]), faster time to meaningful pain relief ($p=0.058$ [nominal; post-hoc]), longer time to first rescue medication, including opioid rescue ($p\leq0.015$ [nominal; post-hoc]), and with PGA of "very good" or "excellent" ($p=0.021$ [nominal; post-hoc]).

Comparison of MR-107A-02 with Standard of Care (Tramadol) for the Treatment of Acute Pain:

An analysis was also performed to estimate the difference in efficacy between MR-107A-02 and tramadol in treating acute pain following herniorrhaphy surgery. The results demonstrated that MR-107A-02 provided significantly greater pain relief than tramadol, as measured by the primary exploratory endpoint, $SPID_{0-48}$, ($p=0.025$ [nominal; post hoc]), indicating an advantage over tramadol.

Although no formal comparisons were made between MR-107A-02 and tramadol for other endpoints, participants in the MR-107A-02 group reported similar or better pain control as those in the Tramadol group with numerically larger LS mean SPIDs at each time interval evaluated, consistent numerically lower PIDs from 2 through 48 hours following study drug administration, suggesting a more robust and sustained analgesic effect.

The proportions of participants experiencing overall pain reductions from baseline of ≥30% or ≥50% were similar in the MR-107A-02 and the Tramadol groups, indicating comparable pain relief from both treatments. In addition, participants in the MR-107A-02 group achieved meaningful pain relief faster than those in the Tramadol group, further supporting the potential of MR-107A-02 to deliver rapid onset of pain relief. The time to first rescue medication was longer in the MR-107A-02 group, than in the Tramadol group, consistent with the observed analgesic efficacy.

Regarding PGA, during the out-patient treatment phase, a numerically higher proportion of participants in the MR-107A-02 group reported "very good" or "excellent" pain control than in the Tramadol group, which suggests that participants experienced more effective results during the out-patient treatment phase with MR-107A-02 than with tramadol.

For OBAS at 24 and 48 hours after the first dose and at Follow-up, participants in the MR-107A-02 group had lower mean OBAS than those in the Tramadol group. This suggests a better overall benefit with MR-107A-02 than with tramadol, including pain relief and fewer side effects. The MR-107A-02 and Placebo groups reported high MPADSS scores from 24 hours post-dose through Follow-up; at 24 hours the MR-107A-02 group demonstrated higher mean MPADSS score compared to the Placebo group. Therefore, with a higher mean score by 24 hours post-dose, participants in the MR-107A-02 group reached the minimum discharge criteria more reliably than those in the Placebo group despite their lower use of both APAP and opioid rescue medications; this shows a direct patient benefit related to reduced opioid analgesic use, such as reliable functional recovery for allowing discharge.

For NRS-R, participants in the MR-107A-02 group numerically lower LS mean PIDs than the Tramadol group from 2 through 48 hours following study drug administration.

A numerically larger proportion of participants in the MR-107A-02 group than in the Tramadol group took no rescue medication during the in-patient treatment phase, out-patient treatment phase, and entire treatment phase. This implies that MR-107A-02 may provide better pain control on its own than tramadol, consistent with the outcome for $SPID_{0-48}$. This is further supported by the finding that participants in the MR-107A-02 group used numerically less APAP as rescue medication than those in the Tramadol group during the in-patient treatment phase and the entire treatment phase and waited longer to take their first rescue medication than those in the Tramadol group.

Improved Patient-Centered Outcomes:

MR-107A-02 consistently outperformed placebo and tramadol in key patient-reported outcome measures, which reflect the real-world impact of analgesic interventions on recovery and comfort. Participants in the MR-107A-02 group reported consistently lower NRS-A pain and OBAS scores than those in the Tramadol and Placebo groups across timepoints, which reflected improved analgesic benefit with fewer side effects. During the entire treatment phase and during the in-patient treatment phase, participants in the MR-107A-02 group reported the lowest amount of APAP used, suggesting that MR-107A-02 may offer better baseline pain control than Tramadol. These findings collectively support the conclusion that MR-107A-02 not only manages pain effectively but also enhances the overall recovery experience by improving comfort and reducing the need for supportive medications.

Favorable Safety and Tolerability Profile:

MR-107A-02 was well tolerated in this study. No deaths were reported at any time during the study. Two participants in the in-patient treatment phase and 4 participants in the out-patient treatment phase reported TEAEs of special interest. No serious or severe TEAEs were reported in the MR-107A-02 group in the in-patient treatment phase; three participants each reported serious TEAEs and severe TEAEs in the out-patient treatment phase.

During the in-patient treatment phase, a total of 237 (41.4%) participants reported 443 TEAEs. The incidence of TEAEs was higher in the Tramadol and Placebo groups (45.2% and 45.8%, respectively) than in the MR-107A-02 group (35.2%). One hundred seven (18.7%) participants reported 181 TEAEs related to study drug; the incidence of related TEAEs was similar in all three treatment groups. Most TEAEs were either mild or moderate in severity with only 4 (0.7%) participants overall reporting severe TEAEs. Notably, all severe TEAEs were reported in the Placebo group, and no severe TEAEs were reported in the MR-107A-02 group. Two (0.3%) participants overall (1 each in the Placebo and Tramadol groups) reported one TEAE leading to study discontinuation (PTs of constipation and ileus). One (0.2% overall) participant in the Placebo group reported the serious TEAE of ileus. No serious TEAEs were reported in the MR-107A-02 group during the in-patient treatment phase. A total of 5 (0.9%) participants reported at least one TEAE leading to treatment discontinuation (1 [0.4%] participant in the MR-107A-02 group, 3 [2.6%] participants in the Tramadol group, and 1 [0.4%] participant in the Placebo group). Reported PTs included constipation (1 [0.4%] and 1 [0.9%] participant in the MR-107A-02 and Tramadol group, respectively), abdominal pain, ileus, and dehydration (1 [0.4%] participant each in the Placebo group), alanine aminotransferase increased, aspartate aminotransferase increased, and dizziness (1 [0.9%] participant each in the Tramadol group).

There was a lower incidence of ORAEs during the in-patient treatment phase in the MR-107A-02 group (19.1%) than in the Tramadol group (33.9%)—an absolute reduction of 14.8 percentage points and a relative reduction of approximately 44% of experiencing an ORAE. The incidence of ORAEs in the MR-107A-02 group was even slightly lower than that in the Placebo group (26.0%).

During the out-patient treatment phase, a total of 198 (35.5%) participants reported 419 TEAEs with similar proportions of participants reporting TEAEs among the treatment groups. Sixty-three (11.3%) participants reported 101 TEAEs related to study drug. Ninety-one (16.3%) participants reported 115 opioid-related TEAEs. Most TEAEs were either mild or moderate in severity, with 4 (0.7%) participants overall reporting at least one severe TEAE (3 [1.3%] participants in the MR-107A-02 group and 1 [0.4%] participant in the Tramadol Placebo group; also counted in the All-Placebo group). Overall, 4 (0.7%) participants reported 4 serious TEAEs (3 [1.3%] participants in the MR-107A-02 group and 1 [0.4%] participant in the Placebo group; also counted in the All Placebo group) with PTs of groin abscess, postoperative wound infection, and peptic ulcer hemorrhage (1 [0.4%] participant each in the MR-107A-02 group), and acute kidney injury (1 [0.4%] participant in the Placebo group). One TEAE that led to study discontinuation was reported in the Placebo group (PT of gout). Six (1.1%) participants overall reported at least one TEAE leading to treatment discontinuation. Treatment-emergent AEs leading to treatment discontinuation in the MR-107A-02 group consisted of nausea, mouth swelling, peptic ulcer hemorrhage, anemia postoperative, and dyspnea in 1 (0.4%) participant each.

No renal toxicity or hepatotoxicity concerns were identified, and no clinically relevant trends over time or treatment group differences in vital signs, laboratory parameters, or ECGs were observed.

Benefit-Risk Profile of MR-107A-02 in the Context of the Opioid Crisis:

In comparison to tramadol, MR-107A-02 demonstrated similar or superior pain relief as shown in post-hoc analysis, reinforcing the effectiveness of MR-107A-02 as a non-opioid alternative for moderate to severe acute pain. The clinical significance of this finding is underscored by the ability of MR-107A-02 to achieve efficacy with a reduced burden of side effects typically encountered with opioids. While Tramadol demonstrated analgesic efficacy, it was associated with a substantially higher rate of ORAEs and greater overall treatment burden (e.g., higher rates of treatment discontinuation during the in-patient treatment phase). Specifically: 33.9% of participants in the Tramadol group experienced ORAEs during the in-patient treatment phase, compared with 19.1% in the MR-107A-02 group—an absolute reduction of 14.8 percentage points and a relative reduction of approximately 44% of experiencing an ORAE. Tramadol was also linked to a higher rate of study drug-related TEAEs during the in-patient treatment phase (20.9%) than MR-107A-02 (18.3%). On the contrary, MR-107A-02 was associated with less constipation, nausea, and dizziness than tramadol-factors that are common barriers to recovery and discharge in post-surgical care. These findings underscore the therapeutic advantage of MR-107A-02 in providing effective pain relief while minimizing the risks associated with opioid analgesics.

The results of this study are especially significant in the context of the ongoing opioid crisis in the US, where overprescription and prolonged opioid use for postoperative pain remain key contributors to opioid dependence and misuse. Acute pain episodes—particularly those following surgery—are often the gateway to long-term opioid use. Therefore, it is crucial to identify and implement effective non-opioid alternatives. The ability of MR-107A-02 to deliver strong analgesia while reducing or eliminating the need for opioids directly supports opioid stewardship efforts. The marked reduction in ORAEs, lower opioid rescue consumption, and higher proportions of opioid-free patients represent the clinically meaningful strategy for MR-107A-02 to reduce opioid exposure without compromising pain control.

Overall Conclusions from Study 3002

MR-107A-02 (15 mg BID) demonstrated clear analgesic efficacy, with faster onset of pain relief, a clinically important opioid-sparing effect, and improvements in patient-reported outcomes when compared to placebo. MR-107A-02 (15 mg BID) also showed better analgesic efficacy and improvements in patient-reported outcomes when compared to tramadol. These benefits were achieved in parallel with a favorable safety profile, including lower rates of TEAE and reduced opioid-related complications.

The ability of MR-107A-02 to provide effective pain control with lower opioid use addresses a key need in acute moderate to severe pain management.

Discussion of Studies 3001 and 3002

MR-107A-02 demonstrated pain control versus placebo across two surgical pain models: Bunionectomy and Herniorrhaphy (see FIG. 33). $SPID_{0-48}$ h of MR-107A-02 versus placebo was consistent in both studies. MR-107A-02 showed a significantly higher $SPID_{0-48}$ h when compared with placebo. MR-107A-02 furthermore demonstrated pain control relative to an opioid comparator (tramadol) across these same two surgical pain models. MR-107A-02 showed a significantly higher $SPID_{0-48}$ h when compared with active control, tramadol (see FIG. 34). The time to perceptible and meaningful pain relief were measured using the Double Stopwatch Method in both of these surgical pain models for MR-107A-02, tramadol and placebo (see FIG. 35).

FIG. 36 is a depiction of the analysis of rescue opioid usage in both the bunionectomy and herniorrhaphy surgical studies. In the bunionectomy study, the MR-107A-02 group had 57% opioid-free patients, whereas in the placebo group there were 33% opioid-free patients ($p<0.001$). In the herniorrhaphy study, the MR-107A-02 group had 73% opioid-free patients versus 59% in the placebo group ($p=0.002$). In the bunionectomy study, the MR-107A-02 group had 59% lower mean opioid use versus the placebo group ($p<0.001$). In the herniorrhaphy study, the MR-107A-02 group had 35% lower mean opioid use versus the placebo group ($p=0.039$).

Analgesic Efficacy

The results of Study 3001 and Study 3002 show that MR-107A-02 achieved analgesic efficacy in both a bony pain model (bunionectomy) as well as in a soft tissue model (herniorrhaphy) for acute pain. The results were highly significant versus placebo. In both studies, MR-107A-02 also showed superior efficacy compared to the opioid comparator, tramadol (as a post-hoc analysis). There is an unmet need for oral analgesic medications with efficacy in the moderate-to-severe pain range, which is expected following discharge of patients after outpatient surgeries, for example. Therefore, MR-107A-02 fills a gap between the current approved oral NSAIDs and oral opioid medications. Results of the Phase 3 primary efficacy analysis are provided in Table 69, FIG. 10 (Study 3001), and FIG. 20 (Study 3002).

TABLE 69

MR-107A-02 Phase 3 Primary Endpoint - $SPID_{0\text{-}48\ h}$ (NRS-R) - Analysis of Covariance With Multiple Imputation - Meloxicam vs. Placebo (Full Analysis Set)

| Variable Statistic | Study 3001 (Bunionectomy) Meloxicam 15 mg BID N = 137 | Study 3001 (Bunionectomy) Placebo N = 136 | Study 3002 (Herniorrhaphy) Meloxicam 15 mg BID N = 230 | Study 3002 (Herniorrhaphy) Placebo N = 227 |
|---|---|---|---|---|
| $SPID_{0\text{-}48\ h}$ | | | | |
| n | 134 | 133 | 222 | 219 |
| Mean (SD) | 157.9 (100.21) | 85.0 (90.56) | 161.8 (87.45) | 112.5 (86.34) |
| Min, Max | −59.5, 387.3 | −102.7, 305.7 | −55.9, 392.6 | −102.5, 363.4 |
| LS Mean (SE) | 183.9 (10.64) | 101.2 (10.83) | 163.1 (8.99) | 113.0 (9.16) |
| CI[a] | (163.0, 204.7) | (80.0, 122.4) | (145.5, 180.7) | (95.0, 131.0) |
| Difference in LS Means (SE) vs Placebo | 82.7 (10.54) | | 50.1 (7.48) | |
| CI for Difference in LS Means[a] | (62.0, 103.4) | | (35.4, 64.8) | |
| p-value for Difference[b] | <0.001 | | <0.001 | |

CI = confidence interval; LS = least squares; NRS-R = Numerical Rating Scale - At Rest; SD = standard deviation; SE = standard error; SPID = summed pain intensity difference.

[a]95% CI for Meloxicam and Placebo.

[b]2-sided p-value.

Example III C. Post-Hoc Analysis of Moderate Pain and Severe Pain

A post-hoc subgroup analysis aimed to assess the efficacy of MR-107A-02 separately in patients with moderate pain or severe pain across the Phase 3 trials in both bony (bunionectomy) and soft tissue (herniorrhaphy) surgical pain models was conducted.

Patients reporting pain scores≥4 on NRS-R and/or NRS-A were randomized to receive MR-107A-02 (15 mg BID), placebo, or tramadol (50 mg QID) in bunionectomy and herniorrhaphy studies. The primary endpoint was the summed pain intensity difference over 0-48 hours (SPID0-48) based on NRS-R (bunionectomy)/NRS-A (herniorrhaphy) for MR-107A-02 versus placebo. In this post-hoc analysis, patients were stratified by baseline pain intensity (moderate: NRS 4-6; severe: NRS 7-10). Least squares (LS) mean pain intensity scores were compared between MR-107A-02 and placebo within each pain subgroup.

Across both studies, 192 patients presented with moderate pain and 536 with severe pain at baseline. MR-107A-02 significantly improved SPID0-48 versus placebo across both pain subgroups. In bunionectomy, MR-107A-02 demonstrated an LS mean $SPID_{0\text{-}48}$ of 134.94 vs 67.40 in moderate pain (LSMD: 67.54; $p=0.001$) and 202.25 vs 112.0 in severe pain (LSMD: 90.25; $p<0.001$). Similarly, in herniorrhaphy, MR-107A-02 showed a LS mean SPID0-48 of 104.16 vs 68.77 in moderate pain (LSMD: 35.39; $p=0.013$) and 189.25 vs 134.21 in severe pain (LSMD: 55.04; $p<0.001$).

Example IV. Food Effect Study

This study was a single-dose, randomized, six-period, six-treatment crossover study investigating the bioequivalence of MR-107A-02 Tablets, 15 mg, compared to a different investigational product (MECC-SA), following administration of a single, oral dose of 15 mg (1×15 mg) in 32 healthy, adult subjects under fasting, low-fat fed, and high-fat fed conditions.

Fasting Administration Conditions (Periods 1 and 2): Following an overnight fast of at least 10 hours, each subject received a single, oral 15-mg dose of either MR-107A-02 Tablets or MECC-SA along with 240 mL of ambient temperature water.

Low-Fat Fed Administration Conditions (Periods 3 and 4): Following a standardized low-fat, non-vegetarian breakfast consisting of 1 boiled egg, one packet of flavored instant oatmeal made with water, and 8 ounces of 1% fat milk that was preceded by an overnight fast of at least 10 hours, each subject received a single, oral dose of either MR-107A-02 Tablets, 15 mg meloxicam, or MECC-SA along with 240 mL of ambient temperature water.

High-Fat Fed Administration Conditions (Periods 5 and 6): Following a standardized high-fat, non-vegetarian breakfast, consisting of 2 eggs fried in butter, 2 strips of bacon, 2 slices of toast with butter, 4 ounces of hash brown potatoes, and 8 ounces of whole milk, that was preceded by an overnight fast of at least 10 hours, each subject received a single, oral dose of either MR-107A-02 Tablets, 15 mg meloxicam, or MECC-SA along with 240 mL of ambient temperature water.

A summary of the mean PK parameters for the MR-107A-02 formulation data is presented in Table 67, and a summary of the food-effect statistical comparison is presented in Table 68. Under high-fat fed conditions, the rate of meloxicam absorption following an oral administration of a 15 mg single-dose MR-107A-02 is slowed with an ~24% reduction in $C_{max}$ and longer $T_{max}$ compared to under fasting conditions. Low-fat fed conditions had a similar effect on the rate of meloxicam absorption with ~22% reduction in $C_{max}$ but did not delay $T_{max}$ as much as observed under high-fat conditions. The overall extent of absorption (LNAUC0-t and LNAUC0-inf) was bioequivalent across all 3 conditions.

TABLE 67

Summary of Mean (% CV) Meloxicam PK Parameters for Meloxicam Tablets MR-107A-02 Under Fasting, Low-Fat Fed, and High-Fat Fed Conditions

| Parameter | Treatment A Fasting (n = 30) | Treatment A Low-fat Fed (n = 29) | Treatment A High-fat Fed (n = 29) |
|---|---|---|---|
| $AUC_{0-inf}$ (ng * hr/mL) | 44706.0 (39.3%) | 41495.5 (37.9%) | 42604.9 (40.4%) |
| $AUC_{0-t}$ (ng * hr/mL) | 40111.6 (30.8%) | 37520.4 (30.5%) | 38094.3 (31.3%) |
| $C_{max}$ (ng/mL) | 2069.5 (26.1%) | 1620.7 (17.6%) | 1569.2 (20.7%) |
| $AUC_{0-1\ h}$ (ng * hr/mL) | 1327.4 (35.9%) | 461.8 (44.6%) | 409.6 (66.1%) |
| $AUC_{0-2\ h}$ (ng * hr/mL) | 3153.6 (26.5%) | 1767.6 (23.0%) | 1379.1 (50.4%) |
| $AUC_{0-3\ h}$ (ng * hr/mL) | 4825.8 (23.6%) | 3270.7 (16.9%) | 2565.7 (41.1%) |
| $AUC_{0-4\ h}$ (ng * hr/mL) | 6413.3 (22.2%) | 4834.6 (15.6%) | 3873.4 (34.3%) |
| $AUC_{0-6\ h}$ (ng * hr/mL) | 9040.0 (21.0%) | 7664.0 (15.9%) | 6702.2 (25.2%) |
| $k_{el}$ ($hr^{-1}$) | 0.0396 (31.0%) | 0.0401 (29.0%) | 0.0400 (31.1%) |
| $t_{1/2}$ (hr) | 19.47 (37.2%) | 18.85 (32.0%) | 19.29 (36.3%) |
| $t_{max}$ (hr)[a] | 0.75 (0.50-4.00) | 3.00 (1.50-4.00) | 5.00 (1.00-10.03) |

[a]Reported as Median (Range)
Treatment A: MR-107A-02, 15 mg meloxicam

TABLE 68

Statistical Summary of Food Effect Comparison for Meloxicam MR-107A-02 Tablets

| | Geometric LSMeans Ratio* (90% Confidence Interval)** | | |
|---|---|---|---|
| Parameter | High-Fat Fed/ Fasting | Low-Fat Fed/ Fasting | High-Fat/ Low-Fat |
| $LNAUC_{0-inf}$ (ng * hr/mL) | 0.95 (92.38%-98.29%) | 0.93 (90.10%-96.92%) | 1.02 (98.45%-105.61%) |
| $LNAUC_{0-t}$ (ng * hr/mL) | 0.95 (92.02%-97.84%) | 0.94 (90.74%-96.69%) | 1.01 (98.16%-104.54%) |
| $LNC_{max}$ (ng/mL) | 0.76 (71.69%-79.66%) | 0.78 (74.44%-82.76%) | 0.96 (91.74%-101.05%) |
| $AUC_{0-1\ h}$ (ng * hr/mL) | 0.26 (20.37%-34.11%) | 0.33 (27.91%-39.33%) | 0.80 (62.33%-101.53%) |
| $LNAUC_{0-2\ h}$ (ng * hr/mL) | 0.39 (32.96%-47.06%) | 0.56 (51.21%-60.50%) | 0.71 (59.38%-84.31%) |
| $LNAUC_{0-3\ h}$ (ng * hr/mL) | 0.49 (42.90%-57.04%) | 0.68 (64.20%-71.50%) | 0.73 (63.48%-83.97%) |
| $LNAUC_{0-4\ h}$ (ng * hr/mL) | 0.58 (51.21%-64.69%) | 0.75 (72.31%-78.54%) | 0.76 (67.99%-85.80%) |
| $LNAUC_{0-6\ h}$ (ng * hr/mL) | 0.73 (67.14%-78.51%) | 0.85 (81.72%-87.65%) | 0.86 (79.04%-93.10%) |

*Ratio (A/B) = $e^{[LSMEAN\ of\ (LNA\ -LNB)]}$;
**Used Natural Log Transformed Parameter

Example V. Dissolution and Absorption of Novel Meloxicam Composition

FIG. 32 shows the PK profiles of MR-107A-02 and MOBIC® from the bioequivalence study described in US 2024/0277726. MR-107A-02 had more rapid absorption than did MOBIC® (see FIG. 32).

Example VI. PK Comparison Across Studies

The following table 70 is a summary of the studies described herein.

TABLE 70

Summary of Studies

| Type of Study | Identifier | Objective | Design and Type of Control | Test Product(s); Dosage Regimen; Route of Administration | Number of Subjects for pK | Healthy Subjects or Patients | Duration and Type of Sampling |
|---|---|---|---|---|---|---|---|
| BA/BE | US 2024/ 0277726 | Comparative Bioavailability | 2-way Fasting Cross-over Randomized | MR-107A-02 Tablets and MOBIC Tablets, 15 mg single dose, oral | 16 males | Healthy | 0-72 hours Full Profile |
| BA/BE | Example IV | Comparative Bioavailability | 6-way Fasting, Low-Fat Fed, and High-Fat Fed, Cross-over, Randomized | MR-107A-02 and another investigative drug | 20 males, 10 females; 30 total | Healthy | 0-72 hours Full Profile |
| Efficacy. Safety | Example II | Efficacy, Safety, Dose-Response | Randomized, Double-blind, Placebo-controlled | MR-107A-02 Tablets, Placebo Tablets, 1.25 mg, 5 mg and 15 mg, Two Doses on Day 1, oral | 16 males, 11 females; 27 total (15 mg only) | Molar Extraction Surgery Patients | 0-24 hours Sparse Sampling |
| Efficacy, Safety | Study 3001 (Ex. IIIA) | Efficacy, Safety | Randomized, Double-blind, Placebo-controlled, Active Comparator | MR-107A-02 Tablets 15 mg, Placebo Tablets, Tramadol Capsules 10 mg; meloxicam BID Dosing, Oral | 5 males, 59 females, 64 total | Bunionectomy Surgery Patients | 0-48 hours Sparse Sampling |
| Efficacy, Safety | Study 3002 (Ex. IIIB) | Efficacy, Safety | Randomized, Double-blind, Placebo-controlled, Active Comparator | MR-107A-02 Tablets 15 mg, Placebo Tablets, Tramadol Capsules 10 mg; meloxicam BID Dosing, Oral | 120 males, 3 females; 123 total | Herniorrhaphy SPatientsurgery | 0-48 hours Sparse Sampling |

The following Table 71 provides a comparison of mean PK parameters after the first MR-107A-02 dose across the studies.

TABLE 71

Comparison of Mean (% CV) PK Parameters after the First MR-107A-02 Dose Across Studies

| Study | n | $C_{max}$ (ng/mL) | $T_{max}$[1] (hr) | $pAUC_{0\text{-}4\ hr}$ (ng * hr/mL) | $pAUC_{0\text{-}12\ hr}$ (ng * hr/mL) |
|---|---|---|---|---|---|
| US 2024/0277726 BA/BE (Single-dose, fasting) | 16 | 2786.1 (20.0%) | 0.75 (0.33-3.5) | 8374.0 (14.2%) | N/A |
| Example IV BA/BE (Single-dose, fasting) | 30 | 2069.5 (26.1%) | 0.75 (0.50-4.0) | 6413.3 (22.2%) | N/A |
| Example II Efficacy and Safety (BID dose for 24 hours) | 27 | 2517.9 (21.6%) | 0.97 (0.47-6.0) | 7218.7 (19.0%) | 16633.8 (16.7%) |
| Study 3001 (Ex. IIIA) (BID dose for 48 hours) | 60 | 1964.6 (30.1%) | 1.0 (0.25-12.0) | 5460.8 (36.8%) | 15003.7 (24.5%) |
| Study 3002 (Ex. IIIB) (BID dose for 48 hours) | 120 | 1317.6 (32.3%) | 2.2 (0.23-12.4) | 3265.7 (50.4%) | 10759.5 (29.5%) |

[1]Median (Min – Max)

FIG. 39 overlays the mean meloxicam profiles for the 0-12 hours' time period across the study in US 2024/0277726, the studies in Examples IV (food effect) and II (dose response), and the 3001 and 3002 studies.

FIG. 40 overlays the mean meloxicam concentrations profiles from the study of Example II (food effect) and Studies 3001 and 3002.

FIG. 22 overlays the mean meloxicam concentrations profiles for the 0-24 hours' time period for the study in US 2024/0277726, the studies in Examples IV (food effect) and II (dose response), and the 3001 and 3002 studies.

The following Table 72 provides a comparison of MR-107A-02 and MOBIC PK parameters from the study described in US 2024/0277726.

TABLE 72

MR-107A-02 vs MOBIC PK Parameter Comparison

| Parameter | Treatment A (n = 16) | Treatment B (n = 16) | Geometric LSMEANS Ratio (A/B)* | 90% Confidence Interval** |
|---|---|---|---|---|
| $AUC_{0\text{-}inf}$ (ng * hr/mL) | 55910.2 (44.3%) | 48233.5 (36.4%) | 1.13 | 108.02%-119.00% |
| $AUC_{0\text{-}t}$ (ng * hr/mL) | 49700.4 (32.4%) | 42834.5 (26.2%) | 1.14 | 109.37%-119.24% |
| $C_{max}$ (ug/mL) | 2786.1 (20.0%) | 1611.1 (15.4%) | 1.72 | 159.92%-184.44% |
| $AUC_{0\text{-}1h}$ (ng * hr/mL) | 1756.8 (22.9%) | 107.9 (88.6%) | 22.65 | 1587.74%-3232.40% |
| $AUC_{0\text{-}2\ h}$ (ng * hr/mL) | 4154.7 (15.7%) | 630.6 (85.2%) | 10.08 | 669.51%-1520.15% |
| $AUC_{0\text{-}4\ h}$ (ng * hr/mL) | 8374.0 (14.2%) | 2854.5 (48.7%) | 3.33 | 266.30%-417.64% |
| $AUC_{0\text{-}6\ h}$ (ng * hr/mL) | 11736.7 (14.3%) | 5607.5 (26.8%) | 2.15 | 190.99%-242.44% |
| $k_{el}$ ($hr^{-1}$) | 0.039 (34.8%) | 0.040 (31.5%) | | |
| $t_{1/2}$ (hr) | 19.75 (37.7%) | 19.25 (34.6%) | | |
| $t_{max}$ (hr)[a] | 0.75 (0.33-3.50) | 4.00 (2.00-8.00) | | |

*Ratio (A/B) = $e^{[LSMEAN\ of\ (LNA\ -LNB)]}$;

**Used Natural Log Transformed Parameter;

[a]Reported as Median (Range)

Treatment A: Meloxicam Tablets, 15 mg (Lot No. 2020565)

Treatment B: MOBIC Tablets, 15 mg (Lot No. 958185)

The study of Example IV ("food effect study") demonstrates that higher meloxicam blood plasma concentrations were obtained for subjects receiving MR-107A-02 under fasting conditions relative to those receiving MR-107A-02 under non-fasting conditions. From the food effect study, it was also observed that subjects under fasting conditions obtained higher meloxicam blood concentrations at an earlier time point (i.e., <1h) compared to subjects who received a low fat or a high fat meal. The PK profiles of the post-operative patients from Study 3001 and Study 3002 show a $T_{max}$ relatively comparable (i.e. two hours or less) to the fasted subjects in the food effect study, and the subjects who received a low-fat meal in the food effect study obtained $T_{max}$ at 3 hours. In these three cases, the $T_{max}$ was earlier than the 5 hours to $T_{max}$ observed in the subjects who received the high-fat meal in the food effect study (see FIG. 40).

Furthermore, the post-operative patients receiving MR-107A-02 in the dental surgery study (Example II) and in Studies 3001 and 3002, as well as the healthy fasted subjects who received MR-107A-02 in the study in US 2024/0277726 ("Phase I MOBIC study"), obtained peak meloxicam blood plasma concentrations at an earlier time point compared to the fasted subject in the Phase I MOBIC study who received MOBIC (see FIG. 39).

Lastly, patients receiving MR-107A-02 exhibited a faster $T_{max}$ (i.e., 0.75 h) compared to patients receiving MOBIC (i.e., 4.0 h), which is indicative of a faster onset of pain relief as was observed for patients in the disclosed studies.

A summary of the analysis population demographics and baseline characteristics of the subjects included in the population PK analysis is presented in the following Table 73:

TABLE 73

| Population PK Analysis Demographics and Baseline Characteristics STUDY | | | | | | |
|---|---|---|---|---|---|---|
| | Total (n = 316) | MELO-1001 (n = 16) | MR-1001 (n = 31) | MELO-2001 (n = 83) | MR-3001 (n = 63) | MR-3002 (n = 123) |
| Subject type | | | | | | |
| BSP | 63 (19.9%) | 0 (0%) | 0 (0%) | 0 (0%) | 63 (100%) | 0 (0%) |
| DSP | 83 (26.3%) | 0 (0%) | 0 (0%) | 83 (100%) | 0 (0%) | 0 (0%) |
| HSP | 123 (38.9%) | 0 (0%) | 0 (0%) | 0 (0%) | 0 (0%) | 123 |
| HV | 47 (14.9%) | 16 (100%) | 31 (100%) | 0 (0%) | 0 (0%) | 0 (0%) |
| Age (years) | | | | | | |
| Mean (SD) | 38.7 (15.9) | 33.1 (5.29) | 39.5 (9.36) | 19.1 (1.63) | 48 (12.2) | 47.7 (12.6) |
| Median | 39 | 32 | 41 | 18 | 49 | 48 |
| [Min, Max] | [18, 76] | [26, 42] | [19, 54] | [18, 24] | [19, 74] | [22, 76] |
| Sex | | | | | | |
| F | 105 (33.2%) | 0 (0%) | 10 (32.3%) | 34 (41%) | 58 (92.1%) | 3 (2.44%) |
| M | 211 (66.8%) | 16 (100%) | 21 (67.7%) | 49 (59%) | 5 (7.94%) | 120 (97.6%) |
| Race | | | | | | |
| AMERICAN INDIAN OR ALASKA NATIVE | 1 (0.316%) | 0 (0%) | 0 (0%) | 0 (0%) | 0 (0%) | 1 (0.813%) |
| ASIAN | 22 (6.96%) | 16 (100%) | 1 (3.23%) | 1 (1.2%) | 2 (3.17%) | 2 (1.63%) |
| BLACK OR AFRICAN AMERICAN | 39 (12.3%) | 0 (0%) | 2 (6.45%) | 2 (2.41%) | 22 (34.9%) | 13 (10.6%) |
| MULTIPLE | 4 (1.27%) | 0 (0%) | 0 (0%) | 1 (1.2%) | 1 (1.59%) | 2 (1.63%) |
| OTHER | 1 (0.316%) | 0 (0%) | 1 (3.23%) | 0 (0%) | 0 (0%) | 0 (0%) |
| WHITE | 249 (78.8%) | 0 (0%) | 27 (87.1%) | 79 (95.2%) | 38 (60.3%) | 105 (85.4%) |
| Baseline weight (kg) | | | | | | |
| Mean (SD) | 78.3 (16.9) | 58.1 (5.5) | 75.3 (11.1) | 71.3 (15.2) | 76.5 (15.5) | 87.2 (15.9) |
| Median | 76 | 58.7 | 74.5 | 68.5 | 74.2 | 86 |
| [Min, Max] | [44.1, 129] | [50.2,65.8] | [49.2, 92.9] | [44.1, 120] | [48, 115] | [52.1, 129] |
| Baseline eGFR (mL/min/1.73 m^2) | | | | | | |
| Mean (SD) | 103 (17.5) | 116 (10.6) | 102 (12.4) | 117 (13.4) | 96.5 (17.3) | 96.2 (15.7) |
| Median | 104 | 116 | 101 | 119[ | 99 | 96.3 |
| [Min, Max] | [55, 136] | [95.2, 133] | [80.2, 124] | [84, 136] | [55, 133] | [55, 127] |

MELO-1001 is the study described in US 2004/0277726
MR-1001 is the study of Example IV herein
MELO-2001 is the study of Example II herein
MELO-3001 is the study of Example IIIA herein
MELO-3002 is the study of Example IIIB herein Table 74 shows the number of subjects and number of samples forming the population PK data pool. The population PK included subjects from the studies described in US 2024/0277726 (crossover: fasting vs MOBIC), Example IV (crossover: fed and fasted vs MECC-SA), Example II (dental surgery), Example IIIA (bunion surgery), and Example IIIB (hernia surgery).

Food intake across the studies used to form the population PK pool was compared. Subjects in the US 2024/0277726 fasted overnight for at least 10 hours before the drug was administered, and the fast was maintained for at least 4 hours after dosing. Prior to surgery, subjects in the study of Example II (dental surgery) were requested to fast and were allowed to eat 2 hours following first dose. The meal served after fasting period in both these studies was low-fat type. However, for the sake of PK modeling, subjects in these two studies were assumed to be on fasting meal type. Subjects in Study 3001 and Study 3002 consumed low-fat meals at various time points during dosing. At each dose level, subjects were classified as either fasting or low-fat meal type based on the timing of their prior meal. If a subject had consumed a meal within two hours before dose administration, they were considered to be in the low-fat meal type category; otherwise, they were classified as fasting.

TABLE 74

| PK Observations Included in Population Modeling Analysis Stratified by Study and Dose Administered | | | | | |
|---|---|---|---|---|---|
| Study | Dose (mg) | Total PK Samples (n) | BLQ n(%) | Included n(%) | Missing n(%) |
| MELO-1001 | 15.0 | 400 | 18 (4.5) | 400 (100.0%) | 0 (0.0) |
| MR-1001 | 15.0 | 1780 | 113 (6.3) | 1778 (99.9%) | 2 (0.1) |
| MELO-2001 | 1.25 | 504 | 35 (6.9) | 504 (100.0%) | 0 (0.0) |
| MELO-2001 | 5.0 | 491 | 28 (5.7) | 491 (100.0%) | 0 (0.0) |
| MELO-2001 | 15.0 | 486 | 28 (5.8) | 486 (100.0%) | 0 (0.0) |
| MR-3001 | 15.0 | 549 | 64 (11.7) | 549 (100.0%) | 0 (0.0) |
| MR-3002 | 15.0 | 1085 | 167 (15.4) | 1085 (100.0%) | 0 (0.0) |

Program: reports/nda-report/ppk-er shell.qmd:567
Abbreviations: BLQ = Below Quantification Limit
All BLQ values were set to 0 and were included for population PK modelling.

A total of 318 subjects contributed to 4825 plasma samples for the population PK analysis. Two observations were excluded due to missing data in the dataset, and an additional three observations were excluded as they were associated with protocol deviations. All observations that were BLQ were recorded during early post-dose time points following dose administration. These BLQ values were set to zero and retained in the analysis.

The PK profiles following administration of MR-107A-02 were overlayed. Overlay plots were limited to the 15 mg dose. Exploratory plots after MR-107A-02 administration in the study of Example IV (dental surgery) show a rapid absorption and linear disposition of the drug.

In order to model the effects of different conditions on efficacy based on reduction in NRS score, covariates were chosen and PK simulations were generated. The impact of each covariate on selected model parameters was analyzed. Potentially clinically relevant effects were observed for the Ka in subjects undergoing dental and hernia surgeries. Additionally, meal type had a clinically relevant impact on Ka. In contrast, covariate effects related to hernia status (on exposure), age, and sex (on bioavailability) were not clinically relevant.

The final covariate model for MR-107A-02 was applied to simulate meloxicam concentration-time profiles under varying meal type conditions (fasting, low-fat, and high-fat). Meal type was incorporated as a covariate, with fasting and low-fat conditions selected to align with the dietary protocols of Study 3001 and Study 3002. These simulated concentration profiles were subsequently integrated with the developed NRS model to predict changes in pain scores over time. As further explained below, this enabled evaluation of whether the onset of analgesic effect is influenced by meal type under repeated dosing conditions.

A sequential modeling approach was employed for exposure-response (E-R) analysis, beginning with a placebo model followed by a drug effect model. Individual observed meloxicam concentrations were linked to the corresponding NRS scores to characterize the relationship between drug exposure and response.

Table 75 below shows the E-R population baseline characteristics for Study 3001.

TABLE 75

E-R Analysis Population Baseline Characteristics

| | Treatment Arm | | |
|---|---|---|---|
| | Total (n-128) | Meloxicam 15 mg BID (n = 64) | Placebo (n = 64) |
| Baseline NRS Score | | | |
| Mean (SD) | 7.35 (1.63) | 7.14 (1.63) | 7.56 (1.61) |
| Median [Min, Max] | 7 [3, 10] | 7 [3, 10] | 8 [4, 10] |
| Sex (n, %) | | | |
| F | 111 (86.7%) | 59 (92.2%) | 52 (81.2%) |
| M | 17 (13.3%) | 5 (7.81%) | 12 (18.8%) |
| Age (years) | | | |
| Mean (SD) | 48.6 (12.9) | 48.2 (12.2) | 49.1 (13.7) |
| Median [Min, Max] | 50 [19, 74] | 49.5 [19, 74] | 50 [19, 72] |
| Race (n, %) | | | |
| AMERICAN INDIAN OR ALASKA NATIVE | 2 (1.56%) | 0 (0%) | 2 (3.12%) |
| ASIAN | 5 (3.91%) | 2 (3.12%) | 3 (4.69%) |
| BLACK OR AFRICAN AMERICAN | 39 (30.5%) | 22 (34.4%) | 17 (26.6%) |
| MULTIPLE | 1 (0.781%) | 1 (1.56%) | 0 (0%) |
| WHITE | 81 (63.3%) | 39 (60.9%) | 42 (65.6%) |
| Baseline Estimated Glomerular Filtration Rate | | | |
| Mean (SD) | 96.2 (17.7) | 96.6 (17.2) | 95.9 (18.3) |
| Median [Min, Max] | 98.6 [53.1, 133] | 99.7 [55, 133] | 96.8 [53.1, 129] |

Program: reports/nda-report/ppk-er-shell.qmd:741

Abbreviations: SD, standard deviation; Min, minimum; Max, maximum.

-

Table 76 below shows the E-R population baseline characteristics for Study 3002.

TABLE 76

E-R Analysis Population Demographics and Baseline Characteristics

| | Treatment Arm | | |
|---|---|---|---|
| | Total (n = 226) | Meloxicam 15 mg BID (n = 121) | Placebo (n = 105) |
| Baseline NRS Score | | | |
| Mean (SD) | 7.6 (1.67) | 7.61 (1.61) | 7.58 (1.74) |
| Median [Min, Max] | 8 [4, 10] | 8 [4, 10] | 8 [4, 10] |

TABLE 76-continued

| E-R Analysis Population Demographics and Baseline Characteristics | | | |
|---|---|---|---|
| | Treatment Arm | | |
| | Total (n = 226) | Meloxicam 15 mg BID (n = 121) | Placebo (n = 105) |
| Sex (n, %) | | | |
| F | 10 (4.42%) | 3 (2.48%) | 7 (6.67%) |
| M | 216 (95.6%) | 118 (97.5%) | 98 (93.3%) |
| Age (years) | | | |
| Mean (SD) | 48.6 (12.1) | 47.7 (12.6) | 49.6 (11.4) |
| Median [Min, Max] | 49 [22, 80] | 48 [22, 76] | 51 [22, 80] |
| Race (n, %) | | | |
| AMERICAN INDIAN OR ALASKA NATIVE | 2 (0.885%) | 1 (0.826%) | 1 (0.952%) |
| ASIAN | 2 (0.885%) | 2 (1.65%) | 0 (0%) |
| BLACK OR AFRICAN AMERICAN | 20 (8.85%) | 13 (10.7%) | 7 (6.67%) |
| MULTIPLE | 1 (0.442%) | 0 (0%) | 1 (0.952%) |
| NOT REPORTED | 1 (0.442%) | 0 (0%) | 1 (0.952%) |
| OTHER | 5 (2.21%) | 2 (1.65%) | 3 (2.86%) |
| WHITE | 195 (86.3%) | 103 (85.1%) | 92 (87.6%) |
| Baseline Estimated Glomerular Filtration Rate | | | |
| Mean (SD) | 95.2 (15.2) | 96.3 (15.7) | 93.9 (14.4) |
| Median [Min, Max] | 95.8 [50.6, 128] | 96.6 [55, 127] | 95 [50.6, 128] |

Program: reports/nda-report/ppk-er-shell.qmd:962
Abbreviations: SD, standard deviation; Min, minimum; Max, maximum.

An E-R model was applied to simulate NRS scores at 0.5-hour intervals up to 48 hours post-dose. Simulations were conducted under both fasting and fed (low-fat and high-fat meal conditions) to evaluate the onset and magnitude of drug effect across different prandial states. A total of 1,000 subjects were simulated to assess the impact of meal type on the onset of effect on NRS scores. Comparisons between meal types showed that the differences in cumulative probabilities remained below 20% across all time points, indicating a high degree of similarity in drug response between the fasting and fed conditions. This analysis and modeling suggested that the influence of meal type (fasting, low-fat or high-fat) on the onset and intensity of drug effect was minimal.

From the above-described analyses of the PK populations of the studies, clinically relevant effects on the Ka were observed for both meal type and subject type. Subjects who underwent dental and hernia surgeries demonstrated significantly different Ka values compared to healthy individuals. Also, low-fat and high-fat meal types showed clinically relevant differences from fasting conditions, based on their Ka estimates and CIs. In contrast, the effect observed in bunion surgery subjects was less conclusive. Note, the drug administration timing varied across subject types, which may have contributed to the observed differences in Ka. Specifically, dental and hernia subject received the drug within hours of surgery, whereas bunion subjects were dosed on the day following surgery, which might have influenced absorption dynamics.

Modeling and analyses of NRS scores from Study 3001 and Study 3002, after censoring observations post-rescue medication, illustrate changes in pain over time for both the MR-107A-02 15 mg BID treatment and placeboes arms. At baseline, a large proportion of subjects in both study drug and placebo groups reported NRS scores≥6. As time progressed, the proportion of subjects with higher NRS scores declined in both arms. In the placebo group, reduction in NRS scores was observed over the 48-hour period indicating a time-related change in reported pain levels. In contrast, the MR-107A-02 treatment arms showed an earlier and more consistent decrease, with fewer subjects reporting scores≥8 from 8 hours post-first dose onward.

What is claimed is:

1. A method of treating moderate to severe pain in an individual in need thereof comprising administering a solid oral meloxicam composition to the individual, wherein the composition comprises an amount of meloxicam or a pharmaceutically acceptable meloxicam salt equivalent to 15 mg meloxicam, the individual's pain before administration of the composition is at a level the same as an adult human reporting a pain level of about from 4.0 to about 10.0 on a pain NRS, and the time to the individual's first meaningful pain relief is about 5.5 hours or less following administration of the composition.

2. The method of claim 1 wherein the time to the individual's first meaningful pain relief is between about 2 hours to about 5.5 hours following administration of the composition.

3. The method of claim 2 wherein the time to the first meaningful pain relief is between about 2.4 hours and 3.7 hours following administration of the composition.

4. The method of claim 1 wherein the pain before administration of the composition is severe and is at a level the same as an adult human reporting a pain level of about 7.0 to about 10.0 on a pain NRS.

5. The method of claim 1 wherein the pain before administration of the composition is moderate and is at a level the same as an adult human reporting a pain level of from about 4.0 to about 6.0 on a pain NRS.

6. The method of claim 1 wherein the composition is administered to the individual about every 12 hours and wherein the individual's pain level decreases for about 48 hours after a first administration of the composition.

7. The method of claim 1 wherein the pain comprises acute pain.

8. The method of claim 1 wherein the pain comprises procedural pain.

9. The method of claim 8 wherein the individual has undergone a surgery.

10. The method of claim 1 wherein the composition is administered to the individual without food or when the individual is in a semi-fasted state.

11. The method of claim 1 wherein the composition is administered to the individual about every 12 hours for 30 days or less.

12. The method of claim 11 wherein the composition is administered to the individual about every 12 hours for 7 days or less.

13. The method of claim 12 wherein the composition is administered four times to the individual about every 12 hours for 2 days (48 hours) or less.

14. The method of claim 12 wherein the treatment is without significant risk to the individual of a gastrointestinal bleeding adverse event.

15. The method of claim 12 wherein the treatment is without significant risk to the individual of a cardiovascular event.

16. The method of claim 1 wherein the individual exhibits opioid-sparing behavior after administration of the composition.

17. The method of claim 16 wherein the individual does not receive an opioid analgesic for at least about 48 hours after administration of the composition.

18. The method of claim 1 wherein the individual does not receive a rescue pain medication before experiencing meaningful pain relief following administration of the composition.

19. The method of claim 1 wherein the meloxicam or pharmaceutically acceptable meloxicam salt is in alkaline surroundings in the composition.

20. The method of claim 1 wherein the composition comprises one or more alkalizing agents and one or more hydrophilic polymers.

21. The method of claim 1 wherein the composition comprises sodium bicarbonate and an excipient selected from copovidone, hypromellose, or a combination of copovidone and hypromellose.

22. The method of claim 21 comprising granules or pellets of meloxicam.

23. A method of treating moderate to severe pain in an individual in need thereof comprising administering a solid oral meloxicam composition to the individual, wherein the composition comprises 15 mg of meloxicam, and wherein the individual's pain about 48 hours from the time of administration of the composition is relieved by a degree corresponding to a 48-hour summed pain intensity difference ($SPID_{0-48}$) of from about 163.0 to about 204.7 or from about 145.5 to about 180.7 using an 11-point NRS (zero to 10) for pain intensity.

24. The method of claim 23, wherein the individual feels pain at the time of administration of the composition at a level corresponding to about from 4.0 to about 10.0 using an 11-point NRS (zero to 10) for pain intensity.

25. The method of claim 24, wherein the composition is in the form of a tablet or tablets.

26. A method of treating moderate to severe pain in an individual in need thereof comprising administering a solid oral meloxicam composition to the individual, wherein the composition comprises 15 mg of meloxicam, and wherein the composition provides a least squares mean summed pain intensity difference over 48 hours (least squares mean $SPID_{0-48}$) using an 11-point pain NRS (zero to 10) in a population of clinical study subjects of from about 163.0 to about 204.7 or from about 145.5 to about 180.7.

27. The method of claim 26 wherein the individual feels pain around the time of administration of the composition at a level corresponding to about from 4.0 to about 10.0 on an 11-point pain NRS (zero to 10).

28. The method of claim 26 wherein the composition is in the form of a tablet or tablets.

29. The method of claim 27 wherein the composition is in the form of a tablet or tablets.

* * * * *